(12) United States Patent
Bergstrom et al.

(10) Patent No.: US 7,473,688 B2
(45) Date of Patent: *Jan. 6, 2009

(54) INDOLOBENZAZEPINE HCV NS5B INHIBITORS

(75) Inventors: Carl P. Bergstrom, Madison, CT (US); John A. Bender, Middletown, CT (US); Robert G. Gentles, Wallingford, CT (US); Piyasena Hewawasam, Middletown, CT (US); Thomas W. Hudyma, Durham, CT (US); John F. Kadow, Wallingford, CT (US); Scott W. Martin, Middletown, CT (US); Alicia Regueiro-Ren, Middletown, CT (US); Kap-Sun Yeung, Madison, CT (US); Yong Tu, Cheshire, CT (US); Katharine A. Grant-Young, Madison, CT (US); Xiaofan Zheng, Cheshire, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 113 days.

This patent is subject to a terminal disclaimer.

(21) Appl. No.: 11/516,435

(22) Filed: Sep. 6, 2006

(65) Prior Publication Data

US 2007/0078122 A1    Apr. 5, 2007

Related U.S. Application Data

(60) Provisional application No. 60/771,501, filed on Feb. 8, 2006, provisional application No. 60/716,693, filed on Sep. 13, 2005.

(51) Int. Cl.
*A61K 31/55* (2006.01)
*A61P 31/00* (2006.01)
*C07D 223/14* (2006.01)

(52) U.S. Cl. .................. 514/214.01; 540/576
(58) Field of Classification Search ............ 514/214.01; 540/576

See application file for complete search history.

(56) References Cited

U.S. PATENT DOCUMENTS

2006/0046983 A1   3/2006   Hudyma et al. ........ 514/211.09

FOREIGN PATENT DOCUMENTS

| WO | WO 2005/080399 A1 | 9/2005 |
| WO | WO 2006/046030 A2 | 5/2006 |
| WO | WO 2006/046039 A2 | 5/2006 |
| WO | WO 2007/029029 A2 | 3/2007 |

*Primary Examiner*—Brenda L Coleman
(74) *Attorney, Agent, or Firm*—James Epperson

(57) ABSTRACT

The invention encompasses compounds and salts of Formulas I, II, III, and IV as well as compositions and methods of using the compounds. The compounds have activity against hepatitis C virus (HCV) and are useful in treating those infected with HCV.

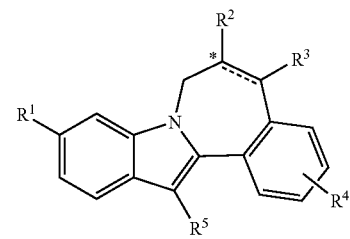

I

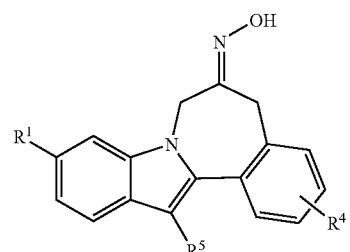

II

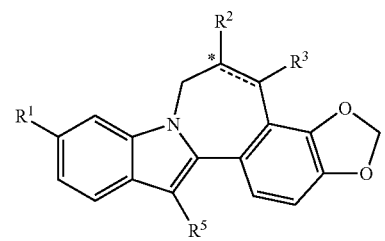

III

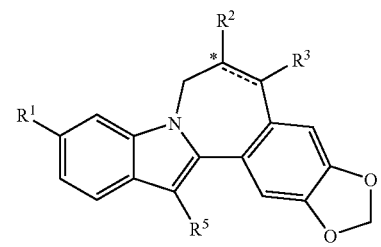

IV

15 Claims, No Drawings

INDOLOBENZAZEPINE HCV NS5B INHIBITORS

CROSS REFERENCE TO RELATED APPLICATIONS

This application claims the benefit of U.S. Provisional Application Ser. No. 60/716,693 filed Sep. 13, 2005 and Ser. No. 60/771,501 filed Feb. 8, 2006.

BACKGROUND OF THE INVENTION

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

HCV NS5B inhibitors have been disclosed. See WO 2006/046039; WO 2006/046030; WO 2006/029912; WO 2005/080399; WO 2005014543; WO 200307945; WO 2003010140; WO 2003010141; WO 200204425; WO 200147883; Harper, S. A. et al. *J. Med. Chem.* 2005, 48, 4547; and Harper, S. A. et al. *J. Med. Chem.* 2005, 48, 1314, and references cited therein.

DESCRIPTION OF THE INVENTION

The invention encompasses compounds of formulas I, II, III, and IV, and pharmaceutically acceptable salts and solvates thereof, and compositions and methods of treatment using these compounds.

One aspect of the invention is a compound of formula I

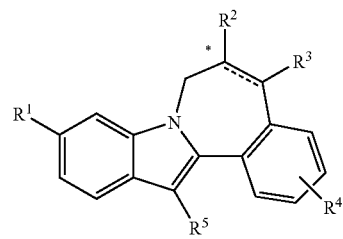

wherein:
$R^1$ is $CO_2R^6$ or $CONR^7R^8$;
$R^2$ is $CO_2R^6$, $CO_2$benzyl, $CONR^9R^{10}$, $NHCO_2$(alkyl), $NHCO_2$benzyl, $NHCO$(alkyl), $NHCO$(cycloalkyl), $NHCOR^{14}$, $NHCO((R^{15})$alkyl), $NHCO((R^{16})$alkyl), $NHCO$(tetrahydropyranyl), $NHCO$(methoxycycloalkyl), $NHCON(R^6)_2$, $NHCON(R^6)((N(R^6)_2)$alkyl), $NHCON(R^6)((CO_2R^6)$alkyl), $NHCON(R^6)((CON(R^6)_2)$alkyl), $NHCON(R^6)((COR^{15})$alkyl), $NHCON(R^6)((tetrahydropyranyl)alkyl),

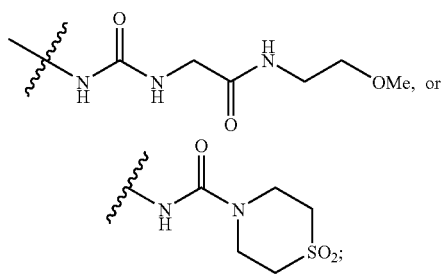

$R^3$ is hydrogen or alkyl;
$R^4$ is hydrogen, halo, alkyl, alkoxy, or benzyloxy;
$R^5$ is $C_{5-7}$cycloalkyl;
$R^6$ is hydrogen, alkyl, or cycloalkyl;
$R^7$ is hydrogen, alkyl, cycloalkyl, alkoxy, aminoalkyl, (alkylamino)alkyl, (dialkylamino)alkyl, $(CO_2R^6)$alkyl, (CON ($R^6$)($R^6$))alkyl, (alkyl)CONH, tetrazolyl, tetrahydropyranyl, sulfolanyl, $SO_2R^{11}$, $SO_2R^{12}$, or ($R^{13}$)alkyl;

$R^8$ is hydrogen, alkyl, or cycloalkyl;

or $NR^7R^8$ taken together is pyrrolidinyl, piperidinyl, piperazinyl, piperazinyl, homomorpholinyl, homopiperidinyl, morpholinyl, or thiomorpholinyl, and is substituted with 0-2 substituents selected from halo, alkyl, and haloalkyl;

$R^9$ is hydrogen, alkyl, cycloalkyl, hydroxyalkyl, dihydroxyalkyl, (alkoxy)alkyl, aminoalkyl, (alkylamino)alkyl, (dialkylamino)alkyl, ($R^{12}$)alkyl, (CHO)alkyl, ($CO_2R^6$)alkyl, ($CON(R^6)_2$)alkyl, ($COR^{12}$)alkyl, ($COR^{15}$)alkyl, ($R^{16}$)alkyl, ((alkoxyalkyl)amido)alkyl, (alkylamido)alkyl, (tetrahydrofuranyl)alkyl, (dioxolanyl)alkyl, (alkylCO)($R^6$)amino, ((alkylCO)($R^6$)amino)alkyl, tetrahydropyranyl, or sulfolanyl;

$R^{10}$ is hydrogen, alkyl, cycloalkyl, hydroxyalkyl, dihydroxyalkyl, (alkoxy)alkyl, aminoalkyl, (alkylamino)alkyl, (dialkylamino)alkyl, ($R^{12}$)alkyl, (CHO)alkyl, ($CO_2R^6$)alkyl, ($CON(R^6)_2$)alkyl, ($COR^{12}$)alkyl, ($COR^{15}$)alkyl, ($R^{16}$)alkyl, ((alkoxyalkyl)amido)alkyl, (alkylamido)alkyl, (tetrahydrofuranyl)alkyl, (dioxolanyl)alkyl, (alkylCO)($R^6$)amino, ((alkylCO)($R^6$)amino)alkyl, tetrahydropyranyl, or sulfolanyl;

or $NR^9R^{10}$ taken together is azetidinyl, pyrrolidinyl, piperidinyl, piperazinyl, homomorpholinyl, homopiperidinyl, morpholinyl, or thiomorpholinyl, and is substituted with 0-4 substituents selected from the group consisting of halo, hydroxy, $OPO(OR^6)_2$, alkoxy, alkyl, cycloalkyl, (cycloalkyl)alkyl, haloalkyl, hydroxyalkyl, alkoxyalkyl, (hydroxy)alkoxyalkyl, (alkoxy)alkyl, amino, alkylamino, dialkylamino, (alkylCO)($R^6$)amino, (alkoxyCO)($R^6$)amino, (alkoxyalkylCO)($R^6$)amino, (alkylCO)alkylamino, (cycloalkyl)($PhSO_2$)amino, $CO_2R^6$, $CON(R^6)_2$, CONH(alkenyl), ($R^{12}$)CO, (alkyl)CO, (cycloalkyl)CO, (hydroxyalkyl)CO, ((hydroxy)cycloalkyl)CO, (aminoalkyl)CO, (acetoxyalkyl)CO, PhCO, (furanyl)CO, (benzodioxanyl)CO, (alkyl)$CO_2$, $SO_2R^{11}$, $SO_2R^{12}$, ($CO_2R^6$)alkyl, ($CON(R^6)_2$)alkyl, ($COR^{12}$)alkyl, (alkylCO)($R^6$)aminoalkyl, (PhCONH)alkyl, ($R^{12}$)alkyl, $R^{12}$, phenyl, methoxyphenyl, pyrrolyl, furanyl, thienyl, imidazolyl, isoxazolyl, oxazolyl, thiazolyl, triazolyl, oxadiazolyl, pyridinyl, pyrimidinyl, pyrazinyl, triazinyl, pyrazolyl,

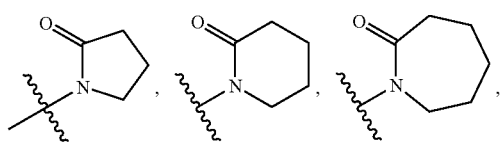

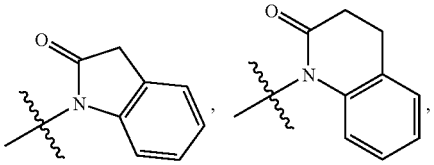

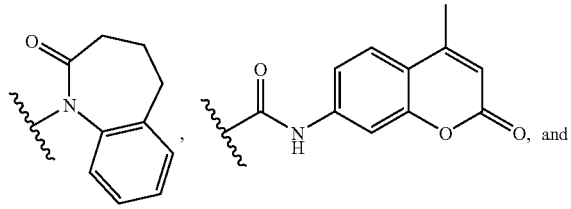

-continued

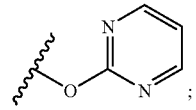

;

or $NR^9R^{10}$ taken together is

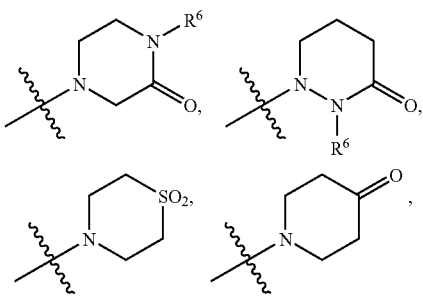

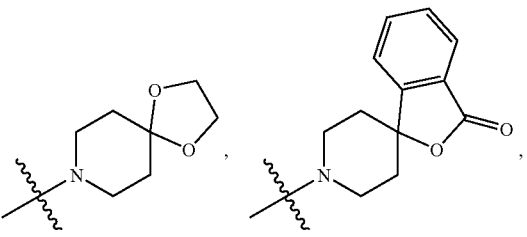

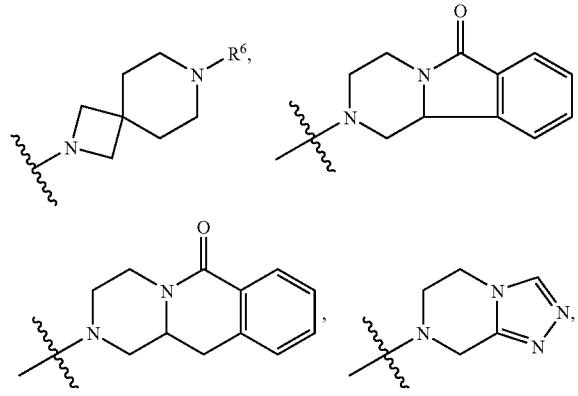

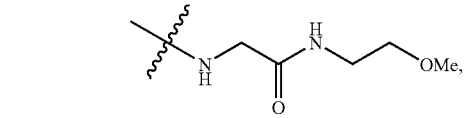

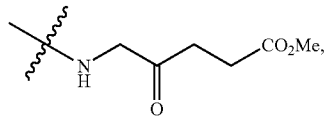

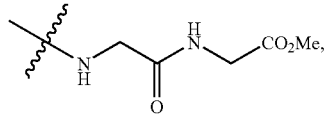

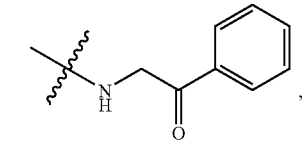

-continued

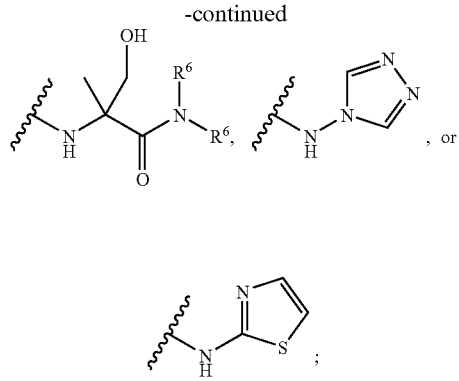

or NR⁹R¹⁰ taken together is a [2.2.1] or [2.2.2] bridged bicyclic amine wherein the bicycle contains 0-1 NR⁶, NCO₂R⁶, or O;

R¹¹ is alkyl, haloalkyl, cycloalkyl, alkoxy, amino, alkylamino, dialkylamino, ((R⁶)(R⁶)N)alkylamino, (((R⁶)(R⁶)N)alkyl)₂amino, N,O-dimethylhydroxylamino, or phenyl, wherein the phenyl is substituted with 0-2 substituents selected from the group consisting of halo, alkyl, haloalkyl, and alkoxy;

R¹² is pyrrolidinyl, piperidinyl, piperazinyl, homomorpholinyl, homopiperidinyl, morpholinyl, or thiomorpholinyl, and is substituted with 0-2 substituents selected from halo, alkyl, haloalkyl, and alkoxy;

R¹³ is pyrrolidinyl, piperidinyl, piperazinyl, homomorpholinyl, homopiperidinyl, morpholinyl, thiomorpholinyl, tetrahydrofuranyl, furanyl, thienyl, pyrrolyl, pyrazolyl, imidazolyl, isoxazolyl, oxazolyl, triazolyl, oxadiazolyl, tetrazolyl, pyridinyl, pyrazinyl, pyrimidinyl, imidazopyridinyl, or benzimidazole, and is substituted with 0-2 alkyl substituents;

R¹⁴ is azetidine, pyrrolidinyl, piperidinyl, piperazinyl, piperazinyl, homomorpholinyl, homopiperidinyl, morpholinyl, thiomorpholinyl, or S,S-dioxothiomorpholinyl, and is substituted with 0-3 substituents selected from halo, alkyl, hydroxy, alkoxy, aminoalkyl, (alkylamino)alkyl, (dialkylamino)alkyl, (CO₂R⁶)alkyl, (CON(R⁶)₂)alkyl, ((R⁶CO)(R⁶)amino)alkyl, (R¹⁵)alkyl, (R⁶CO)(R⁶)amino, R¹⁵, alkylCO, CF₃CO, CO₂R⁶, CON(R⁶)₂, or SO₂R⁶;

or R¹⁴ is a [2.2.1] or [2.2.2] bridged bicyclic amine wherein the bicycle contains 0-1 O;

R¹⁵ is azetidinyl, pyrrolidinyl, piperidinyl, piperazinyl, homomorpholinyl, homopiperidinyl, morpholinyl, or thiomorpholinyl, and is substituted with 0-2 halo, alkyl, or alkoxy substituents;

R¹⁶ is pyrazolyl, imidazolyl, isoxazolyl, oxazolyl, thiazolyl, triazolyl, oxadiazolyl, tetrazolyl, or pyridinyl, and is substituted with 0-2 alkyl substituents; and the dashed line is either a single bond or a double bond, provided that if the dashed line is a single bond, the carbon bearing the asterisk is either of the R configuration, the S configuration, or a mixture of R and S;

or a pharmaceutically acceptable salt thereof.

Another aspect of the invention is a compound of formula I

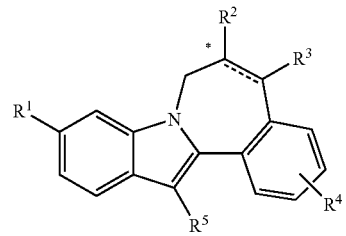

wherein:
R¹ is CONR⁷R⁵;
R² is CO₂R⁶, CO₂benzyl, CONR⁹R¹⁰, NHCO₂(alkyl), NHCO₂benzyl, NHCO(alkyl), NHCO(cycloalkyl), NHCOR¹⁴, NHCO((R¹⁵)alkyl), NHCO((R¹⁶)alkyl), NHCO(tetrahydropyranyl), NHCO(methoxycycloalkyl), NHCON(R⁶)₂, NHCON(R⁶)((N(R⁶)₂)alkyl), NHCON(R⁶)((CO₂R⁶)alkyl), NHCON(R⁶)((CON(R⁶)₂)alkyl), NHCON(R⁶)((COR¹⁵)alkyl), NHCON(R⁶)((tetrahydropyranyl)alkyl),

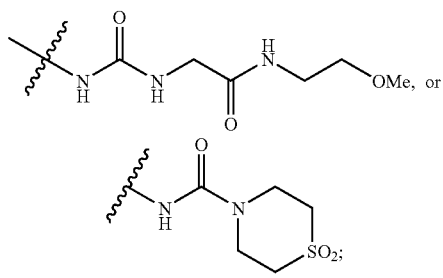

R³ is hydrogen or alkyl;
R⁴ is hydrogen, halo, alkyl, alkoxy, or benzyloxy;
R⁵ is C₅₋₇cycloalkyl;
R⁶ is hydrogen, alkyl, or cycloalkyl;
R⁷ is (CO₂R⁶)alkyl, (CON(R⁶)(R⁶))alkyl, (alkyl)CONH, tetrazolyl, tetrahydropyranyl, sulfolanyl, SO₂R¹¹, SO₂R¹², or (R¹³)alkyl;
R⁸ is hydrogen, alkyl, or cycloalkyl;
or NR⁷R⁸ taken together is pyrrolidinyl, piperidinyl, piperazinyl, piperazinyl, homomorpholinyl, homopiperidinyl, morpholinyl, or thiomorpholinyl, and is substituted with 0-2 substituents selected from halo, alkyl, and haloalkyl;
R⁹ is hydrogen, alkyl, cycloalkyl, hydroxyalkyl, dihydroxyalkyl, (alkoxy)alkyl, aminoalkyl, (alkylamino)alkyl, (dialkylamino)alkyl, (R¹²)alkyl, (CHO)alkyl, (CO₂R⁶)alkyl, (CON(R⁶)₂)alkyl, (COR¹²)alkyl, (COR¹⁵)alkyl, (R¹⁶)alkyl, ((alkoxyalkyl)amido)alkyl, (alkylamido)alkyl, (tetrahydrofuranyl)alkyl, (dioxolanyl)alkyl, (alkylCO)(R⁶)amino, ((alkylCO)(R⁶)amino)alkyl, tetrahydropyranyl, or sulfolanyl;
R¹⁰ is hydrogen, alkyl, cycloalkyl, hydroxyalkyl, dihydroxyalkyl, (alkoxy)alkyl, aminoalkyl, (alkylamino)alkyl, (dialkylamino)alkyl, (R¹²)alkyl, (CHO)alkyl, (CO₂R⁶)alkyl, (CON(R⁶)₂)alkyl, (COR¹²)alkyl, (COR¹⁵)alkyl, (R¹⁶)alkyl, ((alkoxyalkyl)amido)alkyl, (alkylamido)alkyl, (tetrahydrofuranyl)alkyl, (dioxolanyl)alkyl, (alkylCO)(R⁶)amino, ((alkylCO)(R⁶)amino)alkyl, tetrahydropyranyl, or sulfolanyl;
or NR⁹R¹⁰ taken together is azetidinyl, pyrrolidinyl, piperidinyl, piperazinyl, homomorpholinyl, homopiperidinyl, morpholinyl, or thiomorpholinyl, and is substituted with 0-4 substituents selected from the group consisting of halo, hydroxy, OPO(OR$^6$)$_2$, alkoxy, alkyl, cycloalkyl, (cycloalkyl)alkyl, haloalkyl, hydroxyalkyl, alkoxyalkyl, (hydroxy)alkoxyalkyl, (alkoxy)alkyl, amino, alkylamino, dialkylamino, (alkylCO)(R$^6$)amino, (alkoxyCO)(R$^6$)amino, (alkoxyalkylCO)(R$^6$)amino, (alkylCO)alkylamino, (cycloalkyl)(PhSO$_2$)amino, CO$_2$R$^6$, CON(R$^6$)$_2$, CONH(alkenyl), (R$^{12}$)CO, (alkyl)CO, (cycloalkyl)CO, (hydroxyalkyl)CO, ((hydroxy)cycloalkyl)CO, (aminoalkyl)CO, (acetoxyalkyl)CO, PhCO, (furanyl)CO, (benzodioxanyl)CO, (alkyl)CO$_2$, SO$_2$R$^{11}$, SO$_2$R$^{12}$, (CO$_2$R$^6$)alkyl, (CON(R$^6$)$_2$)alkyl, (COR$^{12}$)alkyl, (alkylCO)(R$^6$)aminoalkyl, (PhCONH)alkyl, (R$^{12}$)alkyl, R$^{12}$, phenyl, methoxyphenyl, pyrrolyl, furanyl, thienyl, imidazolyl, isoxazolyl, oxazolyl, thiazolyl, triazolyl, oxadiazolyl, pyridinyl, pyrimidinyl, pyrazinyl, triazinyl, pyrazolyl,

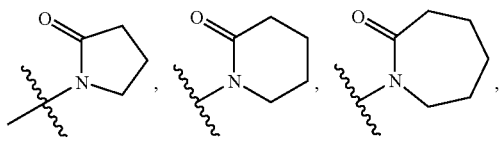

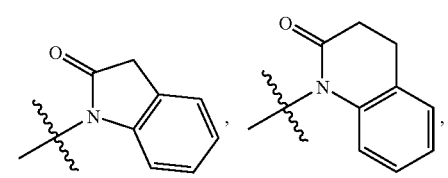

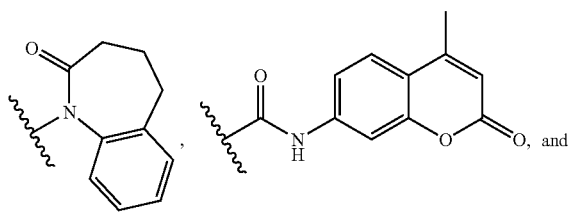

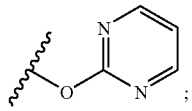

or NR$^9$R$^{10}$ taken together is

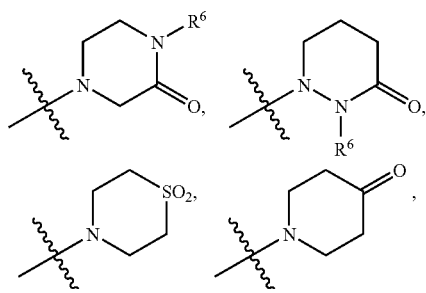

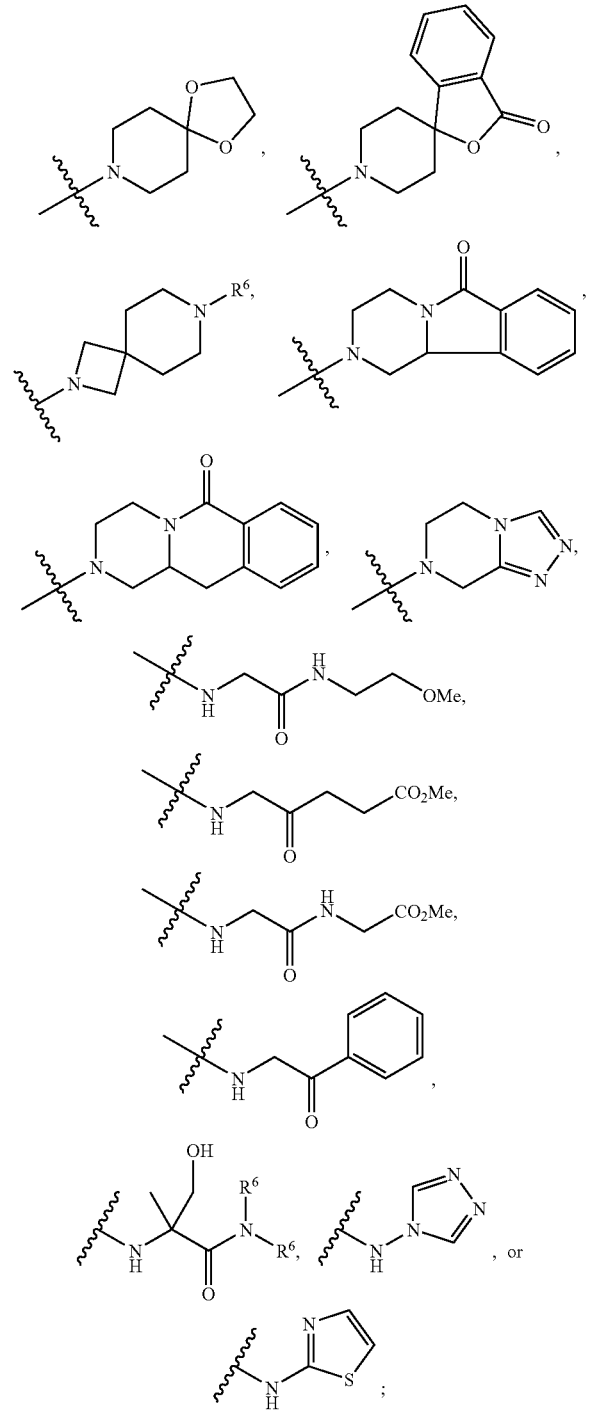

or NR$^9$R$^{10}$ taken together is a [2.2.1] or [2.2.2] bridged bicyclic amine wherein the bicycle contains 0-1 NR, NCO$_2$R$^6$, or O;

R$^{11}$ is haloalkyl, alkoxy, ((R$^6$)(R$^6$)N)alkylamino, (((R$^6$)(R$^6$)N)alkyl)$_2$amino, N,O-dimethylhydroxylamino;

R$^{12}$ is pyrrolidinyl, piperidinyl, piperazinyl, homomorpholinyl, homopiperidinyl, morpholinyl, or thiomorpholinyl, and is substituted with 0-2 substituents selected from halo, alkyl, haloalkyl, and alkoxy;

R[13] is pyrrolidinyl, piperidinyl, piperazinyl, homomorpholinyl, homopiperidinyl, morpholinyl, thiomorpholinyl, or tetrahydrofuranyl, and is substituted with 0-2 alkyl substituents;

R[14] is azetidine, pyrrolidinyl, piperidinyl, piperazinyl, piperazinyl, homomorpholinyl, homopiperidinyl, morpholinyl, thiomorpholinyl, or S,S-dioxothiomorpholinyl, and is substituted with 0-3 substituents selected from halo, alkyl, hydroxy, alkoxy, aminoalkyl, (alkylamino)alkyl, (dialkylamino)alkyl, $(CO_2R^6)$alkyl, $(CON(R^6)_2)$alkyl, $((R^6CO)(R^6)$amino)alkyl, $(R^{15})$alkyl, $(R^6CO)(R^6)$amino, $R^{15}$, alkylCO, $CF_3CO$, $CO_2R^6$, $CON(R^6)_2$, or $SO_2R^6$;

or R[14] is a [2.2.1] or [2.2.2] bridged bicyclic amine wherein the bicycle contains 0-1 O;

R[15] is azetidinyl, pyrrolidinyl, piperidinyl, piperazinyl, homomorpholinyl, homopiperidinyl, morpholinyl, or thiomorpholinyl, and is substituted with 0-2 halo, alkyl, or alkoxy substituents;

R[16] is pyrazolyl, imidazolyl, isoxazolyl, oxazolyl, thiazolyl, triazolyl, oxadiazolyl, tetrazolyl, or pyridinyl, and is substituted with 0-2 alkyl substituents; and the dashed line is either a single bond or a double bond, provided that if the dashed line is a single bond, the carbon bearing the asterisk is either of the R configuration, the S configuration, or a mixture of R and S;

or a pharmaceutically acceptable salt thereof.

Another aspect of the invention is a compound of formula I

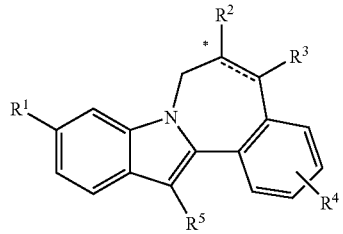

wherein:
R[1] is $CO_2R^6$ or $CONR^7R^8$;
R[2] is $CONR^9R^{10}$, $CO_2$benzyl, $NHCO_2$(alkyl), $NHCO_2$benzyl, NHCO(alkyl), NHCO(cycloalkyl), NHCOR[14], NHCO((R[15])alkyl), NHCO((R[16])alkyl), NHCO(tetrahydropyranyl), NHCO(methoxycycloalkyl), $NHCON(R^6)_2$, $NHCON(R^6)((N(R^6)_2)$alkyl), $NHCON(R^6)((CO_2R^6)$alkyl), $NHCON(R^6)((CON(R^6)_2)$alkyl), $NHCON(R^6)((COR^{15})$alkyl), $NHCON(R^6)((tetrahydropyranyl)$alkyl),

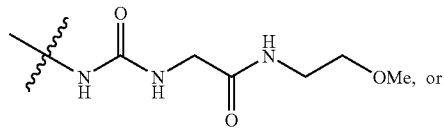

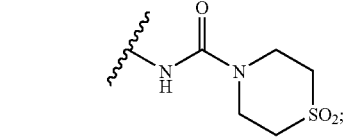

R[3] is hydrogen or alkyl;
R[4] is hydrogen, halo, alkyl, alkoxy, or benzyloxy;

R[5] is $C_{5-7}$cycloalkyl;
R[6] is hydrogen, alkyl, or cycloalkyl;
R[7] is hydrogen, alkyl, cycloalkyl, alkoxy, aminoalkyl, (alkylamino)alkyl, (dialkylamino)alkyl, $(CO_2R^6)$alkyl, $(CON(R^6)(R^6))$alkyl, (alkyl)CONH, tetrazolyl, tetrahydropyranyl, sulfolanyl, $SO_2R^{11}$, $SO_2R^{12}$, or $(R^{13})$alkyl;
R[8] is hydrogen, alkyl, or cycloalkyl;
or $NR^7R^8$ taken together is pyrrolidinyl, piperidinyl, piperazinyl, piperazinyl, homomorpholinyl, homopiperidinyl, morpholinyl, or thiomorpholinyl, and is substituted with 0-2 substituents selected from halo, alkyl, and haloalkyl;
R[9] is cycloalkyl, dihydroxyalkyl, (alkoxy)alkyl, $(R^{12})$alkyl, (CHO)alkyl, $(CO_2R^6)$alkyl, $(CON(R^6)_2)$alkyl, $(COR^{12})$alkyl, $(COR^{15})$alkyl, ((alkoxyalkyl)amido)alkyl, (alkylamido)alkyl, (tetrahydrofuranyl)alkyl, (dioxolanyl)alkyl, $(alkylCO)(R^6)$amino, $((alkylCO)(R^6)$amino)alkyl, tetrahydropyranyl, or sulfolanyl;
R[10] is hydrogen, alkyl, cycloalkyl, hydroxyalkyl, dihydroxyalkyl, (alkoxy)alkyl, aminoalkyl, (alkylamino)alkyl, (dialkylamino)alkyl, $(R^{12})$alkyl, (CHO)alkyl, $(CO_2R^6)$alkyl, $(CON(R^6)_2)$alkyl, $(COR^{12})$alkyl, $(COR^{15})$alkyl, $(R^{16})$alkyl, ((alkoxyalkyl)amido)alkyl, (alkylamido)alkyl, (tetrahydrofuranyl)alkyl, (dioxolanyl)alkyl, $(alkylCO)(R^6)$amino, $((alkylCO)(R^6)$amino)alkyl, tetrahydropyranyl, or sulfolanyl;
or $NR^9R^{10}$ taken together is azetidinyl, pyrrolidinyl, piperidinyl, piperazinyl, homomorpholinyl, homopiperidinyl, morpholinyl, or thiomorpholinyl, and is substituted with 0-4 substituents selected from the group consisting of halo, hydroxy, $OPO(OR^6)_2$, alkoxy, alkyl, cycloalkyl, (cycloalkyl)alkyl, haloalkyl, hydroxyalkyl, alkoxyalkyl, (hydroxy)alkoxyalkyl, (alkoxy)alkyl, amino, alkylamino, dialkylamino, $(alkylCO)(R^6)$amino, $(alkoxyCO)(R^6)$amino, $(alkoxyalkylCO)(R^6)$amino, (alkylCO)alkylamino, $(cycloalkyl)(PhSO_2)$amino, $CO_2R^6$, $CON(R^6)_2$, CONH(alkenyl), $(R^{12})CO$, (alkyl)CO, (cycloalkyl)CO, (hydroxyalkyl)CO, ((hydroxy)cycloalkyl)CO, (aminoalkyl)CO, (acetoxyalkyl)CO, PhCO, (furanyl)CO, (benzodioxanyl)CO, $(alkyl)CO_2$, $SO_2R^{11}$, $SO_2R^{12}$, $(CO_2R^6)$alkyl, $(CON(R^6)_2)$alkyl, $(COR^{12})$alkyl, $(alkylCO)(R^6)$aminoalkyl, (PhCONH)alkyl, $(R^{12})$alkyl, $R^{12}$, phenyl, methoxyphenyl, pyrrolyl, furanyl, thienyl, imidazolyl, isoxazolyl, oxazolyl, thiazolyl, triazolyl, oxadiazolyl, pyridinyl, pyrimidinyl, pyrazinyl, triazinyl, pyrazolyl,

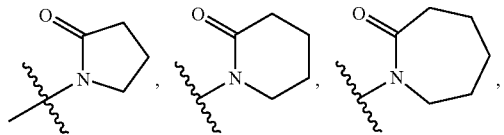

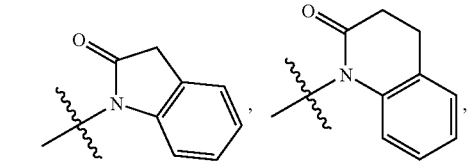

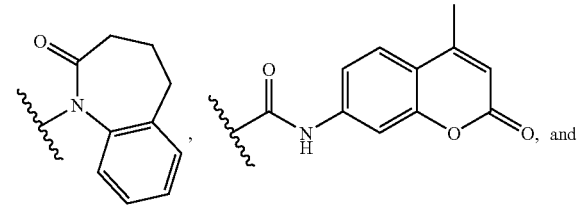

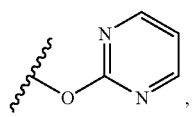

provided that if NR⁹R¹⁰ is pyrrolidinyl, piperidinyl, piperazinyl, homomorpholinyl, homopiperidinyl, morpholinyl, or thiomorpholinyl it cannot be substituted with 0-2 substituents selected from alkyl, hydroxy, amino, alkylamino, dialkylamino, pyrrolidinyl, piperdinyl or pyridinyl;

or NR⁹R¹⁰ taken together is

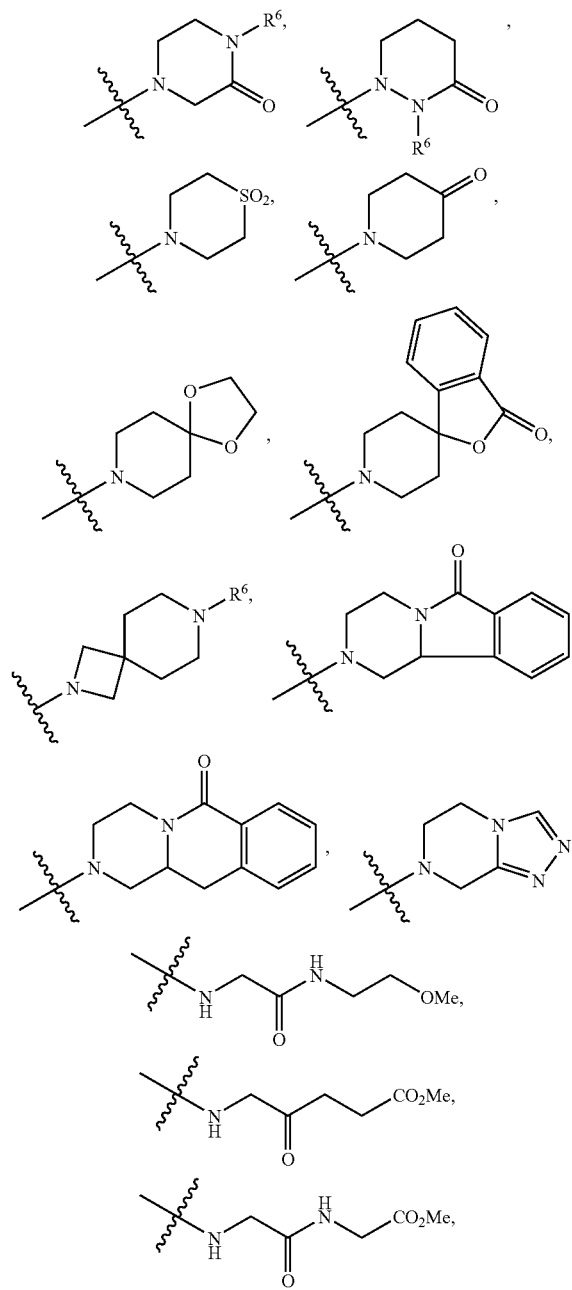

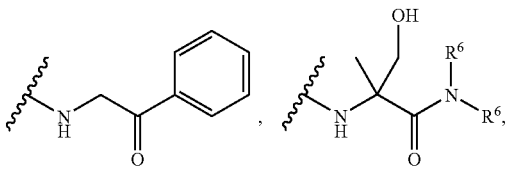

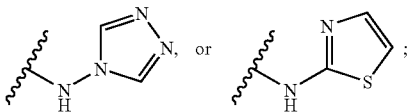

or NR⁹R¹⁰ taken together is a [2.2.1] or [2.2.2] bridged bicyclic amine wherein the bicycle contains 0-1 NR⁶, NCO₂R⁶, or O;

R¹¹ is alkyl, haloalkyl, cycloalkyl, alkoxy, amino, alkylamino, dialkylamino, ((R⁶)(R⁶)N)alkylamino, (((R⁶)(R⁶)N)alkyl)₂amino, N,O-dimethylhydroxylamino, or phenyl, wherein the phenyl is substituted with 0-2 substituents selected from the group consisting of halo, alkyl, haloalkyl, and alkoxy;

R¹² is pyrrolidiyl, ylainyl, pierdineriyl, homomorpholinyl, homopiperidinyl, morpholinyl, or thiomorpholinyl, and is substituted with 0-2 substituents selected from halo, alkyl, haloalkyl, and alkoxy;

R¹³ is pyrrolidinyl, piperidinyl, piperazinyl, homomorpholinyl, homopiperidinyl, morpholinyl, thiomorpholinyl, tetrahydrofuranyl, furanyl, thienyl, pyrrolyl, pyrazolyl, imidazolyl, isoxazolyl, oxazolyl, triazolyl, oxadiazolyl, tetrazolyl, pyridinyl, pyrazinyl, pyrimidinyl, imidazopyridinyl, or benzimidazole, and is substituted with 0-2 alkyl substituents;

R¹⁴ is azetidine, pyrrolidinyl, piperidinyl, piperazinyl, piperazinyl, homomorpholinyl, homopiperidinyl, morpholinyl, thiomorpholinyl, or S,S-dioxothiomorpholinyl, and is substituted with 0-3 substituents selected from halo, alkyl, hydroxy, alkoxy, aminoalkyl, (alkylamino)alkyl, (dialkylamino)alkyl, (CO₂R⁶)alkyl, (CON(R⁶)₂)alkyl, ((R⁶CO)(R⁶)amino)alkyl, (R¹⁵)alkyl, (R⁶CO)(R⁶)amino, R¹⁵, alkylCO, CF₃CO, CO₂R⁶, CON(R⁶)₂, or SO₂R⁶;

or R¹⁴ is a [2.2.1] or [2.2.2] bridged bicyclic amine wherein the bicycle contains 0-1 O;

R¹⁵ is azetidinyl, pyrrolidinyl, piperidinyl, piperazinyl, homomorpholinyl, homopiperidinyl, morpholinyl, or thiomorpholinyl, and is substituted with 0-2 halo, alkyl, or alkoxy substituents; and the dashed line is either a single bond or a double bond, provided that if the dashed line is a single bond, the carbon bearing the asterisk is either of the R configuration, the S configuration, or a mixture of R and S;

or a pharmaceutically acceptable salt thereof.

Another aspect of the invention is a compound of formula I wherein:
R¹ is $CO_2R^6$ or $CONR^7R^8$;
R² is $CO_2R^6$, $CO_2$benzyl, $CONR^9R^{10}$, $NHCO_2$(alkyl), $NHCO_2$benzyl, NHCO(alkyl), NHCO(cycloalkyl), $NHCOR^{14}$, NHCO(($R^{15}$)alkyl), NHCO(tetrahydropyranyl), NHCO(methoxycycloalkyl), $NHCON(R^6)_2$, $NHCON(R^6)((CO_2R^6)$alkyl), $NHCON(R^6)((CON(R^6)_2)$alkyl), or $NHCON(R^6)((COR^{15})$alkyl);
R³ is hydrogen or alkyl;
R⁴ is hydrogen, halo, alkyl, alkoxy, or benzyloxy;
R⁵ is $C_{5-7}$cycloalkyl;
R⁶ is hydrogen or alkyl;
R⁷ is hydrogen, alkyl, cycloalkyl, alkoxy, aminoalkyl, (alkylamino)alkyl, (dialkylamino)alkyl, $(CO_2R^6)$alkyl, $(CON(R^6)(R^6))$alkyl, (alkyl)CONH, tetrazolyl, tetrahydropyranyl, sulfolanyl, $SO_2R^{11}$, $SO_2R^{12}$, or $(R^{13})$alkyl;
R⁸ is hydrogen, alkyl, or cycloalkyl;
or $NR^7R^8$ taken together is pyrrolidinyl, piperidinyl, piperazinyl, piperazinyl, homomorpholinyl, homopiperidinyl, morpholinyl, or thiomorpholinyl, and is substituted with 0-2 substituents selected from halo, alkyl, and haloalkyl;
R⁹ is hydrogen, alkyl, cycloalkyl, hydroxyalkyl, dihydroxyalkyl, (alkoxy)alkyl, aminoalkyl, (alkylamino)alkyl, (dialkylamino)alkyl, $(R^{12})$alkyl, $(CO_2R^6)$alkyl, $(CON(R^6)_2)$alkyl, $(COR^{12})$alkyl, $(COR^{15})$alkyl, $(R^{16})$alkyl, ((alkoxyalkyl)amido)alkyl, (alkylamido)alkyl, (tetrahydrofuranyl)alkyl, (dioxolanyl)alkyl, (alkylCO)($R^6$)amino, ((alkylCO)($R^6$)amino)alkyl, tetrahydropyranyl, or sulfolanyl;
R¹⁰ is hydrogen, alkyl, cycloalkyl, hydroxyalkyl, (alkoxy)alkyl, aminoalkyl, (alkylamino)alkyl, or (dialkylamino)alkyl;
or $NR^9R^{10}$ taken together is azetidinyl, pyrrolidinyl, piperidinyl, piperazinyl, homomorpholinyl, homopiperidinyl, morpholinyl, or thiomorpholinyl, and is substituted with 0-4 substituents selected from the group consisting of halo, hydroxy, alkyl, haloalkyl, hydroxyalkyl, alkoxy, (alkoxy)alkyl, amino, alkylamino, dialkylamino, (alkylCO)amino, (alkylCO)(alkyl)amino, (alkylCO)alkylamino, (cycloalkyl)(PhSO₂)amino, $CO_2R^6$, $CON(R^6)_2$, CONH(alkenyl), $(R^{12})CO$, (alkyl)CO, (cycloalkyl)CO, (hydroxyalkyl)CO, (aminoalkyl)CO, (acetoxyalkyl)CO, PhCO, (furanyl)CO, (benzodioxanyl)CO, $(alkyl)CO_2$, $SO_2R^{11}$, $SO_2R^{12}$, $(CO_2R^6)$alkyl, $(CON(R^6)_2)$alkyl, $(COR^{12})$alkyl, (PhCONH)alkyl, $(R^{12})$alkyl, $R^{12}$, phenyl, methoxyphenyl, pyrrolyl, furanyl, thienyl, imidazolyl, isoxazolyl, oxazolyl, thiazolyl, triazolyl, oxadiazolyl, pyridinyl, pyrimidinyl, pyrazinyl, triazinyl, pyrazolyl, or $NR^9R^{10}$ taken together is

;

-continued

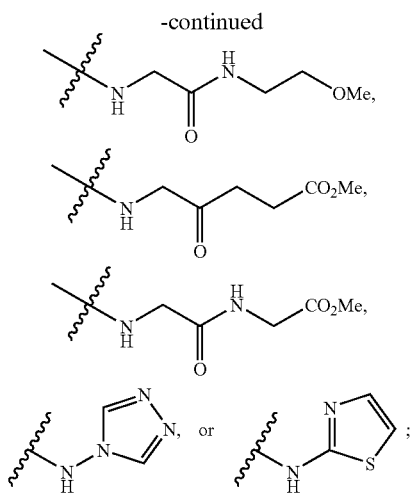

or $NR^9R^{10}$ taken together is a [2.2.1] or [2.2.2] bridged bicyclic amine wherein the bicycle contains 0-1 $NR^6$, $NCO_2R^6$, or O;

$R^{11}$ is alkyl, haloalkyl, cycloalkyl, alkoxy, amino, alkylamino, dialkylamino, N,O-dimethylhydroxylamino, or phenyl, wherein the phenyl is substituted with 0-2 substituents selected from the group consisting of halo, alkyl, haloalkyl, and alkoxy;

$R^{12}$ is pyrrolidinyl, piperidinyl, piperazinyl, homomorpholinyl, homopiperidinyl, morpholinyl, or thiomorpholinyl, and is substituted with 0-2 substituents selected from halo, alkyl, haloalkyl, and alkoxy;

$R^{13}$ is pyrrolidinyl, piperidinyl, piperazinyl, homomorpholinyl, homopiperidinyl, morpholinyl, thiomorpholinyl, tetrahydrofuranyl, furanyl, thienyl, pyrrolyl, pyrazolyl, imidazolyl, isoxazolyl, oxazolyl, triazolyl, oxadiazolyl, tetrazolyl, pyridinyl, pyrazinyl, pyrimidinyl, imidazopyridinyl, or benzimidazole, and is substituted with 0-2 alkyl substituents;

$R^{14}$ is azetidine, pyrrolidinyl, piperidinyl, piperazinyl, homomorpholinyl, homopiperidinyl, morpholinyl, thiomorpholinyl, or S,S-dioxothiomorpholinyl, and is substituted with 0-2 substituents selected from halo, alkyl, alkoxy, aminoalkyl, (alkylamino)alkyl, (dialkylamino)alkyl, $(CO_2R^6)$alkyl, $(CON(R^6)_2)$alkyl, $(R^{15})$alkyl, $(R^6CO)$(alkyl)amino, $R^{15}$, $CF_3CO$, $CO_2R^6$, $CON(R^6)_2$, or $SO_2R^6$;

or $R^{14}$ is a [2.2.1] or [2.2.2] bridged bicyclic amine wherein the bicycle contains 0-1 O;

$R^{15}$ is azetidinyl, pyrrolidinyl, piperidinyl, piperazinyl, homomorpholinyl, homopiperidinyl, morpholinyl, or thiomorpholinyl, and is substituted with 0-2 halo, alkyl, or alkoxy substituents;

$R^{16}$ is pyrazolyl, imidazolyl, isoxazolyl, oxazolyl, thiazolyl, triazolyl, oxadiazolyl, or tetrazolyl, and is substituted with 0-2 alkyl substituents; and the dashed line is either a single bond or a double bond, provided that if the dashed line is a single bond, the carbon bearing the asterisk is either of the R configuration, the S configuration, or a mixture of R and S;

or a pharmaceutically acceptable salt thereof.

Another aspect of the invention is compound of formula I where $R^1$ is $CONR^7R^8$;

$R^7$ is alkoxy, $(CO_2R^6)$alkyl, $(CON(R^6)(R^6))$alkyl, (alkyl)CONH, tetrahydropyranyl, sulfolanyl, $SO_2R^{11}$, $SO_2R^{12}$, or $(R^{13})$alkyl;

$R^8$ is hydrogen, alkyl, or cycloalkyl;

$R^{11}$ is haloalkyl, alkoxy, or N,O-dimethylhydroxylamino;

$R^{12}$ is pyrrolidinyl, piperidinyl, piperazinyl, homomorpholinyl, homopiperidinyl, morpholinyl, or thiomorpholinyl, and is substituted with 0-2 substituents selected from halo, alkyl, haloalkyl, and alkoxy; and $R^{13}$ is pyrrolidinyl, piperidinyl, piperazinyl, homomorpholinyl, homopiperidinyl, morpholinyl, thiomorpholinyl, or tetrahydrofuranyl, and is substituted with 0-2 alkyl substituents.

Another aspect of the invention is compound of formula I where $R^2$ is $CO_2$benzyl, $CONR^9R^{10}$, $NHCO_2$(alkyl), $NHCO_2$benzyl, NHCO(cycloalkyl), $NHCOR^{14}$, $NHCO((R^{15})$alkyl), NHCO(tetrahydropyranyl), NHCO(methoxycycloalkyl), $NHCON(R^6)((CO_2R^6)$alkyl), $NHCON(R^6)((CON(R^6)_2)$alkyl), or $NHCON(R^6)((COR^{15})$alkyl);

$R^6$ is hydrogen or alkyl;

$R^9$ is dihydroxyalkyl, (alkoxy)alkyl, aminoalkyl, (alkylamino)alkyl, (dialkylamino)alkyl, $(R^{12})$alkyl, $(CO_2R^6)$alkyl, $(CON(R^6)_2)$alkyl, $(COR^{12})$alkyl, $(COR^{15})$alkyl, ((alkoxyalkyl)amido)alkyl, (alkylamido)alkyl, (tetrahydrofuranyl)alkyl, (dioxolanyl)alkyl, (alkylCO)($R^6$)amino, ((alkylCO)($R^6$)amino)alkyl, tetrahydropyranyl, or sulfolanyl;

$R^{10}$ is hydrogen, alkyl, cycloalkyl, hydroxyalkyl, (alkoxy)alkyl, aminoalkyl, (alkylamino)alkyl, or (dialkylamino)alkyl;

or $NR^9R^{10}$ taken together is azetidinyl, pyrrolidinyl, piperidinyl, piperazinyl, homomorpholinyl, homopiperidinyl, morpholinyl, or thiomorpholinyl, and $NR^9R^{10}$ is substituted with 1 substituent selected from the group consisting of halo, haloalkyl, hydroxyalkyl, alkoxy, (alkoxy)alkyl, (alkylCO)amino, (alkylCO)(alkyl)amino, (alkylCO)alkylamino, (cycloalkyl)(PhSO$_2$)amino, $CO_2R^6$, $CON(R^6)_2$, CONH(alkenyl), $(R^{12})CO$, (alkyl)CO, (cycloalkyl)CO, (hydroxyalkyl)CO, (aminoalkyl)CO, (acetoxyalkyl)CO, PhCO, (furanyl)CO, (benzodioxanyl)CO, (alkyl)$CO_2$, $SO_2R^{11}$, $SO_2R^{12}$, $(CO_2R^6)$alkyl, $(CON(R^6)_2)$alkyl, $(COR^{12})$alkyl, (PhCONH)alkyl, $(R^{12})$alkyl, piperazinyl, homomorpholinyl, homopiperidinyl, morpholinyl, thiomorpholinyl (where piperazinyl, homomorpholinyl, homopiperidinyl, morpholinyl, or thiomorpholinyl is substituted with 0-2 substituents selected from halo, alkyl, haloalkyl, and alkoxy), phenyl, methoxyphenyl, pyrrolyl, furanyl, thienyl, imidazolyl, isoxazolyl, oxazolyl, thiazolyl, triazolyl, oxadiazolyl, pyrimidinyl, pyrazinyl, triazinyl, pyrazolyl,

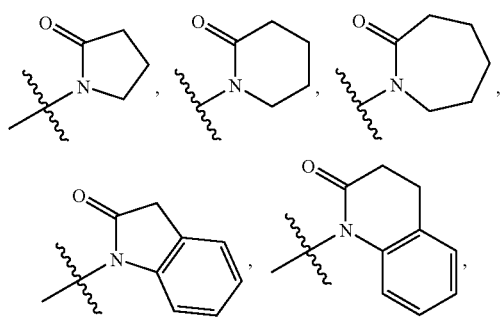

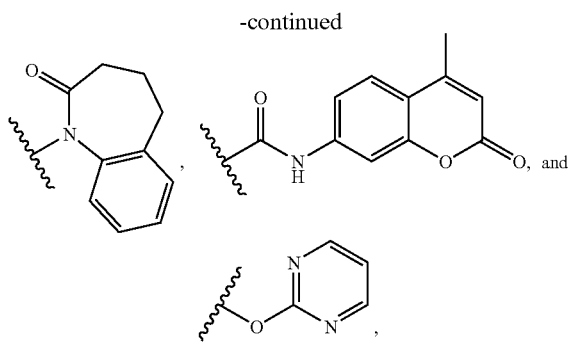

and $NR^9R^{10}$ is further substituted with 0-3 substituents selected from the group consisting of halo, hydroxy, alkyl, haloalkyl, hydroxyalkyl, alkoxy, (alkoxy)alkyl, amino, alkylamino, dialkylamino, (alkylCO)amino, (alkylCO)(alkyl)amino, (alkylCO)alkylamino, (cycloalkyl)(PhSO$_2$)amino, CO$_2$R$^6$, CON(R$^6$)$_2$, CONH(alkenyl), (R$^{12}$)CO, (alkyl)CO, (cycloalkyl)CO, (hydroxyalkyl)CO, (aminoalkyl)CO, (acetoxyalkyl)CO, PhCO, (furanyl)CO, (benzodioxanyl)CO, (alkyl)CO$_2$, SO$_2$R$^{11}$, SO$_2$R$^{12}$, (CO$_2$R$^6$)alkyl, (CON(R$^6$)$_2$)alkyl, (COR$^{12}$)alkyl, (PhCONH)alkyl, (R$^{12}$)alkyl, R$^{12}$, phenyl, methoxyphenyl, pyrrolyl, furanyl, thienyl, imidazolyl, isoxazolyl, oxazolyl, thiazolyl, triazolyl, oxadiazolyl, pyridinyl, pyrimidinyl, pyrazinyl, triazinyl, pyrazolyl,

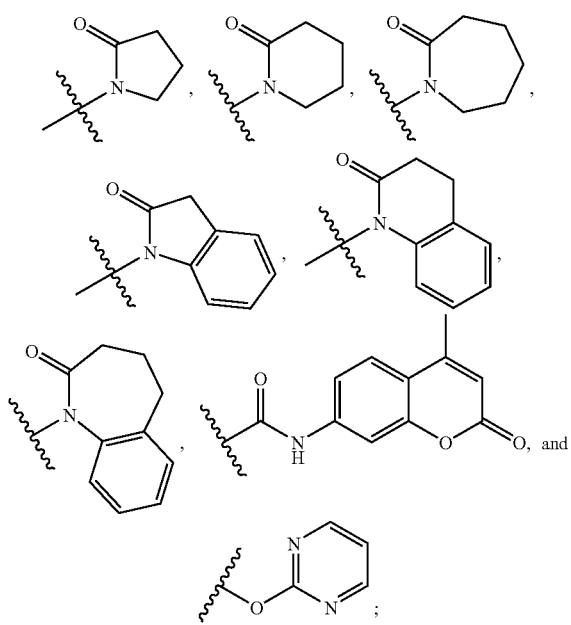

or $NR^9R^{10}$ taken together is

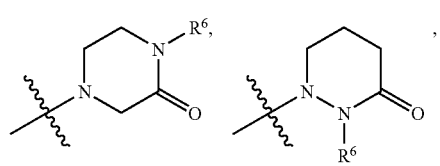

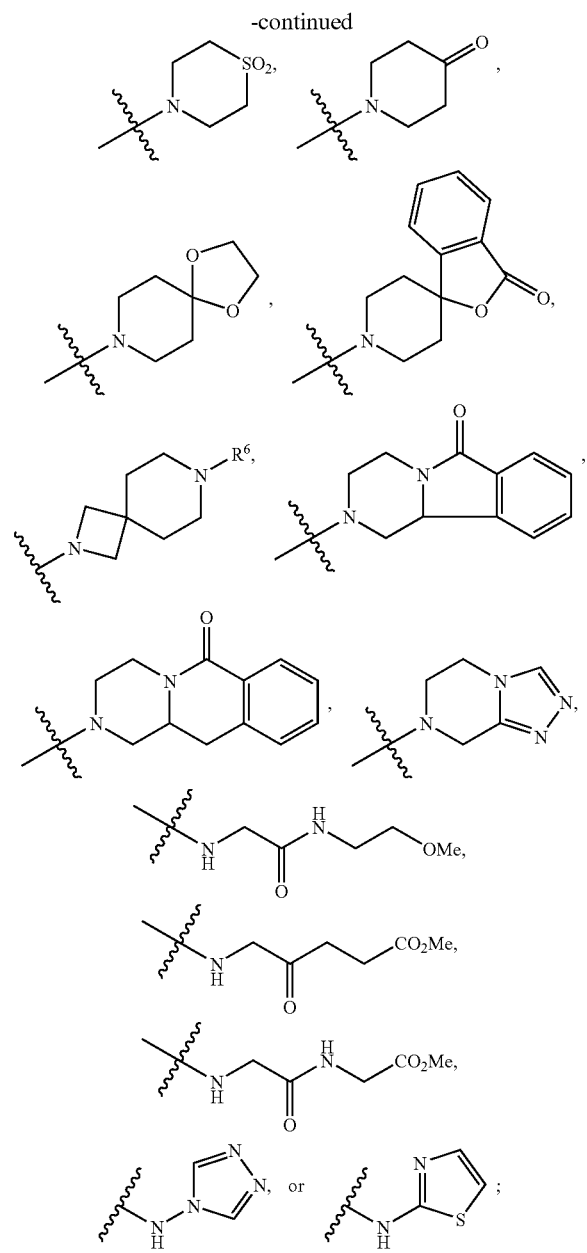

or $NR^9R^{10}$ taken together is a [2.2.1] or [2.2.2] bridged bicyclic amine wherein the bicycle contains 0-1 NR$^6$, NCO$_2$R$^6$, or O;

R$^{11}$ is alkyl, haloalkyl, cycloalkyl, alkoxy, amino, alkylamino, dialkylamino, N,O-dimethylhydroxylamino, or phenyl, wherein the phenyl is substituted with 0-2 substituents selected from the group consisting of halo, alkyl, haloalkyl, and alkoxy;

R$^{13}$ is pyrrolidinyl, piperidinyl, piperazinyl, homomorpholinyl, homopiperidinyl, morpholinyl, thiomorpholinyl, tetrahydrofuranyl, furanyl, thienyl, pyrrolyl, pyrazolyl, imidazolyl, isoxazolyl, oxazolyl, triazolyl, oxadiazolyl, tetrazolyl, pyridinyl, pyrazinyl, pyrimidinyl, imidazopyridinyl, or benzimidazole, and is substituted with 0-2 alkyl substituents;

R$^{14}$ is azetidine, pyrrolidinyl, piperidinyl, piperazinyl, piperazinyl, homomorpholinyl, homopiperidinyl, morpholinyl, thiomorpholinyl, or S,S-dioxothiomorpholinyl, and is substituted with 0-2 substituents selected from halo, alkyl, alkoxy, aminoalkyl, (alkylamino)alkyl, (dialkylamino)alkyl, ($CO_2R^6$)alkyl, ($CON(R^6)_2$)alkyl, ($R^{15}$)alkyl, ($R^6CO$)(alkyl)amino, $R^{15}$, $CF_3CO$, $CO_2R^6$, $CON(R^6)_2$, or $SO_2R^6$;

or $R^{14}$ is a [2.2.1] or [2.2.2] bridged bicyclic amine wherein the bicycle contains 0-1 O; and $R^{15}$ is azetidinyl, pyrrolidinyl, piperidinyl, piperazinyl, homomorpholinyl, homopiperidinyl, morpholinyl, or thiomorpholinyl, and is substituted with 0-2 halo, alkyl, or alkoxy substituents.

Another aspect of the invention is a compound of formula I where the dashed line is a single bond and the carbon bearing the asterisk is of the R configuration.

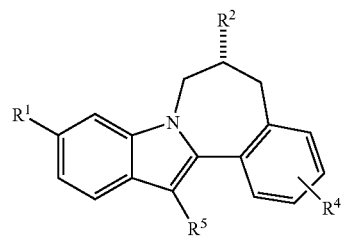

Another aspect of the invention is a compound of formula I where the dashed line is a single bond and the carbon bearing the asterisk is of the S configuration.

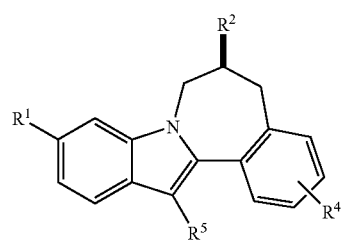

Another aspect of the invention is a compound of formula I wherein the dashed line is a single bond.

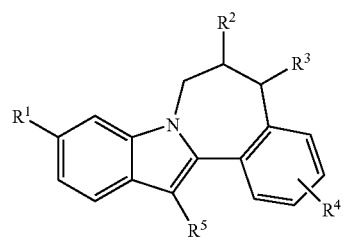

Another aspect of the invention is a compound of formula I wherein the dashed line is a double bond.

Another aspect of the invention is a compound of formula II

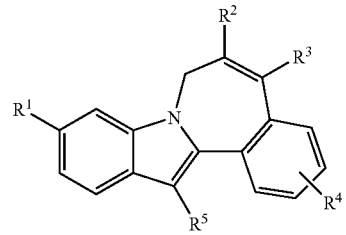

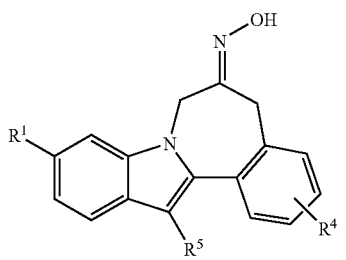

wherein:

$R^1$ is $CO_2R^6$ or $CONR^7R^8$;

$R^4$ is hydrogen, halo, alkyl, alkoxy, or benzyloxy;

$R^5$ is $C_{5-7}$cycloalkyl;

$R^6$ is hydrogen or alkyl;

$R^7$ is hydrogen, alkyl, cycloalkyl, alkoxy, aminoalkyl, (alkylamino)alkyl, (dialkylamino)alkyl, ($CO_2R^6$)alkyl, ($CON(R^6)(R^6)$)alkyl, (alkyl)CONH, tetrazolyl, tetrahydropyranyl, sulfolanyl, $SO_2R^{11}$, $SO_2R^{12}$, or ($R^{13}$)alkyl;

$R^8$ is hydrogen, alkyl, or cycloalkyl;

or $NR^7R^8$ taken together is pyrrolidinyl, piperidinyl, piperazinyl, piperazinyl, homomorpholinyl, homopiperidinyl, morpholinyl, or thiomorpholinyl, and is substituted with 0-2 substituents selected from halo, alkyl, and haloalkyl;

$R^{11}$ is alkyl, haloalkyl, cycloalkyl, alkoxy, amino, alkylamino, dialkylamino, N,O-dimethylhydroxylamino, or phenyl, wherein the phenyl is substituted with 0-2 substituents selected from the group consisting of halo, alkyl, haloalkyl, and alkoxy;

$R^{12}$ is pyrrolidinyl, piperidinyl, piperazinyl, homomorpholinyl, homopiperidinyl, morpholinyl, or thiomorpholinyl, and is substituted with 0-2 substituents selected from halo, alkyl, haloalkyl, and alkoxy; and $R^{13}$ is pyrrolidinyl, piperidinyl, piperazinyl, homomorpholinyl, homopiperidinyl, morpholinyl, thiomorpholinyl, tetrahydrofuranyl, furanyl, thienyl, pyrrolyl, pyrazolyl, imidazolyl, isoxazolyl, oxazolyl, triazolyl, oxadiazolyl, tetrazolyl, pyridinyl, pyrazinyl, pyrimidinyl, imidazopyridinyl, or benzimidazole, and is substituted with 0-2 alkyl substituents;

or a pharmaceutically acceptable salt thereof.

Another aspect of the invention is a compound of formula III

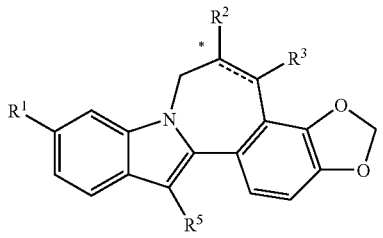

wherein:

$R^1$ is $CO_2R^6$ or $CONR^7R^8$;

$R^2$ is $CO_2R^6$, $CO_2$benzyl, $CONR^9R^{10}$, $NHCO_2$(alkyl), $NHCO_2$benzyl, NHCO(alkyl), NHCO(cycloalkyl), $NHCOR^{14}$, NHCO(($R^{15}$)alkyl), NHCO(tetrahydropyranyl), NHCO(methoxycycloalkyl), $NHCON(R^6)_2$, $NHCON(R^6)((CO_2R^6)alkyl)$, $NHCON(R^6)((CON(R^6)_2)alkyl)$, or $NHCON(R^6)((COR^{15})alkyl)$;

$R^3$ is hydrogen or alkyl;

$R^5$ is $C_{5-7}$cycloalkyl;

$R^6$ is hydrogen or alkyl;

$R^7$ is hydrogen, alkyl, cycloalkyl, alkoxy, aminoalkyl, (alkylamino)alkyl, (dialkylamino)alkyl, $(CO_2R^6)$alkyl, $(CON(R^6)(R^6))$alkyl, (alkyl)CONH, tetrazolyl, tetrahydropyranyl, sulfolanyl, $SO_2R^{11}$, $SO_2R^{12}$, or $(R^{13})$alkyl;

$R^8$ is hydrogen, alkyl, or cycloalkyl;

or $NR^7R^8$ taken together is pyrrolidinyl, piperidinyl, piperazinyl, piperazinyl, homomorpholinyl, homopiperidinyl, morpholinyl, or thiomorpholinyl, and is substituted with 0-2 substituents selected from halo, alkyl, and haloalkyl;

$R^9$ is hydrogen, alkyl, cycloalkyl, hydroxyalkyl, dihydroxyalkyl, (alkoxy)alkyl, aminoalkyl, (alkylamino)alkyl, (dialkylamino)alkyl, $(R^{12})$alkyl, $(CO_2R^6)$alkyl, $(CON(R^6)_2)$alkyl, $(COR^{12})$alkyl, $(COR^{15})$alkyl, $(R^{16})$alkyl, ((alkoxyalkyl)amido)alkyl, (alkylamido)alkyl, (tetrahydrofuranyl)alkyl, (dioxolanyl)alkyl, (alkylCO)($R^6$)amino, ((alkylCO)($R^6$)amino)alkyl, tetrahydropyranyl, or sulfolanyl;

$R^{10}$ is hydrogen, alkyl, cycloalkyl, hydroxyalkyl, (alkoxy)alkyl, aminoalkyl, (alkylamino)alkyl, or (dialkylamino)alkyl;

or $NR^9R^{10}$ taken together is azetidinyl, pyrrolidinyl, piperidinyl, piperazinyl, homomorpholinyl, homopiperidinyl, morpholinyl, or thiomorpholinyl, and is substituted with 0-4 substituents selected from the group consisting of halo, hydroxy, alkyl, haloalkyl, hydroxyalkyl, alkoxy, (alkoxy)alkyl, amino, alkylamino, dialkylamino, (alkylCO)amino, (alkylCO)(alkyl)amino, (alkylCO)alkylamino, (cycloalkyl)(PhSO_2)amino, $CO_2R^6$, $CON(R^6)_2$, CONH(alkenyl), $(R^{12})CO$, (alkyl)CO, (cycloalkyl)CO, (hydroxyalkyl)CO, (aminoalkyl)CO, (acetoxyalkyl)CO, PhCO, (furanyl)CO, (benzodioxanyl)CO, (alkyl)$CO_2$, $SO_2R^{11}$, $SO_2R^{12}$, $(CO_2R^6)$alkyl, $(CON(R^6)_2)$alkyl, $(COR^{12})$alkyl, (PhCONH)alkyl, $(R^{12})$alkyl, $R^{12}$, phenyl, methoxyphenyl, pyrrolyl, furanyl, thienyl, imidazolyl, isoxazolyl, oxazolyl, thiazolyl, triazolyl, oxadiazolyl, pyridinyl, pyrimidinyl, pyrazinyl, triazinyl, pyrazolyl, or $NR^9R^{10}$ taken together is

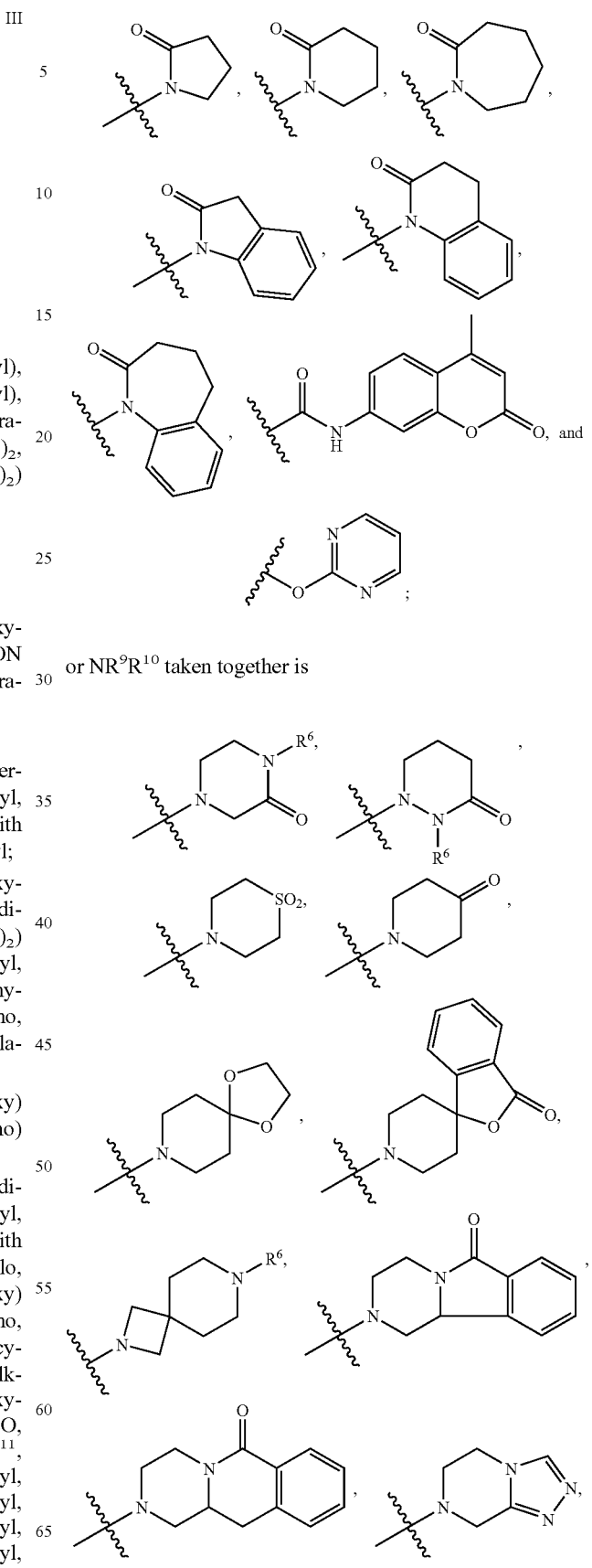

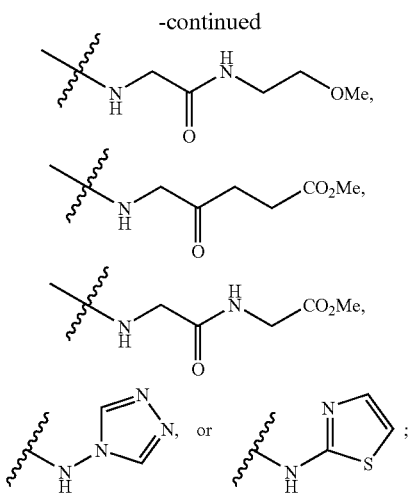

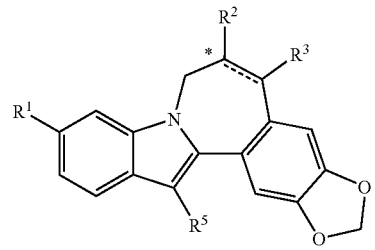

or NR⁹R¹⁰ taken together is a [2.2.1] or [2.2.2] bridged bicyclic amine wherein the bicycle contains 0-1 $NR^6$, $NCO_2R^6$, or O;

$R^{11}$ is alkyl, haloalkyl, cycloalkyl, alkoxy, amino, alkylamino, dialkylamino, N,O-dimethylhydroxylamino, or phenyl, wherein the phenyl is substituted with 0-2 substituents selected from the group consisting of halo, alkyl, haloalkyl, and alkoxy;

$R^{12}$ is pyrrolidinyl, piperidinyl, piperazinyl, homomorpholinyl, homopiperidinyl, morpholinyl, or thiomorpholinyl, and is substituted with 0-2 substituents selected from halo, alkyl, haloalkyl, and alkoxy;

$R^{13}$ is pyrrolidinyl, piperidinyl, piperazinyl, homomorpholinyl, homopiperidinyl, morpholinyl, thiomorpholinyl, tetrahydrofuranyl, furanyl, thienyl, pyrrolyl, pyrazolyl, imidazolyl, isoxazolyl, oxazolyl, triazolyl, oxadiazolyl, tetrazolyl, pyridinyl, pyrazinyl, pyrimidinyl, imidazopyridinyl, or benzimidazole, and is substituted with 0-2 alkyl substituents;

$R^{14}$ is azetidine, pyrrolidinyl, piperidinyl, piperazinyl, piperazinyl, homomorpholinyl, homopiperidinyl, morpholinyl, thiomorpholinyl, or S,S-dioxothiomorpholinyl, and is substituted with 0-2 substituents selected from halo, alkyl, alkoxy, aminoalkyl, (alkylamino)alkyl, (dialkylamino)alkyl, $(CO_2R^6)$alkyl, $(CON(R^6)_2)$alkyl, $(R^{15})$alkyl, $(R^6CO)(alkyl)amino$, $R^{15}$, $CF_3CO$, $CO_2R^6$, $CON(R^6)_2$, or $SO_2R^6$;

or $R^{14}$ is a [2.2.1] or [2.2.2] bridged bicyclic amine wherein the bicycle contains 0-1 O;

$R^{15}$ is azetidinyl, pyrrolidinyl, piperidinyl, piperazinyl, homomorpholinyl, homopiperidinyl, morpholinyl, or thiomorpholinyl, and is substituted with 0-2 halo, alkyl, or alkoxy substituents;

$R^{16}$ is pyrazolyl, imidazolyl, isoxazolyl, oxazolyl, thiazolyl, triazolyl, oxadiazolyl, or tetrazolyl, and is substituted with 0-2 alkyl substituents; and the dashed line is either a single bond or a double bond, provided that if the dashed line is a single bond, the carbon bearing the asterisk is either of the R configuration, the S configuration, or a mixture of R and S;

or a pharmaceutically acceptable salt thereof.

Another aspect of the invention is a compound of formula IV.

Some other aspects which apply to compounds of formula I, II, III, and IV where applicable.

Another aspect of the invention is compound of formula I where $R^3$ is hydrogen.

Another aspect of the invention is compound of formula I where $R^3$ is alkyl.

Another aspect of the invention is compound of formula I where $R^4$ is hydrogen.

Another aspect of the invention is compound of formula I where $R^4$ is chloro.

Another aspect of the invention is compound of formula I where $R^4$ is methoxy.

Another aspect of the invention is compound of formula I where $R^5$ is cyclohexyl.

Another aspect of the invention is compound of formula I where $R^7$ is $SO_2R^{11}$ or $SO_2R^{12}$.

Another aspect of the invention is compound of formula I where $R^7$ is $(R^{13})$alkyl.

Another aspect of the invention is compound of formula I where $R^9$ is $(R^{12})$alkyl.

Another aspect of the invention is compound of formula I where $R^9$ is $(CON(R^6)_2)$alkyl or $(COR^{12})$alkyl.

Another aspect of the invention is compound of formula I where NR⁹R¹⁰ taken together is pyrrolidinyl, piperidinyl, piperazinyl, homomorpholinyl, homopiperidinyl, morpholinyl, or thiomorpholinyl, and is substituted with 1-2 substituents selected from methyl or fluoro.

Another aspect of the invention is compound of formula I where NR⁹R¹⁰ taken together is pyrrolidinyl, piperidinyl, piperazinyl, homomorpholinyl, homopiperidinyl, morpholinyl, or thiomorpholinyl, and is substituted with 1 $R^{12}$.

Another aspect of the invention is compound of formula I where NR⁹R¹⁰ taken together is pyrrolidinyl, piperidinyl, piperazinyl, homomorpholinyl, homopiperidinyl, morpholinyl, or thiomorpholinyl, and is substituted with 1 substituent selected from pyrrolyl, furanyl, thienyl, pyrazolyl, imidazolyl, isoxazolyl, oxazolyl, triazolyl, oxadiazolyl, pyrimidinyl, pyrazinyl, and triazinyl.

Another aspect of the invention is compound of formula I where NR⁹R¹⁰ taken together is pyrrolidinyl, piperidinyl, piperazinyl, homomorpholinyl, homopiperidinyl, morpholinyl, or thiomorpholinyl, and is substituted with 1 substituent selected from the group consisting of $CO_2R^6$, (cycloalkyl)CO, (alkyl)CO, (hydroxyalkyl)CO, (acetoxyalkyl)CO, COPh, $CON(R^6)_2$, and $COR^{12}$.

Another aspect of the invention is compound of formula I where NR⁹R¹⁰ taken together is pyrrolidinyl, piperidinyl, piperazinyl, homomorpholinyl, homopiperidinyl, morpholinyl, or thiomorpholinyl, and is substituted with 1 $SO_2R^{11}$ or $SO_2R^{12}$.

Another aspect of the invention is compound of formula I where NR⁹R¹⁰ taken together has one of the following substitution patterns where R denotes one of the substituents

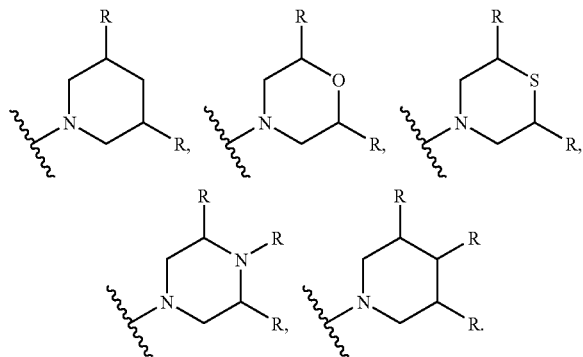

Another aspect of the invention is that any scope of the variables $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and the dashed line is meant to be used with any scope of the remaining variables.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from mono-halo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R. Some compounds were drawn with implied hydrogens.

The following structure illustrates when the dashed line is a single bond.

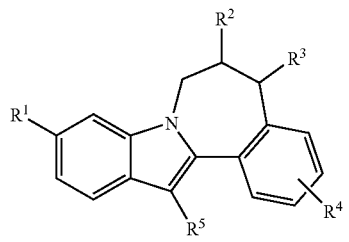

The following structure illustrates when the dashed line is a double bond.

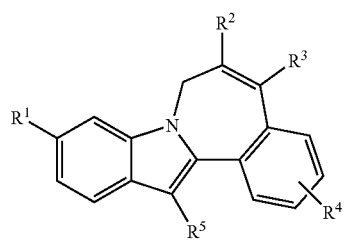

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (for example, the compounds below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art.

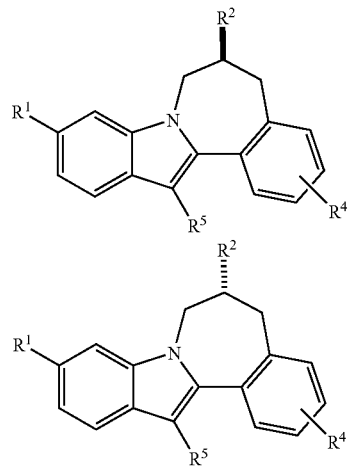

Synthetic Methods

Formula I, II, III, or IV compounds may be made by methods known in the art including those described below. Some reagents and intermediates are known in the art. Other reagents and intermediates can be made by methods known in the art using readily available materials. The variables used to describe the synthesis of formula I, II, III, or IV compounds are intended only to illustrate how to make and are not to be confused with variables used in the claims or in other sections of the specification.

Abbreviations used within the schemes generally follow conventions used in the art. Some examples are as follows: THF means tetrahydrofuran; DMF means N,N-dimethylformamide; RCM means ring-closing methasis; Boc means tert-butoxycarbonyl; TFA means trifluroacetic acid; DMA means N,N-dimethylacetamide; PPh₃ means triphenylphosphine; OAc means acetate; Me means methyl; COD (or cod) means 1,5-cyclooctadiene; dtbpy means 4,4'-di-tert-butyl-2,2'-bipyridine; dba means dibenzylideneacetone; Xantphos means 4,5-bis(diphenylphosphino)-9,9-dimethylxanthine; aq means aqueous; EtOH means ethanol; MeOH means methanol; TBTU means 2-(1H-benzotriazole-1-yl)-1,1,3,3-tetramethyluronium tetrafluroborate; DMSO means dimethylsulfoxide; HATU means O-(7-azabenzotriazol-1-yl)-N,N,N',N'-tetramethyluronium hexafluorophosphate; EEDQ means 2-ethoxy-1-ethoxycarbonyl-1,2-dihydroquinoline; WSC means 1-[3-(dimethylamino)propyl]-3-ethylcarbodiimide hydrochloride; DMAP means 4-dimethylaminopyridine; n-Bu means n-butyl; BEMP means 2-tert-butylimino-2-diethylamino-1,3-dimethylperhydro-1,3,2-diazaphosphorine, polymer-bound; DIPEA means diisopropylethylamine; and TEA means triethylamine.

Some compounds of formula I, II, III, or IV can be according to Schemes 1 and 2. Indole 7 can be made from 6-carboxyindole by condensation with an appropriate ketone. After hydrogenation and esterification, the indole can be selectively brominated and coupled with a variety of aryl compounds, including aryl boronic compounds. Indole 7 can then be alkylated and compound 14 generated by metathesis.

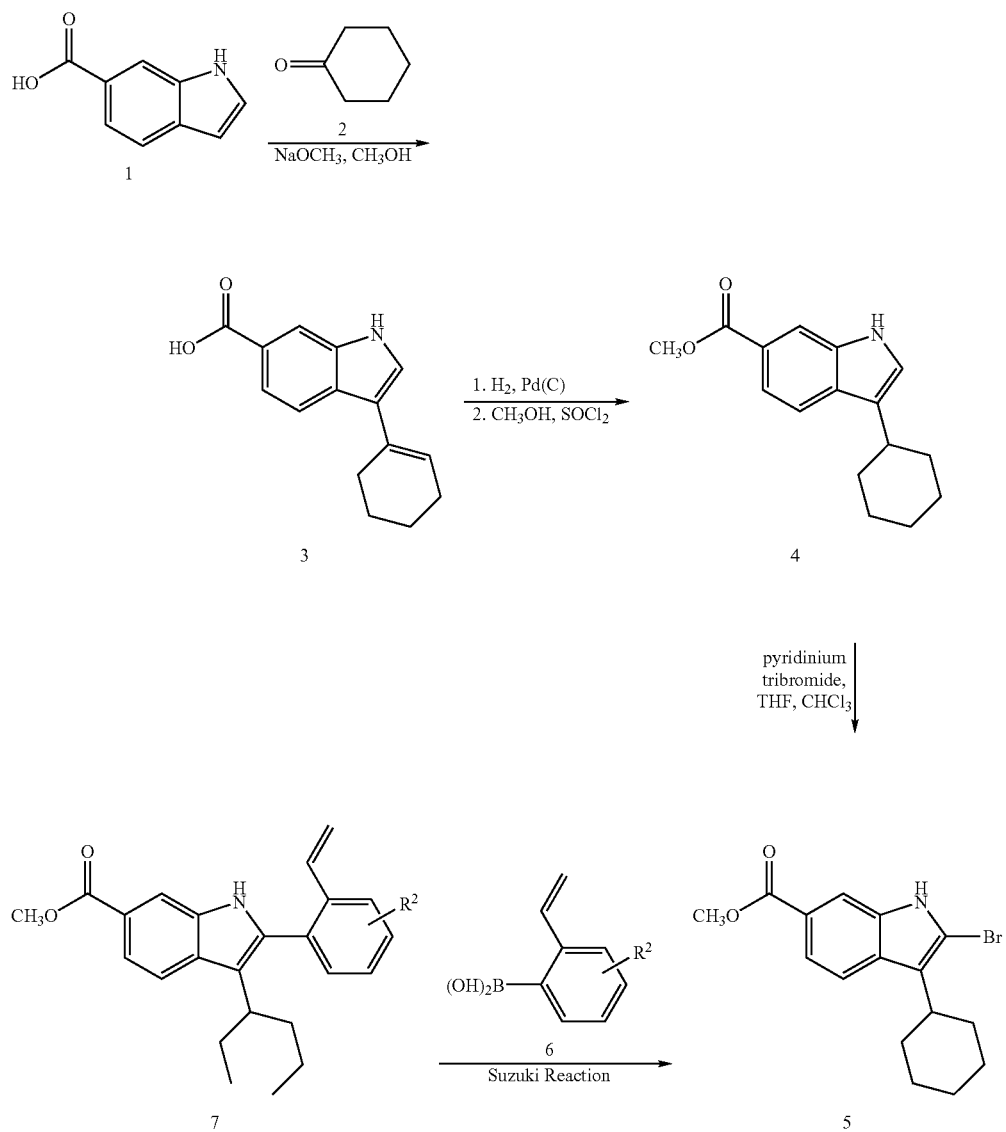

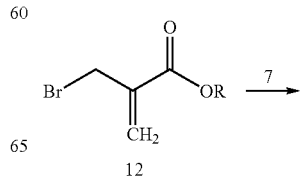

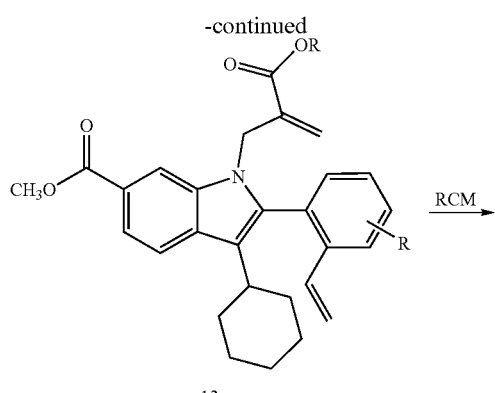

13

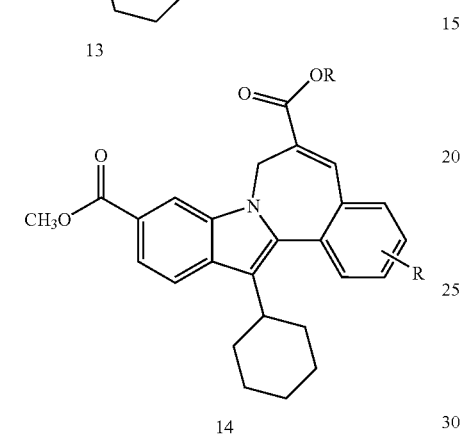

14

Further elaboration of ester 14 can selectively convert it to carboxylic acid 14a. For example, as shown in Scheme 3, partial hydrogenation of the benzyl ester 14 (R=benzyl), selective base-catalyzed hydrolysis of the dimethyl ester 14 (R=methyl), and cleavage of the tert-butyl ester 14 (R=tert-butyl) with trifluoroacetic acid can provide acid 14a. Reduction of 14a with hydrogen and palladium can give saturated acid 14b.

Alternatively, some esters of formula I can be selectively hydrolyzed at the indolic ester followed by functionalization at this moiety. Subsequent transformations can then be attended to at the bridged ester moiety.

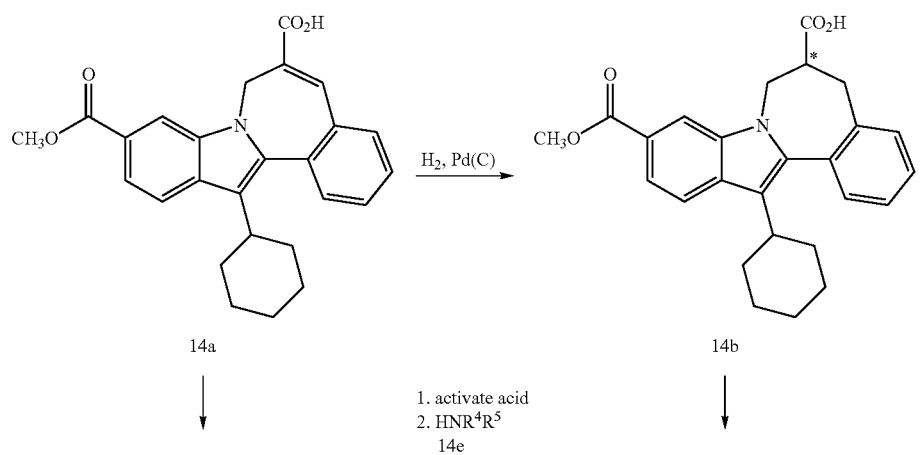

Scheme 3.

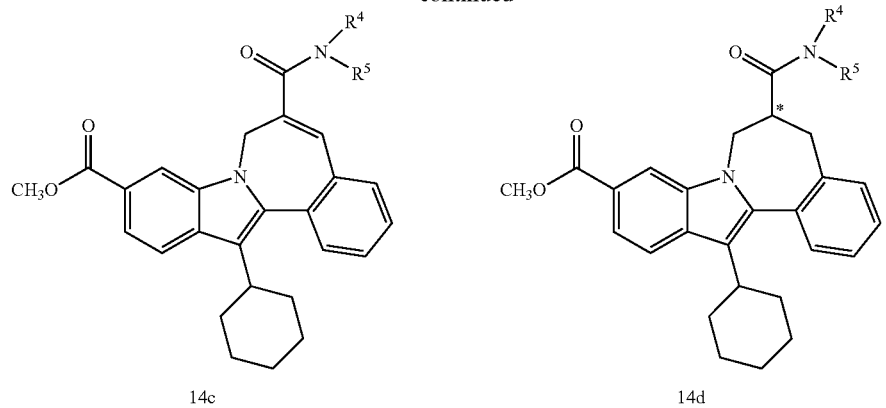

14c

14d

Carboxylic acids 14a and 14b can be transformed into their respective amides. The acids can be activated for the coupling reaction by conversion to their acid chlorides with, for example, oxalyl chloride or thionyl chloride. Alternatively, TBTU (2-(1H-benzotriazole-1-yl)-1,1,3,3-tetramethyluronium tetrafluroborate) is used to effect the coupling of the acids with amines. DMF, DMSO, and THF can be used as solvents. Compounds 14c and 14d can be transformed to compounds 14f and 14g by methods known in the art. Compounds 14f and 14g can be further elaborated at the carboxylic acid position.

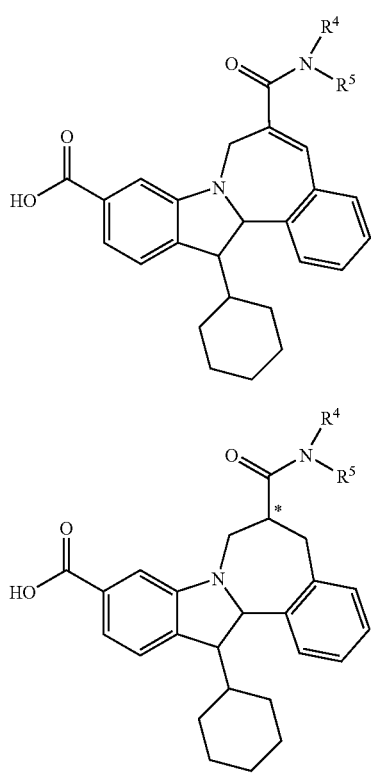

14f

14g

General procedure for the preparation of some 13-cyclohexyl-7H-indolo[2,1-a][2]benzazepine-6,10-dicarboxylic acid, diesters.

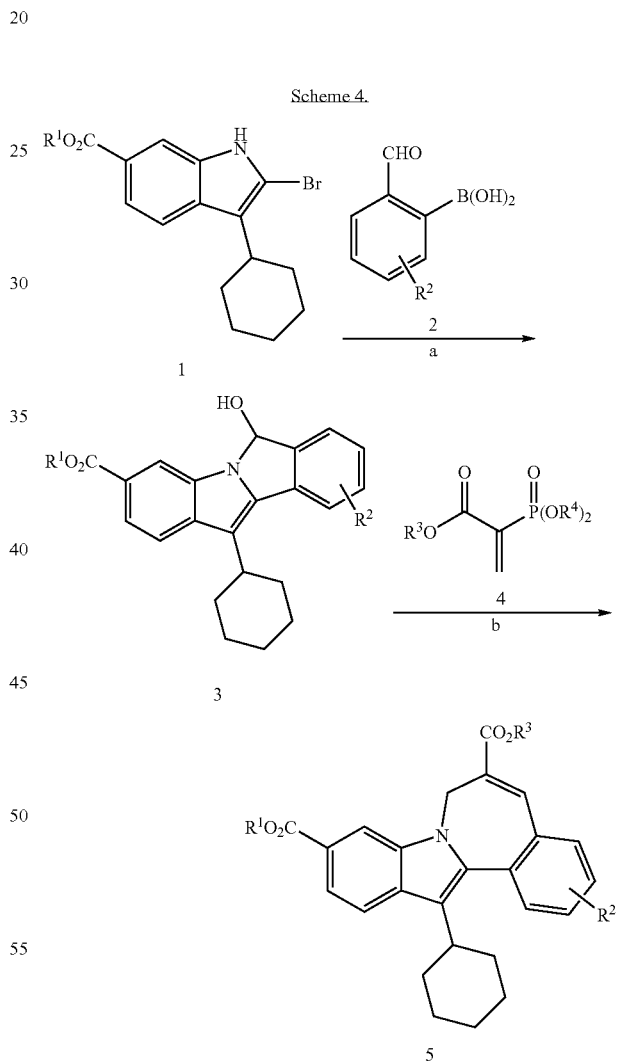

Scheme 4.

(a) 1.2 equiv of 2, LiCl (3 equiv), Pd(PPh$_3$)4 (0.04 equiv), 1M Na$_2$CO$_3$, EtOH-toluene, 85-90° C. (b) 1.2-1.5 equiv of 4, Cs$_2$CO$_3$ (1.2 equiv), DMF, 50-60° C.

An alternate route to some formula I compounds is shown in Scheme 5.

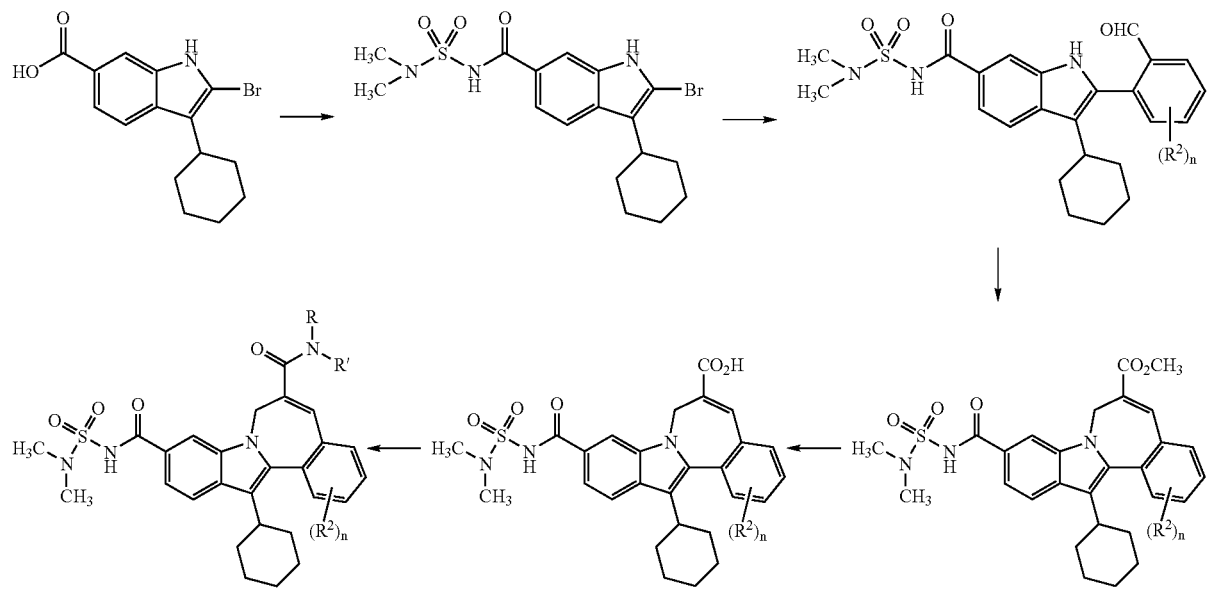
Some sulfamides can be made according to Scheme 6.
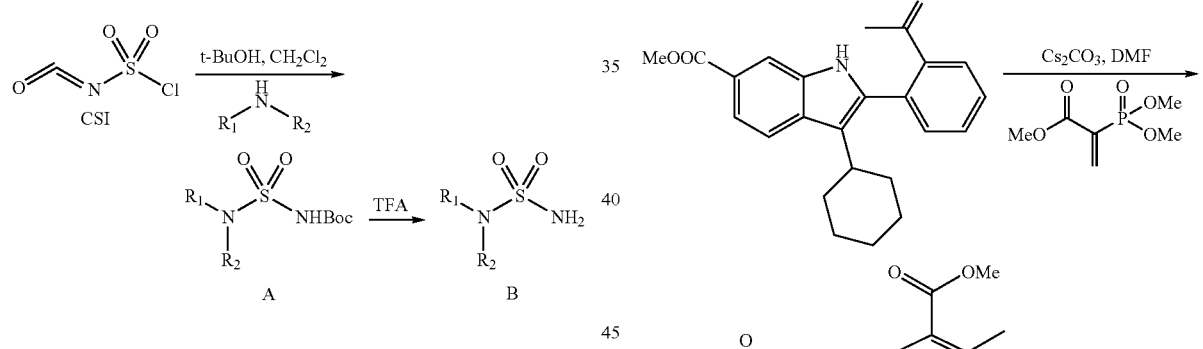
Other formula I compounds can be made according to Scheme 7.
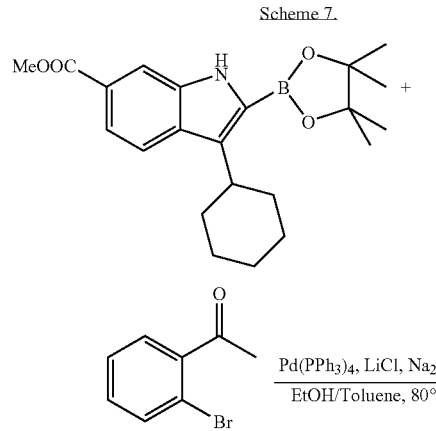
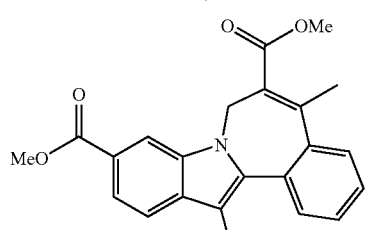
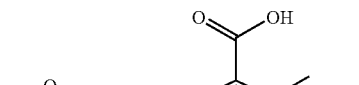

-continued

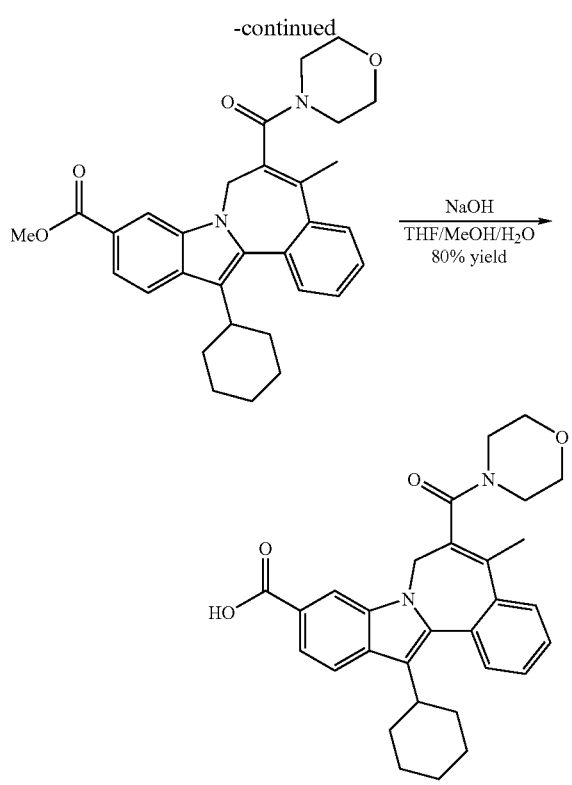

Other compounds are described in the specific embodiments section.

Biological Methods

Some Formula I, II, III, or IV compounds demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 μg/ml and the cells were grown overnight at 20° C.

Cell pellets (3L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 μm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 μl in 96 well plates (Costar 3912). The assay buffer is composed of 20 mM Hepes, pH 7.5, 2.5 mM KCl, 2.5 mM MgCl2, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at 0.6 μCi (0.29 μM total UTP). Reactions were initiated by the addition of enzyme, incubated at 30° C. for 60 min, and stopped by adding 25 g of 50 mM EDTA containing SPA beads (4 μg/μl, Amersham RPNQ 0007). Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 mM primer and 0.67 μg/μl beads. Order of addition in the assay: Enzyme (14 nM) was added to diluted compound followed by the addition of a mixture of template (0.2 nM), 3H-UTP (0.6 μCi, 0.29 μM), and primer-bound beads, to initiate the reaction; concentrations given are final. Reactions were allowed to proceed for 4 hours at 30° C.

IC50 values for compounds were determined using seven different [I]. IC50 values were calculated from the inhibition using the formula $y=A+((B-A)/(1+((C/x)^D)))$.

FRET Assay Preparation. To perform the HCV FRET screening assay, 96-well cell culture plates were used. The FRET peptide (Anaspec, Inc.) (Taliani et al., *Anal. Biochem.* 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with dH2O, NaCl added to 150 mM final, the FRET peptide diluted to 20 uM final from a 2 mM stock.

To prepare plates, HCV replicon cells, with or without a Renilla luciferase reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a CO2 incubator at 37° C.

Assays. Subsequent to addition of the test compounds described above (FRET Assay Preparation), at various times the plate was removed and Alamar blue solution (Trek Diagnostics, #00-100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naïve Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values for a protease inhibitor titration were calculated as the concentration which caused a 50% reduction in FRET or luciferase activity. The two numbers generated for the compound plate, percent cytoxicity and percent activity were used to determine compounds of interest for further analysis.

Representative data for some Formula I, II, III, and IV compounds are reported in Table 1.

TABLE 1

| Structure | $IC_{50}$* | $EC_{50}$* |
|---|---|---|
|  | B | E |
|  | B | E |

TABLE 1-continued
| Structure | IC$_{50}$* | EC$_{50}$* |
|---|---|---|
| 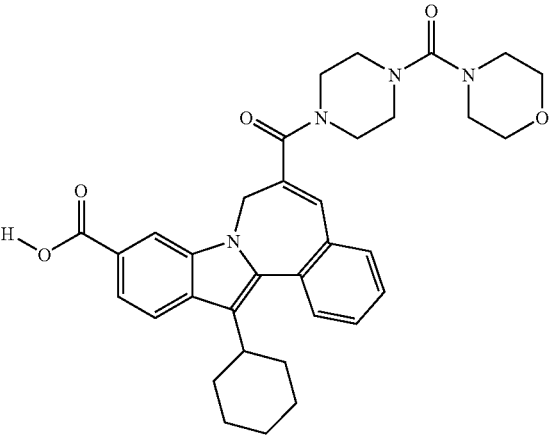 | B | E |
| 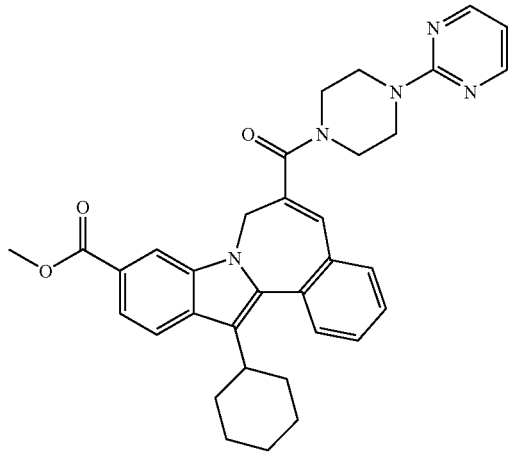 | | |
| 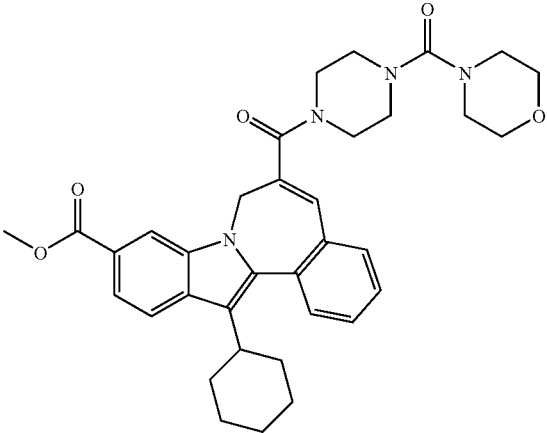 | | |

TABLE 1-continued

| Structure | IC$_{50}$* | EC$_{50}$* |
|---|---|---|
| | B | E |
| | B | E |
| | B | E |

TABLE 1-continued

| Structure | IC$_{50}$* | EC$_{50}$* |
|---|---|---|
| | B | E |
| | B | E |
| | B | E |

TABLE 1-continued

| Structure | IC$_{50}$* | EC$_{50}$* |
|---|---|---|
| | B | E |
| | B | E |
| | B | E |

TABLE 1-continued

| Structure | IC$_{50}$* | EC$_{50}$* |
|---|---|---|
| | B | E |
| | B | E |
| | B | E |

TABLE 1-continued

| Structure | IC$_{50}$* | EC$_{50}$* |
|---|---|---|
| | B | E |
| | B | E |
| | B | E |

TABLE 1-continued

| Structure | IC$_{50}$* | EC$_{50}$* |
|---|---|---|
| | B | E |
| | B | E |
| | B | E |

TABLE 1-continued

| Structure | IC$_{50}$* | EC$_{50}$* |
|---|---|---|
| | B | E |
| | B | E |
| | B | E |

TABLE 1-continued

| Structure | IC$_{50}$* | EC$_{50}$* |
|---|---|---|
| | B | E |
| | B | E |
| | B | E |

TABLE 1-continued

| Structure | IC$_{50}$* | EC$_{50}$* |
|---|---|---|
| (structure) | B | E |
| (structure) | B | E |
| (structure) | B | E |

TABLE 1-continued

| Structure | IC$_{50}$* | EC$_{50}$* |
|---|---|---|
| | B | E |
| | B | D |
| | B | E |

TABLE 1-continued
| Structure | IC$_{50}$* | EC$_{50}$* |
|---|---|---|
| 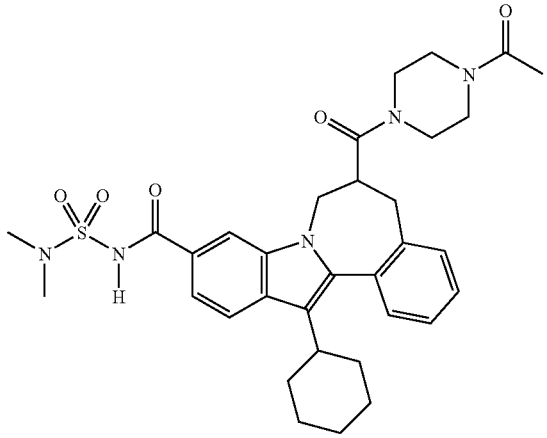 | B | E |
| 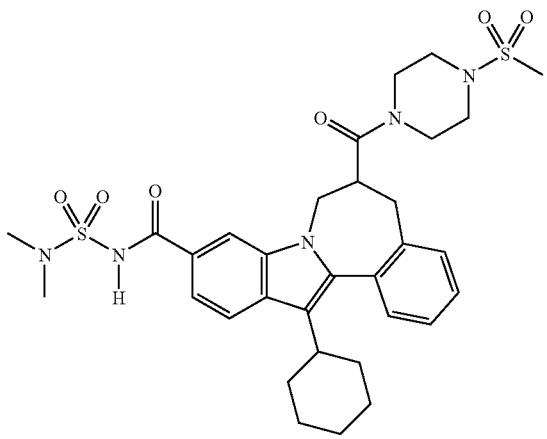 | B | E |
| 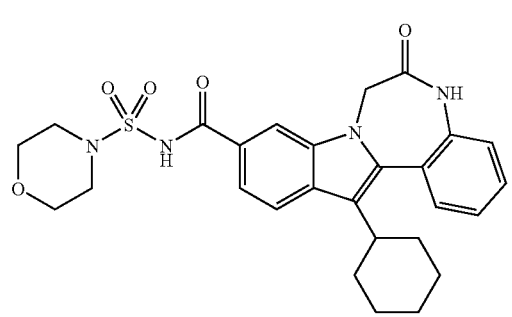 | B | E |
| 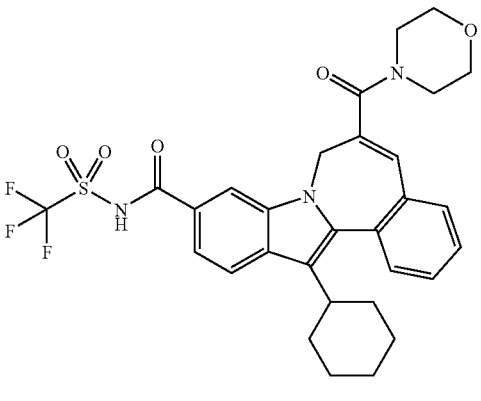 | B | D |

TABLE 1-continued

| Structure | IC$_{50}$* | EC$_{50}$* |
|---|---|---|
| | B | E |
| | B | E |
| | B | E |
| | B | E |

TABLE 1-continued
| Structure | IC$_{50}$* | EC$_{50}$* |
|---|---|---|
| 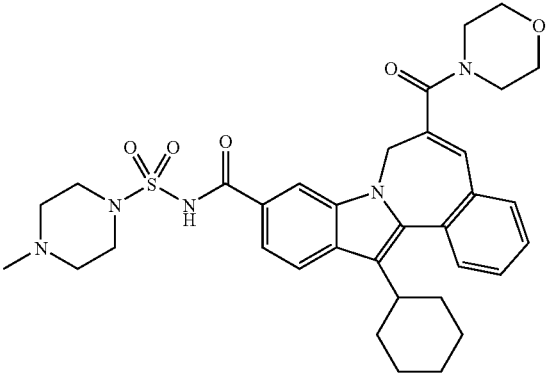 | B | E |
| 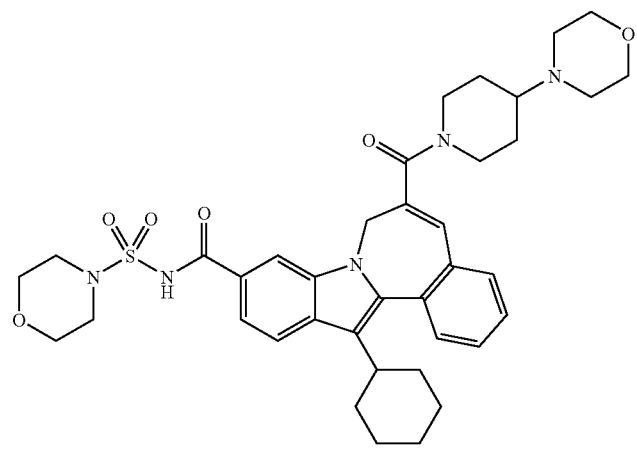 | B | E |
| 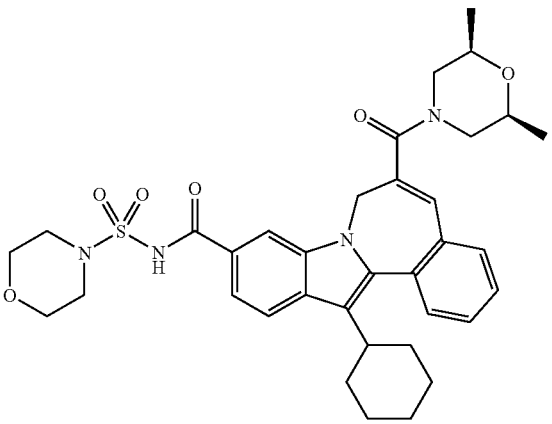 | B | E |

TABLE 1-continued

| Structure | IC$_{50}$* | EC$_{50}$* |
|---|---|---|
| | B | E |
| | B | E |
| | B | C |
| | B | E |

TABLE 1-continued

| Structure | IC$_{50}$* | EC$_{50}$* |
|---|---|---|
| | B | E |
| | | |
| | B | E |
| | B | E |

TABLE 1-continued

| Structure | IC$_{50}$* | EC$_{50}$* |
|---|---|---|
| | B | E |
| | B | E |
| | B | E |

TABLE 1-continued

| Structure | IC$_{50}$* | EC$_{50}$* |
|---|---|---|
| | B | D |
| | B | D |
| | B | D |

TABLE 1-continued
| Structure | IC$_{50}$* | EC$_{50}$* |
|---|---|---|
| 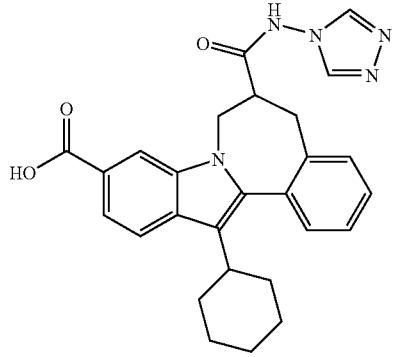 | B | C |
| 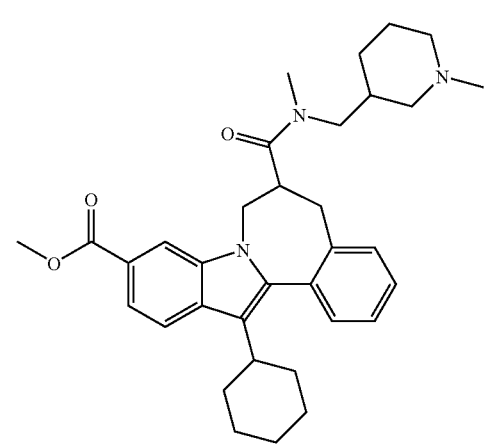 | B | E |
| 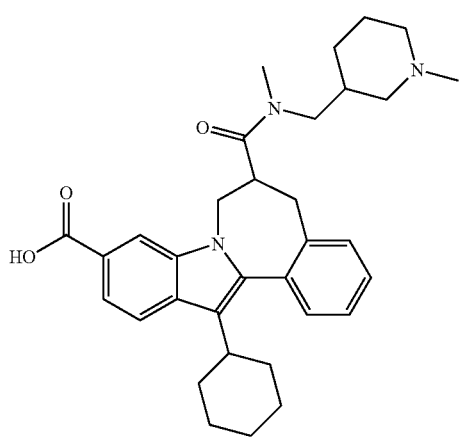 | B | E |

TABLE 1-continued
| Structure | IC$_{50}$* | EC$_{50}$* |
|---|---|---|
| 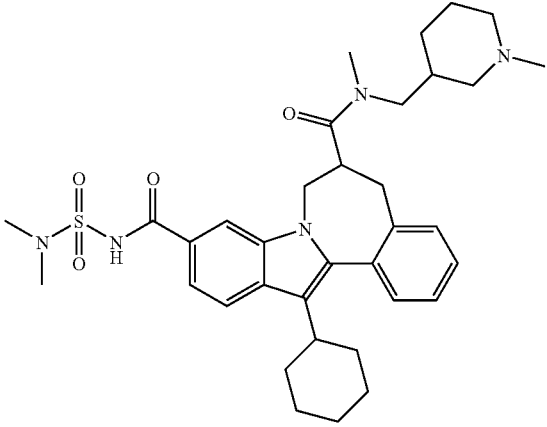 | B | F |
| 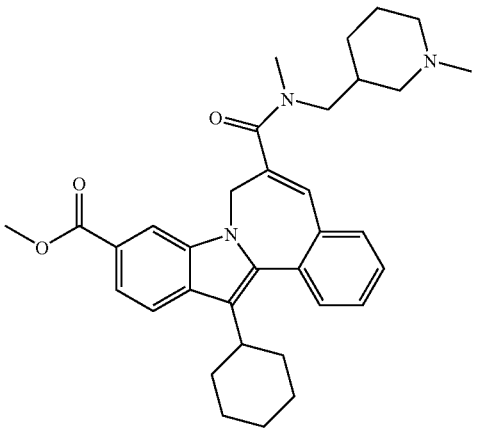 | B | D |
| 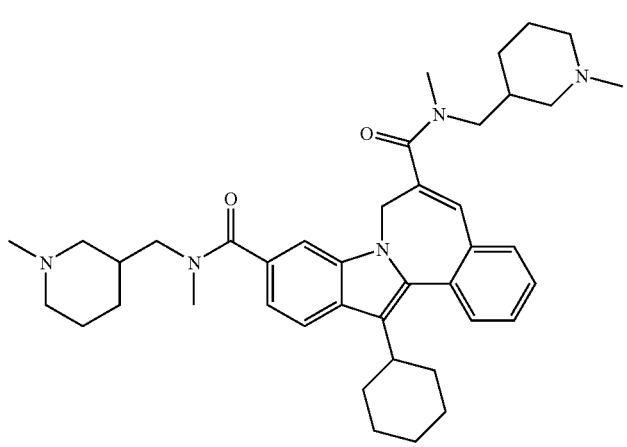 | B | D |

TABLE 1-continued

| Structure | IC$_{50}$* | EC$_{50}$* |
|---|---|---|
| | B | E |
| | B | E |
| 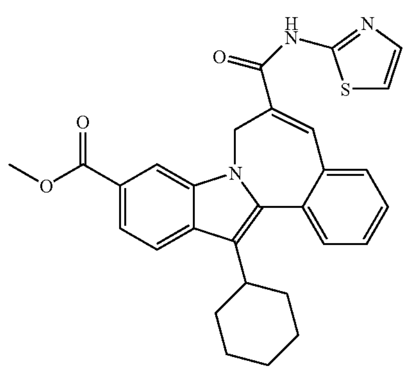 | K | D |
| | B | D |

TABLE 1-continued

| Structure | IC$_{50}$* | EC$_{50}$* |
|---|---|---|
| | B | E |
| | B | E |
| 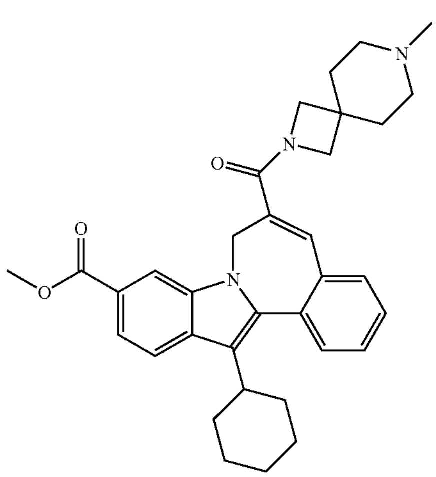 | A | D |

TABLE 1-continued
| Structure | IC$_{50}$* | EC$_{50}$* |
|---|---|---|
| 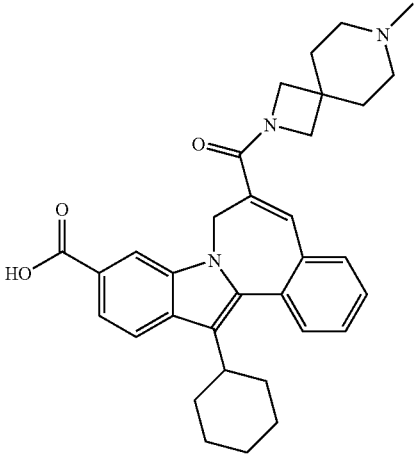 | B | E |
| 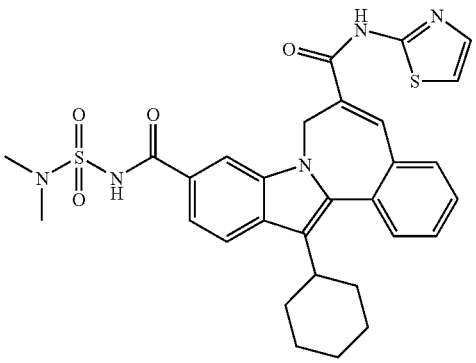 | B | E |
| 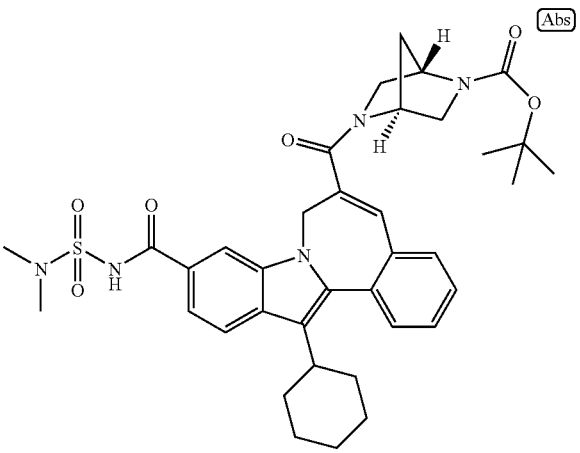 | B | E |

TABLE 1-continued
| Structure | IC$_{50}$* | EC$_{50}$* |
|---|---|---|
| 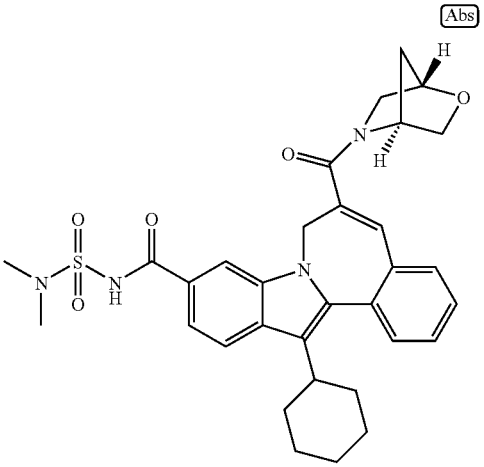 | B | E |
| 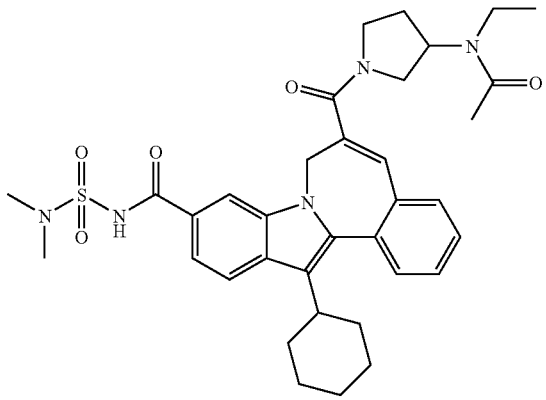 | B | E |
| 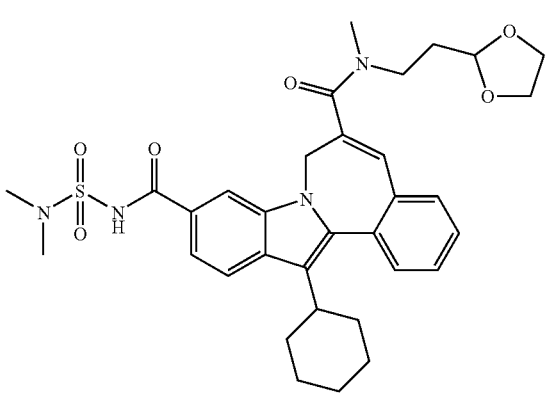 | B | E |

TABLE 1-continued
| Structure | IC$_{50}$* | EC$_{50}$* |
|---|---|---|
| 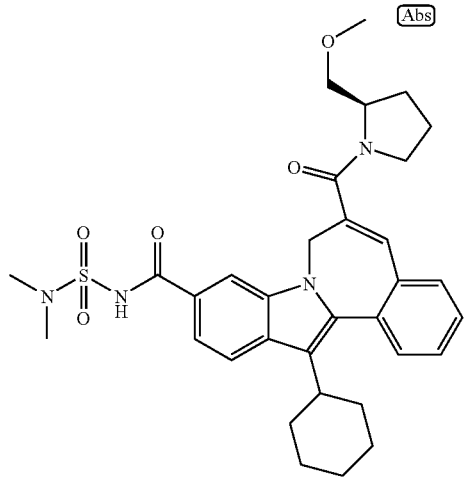 | B | E |
| 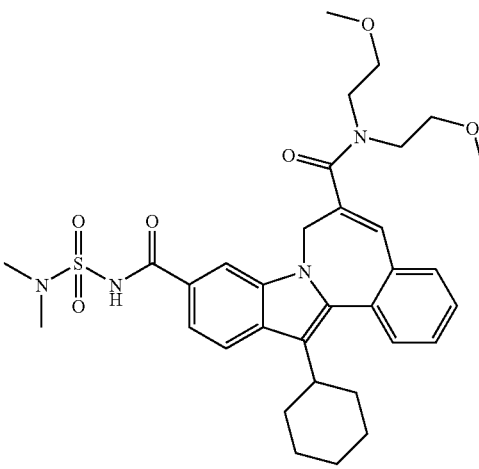 | B | E |
| 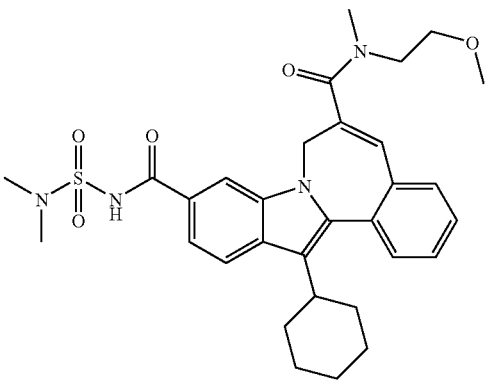 | B | E |

TABLE 1-continued
| Structure | IC$_{50}$* | EC$_{50}$* |
|---|---|---|
| 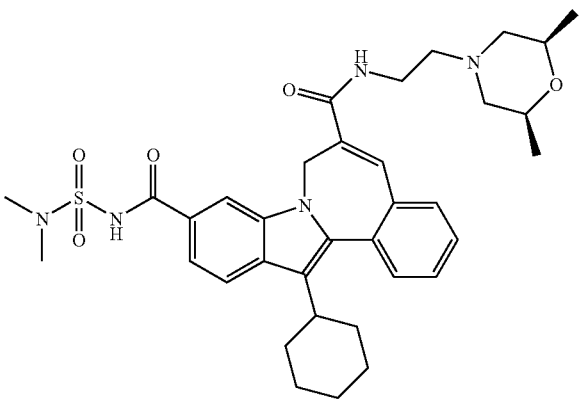 | B | E |
| 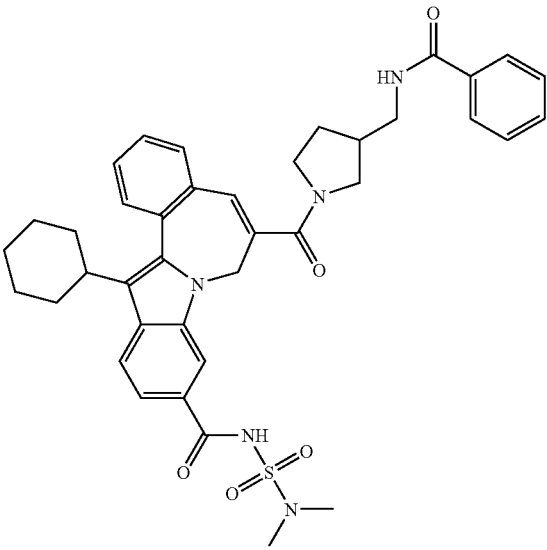 | B | E |
| 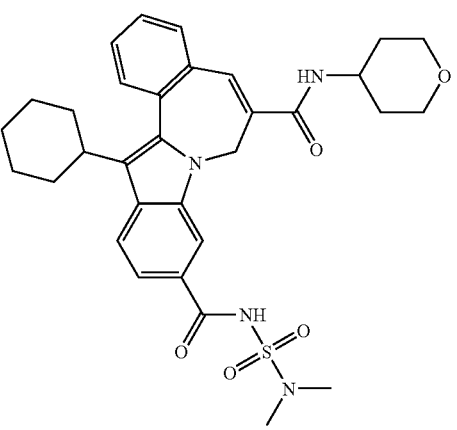 | B | E |

TABLE 1-continued

| Structure | IC$_{50}$* | EC$_{50}$* |
|---|---|---|
| 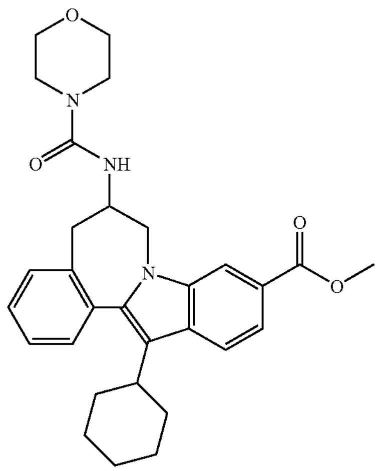 | A | G |
| | B | E |
| | B | E |

TABLE 1-continued

| Structure | IC$_{50}$* | EC$_{50}$* |
|---|---|---|
| 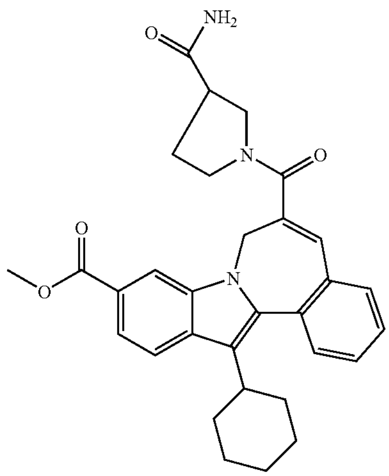 | A | D |
| | B | D |
| | B | E |

TABLE 1-continued

| Structure | IC$_{50}$* | EC$_{50}$* |
|---|---|---|
| (structure) | B | E |
| (structure) | B | E |
| (structure) | B | E |

TABLE 1-continued

| Structure | IC$_{50}$* | EC$_{50}$* |
|---|---|---|
| (structure) | A | G |
| (structure) | B | E |
| (structure) | B | E |

TABLE 1-continued
| Structure | IC$_{50}$* | EC$_{50}$* |
|---|---|---|
| 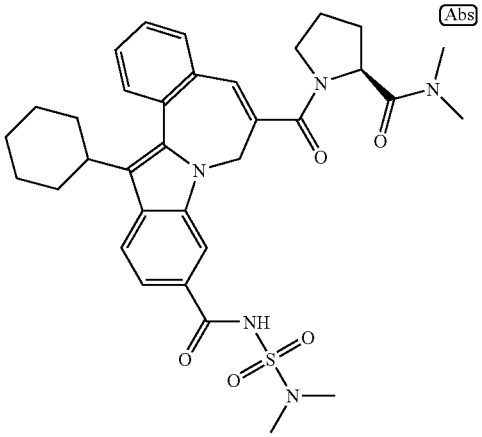 | B | E |
| 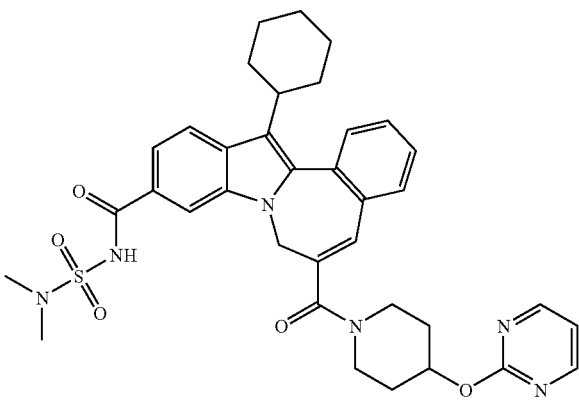 | B | E |
| 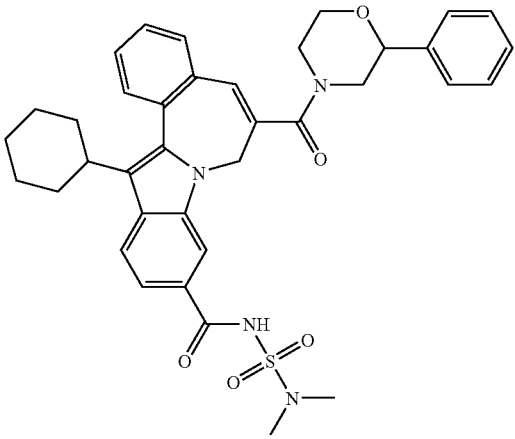 | B | D |

TABLE 1-continued

| Structure | IC$_{50}$* | EC$_{50}$* |
|---|---|---|
| | B | E |
| | B | E |
| | B | E |

TABLE 1-continued
| Structure | IC$_{50}$* | EC$_{50}$* |
|---|---|---|
| 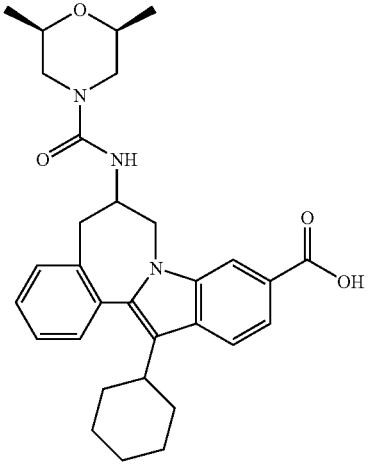 | B | E |
| 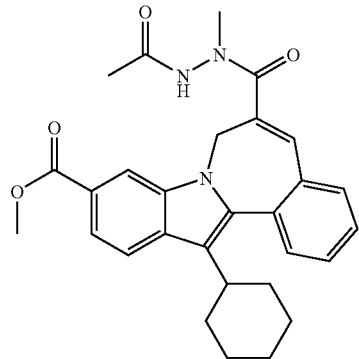 | A | D |
| 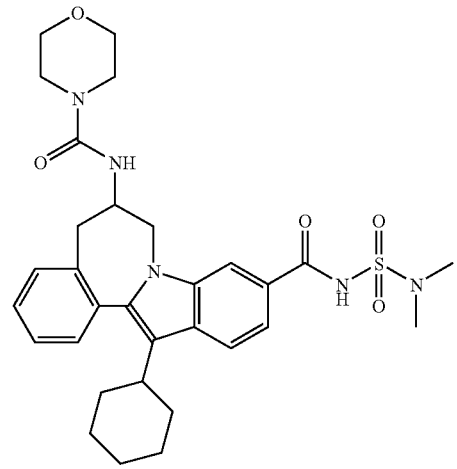 | B | E |

TABLE 1-continued
| Structure | IC$_{50}$* | EC$_{50}$* |
|---|---|---|
| 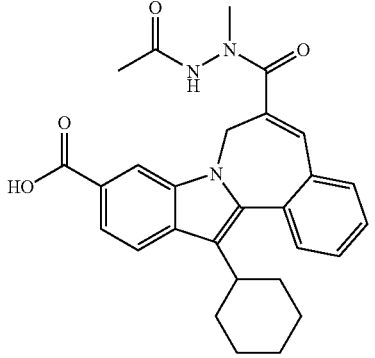 | B | D |
| 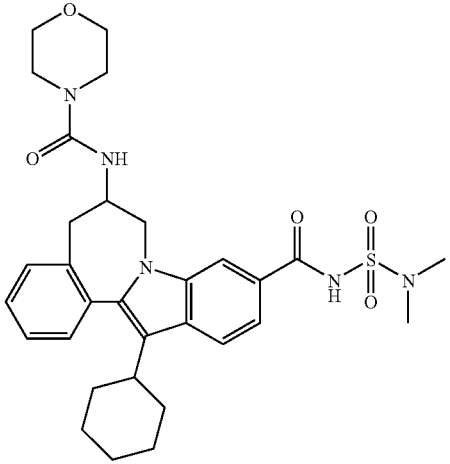 | B | E |
| 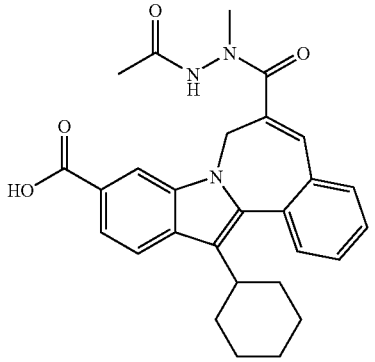 | B | D |
| 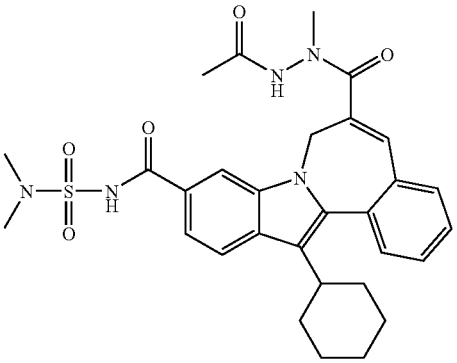 | B | E |

TABLE 1-continued
| Structure | IC$_{50}$* | EC$_{50}$* |
|---|---|---|
| 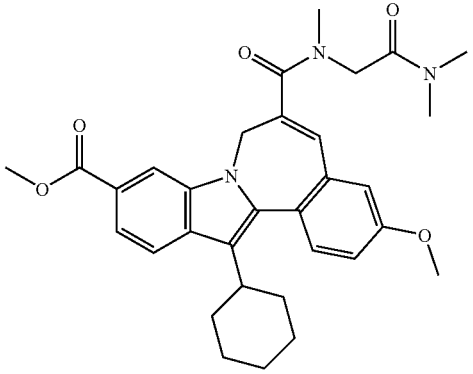 | | |
| 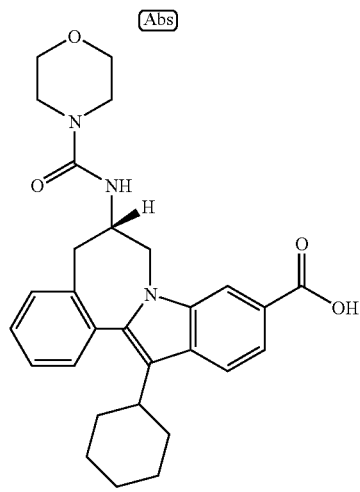 [Abs] | B | E |
| 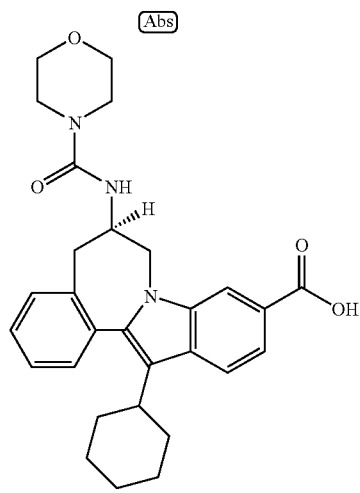 [Abs] | B | E |

TABLE 1-continued

| Structure | IC$_{50}$* | EC$_{50}$* |
|---|---|---|
| | B | E |
| | B | E |
| | | |

TABLE 1-continued

| Structure | IC$_{50}$* | EC$_{50}$* |
|---|---|---|
| | B | E |
| | B | E |
| 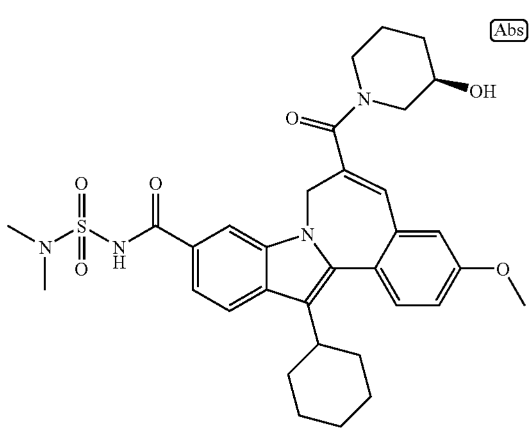 | B' | |

TABLE 1-continued

| Structure | IC$_{50}$* | EC$_{50}$* |
|---|---|---|
| (structure) | A | D |
| (structure) | B | E |
| (structure) | K | D |

TABLE 1-continued

| Structure | IC$_{50}$* | EC$_{50}$* |
|---|---|---|
| | B | E |
| | B | E |
| | B | E |

TABLE 1-continued

| Structure | IC$_{50}$* | EC$_{50}$* |
|---|---|---|
| | B | E |
| 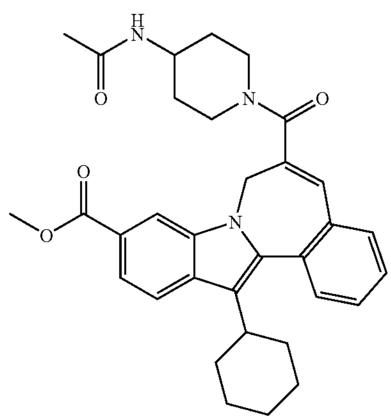 | N | D |
| | B | E |

TABLE 1-continued

| Structure | IC$_{50}$* | EC$_{50}$* |
|---|---|---|
| | B | E |
| | B | E |
| | B | E |

TABLE 1-continued
| Structure | IC$_{50}$* | EC$_{50}$* |
|---|---|---|
| 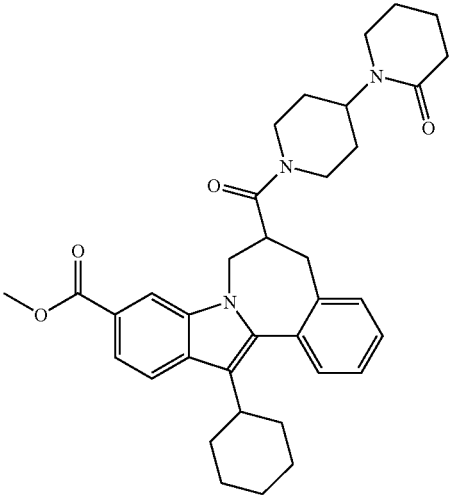 | A | E |
| 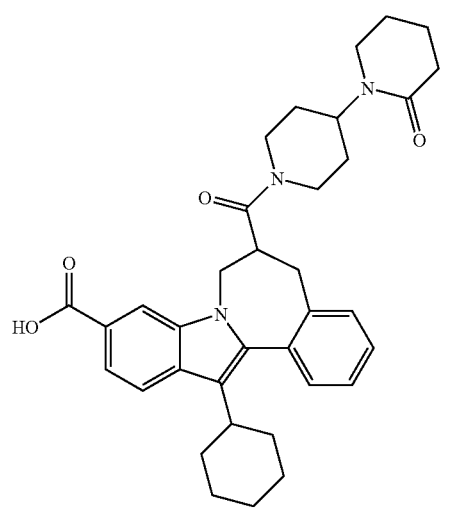 | B | E |
| 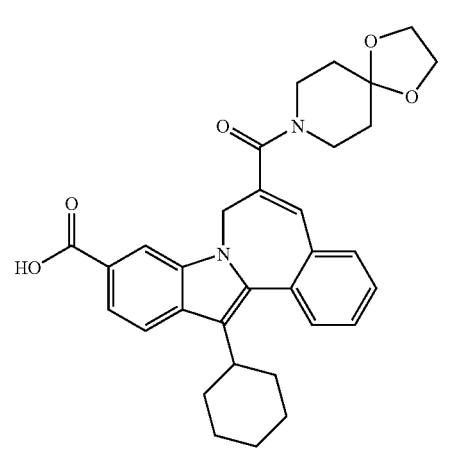 | B | E |

TABLE 1-continued
| Structure | IC$_{50}$* | EC$_{50}$* |
|---|---|---|
| 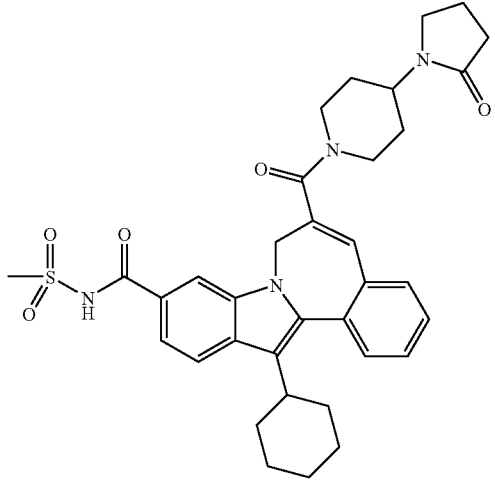 | B | D |
| 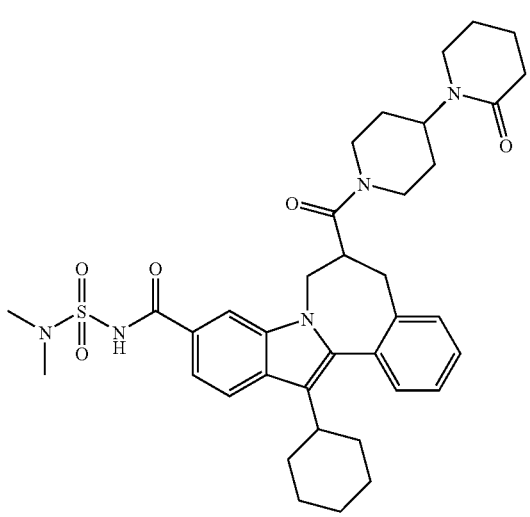 | B | E |
| 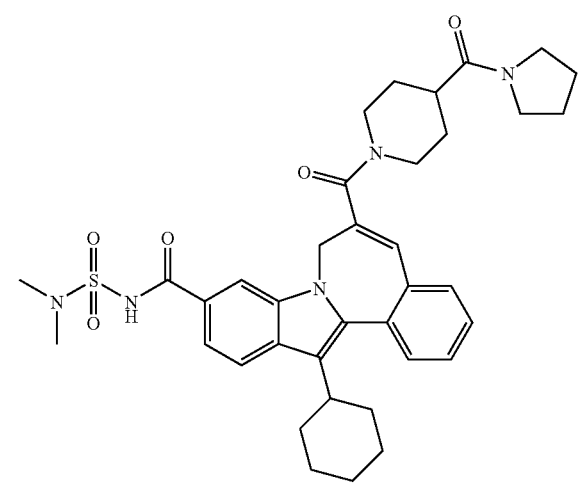 | B | E |

TABLE 1-continued
| Structure | IC$_{50}$* | EC$_{50}$* |
|---|---|---|
| 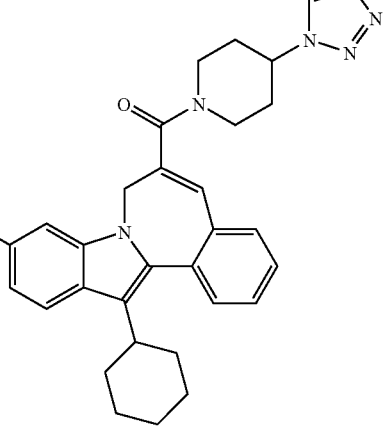 | B | E |
| 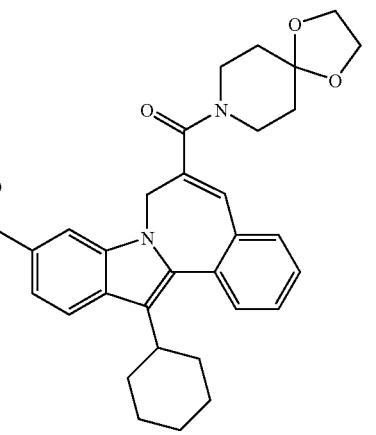 | B | E |
| 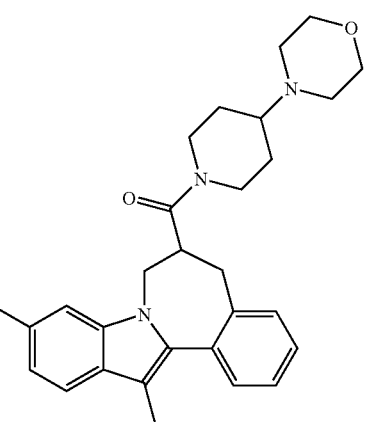 | B | E |

TABLE 1-continued

| Structure | IC$_{50}$* | EC$_{50}$* |
|---|---|---|
| 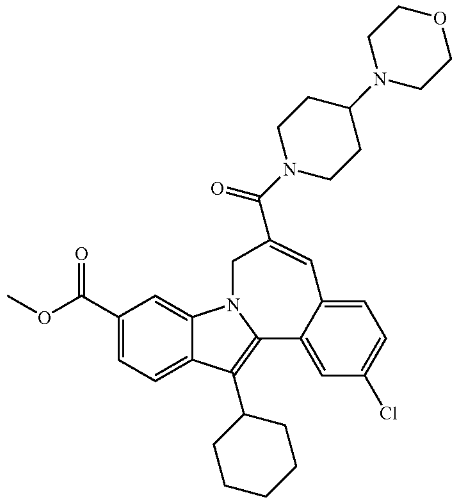 | K | D |
| 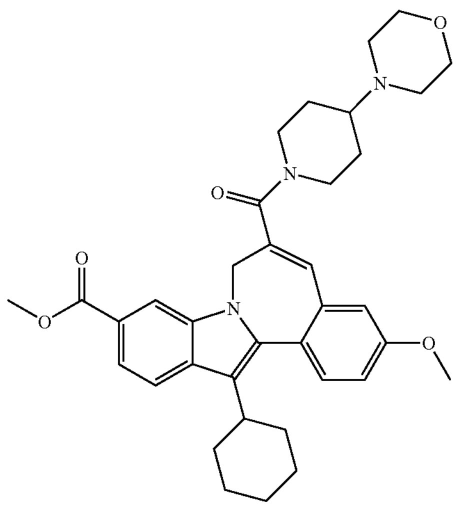 | A | D |
| 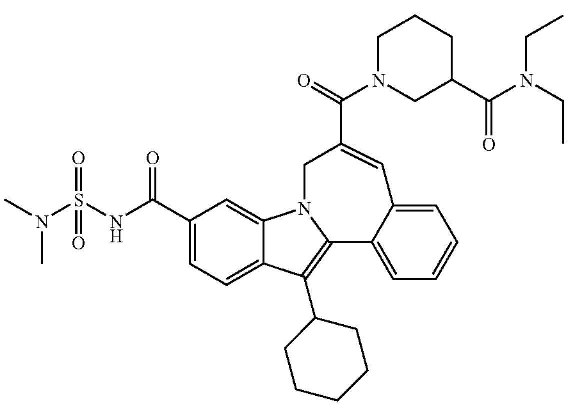 | B | E |

TABLE 1-continued
| Structure | IC$_{50}$* | EC$_{50}$* |
|---|---|---|
| 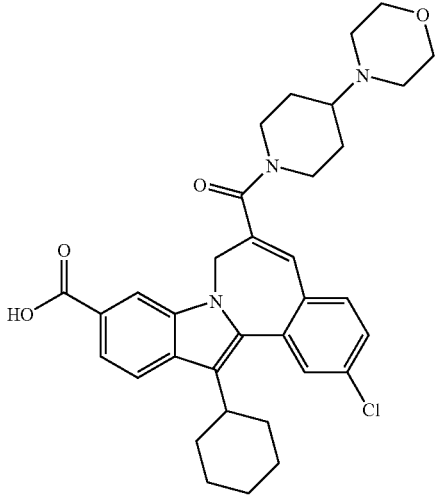 | A | D |
| 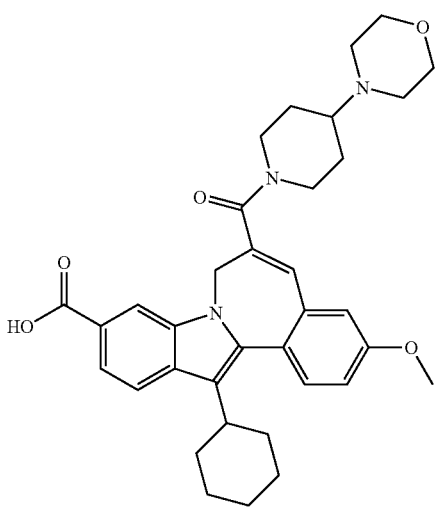 | B | E |
| 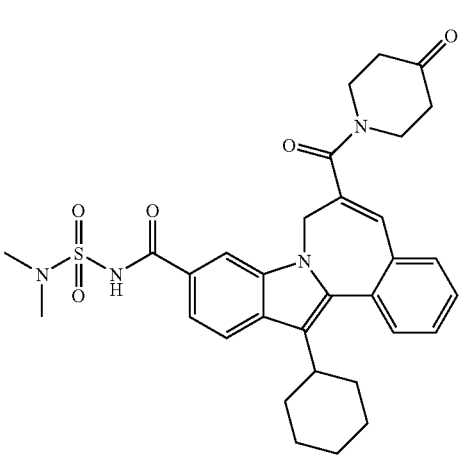 | B | E |

TABLE 1-continued

| Structure | IC$_{50}$* | EC$_{50}$* |
| --- | --- | --- |
| | B | E |
| | B | E |
| | B | E |
| | B | E |

TABLE 1-continued

| Structure | IC$_{50}$* | EC$_{50}$* |
|---|---|---|
| | B | E |
| | B | E |
| 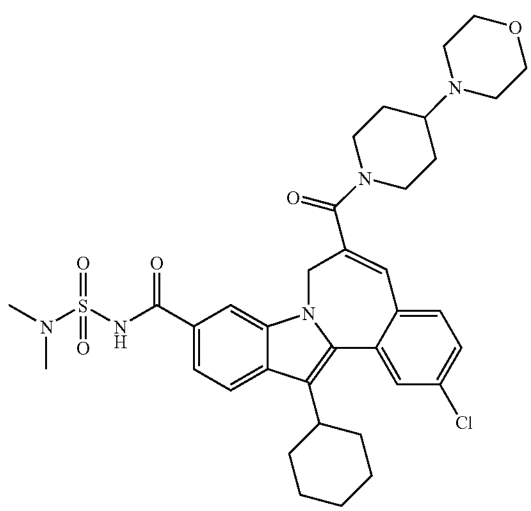 | A | D |

TABLE 1-continued

| Structure | IC$_{50}$* | EC$_{50}$* |
|---|---|---|
| | B | G |
| | B | E |
| | B | D |

TABLE 1-continued

| Structure | IC₅₀* | EC₅₀* |
|---|---|---|
| (structure) | B | D |
| (structure) | B | H |
| (structure) | A | H |
| (structure) | A | H |

TABLE 1-continued
| Structure | IC$_{50}$* | EC$_{50}$* |
|---|---|---|
| 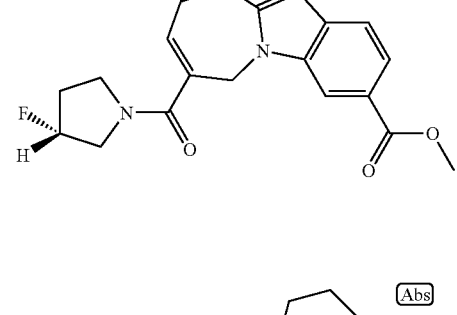 | N | H |
| 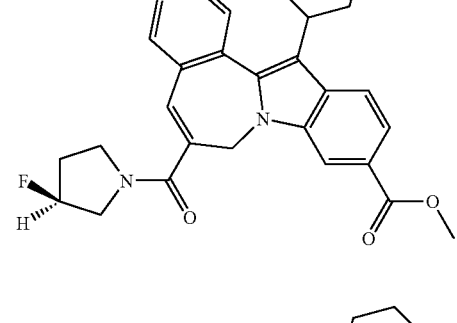 | A | H |
| 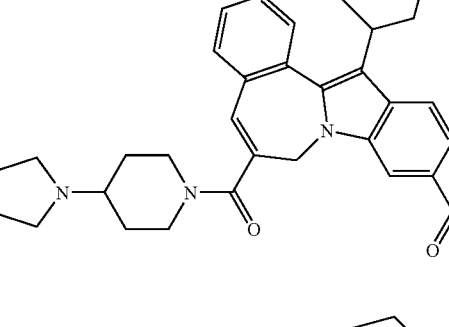 | A | H |
| 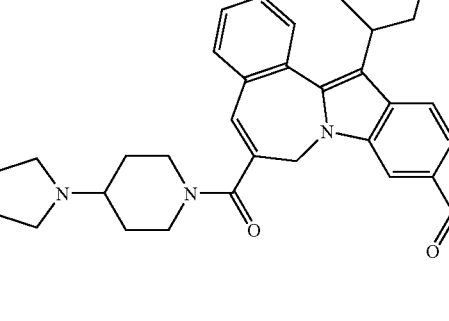 | A | J |

TABLE 1-continued
| Structure | IC$_{50}$* | EC$_{50}$* |
|---|---|---|
| 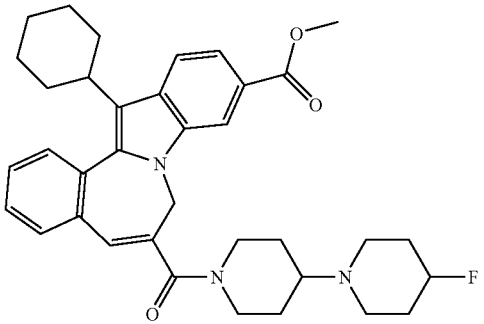 | A | H |
| 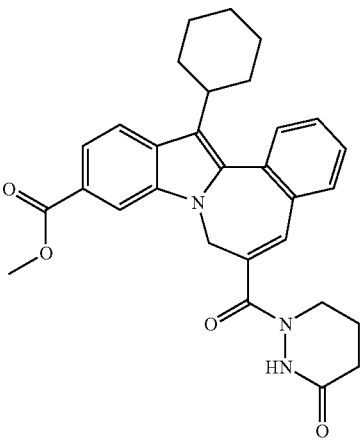 | A | D |
| 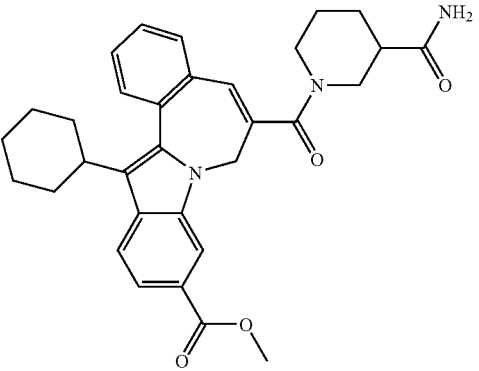 | A | D |
| 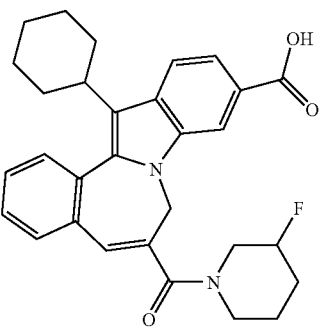 | B | D |

TABLE 1-continued

| Structure | IC$_{50}$* | EC$_{50}$* |
|---|---|---|
| | B | E |
| | B | E |
| | B | E |
| | B | E |

TABLE 1-continued

| Structure | IC$_{50}$* | EC$_{50}$* |
|---|---|---|
| (structure) | B | E |
| (structure) | B | E |
| (structure) | B | E |
| (structure) | B | D |

TABLE 1-continued
| Structure | IC$_{50}$* | EC$_{50}$* |
|---|---|---|
| 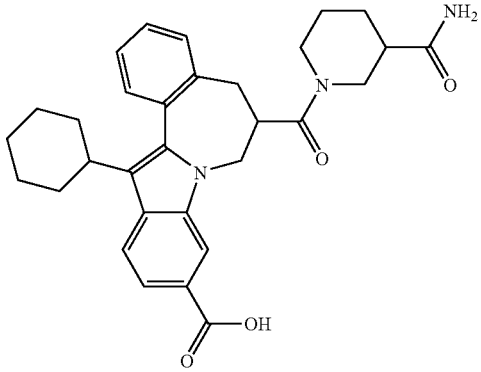 | B | D |
| 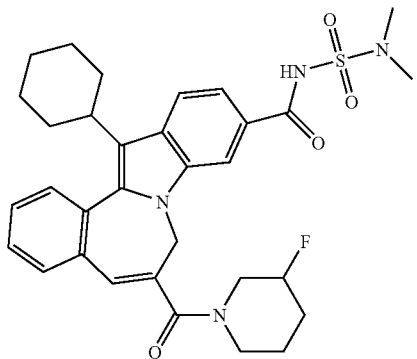 | B | E |
| 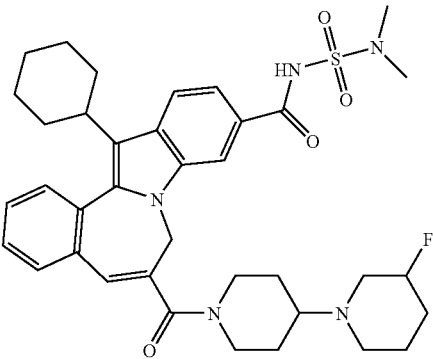 | B | E |
| 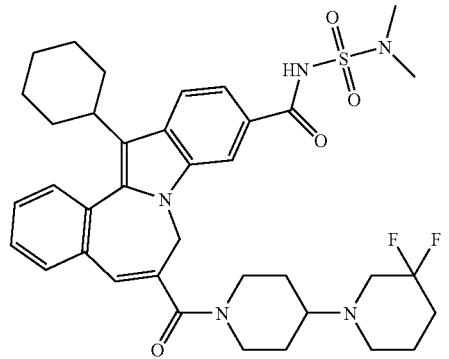 | B | E |

TABLE 1-continued

| Structure | IC$_{50}$* | EC$_{50}$* |
|---|---|---|
| | B | E |
| | B | E |
| | B | E |

TABLE 1-continued
| Structure | IC$_{50}$* | EC$_{50}$* |
|---|---|---|
| 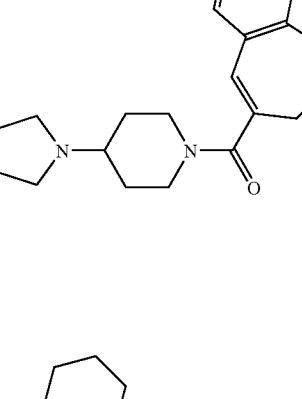 | B | E |
| 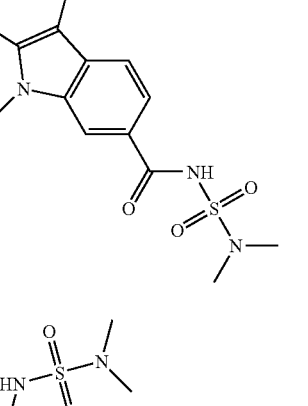 | B | E |
| 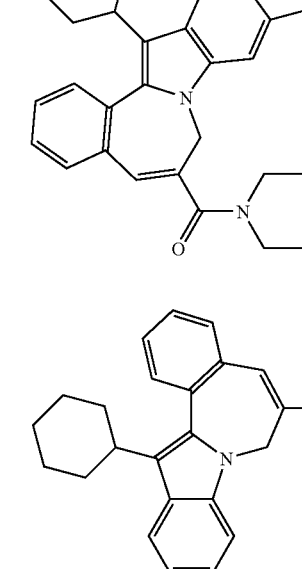 | B | E |
| 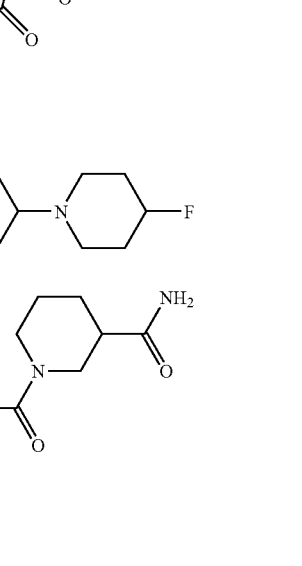 | K | C** |

TABLE 1-continued

| Structure | IC$_{50}$* | EC$_{50}$* |
|---|---|---|
| (structure) | B | D |

A > 1 μM;
B 0.01 μM-1 μM;
C > 10 μM;
D 1 μM-10 μM;
E 1.0 μM-0.07 μM.
IC$_{50}$ values were determined using the preincubation protocol.
EC$_{50}$ values were determined using the FRET assay.

Data for some additional Formula I, II, III, and IV compounds are shown in Table 1a below.

TABLE 1a

| Structure | IC$_{50}$* | EC$_{50}$* |
|---|---|---|
| (structure) | B | E |
| (structure) | B | E |

TABLE 1a-continued

| Structure | IC$_{50}$* | EC$_{50}$* |
|---|---|---|
| | B | E |
| | B | |
| | B | |
| | B | |

TABLE 1a-continued
| Structure | IC$_{50}$* | EC$_{50}$* |
| --- | --- | --- |
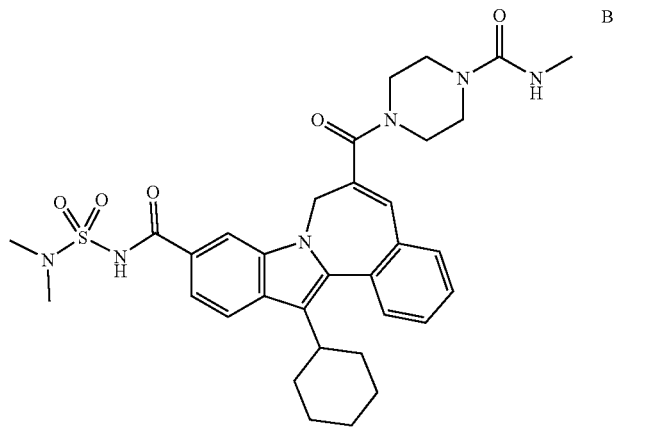
B
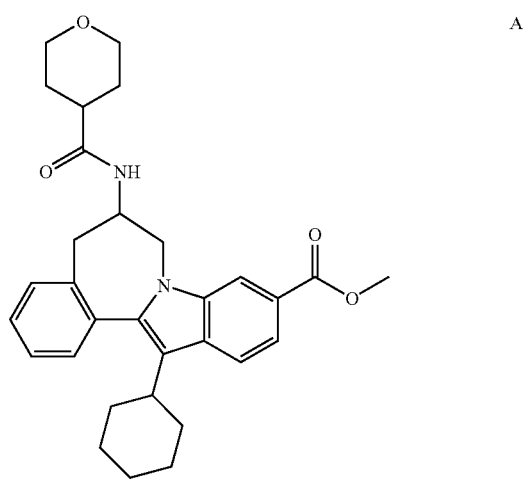
A
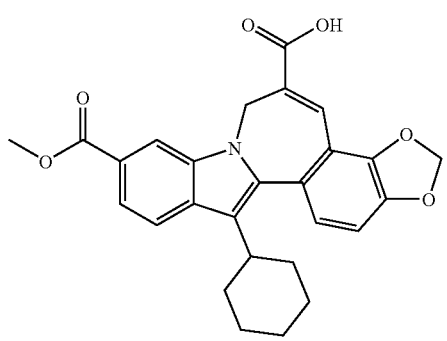

TABLE 1a-continued

| Structure | IC$_{50}$* | EC$_{50}$* |
|---|---|---|
| | | B |
| | | B |
| | | |

TABLE 1a-continued

| Structure | IC$_{50}$* | EC$_{50}$* |
|---|---|---|
| | | B |
| | | B |

TABLE 1a-continued
| Structure | IC$_{50}$* | EC$_{50}$* |
|---|---|---|
| 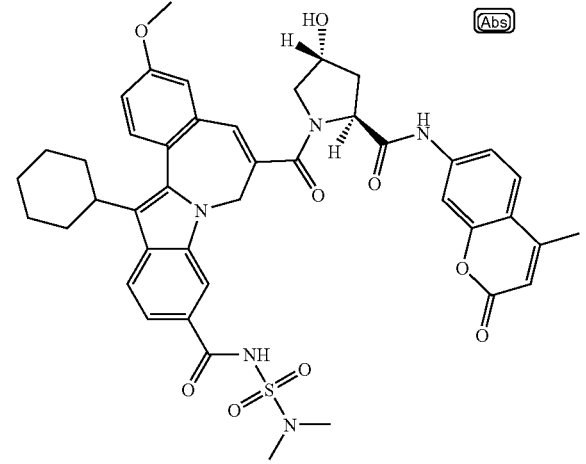 | B | |
| 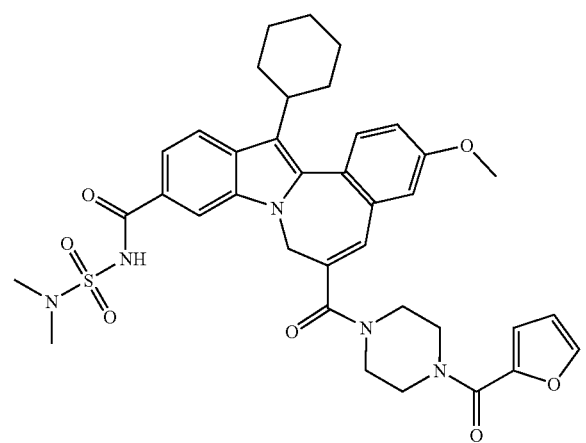 | B | |
| 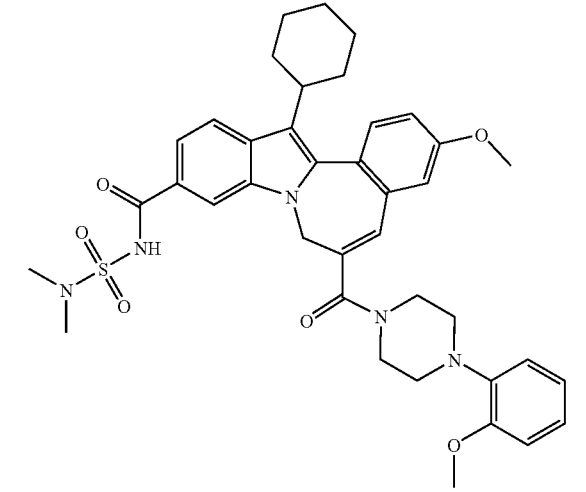 | B | |

TABLE 1a-continued
| Structure | IC$_{50}$* | EC$_{50}$* |
|---|---|---|
| 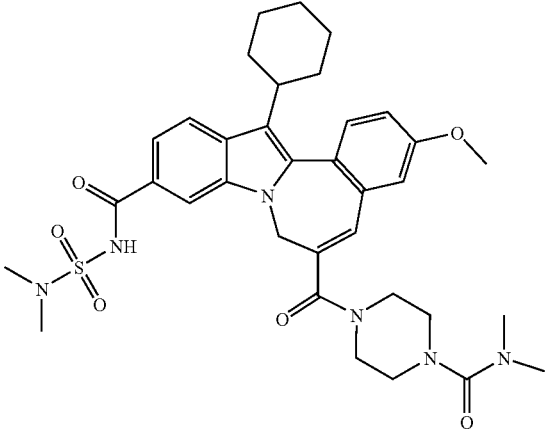 | B | |
| 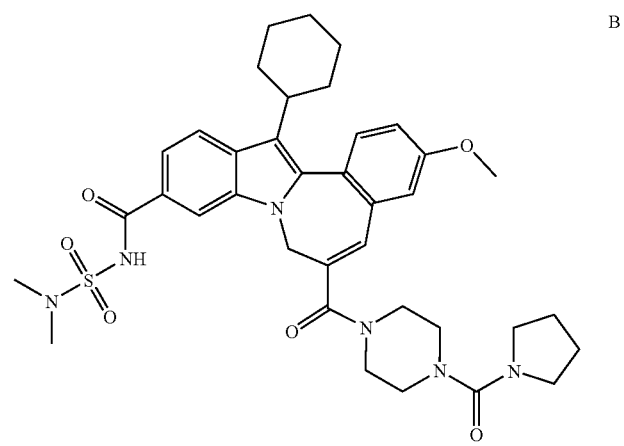 | B | |
| 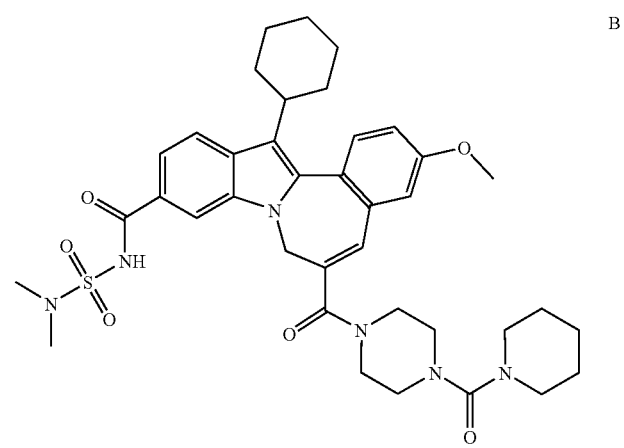 | B | |

TABLE 1a-continued
| Structure | IC$_{50}$* | EC$_{50}$* |
|---|---|---|
| 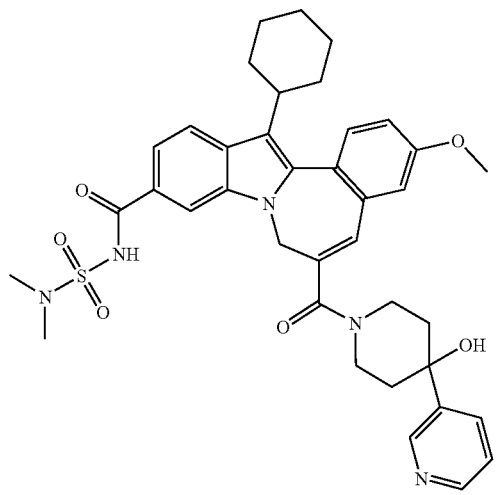 | B | |
| 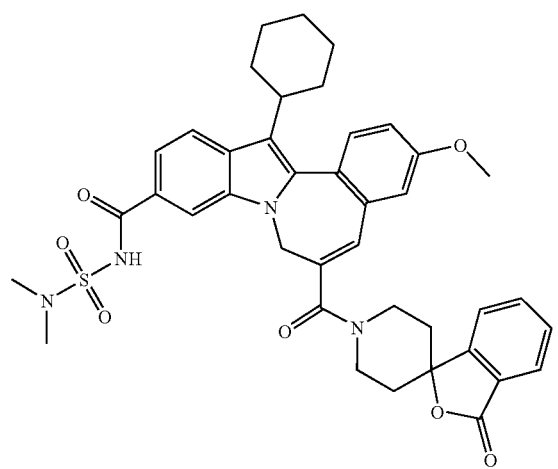 | B | |
| 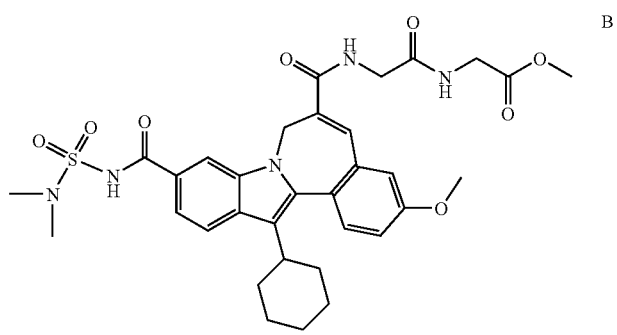 | B | |

TABLE 1a-continued
| Structure | IC$_{50}$* | EC$_{50}$* |
|---|---|---|
| 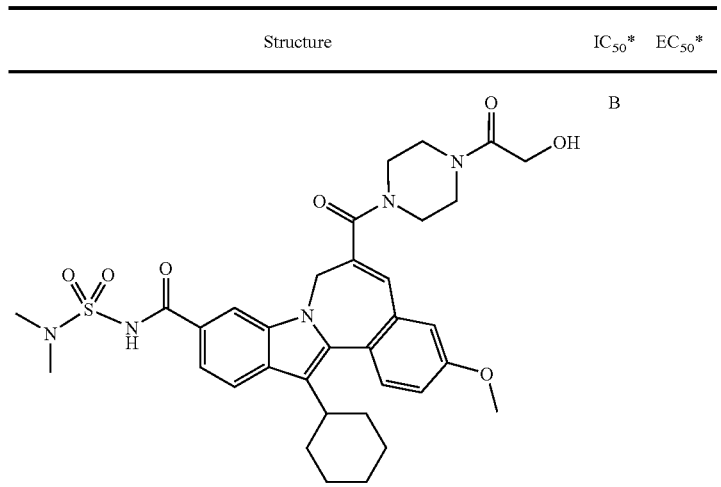 | B | |
| 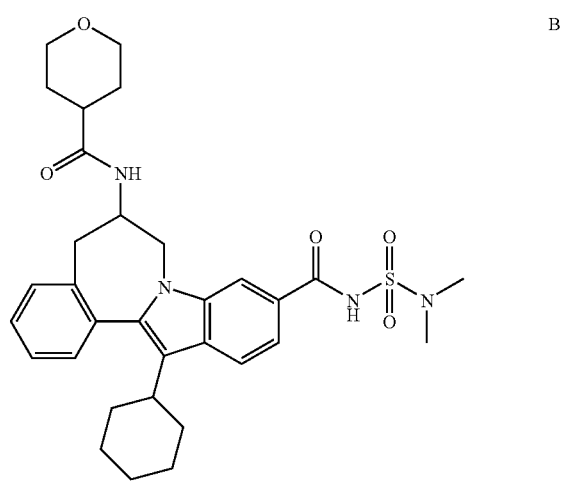 | B | |
| 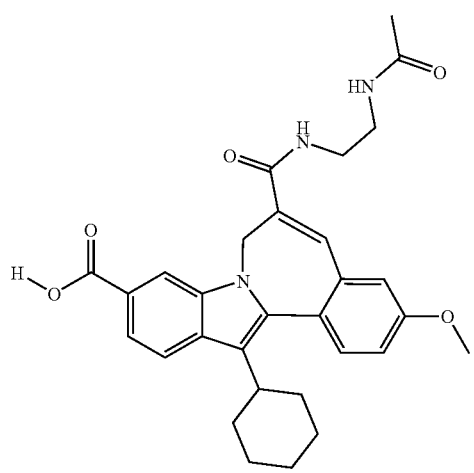 | | |

TABLE 1a-continued
| Structure | IC$_{50}$* | EC$_{50}$* |
|---|---|---|
| 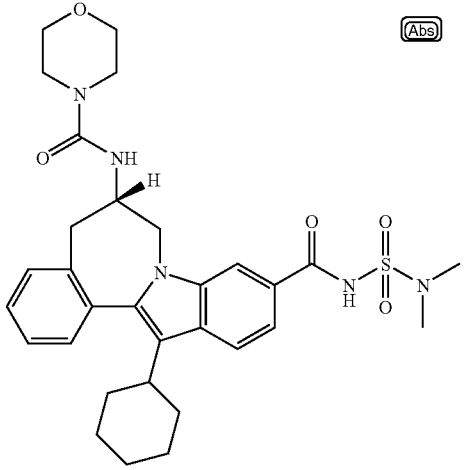 | | B |
| 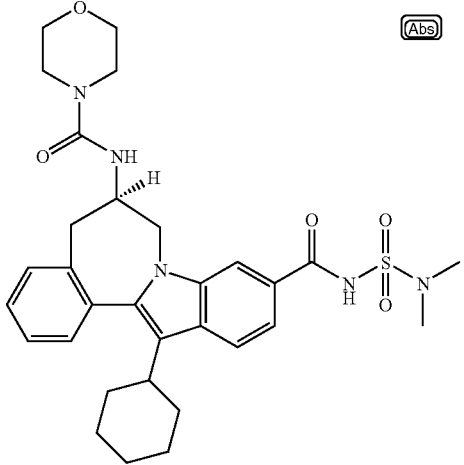 | | B |
| 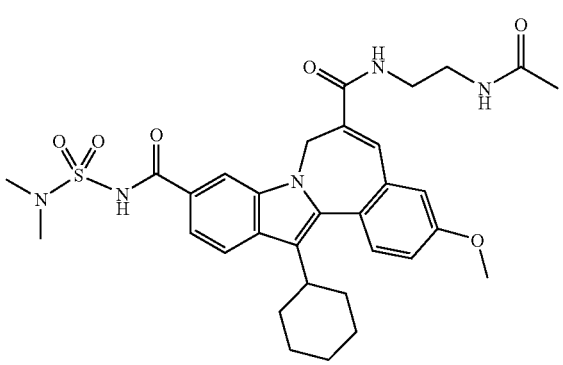 | | B |

TABLE 1a-continued
| Structure | IC$_{50}$* | EC$_{50}$* |
|---|---|---|
| 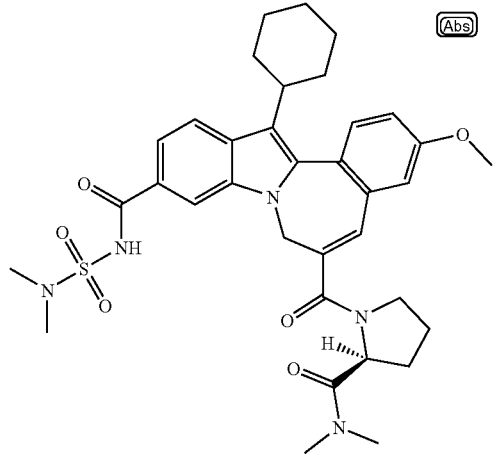 | B | |
| 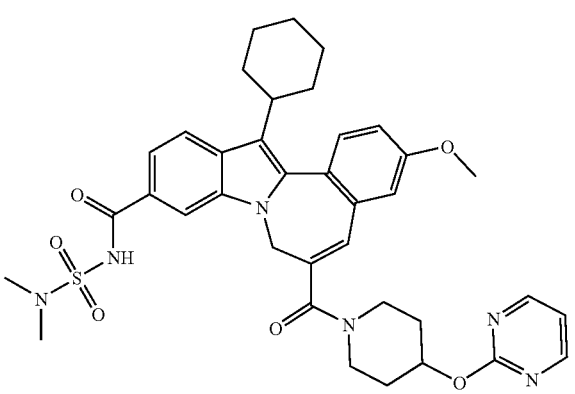 | B | |
| 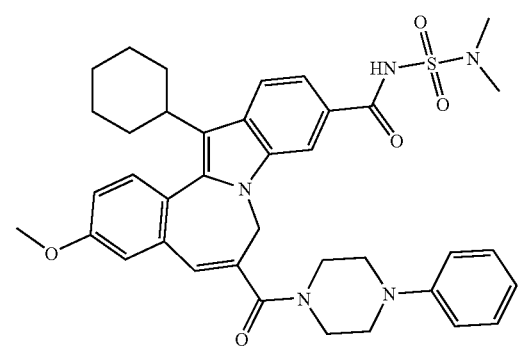 | | |

TABLE 1a-continued
| Structure | IC$_{50}$* | EC$_{50}$* |
|---|---|---|
| 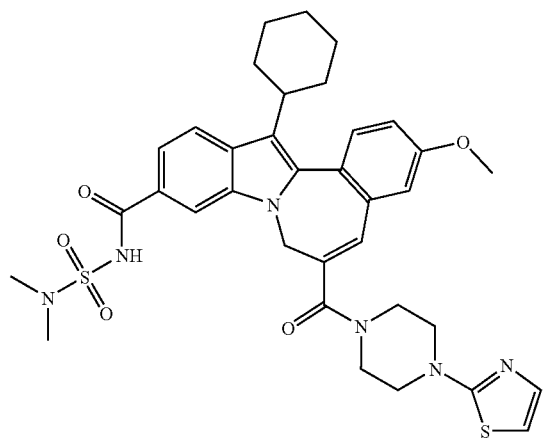 | | B |
| 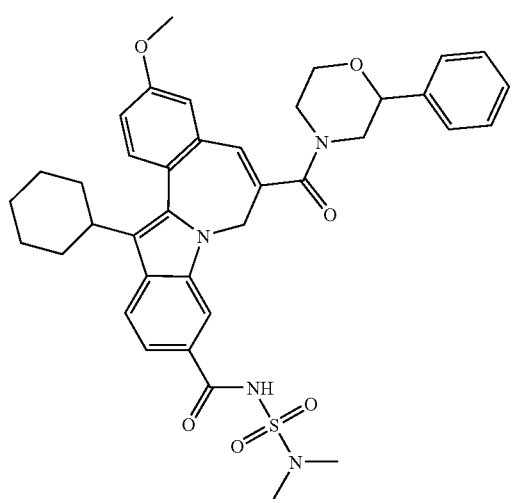 | | B |
| 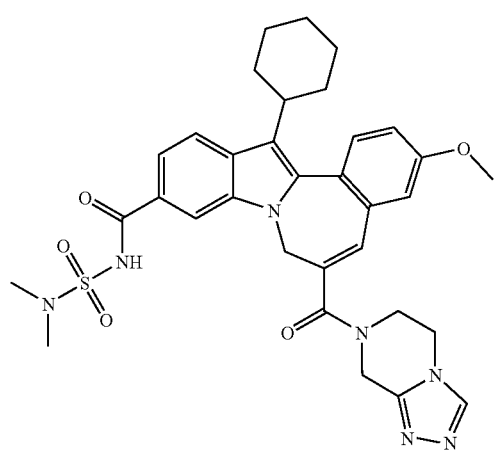 | | B |

TABLE 1a-continued
| Structure | IC$_{50}$* | EC$_{50}$* |
|---|---|---|
| 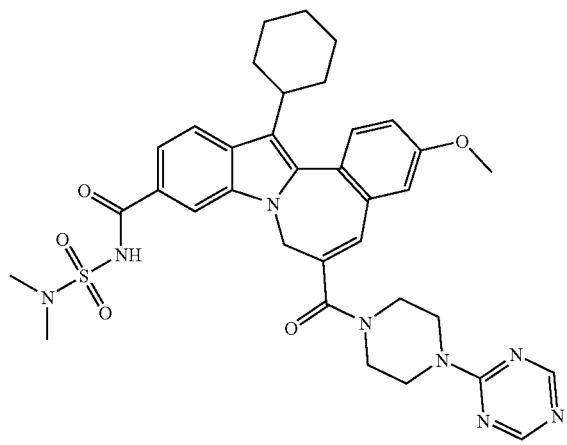 | | B |
| 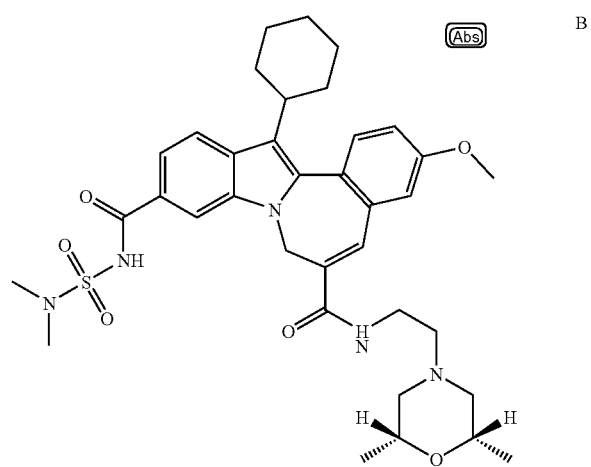 | | B |
| 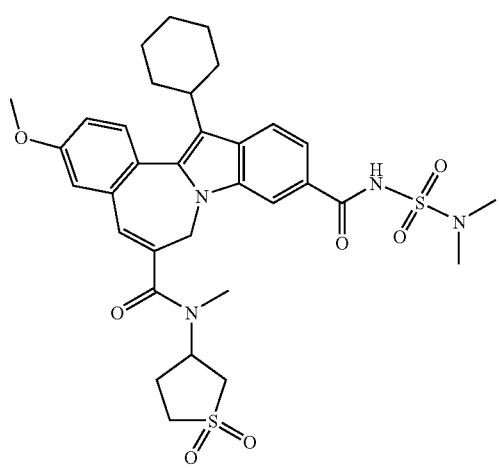 | | B |

TABLE 1a-continued
| Structure | IC$_{50}$* | EC$_{50}$* |
|---|---|---|
| 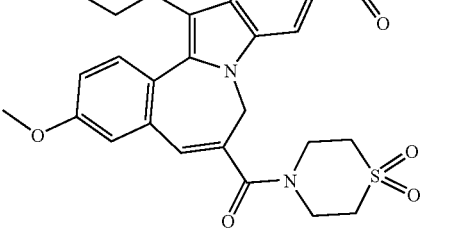 | B | |
| 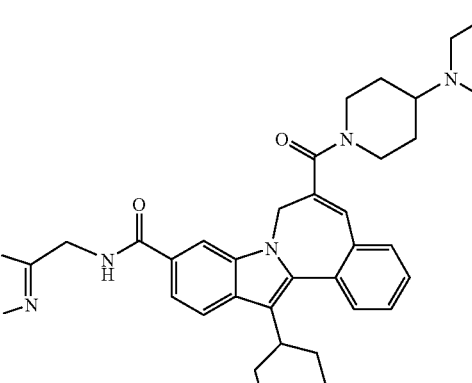 | B | |
| 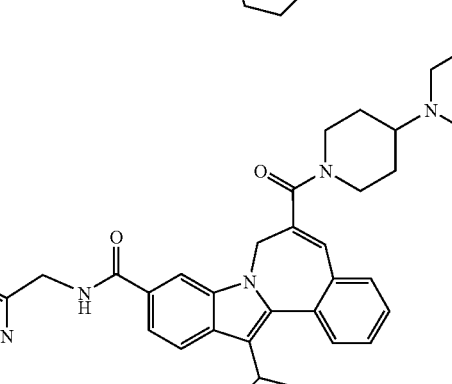 | B | |
| 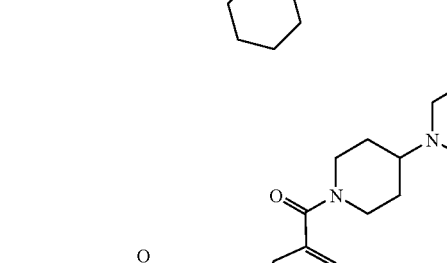 | B | |

TABLE 1a-continued
| Structure | IC$_{50}$* | EC$_{50}$* |
| --- | --- | --- |
| 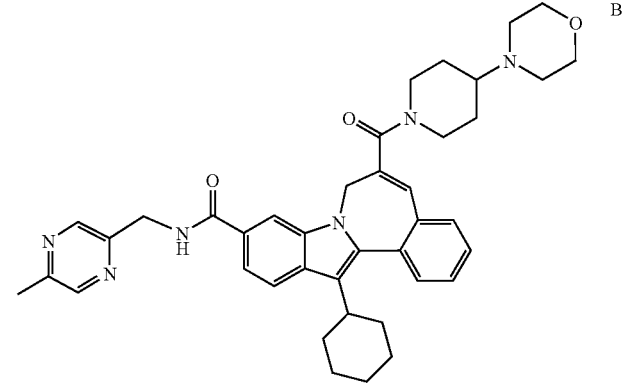 | B | |
| 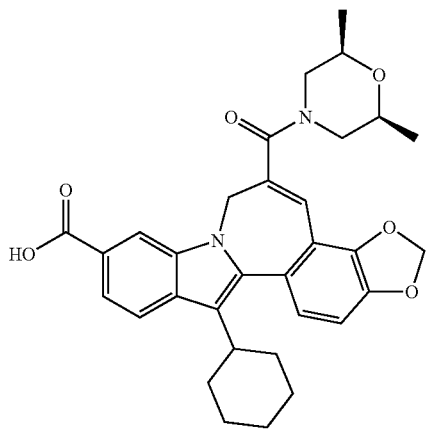 | B | |
| 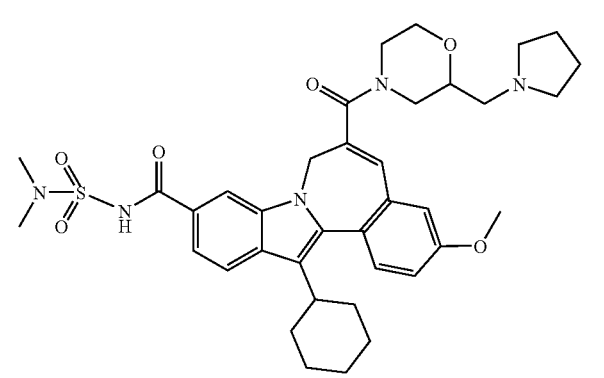 | B | |

TABLE 1a-continued
| Structure | IC$_{50}$* | EC$_{50}$* |
|---|---|---|
| 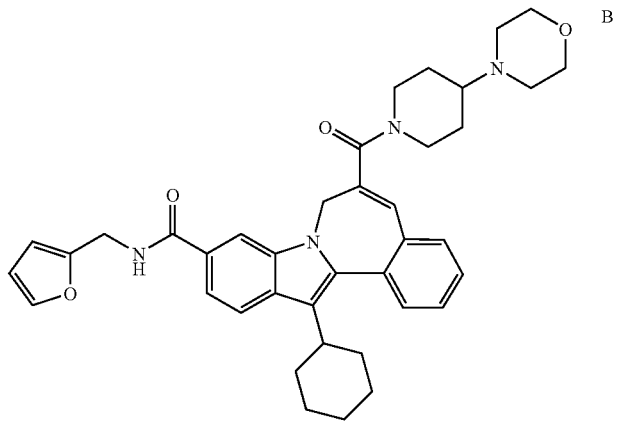 | B | |
|  | B | |
|  | B | |

TABLE 1a-continued
| Structure | IC$_{50}$* | EC$_{50}$* |
|---|---|---|
| 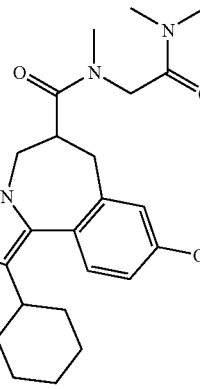 | B | |
| 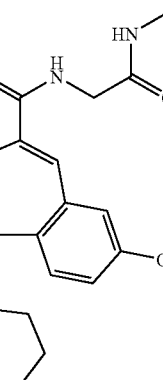 | B | |
| 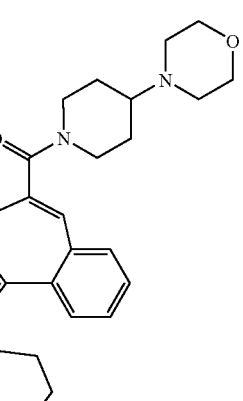 | B | |
| 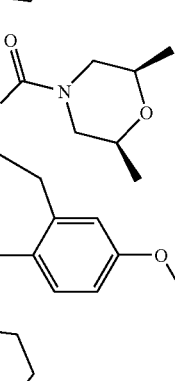 | B | E |

TABLE 1a-continued
| Structure | IC$_{50}$* | EC$_{50}$* |
| --- | --- | --- |
| 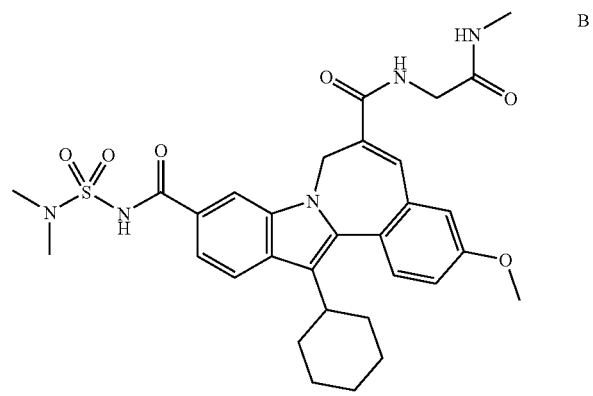 | B | |
| 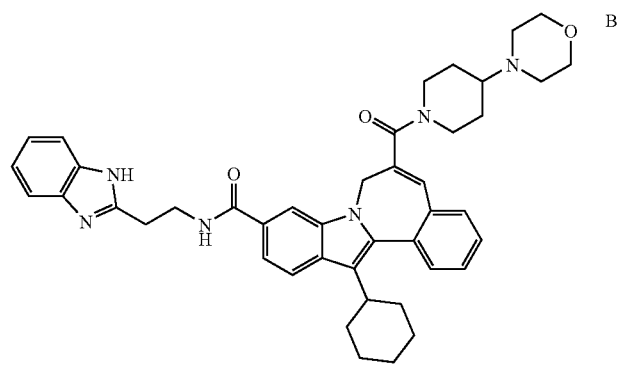 | B | |
| 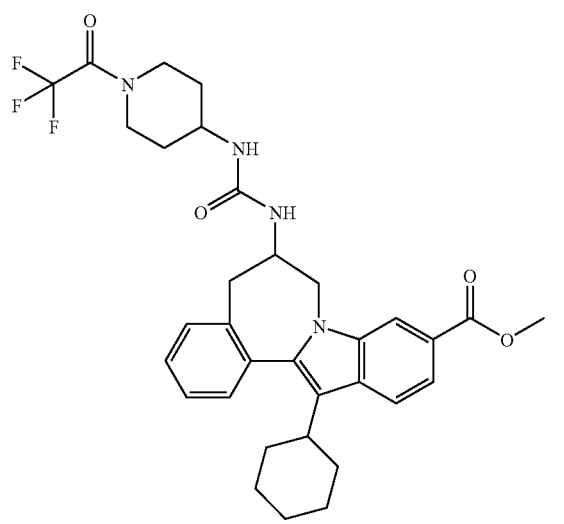 | A | |

TABLE 1a-continued
| Structure | IC$_{50}$* | EC$_{50}$* |
|---|---|---|
| 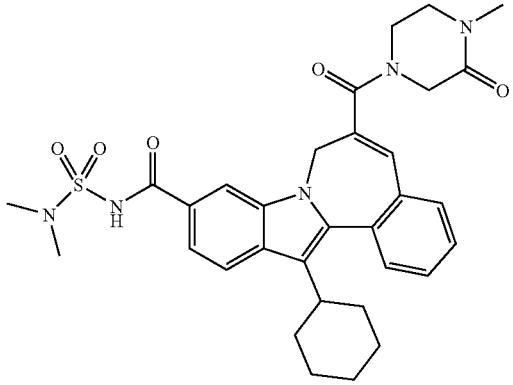 | B | |
| 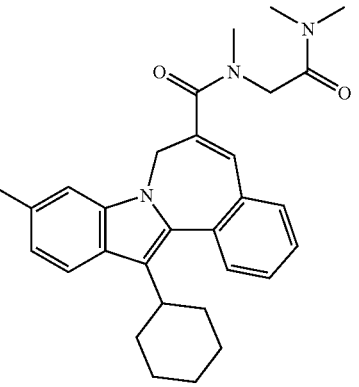 | B | |
| 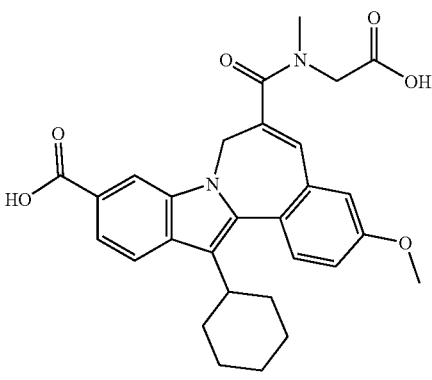 | B | |
| 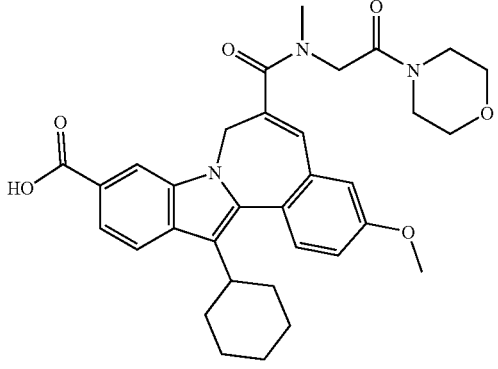 | B | |

TABLE 1a-continued
| Structure | IC$_{50}$* | EC$_{50}$* |
|---|---|---|
| 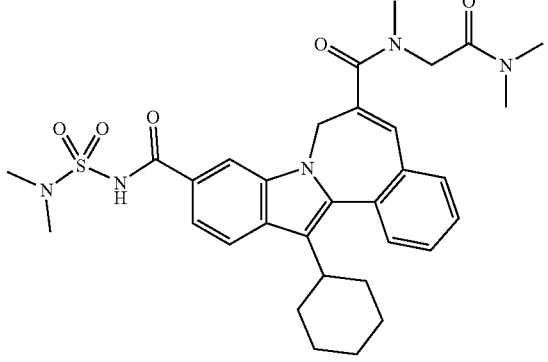 | B | |
| 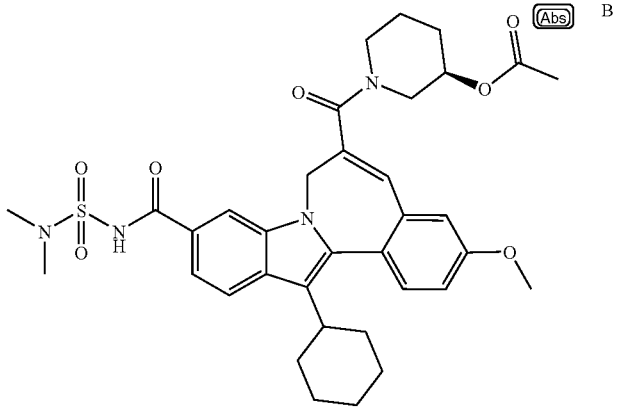 | B | |
| 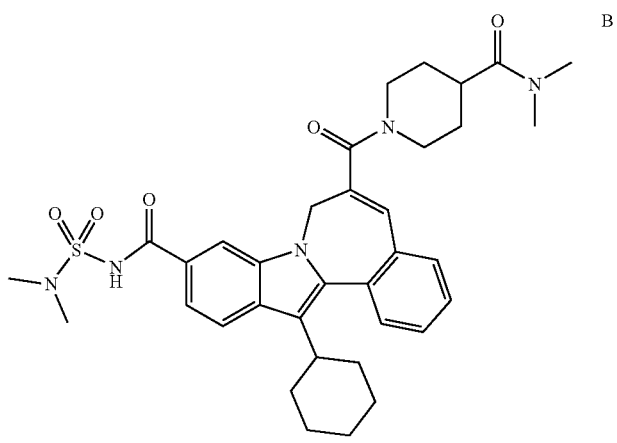 | B | |
| 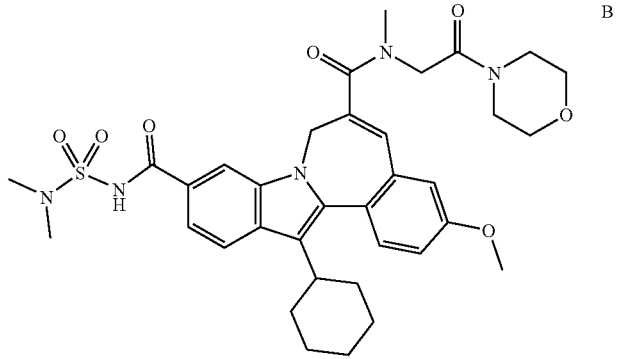 | B | |

TABLE 1a-continued
| Structure | IC$_{50}$* | EC$_{50}$* |
|---|---|---|
| 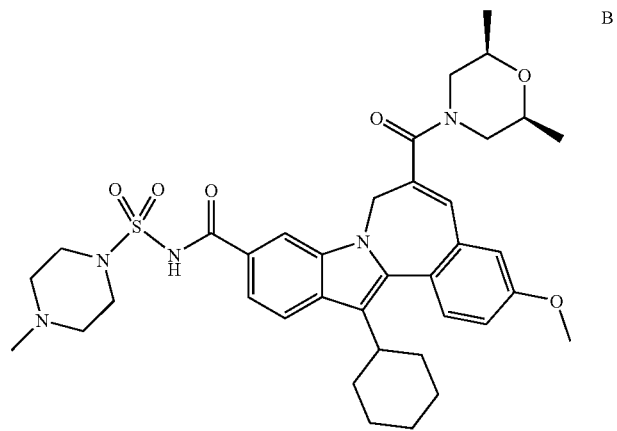 | B | |
| 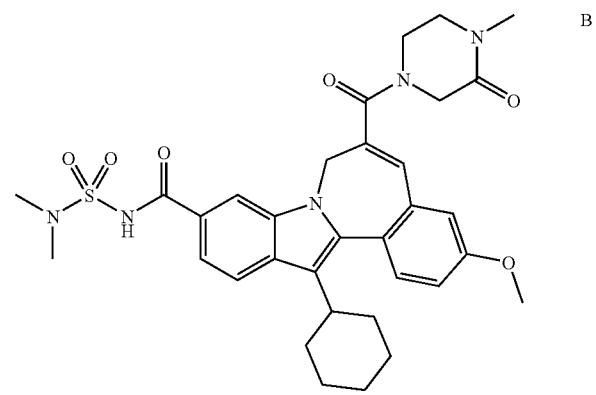 | B | |
| 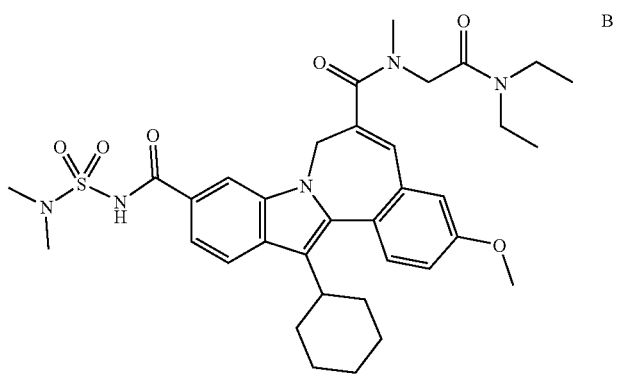 | B | |
| 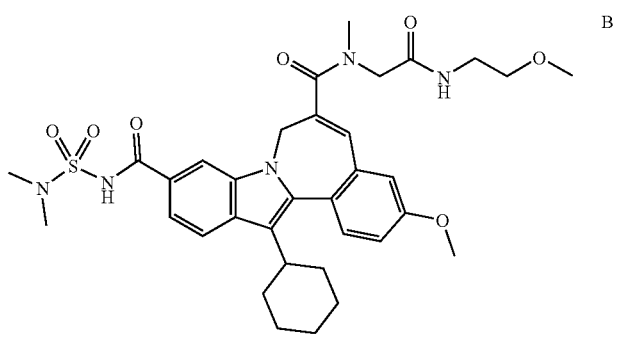 | B | |

TABLE 1a-continued
| Structure | IC$_{50}$* | EC$_{50}$* |
|---|---|---|
| 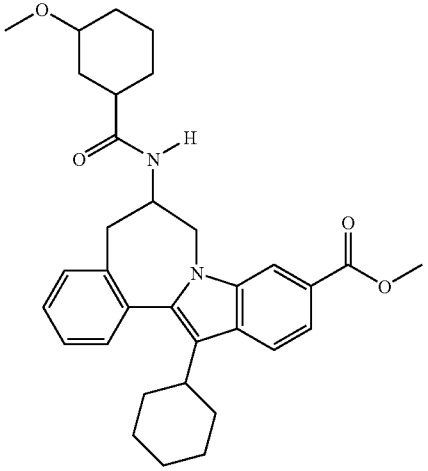 | A | |
| 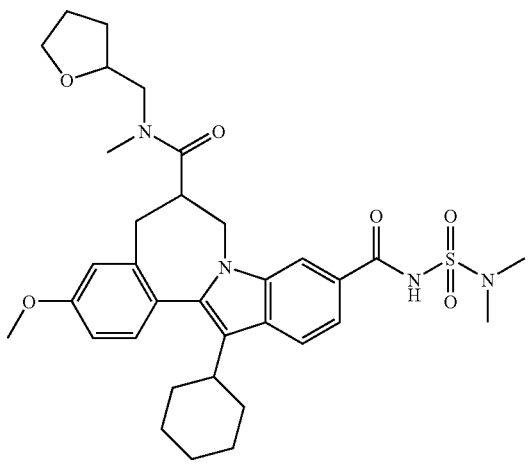 | B | |
| 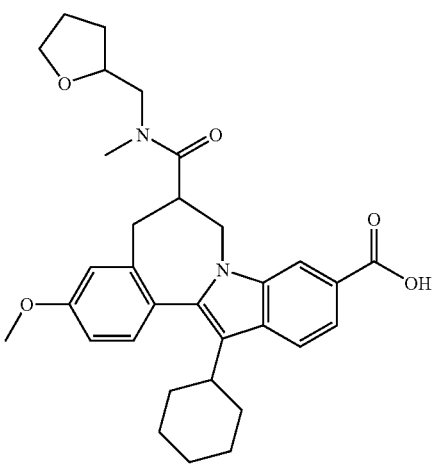 | B | |

TABLE 1a-continued
| Structure | IC$_{50}$* | EC$_{50}$* |
| --- | --- | --- |
| 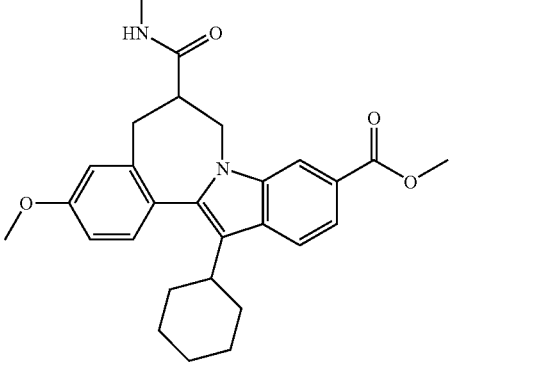 | | A |
| 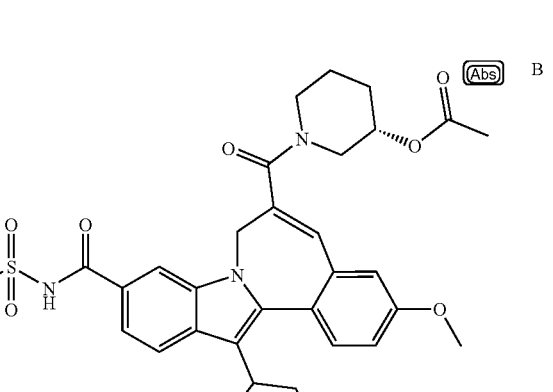 | | B |
| 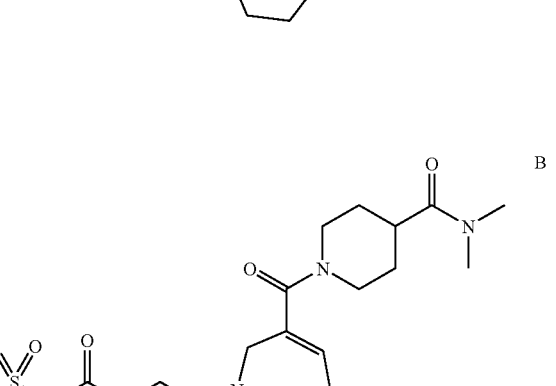 | | B |

TABLE 1a-continued
| Structure | IC$_{50}$* | EC$_{50}$* |
|---|---|---|
| 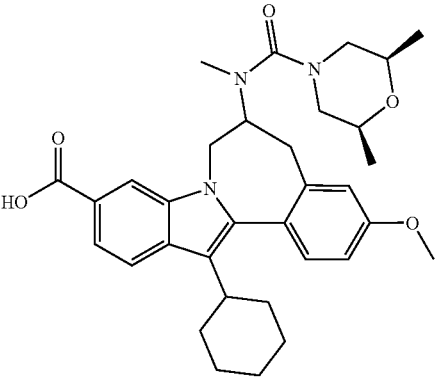 | B | |
| 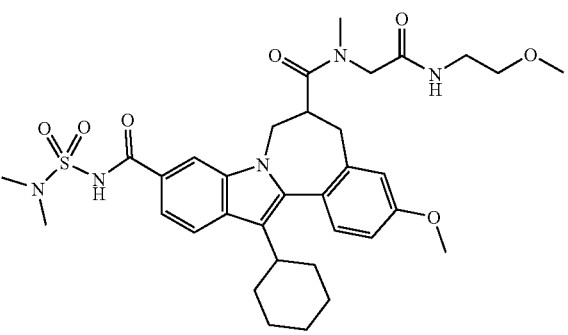 | B | |
| 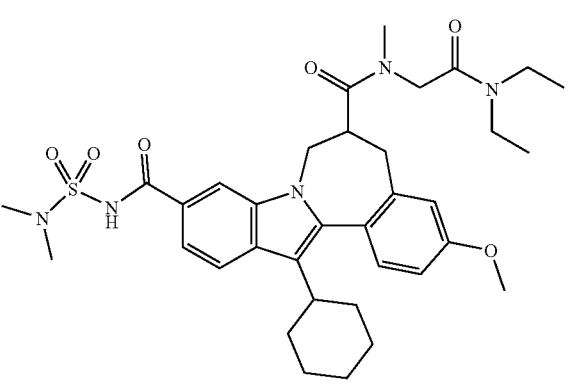 | B | |
| 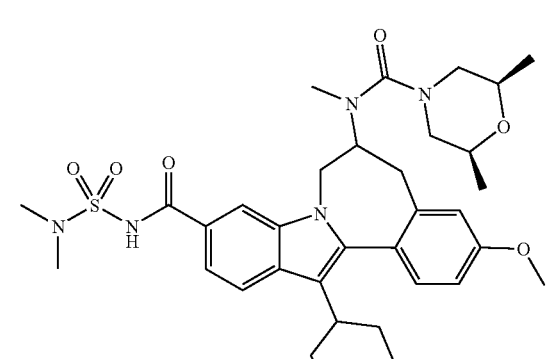 | B | |

TABLE 1a-continued
| Structure | IC$_{50}$* | EC$_{50}$* |
|---|---|---|
| 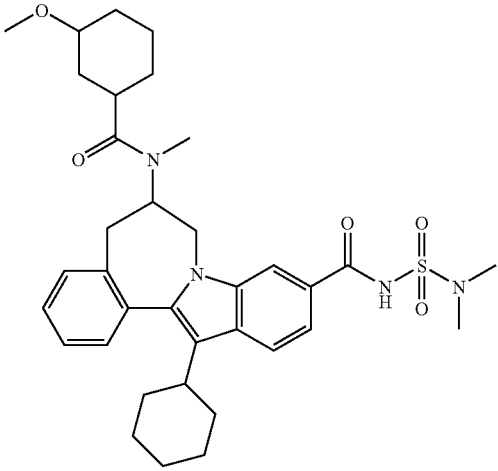 | | B |
| 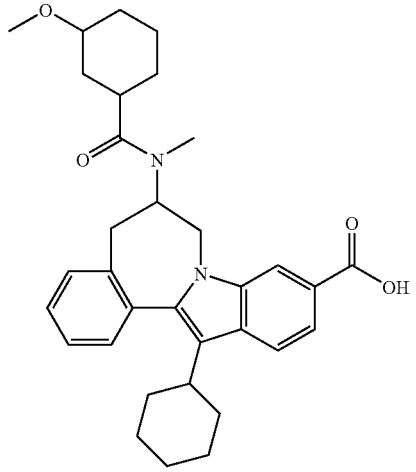 | | B |
| 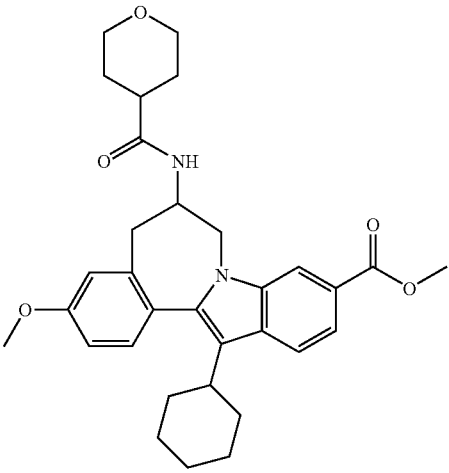 | | B |

TABLE 1a-continued
| Structure | IC$_{50}$* | EC$_{50}$* |
| --- | --- | --- |
| 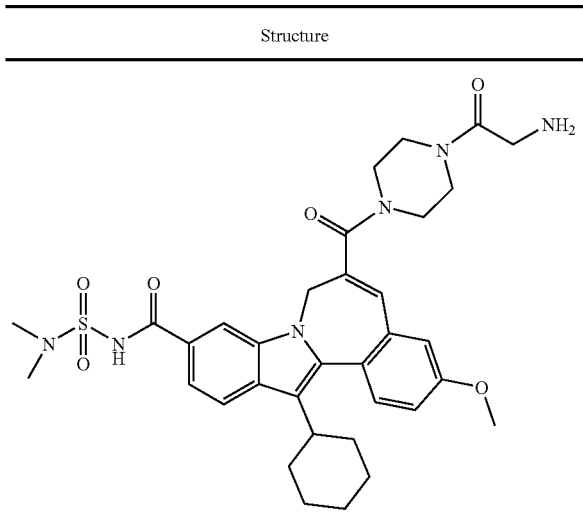 | F | |
| 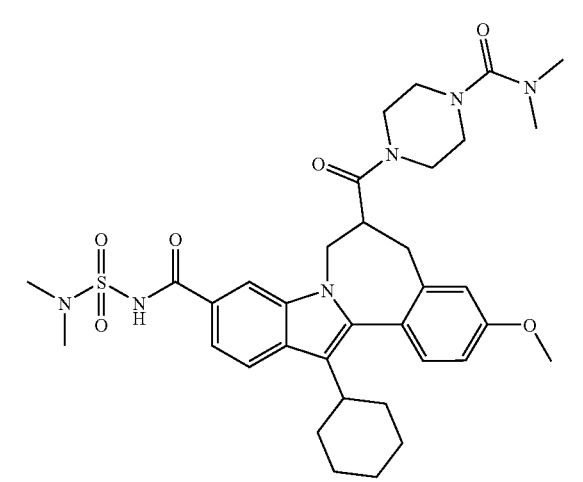 | B | |
| 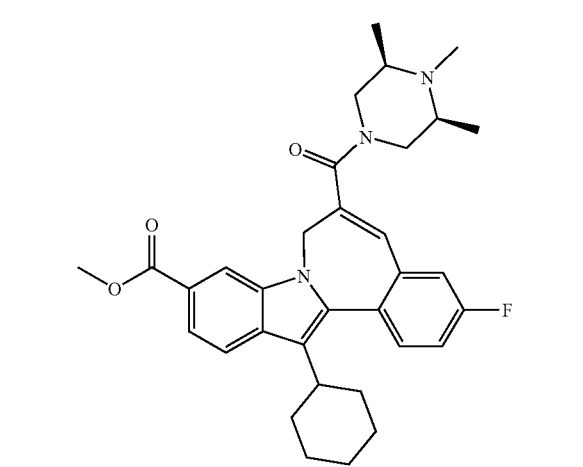 | B | |

TABLE 1a-continued
| Structure | IC$_{50}$* | EC$_{50}$* |
|---|---|---|
| 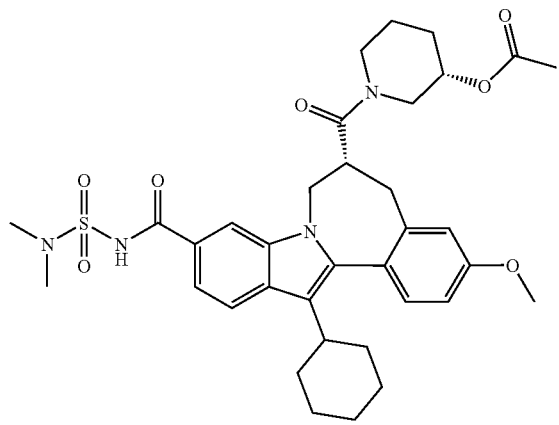 | B | |
| 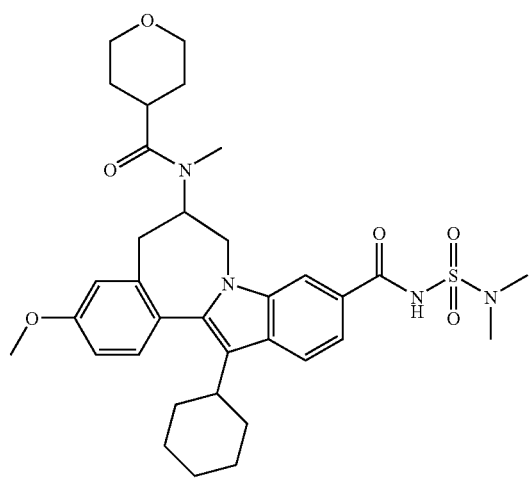 | B | |
| 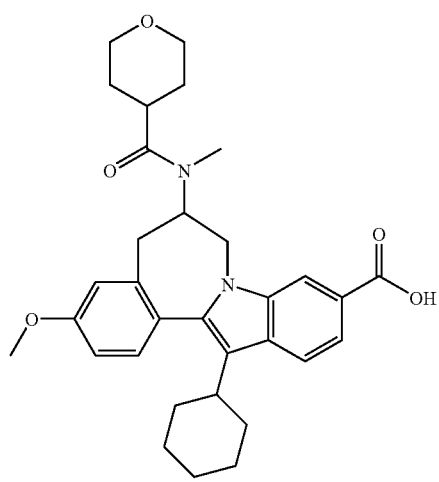 | F | |

TABLE 1a-continued

| Structure | IC$_{50}$* | EC$_{50}$* |
|---|---|---|
| | | B |
| | | B |
| | | B |

TABLE 1a-continued

| Structure | IC$_{50}$* | EC$_{50}$* |
|---|---|---|
| | | B |
| | | B |
| | | B |

TABLE 1a-continued

| Structure | IC₅₀* | EC₅₀* |
|---|---|---|
| | | B |
| | | B |
| | | B |

TABLE 1a-continued

| Structure | IC$_{50}$* | EC$_{50}$* |
|---|---|---|

TABLE 1a-continued

| Structure | IC$_{50}$* | EC$_{50}$* |
|---|---|---|

TABLE 1a-continued
| Structure | IC$_{50}$* | EC$_{50}$* |
|---|---|---|
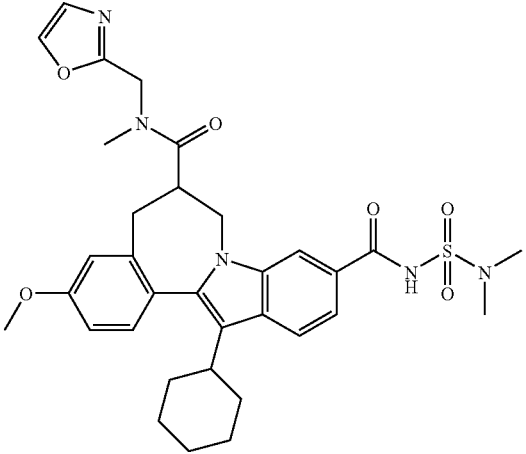
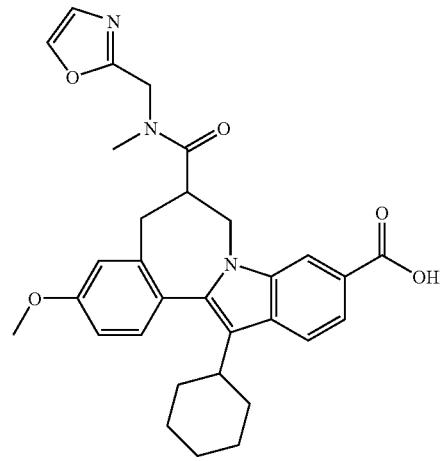
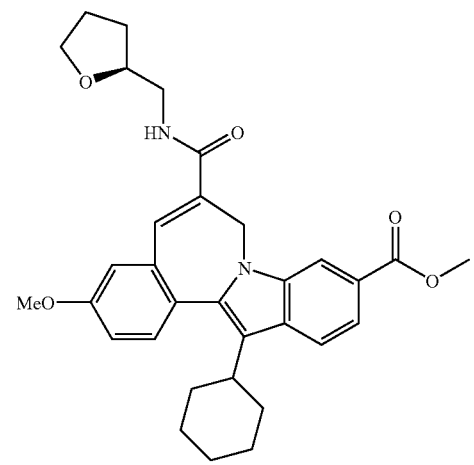

TABLE 1a-continued

| Structure | IC$_{50}$* | EC$_{50}$* |
|---|---|---|

TABLE 1a-continued

| Structure | IC₅₀* | EC₅₀* |
|---|---|---|
| 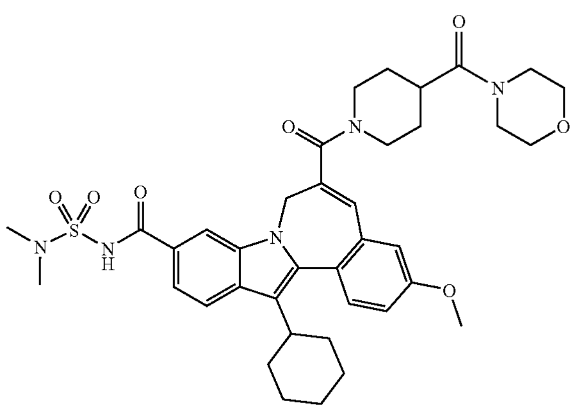 | B | E |
| 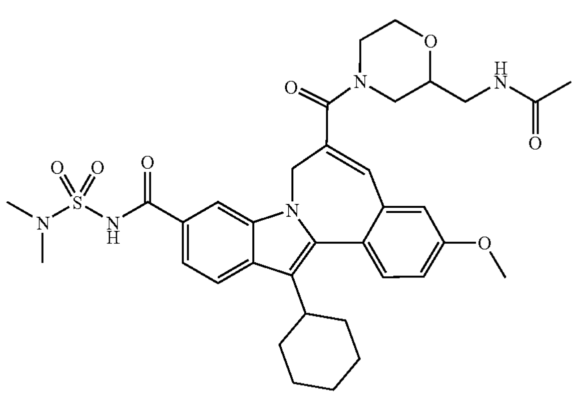 | F | E |

TABLE 1a-continued

| Structure | IC$_{50}$* | EC$_{50}$* |
| --- | --- | --- |
| (structure) | B | E |
| (structure) | B | E |
| (structure) | B | E |

TABLE 1a-continued
| Structure | IC$_{50}$* | EC$_{50}$* |
|---|---|---|
| Chiral 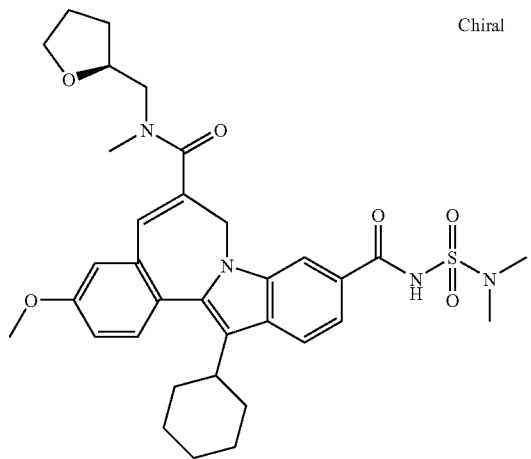 | B | E |
| Chiral 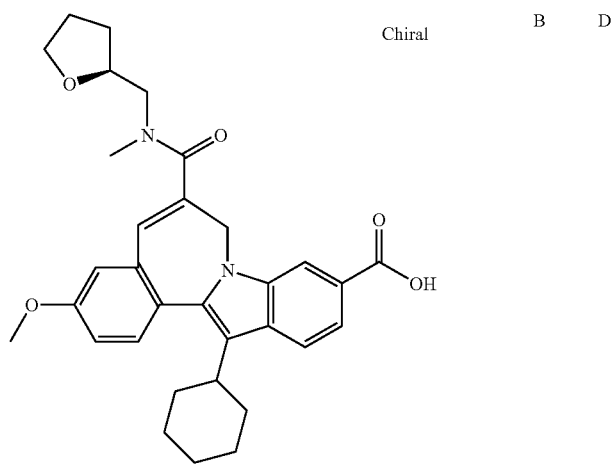 | B | D |
| 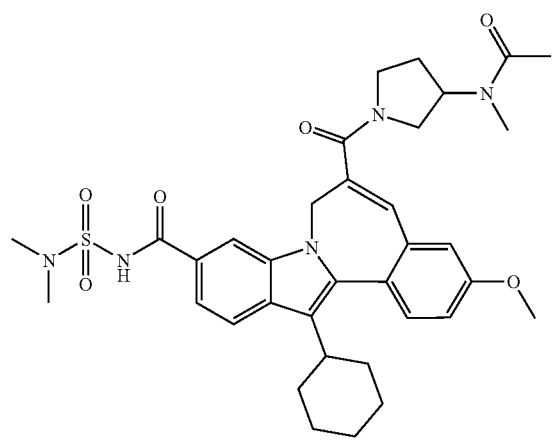 | | |

TABLE 1a-continued
| Structure | IC$_{50}$* | EC$_{50}$* |
|---|---|---|
| 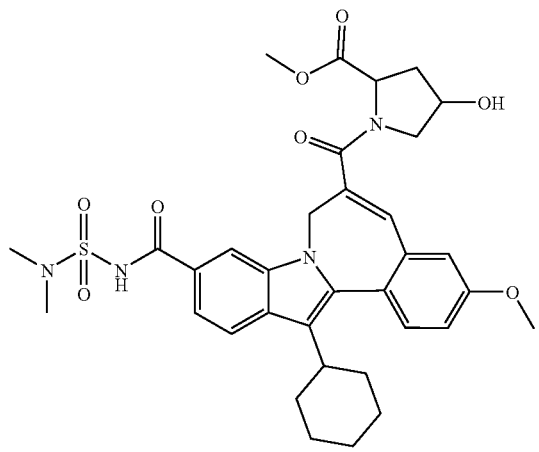 | | |
| 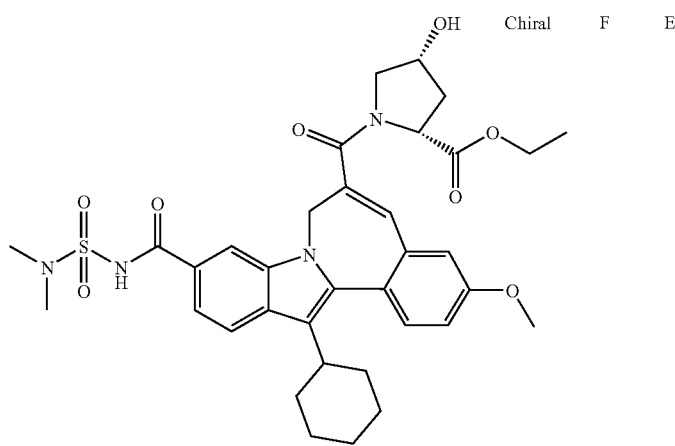 Chiral | F | E |
| 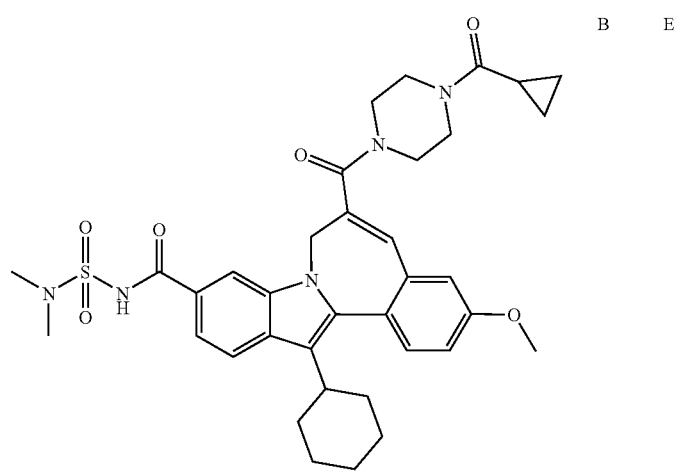 | B | E |

TABLE 1a-continued
| Structure | IC$_{50}$* | EC$_{50}$* |
|---|---|---|
| 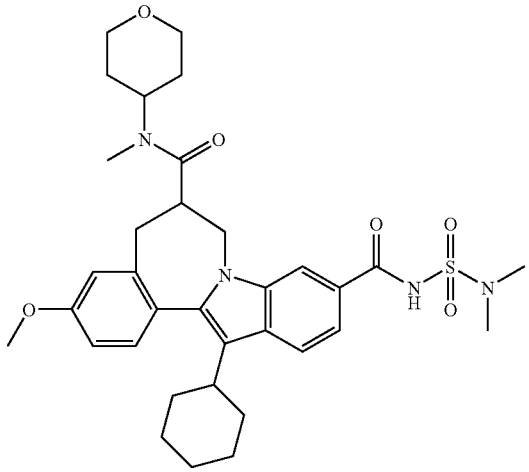 | B | E |
| 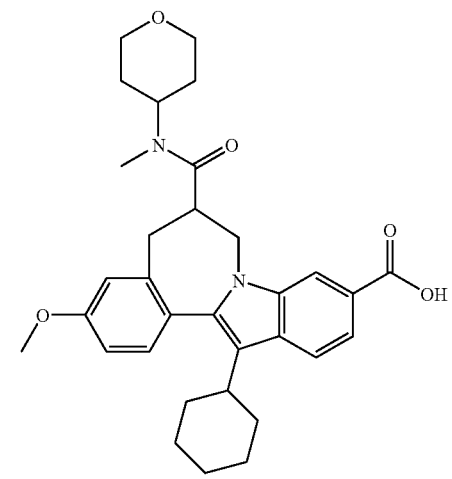 | F | E |
| 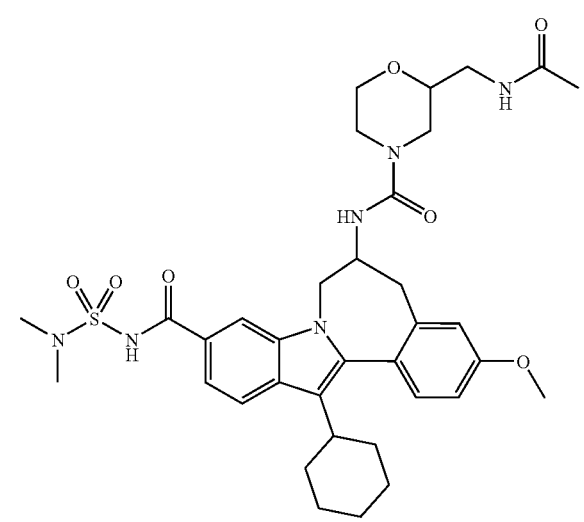 | F | E |

TABLE 1a-continued
| Structure | IC$_{50}$* | EC$_{50}$* |
|---|---|---|
| 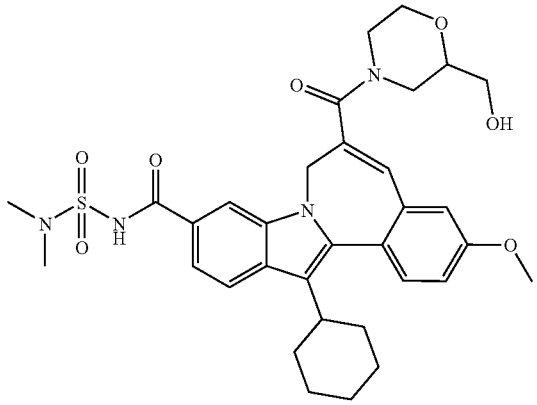 | B | E |
| 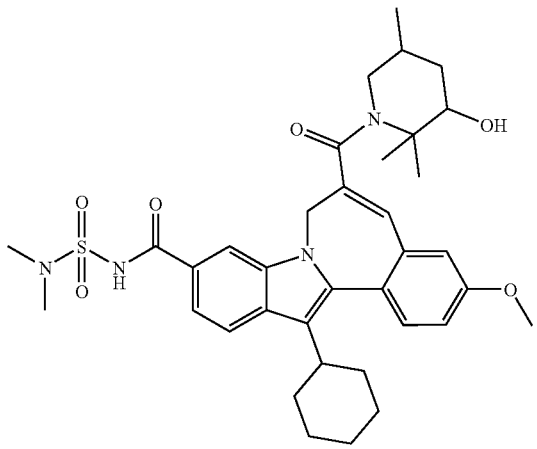 | F | E |
| 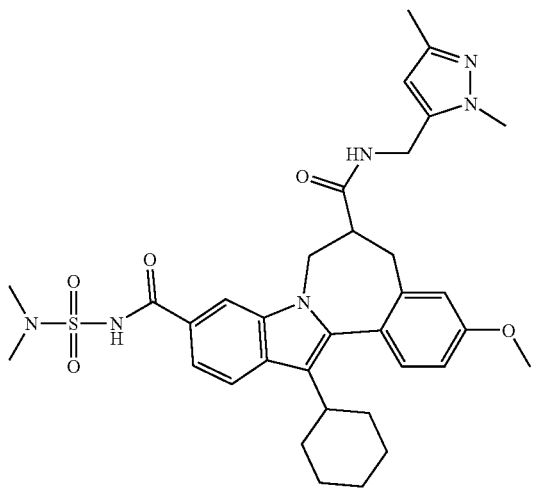 | B | E |

TABLE 1a-continued

| Structure | IC$_{50}$* | EC$_{50}$* |
|---|---|---|
| | B | E |
| 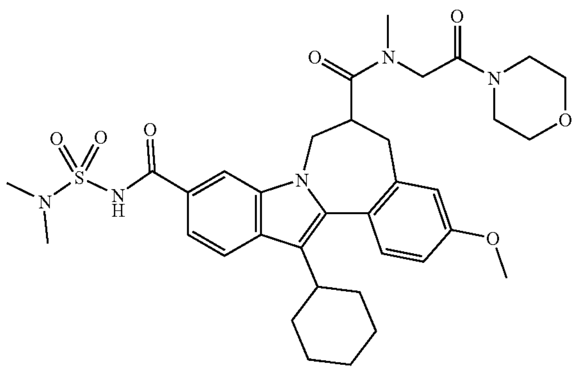 | F | E |
| | B | E |

TABLE 1a-continued
| Structure | IC$_{50}$* | EC$_{50}$* |
|---|---|---|
| 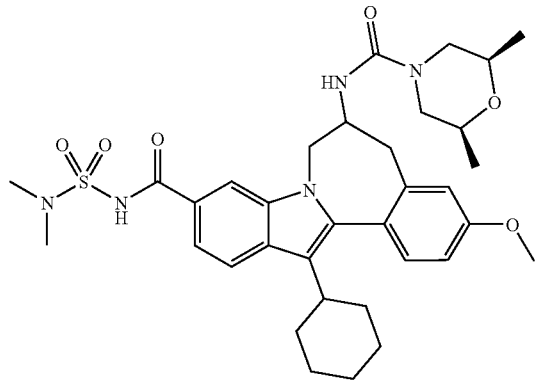 | B | E |
| 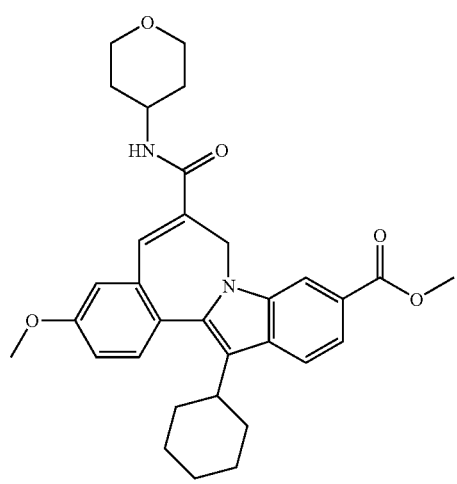 | B | E |
| 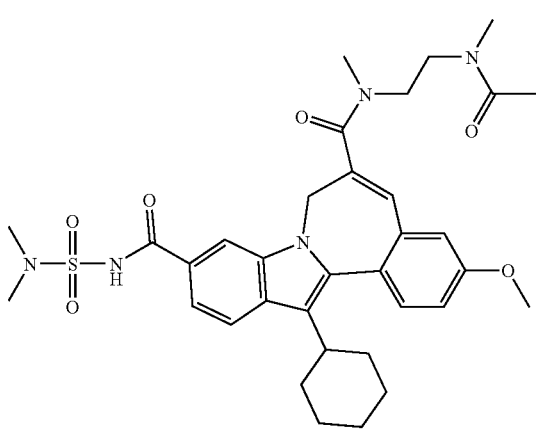 | B | E |

TABLE 1a-continued
| Structure | IC$_{50}$* | EC$_{50}$* |
|---|---|---|
| 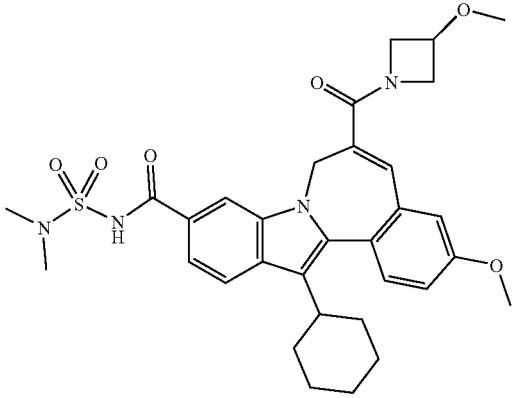 | F | E |
| 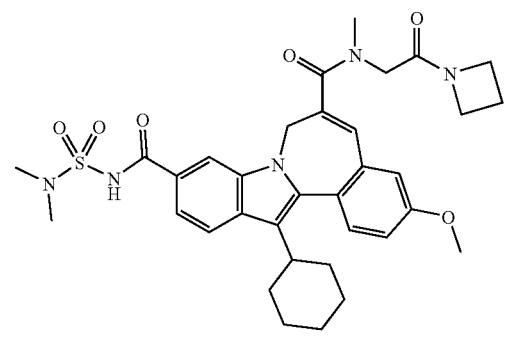 | B | E |
| 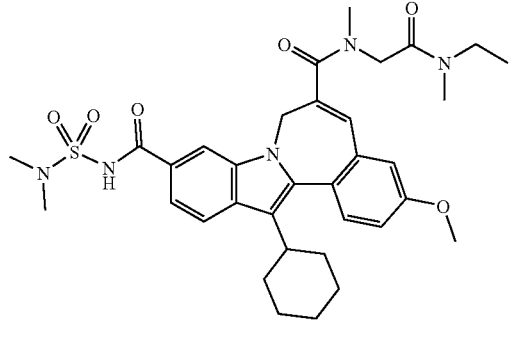 | B | E |
| 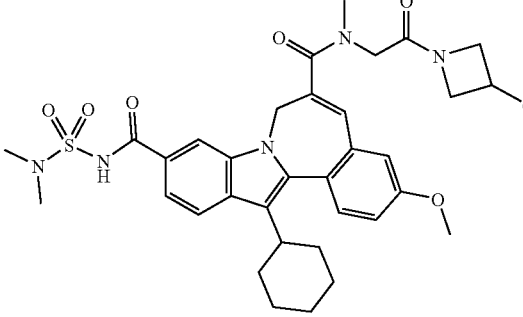 | B | E |

TABLE 1a-continued

| Structure | IC$_{50}$* | EC$_{50}$* |
|---|---|---|
| | B | E |
| | B | E |
| | B | E |

TABLE 1a-continued
| Structure | IC$_{50}$* | EC$_{50}$* |
|---|---|---|
| 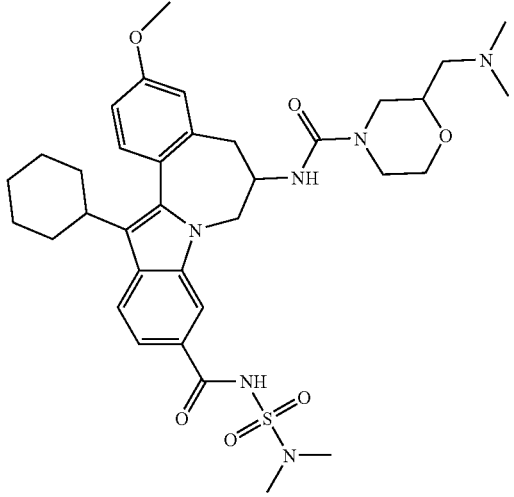 | B | E |
| 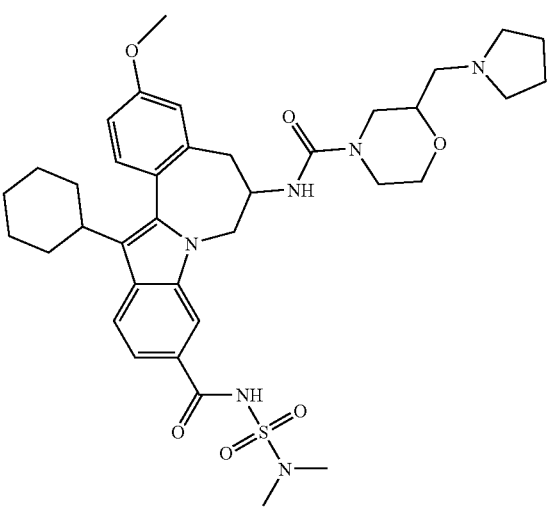 | B | E |
| 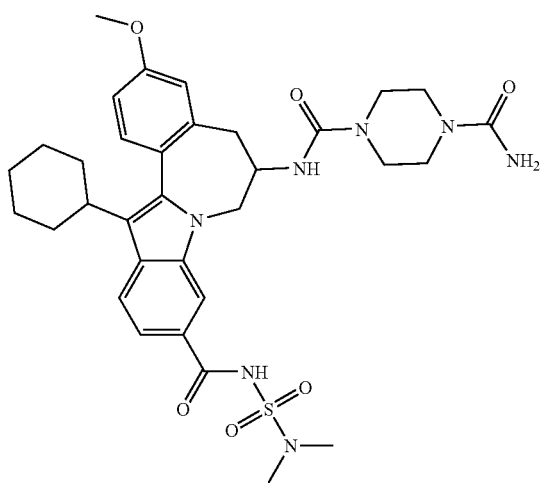 | B | E |

TABLE 1a-continued

| Structure | IC$_{50}$* | EC$_{50}$* |
|---|---|---|
| | B | E |
| | B | E |
| | B | E |

TABLE 1a-continued

| Structure | IC$_{50}$* | EC$_{50}$* |
|---|---|---|
| | B | E |
| | B | E |
| | B | E |

TABLE 1a-continued

| Structure | IC$_{50}$* | EC$_{50}$* |
|---|---|---|
| | B | E |
| | B | E |
| | B | E |

TABLE 1a-continued
| Structure | IC$_{50}$* | EC$_{50}$* |
|---|---|---|
| 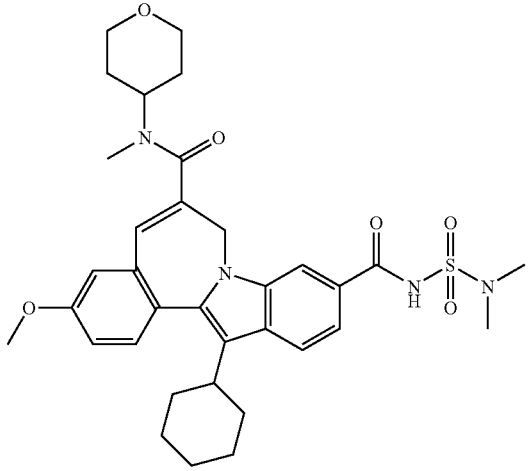 | B | G |
| 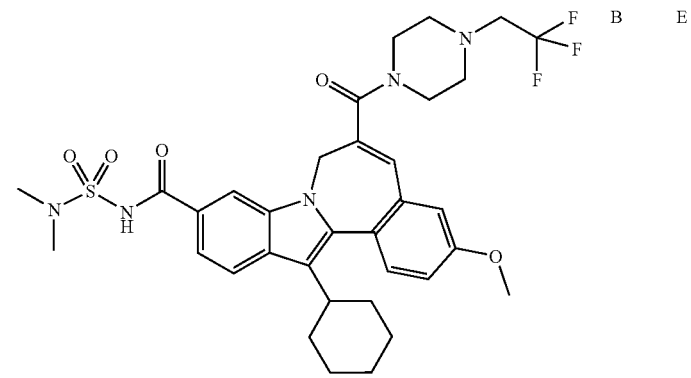 | B | E |
| 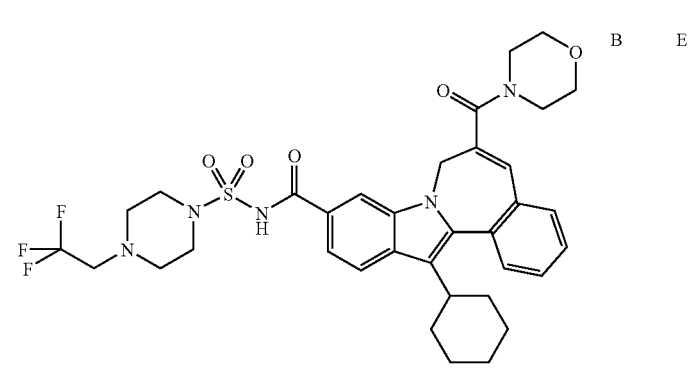 | B | E |

TABLE 1a-continued
| Structure | IC$_{50}$* | EC$_{50}$* |
|---|---|---|
| 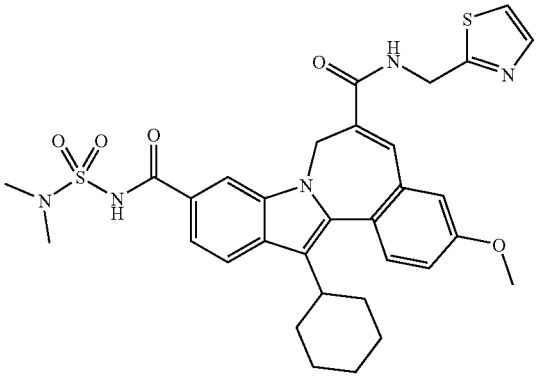 | B | E |
A > 1 µM;
B 0.01 µM-1 µM;
C > 10 µM;
D > 1 µM-10 µM;
E 1.0 µM-0.03 µM;
F < 0.02 µM;
G > 0.12 µM
IC$_{50}$ values were determined using the preincubation protocol.
EC$_{50}$ values were determined using the FRET assay.
Data for some additional Formula I, II, III, and IV compounds are shown in Table 1b below.
TABLE 1b
| Structure | IC$_{50}$* | EC$_{50}$* |
|---|---|---|
| 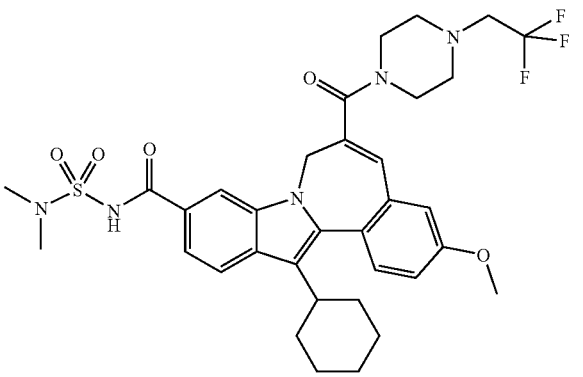 | B | E |

TABLE 1b-continued
| Structure | IC$_{50}$* | EC$_{50}$* |
|---|---|---|
| 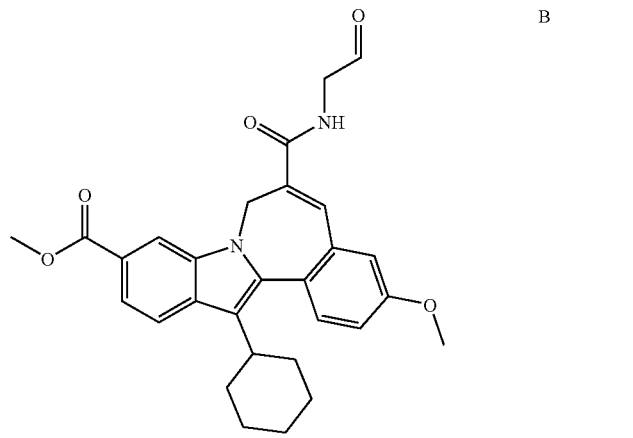 | B | |
| 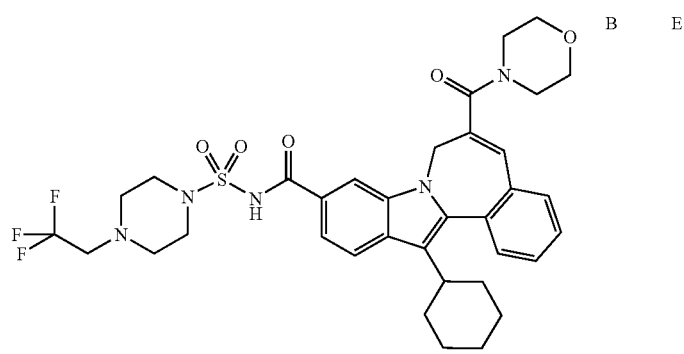 | B | E |
| 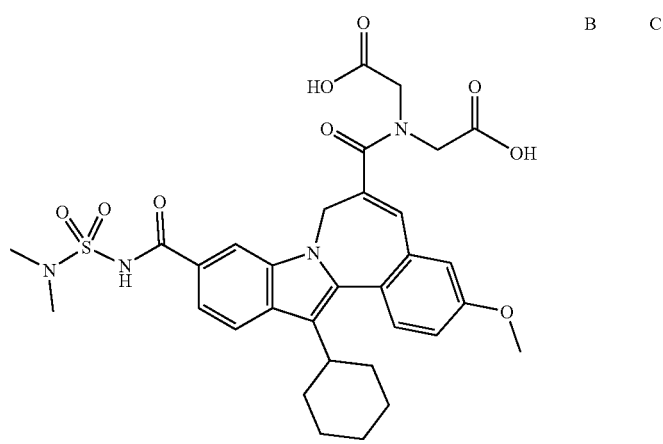 | B | C |

TABLE 1b-continued
| Structure | IC$_{50}$* | EC$_{50}$* |
|---|---|---|
| 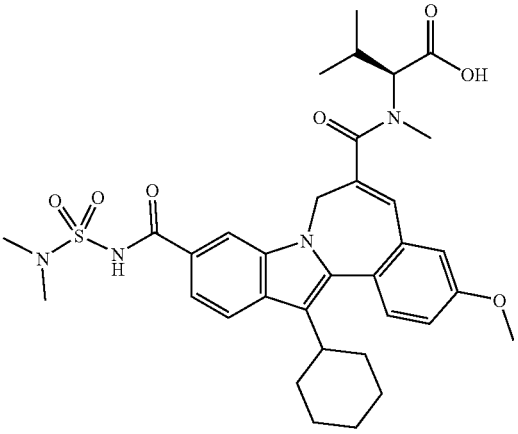 | F | E |
| 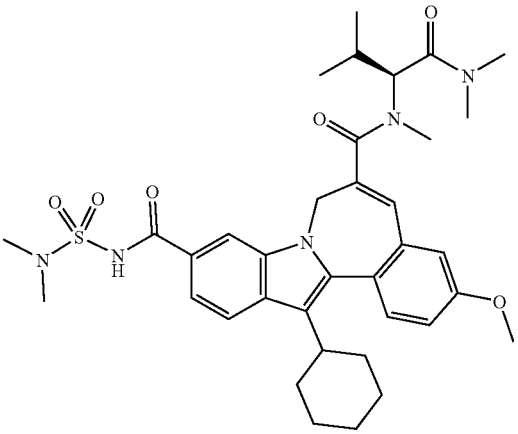 | F | E |
| 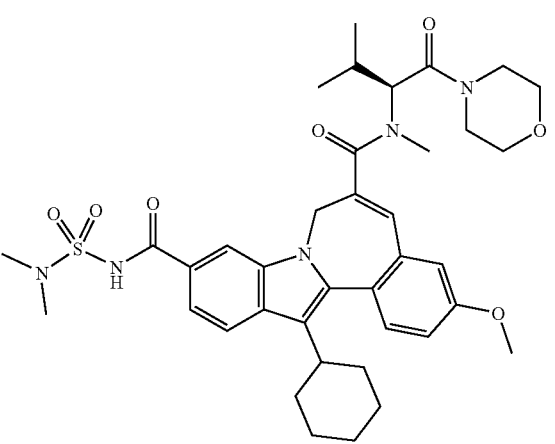 | B | E |

TABLE 1b-continued
| Structure | IC$_{50}$* | EC$_{50}$* |
|---|---|---|
| 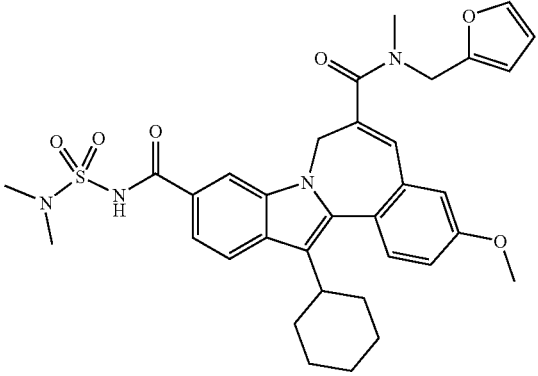 | F | E |
| 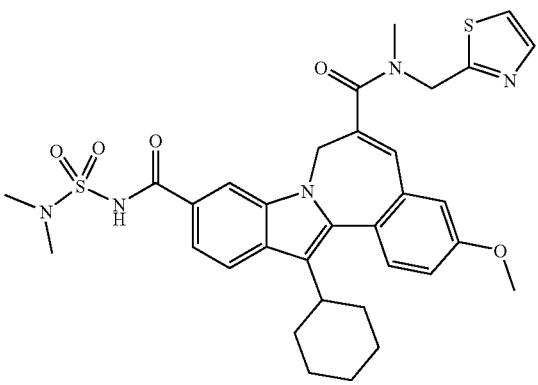 | F | E |
| 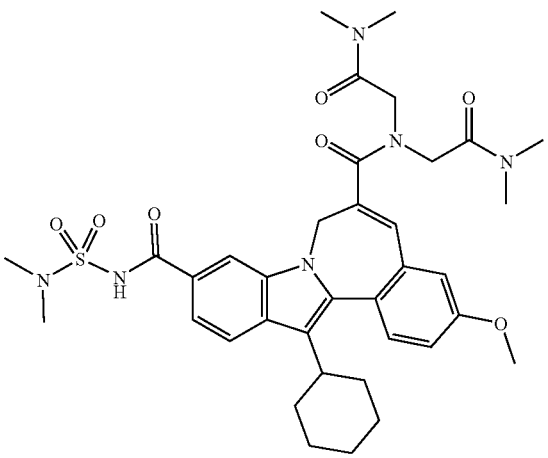 | F | E |

TABLE 1b-continued

| Structure | IC$_{50}$* | EC$_{50}$* |
|---|---|---|
| (Chiral) | B | E |
| (Chiral) | F | |
| (Chiral) | F | |
| (Chiral) | F | |

TABLE 1b-continued
| Structure | IC$_{50}$* | EC$_{50}$* |
|---|---|---|
| 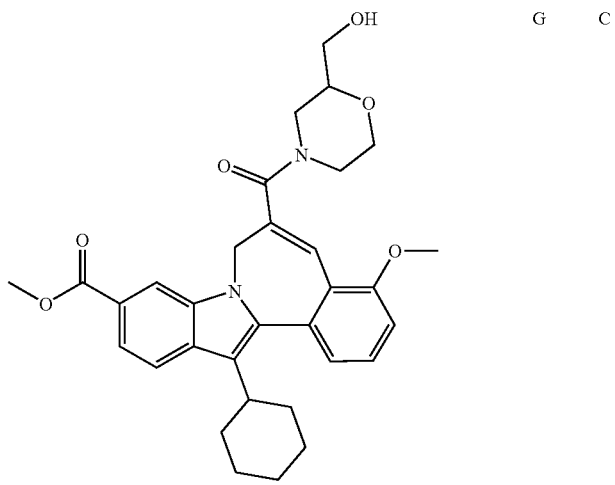 | G | C |
| 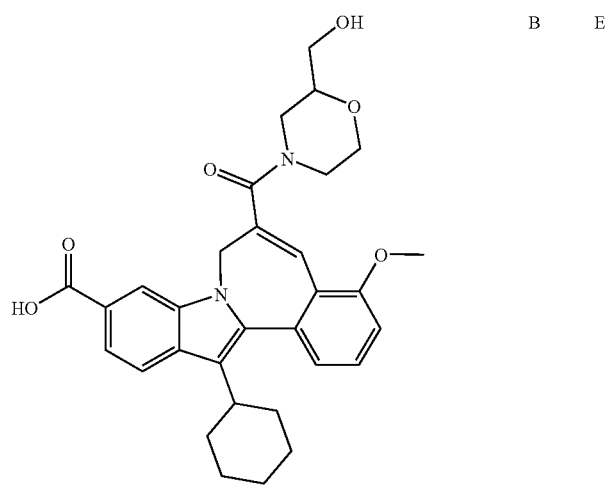 | B | E |
| 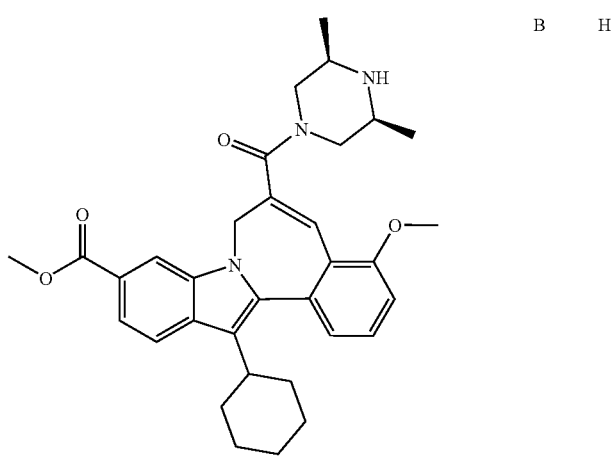 | B | H |

TABLE 1b-continued
| Structure | IC$_{50}$* | EC$_{50}$* |
|---|---|---|
| 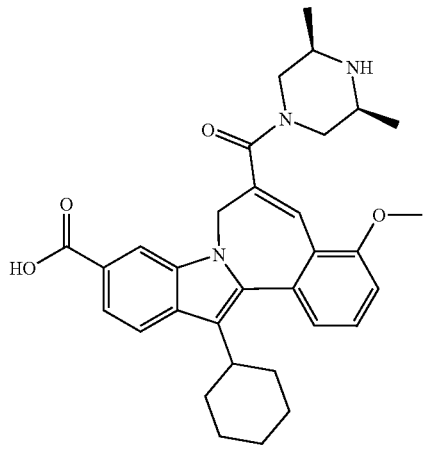 | B | E |
| 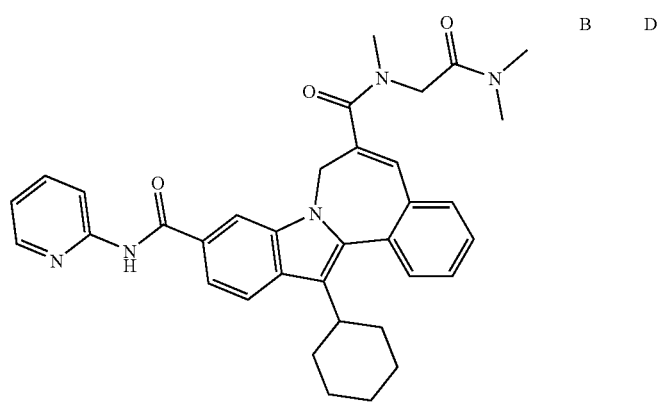 | B | D |
| 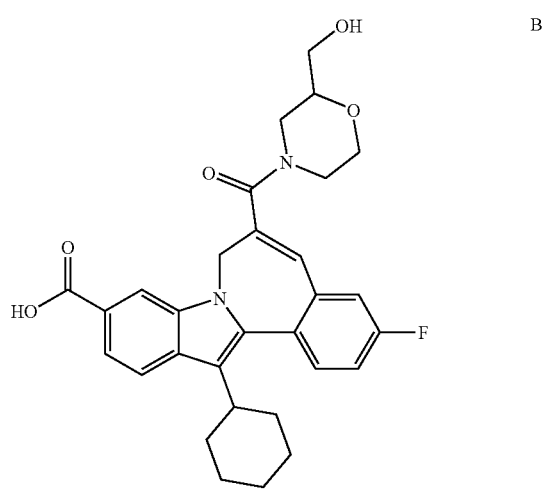 | B | |

TABLE 1b-continued
| Structure | IC$_{50}$* | EC$_{50}$* |
|---|---|---|
| 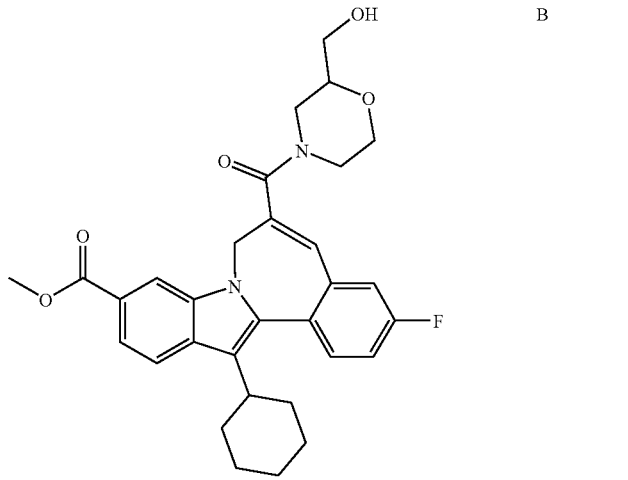 | B | |
| 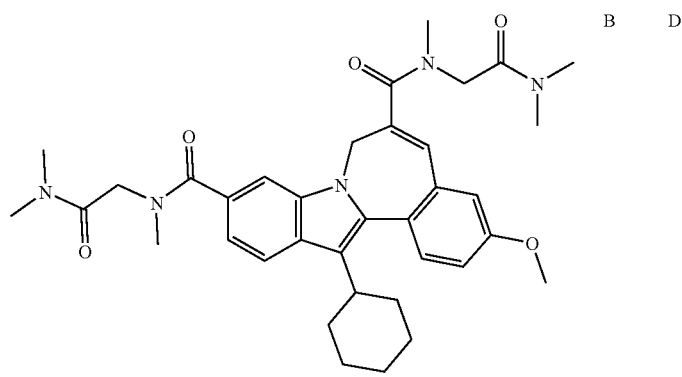 | B | D |
| 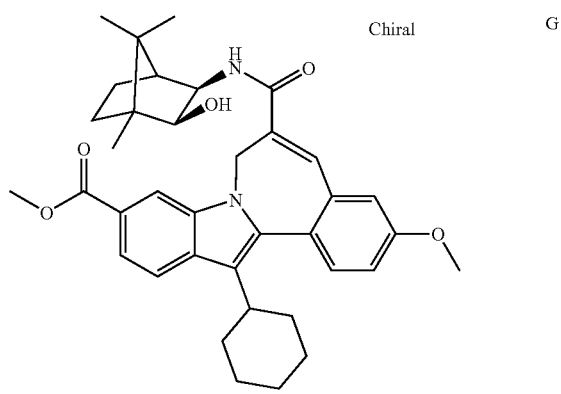 Chiral | G | |

TABLE 1b-continued
| Structure | IC$_{50}$* | EC$_{50}$* |
|---|---|---|
| 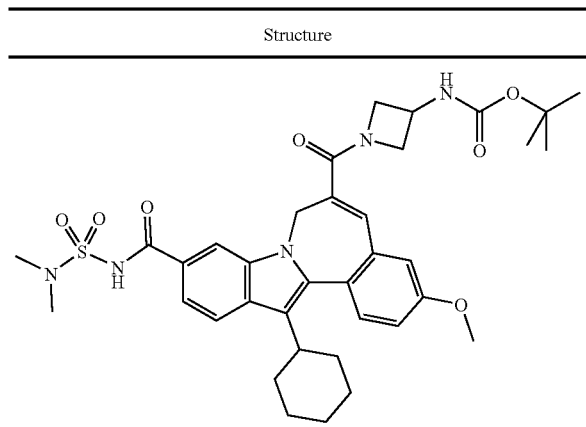 | B | E |
| 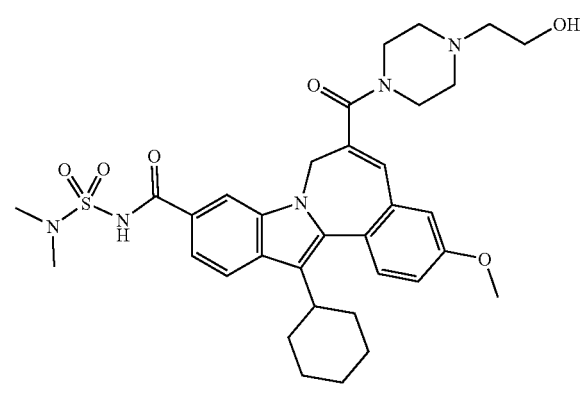 | B | E |
| 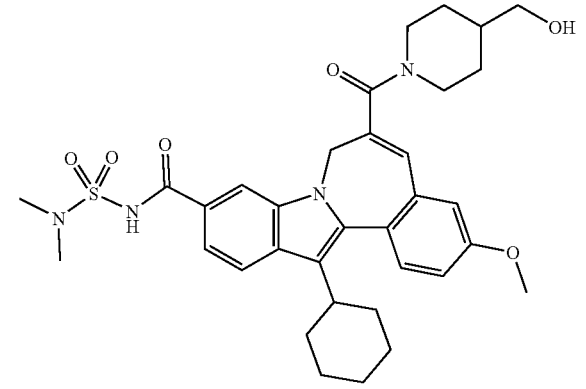 | B | E |
| 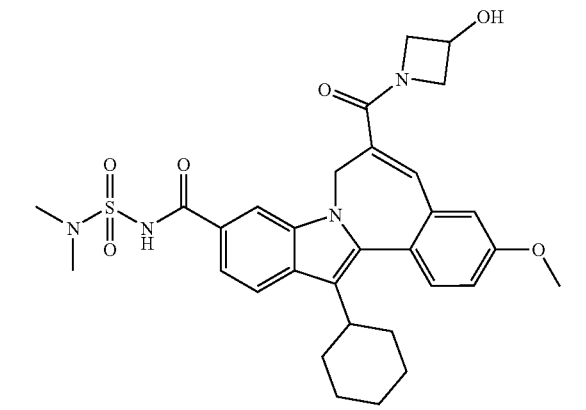 | B | E |

TABLE 1b-continued

| Structure | IC$_{50}$* | EC$_{50}$* |
|---|---|---|
| | B | D |
| | B | E |
| | B | E |
| | B | E |

TABLE 1b-continued

| Structure | IC$_{50}$* | EC$_{50}$* |
|---|---|---|
| | B | E |
| | B | E |
| | B | E |

TABLE 1b-continued

| Structure | IC$_{50}$* | EC$_{50}$* |
|---|---|---|
| (Chiral structure) | B | E |
| (Chiral structure) | B | E |
| (Structure) | B | R |

TABLE 1b-continued

| Structure | IC$_{50}$* | EC$_{50}$* |
|---|---|---|
| | B | E |
| | B | E |
| | B | E |
| | B | E |

TABLE 1b-continued

| Structure | IC$_{50}$* | EC$_{50}$* |
|---|---|---|
| | B | E |
| | B | C |
| Chiral | B | E |
| | B | E |

TABLE 1b-continued
| Structure | IC$_{50}$* | EC$_{50}$* |
|---|---|---|
| 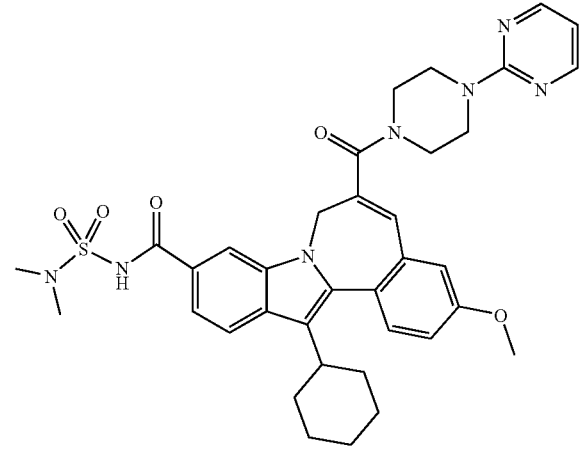 | F | E |
| 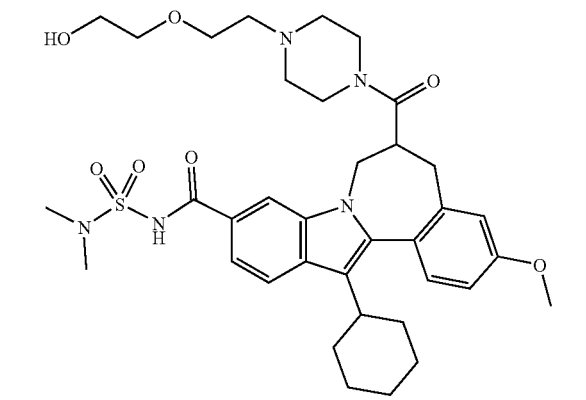 | B | E |
| 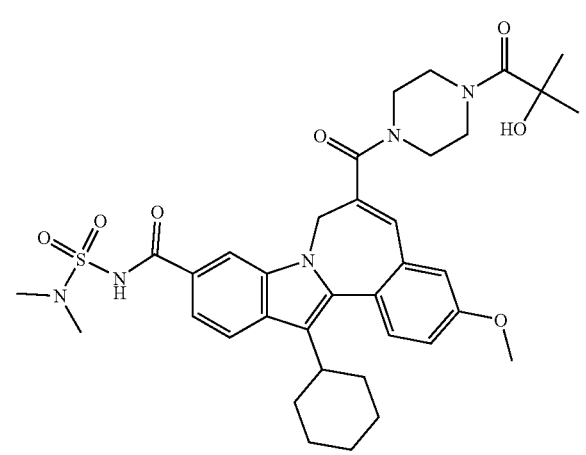 | B | E |

TABLE 1b-continued
| Structure | IC$_{50}$* | EC$_{50}$* |
| --- | --- | --- |
| 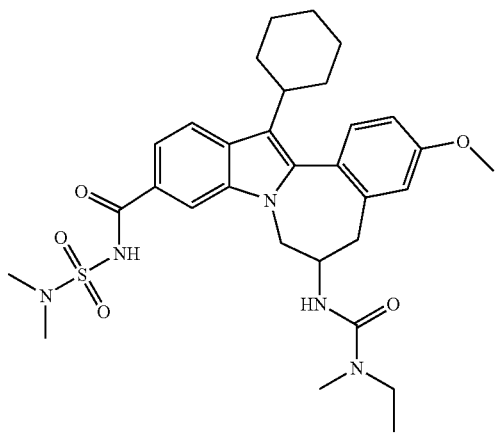 | B | E |
| 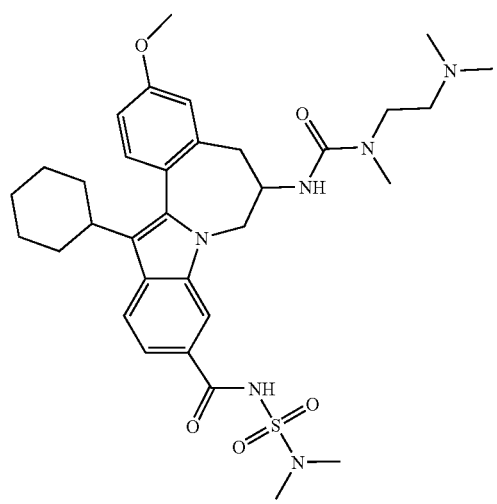 | B | E |
| 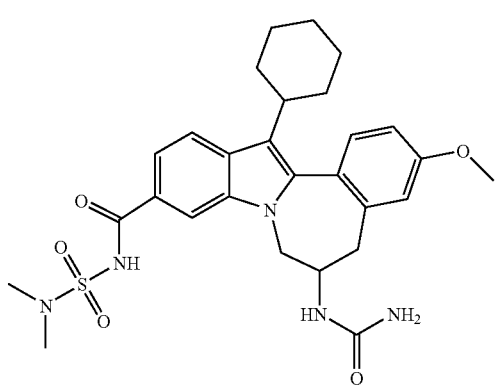 | B | E |

TABLE 1b-continued
| Structure | IC$_{50}$* | EC$_{50}$* |
|---|---|---|
| 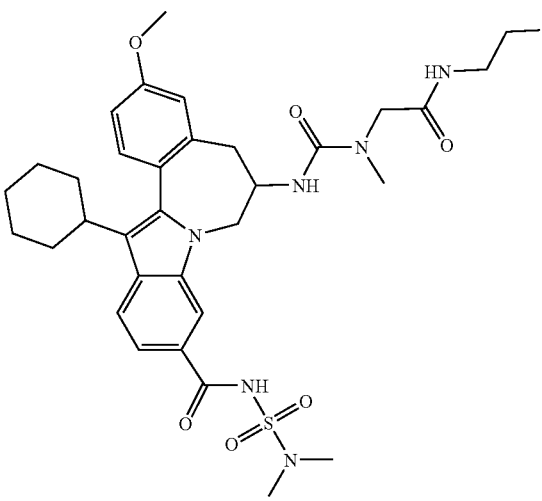 | B | E |
| 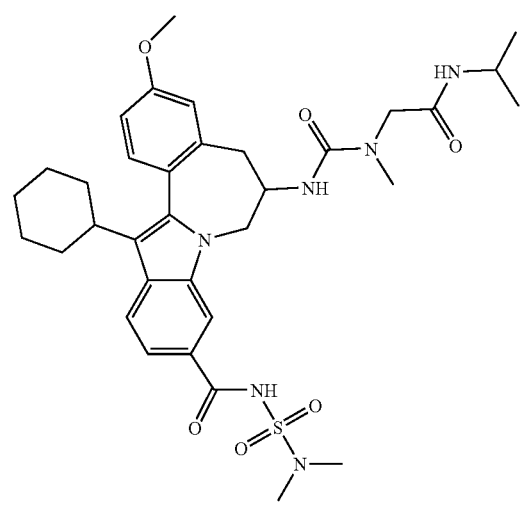 | B | E |
| 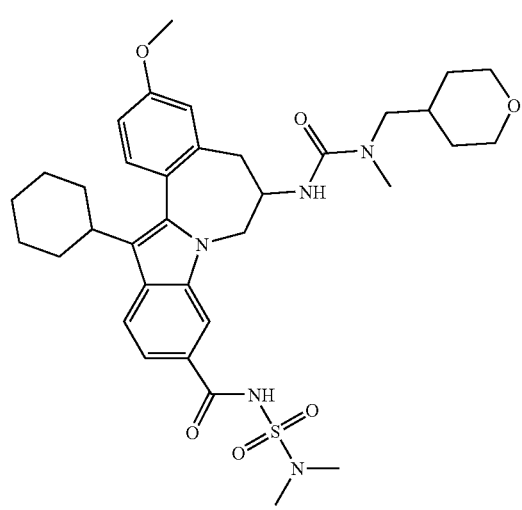 | B | E |

TABLE 1b-continued

| Structure | IC$_{50}$* | EC$_{50}$* |
| --- | --- | --- |
| | B | E |
| | B | E |
| | B | E |

TABLE 1b-continued

| Structure | IC$_{50}$* | EC$_{50}$* |
|---|---|---|
| | B | E |
| | B | E |
| | B | E |

TABLE 1b-continued
| Structure | IC$_{50}$* | EC$_{50}$* |
| --- | --- | --- |
| 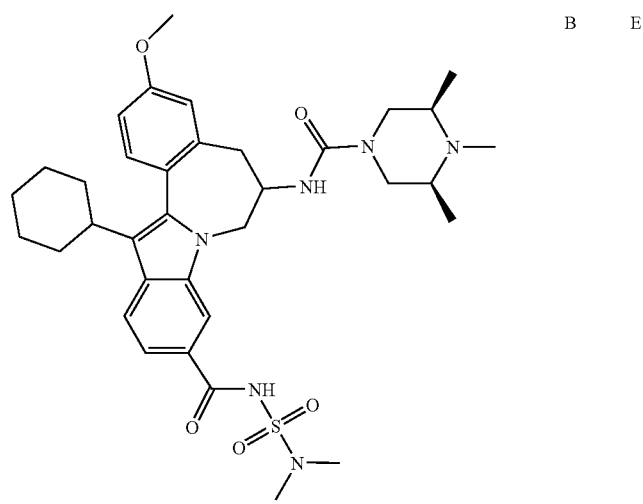 | B | E |
| 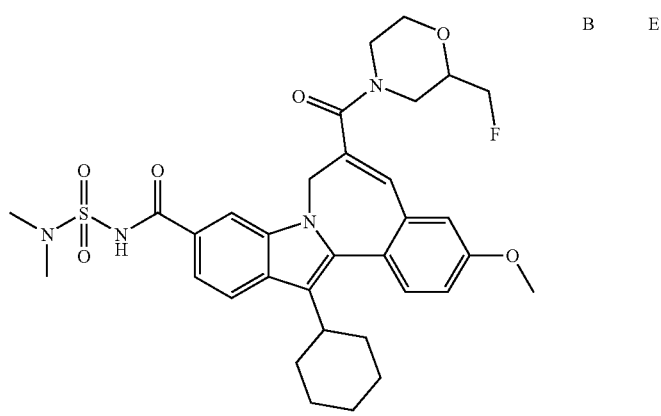 | B | E |
| | B | E |

TABLE 1b-continued
| Structure | IC$_{50}$* | EC$_{50}$* |
|---|---|---|
| 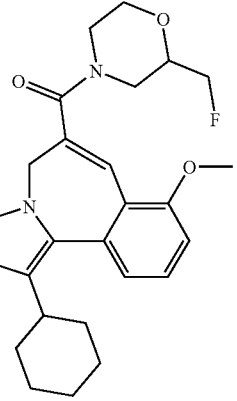 | B | E |
| 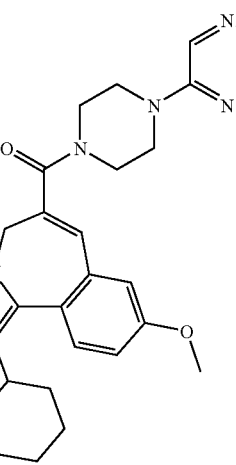 | B | E |
| 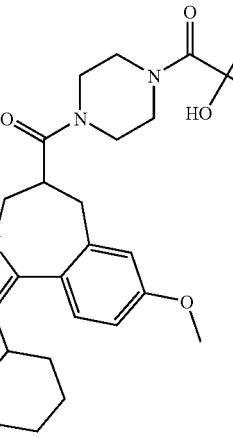 | B | E |

TABLE 1b-continued
| Structure | IC$_{50}$* | EC$_{50}$* |
|---|---|---|
| 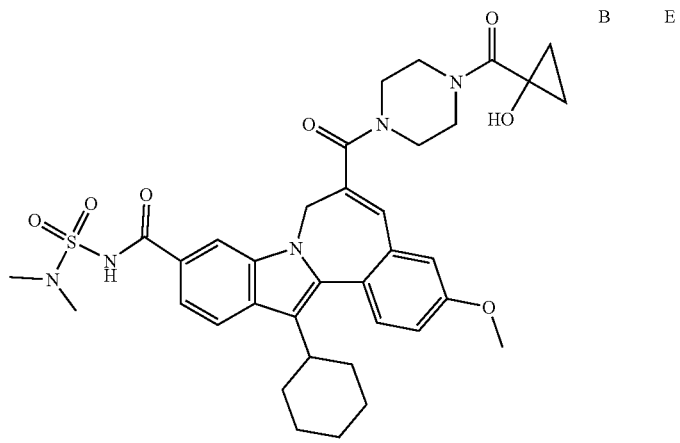 | B | E |
|  | B | E |
| 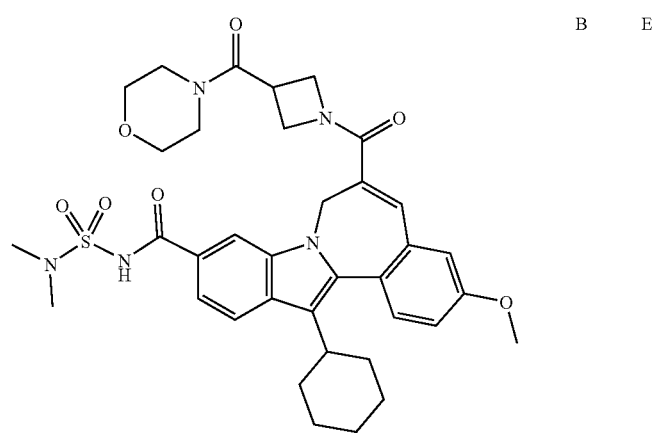 | B | E |

TABLE 1b-continued
| Structure | IC$_{50}$* | EC$_{50}$* |
|---|---|---|
| 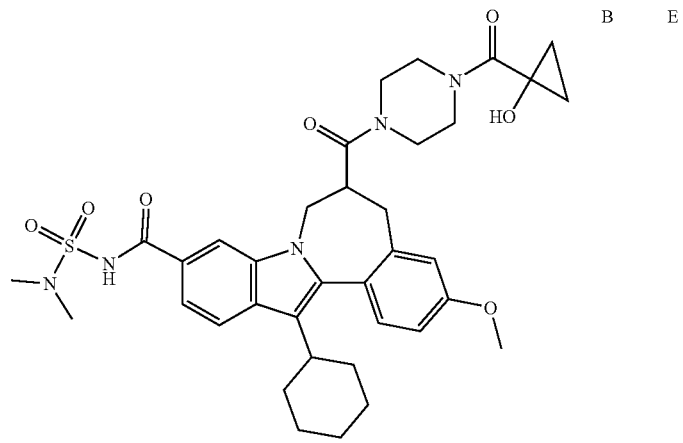 | B | E |
| 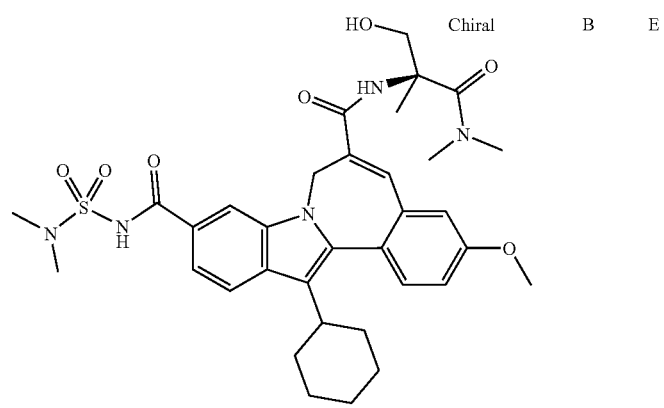 | B | E |
| 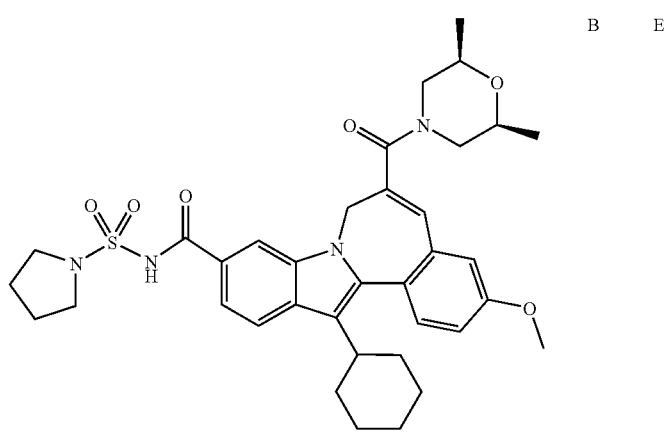 | B | E |

TABLE 1b-continued

| Structure | IC$_{50}$* | EC$_{50}$* |
|---|---|---|
| | B | E |
| | B | E |
| | B | E |
| | B | E |

TABLE 1b-continued

| Structure | IC$_{50}$* | EC$_{50}$* |
|---|---|---|
| (structure) | B | E |
| (structure) | B | E |
| (structure) | B | E |

A > 1 μM;
B 0.02 μM-1 μM;
C > 10 μM;
D > 1 μM-10 μM;
E 1.0 μM-0.03 μM;
F < 0.02 μM;
G > 12.5 μM;
H > 0.37 μM;
IC$_{50}$ values were determined using the preincubation protocol.
EC$_{50}$ values were determined using the FRET assay.

Additionally, compounds disclosed in U.S. patent application Ser. No. 11/181,639, filed Jul. 14, 2005 were shown to have activity in these assays (see Table 2).

TABLE 2

Structure

TABLE 2-continued

Structure (Chiral)

TABLE 2-continued
Structure
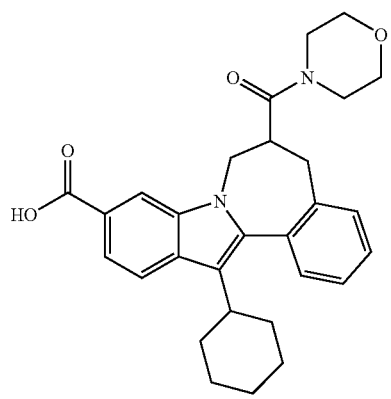
(Chiral)
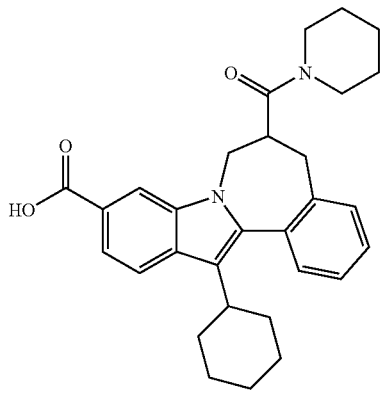
(Chiral)
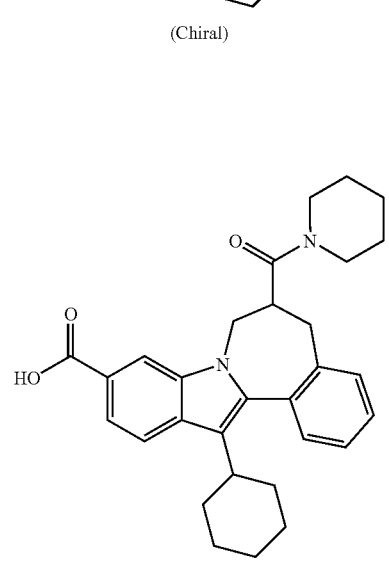
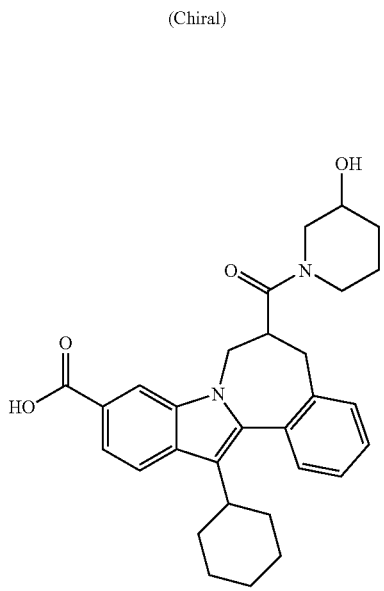
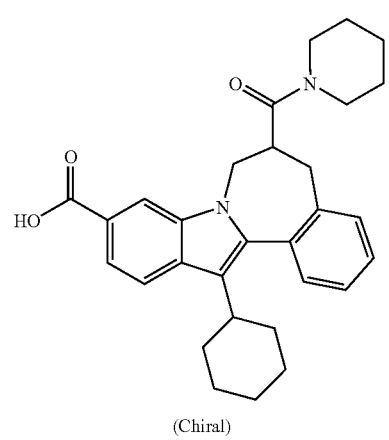
(Chiral)
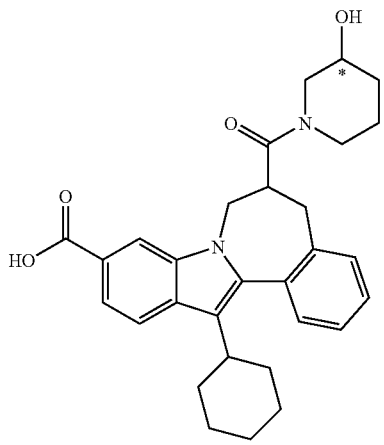
(Chiral*)

TABLE 2-continued
| Structure | Structure |
|---|---|
| 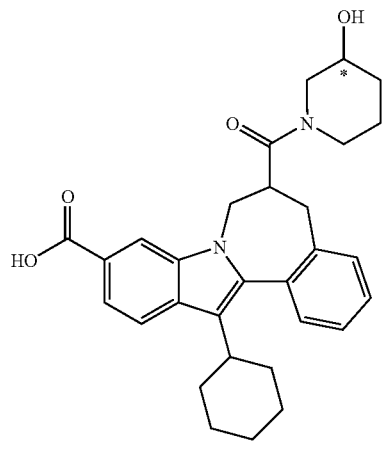 (Chiral*) | 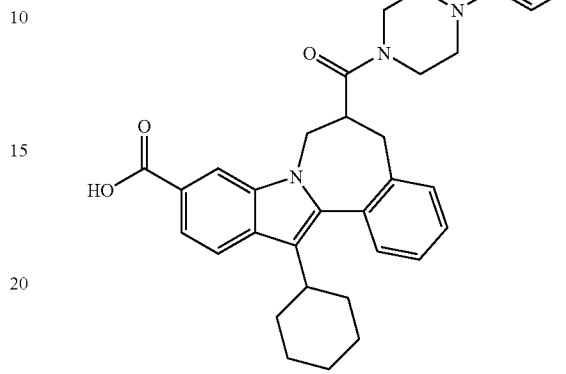 |
| 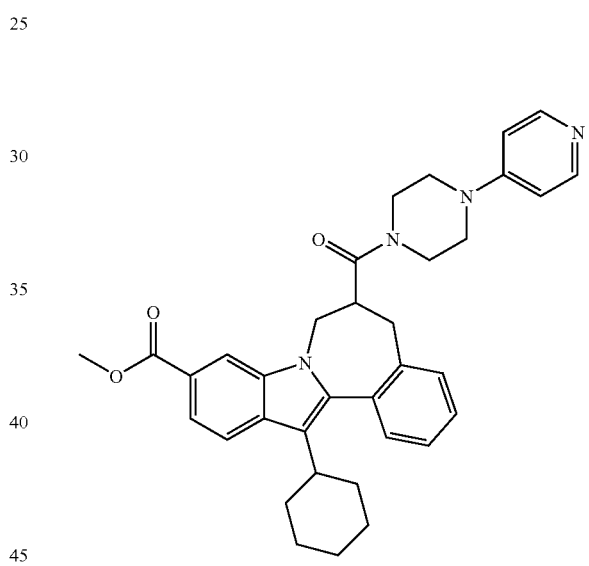 | 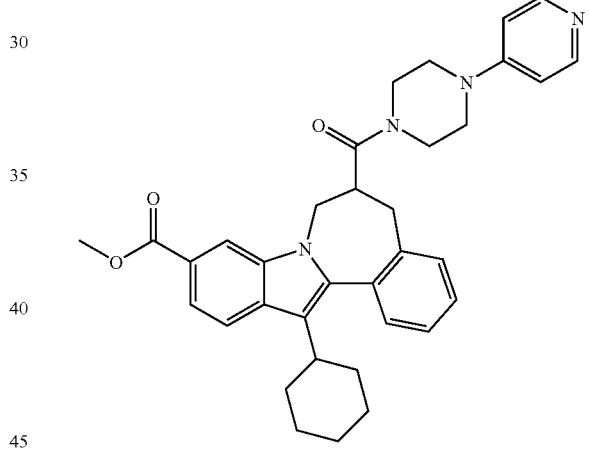 |
| 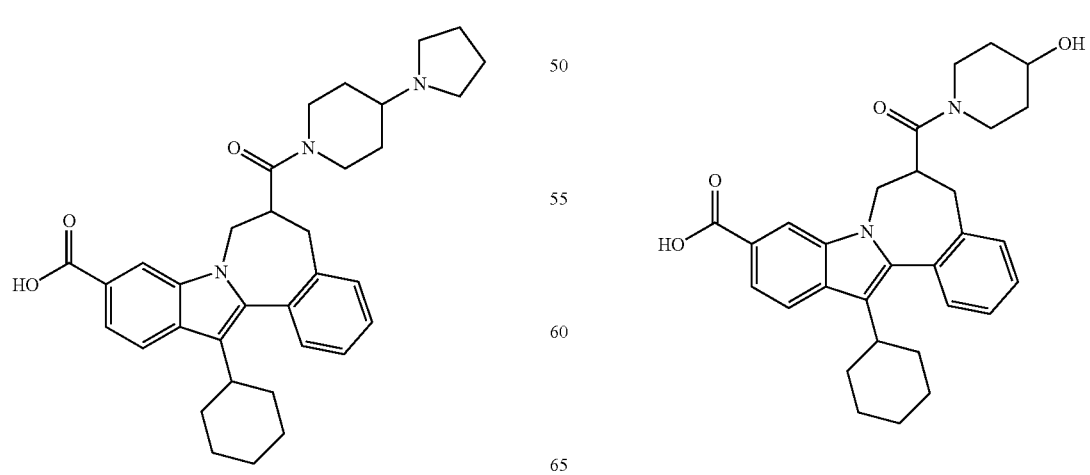 | 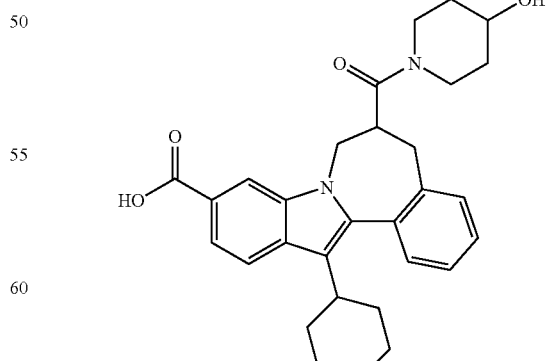 |

TABLE 2-continued
Structure
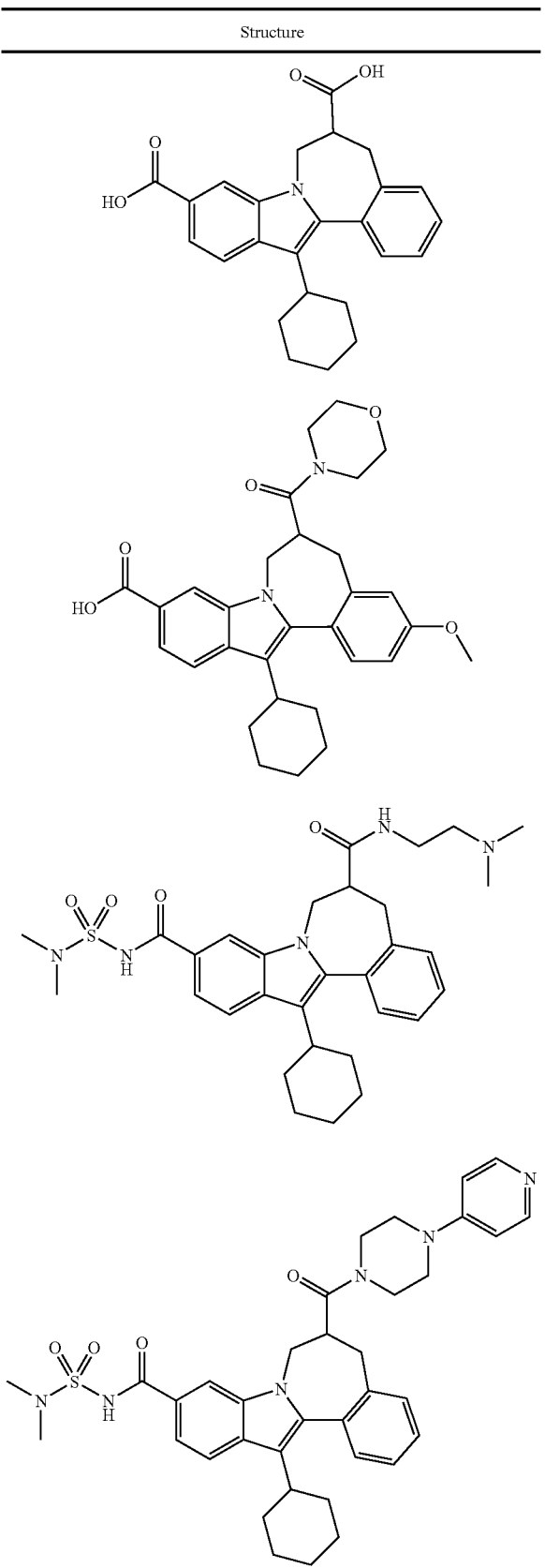
TABLE 2-continued
Structure
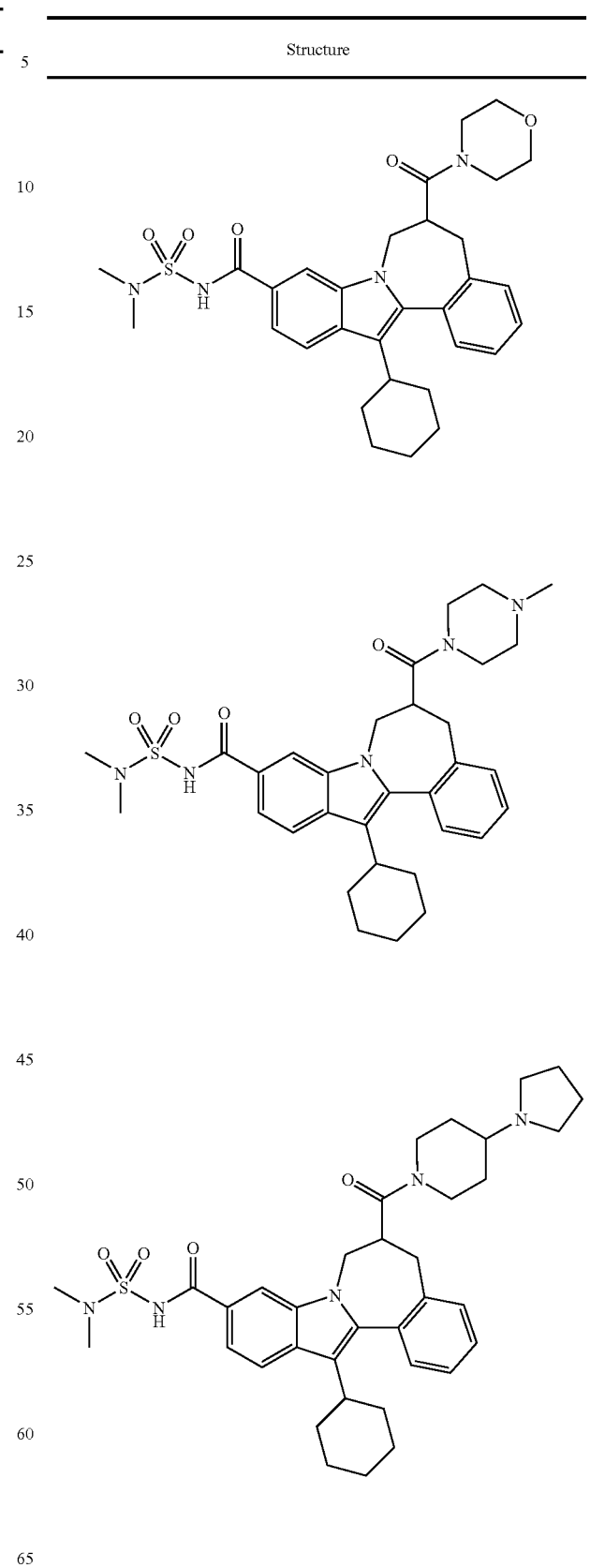

TABLE 2-continued
Structure
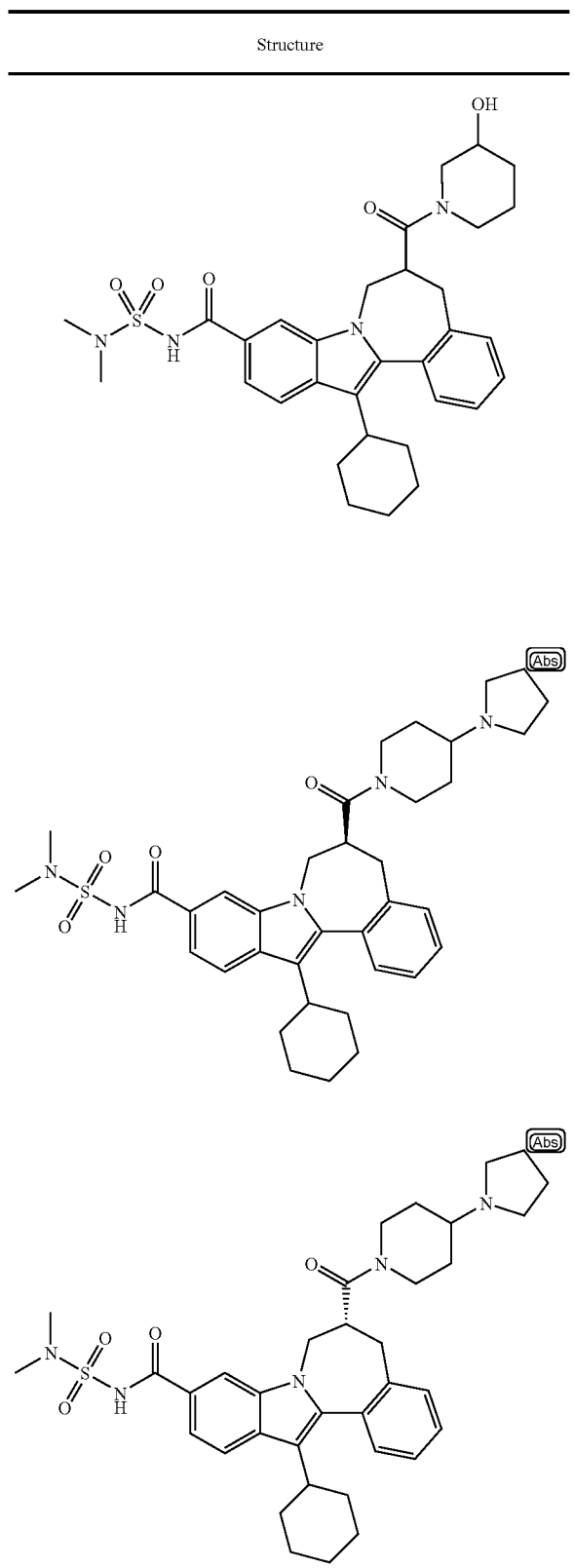
TABLE 2-continued
Structure
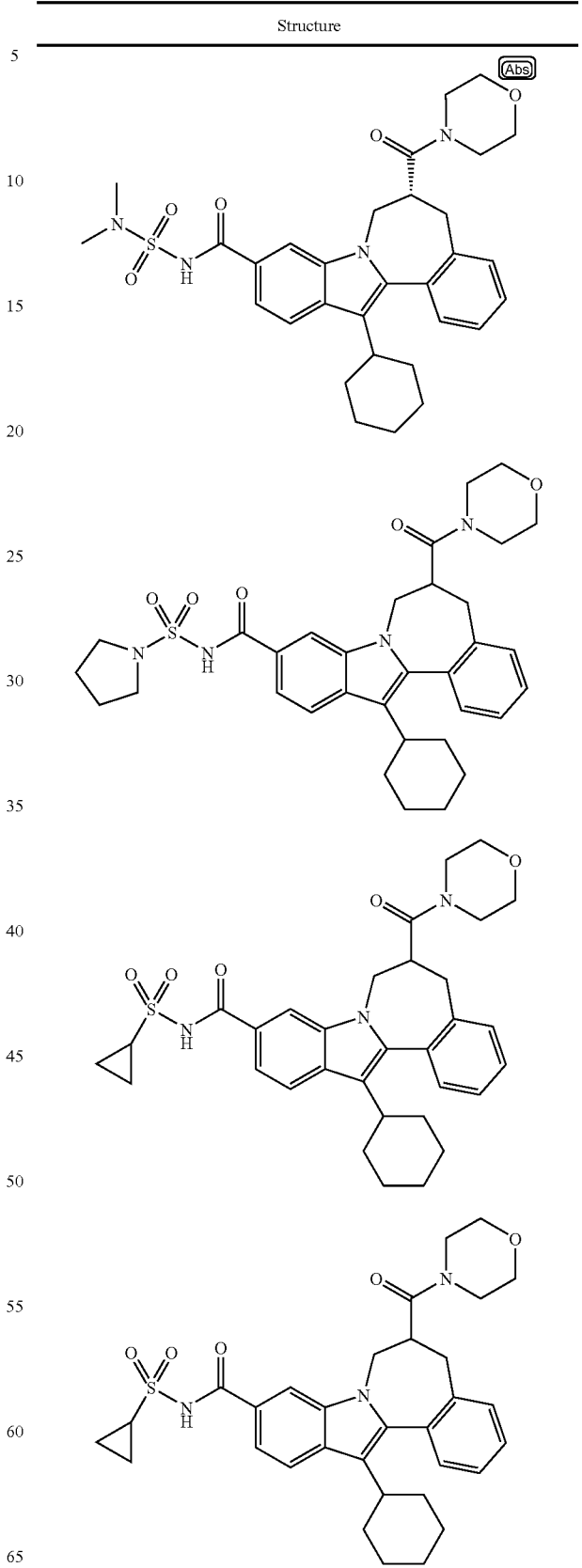

TABLE 2-continued
Structure
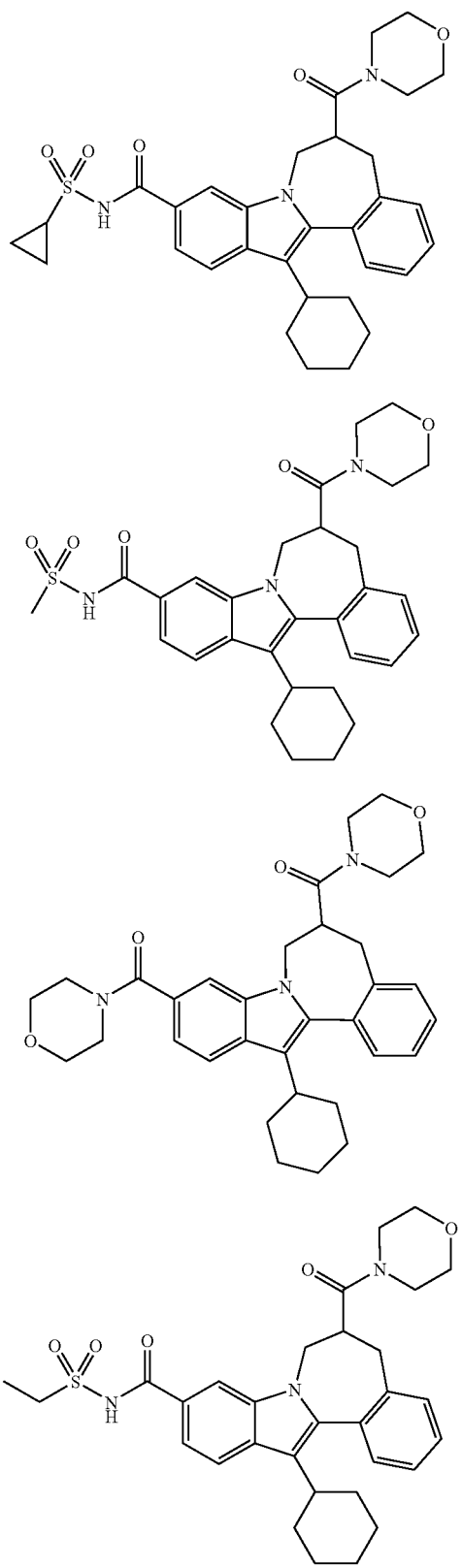
TABLE 2-continued
Structure
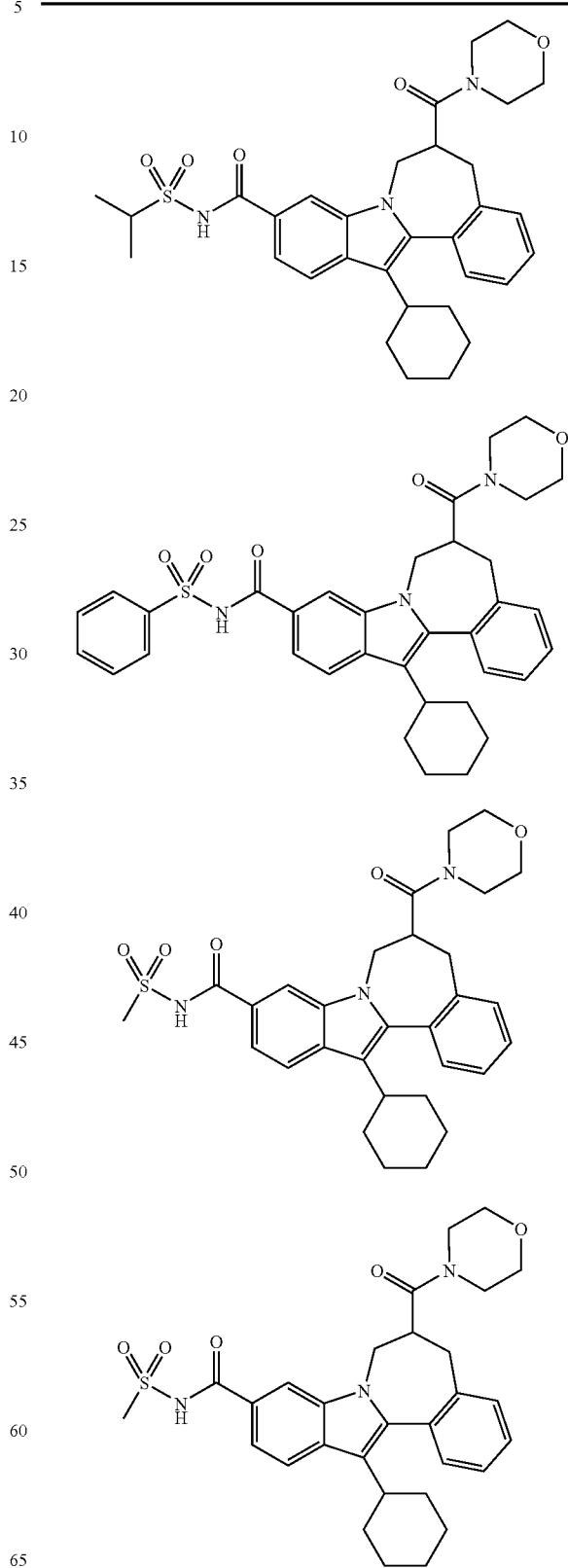

TABLE 2-continued
Structure
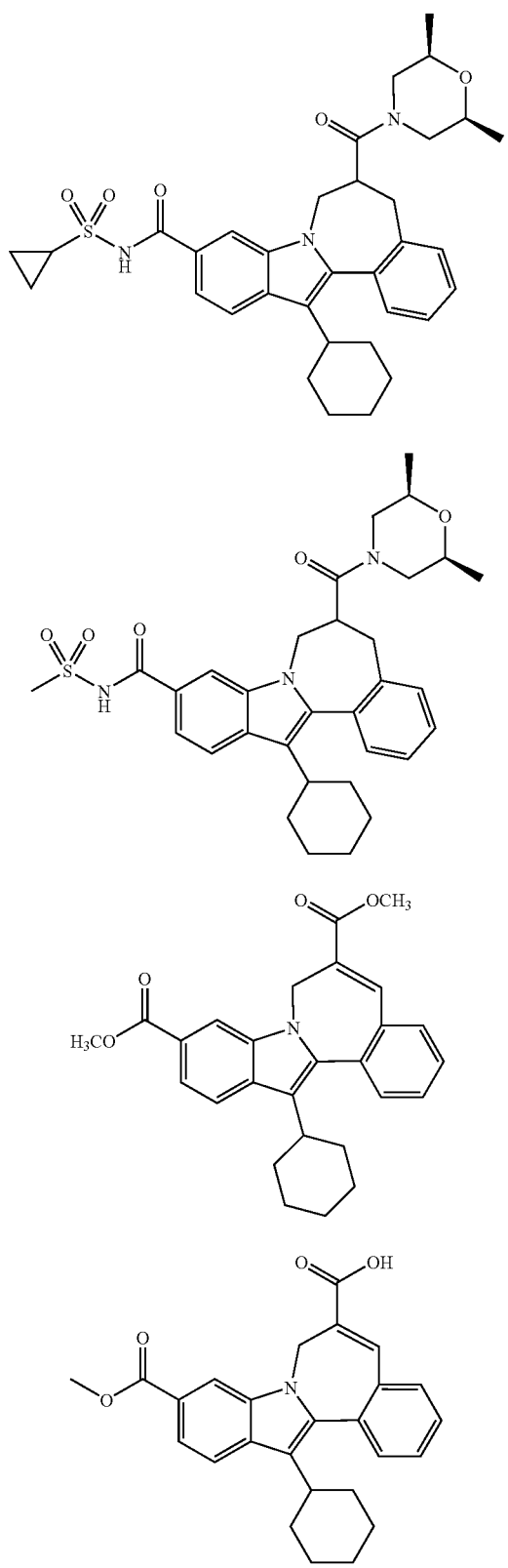
TABLE 2-continued
Structure
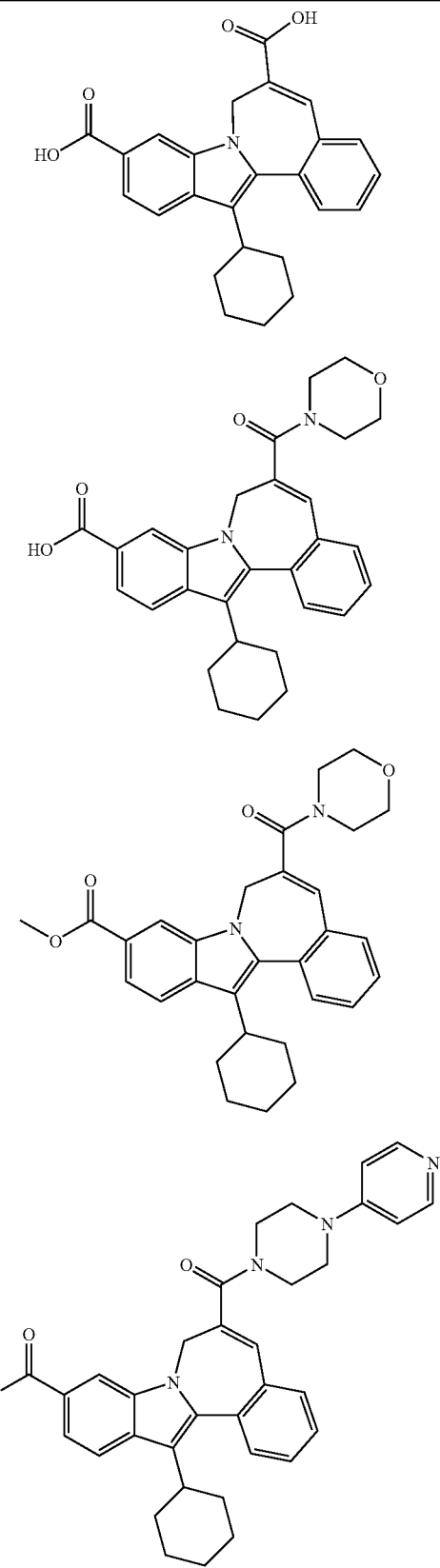

TABLE 2-continued
Structure
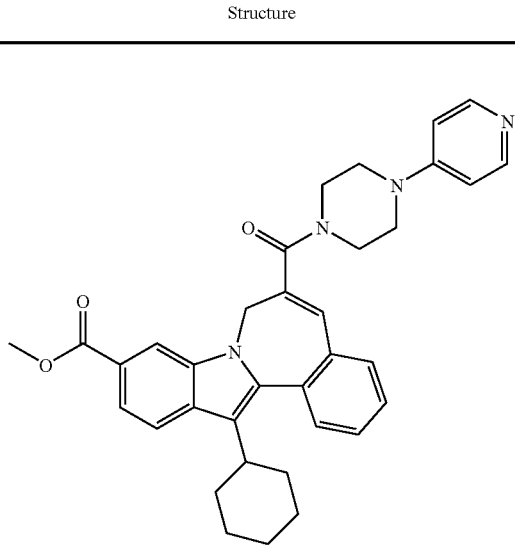
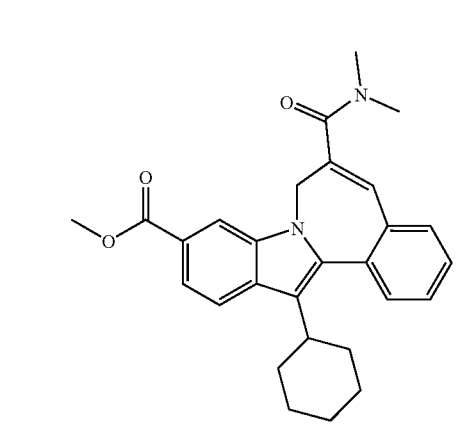
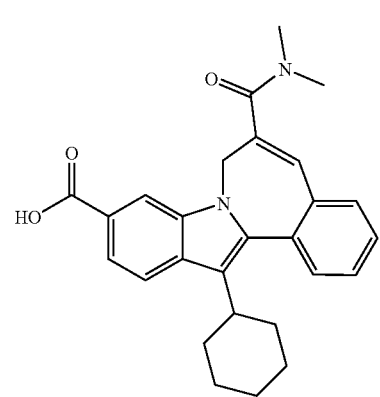
TABLE 2-continued
Structure
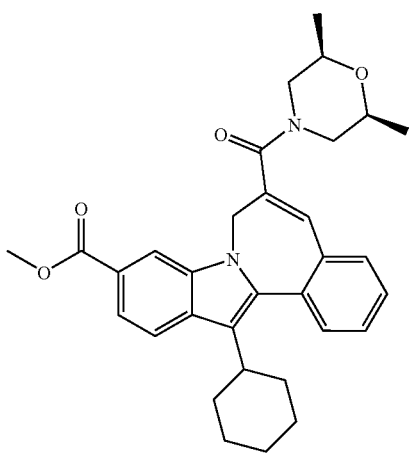
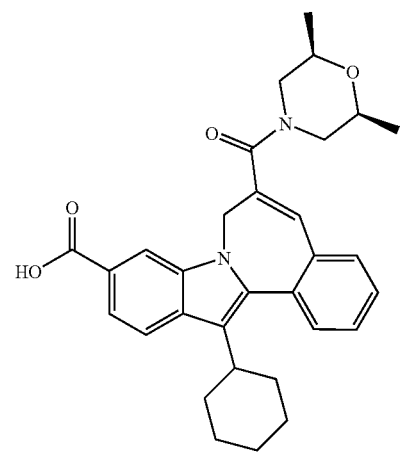
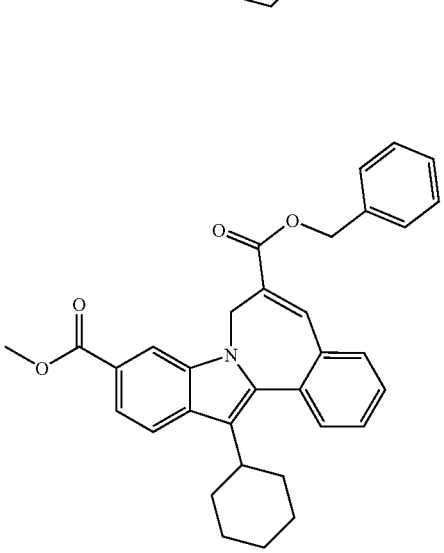

TABLE 2-continued
Structure
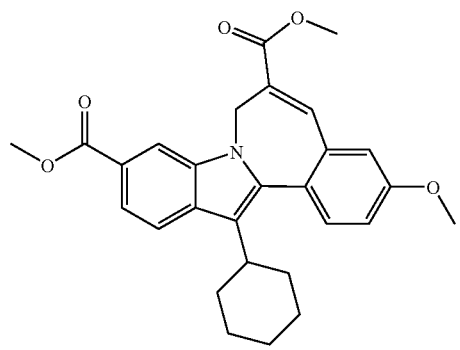
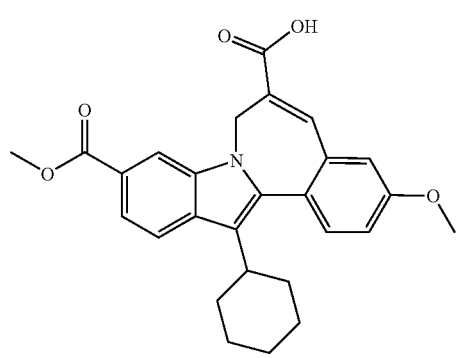
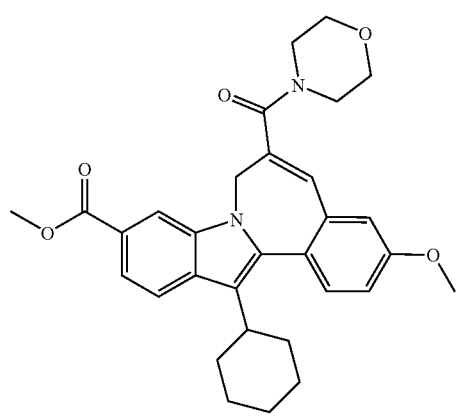
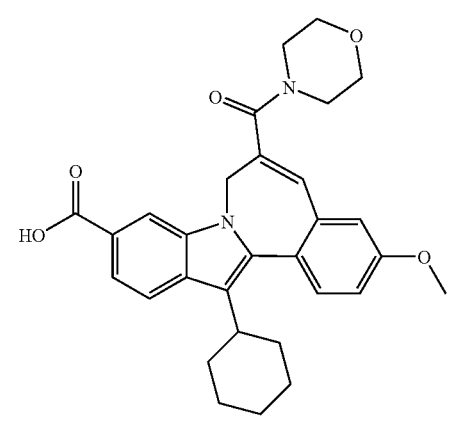
TABLE 2-continued
Structure
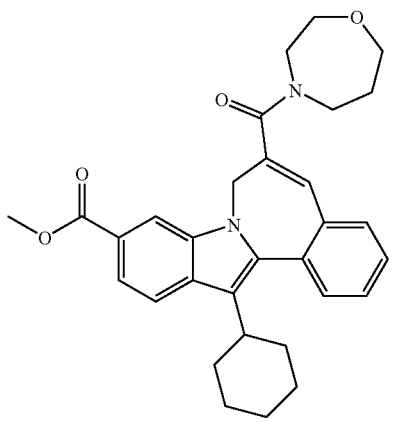
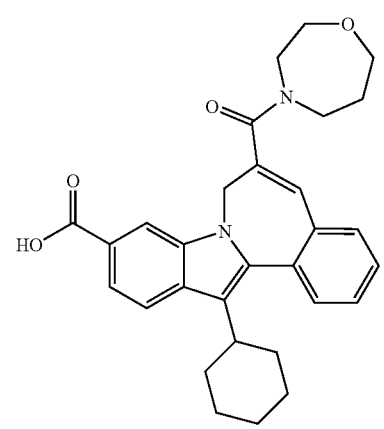
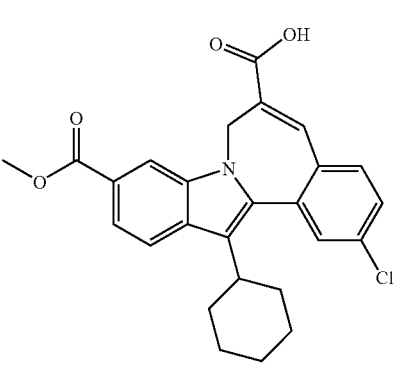
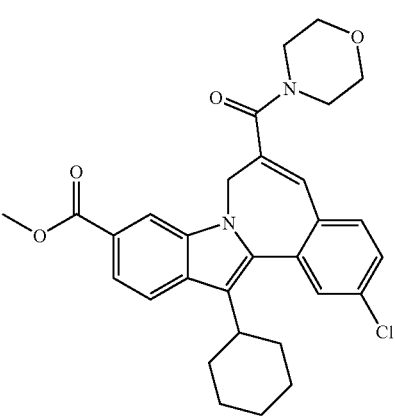

TABLE 2-continued
Structure
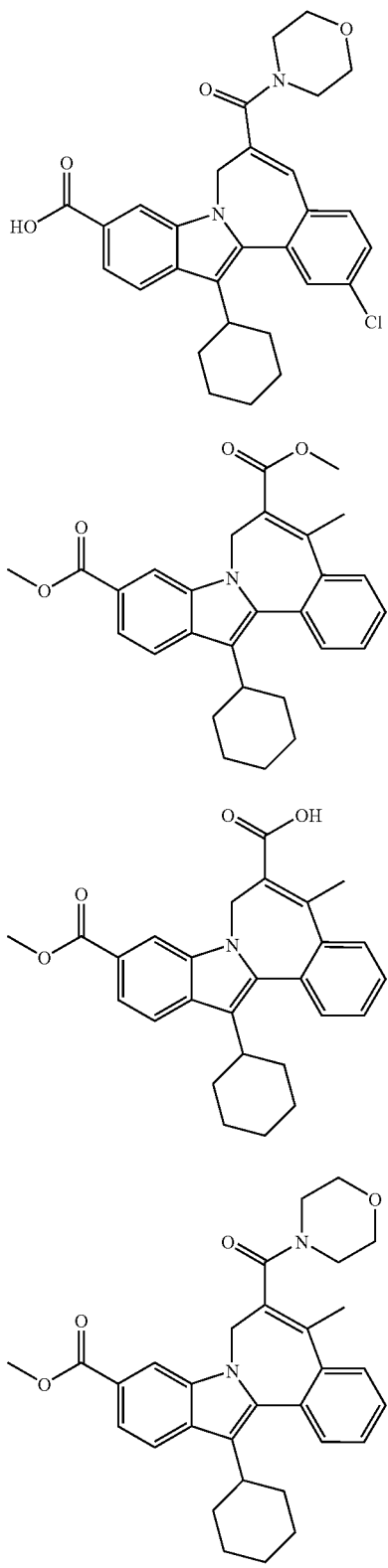
TABLE 2-continued
Structure
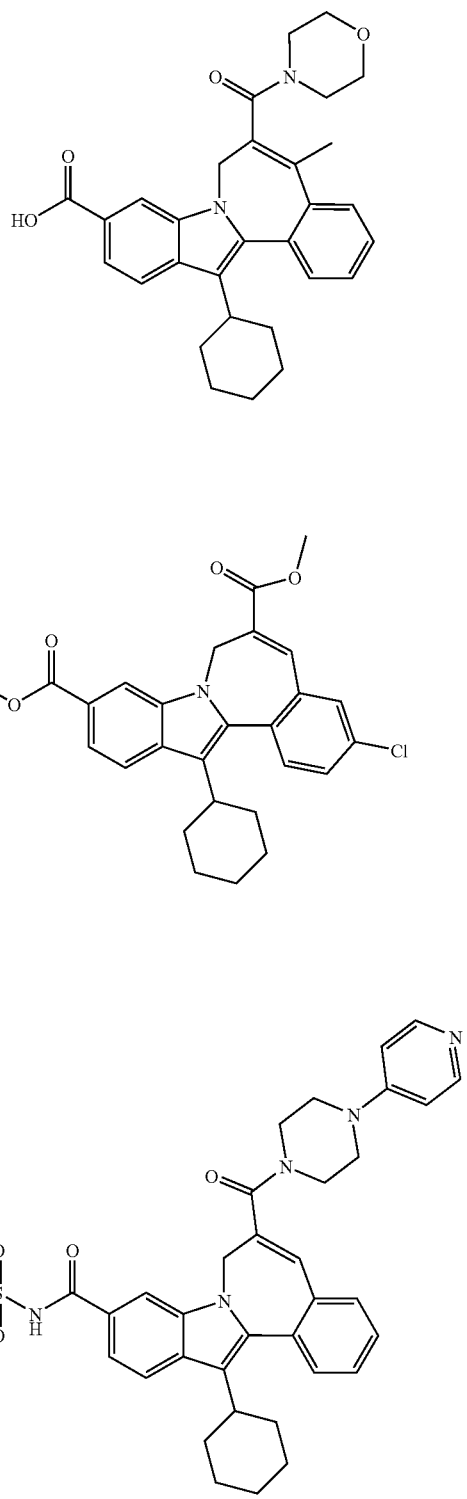

TABLE 2-continued
| Structure |
|---|
| 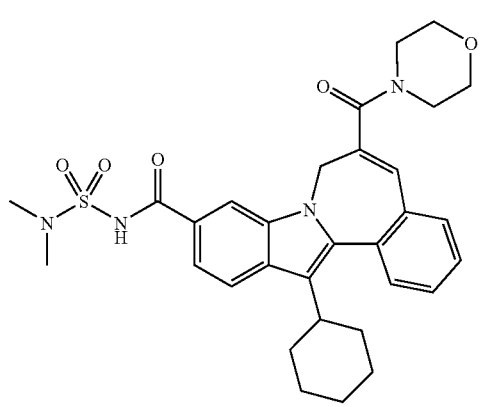 |
| 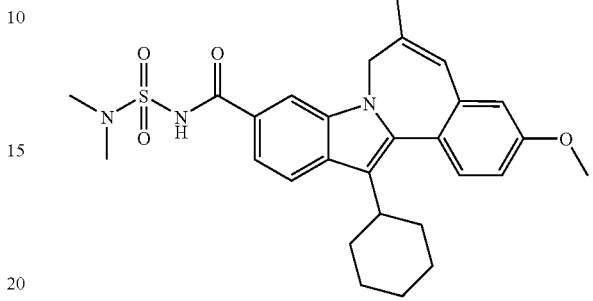 |
| 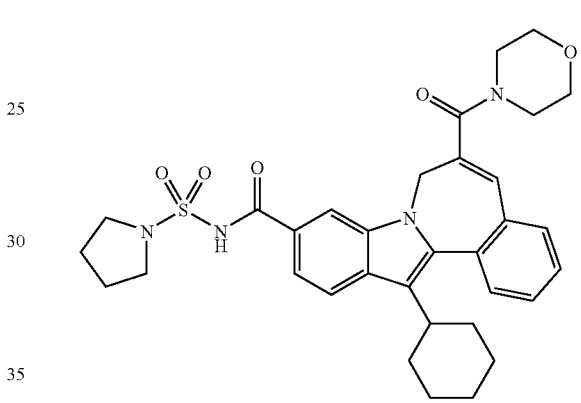 |
TABLE 2-continued
| Structure |
|---|
| 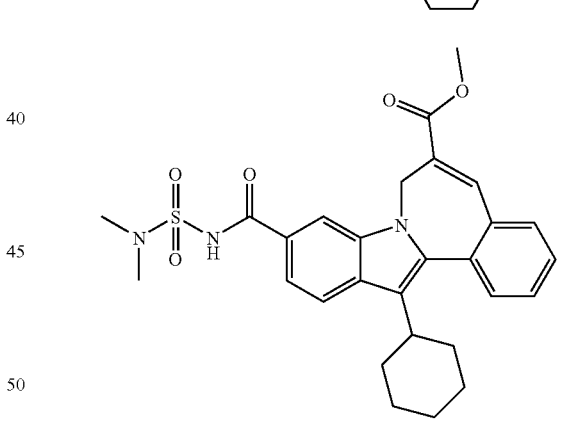 |
| 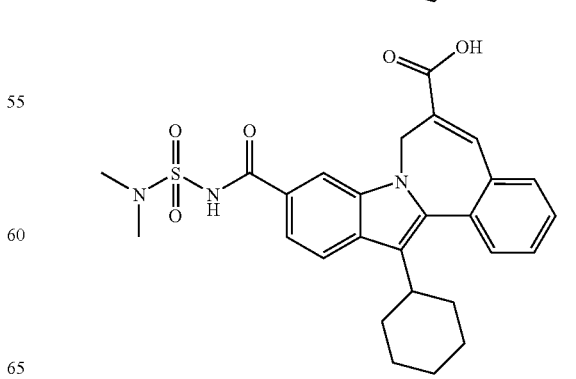 |

TABLE 2-continued
Structure
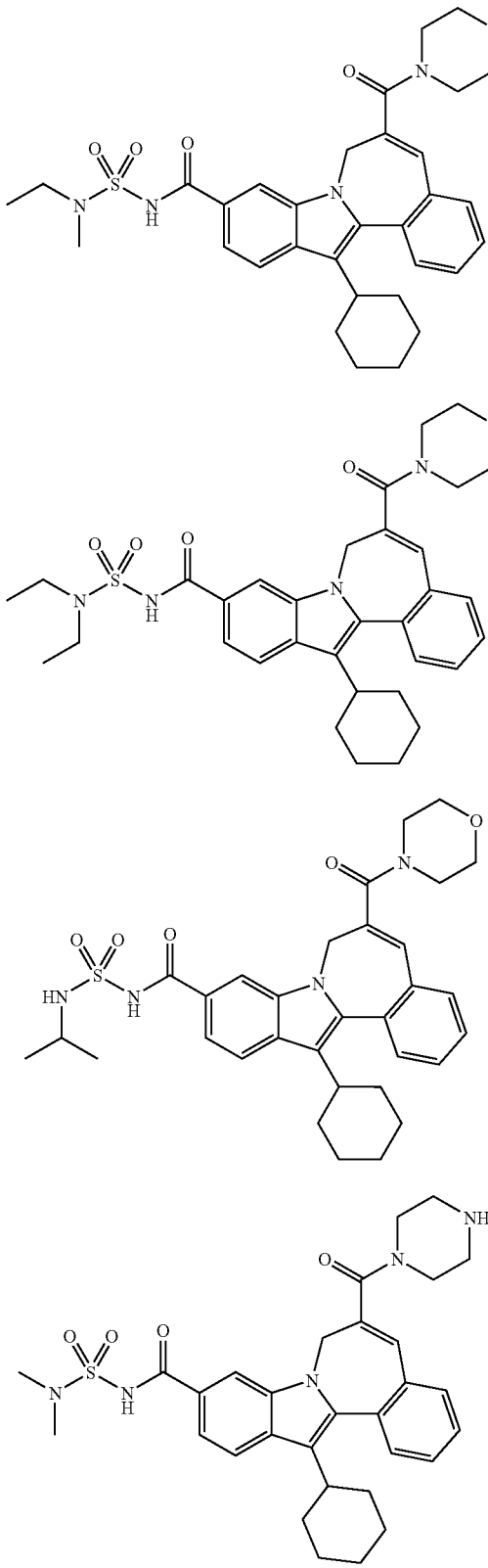
TABLE 2-continued
Structure
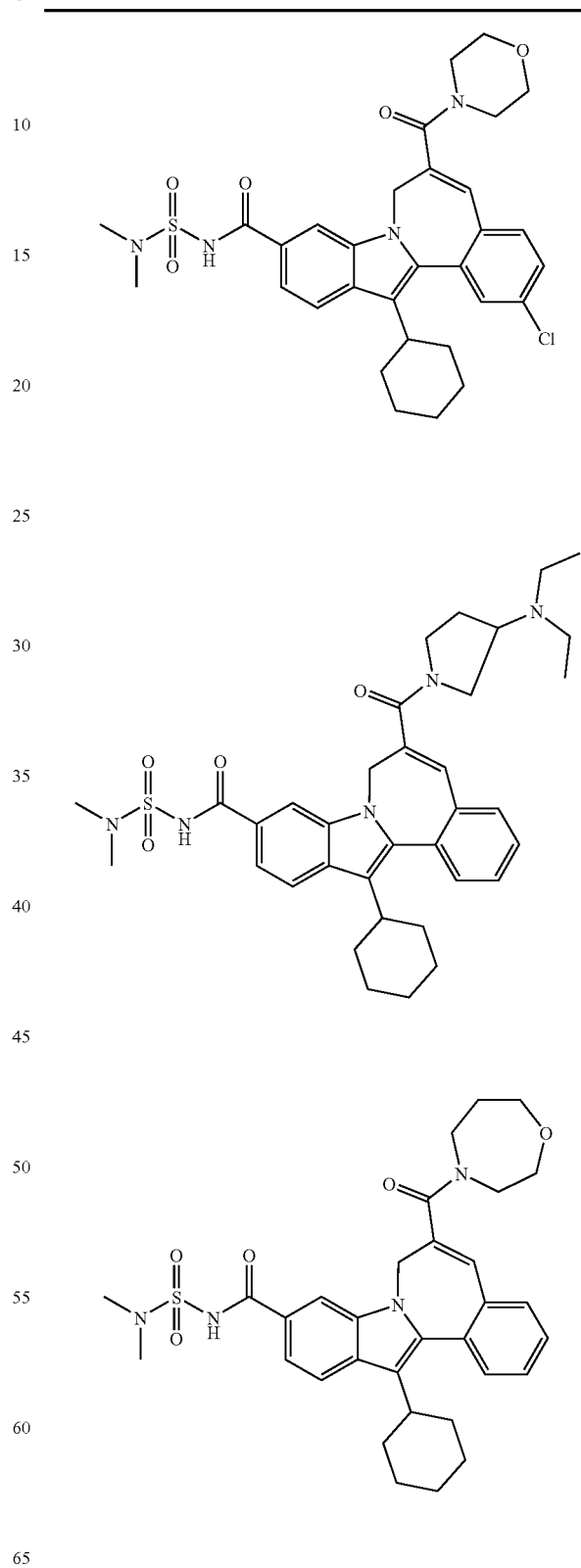

TABLE 2-continued
Structure
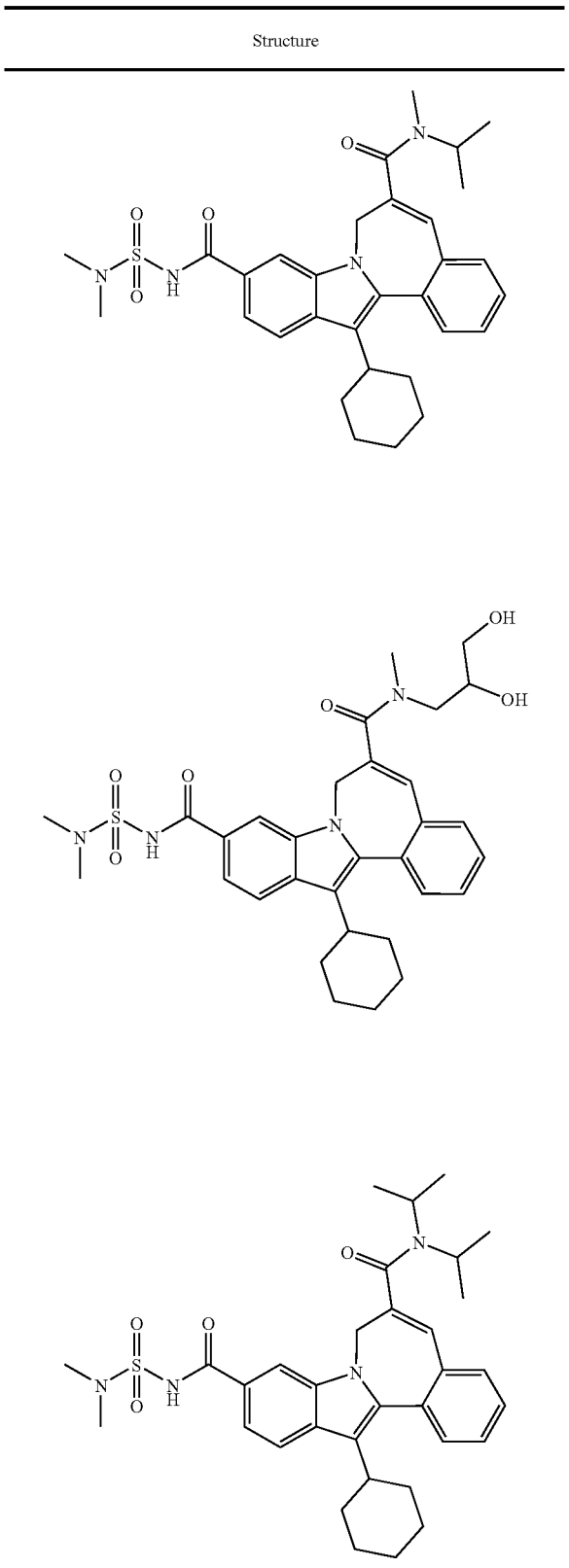
TABLE 2-continued
Structure
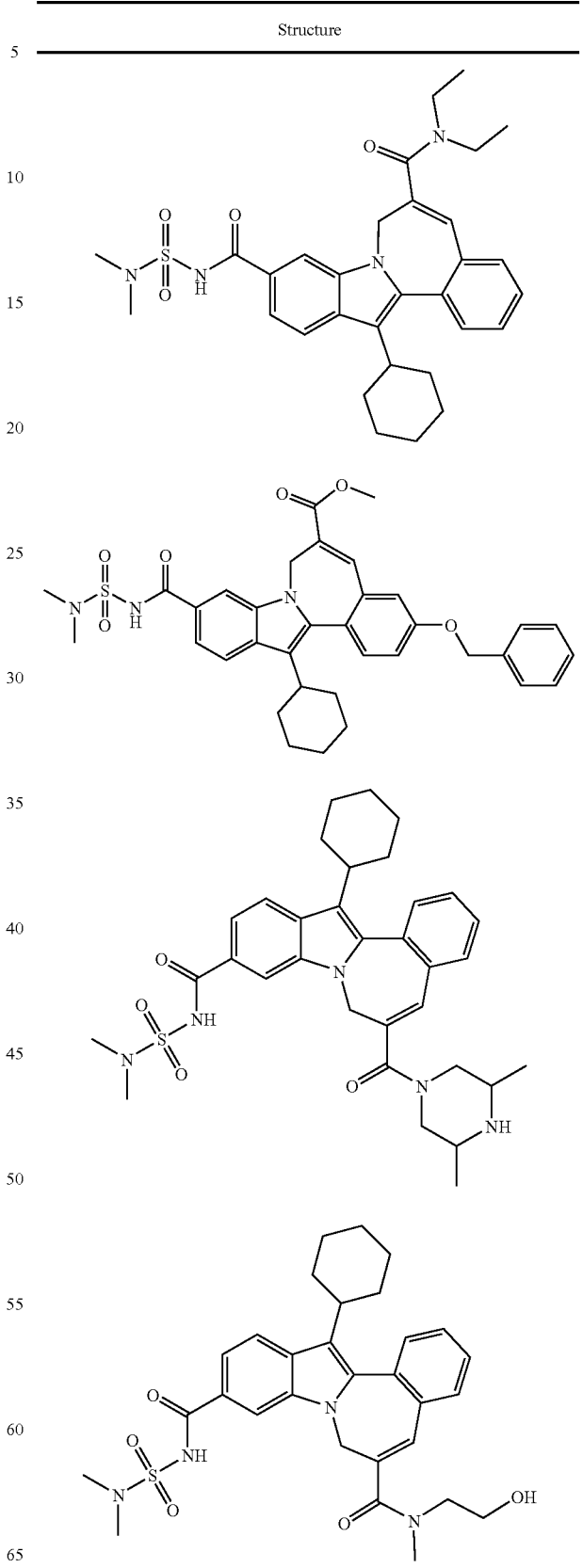

TABLE 2-continued
Structure
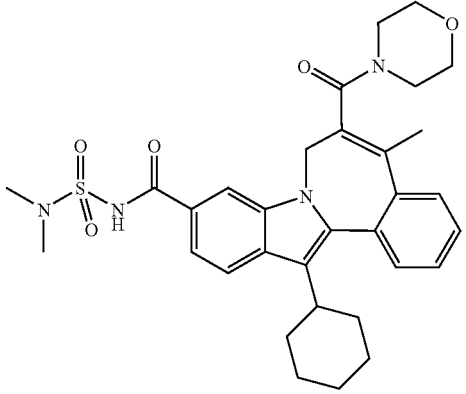
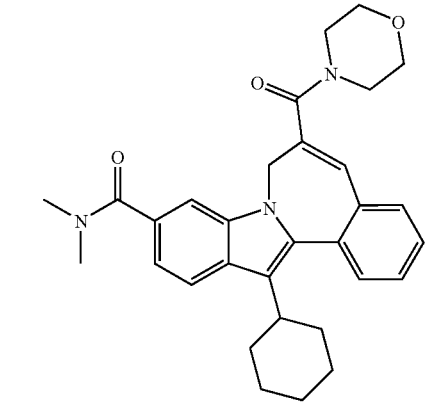
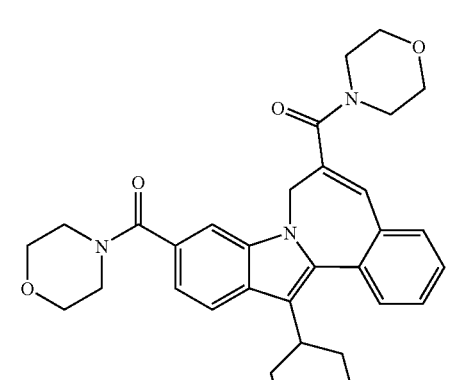
TABLE 2-continued
Structure
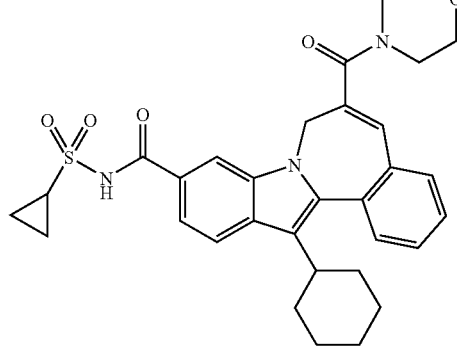
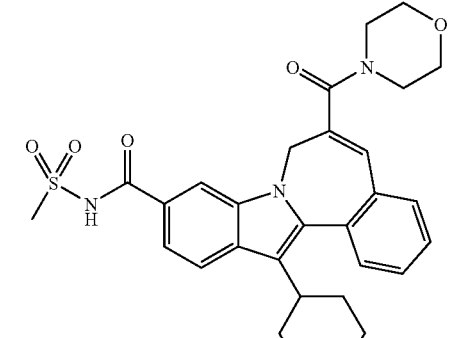
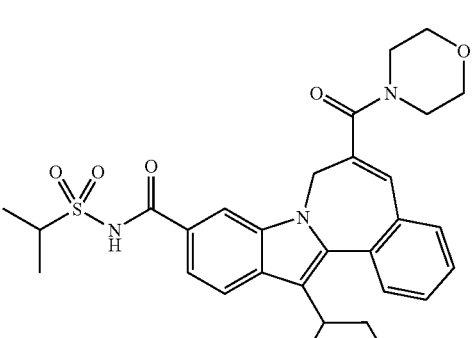
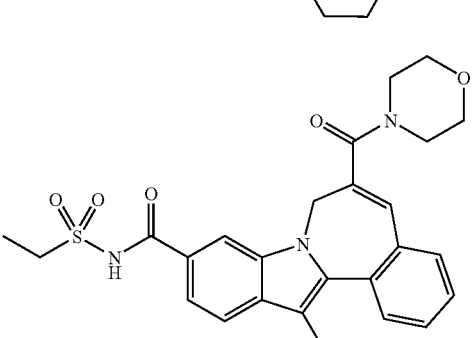

TABLE 2-continued

Structure

[Chemical structure: tert-butylsulfonamide-substituted indole-fused azepine with morpholine amide and cyclohexyl group]

[Chemical structure: phenylsulfonamide-substituted indole-fused azepine with morpholine amide and cyclohexyl group]

[Chemical structure: dimethylurea-substituted indole-fused azepine with morpholine amide and cyclohexyl group]

Pharmaceutical Compositions and Methods of Treatment

Formula I, II, III, and IV compounds demonstrate activity against HCV NS5B and can be useful in treating HCV and HCV infection. Therefore, another aspect of the invention is a composition comprising a compound of formula I, II, III, or IV, or a pharmaceutically acceptable salt or solvate thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound of formula I, II, III, or IV, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound of formula I, II, III, or IV or a pharmaceutically acceptable salt thereof.

Another aspect of the invention is a method of inhibiting the function of the HCV NS5B protein comprising contacting the HCV NS5B protein with a compound of formula I, II, III, or IV or a pharmaceutically acceptable salt thereof.

Another aspect of the invention is a method of treating an HCV infection in a patient comprising administering to the patient a therapeutically effective amount of a compound of formula I, II, III, or IV or a pharmaceutically acceptable solvate or salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound of formula I, II, III, or IV, or a pharmaceutically acceptable solvate or salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound of Formula I, II, III, or IV or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound of Formula I, II, III, or IV will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 3.

TABLE 3

| Brand Name | Type of Inhibitor or Target | Source Company |
|---|---|---|
| Omega IFN | IFN-ω | BioMedicines Inc., Emeryville, CA |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon —α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/SciClone Pharmaceuticals Inc, San Mateo, CA |
| Levovirin | IMPDH inhibitor | Ribapharm Inc., Costa Mesa, CA |
| Viramidine | IMPDH inhibitor | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |

TABLE 3-continued

| Brand Name | Type of Inhibitor or Target | Source Company |
|---|---|---|
| Zadazim | immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| T67 | β-tubulin inhibitor | Tularik Inc., South San Francisco, CA |
| VX-497 | IMPDH inhibitor | Vertex Pharmaceuticals Inc., Cambridge, MA |
| VX-950/LY-570310 | serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-002 | monoclonal antibody | XTL Biopharmaceuticals Ltd., Rehovot, Isreal |

DESCRIPTION OF SPECIFIC EMBODIMENTS

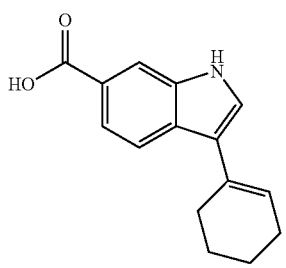

Intermediate 1

3-Cyclohexenyl-1H-indole-6-carboxylic acid. Cyclohexanone (96 mL, 0.926 mol) was added to a stirred solution of methyl indole-6-carboxylic acid (50.0 g, 0.335 mol) in methanol (920 mL) at 22° C. Methanolic sodium methoxide (416 mL of 25% w/w, 1.82 mol) was added in portions over 10 minutes. The mixture was stirred at reflux for 18 hours, cooled to room temperature, concentrated, diluted with cold water, and acidified with 36% HCl solution. The resulting precipitate was collected by filtration, washed with cold water, and dried over phosphorous pentoxide (0.1 mm) to provide the the title compound as a tan colored solid (80.9 g, 97.5% yield).

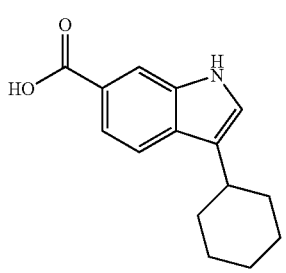

Intermediate 2

3-Cyclohexyl-1H-indole-6-carboxylic acid. 3-Cyclohexenyl-1H-indole-6-carboxylic acid (38 g) was added to a Parr bottle, followed by methanol (100 mL) and THF (100 mL). The bottle was flushed with argon and 10% palladium on carbon (1.2 g) was added. The flask was then evacuated and subsequently refilled with $H_2$ to a pressure of 55 psi, and the resultant mixture was shaken for 18 hours at RT. The catalyst was then removed by filtration through celite. Concentration of the filtrate provided the desired product as a pale purple solid (30.6 g, 79%). ESI-MS m/z 244 (MH+).

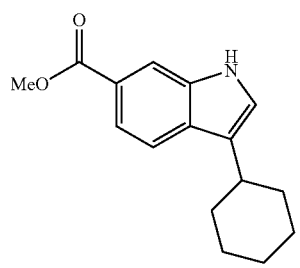

Intermediate 3

Methyl 3-cyclohexyl-1H-indole-6-carboxylate. Thionyl chloride (1 mL) was added to a stirred mixture of 3-cyclohexyl-1H-indole-6-carboxylic acid (30.4 g, 0.125 mol) in methanol (300 mL). The mixture was stirred at reflux for 18 hours, treated with decolorizing carbon, and filtered. The filtrate was concentrated to about 150 mL at which point crystallization occurred. The filtrate was cooled to room temperature and filtered. The solid was washed with cold methanol followed by diethyl ether to provide the desired product as a pale purple solid (22.2 g, 69% yield). ESI-MS m/z 258 (MH+); $^1$H NMR (300 MHz, CDCl$_3$) δ 1.35 (m, 4H), 1.63 (s, 1H), 1.78 (m, 3H), 2.06 (d, J=8.05 Hz, 2H, 3.90 (m, 1H), 7.08 (d, J=1.83 Hz, 1H), 7.62 (s, 1H), 7.65 (s, 1H),7.74 (d, J=1.46 Hz, 1H), 7.77 (d, J=1.46 Hz, 1H), 8.08 (s, 1H).

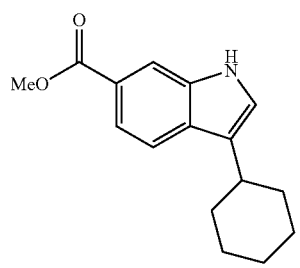

Intermediate 4

Methyl 1H-indole-6-carboxylate. An ethereal solution of diazomethane (620 mL) was added slowly to a cooled, (−15° C.) stirred suspension of 6-indole carboxylic acid (45 g, 0.27 mol.) in diethyl ether (250 mL). Upon addition, the reaction mixture was stirred for a further 1 h at −15° C., after which the reaction was quenched by the slow addition of acetic acid (50 mL). The resultant mixture was then concentrated under reduced pressure, and the residue purified using flash chromatography on silica (60-120), using MDC as eluant.

Intermediate 5

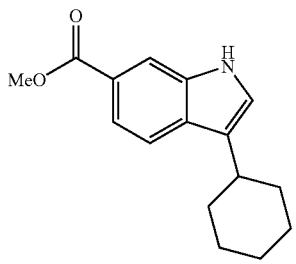

Methyl 3-cyclohexyl-1H-indole-6-carboxylate. Cyclohexanone (42.46 mL, 0.40 mol) was added in a single portion to a stirred solution of methyl indole-6-carboxylate (47.8 g, 0.27 m) in dry dichloromethane (500 mL). The reaction mixture was then cooled to 10° C. and trifluoroacetic acid (63.13 mL, 0.8 m) was added dropwise followed by triethyl silane (174.5 mL, 1.09 m). Upon addition, the temperature was allowed to rise to rt, after which it was stirred for a further 12 h. Dichloromethane (200 mL) was then added and the reaction mixture was washed successively with with 10% sodium bicarbonate solution and brine. The organic layer dried over sodium sulfate, filtered and concentrated under vacuum. The resultant residuce was purified by flash chromatography on silica (60-120) using hexane-ethyl acetate (9.5:0.5) mixture as eluant. Homogeneous fractions were combined and evaporated to give 60 g of the desired product (85%). Analytical data on this material was consistant with that observed with a sample prepared by the alternative route described above.

Intermediate 6

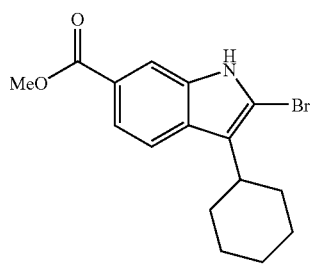

Methyl 2-bromo-3-cyclohexyl-2-1H-indole-6-carboxylate. Dry pyridinium tribromide (12.0 g, 38 mmol) was added in one portion to a stirred and cooled (ice/water bath) solution of methyl 3-cyclohexyl-1H-indole-6-carboxylate (7.71 g, 30 mmol) in a mixture of THF (80 mL) and chloroform (80 mL). The flask was removed from the cooling bath and stirring was continued for 2 hours at room temperature. The mixture was sequentially washed with 1M NaHSO$_3$ (2×50 mL) and 1N HCl (50 mL). It was then dried over anhydrous sodium sulfate, filtered, and concentrated. The concentrate was treated with hexanes and the resulting precipitate was collected by filtration to provide the desired product as an off-white solid (5.8 g, 58%). $^1$H NMR (300 MHz, CDCl$_3$) δ 1.38 (m, 3H), 1.85 (m, 7H), 2.81 (m, 1H), 7.71 (m, 2H), 8.03 (s, 1H), 8.47 (s, 1H).

The hexane mother liquor was concentrated and the residue was dissolved in hexane/ethyl acetate (5:1). The solution was passed through a pad of silica gel with the same solvents. Concentration of the eluate followed by the addition of hexane (10 mL) resulted in the precipitation of additional product which was collected by filtration to provide 2.8 g (28%) of the desired product.

Intermediate 7

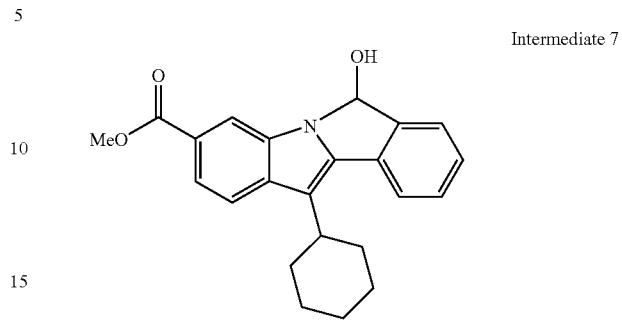

Methyl 11-cyclohexyl-6-hydroxy-6H-isoindolo[2,1-a]indole-3-carboxylate. A stirred mixture of methyl 2-bromo-3-cyclohexyl-1H-indole-6-carboxylate (10.1 g, 30 mmol), 2-formylphenylboronic acid (5.4 g, 36 mmol), LiCl (3.8 g (90 mmol) and Pd (PPh$_3$)$_4$ (1.6 g, 1.38 mmol) in 1M Na$_2$CO$_3$ (40 mL) and 1:1 EtOH-toluene (180 mL) was heated under nitrogen at 85° C. for 3 hours. The reaction mixture was then cooled to RT, and extracted with EtOAc (2×100 mL). The extracts were washed sequentially with water and brine, then dried (MgSO$_4$), filtered and conventrated in-vacuo to afforded 13.3 g of crude product. This material was triturated with DCM and hexanes to provide pure desired product (7.52 g, 70%). LC-MS: m/e 360 (M−H); 344 (M−17)$^+$. $^1$H NMR (400 MHz, CHLOROFORM-D) δ ppm 1.33-1.60 (m, 4 H) 1.77-2.01 (m, 6H) 2.80 (d, J=11.83 Hz, 1 H) 3.02-3.18 (m, 1 H) 3.89 (s, 3 H) 6.49 (d, J=11.33 Hz, 1 H) 7.34 (t, J=7.55 Hz, 1 H) 7.46 (t, J=7.55 Hz, 1 H) 7.62 (d, J=7.30 Hz, 1 H) 7.66-7.74 (m, 2 H) 7.77 (d, J=7.81 Hz, 1 H) 8.21 (s, 1 H).

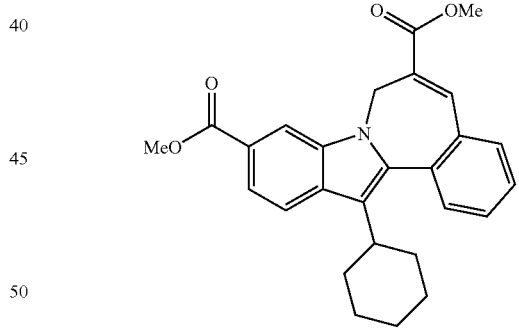

Methyl 13-cyclohexyl-6-(methoxycarbonyl)-7H-indolo[2, 1-a][2]benzazepine-10-carboxylate. A stirred suspension of methyl 11-cyclohexyl-6-hydroxy-6H-isoindolo[2,1-a]indole-3-carboxylate (3.61 g, 10 mmol), Cs$_2$CO$_3$ (3.91 g, 12 mmol) and trimethyl 2-phosphonoacetate (2.86g, 14 mmol) in an. DMF (40 mL) was heated at 60° C. under nitrogen for 3 h. The resultant yellow suspension was cooled to rt and water was added with vigorous stirring. A yellow precipitate formed which was collected by filtration. The solid was washed with water, and then air dried overnight to afford the title compound as a yellow powder (4.124 g, 96%). LC/MS: m/e 430 (MH$^+$); $^1$H NMR (400 MHz, CHLOROFORM-D) δ ppm 1.30-1.46 (m, J=14.86 Hz, 2 H) 1.55 (s, 2 H) 1.77 (s, 2 H) 1.85-2.18 (m, 4 H) 2.76-2.89 (m, 1 H) 3.84 (s, 3 H) 3.95 (s, 3

H) 4.19 (s, 1 H) 5.68 (s, 1 H) 7.38-7.63 (m, 4 H) 7.74 (dd, J=8.44, 1.39 Hz, 1 H) 7.81-7.98 (m, 2 H) 8.29 (d, J=1.01 Hz, 1 H).

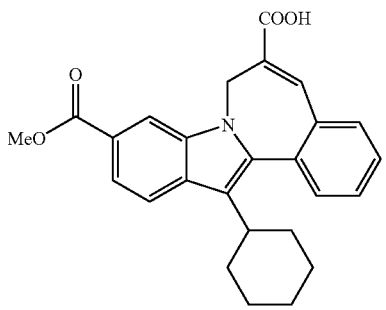

Methyl 13-cyclohexyl-6-(carboxy)-5H-indolo[2,1-a][2]benzazepine-10-carboxylate. Methyl 13-cyclohexyl-6-(methoxycarbonyl)-7H-indolo[2,1-a][2]benzazepine-10-carboxylate (308 mg, 0.72 mmol) was dissolved in N,N-dimethylformamide (5 mL) and treated with LiOH (173 mg, 7.2 mmol). The mixture was heated at 50° C. for 4 hr, after which the solvent was removed in vacuo. The residue was dissolved in H$_2$O (5 mL) and the resultant mixture was acidified by the addition of a 10% aqueous HCL solution. A precipitate formed which was collected by filtration and air dried to afford the title compound as a bright yellow solid (290 mg, 97%). ESI-MS m/z [M+1]=415.

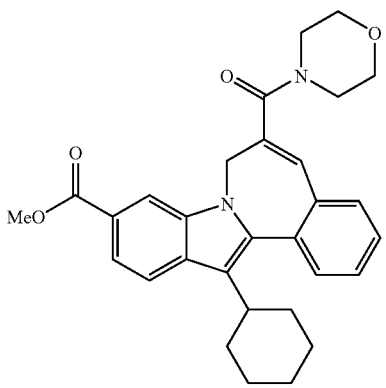

Methyl 13-cyclohexyl-6-(morpholinylcarbonyl)-5H-indolo[2,1-a][2]benzazepine-10-carboxylate. TBTU (145 mg, 0.45 mmol) was added to a stirred solution of Methyl 13-cyclohexyl-6-(carboxy)-5H-indolo[2,1-a][2]benzazepine-10-carboxylate (125 mg, 0.30 mmol), morpholine (26 μL, 0.30 mmol), and N,N-diisopropylethylamine 200 μL, 1.15 mmol) in DMF (2 mL). The mixture was stirred at 22° C. for 20 min. The resulting solution was then injected onto a Shimadzu reverse phase preparative HPLC. The product containing fraction was concentrated on a Speed Vac® to leave methyl 13-cyclohexyl-6-(morpholinylcarbonyl)-5H-indolo[2,1-a][2]benzazepine-10-carboxylic acid as a yellow solid (64 mg, 44%). ESI-MS m/z 487 (MH$^+$); $^1$H NMR (500 MHz, CDCl$_3$) δ 1.21 (m, 1 H), 1.34-1.55 (m, 3 H), 1.77 (m, 2 H), 1.91 (m, 1 H), 2.06 (m, 3 H), 2.83 (m, 1 H), 2.97-3.85 (m, 8 H), 3.97 (s, 3 H), 4.45 (m, 1 H), 5.07 (m, 1 H), 6.89 (s, 1 H), 7.41 (d, 1 H), 7.49 (m, 2 H), 7.57 (m, 1 H), 7.75 (m, 1 H), 7.89 (d, J=8.55 Hz, 1 H), 8.15 (s, 1 H).

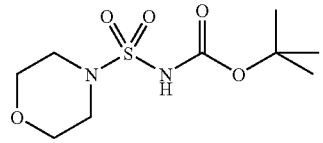

A t-butanol (1.32 mL, 14 mmol) solution in CH$_2$Cl$_2$ (6 mL) was added dropwise to the solution of CSI (1.24 mL, 14 mmol) of CH$_2$Cl$_2$ (20 mL) at 0° C. The generated solution was stirred for 1.5 h at 0° C. A solution of morpholine (1.23 mL, 14 mmol) and triethylamine (5.9 mL, 42 mmol) in CH$_2$Cl$_2$ (10 mL) was added dropwise. The generated reaction mixture was stirred for 1 h at 0° C. and 1 h at r.t. The solvents were removed in vacuo and the residue was partitioned between EtOAc and cold 1N HCl. The organic layer was washed with cold 1N HCl, brine, dried (MgSO$_4$), and removed the solvent to afford A-1 as a white solid (2.16 g, 92%). $^1$H NMR (400 MHz, CHLOROFORM-D) δ ppm 1.48 (s, 9 H) 3.30-3.44 (m, 4 H) 3.66-3.80(m, 4 H) 7.19 (s, 1 H).

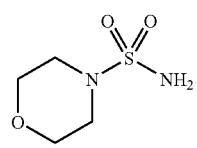

Dissolved A-1 (2.16 g, 13 mmol) in TFA (2 mL) and CH$_2$Cl$_2$ (2 mL) and stirred the mixture at r.t. for 5 h. Removed the solvents in vacuo to afford B-1 as a beige solid (1.35 g, 100%). $^1$H NMR (400 MHz, CHLOROFORM-D) δ ppm 3.10-3.39 (m, 4 H) 3.63-3.96 (m, 4 H).

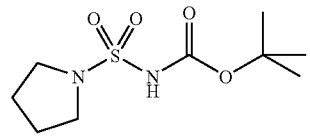

$^1$H NMR (400 MHz, CHLOROFORM-D) δ ppm 1.47 (s, 9 H) 1.85-1.98 (m, 4 H) 3.42-3.57 (m, 4 H) 7.00 (s, 1 H).

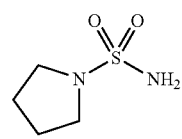

$^1$H NMR (400 MHz, MeOD) δ ppm 1.85-1.93 (m, 4 H) 3.17-3.28 (m, 4 H).

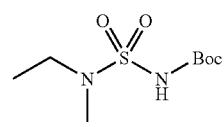

$^1$H NMR (400 MHz, CHLOROFORM-D) δ ppm 1.20 (t, J=7.18 Hz, 3 H) 1.47 (s, 9 H) 2.95 (s, 3 H) 3.35 (q, J=7.05 Hz, 2 H) 7.00 (s, 1 H).

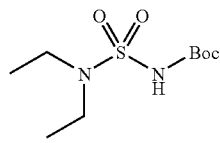

¹H NMR (400 MHz, CHLOROFORM-D) δ ppm 1.20 (t, J=7.18 Hz, 6 H) 1.47 (s, 9 H) 3.41 (q, J=7.30 Hz, 3 H) 7.04 (s, 1 H).

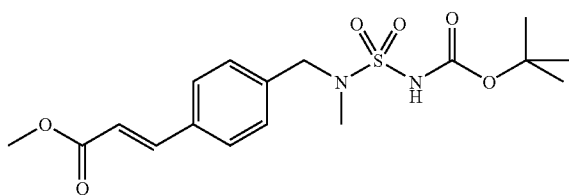

¹H NMR (400 MHz, CHLOROFORM-D) δ ppm 1.50 (s, 9 H) 2.84 (s, 3 H) 3.80 (s, 3 H) 4.48 (s, 2 H) 6.43 (d, J=16.12 Hz, 1 H) 7.36 (d, J=8.06 Hz, 2 H) 7.48-7.54 (m, J=8.06 Hz, 2 H) 7.67 (d, J=15.86 Hz, 1 H).

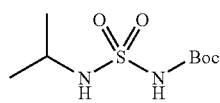

¹H NMR (400 MHz, CHLOROFORM-D) δ ppm 1.21 (d, J=6.55 Hz, 6 H) 1.48 (s, 9 H) 3.47-3.66 (m, 1 H).

094

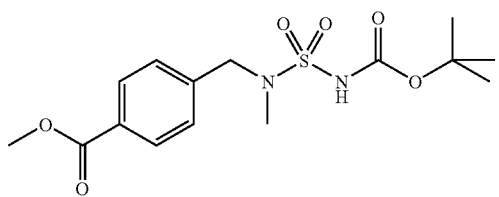

¹H NMR (400 MHz, CHLOROFORM-D) δ ppm 1.49 (s, 9 H) 2.83 (s, 3 H) 3.90 (s, 3 H) 4.52 (s, 2 H) 7.40 (d, J=8.06 Hz, 2 H) 8.01 (d, J=8.31 Hz, 2 H).

098

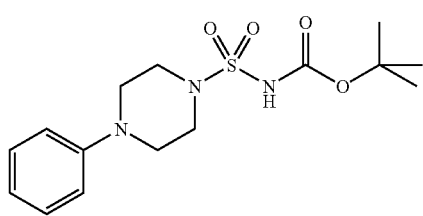

¹H NMR (400 MHz, CHLOROFORM-D) δ ppm 3.20-3.28 (m, 4 H) 3.51-3.57 (m, 4 H) 6.88-6.98 (m, J=8.31 Hz, 2 H) 7.21-7.31 (m, 2 H).

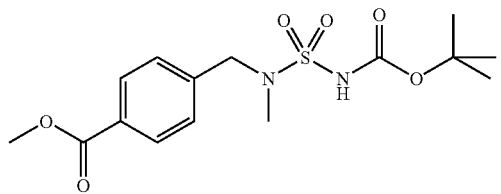

¹H NMR (400 MHz, CHLOROFORM-D) δ ppm 1.49 (s, 9 H) 2.83 (s, 3 H) 3.90 (s, 3 H) 4.52 (s, 2 H) 7.40 (d, J=8.06 Hz, 2 H) 8.01 (d, J=8.31 Hz, 2 H).

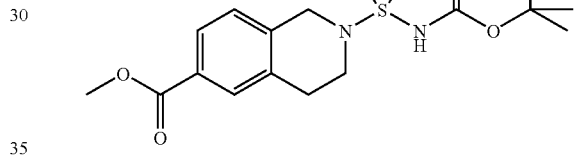

¹H NMR (400 MHz, CHLOROFORM-D) δ ppm 1.50 (s, 9 H) 2.83 (s, 3 H) 4.45 (s, 2 H) 7.29-7.44 (m, 5 H).

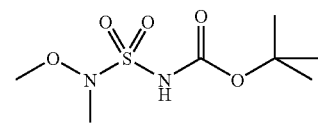

¹H NMR (500 MHz, CHLOROFORM-D) δ ppm 1.42 (s, 9 H) 3.00 (t, J=5.80 Hz, 2 H) 3.68 (t, J=5.95 Hz, 2 H) 3.90 (s, 3 H) 4.65 (s, 2 H) 7.05 (s, 1 H) 7.16 (d, J=7.94 Hz, 1 H) 7.79-7.92 (m, 2 H).

¹H NMR (400 MHz, CHLOROFORM-D) δ ppm 1.48 (s, 9 H) 3.08 (s, 3 H) 3.76 (s, 3 H) 4.95 (s, 1 H).

A t-butanol (1.32 mL, 14 mmol) solution in CH₂Cl₂ (5 mL) was added dropwise to the solution of CSI (1.24 mL, 14 mmol) of CH₂Cl₂ (20 mL) at 0° C. The generated solution was stirred for 1.5 h at 0° C. A solution of 1-methylpiperazine (1.52 mL, 14 mmol) and in CH₂Cl₂ (5 mL) was added dropwise at 0° C. After stirred for 5 min at 0° C., removed the bath and stirred at r.t. for 4 h. The reaction mixture was diluted with ether and filtered to afford a white solid (2.72 g, 69%). $^1$H NMR (400 MHz, MeOD) δ ppm 1.49 (s, 9 H) 2.92 (s, 3 H) 3.38 (s, 4 H) 3.65 (s, 4 H).

341

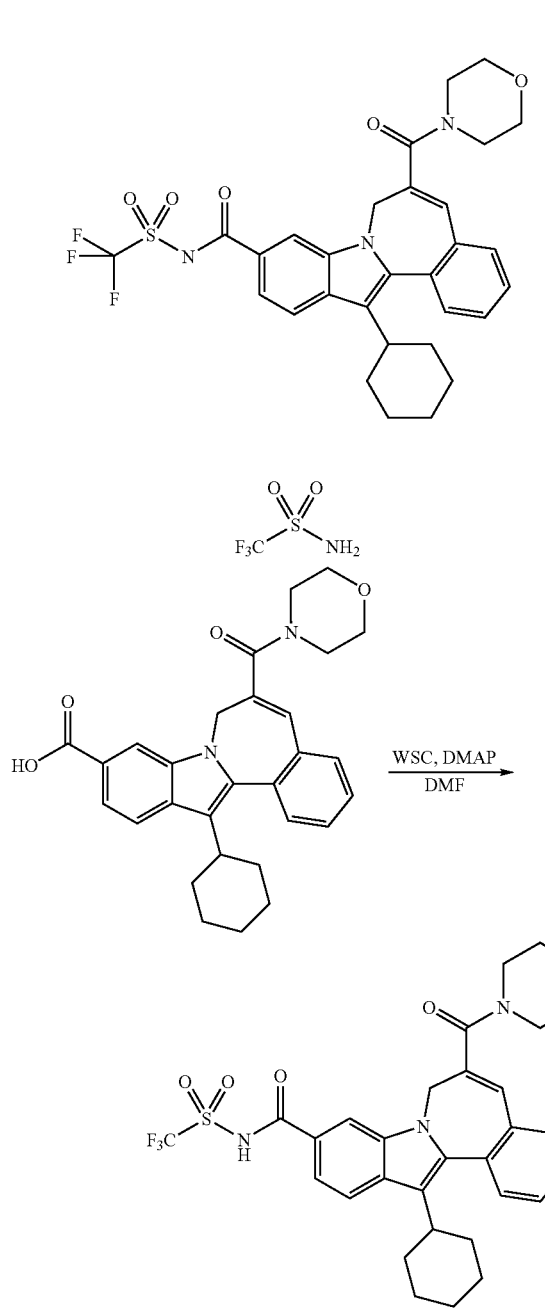

342

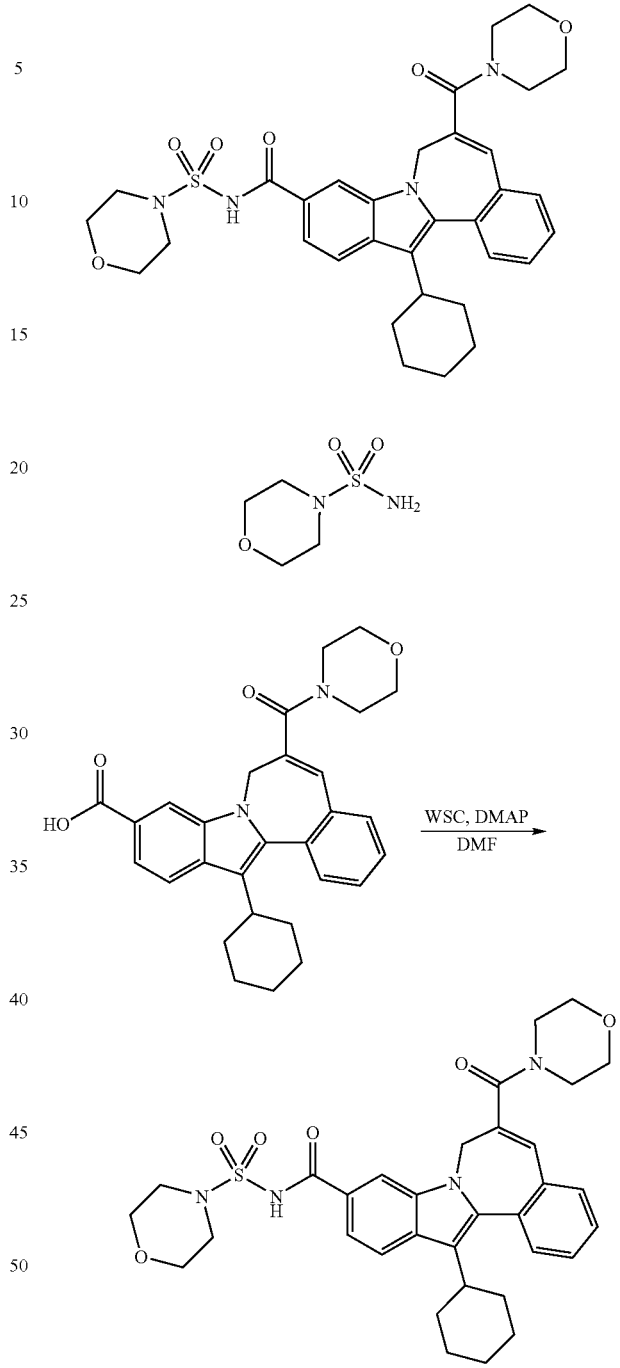

A mixture of trifluoromethanesulfonamide (89 mg, 0.6 mmol), added acid 2 (56 mg, 0.12 mmol), DMAP (89 mg, 0.73 mmol), N1-((ethylimino)methylene)-N3,N3-dimethylpropane-1,3-diamine hydrochloride (57 mg, 0.27 mmol) in DMF (1.5 mL) was stirred o/n and purified by prep HPLC to afford the product as a solid (17.6 mg, 24 %). $^1$H NMR (400 MHz, CHLOROFORM-D) δ ppm 1.29-1.52 (m, 4 H) 1.66-1.79 (m, 2 H) 2.03 (s, 4 H) 2.79 (s, 1 H) 3.26-3.74 (m, 8 H) 4.21 (s, 1 H) 5.06 (s, 1 H) 6.89 (s, 1 H) 7.33-7.60 (m, 4 H) 7.68 (d, J=8.31 Hz, 1 H) 7.83-7.91 (m, 1 H) 8.33 (s, 1 H). LC-MS (retention time: 3.04; MS m/z 602 (M+H).

A mixture of morpholine-4-sulfonamide (46 mg, 0.28 mmol), added acid 1 (40 mg, 0.08 mmol), DMAP (82 mg, 0.67 mmol), N1-((ethylimino)methylene)-N3,N3-dimethylpropane-1,3-diamine hydrochloride (57 mg, 0.30 mmol) in DMF (1.5 mL) was stirred o/n and purified by prep HPLC to afford the product as a solid (16 mg, 30%) $^1$H NMR (400 MHz, CHLOROFORM-D) δ ppm 1.21-1.62 (m, 4 H) 1.90 (d, J=112.30 Hz, 6 H) 2.83 (s, 1 H) 3.28-3.88 (m, 16 H) 4.36 (s, 1 H) 5.12 (s, 1 H) 6.89 (s, 1 H) 7.35-7.63 (m, 5 H) 7.80-7.94 (m, 1 H) 8.14 (s, 1 H) LC-MS (retention time: 2.97; MS m/z 619 (M+H).

343

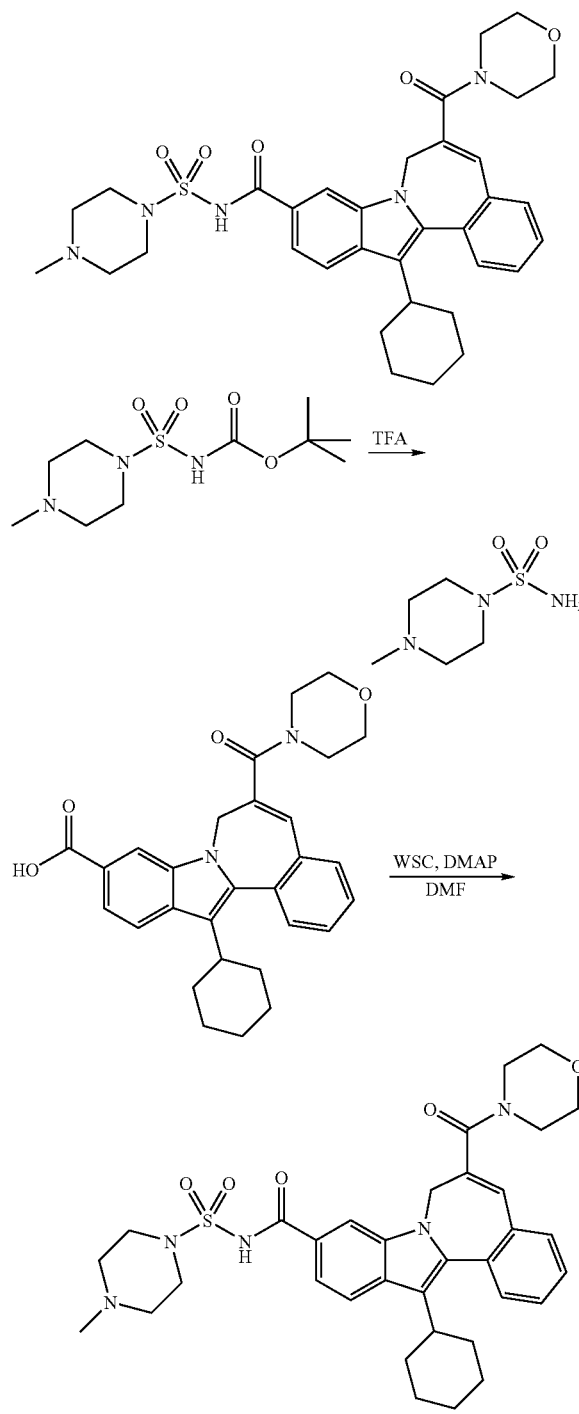

tert-butyl 4-methylpiperazin-1-ylsulfonylcarbamate (89 mg, 0.32 mmol) was dissolved in TFA/DCM (1/1, 1 mL) and stirred for 2 h. removed the solvents in vacuo and added acid 2 (40 mg, 0.1 mmol), DMAP (129 mg, 1.06 mmol), N1-((ethylimino)methylene)-N3,N3-dimethylpropane-1,3-diamine hydrochloride (61 mg, 0.3 mmol), DMF (1.5 mL). The mixture was stirred o/n and purified by prep HPLC to afford the product as a solid (6.3 mg, 9%). $^1$H NMR (400 MHz, CHLOROFORM-D) δ ppm 1.39 (d, J=7.30 Hz, 4 H) 1.76 (s, 2 H) 2.08 (d, J=12.84 Hz, 4 H) 2.75-2.91 (m, 4 H) 3.40-3.91

344

(m, 16 H) 4.22-4.42 (m, J=-18.13 Hz, 1 H) 5.15 (s, 1 H) 6.88 (s, 1 H) 7.41 (dd, J=7.30, 1.51 Hz, 1 H) 7.47-7.56 (m, 3 H) 7.55-7.62 (m, 1 H) 7.84-7.96 (m, J=8.81, 8.81 Hz, 1 H) 8.08 (s, 1 H): LC-MS (retention time: 2.71; MS m/z 632 (M+H).

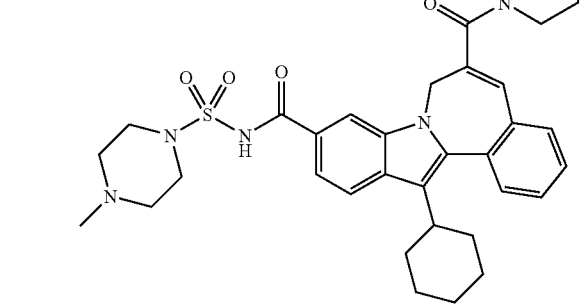

The Boc sulfamide (102 mg, 0.63 mmol) was dissolved in TFA/DCM (1/1, 1 mL) and stirred for 2 h. removed the solvents in vacuo and added acid 2 (40 mg, 0.1 mmol), DMAP (100 mg, 0.82 mmol), N1-((ethylimino)methylene)-N3,N3-dimethylpropane-1,3-diamine hydrochloride (57 mg, 0.3 mmol), DMF (1.5 mL). The mixture was stirred o/n and purified by prep HPLC to afford the product as a solid (10.4 mg, 20%). $^1$H NMR (400 MHz, CHLOROFORM-D) δ ppm 1.13-2.18 (m, 10 H) 2.78-2.87 (m, 1 H) 3.26 (s, 3 H) 3.32-3.71 (m, 8 H) 3.82 (s, 3 H) 4.35 (s, 1 H) 5.12 (s, 1 H) 6.87(s, 1

345

H)7.34-7.63(m,4H) 7.82-7.87(m, 1 H) 7.91 (d, J=8.56 Hz, 1 H) 8.10 (s, 1 H), LC-MS (retention time: 3.00 ), MS m/z 593 (M$^+$+1).

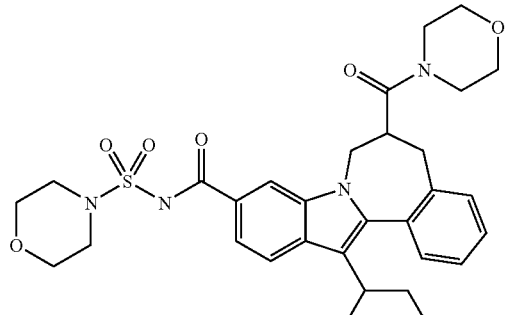

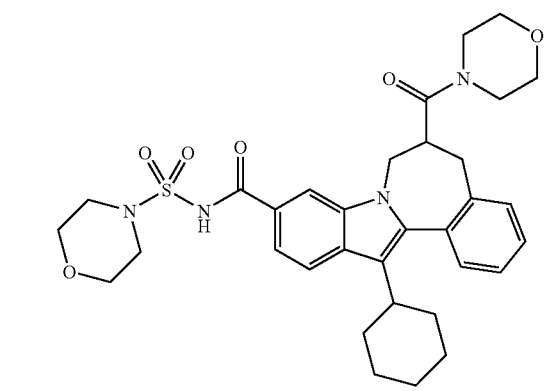

A suspension of compound 18 (7.9 mg, 0.17 mmol) and small amount of Pd/C (10%) in THF/MeOH (1/2, 6 mL) was stirred under H$_2$ balloon pressure for 4 h. Filtered off the solid and removed the solvents in vacuo to afford the product as a colorless solid (6.7 mg, 84%). $^1$H NMR (400 MHz, CHLOROFORM-D) δ ppm 1.21-1.62 (m, 4 H) 1.75 (s, 2 H) 1.85-2.12 (m, 4 H) 2.86-2.96 (m, 3 H) 3.08-3.87 (m, 17 H) 4.08-4.42 (m, 1 H) 4.52-4.71 (m, J=14.86 Hz, 1 H) 7.31-7.65 (m, 5 H) 7.75-8.05 (m, 2 H) LC-MS (retention time: 3.08 ; MS m/z 621 (M+H).

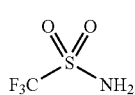

346

-continued

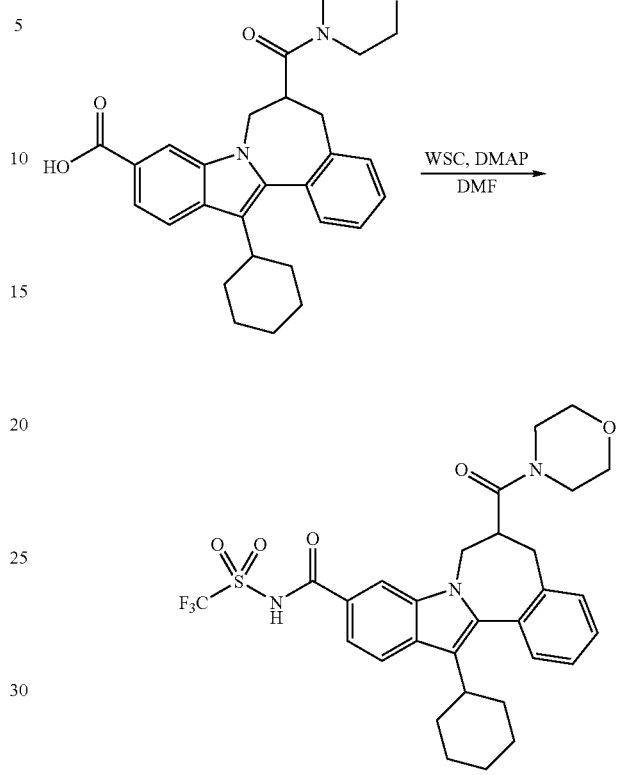

A mixture of trifluoromethanesulfonamide (49 mg, 0.33 mmol), acid (31 mg, 0.07 mmol), DMAP (40 mg, 0.33 mmol), N1-((ethylimino)methylene)-N3,N3-dimethylpropane-1,3-diamine hydrochloride (31 mg, 0.16 mmol) in DMF (1.5 mL) was stirred o/n and purified by prep HPLC to afford the product as a glass (4.2 mg, 10%). LC-MS (retention time: 3.09; MS m/z 604 (M+H).

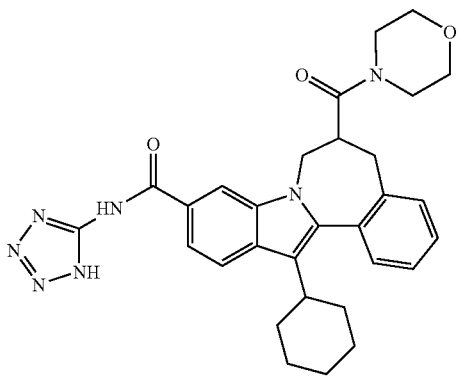

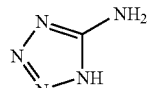

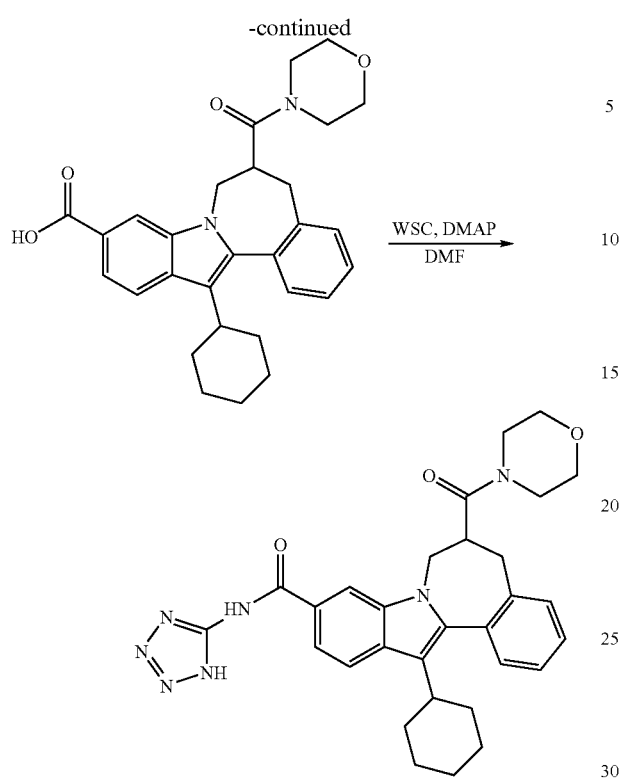

A mixture of (1H-tetrazol-5-amine (45 mg, 0.53 mmol), acid (25 mg, 0.05 mmol), DMAP (100 mg, 0.82 mmol), N1-((ethylimino)methylene)-N3,N3-dimethylpropane-1,3-diamine hydrochloride (80 mg, 0.16 mmol) in DMF (1.5 mL) was stirred o/n and purified by prep HPLC to afford the product as a glass (3.1 mg, 11%). $^1$H NMR (400 MHz, CHLOROFORM-D) δ ppm 1.16-1.59 (m, 4 H) 1.59-1.82 (m, 2 H) 1.82-2.18 (m, 4 H) 2.84-3.00 (m, 4 H) 3.44-3.94 (m, 8 H) 4.18-4.37 (m, 2 H) 4.86 (d, J=15.36 Hz, 2 H) 7.30-7.54 (m, 5 H) 7.77-7.91 (m, J=7.30 Hz, 1 H) 8.45 (s, 1 H); LC-MS (retention time: 2.80 MS m/z 540 (M+H).

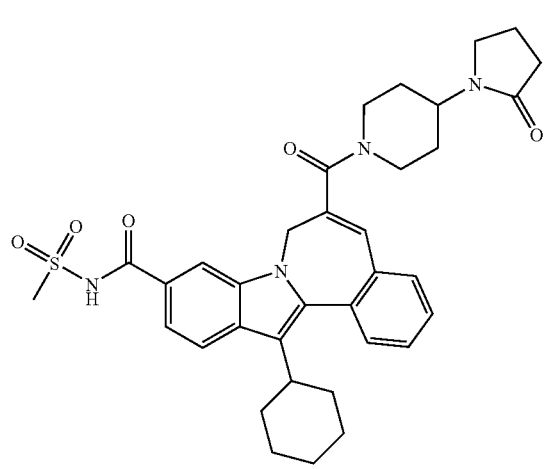

13-Cyclohexyl-N-(methylsulfonyl)-6-[4-(2-oxopyrrolidin-1-yl)piperidine-1-carbonyl]-7H-indolo[2,1-a][2]benzazepine-10-carboxamide. LS/MS: m/e 629 (MH$^+$); $^1$H NMR (400 MHz, CHLOROFORM-D) δ ppm 1.17-1.54 (m, 5 H) 1.64 (s, 2 H) 1.71-1.83 (m, 2 H) 2.01 (s, 6 H) 2.36-2.47 (m, 2 H) 2.83 (d, J=4.28 Hz, 2 H) 3.21-3.53 (m, 6 H) 3.47 (s, 3 H) 3.48 (s, 3 H) 3.92-4.10 (m, 1 H) 4.37 (s, 1 H) 5.02-5.23 (m, 1 H) 6.86 (s, 1 H) 7.36-7.63 (m, 5 H) 7.91 (d, J=8.56 Hz, 1 H) 8.18 (s, 1H).

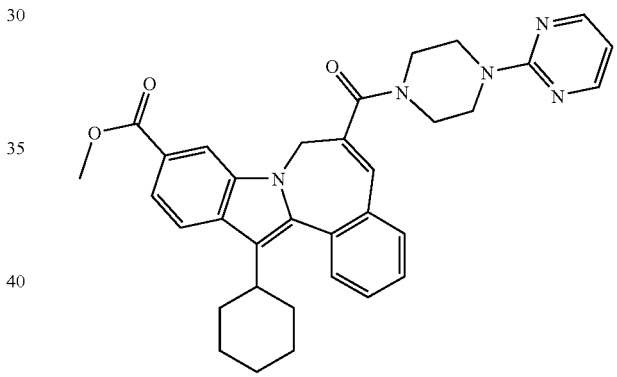

To a stirred solution of methyl 7H-indolo[2,1-a][2]benzazepine-10-carboxylate, 13-cyclohexyl, 6-carboxylic acid (150 mg, 0.36 mmol), 2-(piperazin-1-yl)pyrimidine (63 mg, 0.38 mmol) and triethylamine (0.10 mL) in DMF (2 mL) was added HATU (160 mg, 0.42 mmol). The reaction mixture was stirred at rt for 15 min., diluted with H2O (~4 mL) and the solids were collected by filtration washed with H$_2$O and dried under vacuum overnight to yield 7H-indolo[2,1-a][2]benzazepine-10-carboxylic acid, 13-cyclohexyl-6-[[4-(2-pyrimidinyl)-1-piperazinyl]carbonyl]-, methyl ester (168 mg, 0.30 mmol, 83%) as a yellow solid. $^1$H NMR (500 MHz, CDCl$_3$) δ 8.28 (d, J=4.9 Hz, 2H), 8.16 (br s, 1H), 7.89 (d, J=8.6 Hz, 1H), 7.74 (dd, J=8.6 Hz, 1H), 7.59 (dd, J=7.6, 1.5 Hz, 1H), 7.52-7.45 (m, 2H), 7.40 (dd, J=7.3, 1.5 Hz, 1H), 7.25 (s, 1H), 6.51 (t, J=4.9 Hz, 1H), 5.15 (br s, 1H), 4.43(br s, 1H), 3.91 (s, 3H), 3.80-3.29 (m, 8H), 2.91-2.82 (m, 1H), 2.17-1.14 (m, 10H). LCMS: m/e 562 (M+H)+, ret time 2.07 min, column A, 2 minute gradient.

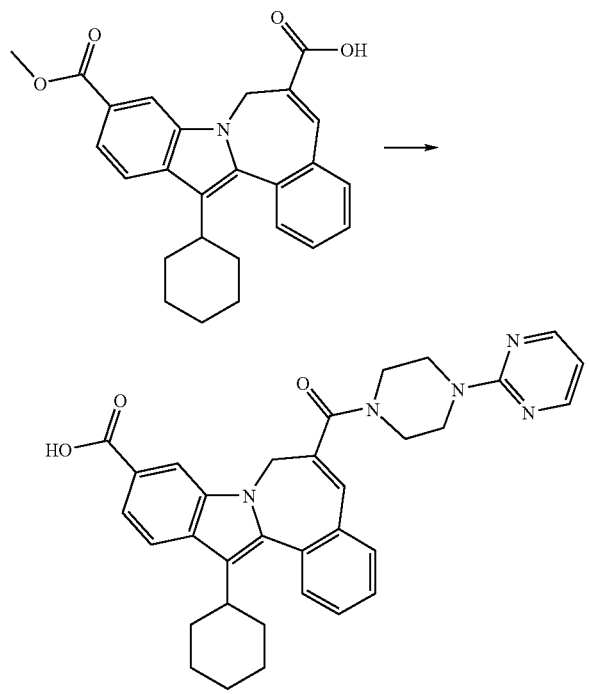

To a stirred solution of methyl 7H-indolo[2,1-a][2]benzazepine-10-carboxylate, 13-cyclohexyl, 6-carboxylic acid (200 mg, 0.48 mmol), 2-(piperazin-1-yl)pyrimidine (95 mg, 0.58 mmol) and triethylamine (0.20 mL, 1.45 mmol) in DMF (3 mL) was added HATU (220 mg, 0.58 mmol). The reaction mixture was stirred at rt for 2 h, diluted with H2O (~6 mL) and the solids were collected by filtration, washed with H2O, dissolved into MeOH//THF (1:1, 4 mL) and treated with 1M aqueous NaOH (0.60 mL). The reaction mixture was stirred and heated at 80° C. with microwave irradiation for 20 min in a sealed tube, additional 1 M aqueous NaOH (0.10 mL.) was added and the reaction was reheated at 80° C. for 10 min. The clear solution was diluted with H2O (1 mL), neutralized with 1M aqueous HCl (0.70 mL) and concentrated to remove organic solvents. The resultant solids were collected by filtration, washed with H2O and dried under vacuum to yield 7H-indolo[2,1-a][2]benzazepine-10-carboxylic acid, 13-cyclohexyl-6-[[4-(2-pyrimidinyl)-1-piperazinyl]carbonyl] (125 mg, 0.23 mmol, 48%) as a light yellow solid. LCMS: m/e 548 (M+H)+, ret time 1.52 min, column A, 2 minute gradient.

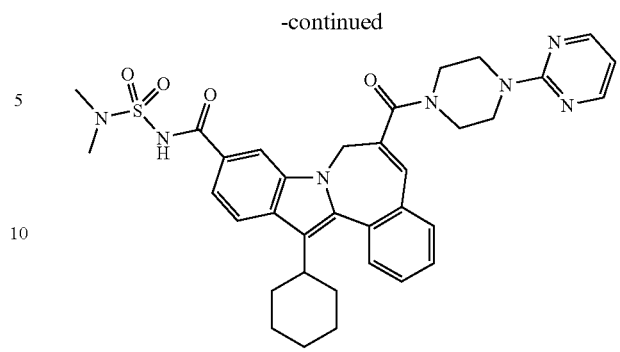

-continued

To a stirred solution of 7H-indolo[2,1-a][2]benzazepine-10-carboxylic acid, 13-cyclohexyl-6-[[4-(2-pyrimidinyl)-1-piperazinyl]carbonyl] (125 mg, 0.23 mmol), N,N-dimethylsulfamide (140 mg, 1.14 mmol) and DMAP (140 mg, 1.14 mmol) in dimethylacetamide (2 mL) was added 1-(3-dimethylaminopropyl)-3-ethylcarbodiimide hydrochloride (175 mg, 0.91 mmol). The reaction solution was stirred at 50° C. overnight, concentrated, purified by preparative HPLC (MeOH/2O with NH4OAc buffer) and repurified by preparative HPLC (MeOH/2O with TFA buffer) to yield 7H-indolo[2,1-a][2]benzazepine-10-carboxamide, 13-cyclohexyl-N-[(dimethylamino)sulfonyl]-6-[[4-(2-pyrimidinyl)-1-piperazinyl]carbonyl] (44 mg, 0.067 mol, 29%) as a yellow solid. $^1$H NMR (500 MHz, CDCl$_3$) δ 9.23 (br s, 1H), 8.43 (d, J=4.9 Hz, 2H), 8.04 (s, 1H), 7.92 (d, J=8.5 Hz, 1H), 7.60 (br d, J=8.5 Hz, 1H), 7.54-7.45 (m, 3H), 7.42 (br d, J=7.6 Hz, 1H), 6.92 (s, 1H), 6.68 (t, J=4.9 Hz, 1H), 5.16 (br s, 1H), 4.41 (br s, 1H), 3.88-3.46 (m, 8H), 3.03 (s, 6H), 2.90-2.81 (m, 1H), 2.16-1.13 (m, 10H). LCMS: m/e 654 (M+H)+, ret time 2.87 min, column B, 2 minute gradient.

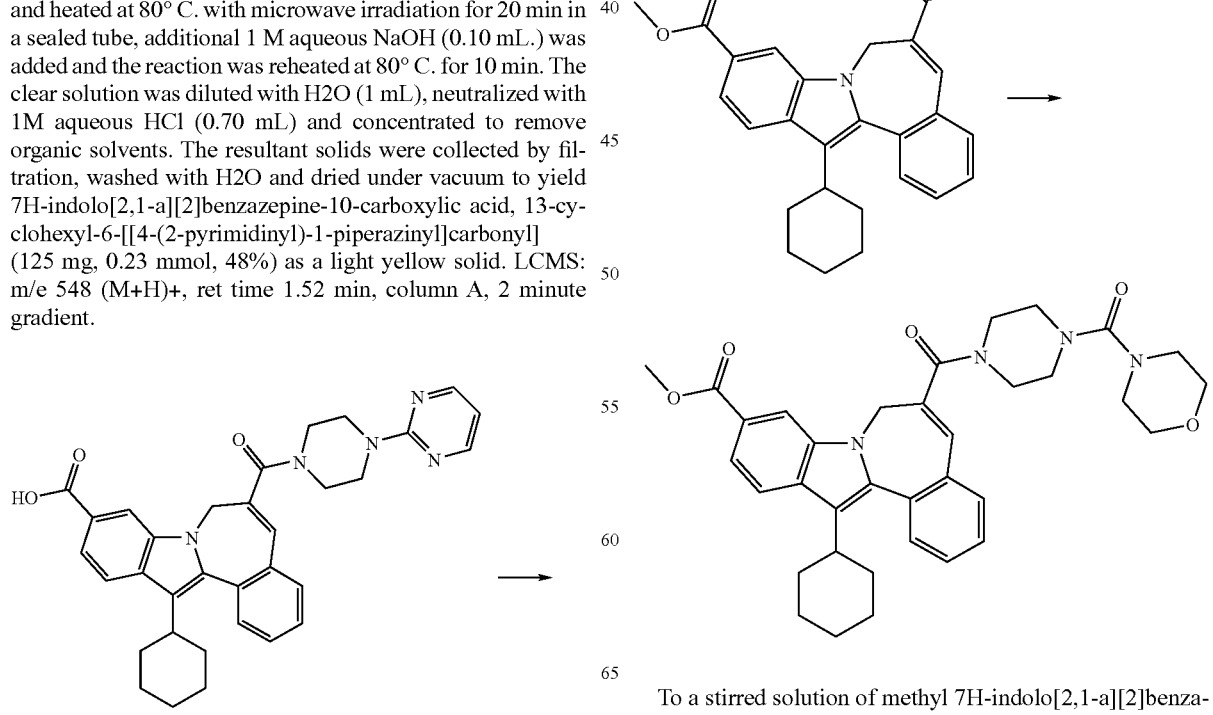

To a stirred solution of methyl 7H-indolo[2,1-a][2]benzazepine-10-carboxylate, 13-cyclohexyl, 6-carboxylic acid (150 mg, 0.36 mmol), 2-(piperazin-1-yl)pyrimidine (76 mg, 0.38 mmol) and triethylamine (0.10 mL) in DMF (2 mL) was added HATU (160 mg, 0.42 mmol). The reaction mixture was stirred at rt for 15 min., diluted with H2O (~4 mL) and the solids were collected, by filtration washed with H2O and dried under vacuum overnight to yield 7H-indolo[2,1-a][2]benzazepine-10-carboxylic acid, 13-cyclohexyl-6-[[4-(4-morpholinylcarbonyl)-1-piperazinyl]carbonyl]-, methyl ester (170 mg, 0.30 mmol, 83%) as a yellow solid. $^1$H NMR (500 MHz, CDCl$_3$) δ 8.15 (s, 1H), 7.88 (d, J=8.5 Hz, 1H), 7.74 (br d, J=8.5 Hz, 1H), 7.58 (br d, J=7.6 Hz, 1H), 7.52-7.44 (m, 2H), 7.39 (br d, J=7.3 Hz, 1H), 6.85 (s, 1H), 5.12(br s, 1H), 4.40 (br s, 1H), 3.94 (s, 3H), 3.72-3.01 (m, 8H), 3.63 (dd, J=4.9, 4.3 Hz, 4H), 3.20 (dd, J=4.9, 4.3 Hz, 4H), 2.88-2.81 (m, 1H), 2.16-1.15 (m, 10H). LCMS: m/e 597 (M+H)+, ret time 1.82 min, column A, 2 minute gradient.

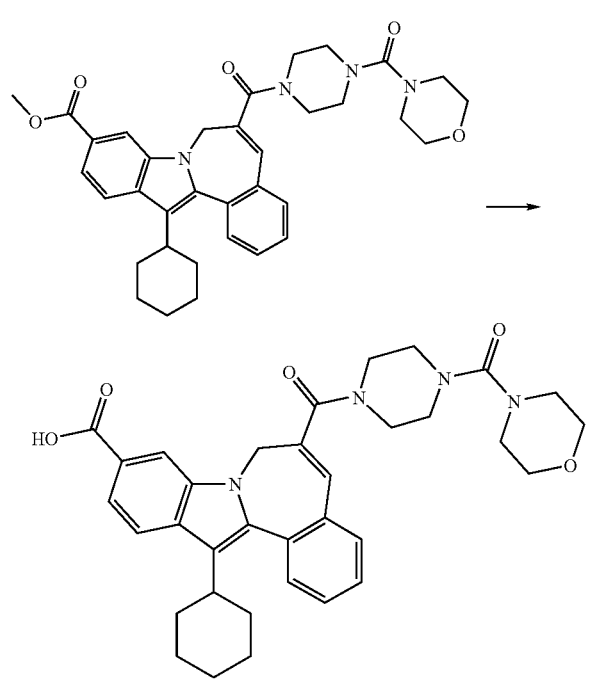

To a solution of 7H-indolo[2,1-a][2]benzazepine-10-carboxylic acid, 13-cyclohexyl-6-[[4-(4-morpholinylcarbonyl)-1-piperazinyl]carbonyl]-, methyl ester (142 mg, 0.24 mmol) in MeOH/THF (1:1, 2 mL) was added 1N aqueous NaOH (0.36 mL, 0.36 mmol). The reaction solution was stirred at rt for 1h, and then at 80° C. for 20 min. The reaction was cooled to rt, diluted with H2O (~2 mL), neutralized with 1N aqueous HCl (0.36 mL, 0.36 mmol) and concentrated to removed organic solvents. The solids were collected by filtration, flushed with water, dissolved into MeOH and purified by preparative HPLC (MeOH/H2O with NH4OAc buffer) to yield 7H-indolo[2,1-a][2]benzazepine-10-carboxylic acid, 13-cyclohexyl-6-[[4-(4-morpholinylcarbonyl)-1-piperazinyl]carbonyl] (78 mg, 0.13 mmol, 56%) as a yellow solid. $^1$H NMR (500 MHz, DMSO-d6) δ 8.19 (s, 1H), 7.89 (d, J=8.6 Hz, 1H), 7.63 (dd, J=8.6, 1.5 Hz, 1H), 7.61-7.53 (m, 4H), 7.02 (s, 1H), 5.18 (br s, 1H), 4.26 (br s, 1H), 3.56 (dd, J=4.9, 4.3 Hz, 4H), 3.53-3.47 (m, 4H), 3.19-3.13 (m, 4H), 3.14 (dd, J=4.9, 4.3 Hz, 4H), 2.84-2.76 (m, 1H), 2.12-1.99 (m, 3H), 1.75-1.10 (m, 7H). LCMS: m/e 583 (M+H)+, ret time 1.28 min, column A, 2 minute gradient.

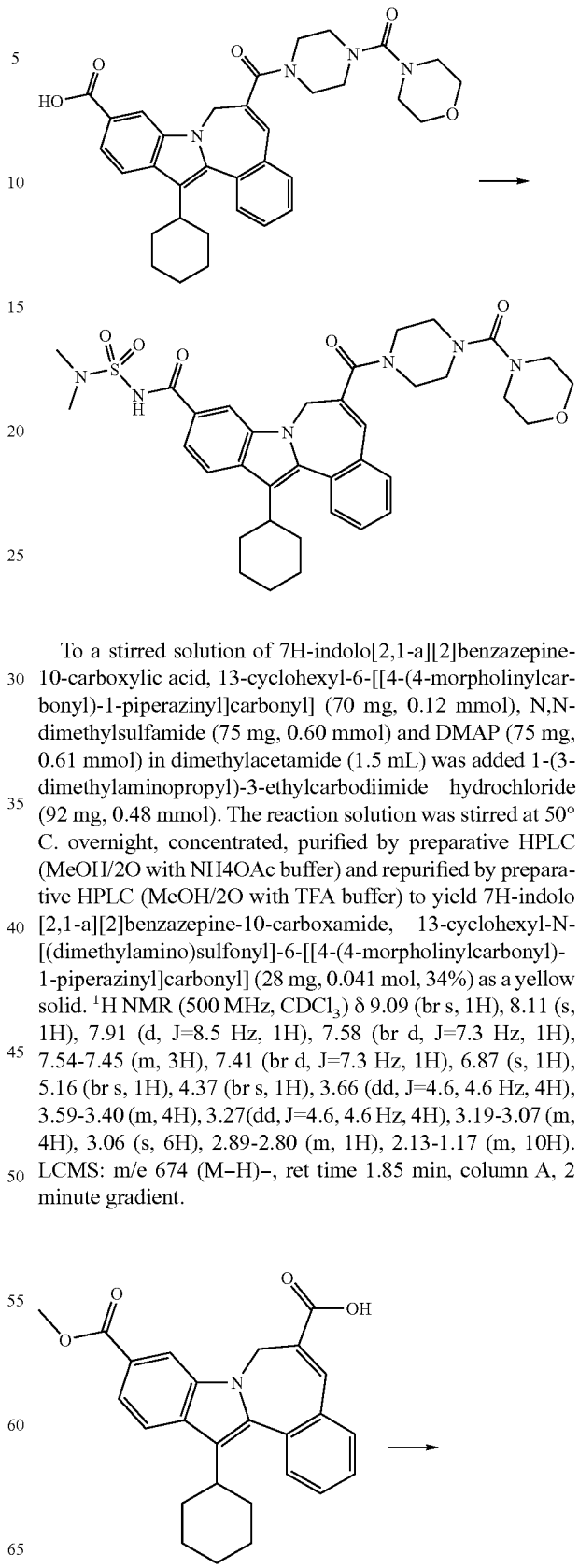

To a stirred solution of 7H-indolo[2,1-a][2]benzazepine-10-carboxylic acid, 13-cyclohexyl-6-[[4-(4-morpholinylcarbonyl)-1-piperazinyl]carbonyl] (70 mg, 0.12 mmol), N,N-dimethylsulfamide (75 mg, 0.60 mmol) and DMAP (75 mg, 0.61 mmol) in dimethylacetamide (1.5 mL) was added 1-(3-dimethylaminopropyl)-3-ethylcarbodiimide hydrochloride (92 mg, 0.48 mmol). The reaction solution was stirred at 50° C. overnight, concentrated, purified by preparative HPLC (MeOH/2O with NH4OAc buffer) and repurified by preparative HPLC (MeOH/2O with TFA buffer) to yield 7H-indolo[2,1-a][2]benzazepine-10-carboxamide, 13-cyclohexyl-N-[(dimethylamino)sulfonyl]-6-[[4-(4-morpholinylcarbonyl)-1-piperazinyl]carbonyl] (28 mg, 0.041 mol, 34%) as a yellow solid. $^1$H NMR (500 MHz, CDCl$_3$) δ 9.09 (br s, 1H), 8.11 (s, 1H), 7.91 (d, J=8.5 Hz, 1H), 7.58 (br d, J=7.3 Hz, 1H), 7.54-7.45 (m, 3H), 7.41 (br d, J=7.3 Hz, 1H), 6.87 (s, 1H), 5.16 (br s, 1H), 4.37 (br s, 1H), 3.66 (dd, J=4.6, 4.6 Hz, 4H), 3.59-3.40 (m, 4H), 3.27(dd, J=4.6, 4.6 Hz, 4H), 3.19-3.07 (m, 4H), 3.06 (s, 6H), 2.89-2.80 (m, 1H), 2.13-1.17 (m, 10H). LCMS: m/e 674 (M−H)−, ret time 1.85 min, column A, 2 minute gradient.

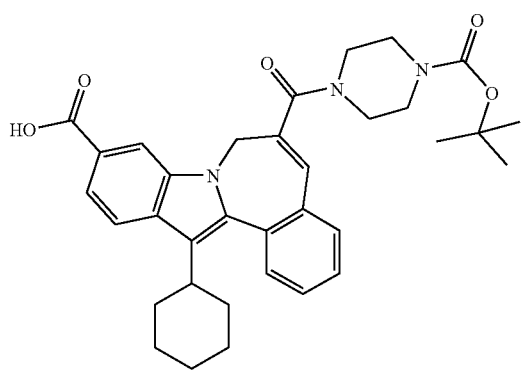

To a stirred solution of methyl 7H-indolo[2,1-a][2]benzazepine-10-carboxylate, 13-cyclohexyl, 6-carboxylic acid (470 mg, 1.13 mmol), tert-butyl piperazine-1-carboxylate (250 mg, 1.36 mmol) and triethylamine (0.30 mL) in DMF (5 mL) was added HATU (520 mg, 1.36 mmol). The reaction mixture was stirred at rt for 1 h, diluted with H2O (~6 mL) and extracted with EtOAc (2×10 mL). The combined organics were washed with brine (10 mL), dried (MgSO4), filtered and concentrated. The residue was dissolved into MeOH//THF (1:1, 10 mL) and treated with 1M aqueous NaOH (1.4 mL). The reaction mixture was stirred and heated at 80° C. with microwave irradiation for 30 min in a sealed tube, additional 1M aqueous NaOH (0.50 mL.) was added and the reaction was reheated at 80° C. for 15 min. The clear solution was diluted with H2O (10 mL), neutralized with 1M aqueous HCl (1.9 mL) and concentrated to remove organic solvents. The resultant solids were collected by filtration, washed with H2O, dried under vacuum and purified by preparative HPLC (MeOH/H2O with NH4OAc buffer) to yield 7H-indolo[2,1-a][2]benzazepine-10-carboxylic acid, 13-cyclohexyl-6-[[4-[(1,1-dimethylethoxy)carbonyl]-1-piperazinyl]carbonyl] (335 mg, 0.59 mmol, 43%) as a yellow solid. $^1$H NMR (500 MHz, CD$_3$OD) δ 8.23 (s, 1H), 7.92 (d, J=8.5 Hz, 1H), 7.75 (dd, J=8.5, 1.2 Hz, 1H), 7.65 (br d, J=6.4 Hz, 1H), 7.60-7.53 (m, 3H), 7.03 (s, 1H), 5.18 (br s, 1H), 4.43 (br s, 1H), 3.42-3.25 (m, 8H), 2.95-2.86 (m, 1H), 2.21-1.19 (m, 10H). LCMS: m/e 568 (M−H)−, ret time 1.36 min, column D, 2 minute gradient.

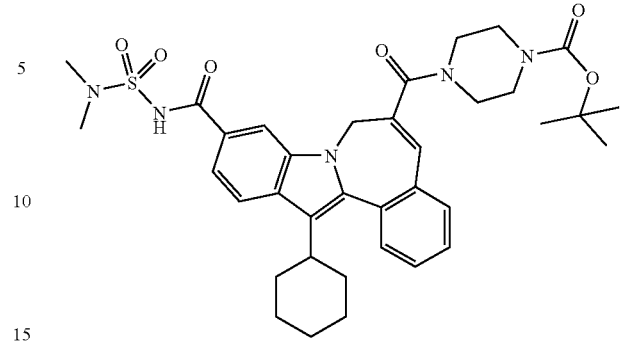

To a stirred solution of 7H-indolo[2,1-a][2]benzazepine-10-carboxylic acid, 13-cyclohexyl-6-[[4-[(1,1-dimethylethoxy)carbonyl]-1-piperazinyl]carbonyl] (100 mg, 0.18 mmol), N,N-dimethylsulfamide (110 mg, 0.89 mmol) and DMAP (110 mg, 0.90 mmol) in dimethylacetamide (2 mL) was added 1-(3-dimethylaminopropyl)-3-ethylcarbodiimide hydrochloride (135 mg, 0.71 mmol). The reaction solution was stirred at 50° C. overnight, concentrated, purified by preparative HPLC (MeOH/2O with NH4OAc buffer) to yield 1-piperazinecarboxylic acid, 4-[[13-cyclohexyl-10-[[[(dimethylamino)sulfonyl]amino]carbonyl]-7H-indolo[2,1-a][2]benzazepin-6-yl]carbonyl]-, 1,1-dimethylethyl ester (49 mg, 0.073 mol, 40%) as a yellow solid. $^1$H NMR (500 MHz, CDCl$_3$) δ 8.10 (s, 1H), 7.91 (d, J=8.6 Hz, 1H), 7.58 (br d, J=7.6 Hz, 1H), 7.63-7.46 (m, 3H), 7.40 (br d, J=7.3 Hz, 1H), 6.87 (s, 1H), 5.15 (br s, 1H), 4.37 (br s, 1H), 3.56-3.22 (m, 8H), 3.06 (s, 6H), 2.89-2.81 (m, 1H), 2.15-1.15 (m, 10H), 1.44 (s, 9H). LCMS: m/e 676 (M+H)+, ret time 2.05 min, column B, 2 minute gradient.

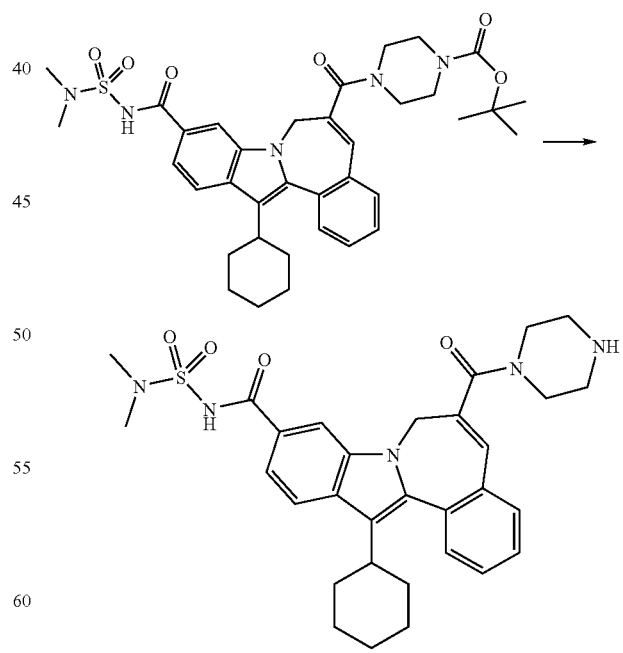

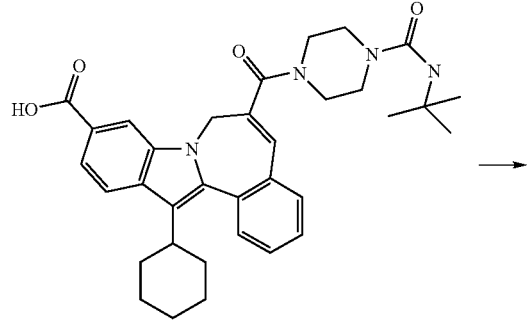

Trifluoroacetic acid (1.5 mL) was added dropwise to a stirred solution of 1-piperazinecarboxylic acid, 4-[[13-cyclohexyl-10-[[[(dimethylamino)sulfonyl]amino]carbonyl]-7H-indolo[2,1-a][2]benzazepin-6-yl]carbonyl]-, 1,1-dimethylethyl ester (77 mg. 0.11 mmol) in CH2Cl2 (1.5 mL). The reaction solution was stirred 2 h, concentrated and the residue was purified by preparative HPLC (MeOH/H2O with TFA buffer) to yield 7H-indolo[2,1-a][2]benzazepine-10-carboxamide, 13-cyclohexyl-N-[(dimethylamino)sulfonyl]-6-(1-piperazinylcarbonyl) (37 mg, 0.06 mmol, 56%) as a yellow solid. ¹H NMR (500 MHz, CDCl₃) δ 9.36 (br s, 1H), 8.25 (s, 1H), 7.87 (d, J=8.2 Hz, 1H), 7.61-7.39 (m, 5H), 6.91 (s, 1H), 5.16 (br s, 1H), 4.31 (br s, 1H), 3.88-3.39 (m, 8H), 2.98 (s, 6H), 2.89-2.75 (m, 1H), 2.11-1.13 (m, 10H). LCMS: m/e 576 (M+H)+, ret time 2.39 min, column B, 3 minute gradient.

dol-2(1H)-yl)carbonyl] (71 mg total, 27 mg from solids and 44 mg from mother liquor, 0.09 mol, 36% over 3 steps) as a yellow solid. ¹H NMR (500 MHz, CDCl₃) δ 8.96 (br s, 1H), 8.15 (s, 1H), 7.94 (d, J=8.6 Hz, 1H), 7.83 (s, 1H), 7.62 (d, J=7.6 Hz, 1H), 7.57-7.38 (m, 7H), 6.96 (s, 1H), 5.20 (br s, 1H), 4.44 (br s, 1H), 4.38-3.70 (m, 3H), 3.23-2.66 (m, 5H), 2.98 (s, 6H), 2.11-1.17 (m, 10H). LCMS: m/e 676 (M–H)–, ret time 1.61 min, column A, 2 minute gradient.

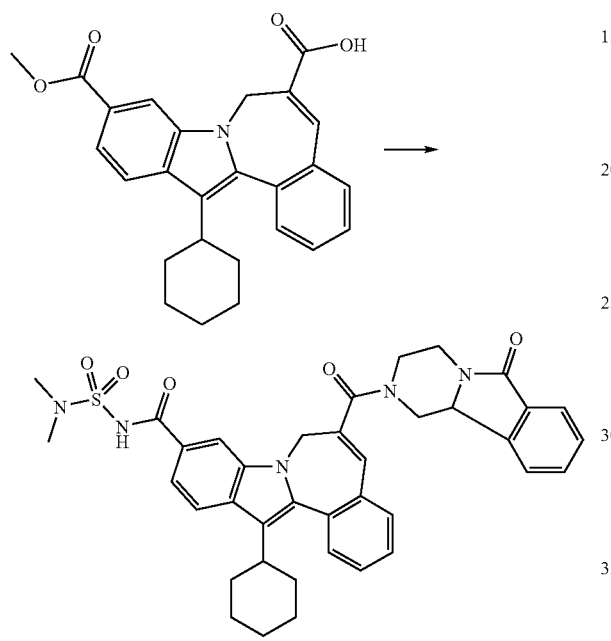

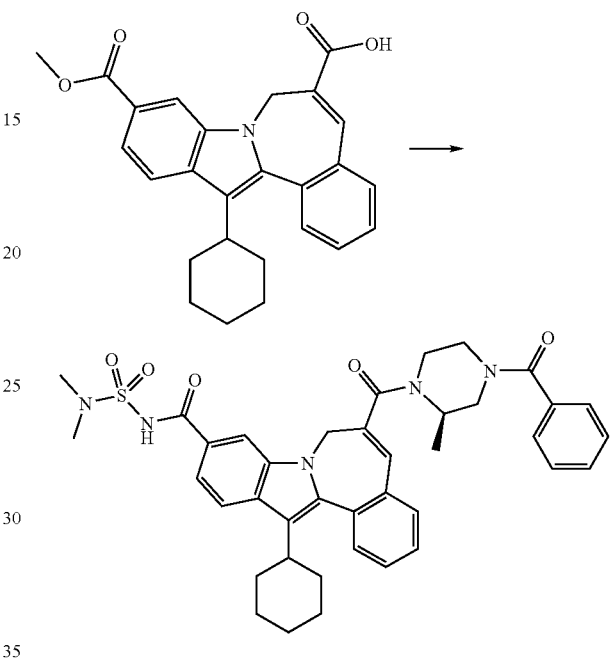

To a stirred solution of methyl 7H-indolo[2,1-a][2]benzazepine-10-carboxylate, 13-cyclohexyl, 6-carboxylic acid (200 mg, 0.48 mmol), 1,2,3,4-tetrahydropyrazino[2,1-a]isoindol-6(10bH)-one hydrochloride (130 mg, 0.58 mmol) and triethylamine (0.20 mL) in DMF (3 mL) was added HATU (220 mg, 0.58 mmol). The reaction mixture was stirred at rt for 1 h, diluted with H2O (~5 mL) stirred for 30 min, and the solids (288 mg) collected by filtration and flushed with H2O. The crude solids were dissolved into MeOH/THF (1:1, 4 mL) and treated with 1M aqueous NaOH (0.75 mL). The reaction mixture was stirred and heated at 80° C. with microwave irradiation for 15 min in a sealed tube. The clear solution was diluted with H2O (5 mL), neutralized with 1M aqueous HCl (0.75 mL) and concentrated to remove organic solvents. The resultant solids (247 mg) were collected by filtration and washed with H2O. To a stirred solution of the crude solids (150 mg, 61% of total collected, ~0.25 mmol), N,N-dimethylsulfamide (155 mg, 1.25 mmol) and DMAP (150 mg, 1.25 mmol) in dimethylacetamide (2 mL) was added 1-(3-dimethylaminopropyl)-3-ethylcarbodiimide hydrochloride (190 mg, 1.0 mmol). The reaction solution was stirred at 50° C. for 2h, diluted with water (5 mL) and the resulting solids were collected by filtration. The mother liquor was concentrated and the solids and the mother liquor were independently purified by preparative HPLC (MeOH/2O with NH4OAc buffer) to yield 7H-indolo[2,1-a][2]benzazepine-10-carboxamide, 13-cyclohexyl-N-[(dimethylamino)sulfonyl]-6-[(3,4,6,10b-tetrahydro-6-oxopyrazino[2,1-a]isoin- To a stirred solution of methyl 7H-indolo[2,1-a][2]benzazepine-10-carboxylate, 13-cyclohexyl, 6-carboxylic acid (200 mg, 0.48 mmol), 3(R)-methyl-1-benzoylpiperazine hydrochloride (130 mg, 0.58 mmol) and triethylamine (0.20 mL) in DMF (3 mL) was added HATU (220 mg, 0.58 mmol). The reaction mixture was stirred at rt for 1 h, diluted with H2O (~5 mL) stirred for 30 min, and the solids (290 mg) collected by filtration and flushed with H2O. The crude solids were dissolved into MeOH/THF (1:1, 4 mL) and treated with 1M aqueous NaOH (0.75 mL). The reaction mixture was stirred and heated at 80° C. with microwave irradiation for 15 min in a sealed tube. The clear solution was diluted with H2O (5 mL), neutralized with 1M aqueous HCl (0.75 mL) and concentrated to remove organic solvents. The resultant solids (257 mg) were collected by filtration and washed with H2O. To a stirred solution of the crude solids (145 mg, 56% of total collected, ~0.25 mmol), N,N-dimethylsulfamide (155 mg, 1.25 mmol) and DMAP (150 mg, 1.25 mmol) in dimethylacetamide (2 mL) was added 1-(3-dimethylaminopropyl)-3-ethylcarbodiimide hydrochloride (190 mg, 1.0 mmol). The reaction solution was stirred at 50° C. for 2 h, diluted with water (5 mL) and the resulting solids were collected by filtration. The mother liquor was concentrated and the solids and the mother liquor were independently purified by preparative HPLC (MeOH/2O with NH4OAc buffer) to yield 7H-indolo[2,1-a][2]benzazepine-10-carboxamide, 6-[[(2R)-4-benzoyl-2-methyl-1-piperazinyl]carbonyl]-13-cyclohexyl-N-[(dimethylamino)sulfonyl] (79 mg total, 52 mg from solids and 27 mg from mother liquor, 0.11 mol, 42% over 3 steps) as a yellow solid. ¹H NMR (500 MHz, CDCl₃) δ 8.21 (s, 1H), 7.88 (d, J=8.6 Hz, 1H), 7.60-7.44 (m, 4H), 7.43-7.32

(m, 6H), 6.82 (br s, 1H), 5.21 (br s, 1H), 4.34 (br s, 1H), 4.58-3.34 (m, 7H), 3.06 (s, 6H), 2.87-2.78(m, 1H), 2.12-1.00 (m, 13H). LCMS: m/e 692 (M−H)−, ret time 1.69 min, column A, 2 minute gradient.

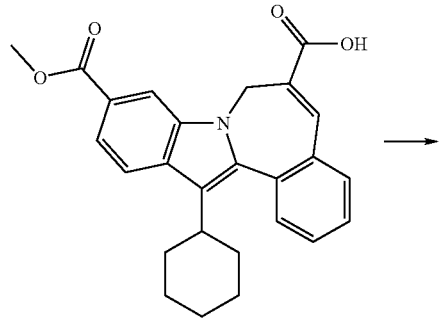

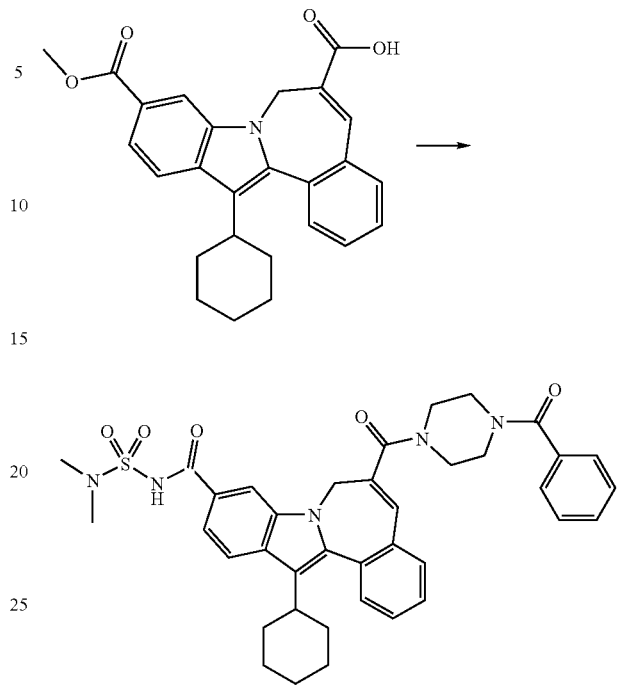

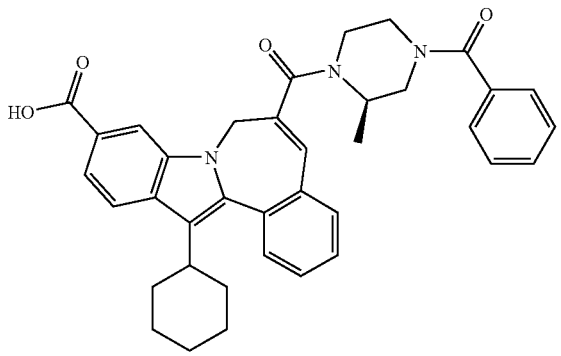

To a stirred solution of methyl 7H-indolo[2,1-a][2]benzazepine-10-carboxylate, 13-cyclohexyl, 6-carboxylic acid (200 mg, 0.48 mmol), 3(R)-methyl-1-benzoylpiperazine hydrochloride (130 mg, 0.58 mmol) and triethylamine (0.20 mL) in DMF (3 mL) was added HATU (220 mg, 0.58 mmol). The reaction mixture was stirred at rt for 1 h, diluted with H2O (~5 mL) stirred for 30 min, and the solids (290 mg) collected by filtration and flushed with H2O. The crude solids were dissolved into MeOH/THF (1:1, 4 mL) and treated with 1M aqueous NaOH (0.75 mL). The reaction mixture was stirred and heated at 80° C. with microwave irradiation for 15 min in a sealed tube. The clear solution was diluted with H2O (5 mL), neutralized with 1M aqueous HCl (0.75 mL) and concentrated to remove organic solvents. The resultant solids were collected by filtration, washed with H2O and dried under vacuum to yield 7H-indolo[2,1-a][2]benzazepine-10-carboxylic acid, 6-[[(2R)-4-benzoyl-2-methyl-1-piperazinyl]carbonyl]-13-cyclohexyl (257 mg, 0.44 mol, 90%). LCMS: m/e 586 (M−H)−, ret time 1.48 min, column A, 2 minute gradient.

To a stirred solution of methyl 7H-indolo[2,1-a][2]benzazepine-10-carboxylate, 13-cyclohexyl, 6-carboxylic acid (200 mg, 0.48 mmol), 3(R)-methyl-1-benzoylpiperazine hydrochloride (130 mg, 0.58 mmol) and triethylamine (0.20 mL) in DMF (3 mL) was added HATU (220 mg, 0.58 mmol). The reaction mixture was stirred at rt for 1 h, diluted with H2O (~5 mL) stirred for 30 min, and the solids (290 mg) collected by filtration and flushed with H2O. The crude solids were dissolved into MeOH/THF (1:1, 4 mL) and treated with 1M aqueous NaOH (0.75 mL). The reaction mixture was stirred and heated at 80° C. with microwave irradiation for 15 min in a sealed tube. The clear solution was diluted with H2O (5 mL), neutralized with 1M aqueous HCl (0.75 mL) and concentrated to remove organic solvents. The resultant solids (257 mg) were collected by filtration and washed with H2O. To a stirred solution of the crude solids (145 mg, 56% of total collected, ~0.25 mmol), N,N-dimethylsulfamide (155 mg, 1.25 mmol) and DMAP (150 mg, 1.25 mmol) in dimethylacetamide (2 mL) was added 1-(3-dimethylaminopropyl)-3-ethylcarbodiimide hydrochloride (190 mg, 1.0 mmol). The reaction solution was stirred at 50° C. for 2 h, diluted with water (5 mL) and the resulting solids were collected by filtration. The mother liquor was concentrated and the solids and the mother liquor were independently purified by preparative HPLC (MeOH/2O with NH4OAc buffer) to yield 7H-indolo[2,1-a][2]benzazepine-10-carboxamide, 6-[(4-benzoyl-1-piperazinyl)carbonyl]-13-cyclohexyl-N-[(dimethylamino)sulfonyl] (79 mg total, 52 mg from solids and 27 mg from mother liquor, 0.11 mol, 42% over 3 steps) as a yellow solid. $^1$H NMR (500 MHz, CDCl$_3$) δ 9.07 (br s, 1H), 8.10 (s, 1H), 7.91 (d, J=8.2 Hz, 1H), 7.59 (d, J=8.6 Hz, 1H), 7.54-7.45 (m, 3H), 7.44-7.35 (m, 6H), 6.89 (s, 1H), 5.16 (br s, 1H), 4.36 (br s, 1H), 3.63-3.37 (m, 8H), 3.07 (s, 6H), 2.90-2.79 (m, 1H), 2.12-1.14 (m, 10H). LCMS: m/e 678 (M−H)−, ret time 1.66 min, column A, 2 minute gradient.

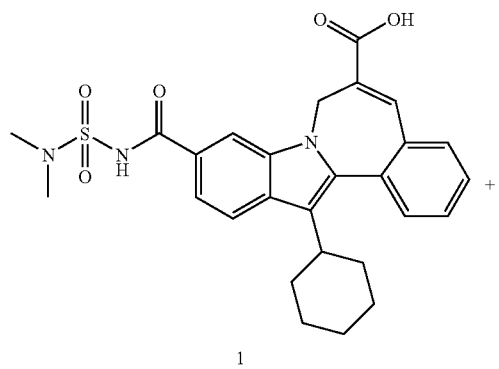

1

$HNR_1R_2$ $\xrightarrow{\text{TBTU}}$
$\text{DMF}$

2

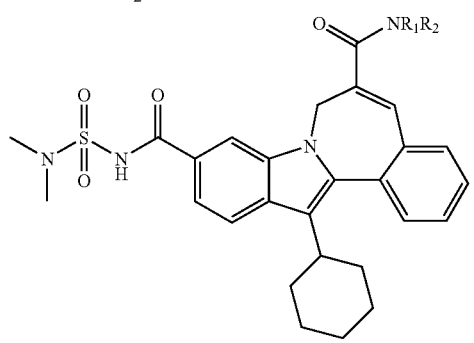

2

To 0.05 mmol of 1 in 1.0 mL of anhydrous N,N-Dimethylformamide (DMF) in a 3 dram vial equipped with a teflon lined screw cap was added 0.15 mmol (3 eq.) of 2-(1H-Benzotriazole-1-yl)-1,1,3,3,-Tetramethyluronium Tetrafluoroborate (TBTU) in 1.0 mL of anhydrous DMF followed by the addition of 0.1 mmol (2 eq.) of amine 2 in 1.0 mL of anhydrous DMF. The reaction was shaken on an Innova 2000 orbital shaker at 240 rpm overnight at room temperature. The reaction volume was then reduced to a total volume of 2.0 mL in a Savant Speedvac and the crude product was purified using a Dionex ELSD triggered preparative HPLC employing acetonitrile/water and 10 mM ammonium acetate buffer with a Sunfire, C18, 21.2 mm×150 mm, 10 μm column at a focused gradient flow rate of 20 mL/min. Postpurification LC/MS data was obtained on a Waters analytical LC/Micromass Platform LC (ESI+) at 220 nm using the following set of conditions: Sunfire 5 μm C18, 4.6×100 mm column, with a focused gradient of 50-95% B (B=HPLC grade acetonitrile), (A=HPLC grade water with 0.1% ammonium acetate), in 7 minutes with a 1 minute hold. All NMR spectra were recorded at room temperature using a Bruker DRX500 spectrometer. The NMR solvent used was 1:1 (by volume) methyl alcohol-$d_4$ ($CD_3OD$)/chloroform-d ($CDCl_3$). Chemical shifts were reported in ppm relative to $CD_3OD$. Coupling constants were reported in hertz. Peak multiplicity was reported using the following abbreviations: s (singlet), d (doublet), t (triplet), m (multiplet), br (broad).

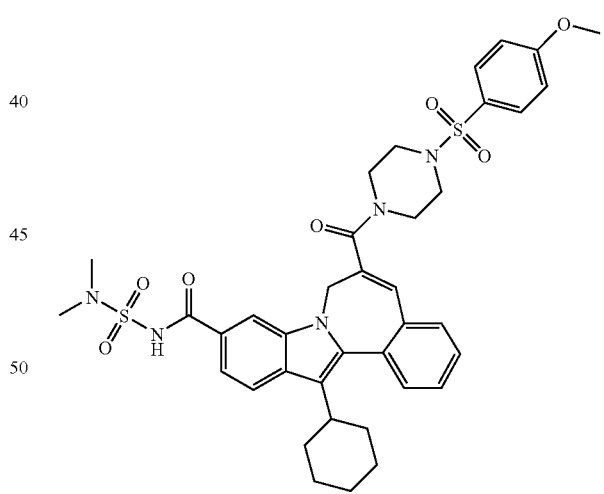

1-piperazinecarboxylic acid, 4-[[13-cyclohexyl-10-[[[(dimethylamino)sulfonyl]amino]carbonyl]-7H-indolo[2,1-a][2]benzazepin-6-yl]carbonyl]-3-methyl-, 1,1-dimethylethyl ester. $^1$H NMR: δ 0.75 (m, 4H), 1.26 (m, 1H), 1.00 (s, 9H), 1.06 (m, 3H), 1.32 (m, 2H), 1.50 (m, 1H), 1.63 (m, 3H), 2.44 (m, 2H), 2.59 (s, 6H), 2.74 (m, 1H), 2.89 (m, 3H), 3.42 (br s, 1H), 3.54 (br s, 1H), 3.96 (m, 1H), 4.67 (m, 1H), 6.47 (br s, 1H), 7.05 (m, 1H), 7.06-7.12 (m, 2H), 7.19 (m, 2H), 7.49 (d, 1H, J=8.71 Hz), 7.63 (br s, 1H). LC/MS: m/z 690.41, Rf 6.1 min., 100% purity.

7H-indolo[2,1-a][2]benzazepine-10-carboxamide, 13-cyclohexyl-N-[(dimethylamino)sulfonyl]-6-[[4-[(4-methoxyphenyl)sulfonyl]-1-piperazinyl]carbonyl]-. $^1$H NMR: δ 1.22 (m, 2H), 1.35-1.50 (br m, 3H), 1.73 (m, 2H), 1.73 (m, 2H), 1.92 (m, 1H), 2.03 (m, 3H), 2.86 (m, 1H), 2.92 (m, 2H), 2.99 (m, 1H), 3.00 (s, 6H), 3.63 (m, 2H), 3.73 (s, 2H), 3.87 (s, 3H), 4.30 (m, 1H), 5.02 (m, 1H), 6.89 (s, 1H), 7.04 (d, 1H, J=8.94 Hz), 7.42-7.51 (br m, 3H), 7.55 (m, 2H), 7.63 (d, 2H, J=8.71 Hz), 7.88 (d, 1H, J=8.47 Hz), 7.97 (s, 1H). LC/MS: m/z 746.27, Rf 4.5 min., 100% purity.

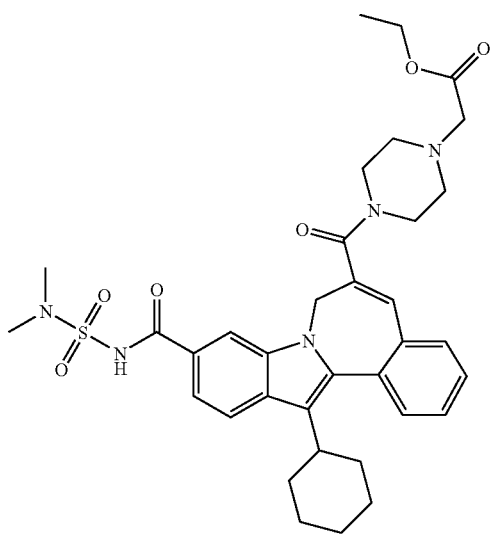

1-piperazineacetic acid, 4-[[13-cyclohexyl-10-[[[(dimethylamino)sulfonyl]amino]carbonyl-7H-indolo[2,1-a][2]benzazepin-6-yl]carbonyl]-, ethyl ester. $^1$H NMR: δ 1.04 (m, 1H), 1.19 (m, 2H), 1.26 (t, 3H, J=7.10 Hz), 1.43 (m, 3H), 1.71 (m, 2H), 1.89 (m, 1H), 2.01 (m, 2H), 2.81 (m, 1H), 2.95 (m, 2H), 2.98 (s, 6H, ), 3.40 (m, 1H), 3.68 (br s, 1H), 4.03 (br s, 2H), 4.26 (m, 2H), 4.32 (m, 1H), 4.75 (m, 2H), 5.09 (m, 1H), 7.03 (s, 1H), 7.04-7.52 (br m, 5H), 7.87 (d, 1H, J=8.48 Hz), 8.02 (s, 1H). LC/MS: m/z 662.35, Rf 3.0 min., 98.6% purity.

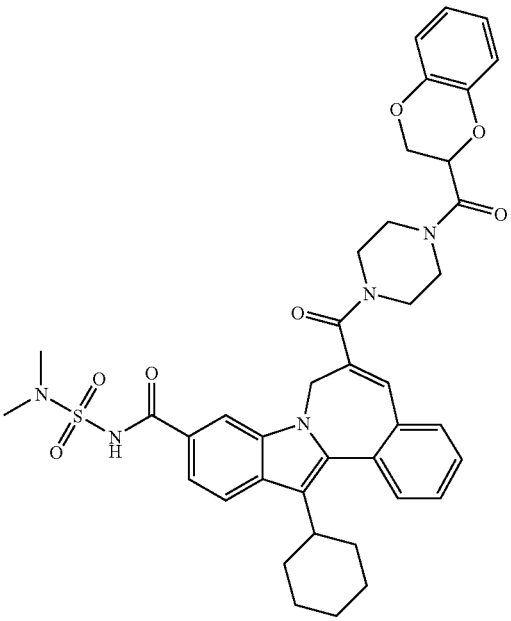

7H-indolo[2,1-a][2]benzazepine-10-carboxamide, 13-cyclohexyl-6-[[4-[(2,3-dihydro-1,4-benzodioxin-2-yl)carbonyl]-1-piperazinyl]carbonyl]-N-[(dimethylamino)sulfonyl]-. $^1$H NMR: δ 0.88 (m, 1H), 1.26 (m, 2H), 1.41-1.55 (m, 3H), 1.77 (m, 2H), 2.05 (m, 1H), 2.09 (m, 2H), 2.90 (m, 1H), 3.04 (m, 6H), 3.47 (m, 1H), 3.63 (m, 2H), 3.75 (m, 3H), 3.86 (m, 1H), 4.29 (m, 1H), 4.42 (m, 2H), 4.95 (m, 1H), 5.15 (m, 1H), 6.84 (m, 3H), 7.00 (s, 1H), 7.52 (m, 2H), 7.59 (m, 4H), 7.92 (d, 2H, J=8.02 Hz), 8.07 (s, 1H). LC/MS: m/z 738.36, Rf 3.9 min., 99.4% purity.

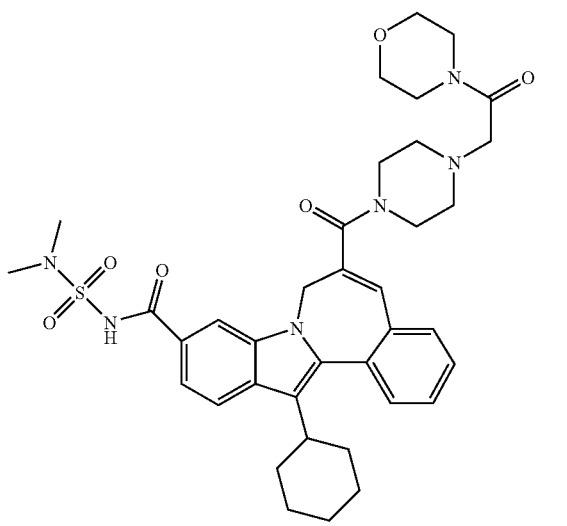

7H-indolo[2,1-a][2]benzazepine-10-carboxamide, 13-cyclohexyl-N-[(dimethylamino)sulfonyl]-6-[[4-[2-(4-morpholinyl)-2-oxoethyl]-1-piperazinyl]carbonyl]-. $^1$H NMR: δ 1.22 (m, 2H), 1.38 (m, 3H), 1.73 (m, 2H), 2.01 (m, 4H), 2.98 (m, 2H), 3.01 (m, 7H), 3.38 (m, 1H), 3.55 (m, 3H), 3.56 (m, 3H), 3.68 (m, 2H), 3.71 (s, 6H), 4.39 (m, 1H), 5.09 (m, 1H), 6.96 (br s, 1H), 7.52 (m, 5H), 7.89 (d, 1H, J=8.47 Hz), 8.06 (s, 1H). LC/MS: m/z 703.39, Rf 1.8 min., 100% purity.

7H-indolo[2,1-a][2]benzazepine-10-carboxamide, 13-cyclohexyl-N-[(dimethylamino)sulfonyl]-6-[[4-(2-methoxyethyl)-1-piperazinyl]carbonyl]-. $^1$H NMR: δ 0.91 (m, 1H), 1.29 (m, 3H), 1.45 (m, 4H), 1.81 (m, 2H), 2.05 (m, 6H), 1.36 (s, 1H), 2.92 (m, 1H), 3.07 (m, 3H), 3.22 (m, 2H), 3.41 (m, 3H), 3.72 (m, 3H), 3.78 (m, 3H), 4.46 (m, 1H), 5.21 (m, 1H), 7.08 (s, 1H), 7.61 (m, 5H), 7.97 (d, 1H, J=8.47 Hz), 8.13 (s, 1H). LC/MS: m/z 634.30, Rf 2.2 min., 99.5% purity.

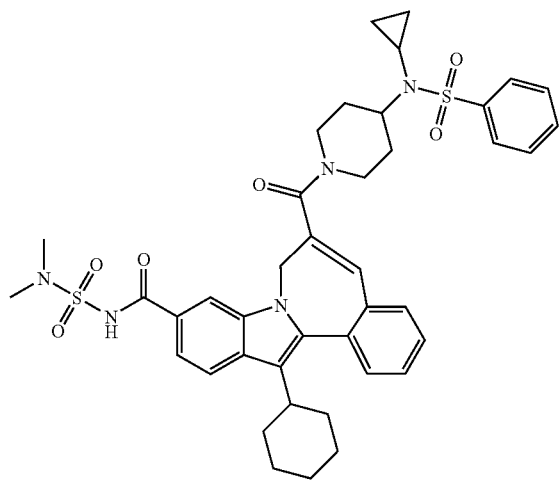

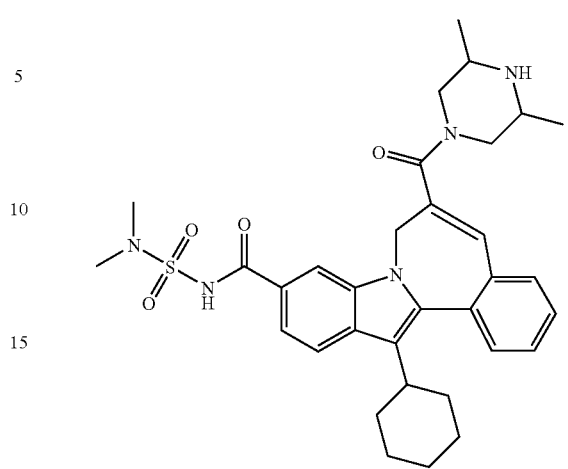

7H-indolo[2,1-a][2]benzazepine-10-carboxamide, 13-cyclohexyl-6-[[4-[cyclopropyl(phenylsulfonyl)amino]-1-piperidinyl]carbonyl]-N-[(dimethylamino)sulfonyl]-. $^1$H NMR: δ 0.78 (m, 4H), 1.23 (m, 2H), 1.40 (m, 2H), 1.57 (m, 1H), 1.77 (m, 4H), 2.02 (m, 5H), 2.82 (m, 2H), 3.00 (s, 6H), 3.72 (m, 4H), 3.95 (m, 1H), 4.36 (m, 1H), 5.07 (m, 1H), 6.88 (br s, 1H), 7.56 (m, 8H), 7.80-7.89 (m, 3H), 8.03 (br s, 1H). LC/MS: m/z 770.36, Rf 5.0 min., 99.1% purity.

7H-indolo[2,1-a][2]benzazepine-10-carboxamide, 13-cyclohexyl-N-[(dimethylamino)sulfonyl]-6-[(3,5-dimethyl-1-piperazinyl)carbonyl]-. $^1$H NMR: δ 0.84 (m, 1H), 1.23 (m, 6H), 1.38 (m, 2H), 1.47 (m, 2H), 1.74 (m, 2H), 1.98 (m, 5H), 2.73 (m, 2H), 2.84 (m, 2H), 3.00 (s, 6H), 3.10 (m, 1H), 3.73 (s, 1H), 4.44 m, 1H), 5.06 (m, 1H), 6.91 (br s, 1H), 7.46-7.61 (br m, 5H), 7.91 (d, 1H, J=8.48 Hz), 8.07 (br s, 1H). LC/MS: m/z 604.26, Rf 1.8 min., 99.4% purity.

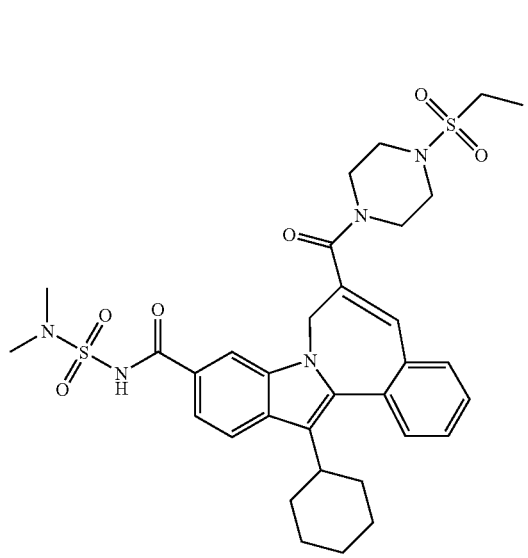

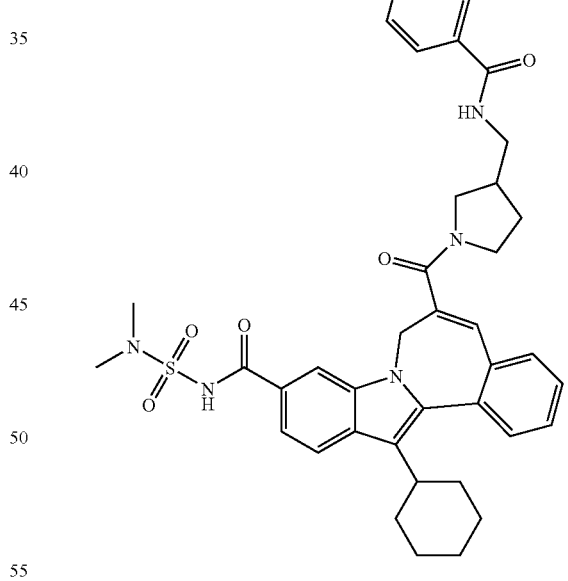

7H-indolo[2,1-a][2]benzazepine-10-carboxamide, 13-cyclohexyl-N-[(dimethylamino)sulfonyl]-6-[[4-(ethylsufonyl)-1-piperazinyl]carbonyl]-. $^1$H NMR: δ 0.90 (m, 1H), 1.29 (m, 2H), 1.36 (t, 3H, J=7.33 Hz), 1.45 (m, 3H), 1.80 (m, 2H), 2.08 (m, 4H), 2.91 (m, 3H), 3.07 (m, 3H), 3.37 (m, 6H), 3.42 (m, 2H), 3.78 (s, 1H), 4.46 (m, 1H), 5.14 (m, 1H), 6.98 (s, 1H), 7.59 (m, 3H), 7.66 (m, 2H), 7.98 (d, 1H, J=8.71 Hz), 8.13 (s, 1H). LC/MS: m/z 668.22, Rf 2.7 min., 100% purity.

7H-indolo[2,1-a][2]benzazepine-10-carboxamide, 6-[[3-[(benzoylamino)methyl]-1-pyrrolidinyl]carbonyl]-13-cyclohexyl-N-[(dimethylamino)sulfonyl]-. H), 1.46 (m, 3H), 1.80 (m, 2H), 2.07 (m, 2H), 2.11 (m, 3H), 2.69 (m, 1H), 2.91 (m, 1H), 3.06 (s, 6H), 3.61 (m, 4), 3.91 (m, 1H), 4.32 (m, 1H), 5.28 (m, 1H), 7.18 (m, 1H), 7.42 (m, 3H), 7.48 (m, 5H), 7.76 (m, 1H), 7.79 (d, 1H, J=7.33 Hz), 7.94 (m, 1H), 8.07 (m, 1H). LC/MS: m/z 694.32, Rf 3.0 min., 100% purity.

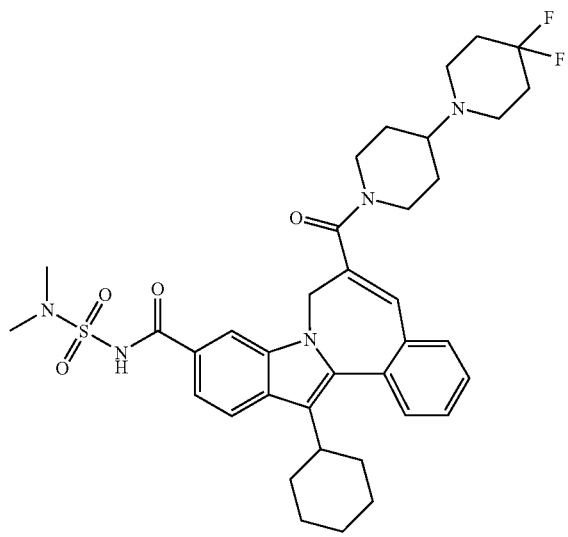

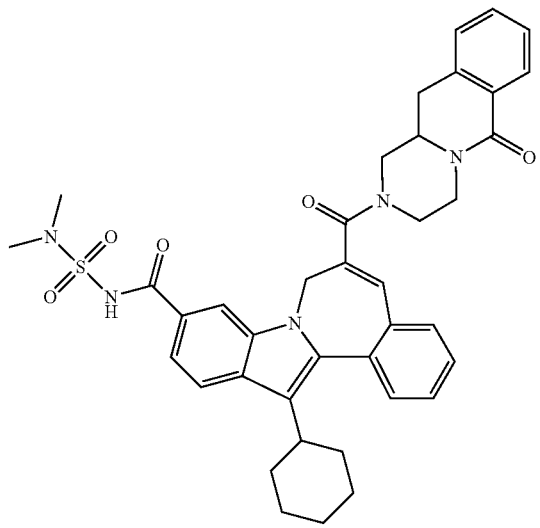

7H-indolo[2,1-a][2]benzazepine-10-carboxamide, 13-cyclohexyl-6-[(4,4-difluoro[1,4'-bipiperidin]-1'-yl)carbonyl]-N-[(dimethylamino)sulfonyl]-. ¹H NMR: δ 0.91 (m, 1H), 1.29 (m, 2H), 1.46 (m, 3H), 1.64 (m, 1H), 1.81 (m, 2H), 1.98 (m, 2H), 2.12 (m, 4H), 2.38 (m, 4H), 2.70 (s, 1H), 2.92 (m, 3H), 3.04 (m, 2H), 3.07 (s, 6H), 3.15 (m, 2H), 3.78 (s, 1H), 4.48 (m, 1H), 5.15 (m, 1H), 6.99 (m, 1H), 7.59 (m, 5H), 7.99 (d, 1H, J=8.48 Hz), 8.13 (s, 1H). LC/MS: m/z 694.34, Rf 3.8 min., 100% purity.

7H-indolo[2,1-a][2]benzazepine-10-carboxamide, 13-cyclohexyl-N-[(dimethylamino)sulfonyl]-6-[(1,3,4,6,11,11a-hexahydro-6-oxo-2H-pyrazino[1,2-b]isoquinolin-2-yl)carbonyl]-. ¹H NMR: δ 1.26 (m, 1H), 1.45 (m, 2H), 1.60 (m, 1H), 1.80 (m, 2H), 1.96 (m, 1H), 2.10 (m, 3H), 2.88 (m, 1H), 2.98 (m, 6H), 3.03 (m, 3H), 3.19 (m, 1H), 3.75 (m, 2H), 4.40 (m, 2H), 4.83 (m, 2H), 5.16 (m, 1H), 7.05 (m, 1H), 7.35 (m, 1H), 7.57 (m, 4H), 7.62 (m, 3H), 7.95 (m, 2H), 8.09 (br s, 1H). LC/MS: m/z 692.31, Rf 3.3 min., 100% purity.

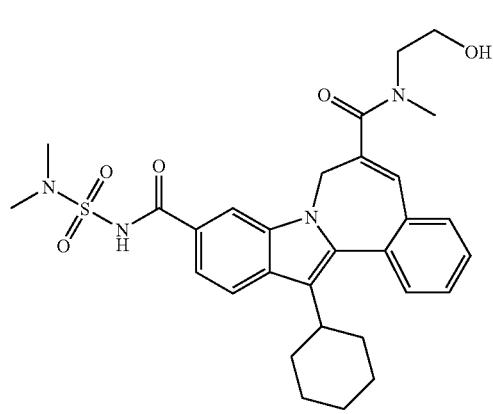

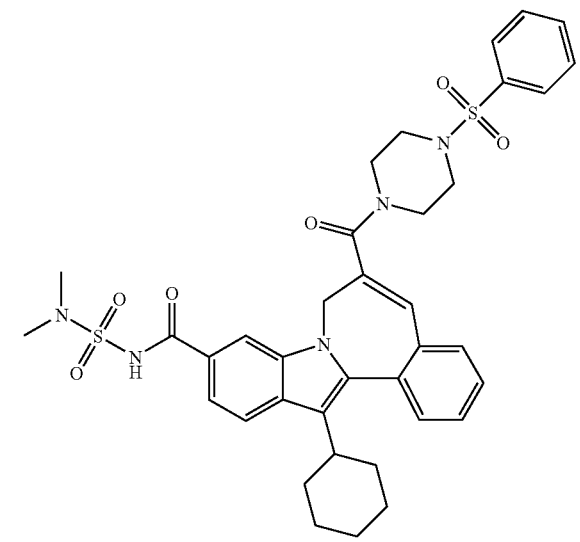

7H-indolo[2,1-a][2]benzazepine-6,10-dicarboxamide, 13-cyclohexyl-N¹⁰-[(dimethylamino)sulfonyl]-N6-(2-hydroxyethyl)-N6-methyl-. ¹H NMR: δ 1.29 (m, 1H), 1.50 (m, 3H), 1.80 (m, 2H), 1.98 (m, 1H), 2.08 (m, 3H), 2.92 (m, 1H), 3.10 (m, 8H), 3.58 (m, 1H), 3.71 (m, 3H), 3.78 (s, 1H), 3.82 (m, 1H), 4.43 (m, 1H), 5.17 (m, 1H), 7.11 (s, 1H), 7.53 (m, 3H), 7.66 (m, 2H), 7.95 (d, 1H, J=8.47 Hz), 8.10 (m, 1H). LC/MS: m/z 565.18, Rf 1.9 min., 100% purity.

7H-indolo[2,1-a][2]benzazepine-10-carboxamide, 13-cyclohexyl-N-[(dimethylamino)sulfonyl-6-[[4-(phenylsulfonyl)-1-piperazinyl]carbonyl]-. ¹H NMR: δ 1.20 (m, 1H), 1.40 (m, 3H), 1.76 (m, 2H), 1.92 (m, 1H), 2.04 (m, 3H), 2.82 (m, 2H), 2.99 (m, 2H), 3.01 (s, 6H), 3.65 (m, 3H), 3.72 (m, 2H), 4.30 (m, 1H), 5.05 (m, 1H), 6.89 (s, 1H), 7.43-7.56 (br m, 4H), 7.60 (m, 3H), 7.69 (m, 3H), 7.89 (d, 1H, J=8.47 Hz), 7.97 (s, 1H). LC/MS: m/z 716.30, Rf 4.1 min., 100% purity.

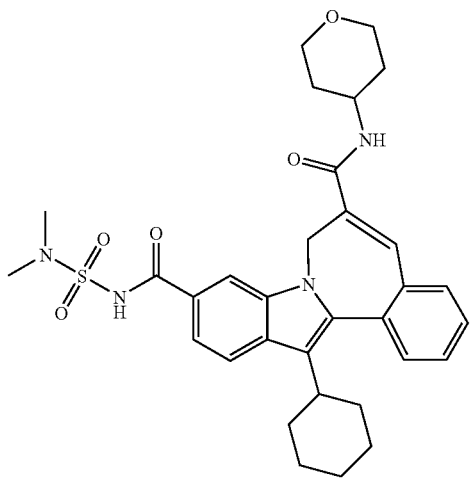

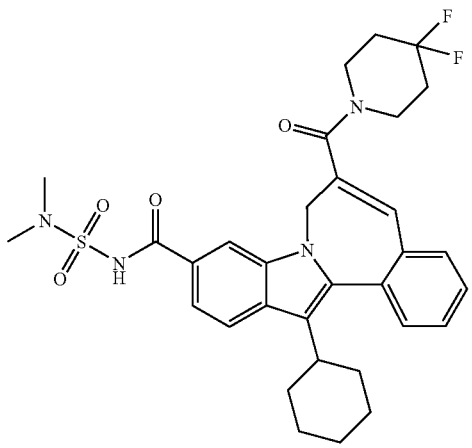

7H-indolo[2,1-a][2]benzazepine-6,10-dicarboxamide, 13-cyclohexyl-N[10]-[(dimethylamino)sulfonyl]-N[6]-(tetrahydro-2H-pyran-4-yl)-. $^1$H NMR: δ 1.24 (m, 2H), 1.51 (m, 3H), 1.63 (m, 1H), 1.77 (m, 2H), 1.94 (m, 2H), 2.06 (m, 2H), 2.65 (s, 1H), 2.87 (m, 1H), 3.04 (s, 6H), 3.51 (m, 3H), 4.01 (m, 3H), 4.14 (m, 1H), 5.61 (m, 1H), 7.53 (m, 4H), 7.60 (m, 2H), 7.89 (d, 1H, J=8.48 Hz), 8.10 (s, 1H). LC/MS: m/z 591.20, Rf 2.6 min., 100% purity.

7H-indolo[2,1-a][2]benzazepine-10-carboxamide, 13-cyclohexyl-6-[(4,4-difluoro-1-piperidinyl)carbonyl]-N-[(dimethylamino)sulfonyl]-. $^1$H NMR: δ 1.26 (m, 1H), 1.41 (m, 2H), 1.53 (m, 2H), 1.77 (m, 3H), 1.95 (m, 3H), 2.08 (m, 3H), 2.87 (m, 1H), 3.04 (s, 6H), 3.68 (m, 4H), 4.42 (m, 1H), 5.13 (m, 1H), 6.98 (s, 1H), 7.52 (m, 3H), 7.59 (m, 2H), 7.91 (d, 1H, J=8.47 Hz), 8.05 (s, 1H). LC/MS: m/z 611.24, Rf 4.0 min., 100% purity.

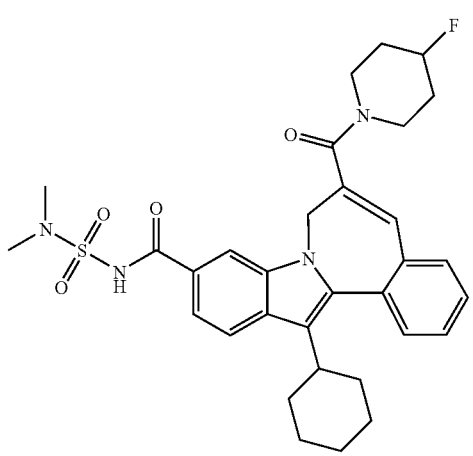

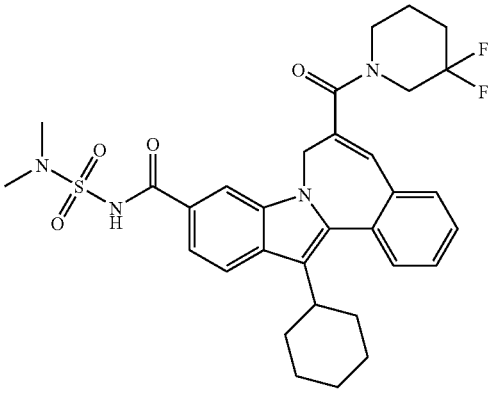

7H-indolo[2,1-a][2]benzazepine-10-carboxamide, 13-cyclohexyl-N-[(dimethylamino)sulfonyl]-6-[(4-fluoro-1-piperidinyl)carbonyl]-. $^1$H NMR: δ 1.23 (m, 1H), 1.45 (m, 3H), 1.74 (m, 3H), 1.83 (m, 1H), 1.92 (m, 1H), 2.05 (m, 3H), 2.86 (m, 1H), 3.02 (s, 6H), 3.54 (m, 2H), 3.72 (m, 3H), 4.38 (m, 1H), 4.89 (m, 1H), 5.08 (m, 1H), 6.95 (s, 1H), 7.51 (m, 3H), 7.59 (m, 2H), 7.90 (d, 1H, J=8.48 Hz), 8.04 (s, 1H). LC/MS: m/z 593.24, Rf 3.5 min., 100% purity.

7H-indolo[2,1-a][2]benzazepine-10-carboxamide, 13-cyclohexyl-6-[(3,3-difluoro-1-piperidinyl)carbonyl]-N-[(dimethylamino)sulfonyl]-. $^1$H NMR: δ 1.29 (m, 1H), 1.41 (m, 2H), 1.57 (m, 2H), 1.80 (m, 3H), 1.99 (m, 1H), 2.11 (m, 4H), 2.87 (m, 1H), 3.07 (s, 6H), 3.51 (m, 1H), 3.78 (m, 3H), 3.82 (m, 1H), 4.42 (m, 1H), 5.15 (m, 1H), 7.04 (s, 1H), 7.58 (m, 3H), 7.66 (m, 2H), 7.96 (d, 1H, J=8.71 Hz), 8.10 (s, 1H). LC/MS: m/z 611.25, Rf 4.0 min., 100% purity.

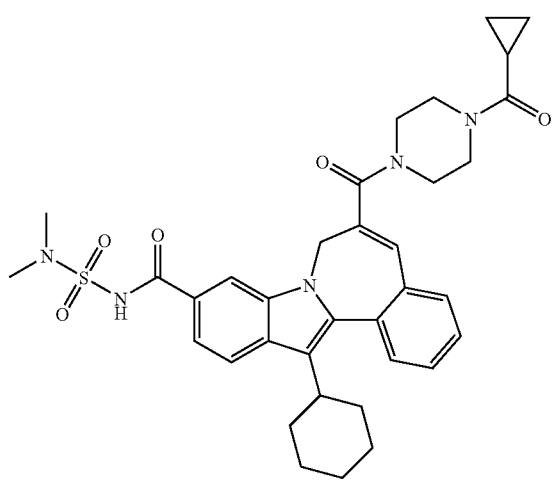

7H-indolo[2,1-a][2]benzazepine-10-carboxamide, 13-cyclohexyl-6-[[4-(cyclopropylcarbonyl)-1-piperazinyl]carbonyl]-N-[(dimethylamino)sulfonyl]-. $^1$H NMR: δ 0.85 (m, 2H), 0.94 (m, 2H), 1.26 (m, 1H), 1.48 (m, 3H), 1.80 (m, 3H), 1.98 (m, 1H), 2.09 (m, 3H), 2.89 (m, 1H), 3.04 (s, 6H), 3.58 (m, 3H), 3.75 (m, 5H), 4.42 (m, 1H), 5.15 (m, 1H), 7.02 (s, 1H), 7.56 (m, 3H), 7.63 (m, 2H), 7.94 (d, 1H, J=8.71 Hz), 8.09 (s, 1H). LC/MS: m/z 644.24, Rf 2.3 min., 99.3% purity.

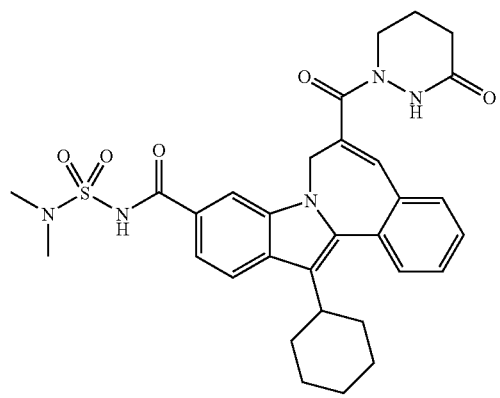

7H-indolo[2,1-a][2]benzazepine-10-carboxamide, 13-cyclohexyl-N-[(dimethylamino)sulfonyl]-6-[(tetrahydro-3-oxo-1(2H)-pyridazinyl)carbonyl]-. $^1$H NMR: (Bruker DPX-300 in CD$_3$OD) δ 1.43 (m, 4H), 1.76 (m, 2H), 1.92 (m, 3H), 2.08 (m, 3H), 2.25 (m, 1H), 2.38 (m, 1H), 2.86 (m, 1H), 3.01 (s, 6H), 3.59 (m, 1H), 3.72-3.88 (m, 1H), 4.36 (m, 1H), 5.26 (m, 1H), 7.18-7.26 (m, 1H), 7.52-7.62 (m, 5H), 7.92 (m, 1H), 8.12 (br s, 1H). LC/MS: m/z 590.34, Rf 1.97 min., 93% purity (Phenomenex 10 µm C18, 4.6×30 mm column; 2 min. gradient with a 1 minute hold employing 10-90% methanol/water/0.1% TFA).

The preparations in the following section uses the general protocols and procedures described below: The diversity amines (0.108 mmol, 1.3 equiv) were weighed directly into successive reactor vessels of a multiposition reactor. To each position in the reactor was then added the carboxylic acid template (500 uL of a 0.172 M stock solution in DMF, 0.086 mmol, 1.0 equiv) followed by 500 uL of a three-component stock solution in DMF containing EDC (0.108 mmol, 1.3 equiv), HOBt (0.108 mmol, 1.3 equiv), and N,N-diisopropylethylamine (0.430 mmol, 5.0 equiv). The reactions were capped with a septum and agitated overnight via orbital shaker at room temperature.

Purification was effected by injecting the reaction mixture directly onto a preparative LCMS system using one of the following conditions:

Analysis Conditions: Column: Waters SunFire Prep C18 OBD, 19×100 mm×5 um; Mobile Phase: (A) 10:90 methanol:water; (B) 90:10 methanol:water; Buffer: 0.1% TFA; Gradient Range: 40-100% B; Gradient Time: 10 min; Flow Rate: 20 mL/min; Analysis Time: 15 min; Detection: Detector 1: UV at 220 nm; Detector 2: MS (ESI+); Fraction Collection: WV-triggered; Fraction Drying: Savant Speedvac.

Analysis Conditions: Column: Phenomenex Luna C18(2), 4.6×50 mm×5 um; Mobile Phase: (A) 10:90 methanol:water; (B) 90:10 methanol:water; Buffer: 0.1% TFA; Gradient Range: 0-100% B; Gradient Time: 4 min; Flow Rate: 4 mL/min; Analysis Time: 5 min; Detection: Detector 1: UV at 220 nm; Detector 2: MS (ESI+); Detector 3: ELSD.

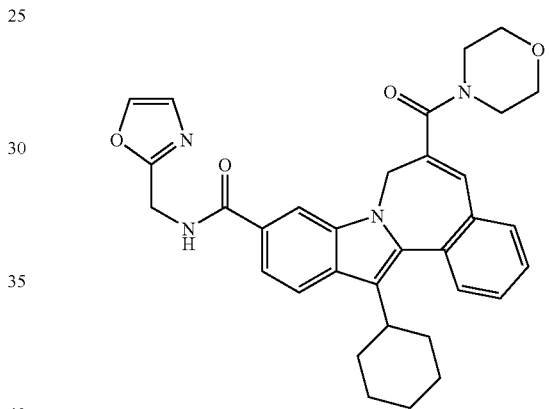

RT = 3.82 min
MS ion 551.34

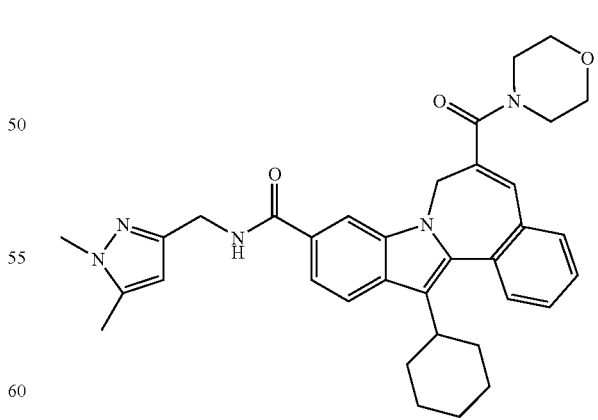

RT = 3.85 min
MS ion 578.59

-continued

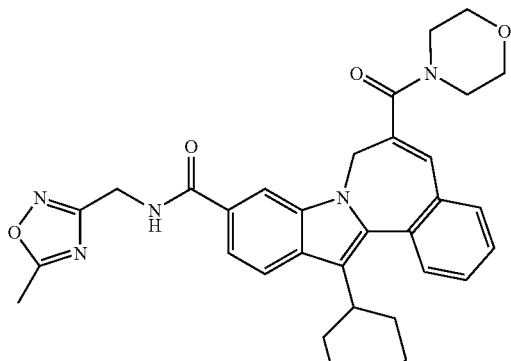

RT = 3.83 min
MS ion = 566.55

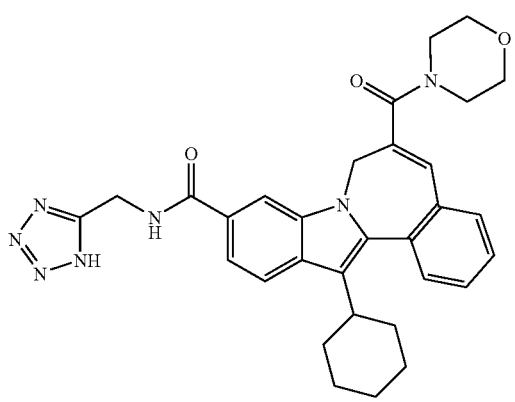

RT = 3.73 min
MS ion = 552.55

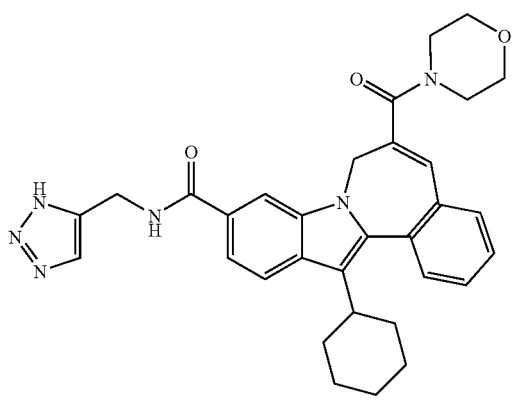

RT = 3.75 min
MS ion = 551.56

For the next set of procedures column 3 is defined as LCMS data:Gradient time: 2min; Flow rate: 4 mL/min; Stop time: Gradient time+1 minute; Starting conc: 0% B; Eluent A: 10% MeOH/90% H2O with 0.1% TFA; Eluent B: 90% MeOH/ 10% H2O with 0.1% TFA; Column 3: Phenomenex-luna 10μ 4.6×50 mm S10.

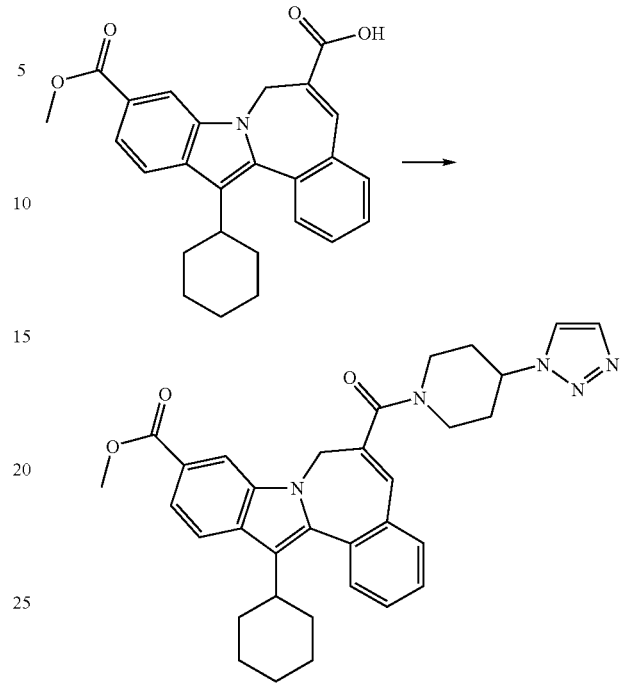

7H-indolo[2,1-a][2]benzazepine-10-carboxylic acid, 1 3-cyclohexyl-6-[[4-(1H-1,2,3-triazol-1-yl)piperidinyl]carbonyl], methyl ester. o a stirred solution of methyl 7H-indolo[2,1-a][2]benzazepine-10-carboxylate, 13-cyclohexyl, 6-carboxylic acid (50 mg, 0.12 mmol), 4-(1H-1,2,3-triazol-1-yl) piperidine (74 mg, 0.48 mmol) and DMAP (58 mg, 0.48 mmol) in DMF (2 mL) was added HATU (182 mg, 0.48 mmol). The reaction mixture was stirred at rt for 22 h, diluted with EtOAc (4 mL) and H2O (~4 mL). The organic phase was separated, dried over Na2SO4 and concentrated in vacuo. The residue was dissolved in methanol and purified using reverse phase prep-HPLC to yield 7H-indolo[2,1-a][2]benzazepine-10-carboxylic acid, 13-cyclohexyl-6-[[4-(1H-1,2,3-triazol-1-yl)piperidinyl]carbonyl], methyl ester. $^1$H NMR (500 MHz, CDCl$_3$) δ 8.28 (d, J=4.9 Hz, 2H), 8.16 (br s, 1H), 7.89 (d, J=8.6 Hz, 1H), 7.74 (dd, J=8.6 Hz, 1H), 7.59 (dd, J=7.6, 1.5 Hz, 1H), 7.52-7.45 (m, 2H), 7.40 (dd, J=7.3, 1.5 Hz, 1H), 7.25 (s, 1H), 6.51 (t, J=4.9 Hz, 1H), 5.15 (br s, 1 H), 4.43(br s, 1H), 3.91 (s, 3H), 3.80-3.29 (m, 8H), 2.91-2.82 (m, 1H), 2.17-1.14 (m, 10H). LCMS: m/e 550 (M+H)+, ret time 2.55 min, column 3, 2 minute gradient.

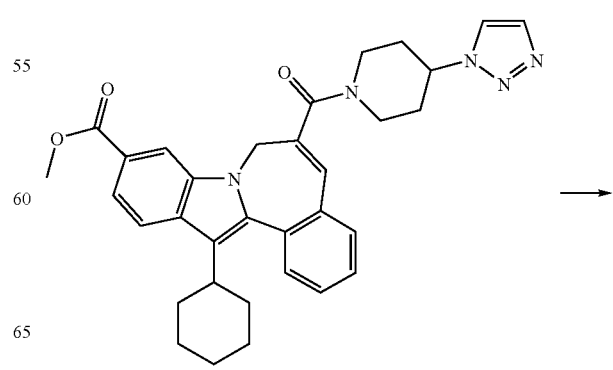

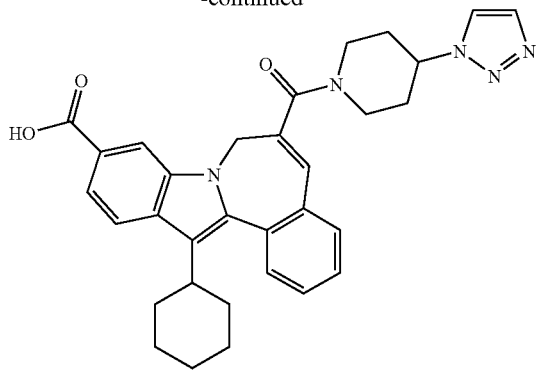

solution was stirred in a sealed tube under nitrogen at 50° C. overnight and purified by reverse phase prep-HPLC to yield 7H-indolo[2,1-a][2]benzazepine-10-carboxamide, 13-cyclohexyl-N-[(dimethylamino)sulfonyl]-6-[[4-(1H-1,2,3-triazol-1-yl)piperidinyl]carbonyl] as a pale yellow solid. $^1$H NMR (500 MHz, CDCl$_3$) δ 7.84 (br s, 1H), 7.92 (s, 1H), 7.87 (d, J=8.5 Hz, 1H), 7.60-7.42 (m, 6H), 6.87 (s, 1H), 5.39 (br s, 1H), 4.75 (br s, 1H), 4.35 (s, 1H), 4.20 (m, 4H), 3.08 (s, 6 H), 2.83 (m, 1H), 2.05-1.35 (m, 14H). LCMS: m/e 642 (M+H)+, ret time 2.18 min, column 3, 2 minute gradient.

7H-indolo[2,1-a][2]benzazepine-10-carboxylic acid, 13-cyclohexyl-6-[[4-(1H-1,2,3-triazol-1-yl)piperidinyl]carbonyl]. To a stirred solution of 7H-indolo[2,1-a][2]benzazepine-10-carboxylic acid, 13-cyclohexyl-6-[[4-(1H-1,2,3-triazol-1-yl)piperidinyl]carbonyl], methyl ester (10 mg, 0.018 mmol), in THF (1 mL) was added TMSSiOK (5 mg, 0.036 mmol). The reaction mixture was stirred at rt for 3.5 h, and purified using reverse phase prep-HPLC to afford 7H-indolo[2,1-a][2]benzazepine-10-carboxylic acid, 13-cyclohexyl-6-[[4-(1H-1,2,3-triazol-1-yl)piperidinyl]carbonyl] as a pale yellow solid. LCMS: m/e 536 (M+H)+, ret time 2.45 min, column 3, 2 minute gradient.

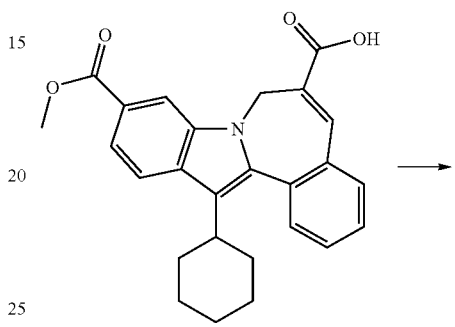

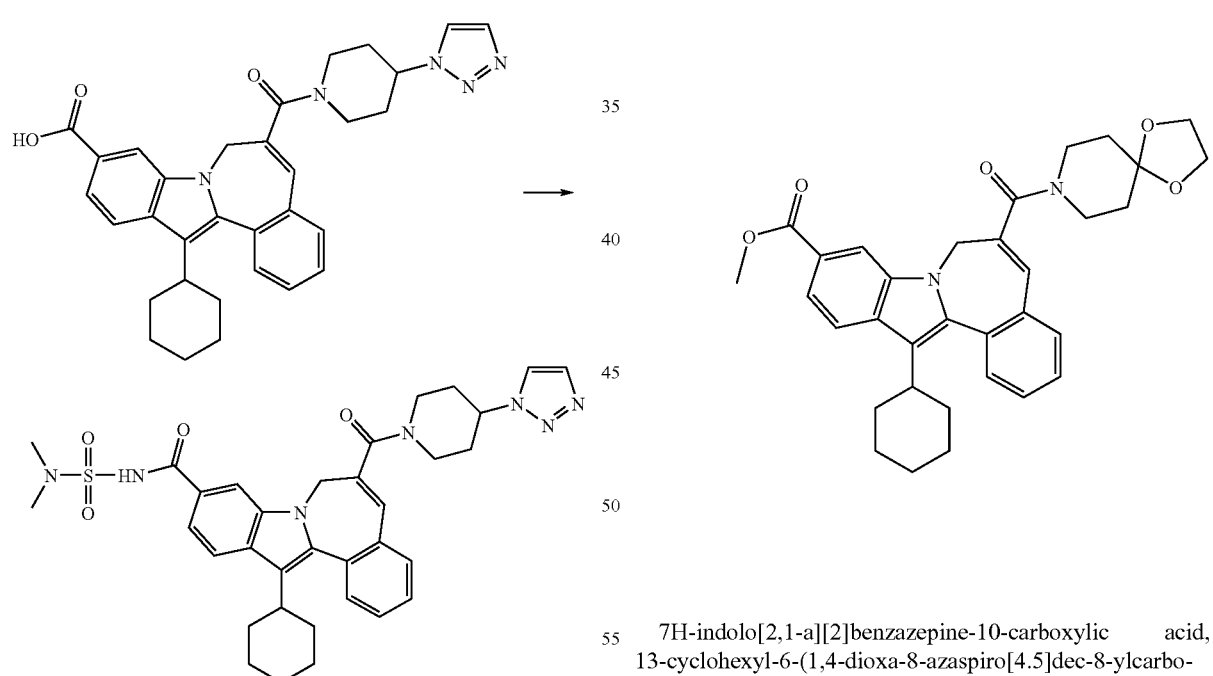

7H-indolo[2,1-a][2]benzazepine-10-carboxamide, 13-cyclohexyl-N-[(dimethylamino)sulfonyl]-6-[[4-(1H-1,2,3-triazol-1-yl)piperidinyl]carbonyl]. To a stirred solution of 7H-indolo[2,1-a][2]benzazepine-10-carboxylic acid, 13-cyclohexyl-6-[[4-(1H-1,2,3-triazol-1-yl)piperidinyl]carbonyl] (30 mg, 0.056 mmol), N,N-dimethylsulfamide (35 mg, 0.28 mmol) and DMAP (34 mg, 0.28 mmol) in dimethylacetamide (1 mL) was added 1-(3-dimethylaminopropyl)-3-ethylcarbodiimide hydrochloride (43 mg, 0.22 mmol). The reaction 7H-indolo[2,1-a][2]benzazepine-10-carboxylic acid, 13-cyclohexyl-6-(1,4-dioxa-8-azaspiro[4.5]dec-8-ylcarbonyl), methyl ester. To a stirred solution of methyl 7H-indolo[2,1-a][2]benzazepine-10-carboxylate, 13-cyclohexyl, 6-carboxylic acid (100 mg, 0.24 mmol), 1,4-dioxa-8-azaspiro[4,5]decane (67 mg, 0.48 mmol) and DMAP (58 mg, 0.48 mmol) in DMF (3 mL) was added HATU (182 mg, 0.48 mmol). The reaction mixture was stirred at rt overnight and purified using reverse phase prep-HPLC to yield 7H-indolo[2,1-a][2]benzazepine-10-carboxylic acid, 13-cyclohexyl-6-(1,4-dioxa-8-azaspiro[4.5]dec-8-ylcarbonyl), methyl ester. LCMS: m/e 541 (M+H)+, ret time 2.47 min, column 3, 2 minute gradient.

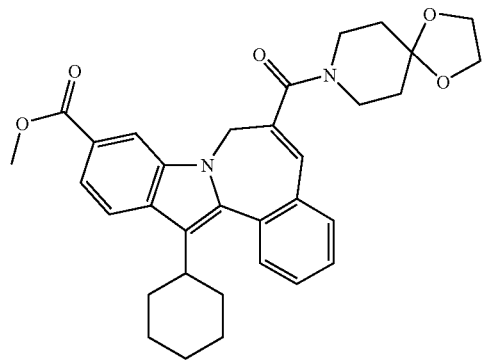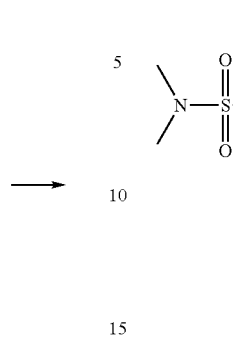

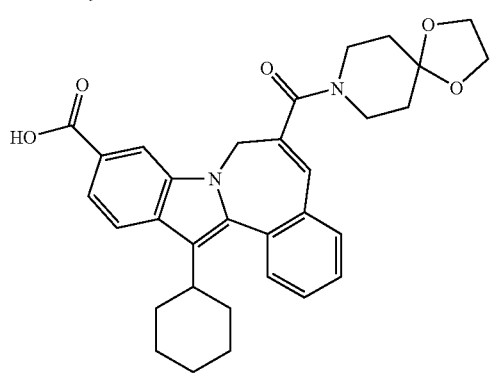

7H-indolo[2,1-a][2]benzazepine-10-carboxylic acid, 13-cyclohexyl-6-(1,4-dioxa-8-azaspiro[4.5]dec-8-ylcarbonyl)-. To a stirred solution of 7H-indolo[2,1-a][2]benzazepine-10-carboxylic acid, 13-cyclohexyl-6-(1,4-dioxa-8-azaspiro[4.5]dec-8-ylcarbonyl), methyl ester (40 mg, 0.018 mmol), in THF (1 mL) and MeOH (1 mL) was added 1 M NaOH (0.12 mL, 0.12 mmol). The reaction mixture was heated in a sealed tube at 70° C. for 7 h; cooled to rt overnight and heated again at 70° C. for 5 h after. The mixture was purified using reverse phase prep-HPLC to afford 7H-indolo[2,1-a][2]benzazepine-10-carboxylic acid, 13-cyclohexyl-6-(1,4-dioxa-8-azaspiro[4.5]dec-8-ylcarbonyl)- as a pale yellow solid. LCMS: m/e 527 (M+H)+, ret time 2.55 min, column 3, 2 minute gradient.

7H-indolo[2,1-a][2]benzazepine-10-carboxamide, 13-cyclohexyl-N-[(dimethylamino)sulfonyl]-6-(1, 4-dioxa-8-azaspiro[4.5]dec-8-ylcarbonyl)-. To a stirred solution of 7H-indolo[2,1-a][2]benzazepine-10-carboxylic acid, 13-cyclohexyl-6-(1,4-dioxa-8-azaspiro[4.5]dec-8-ylcarbonyl)- (30 mg, 0.056 mmol), N,N-dimethylsulfamide (35 mg, 0.28 mmol) and DMAP (34 mg, 0.28 mmol) in dimethylacetamide (1 mL) was added 1-(3-dimethylaminopropyl)-3-ethylcarbodiimide hydrochloride (43 mg, 0.22 mmol). The reaction solution was stirred in a sealed tube under nitrogen at 50° C. overnight and purified by reverse phase prep-HPLC to yield 7H-indolo[2,1-a][2]benzazepine-10-carboxamide, 13-cyclohexyl-N-[(dimethylamino)sulfonyl]-6-(1,4-dioxa-8-azaspiro[4.5]dec-8-ylcarbonyl)- as a pale yellow solid. $^1$H NMR (500 MHz, CDCl$_3$) δ. 9.1 (s, 1H), 8.04 (s, 1H), 7.90 (d, J=8.5 Hz, 1H), 7.58-7.40 (m, 4H), 6.88 (s, 1H), 5.12 (br s, 1H), 4.39 (br s, 1H), 3.93 (s, 4H), 3.70-3.30 (m, 4H), 3.01 (s, 6H), 2.8 (m, 1H), 2.10-1.25 (m, 14H). LCMS: m/e 633 (M+H)+, ret time 2.28 min, column 3, 2 minute gradient.

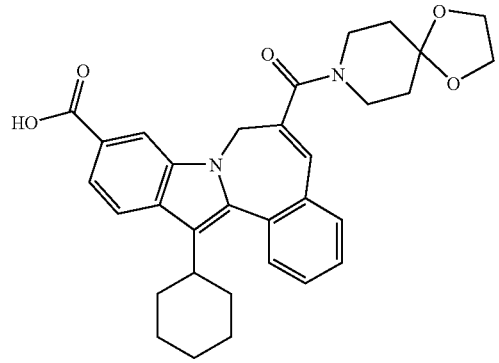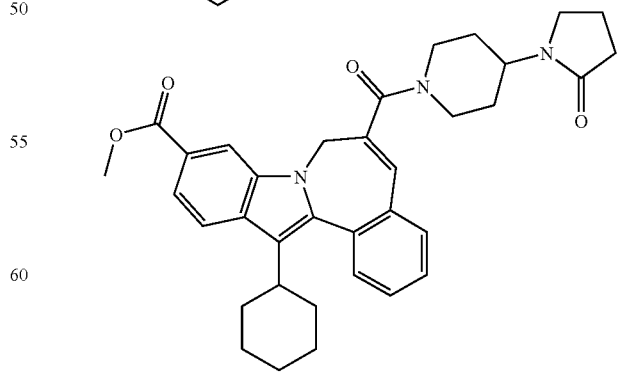

1-cyclohexyl-3-(3-oxo-3-(4-(2-oxopyrrolidin-1-yl)piperidin-1-yl)propyl)-2-phenyl-3H-indene-5-carboxylic acid, methyl ester. To a stirred solution of methyl 7H-indolo[2,1-a][2]benzazepine-10-carboxylate, 13-cyclohexyl, 6-carboxylic acid (100 mg, 0.24 mmol), 4-(N-2-pyrrolidinone)-piperidine hydrochloride (98 mg, 0.48 mmol) and DMAP (58 mg, 0.48 mmol) in DMF (2 mL) was added HATU (182 mg, 0.48 mmol). The reaction mixture was stirred at rt for 22 h and purified using reverse phase prep-HPLC to yield 1-cyclohexyl-3-(3-oxo-3-(4-(2-oxopyrrolidin-1-yl)piperidin-1-yl)propyl)-2-phenyl-3H-indene-5-carboxylic acid, methyl ester. LCMS: m/e 566 (M+H)+, ret time 2.36 min, column 3, 2 minute gradient.

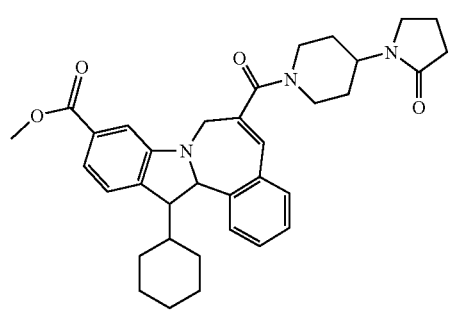

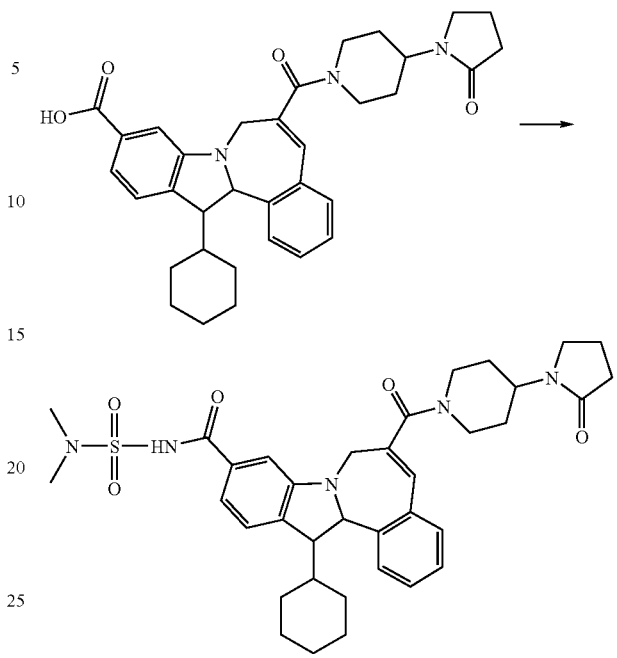

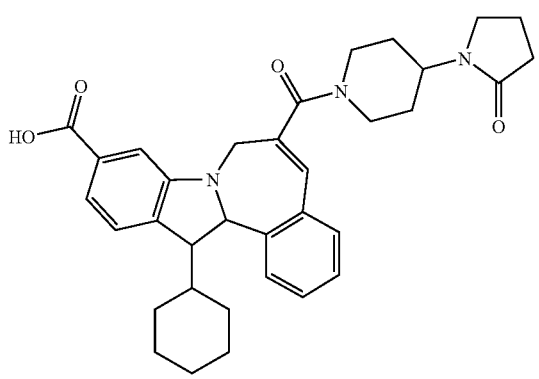

1-cyclohexyl-3-(3-oxo-3-(4-(2-oxopyrrolidin-1-yl)piperidin-1-yl)propyl)-2-phenyl-3H-indene-5-carboxylic acid. To a stirred solution of 1-cyclohexyl-3-(3-oxo-3-(4-(2-oxopyrrolidin-1-yl)piperidin-1-yl)propyl)-2-phenyl-3H-indene-5-carboxylic acid, methyl ester (460 mg, 0.1 mmol), in THF (1 mL) and MeOH (1 mL) was added 1M NaOH (0.16 mL, 0.16 mmol). The reaction mixture was heated in a sealed tube at 70° C. for 4 h. 1M NaOH (0.2 mL, 0.2 mmol) was added and heated for 5 h more. 1N HCl (0.5 mL) was added and the volatiles were removed in vacuo. A precipitate formed and it was collected by filtration and dried at open air to afford 1-cyclohexyl-3-(3-oxo-3-(4-(2-oxopyrrolidin-1-yl)piperidin-1-yl)propyl)-2-phenyl-3H-indene-5-carboxylic acid as a pale yellow solid. LCMS: m/e 552 (M+H)+, ret time 2.10 min, column A, 2 minute gradient.

1-cyclohexyl-N-[(dimethylamino)sulfonyl]3-(3-oxo-3-(4-(2-oxopyrrolidin-1-yl)piperidin-1-yl)propyl)-2-phenyl-3H-indene-5-carboxamide. To a stirred solution of 1-cyclohexyl-3-(3-oxo-3-(4-(2-oxopyrrolidin-1-yl)piperidin-1-yl)propyl)-2-phenyl-3H-indene-5-carboxylic acid, (46 mg, 0.083 mmol), N,N-dimethylsulfamide (51 mg, 0.42 mmol) and DMAP (51 mg, 0.42 mmol) in dimethylacetamide (1 mL) was added 1-(3-dimethylaminopropyl)-3-ethylcarbodiimide hydrochloride (64 mg, 0.33 mmol). The reaction solution was stirred in a sealed tube under nitrogen at 50° C. overnight and purified by reverse phase prep-HPLC to yield 1-cyclohexyl-N-[(dimethylamino)sulfonyl]3-(3-oxo-3-(4-(2-oxopyrrolidin-1-yl)piperidin-1-yl)propyl)-2-phenyl-3H-indene-5-carboxamide as an off-white solid. $^1$H NMR (500 MHz, CDCl$_3$) δ 8.91 (br s, 1H), 8.09 (s, 1H), 7.92 (d, J=8.5 Hz, 1H), 7.57-7.41 (m, 5H), 6.86 (s, 1H), 5.10 (br s, 1H), 4.41 (br s, 1H), 4.05-3.50 (m, 7H), 3.07 (s, 6H), 2.81 (m, 1H), 2.44 (m, 2H), 2.05-1.38 (m, 16H). LCMS: m/e 658 (M+H)+, ret time 2.43 min, column 3, 2 minute gradient. The next set of experimental procedures constitute a the start of a new section which stand alone:

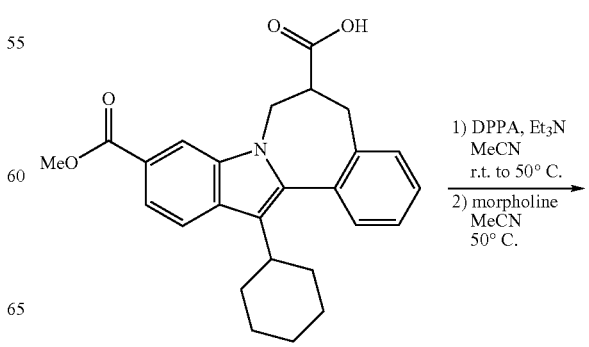

-continued

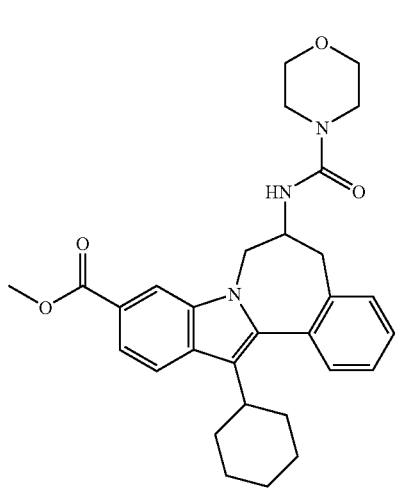

5H-indolo[2,1-a][2]benzazepine-10-carboxylic acid, 13-cyclohexyl-6,7-dihydro-6-[(4-morpholinylcarbonyl)amino]-, methyl ester. To the acid (5H-indolo[2,1-a][2]benzazepine-6,10-dicarboxylic acid, 13-cyclohexyl-6,7-dihydro-, 10-methyl ester) (30 mg, 71.9 µmol) in a round-bottomed flask at r.t. under $N_2$ was added a solution of triethylamine (9 mg, 88.9 µmol) in MeCN (0.6 ml), followed by a solution of diphenylphosphoryl azide (DPPA) (24 mg, 87.2 µmol) in MeCN (0.4 ml). The mixture was stirred at r.t. for 75 min., and then at 50° C. for 1 hr. After cooling to r.t., the mixture was added a solution of morpholine (19 mg, 218 µmol) in MeCN (0.3 ml) and then stirred at 50° C. for 1 hr. The mixture was cooled to r.t. and the volatiles evaporated. The residue obtained was purified by preparative thin layer chromatography (500 µm×20 cm×20 cm plate) using 5% MeOH/$CH_2Cl_2$ as eluent to give the urea, 5H-indolo[2,1-a][2]benzazepine-10-carboxylic acid, 13-cyclohexyl-6,7-dihydro-6-[(4-morpholinylcarbonyl)amino]-, methyl ester (14.4 mg, 40%). $^1$H NMR (500 MHz): ($CD_3OD$) δ 8.02 (s, 1H), 7.90 (d, J=8.5, 1H), 7.72 (d, J=8.5, 1H), 7.52-7.44 (m, 4H), 4.61 (d, J=15.5, 1H), 4.45-4.42 (m, 1H), 3.96 (s, 3H), 3.66-3.59 (overlapping m, 5H), 3.48-3.43 (overlapping m, 3H), 3.33-3.30 (m, 1H), 3.05-2.99 (m, 1H), 2.92 (dd, J=13, 6.5, 1H), 2.50 (t, J=12.5, 1H), 2.16-2.05 (overlapping m, 3H), 1.98-1.96 (b m, 1H), 1.82 (b m, 2H), 1.67-1.64 (b m, 1H), 1.55-1.40 (overlapping m, 2H), 1.36-1.25 (b m, 1H); Analytical HPLC method: Solvent A=10% MeOH—90% $H_2O$—0.1% TFA, Solvent B=90% MeOH—10% $H_2O$—0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=502.31, HPLC $R_t$=2.022 min.

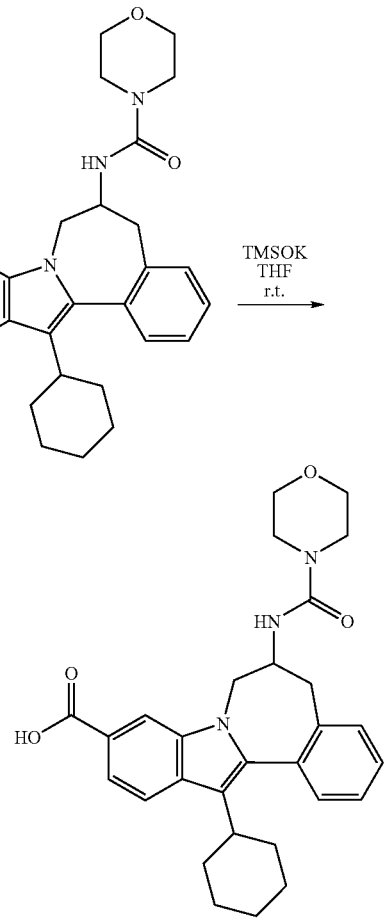

5H-indolo[2,1-a][2]benzazepine-10-carboxylic acid, 13-cyclohexyl-6,7-dihydro-6-[(4-morpholinylcarbonyl)amino]-. To the methyl ester (5H-indolo[2,1-a][2]benzazepine-10-carboxylic acid, 13-cyclohexyl-6,7-dihydro-6-[(4-morpholinylcarbonyl)amino]-, methyl ester) (14.4 mg, 28.7 µmol) in a round-bottomed flask at r.t. under $N_2$ was added a solution of potassium trimethylsilanoate (TMSOK) (82 mg, about 575 µmol, 90% tech) in THF (2 ml), and the mixture stirred at r.t. for 94 hr. The mixture was evaporated to dryness, and the residue added hydrochloric acid (3 ml, 1 N). The white precipitates were filtered, and washed with hexane (3×1 ml) and then dried to give the acid, 5H-indolo[2,1-a][2]benzazepine-10-carboxylic acid, 13-cyclohexyl-6,7-dihydro-6-[(4-morpholinylcarbonyl)amino]- (11.6 mg, 83%). $^1$H NMR (500 MHz): ($CD_3OD$) δ 8.05 (s, 1H), 7.90 (d, J=8.5, 1H), 7.73 (d, J=8.5, 1H), 7.52-7.42 (m, 4H), 4.61 (d, J=15, 1H), 4.45-4.41 (m, 1H), 3.71-3.60 (overlapping m, 5H), 3.47-3.43 (overlapping m, 3H), 3.31-3.29 (m, 1H), 3.04-2.99 (m, 1H), 2.92 (dd, J=13, 7, 1H), 2.50 (t, J=12, 1H), 2.17-2.05 (overlapping m, 3H), 1.99-1.96 (b m, 1H), 1.82 (b m, 2H), 1.68-1.65 (b m, 1H), 1.55-1.41 (overlapping m, 2H), 1.34-1.26 (b m, 1H); Analytical HPLC method: Solvent A=10% MeOH—90% $H_2O$—0.1% TFA, Solvent B=90% MeOH—10%$H_2O$—0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=488.28, HPLC $R_t$=1.938 min.

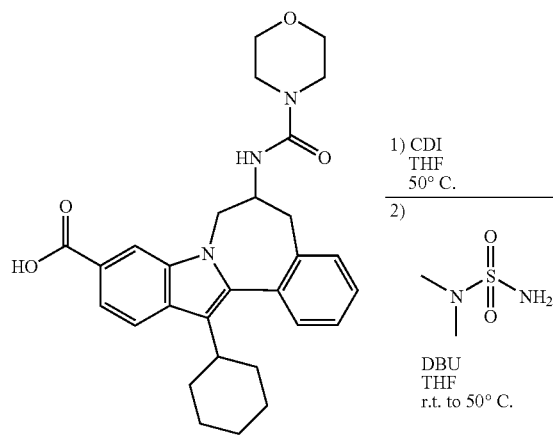

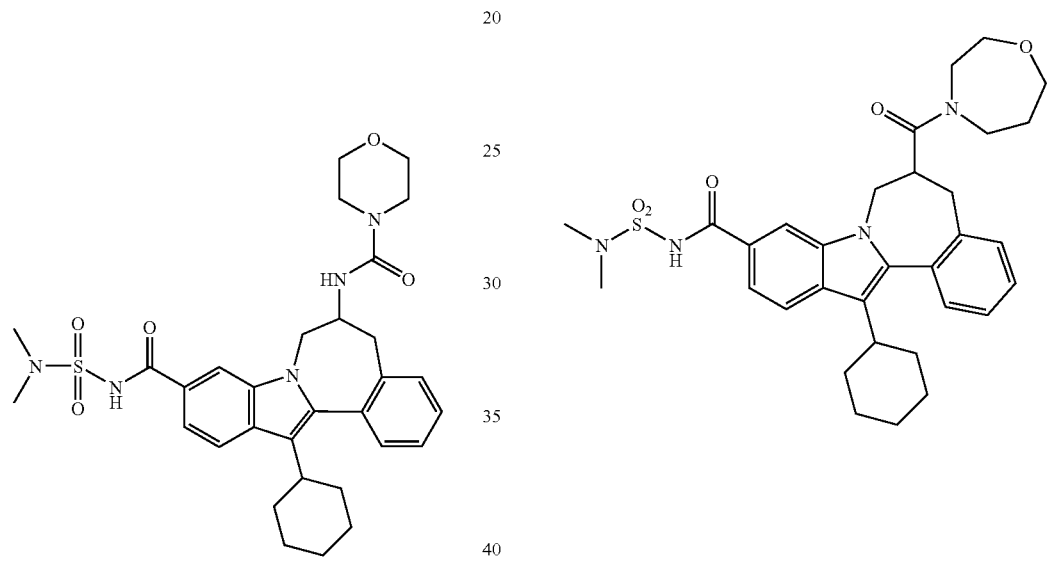

5H-indolo[2,1-a][2]benzazepine-10-carboxamide, 13-cyclohexyl-N-[(dimethylamino)sulfonyl]-6,7-dihydro-6-[(4-morpholinylcarbonyl)amino]-. To the acid (5H-indolo[2,1-a][2]benzazepine-10-carboxylic acid, 13-cyclohexyl-6,7-dihydro-6-[(4-morpholinylcarbonyl)amino]-) (13.6 mg, 27.9 μmol) in a round-bottomed flask at r.t. under $N_2$ was added a solution of 1,1'-carbonyldiimidazole (CDI) (5.9 mg, 36.4 μmol) in THF (1 ml), and the mixture was stirred at 50° C. for 2 hr. After cooling to r.t., the reaction mixture was added a mixture of N,N-dimethylsulfamide (4.5 mg, 36.2 μmol) and DBU (6.2 mg, 40.7 μmol) in THF (0.3 ml), and then stirred at r.t. for 17.5 hr. The reaction was then added another mixture of N,N-dimethylsulfamide (9 mg, 72.5 μmol) and DBU (12 mg, 78.7 μmol) in THF (0.3 ml), and stirred at 50° C. for 8 hr. After cooling to r.t., the volatiles were evaporated and the residue added hydrochloric acid (1.5 ml, 1N). The aqueous mixture was removed by pipet, and the white solid residue purified by preparative thin layer chromatography (500 μm×20 cm×20 cm plate) using 5% MeOH/$CH_2Cl_2$ as eluent to give the amide 5H-indolo[2,1-a][2]benzazepine-10-carboxamide, 13cyclohexyl-N-[(dimethylamino)sulfonyl]-6,7-dihydro-6-[(4-morpholinylcarbonyl)amino]-. $^1$H NMR (500 MHz) : ($CD_3OD$) δ 7.98 (d, J=1.5, 1H), 7.93 (d, J=8.5, 1H), 7.62 (dd, J=1.5, 8.5, 1H), 7.51-7.45 (overlapping m, 4H), 4.64 (d, J=15, 1H), 4.45 (m, 1H), 3.73-3.58 (overlapping m, 6H), 3.50-3.40 (overlapping m, 2H), 3.29 (m, 1H), 3.03 (s overlapping with m, 7H), 2.93 (dd, 1H), 2.50 (t, J=12, 1H), 2.17-2.03 (overlapping m, 3H), 2.00-1.94 (b m, 1H), 1.87-1.77 (b m, 2H), 1.69-1.63 (b m, 1H), 1.57-1.40 (overlapping m, 2H), 1.36 1.25 (b m, 1H); Analytical HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=594.34, HPLC R$_t$=1.895 min.

13-Cyclohexyl-N-[(dimethylamino)sulfonyl]-6-(homomorpholinylcarbonyl)-5H-indolo[2,1-a][2]benzazepine-10-carboxamide. TBTU (22 mg, 0.069 mmol) was added to a stirred solution of 6-carboxy-13-cyclohexyl-N-[(dimethylamino)sulfonyl]-5H-indolo[2,1-a][2]benzazepine-10-carboxamide (25 mg, 0.049 mmol), homomorpholine hydrochloride (8.1 mg, 0.059 mmol), and N,N-diisopropylethylamine (0.3 mL, 1.74 mmol) in DMF (3 mL). The mixture was stirred at 22° C. for 20 min. The resulting solution was concentrated down to the volume of 2 mL on a Speed Vac® and filtered. The filtrate was injected on the Shimadzu preparative liquid chromatograph. The product containing fraction was concentrated on a Speed Vac® to leave the titled compound as a white solid (28 mg, 97 %). ESI-MS m/z 591 (MH$^+$); $^1$H NMR (500 MHz, Solvent) δ 1.16-1.32 (m, 1 H) 1.38-1.55 (m, 4 H) 1.75-1.86 (m, 2 H) 1.90-2.21 (m, 5 H) 2.90 (m, 1 H) 3.04 (s, 6 H) 3.39-3.93 (m, 8 H) 4.42 (m, 1 H) 5.20 (m, 1 H) 7.05 (s, 1 H) 7.57 (m, 3 H) 7.63 (m, 2 H) 7.96 (d, J=8.55 Hz, 1 H) 8.15 (s, 1 H).

The following library of 13-Cyclohexyl-N-[(dimethylamino)sulfonyl]-6-(substituted-aminocarbonyl)-5H-indolo[2,1-a][2]benzazepine-10-carboxamides was synthesized using the protocols described in the preceding section.

| Structure | Physiochemical Data |
|---|---|
| 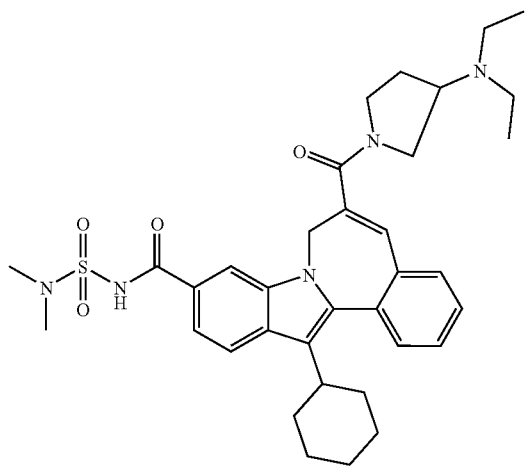 | ESI-MS m/z 631 (MH⁺); Rt 1.71 min |
| 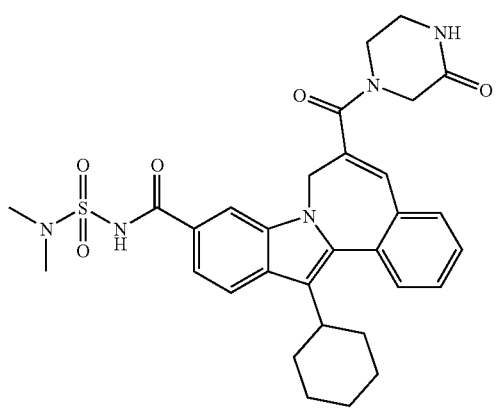 | ESI-MS m/z 590 (MH⁺); Rt 1.85 min |
| 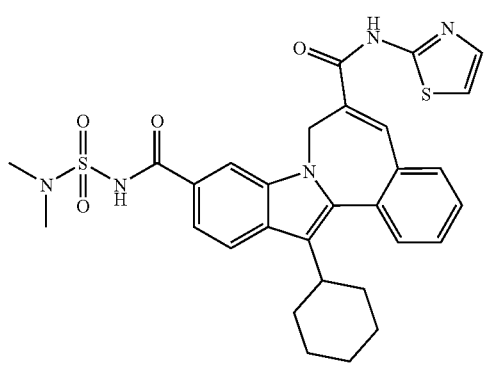 | ESI-MS m/z 590 (MH⁺); Rt 2.03 min |

| Structure | Physiochemical Data |
|---|---|
| 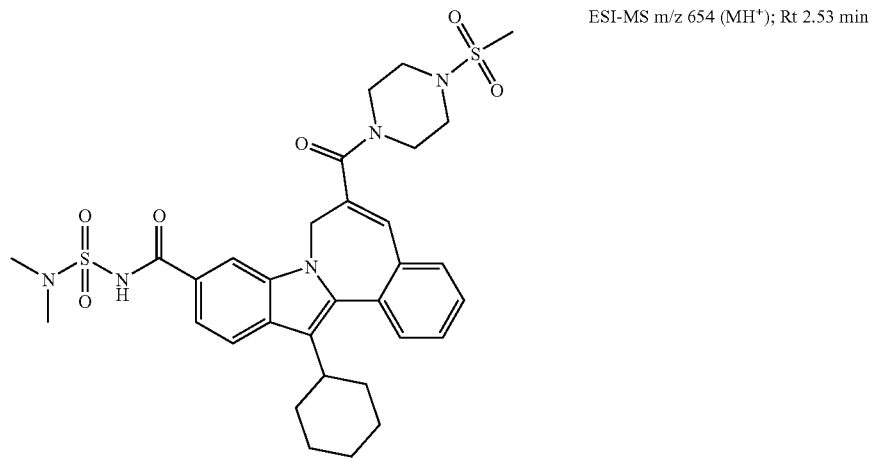 | ESI-MS m/z 654 (MH$^+$); Rt 2.53 min |
| 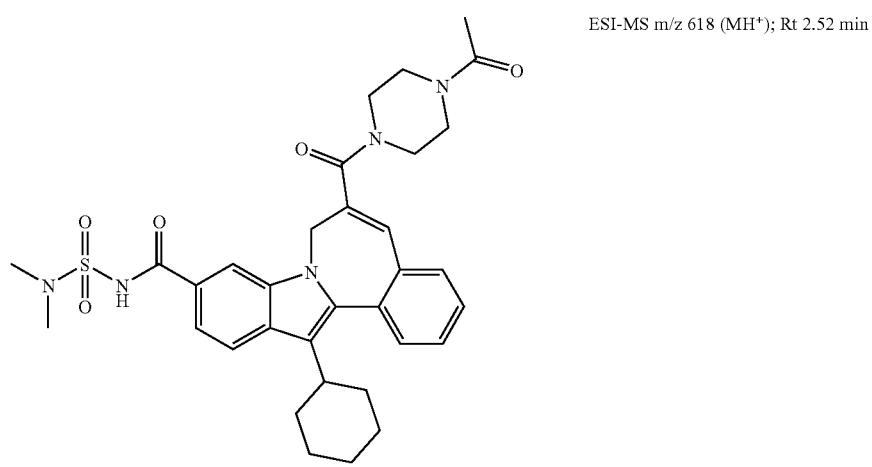 | ESI-MS m/z 618 (MH$^+$); Rt 2.52 min |
| 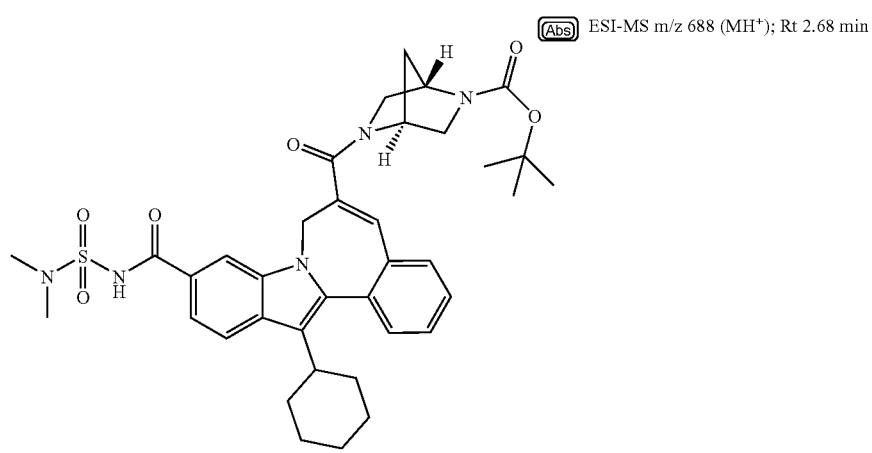 | ESI-MS m/z 688 (MH$^+$); Rt 2.68 min |

| Structure | Physiochemical Data |
|---|---|
| 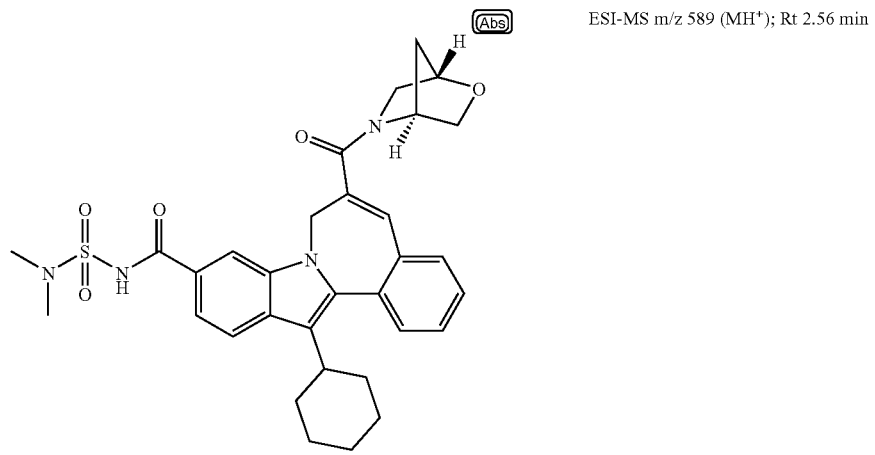 | ESI-MS m/z 589 (MH+); Rt 2.56 min |
| 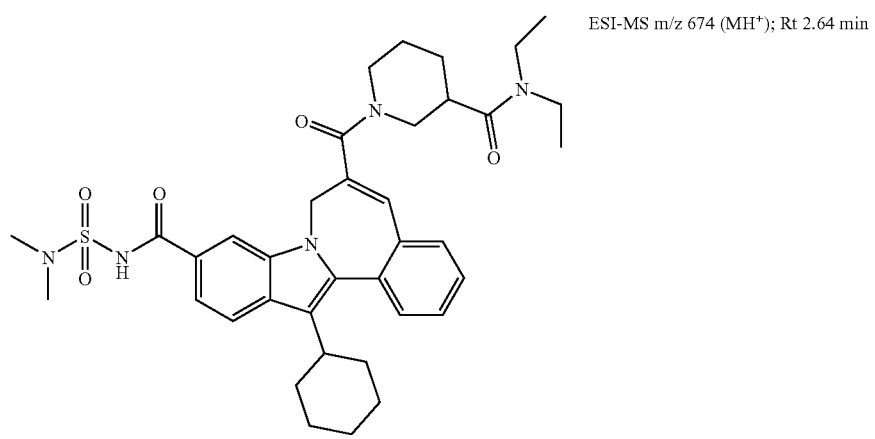 | ESI-MS m/z 674 (MH+); Rt 2.64 min |
| 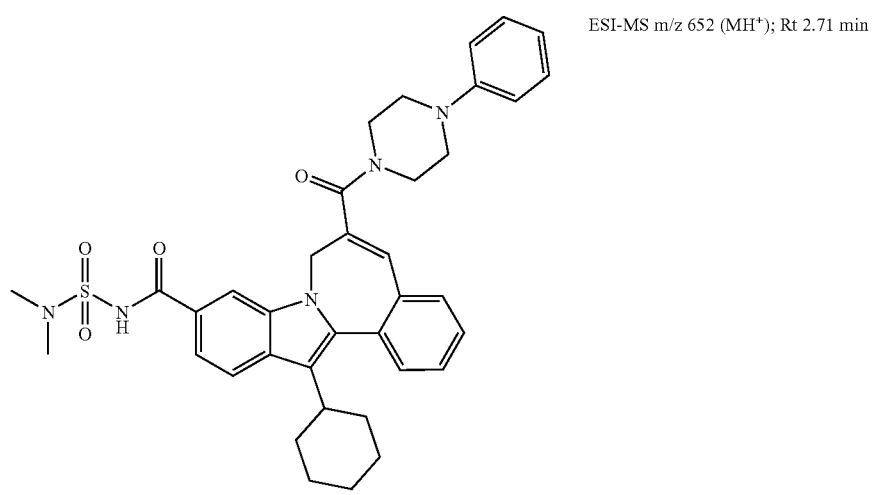 | ESI-MS m/z 652 (MH+); Rt 2.71 min |

-continued
| Structure | Physiochemical Data |
|---|---|
| 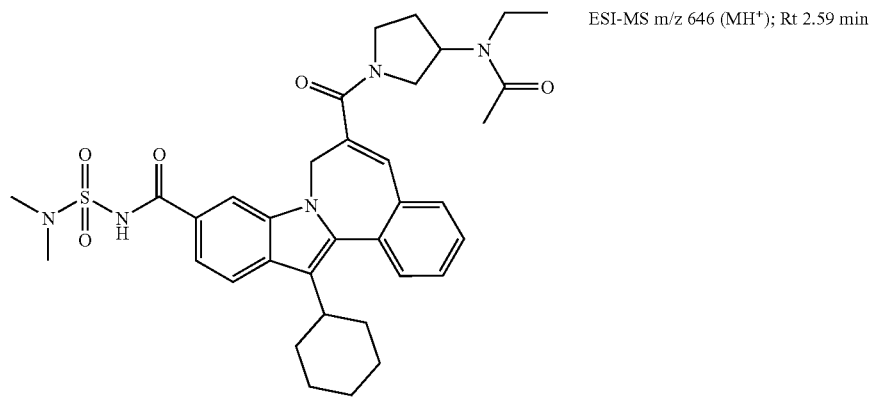 | ESI-MS m/z 646 (MH+); Rt 2.59 min |
| 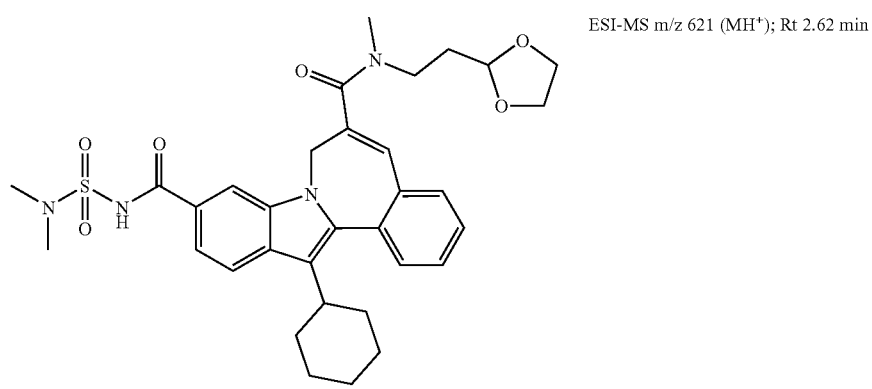 | ESI-MS m/z 621 (MH+); Rt 2.62 min |
| 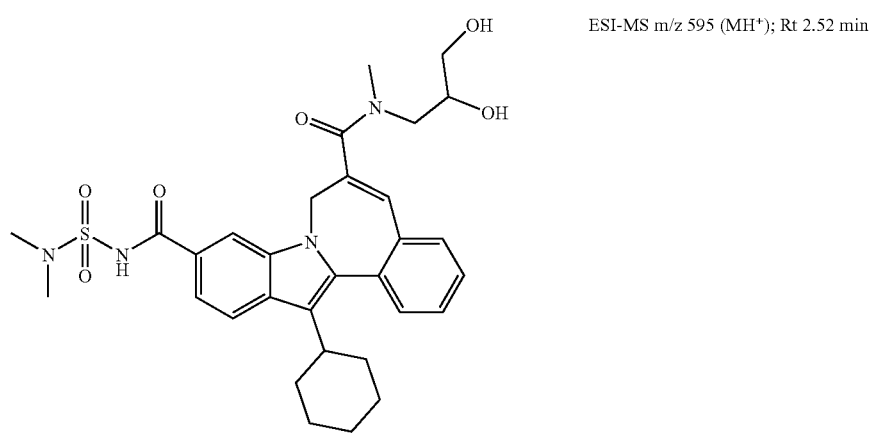 | ESI-MS m/z 595 (MH+); Rt 2.52 min |

| Structure | Physiochemical Data |
|---|---|
| 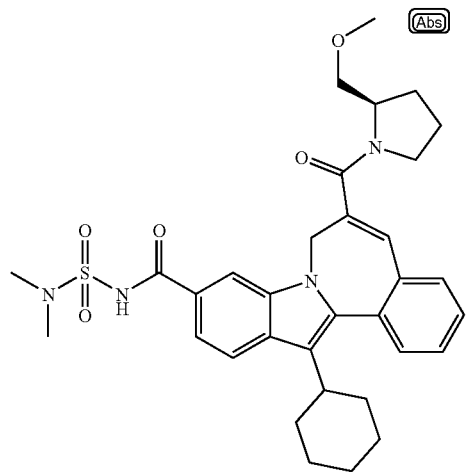 | ESI-MS m/z 605 (MH⁺); Rt 2.65 min |
| 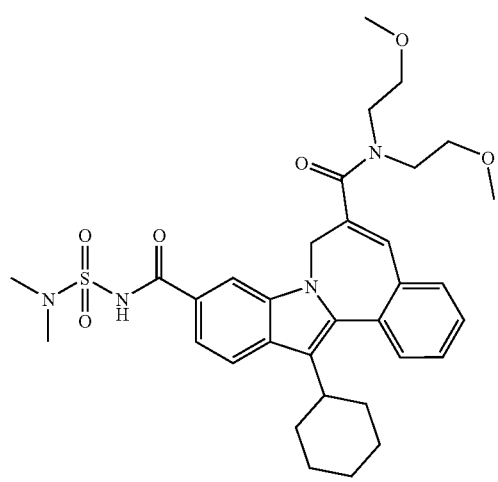 | ESI-MS m/z 623 (MH⁺); Rt 2.64 min |
| 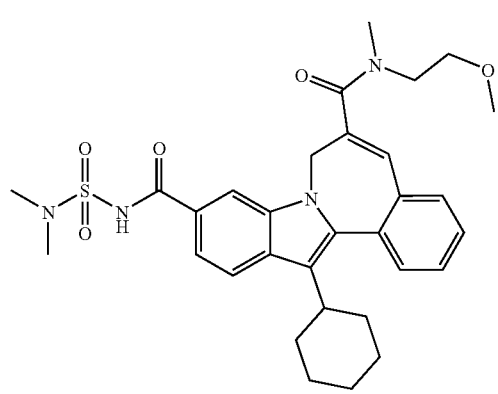 | ESI-MS m/z 579 (MH⁺); Rt 2.61 min |

| Structure | Physiochemical Data |
|---|---|
| 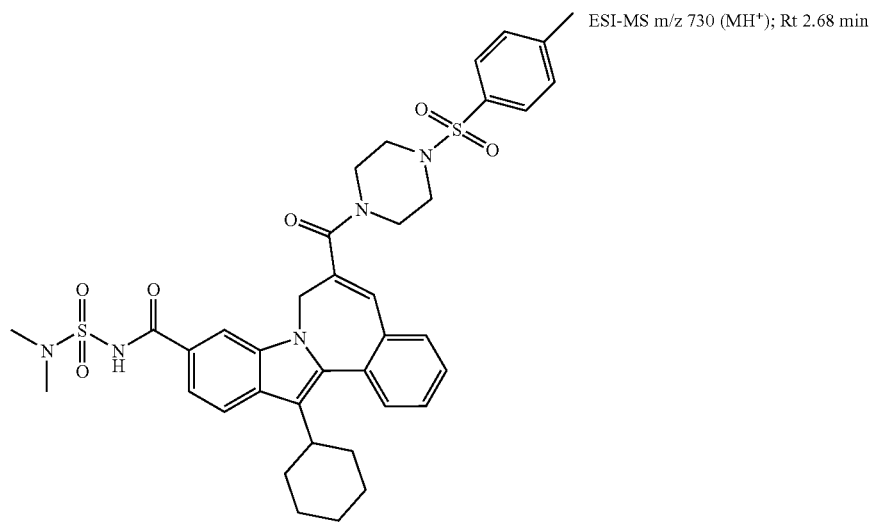 | ESI-MS m/z 730 (MH+); Rt 2.68 min |
| 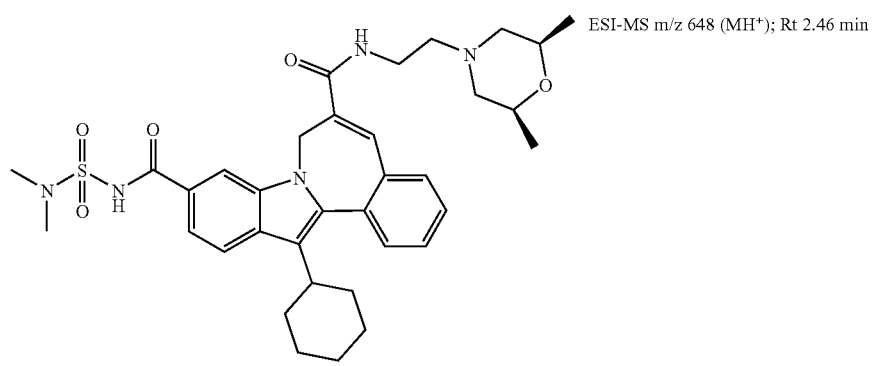 | ESI-MS m/z 648 (MH+); Rt 2.46 min |
| 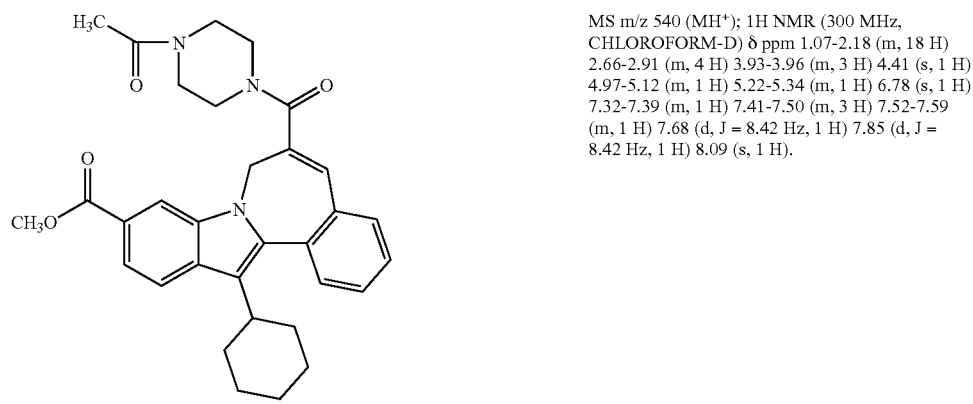 | MS m/z 540 (MH+); 1H NMR (300 MHz, CHLOROFORM-D) δ ppm 1.07-2.18 (m, 18 H) 2.66-2.91 (m, 4 H) 3.93-3.96 (m, 3 H) 4.41 (s, 1 H) 4.97-5.12 (m, 1 H) 5.22-5.34 (m, 1 H) 6.78 (s, 1 H) 7.32-7.39 (m, 1 H) 7.41-7.50 (m, 3 H) 7.52-7.59 (m, 1 H) 7.68 (d, J = 8.42 Hz, 1 H) 7.85 (d, J = 8.42 Hz, 1 H) 8.09 (s, 1 H). |

| Structure | Physiochemical Data |
|---|---|
| 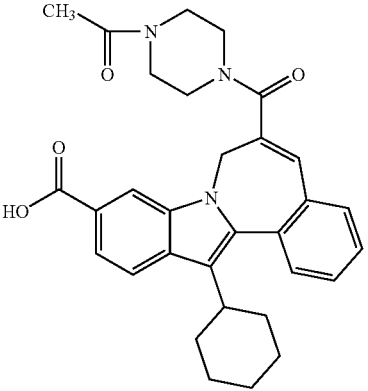 | 1H NMR (500 MHz, DMSO-D6) δ ppm 1.12-1.33 (m, 3 H) 1.37-1.48 (m, 4 H) 1.67-1.76 (m, 4 H) 1.79 (s, 3 H) 1.99-2.12 (m, 4 H) 2.74-2.84 (m, 1 H) 3.78 (s, 1 H) 4.23-4.35 (m, 1 H) 5.07-5.17 (m, 1 H) 6.96 (s, 1 H) 7.57-7.61 (m, 3 H) 7.63 (d, J = 8.24 Hz, 1 H) 7.82 (d, J = 7.32 Hz, 1 H) 7.91 (d, J = 8.55 Hz, 1 H) 8.17 (s, 1 H). |

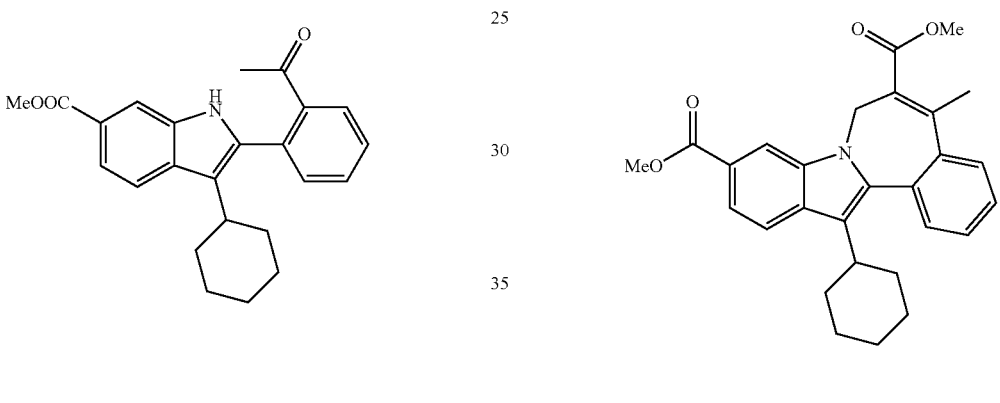

Methyl 2-(2-acetylphenyl)-3-cyclohexyl-1H-indole-6-carboxylate. A 2M aqueous solution of $Na_2CO_3$ (2.5 mL, 5.0 mmol) was added to a mixture of; methyl 3-cyclohexyl-2-(4,4,5,5-tetramethyl-1,3,2-dioxaborolan-2-yl)-1H-indole-6-carboxylate (766 mg, 2.0 mmol), 2'-bromoacetophenone (478 mg, 2.4 mmol) and LiCl (170 mg, 4.0 mmol), in ethanol (5 mL) and toluene (5 mL). The mixture was then degassed by sequentially applying vacuum followed by flushing with $N_2$. $Pd(PPh_3)_4$ (115 mg, 0.1 mmol) was then added and the reaction heated at 80° C. for 4 hr. The reaction mixture was then filtered and concentrated under reduced pressure. The resultant residue was purified by silica gel flash chromatography using hexanes to 20% ethyl acetate in hexanes as eluent to give the title compound as a white foam which could be crushed to a powder, (686 mg, 91% yield). MS m/z 374(M−H−); $^1$H NMR (500 MHz, $CD_3OD$) δ ppm 1.30 (m, 1 H) 1.41-1.64 (m, 3 H) 1.82-2.21 (m, 9 H) 3.26 (m, 1 H) 3.95 (s, 3 H) 7.40 (m, 1 H) 7.49 (m, 1 H) 7.61 (m, 1 H) 7.69 (m, 1 H) 7.79 (m, 1 H) 7.84 (m, 1 H) 8.29 (s, 1 H).

7H-indolo[2,1-a][2]benzazepine-6,10-carboxylic acid, 13-cyclohexyl-5-methyl-, dimethyl ester. To a solution of methyl 2-(2-acetylphenyl)-3-cyclohexyl-1H-indole-6-carboxylate (400 mg, 1.065 mmol) in DMF (10 mL), $Cs_2CO_3$ (521 mg, 1.6 mmol) and trimethyl2-phosphonoacrylate (310 mg, 1.6 mmol) were added. The reaction mixture was heated at 60° C. overnight. It was then quenched by the addition of water after which a precipitate formed. This was collected by filtration, and dried under vacuum to give the crude product as a light yellow solid (380 mg, 80% yield). 10 mg of this material was purified by Prep. reverse phase HPLC to provide pure, 7H-indolo[2,1-a][2]benzazepine-6,10-carboxylic acid, 13-cyclohexyl-5-methyl-, dimethyl ester. MS m/z 444(MH+); $^1$H NMR (500 MHz, $CD_3OD$) δ ppm 1.15-1.66 (m, 4 H) 1.76-1.87 (m, 2 H) 1.97 (m, 1 H) 2.02-2.22 (m, 3 H) 2.49 (s, 3H) 2.95 (m, 1 H) 3.83 (s, 3 H) 3.97 (s, 3 H) 4.09 (d, J=14.65 Hz, 1 H) 5.49 (d, J=14.65 Hz, 1 H) 7.55-7.61 (m, 3 H) 7.70 (dd, J=8.39, 1.37 Hz, 1 H) 7.76 (m, 1 H) 7.88 (d, J=8.55 Hz, 1 H) 8.33 (s, 1 H).

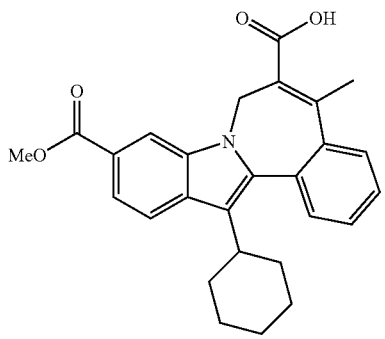

7H-indolo[2,1-a][2]benzazepine-6,10-dicarboxylic acid, 13-cyclohexyl-5-methyl-, 10-methyl ester. To a solution of 7H-indolo[2,1-a][2]benzazepine-6,10-carboxylic acid, 13-cyclohexyl-5-methyl-, dimethyl ester (179, 0.4 mmol) in THF (10 mL), 1M solution of Bu$_4$NOH (0.6 mL, 0.6 mmol) in methanol was added. The reaction mixture was stirred at rt. for two days. It was then concentrated, acidified with 1N HCl solution and extracted with ethyl acetate (2×30 mL). The organic layers were combined, dried (MgSO$_4$), filtered and concentrated in vacuo. The resultant residue was purified by Prep. reverse phase HPLC column to give the title compound as a yellow solid, (90 mg, 52% yield). MS m/z 430(MH$^+$); $^1$H NMR (300 MHz, DMSO-D6) δ ppm 1.10-1.27 (m, 1H) 1.32-1.59 (m, 3 H) 1.64-1.79 (m, 2 H) 1.81-1.94 (m, 1 H) 1.94-2.13 (m, 3 H) 2.41 (s, 3 H) 2.86 (m, 1 H) 3.87 (s, 3 H) 3.98 (d, J=14.64 Hz, 1 H) 5.43 (d, J=14.64 Hz, 1 H) 7.49-7.67 (m, 4 H) 7.74-7.83 (m, 1 H) 7.91 (d, J=8.42 Hz, 1 H) 8.22 (s, 1 H) 13.00 (s, 1 H).

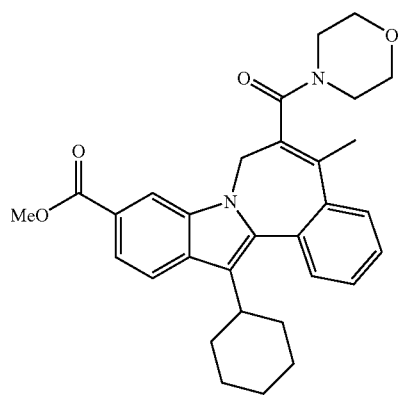

7H-indolo[2,1-a][2]benzazepine-10-carboxylic acid, 13-cyclohexyl-5-methyl-6-(4-morpholinylcarbonyl)-, methyl ester. To a solution of 7H-indolo[2,1-a][2]benzazepine-6,10-dicarboxylic acid, 13-cyclohexyl-5-methyl-, 10-methyl ester (120 mg, 0.28 mmol) in DMSO (3.0 mL), TBTU (135 mg, 0.42 mmol) and DIPEA (0.244 mL, 1.4 mmol) were added. The reaction mixture was stirred at rt for 15 min. Then morpholine (0.037 mL, 0. 42 mmol) was added and the reaction mixture was stirred at rt for overnight. It was then concentrated under reduced pressure and the residue was purified by Prep. reverse phase HPLC to give the title compound as a white solid, (115 mg, 82% yield). MS m/z 499 (MH$^+$); $^1$H NMR (500 MHz, CD$_3$OD) δ ppm Compound exists as a complex mixture of rotamers.

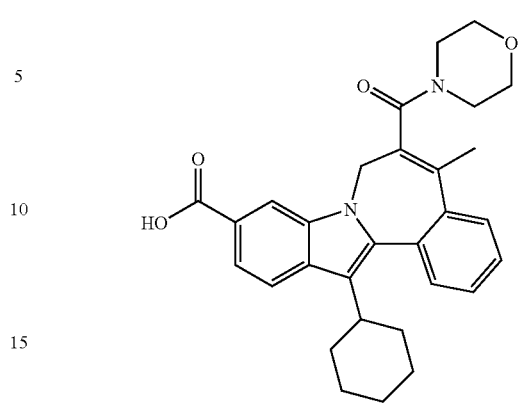

7H-indolo[2,1-a][2]benzazepine-10-carboxylic acid, 13-cyclohexyl-5-methyl-6-(4-morpholinylcarbonyl)-. 2N NaOH solution (1.0 mL) was added to a solution of 7H-indolo[2,1-a][2]benzazepine-10-carboxylic acid, 13-cyclohexyl-5-methyl-6-(4-morpholinylcarbonyl)-, methyl ester (100 mg, 0.2 mmol)in a THF/Methanol mixture (2.0 mL/2.0 mL) in a sealed tube. The reaction mixture was heated at 90° C. under microwave conditions for 10 min. It was then concentrated and acidified with 1N HCl solution after which a precipitate formed. This was collected by filtration and dried under vacuum to provide the title compound as an off-white solid, (75 mg, 77% yield). MS m/z 485(MH$^+$); $^1$H NMR (300 MHz, CD$_3$OD) δ ppm exists as rotamers.

The general methods below were used with the following experimental procedures until indicated otherwise: LCMS data: Stop time: Gradient time+1 minute; Starting conc: 0% B unless otherwise noted; Eluent A: 5% CH$_3$CN/95% H$_2$O with 10 mM NH$_4$OAc (for columns A and D); 10% MeOH/90% H$_2$O with 0.1% TFA (for columns B and C); Eluent B: 95% CH$_3$CN/5% H$_2$O with 10 mM NH$_4$OAc (for columns A and D); 90% MeOH/10% H$_2$O with 0.1% TFA (for columns B and C); Column A: Phenomenex 10μ 4.6×50 mm C18; Column B: Phenomenex C18 10μ 3.0×50 mm; Column C: Phenomenex 4.6×50 mm C18 10μ; Column D: Phenomenex Lina C18 5μ 3.0×50 mm; Column E: Phenomenex 5μ 4.6×5.0 mm C18.

To a slurried solution of methyl 2-bromo-3-cyclohexyl-1H-indole-6-carboxylate (4.3 g, 13 mmol), 4-methoxy-2-formylphenylboronic acid (3.0 g, 17 mmol) and LiCl (2.2 g, 51 mmol) in EtOH/toluene (1:1, 100 mL) was added Pd(PPh$_3$)$_4$ (1.4 g, 1.3 mmol) and then 1M Na$_2$CO$_3$ (aq.) (32 mL, 32 mmol). The reaction solution was flushed with nitrogen and heated at 100° C. for 3 h and cooled to rt. The reaction was concentrated to remove EtOH, diluted with H$_2$O (200 mL) and extracted with EtOAc (2×150 mL). The combined organics were washed with brine (100 mL), dried (MgSO$_4$), filtered and concentrated to dryness. The residue was triturated with CH$_2$Cl$_2$ and the solids were collected by filtrated and washed with Et$_2$O and CH$_2$Cl$_2$ to yield methyl 11-cyclohexyl-6-hydroxy-8-methoxy-6H-isoindolo[2,1-a]indole-3-carboxylate (3.0 g, 8.0 mmol, 63%) as a yellow solid which was used without further purification. LCMS: m/e 374 (M+H)$^+$, ret time 3.09 min, column B, 3 minute gradient.

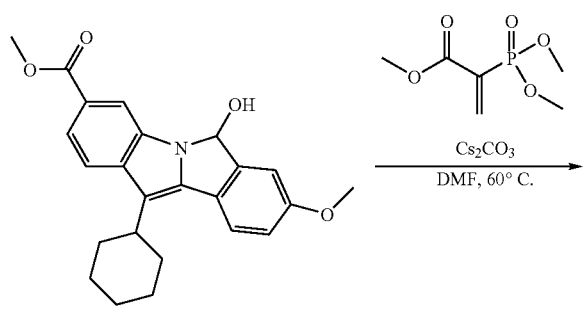

A solution of methyl 11-cyclohexyl-6-hydroxy-8-methoxy-6H-isoindolo[2,1-a]indole-3-carboxylate (2.9 g, 7.4 mmol), methyl 2-(dimethoxyphosphoryl)acrylate (2.6 g, 11 mmol), cesium carbonate (3.6 g, 11 mmol) in DMF (20 mL) was heated at 60° C. for 2 h and cooled to rt. The stirring reaction mixture was diluted with H$_2$O (50 mL) and the precipitates were collected by filtration to yield dimethyl 13-cyclohexyl-3-methoxy-7H-indolo[2,1-a][2]benzazepine-6,10-dicarboxylate (3.3 g, 7.1 mmol, 97%) as a yellow solid which was used without further purification. LCMS: m/e 460 (M+H)$^+$, ret time 3.35 min, column B, 3 minute gradient.

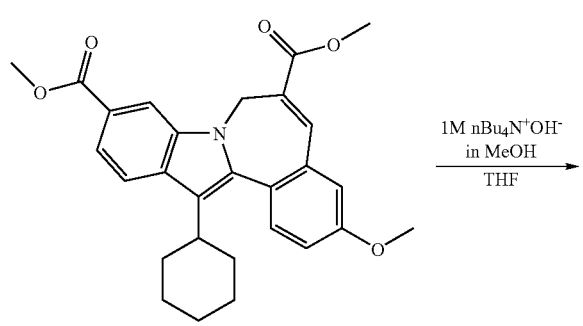

A solution of tetrabutylammonium hydroxide (1M in MeOH, 2.2 mL, 2.2 mmol) was added to a stirring solution of dimethyl 13-cyclohexyl-3-methoxy-7H-indolo[2,1-a][2]benzazepine-6,10-dicarboxylate (1.0 g, 2.2 mmol) in THF (75 mL) and stirred at rt overnight. The reaction mixture was concentrated to ~30 mL, diluted with EtOAc (120 mL), washed with 0.5 M HCl (aq.) (2×50 mL) and brine (40 mL), dried (MgSO$_4$), filtered and concentrated to dryness to yield methyl 7H-indolo[2,1-a][2]benzazepine-10-carboxylate, 13-cyclohexyl, 3-methoxy, 6-carboxylic acid (1.0 g, 2.2 mmol, quant.) as a yellow solid which was used without further purification. LCMS: m/e 446 (M+H)$^+$, ret time 1.54 min, column A, 2 minute gradient.

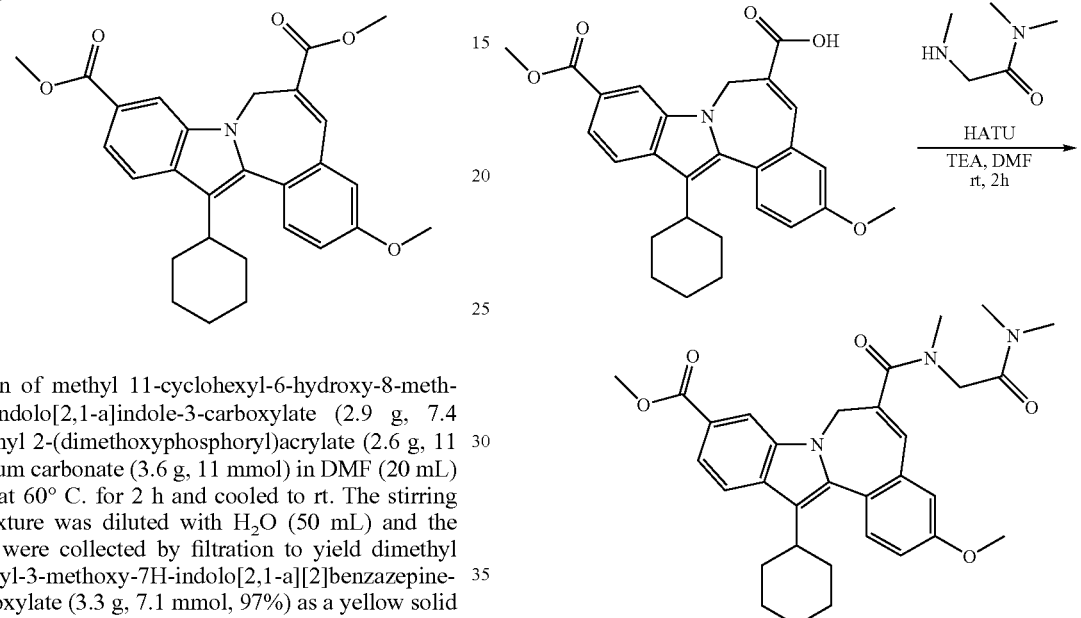

To a stirred solution of methyl 7H-indolo[2,1-a][2]benzazepine-I0-carboxylate, 13-cyclohexyl, 3-methoxy, 6-carboxylic acid (120 mg, 0.27 mmol), 2-N,N-dimethyl-2-(methylamino)acetamide (40 mg, 0.32 mmol) and triethylamine (0.11 mL) in DMF (2 mL) was added HATU (125 mg, 0.32 mmol). The reaction mixture was stirred at rt for 2 h, diluted with H$_2$O (~10 mL) and the resulting solids were collected by filtration, washed with H$_2$O and dried to yield methyl 7H-indolo[2,1-a][2]benzazepine-10-carboxylate, 13-cyclohexyl-3-methoxy-6-[[[2-(dimethylamino)-2-oxoethyl]methylamino]carbonyl]- (127 mg, 0.23 mmol, 87%) as a yellow solid, which was used without further purification. LCMS: m/e 544 (M+H)$^+$, ret time 1.88 min, column A, 2 minute gradient.

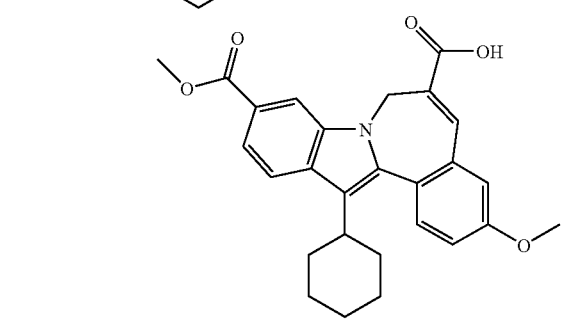

-continued

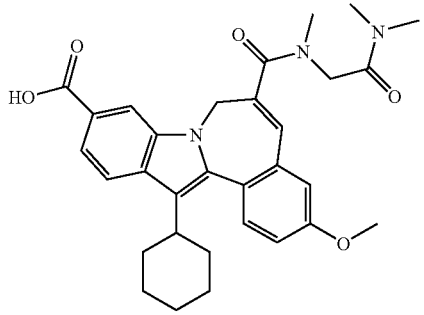

Methyl 7H-indolo[2,1-a][2]benzazepine-10-carboxylate, 13-cyclohexyl-3-methoxy-6-[[[2-(dimethylamino)-2-oxoethyl]methylamino]carbonyl]- (117 mg, 0.21 mmol) was dissolved into THF/MeOH (1:1, 2 mL) and 1M NaOH (aq.) (0.5 mL, 0.5 mmol). The reaction mixture was heated in a sealed tube with microwave irradiation at 85° C. for 20 min. The reaction was cooled, neutralized with 1M HCl (aq.) (0.5 mL, 0.5 mmol) and concentrated to remove organic solvents. The residue was slurried with H$_2$O and the solids were collected by filtration, flushed with H$_2$O, and purified by preparative HPLC to yield 7H-indolo[2,1-a][2]benzazepine-10-carboxylic acid, 13-cyclohexyl-3-methoxy-6-[[[2-(dimethylamino)-2-oxoethyl]methylamino]carbonyl]- (71 mg, 0.13 mmol, 63%) as a yellow solid. Mixture of amide rotamers: $^1$HNMR (500 MHz, CD$_3$OD) δ 8.24 (br s, 1H), 7.88 (d, J=8.4 Hz, 1H), 7.71 (d, J=8.4 Hz, 1H), 7.56 (d, J=8.4 Hz, 1H), 7.18-6.88 (m, 2H), 7.14 (dd, J=8.4, 2.2 Hz, 1H), 5.14 (br s, 1H), 4.49-4.12 (m, 2H), 3.97-3.88 (m, 1H), 3.93 (s, 3H), 3.15-2.83 (m, 7H), 2.56 (s, 1.5H), 2.42 (s, 1.5H), 2.23-1.73 (m, 6H), 1.59-1.17 (m, 4H). LCMS: m/e 530 (M+H)$^+$, ret time 1.40 min, column A, 2 minute gradient.

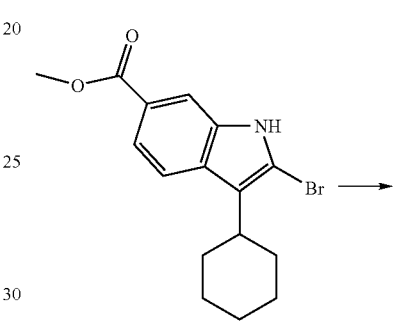

Me$_2$NSO$_2$NH$_2$
EDCl, DMAP
―――――――→
DMA, 50° C.

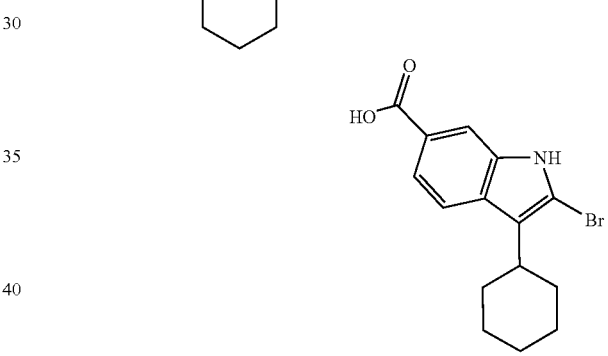

To a stirred solution of 7H-indolo[2,1-a][2]benzazepine-10-carboxylic acid, 13-cyclohexyl-3-methoxy-6-[[[2-(dimethylamino)-2-oxoethyl]methylamino]carbonyl]- (53 mg, 0.10 mmol), N,N-dimethylsulfamide (62 mg, 0.50 mmol) and DMAP (61 mg, 0.50 mmol) in dimethylacetamide (1.5 mL) was added 1-(3-dimethylaminopropyl)-3-ethylcarbodiimide hydrochloride (76 mg, 0.40 mmol). The reaction solution was stirred at 50° C. for 5 h, concentrated under a steam of nitrogen, diluted with MeOH (1 mL) and purified by preparative HPLC (CH$_3$CN/H$_2$O with TFA buffer) to yield 7H-indolo[2,1-a][2]benzazepine-6,10-dicarboxamide, 13-cyclohexyl-N$^6$-[2-(dimethylamino)-2-oxoethyl]-N$^{10}$-[(dimethylamino)sulfonyl]-3-methoxy-N$^6$-methyl- (13 mg, 0.02 mmol, 20%) as a yellow solid. $^1$HNMR (500 MHz, CD$_3$OD) δ 8.19 (s, 0.5H), 8.12 (s, 0.5H), 7.91 (d, J=8.1 Hz, 1H), 7.63 (d, J=8.1 Hz, 1H), 7.60-7.50 (m, 1H), 7.20-6.93 (m, 3H), 5.14 (br s, 1H), 4.46-4.11 (m, 2H), 3.96-3.87 (m, 1H), 3.93 (s, 3H), 3.12-2.86 (m, 13H), 2.45 (br s, 3H), 2.20-1.74 (m, 6H), 1.57-1.19 (m, 4H). LCMS: m/e 636 (M+H)$^+$, ret time 2.82 min, column B, 3 minute gradient.

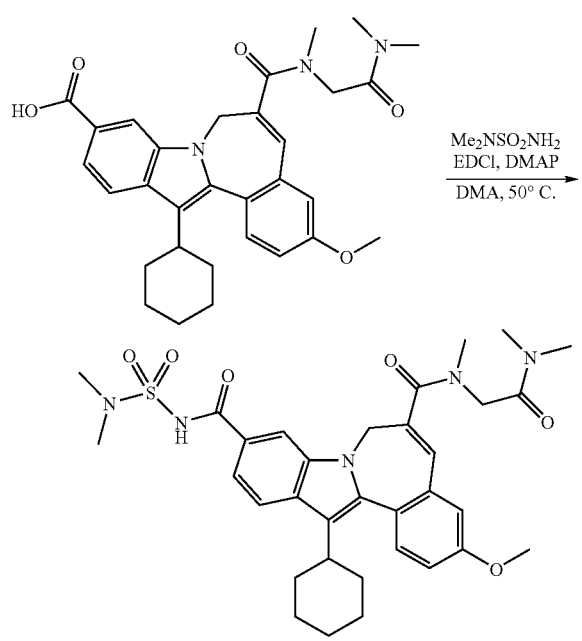

A solution of methyl 2-bromo-3-cyclohexyl-1H-indole-6-carboxylate (20 g, 60 mmol) and LiOH (3.8 g, 160 mmol) in MeOH/THF/H$_2$O (1:1:1, 300 mL) was heated at 90° C. for 2 h. The reaction mixture was cooled in an ice/H$_2$O bath, neutralized with 1M HCl (~160 mL) diluted with H$_2$O (250 mL) and stirred for 1 h at rt. The precipitates were collected by filtration rinse with H$_2$O and dried to yield 2-bromo-3-cyclohexyl-1H-indole-6-carboxylic acid (quant.) which was used without further purification.

Carbonyl diimidazole (6.0 g, 37 mmol) was added to a solution of 2-bromo-3-cyclohexyl-1H-indole-6-carboxylic acid (10 g, 31 mmol) in THF (30 mL) and the reaction was stirred at 50° C. for 2 h (a white precipitate had formed). The reaction was cooled to rt and treated with N,N-dimethylsulfamide (4.6 g, 37 mmol). Then DBU (6.7 mL) in THF (20 mL) was added dropwise and the reaction was stirred at rt overnight. The solution was diluted with EtOAc (300 mL) and washed with H$_2$O (150 mL), 1N aqueous HCl (2×100 mL) and brine (100 mL). The combined aqueous layers were extracted with EtOAc (200 mL) and the organic layer was washed with 1N aqueous HCl (150 mL) and brine (50 mL). The combined organic layers were dried (MgSO$_4$), filtered and concentrated to an oil. The oil was diluted with Et$_2$O and concentrated to a semi-solid which was triturated with Et₂O to yield 2-bromo-3-cyclohexyl-N-[(dimethylamino)sulfonyl]-indole-6-carboxamide (6.1 g, 14 mmol, 46%) as a light yellow solid. The organic washes where concentrated and purified by silica gel chromatography (20-35% EtOAc/hexanes) to yield additional 2-bromo-3-cyclohexyl-N-[(dimethylamino)sulfonyl]-indole-6-carboxamide (2.5 g, 6 mmol, 19%). ¹HNMR (500 MHz, CD₃OD) δ 7.90 (d, J=1.8 Hz, 1H), 7.77 (d, J=8.5 Hz, 1H), 7.56 (dd, J=1.8, 8.5 Hz, 1H), 3.01 (s, 6H), 2.93-2.86 (m, 1H), 2.04-1.76 (m, 7H), 1.54-1.37 (m, 3H). LCMS: m/e 426 (M−H)⁻, ret time 1.55 min, column A, 2 minute gradient.

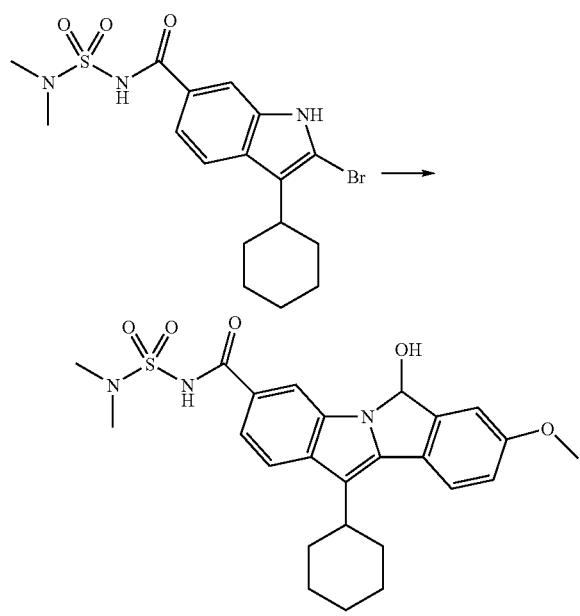

To a slurried solution of 2-bromo-3-cyclohexyl-N-[(dimethylamino)sulfonyl]-indole-6-carboxamide (4.3 g, 10 mmol), 4-methoxy-2-formylphenylboronic acid (2.5 g, 14 mmol) and LiCl (1.05 g, 25 mmol) in EtOH/toluene (1:1, 80 mL) was added Pd(PPh₃)₄ (1.12 g, 1.0 mmol) and then 1M Na₂CO₃ (aq.) (30 mL, 30 mmol). The reaction solution was flushed with nitrogen and heated at 85° C. for 18 h and cooled to rt. The reaction was diluted with EtOAc (200 mL), washed with 0.5N aqueous HCl (100 mL) and brine (50 mL), dried (MgSO₄), filtered and concentrated to yield 11-cyclohexyl-N-[(dimethylamino)sulfonyl]-6-hydroxy-8-methoxy-6H-isoindolo[2,1-a]indole-3-carboxamide which was used without further purification. LCMS: m/e 482 (M−H)⁻, ret time 1.63 min, column A, 2 minute gradient.

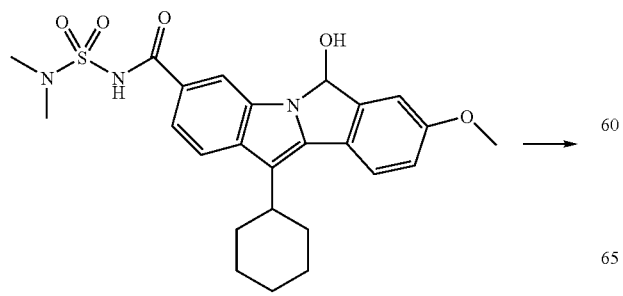

-continued

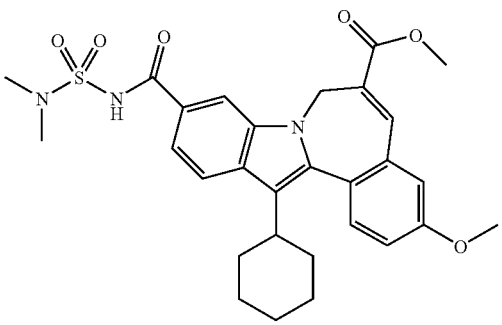

A solution of 11-cyclohexyl-N-[(dimethylamino)sulfonyl]-6-hydroxy-8-methoxy-6H-isoindolo[2,1-a]indole-3-carboxamide (10 mmol, crude from previous experiment), methyl 2-(dimethoxyphosphoryl)acrylate (2.9 g, 15 mmol), cesium carbonate (3.9 g, 12 mmol) in DMF (30 mL) was heated at 60° C. for 3h. Additional methyl 2-(dimethoxyphosphoryl)acrylate (1.2 g, 6 mmol) was added and the reaction was heated at 70° C. for 2 h. Additional methyl 2-(dimethoxyphosphoryl)acrylate (0.8 g, 4 mmol), cesium carbonate (1.6 g, 5 mmol) and DMF (6 mL) were added and the react was heated at 60° C. for 10 h and cooled to rt. The stirring reaction mixture was diluted with H₂O (150 mL), neutralized with 1N aqueous HCl and the precipitates were collected by filtration. The solids were purified by silica gel chromatography (Biotage Horizon, 65M, 25-50% EtOAc/hexanes) to yield methyl 13-cyclohexyl-N-[(dimethylamino)sulfonyl]-3-methoxy-7H-indolo[2,1-a][2]benzazepine-6-carboxylate-10-carboxamide (4.0 g, 7.2 mmol, 72% over two steps) as a yellow solid. ¹HNMR (300 MHz, CDCl₃) δ 8.67 (s, 1H), 8.09 (s, 1H), 7.86 (d, J=8.4 Hz, 1H), 7.80 (s, 1H), 7.50 (d, J=8.4 Hz, 1H), 7.42 (d, J=8.8 Hz, 1H), 7.08 (dd, J=2.6, 8.8 Hz, 1H), 6.98 (d, J=2.6 Hz, 1H), 5.75-5.51 (m, 1H), 4.29-4.01 (m, 1H), 3.89 (s, 3H), 3.82 (s, 3H), 3.05 (s, 6H), 2.87-2.73 (m, 1H), 2.11-1.12 (m, 10H). LCMS: m/e 550 (M−H)⁻, ret time 3.21 min, column A, 4 minute gradient.

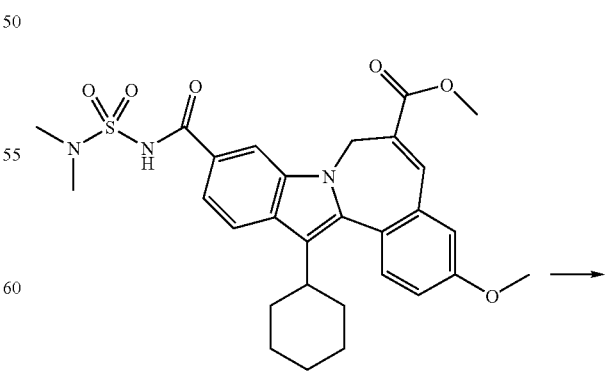

-continued

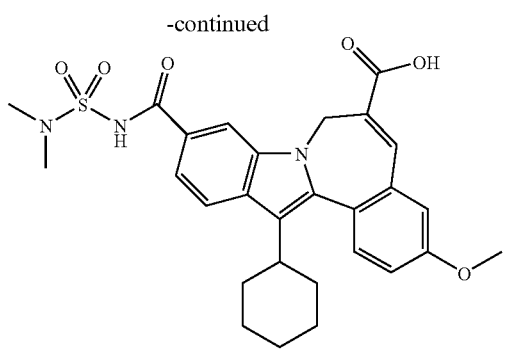

Added 1M NaOH (aq.) (5 mL, 5 mmol) to a solution of methyl 13-cyclohexyl-N-[(dimethylamino)sulfonyl]-3-methoxy-7H-indolo[2,1-a][2]benzazepine-6-carboxylate-10-carboxamide (900 mg, 1.6 mmol) in THF/MeOH (1:1, 14 mL) and heated the reaction mixture in a sealed tube with microwave irradiation at 85° C. for 30 min. The reaction was cooled, neutralized with 1M HCl (aq.) (5 mL, 5.0 mmol) and concentrated to remove organic solvents. The residue was slurried with H$_2$O and the solids were collected by filtration, flushed with H$_2$O and dried to yield 13-cyclohexyl-N-[(dimethylamino)sulfonyl]-3-methoxy-7H-indolo[2,1-a][2]benzazepine-10-carboxamide-6-carboxylic acid (807 mg, 1.5 mmol, 92%) as a yellow solid. LCMS: m/e 536 (M−H)$^-$, ret time 2.18 min, column A, 4 minute gradient.

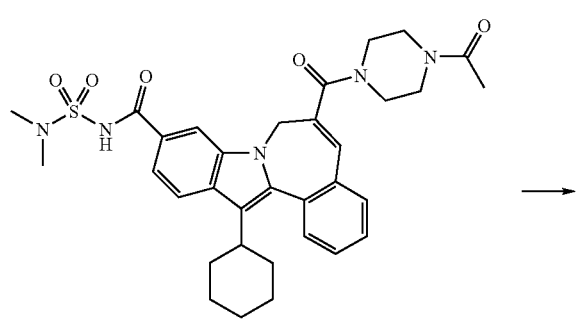

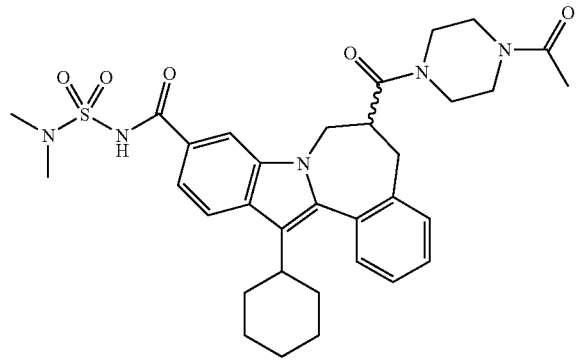

10% Palladium on carbon (200 mg, 0.19 mmol) was added to a solution of 7H-indolo[2,1-a][2]benzazepine-10-carboxamide, 6-[(4-acetyl-1-piperazinyl)carbonyl]-13-cyclohexyl-N-[(dimethylamino)sulfonyl]- (79 mg, 0.13 mmol) in MeOH (10 mL) and the reaction mixture was vacuum flushed with nitrogen (3×) and then with hydrogen (3×). The reaction mixture was stirred under a balloon of hydrogen for 3 d, filtered through a pad of celite and concentrated. The residue was purified by preparative HPLC (MeOH/H$_2$O with an NH$_4$OAc buffer) to yield 5H-indolo[2,1-a][2]benzazepine-10-carboxamide, 6-[(4-acetyl-1-piperazinyl)carbonyl]-13-cyclohexyl-N-[(dimethylamino)sulfonyl]-6,7-dihydro- (16 mg, 0.03 mmol, 20%) as a white powder. Mixture of atrope diastereomers: $^1$HNMR (500 MHz, CD$_3$OD) δ 8.09 (s. 0.3H), 7.99 (s. 0.7H), 7.91 (d, J=8.6 Hz, 0.3H), 7.89 (d, J=8.6 Hz, 0.7H), 7.63 (d, J=7.9 Hz, 0.3H), 7.59 (d, J=7.9 Hz, 0.7H), 7.52-7.28 (m, 4H), 4.64-4.56 (m, 0.7H), 4.50 (dd, J=6.1, 14.0 Hz, 0.3H), 4.14-4.05 (m, 0.3H), 3.94-3.57 (m, 9H), 3.02 (s, 4H), 3.01 (s, 2H), 2.98-2.91 (m, 1H), 2.88-2.68 (m, 2H), 2.19 (s, 2H), 2.11 (s, 1H), 2.16-1.91 (m, 4H), 1.87-1.76 (m, 2H) 1.67-1.22 (m, 4H). LCMS: m/e 618 (M−H)$^-$, ret time 1.59 min, column A, 3 minute gradient.

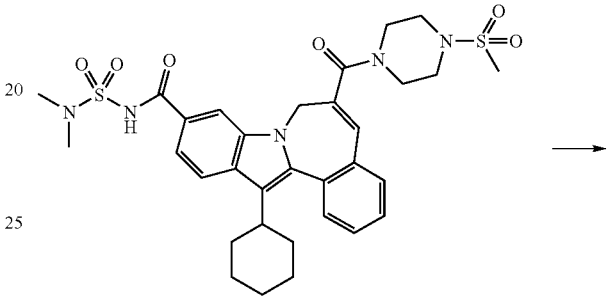

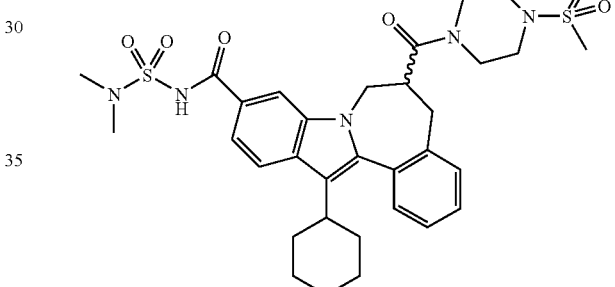

10% Palladium on carbon (84 mg, 0.08 mmol) was added to a solution of 7H-indolo[2,1-a][2]benzazepine-10-carboxamide, 13-cyclohexyl-N-[(dimethylamino)sulfonyl]-6-[[4-(methylsulfonyl)-1-piperazinyl]carbonyl]- (84 mg, 0.14 mmol) in MeOH (6 mL) and the reaction mixture was vacuum flushed with nitrogen (3×) and then with hydrogen (3×). The reaction mixture was stirred under a balloon of hydrogen for 1 d. Additional 10% palladium on carbon (100 mg, 0.9 mmol) was added and the reaction mixture was vacuum flushed with nitrogen (3×), with hydrogen (3×) and then stirred under a balloon of hydrogen for 3 d. The reaction mixture was filtered through a pad of celite and concentrated. The residue was purified by preparative HPLC (MeOH/H$_2$O with an NH$_4$OAc buffer) to yield 5H-indolo[2,1-a][2]benzazepine-10-carboxamide, 13-cyclohexyl-N-[(dimethylamino)sulfonyl]-6,7-dihydro-6-[[4-(methylsulfonyl)-1-piperazinyl]carbonyl]- (39 mg, 0.06 mmol, 44%) as a yellow solid. Mixture of atrope diastereomers: $^1$HNMR (500 MHz, CD$_3$OD) δ 8.10 (s. 0.3H), 8.02 (s. 0.7H), 7.92 (d, J=8.6 Hz, 0.3H), 7.90 (d, J=8.6 Hz, 0.7H), 7.63 (d, J=8.5 Hz, 0.3H), 7.58 (d, J=8.5 Hz, 0.7H), 7.53-7.31 (m, 4H), 4.64-4.47 (m, 1H), 4.15-3.64 (m, 5H), 3.55-3.27 (m, 5H), 3.04-2.96 (m, 9H), 2.94-2.76 (m, 3H), 2.19-1.23 (m, 10H). LCMS: m/e 654 (M−H)$^-$, ret time 1.73 min, column A, 3 minute gradient.

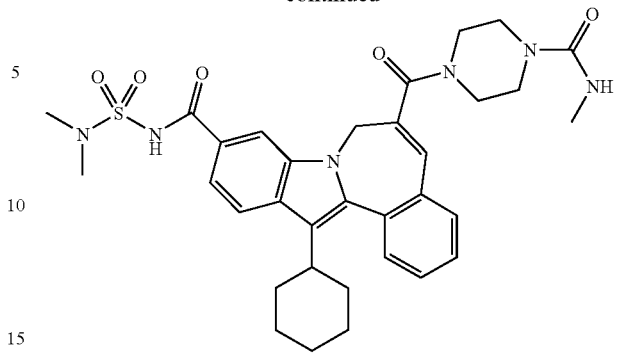

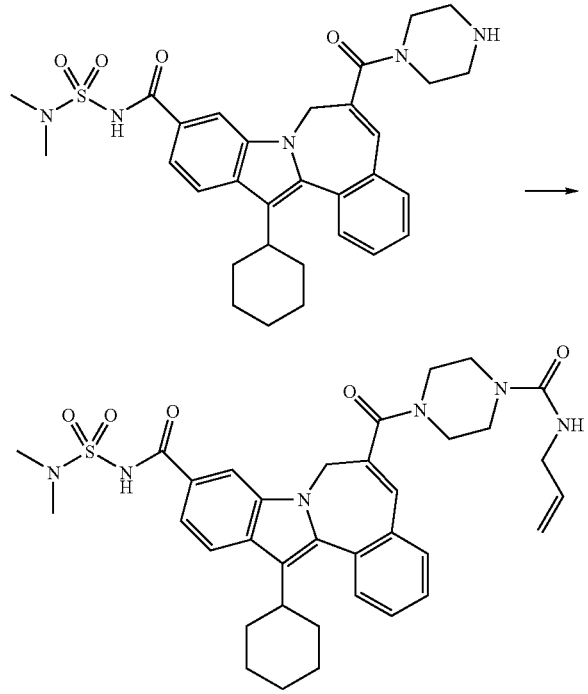

Allyl isocyanate (94 mg, 1.1 mmol) was added to a solution of 7H-indolo[2,1-a][2]benzazepine-10-carboxamide, 13-cyclohexyl-N-[(dimethylamino)sulfonyl]-6-(1-piperazinylcarbonyl) (40 mg. 0.07 mmol) in CH$_2$Cl$_2$ (1 mL) and stirred at rt for 2 h. The reaction was concentrated to dryness, slurried with Et$_2$O, filtered, and the solids were purified by preparative HPLC (MeOH/H$_2$O with an NH$_4$OAc buffer) to yield 7H-indolo[2,1-a][2]benzazepine-10-carboxamide, 13-cyclohexyl-N-[(dimethylamino)sulfonyl]-6-[[4-[(2-propenylamino)carbonyl]-1-piperazinyl]carbonyl]- (15 mg, 0.02 mmol, 32%) as a yellow powder. $^1$HNMR (500 MHz, CD$_3$OD) δ 8.17 (s. 1H), 7.95 (d, J=8.6 Hz, 1H), 7.68-7.53 (m, 5H) 7.06 (s, 1H), 5.90-5.81 (m, 1H), 5.25-5.15 (m, 1H), 5.15 (dd, J=1.6, 17.3 Hz, 1H), 5.07 (dd, J=1.6, 10.4 Hz, 1H), 4.47-4.35 (m, 1H), 3.80-3.74 (m, 2H), 3.67-3.27 (m, 8H), 3.01 (s, 6H), 2.95-2.85 (m, 1H), 2.20-1.18 (m, 10H). LCMS: m/e 659 (M+H)$^+$, ret time 2.79 min, column B, 3 minute gradient.

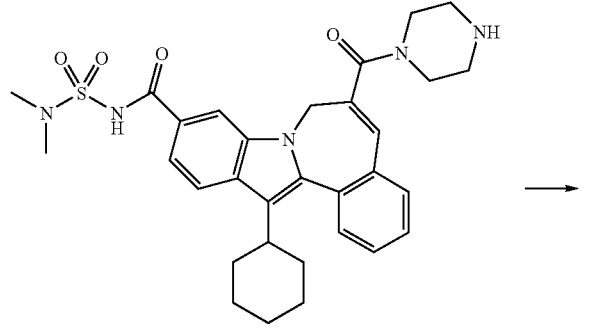

-continued

Methyl isocyanate (94 mg, 1.6 mmol) was added to a solution of 7H-indolo[2,1-a][2]benzazepine-10-carboxamide, 13-cyclohexyl-N-[(dimethylamino)sulfonyl]-6-(1-piperazinylcarbonyl) (40 mg. 0.07 mmol) in CH$_2$Cl$_2$ (1 mL) and stirred at rt for 2 h. The reaction was concentrated to dryness, slurried with Et$_2$O and filtered. The solids were dissolved into DMF and purified by preparative HPLC (MeOH/H$_2$O with a TFA buffer) to yield 7H-indolo[2,1-a][2]benzazepine-10-carboxamide, 13-cyclohexyl-N-[(dimethylamino)sulfonyl]-6-[[4-[(methylamino)carbonyl]-1-piperazinyl]carbonyl]- (13 mg, 0.02 mmol, 30%) as a yellow solid. $^1$HNMR (500 MHz, CD$_3$OD) δ 8.16 (s. 1H), 7.97 (d, J=8.6 Hz, 1H), 7.69-7.53 (m, 5H) 7.06 (s, 1H), 5.25-5.14 (m, 1H), 4.46-4.34 (m, 1H), 3.68-3.23 (m, 8H), 3.03 (s, 6H), 2.95-2.85 (m, 1H), 2.72 (s, 3H), 2.20-1.74 (m, 6H), 1.57-1.17 (m, 4H). LCMS: m/e 631 (M−H)$^−$, ret time 1.54 min, column A, 3 minute gradient.

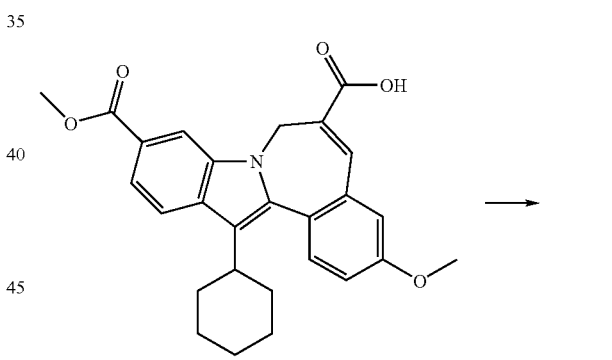

To a stirred solution of methyl 7H-indolo[2,1-a][2]benzazepine-10-carboxylate, 13-cyclohexyl, 3-methoxy, 6-carboxylic acid (120 mg, 0.27 mmol), N-(2-aminoethyl)acetamide (45 mg, 0.44 mmol) and triethylamine (0.11 mL) in DMF (2 mL) was added HATU (125 mg, 0.32 mmol). The reaction mixture was stirred at rt for 2 h, concentrated and purified by preparative HPLC (CH₃CN/H₂O with a TFA buffer) to yield methyl 7H-indolo[2,1-a][2]benzazepine-10-carboxamide-6-carboxylate, N⁶-[2-(acetylamino)ethyl]-13-cyclohexyl-3-methoxy (54 mg, 0.10 mmol, 38%) as a yellow solid. LCMS: m/e 528 (M–H)⁻, ret time 1.83 min, column A, 2 minute gradient.

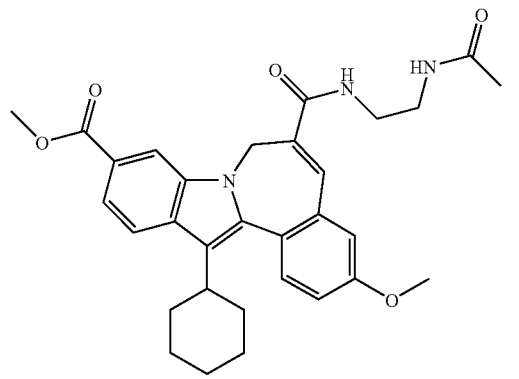

Added 1M NaOH (aq.) (0.4 mL, 0.4 mmol) to a solution of methyl 7H-indolo[2,1-a][2]benzazepine-10-carboxamide-6-carboxylate, N⁶-[2-(acetylamino)ethyl]-13-cyclohexyl-3-methoxy (54 mg, 0.10 mmol) in THF/MeOH (1:1, 2 mL) and heated the reaction mixture in a sealed tube with microwave irradiation at 85° C. for 20 min. The reaction was cooled, neutralized with 1M HCl (aq.) (0.4 mL, 0.4 mmol) and concentrated to remove organic solvents. The residue was slurried with H₂O and the solids were collected by filtration, flushed with H₂O and dried to yield 7H-indolo[2,1-a][2]benzazepine-10-carboxamide-6-carboxylic acid, N⁶-[2-(acetylamino)ethyl]-13-cyclohexyl-3-methoxy (44 mg, 0.09 mmol, 90%) as a yellow powder. ¹HNMR (500 MHz, CD₃OD) δ 8.29 (s, 1H), 7.86 (d, J=8.2 Hz, 1H), 7.71 (d, J=8.2 Hz, 1H), 7.59 (d, J=8.5 Hz, 1H), 7.50 (s, 1H), 7.18 (d, J=8.5 Hz, 1H), 7.14 (s, 1H), 5.72-5.59 (m, 1H), 4.23-4.10 (m, 1H), 3.95 (s, 3H), 3.49-3.27 (m, 4H), 2.93-2.85 (m, 1H), 2.20-1.75 (m, 6H), 1.89 (s, 3H), 1.58-1.18 (m, 4H). LCMS: m/e 514 (M–H)⁻, ret time 1.35 min, column A, 3 minute gradient.

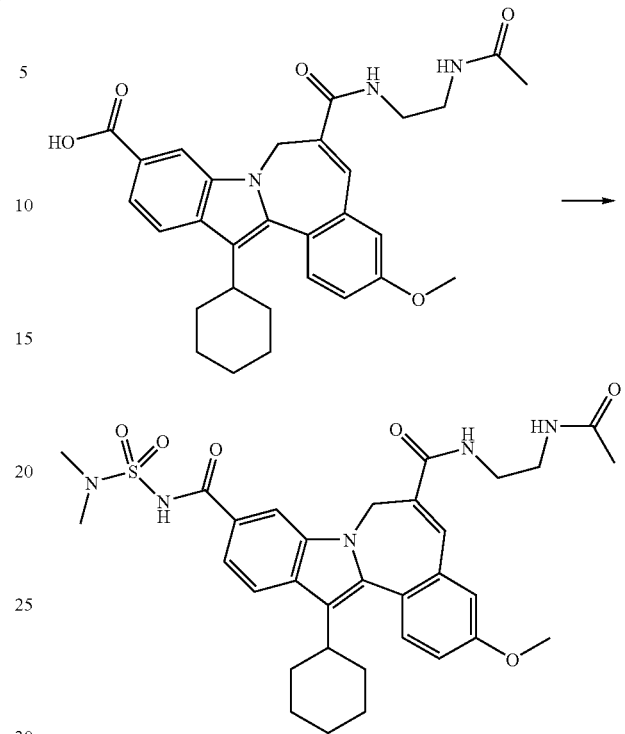

To a stirred solution of 7H-indolo[2,1-a][2]benzazepine-10-carboxamide-6-carboxylic acid, N⁶-[2-(acetylamino)ethyl]-13-cyclohexyl-3-methoxy (33 mg, 0.06 mmol), N,N-dimethylsulfamide (64 mg, 0.51 mmol) and DMAP (40 mg, 0.32 mmol) in dimethylacetamide (0.5 mL) was added 1-(3-dimethylaminopropyl)-3-ethylcarbodiimide hydrochloride (50 mg, 0.26 mmol). The reaction solution was stirred at rt 1 h and then at 45° C. for 2 h, diluted with MeOH (1 mL) and purified by preparative HPLC (CH₃CN/H₂O with TFA buffer) to yield 7H-indolo[2,1-a][2]benzazepine-6,10-dicarboxamide, N⁶-[2-(acetylamino)ethyl]-13-cyclohexyl-N¹⁰-[(dimethylamino)sulfonyl]-3-methoxy- (12 mg, 0.02 mmol, 30%) as a yellow solid. ¹HNMR (500 MHz, CDCl₃) δ 10.12 (s, 1H), 8.71 (s, 1H), 7.92 (d, J=8.5 Hz, 1H), 7.84 (s, 1H), 7.81 (dd, J=1.2, 8.5 Hz, 1H), 7.77 (br s, 1H), 7.50 (d, J=8.5 Hz, 1H), 7.08 (dd, J=2.8, 8.6 Hz, 1H), 7.03 (d, J=2.8 Hz, 1H), 6.35 (br t, J=6.1 Hz, 1H), 5.24-5.11 (m, 1H), 4.39-4.25 (m, 1H), 3.95 (s, 3H), 3.62-3.23 (m, 4H), 3.03 (s, 6H), 2.87-2.79 (m, 1H), 2.21-1.70 (m, 6H), 2.19 (s, 3H), 1.61-1.14 (m, 4H). LCMS: m/e 620 (M–H)⁻, ret time 2.43 min, column E, 4 minute gradient.

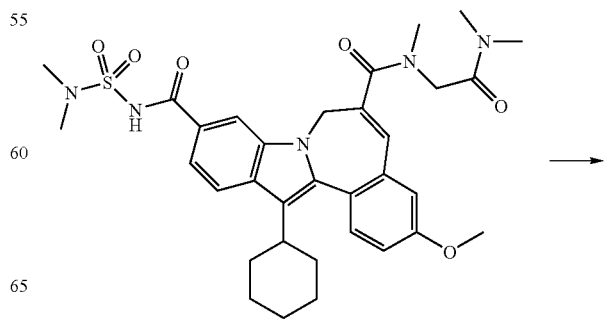

-continued

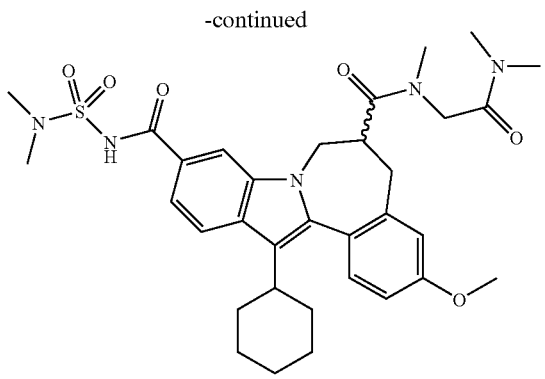

10% Palladium on carbon (80 mg, 0.08 mmol) was added to a solution of 7H-indolo[2,1-a][2]benzazepine-6,10-dicarboxamide, 13-cyclohexyl-$N^6$-[2-(dimethylamino)-2-oxoethyl]-$N^{10}$-[(dimethylamino)sulfonyl]-3-methoxy-$N^6$-methyl- (35 mg, 0.06 mmol) in MeOH (2 mL) and the reaction mixture was vacuum flushed with nitrogen (3×) and then with hydrogen (3×). The reaction mixture was stirred under a balloon of hydrogen for 2.5 d, filtered through a pad of celite and concentrated. The residue was purified by preparative HPLC (MeOH/$H_2O$ with an $NH_4OAc$ buffer) to yield 5H-indolo[2,1-a][2]benzazepine-6,10-dicarboxamide, 13-cyclohexyl-$N^6$-[2-(dimethylamino)-2-oxoethyl]-$N^{10}$-[(dimethylamino)sulfonyl]-6,7-dihydro-3-methoxy-$N^6$-methyl- (6 mg, 0.01 mmol, 20%) as an off-white solid. $^1$HNMR (500 MHz, $CDCl_3$) δ 11.11 (s, 1H), 8.09 (s. 1H), 7.74 (d, J=8.6 Hz, 1H), 7.71 (dd, J=1.2, 8.6 Hz, 1H), 7.34 (d, J=8.2 Hz, 1H), 6.96-6.90 (m, 2H), 4.85 (d, J=15.9 Hz, 1H), 4.58 (d, J=14.7 Hz, 1H), 4.04-3.84 (m, 3H), 3.89 (s, 3H), 3.51-3.45 (m, 1H), 3.35 (s, 3H), 3.40-3.20 (m, 3H), 3.09-3.01 (m, 1H), 3.04 (s, 3H), 3.03 (s, 6H), 3.00 (s, 3H), 2.64-2.58 (m, 1H), 2.10-1.19 (m, 10H). LCMS: m/e 636 (M–H)$^-$, ret time 2.69 min, column E, 4 minute gradient.

To a stirred solution of methyl 7H-indolo[2,1-a][2]benzazepine-10-carboxylate, 13-cyclohexyl, 3-methoxy, 6-carboxylic acid (120 mg, 0.27 mmol), 2-amino-N-methylacetamide hydrochloride (52 mg, 0.432 mmol) and triethylamine (0.15 mL) in DMF (2 mL) was added HATU (125 mg, 0.32 mmol). The reaction mixture was stirred at rt for 3 h, diluted with $H_2O$ (~10 mL) and the resulting solids were collected by filtration, washed with $H_2O$ and dried to yield methyl 7H-indolo[2,1-a][2]benzazepine-10-carboxylate, 13-cyclohexyl-3-methoxy-6-[[[2-(methylamino)-2-oxoethyl]amino]carbonyl]- (140 mg, 0.27 mmol, quant.) as a yellow solid, which was used without further purification.

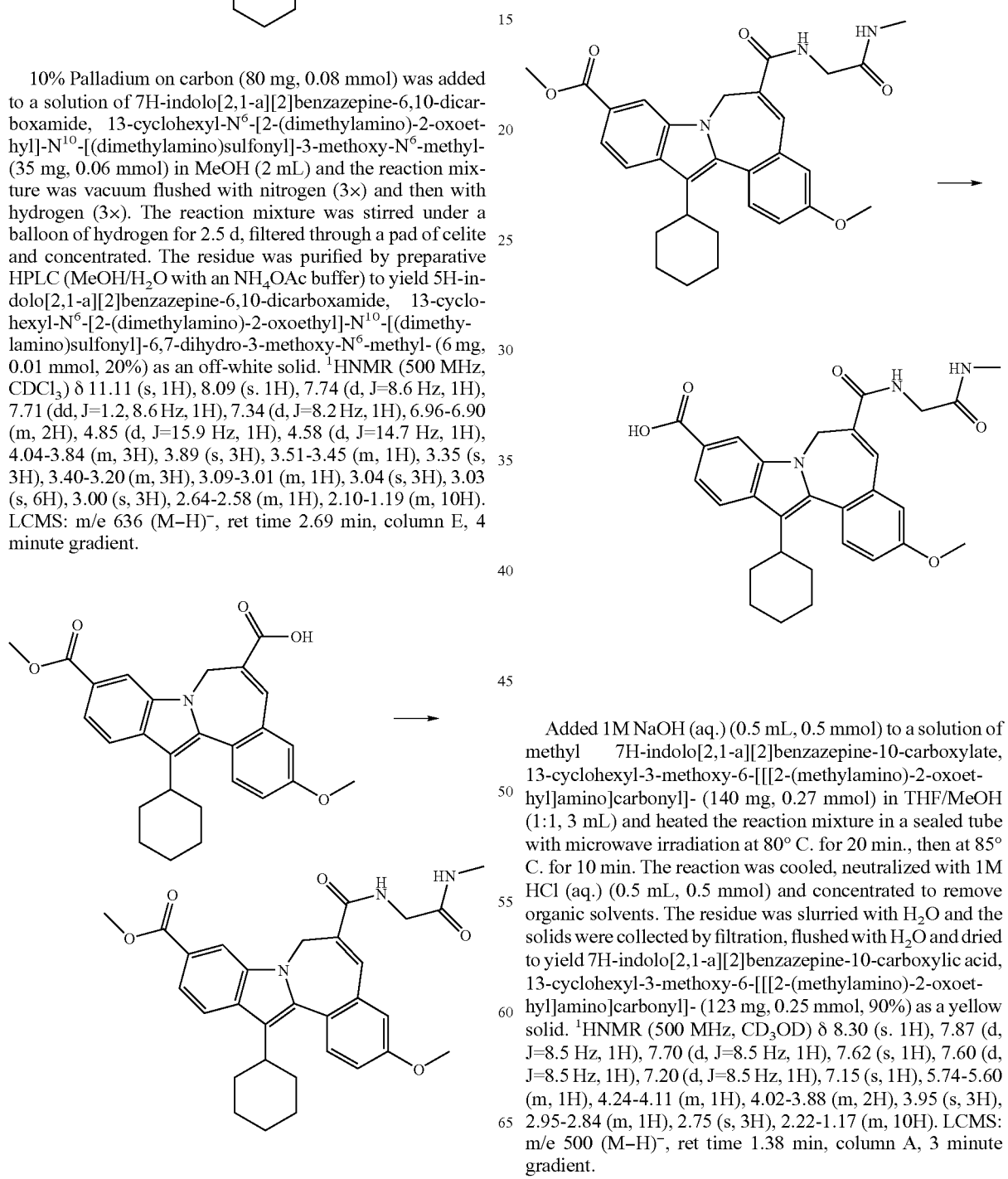

Added 1M NaOH (aq.) (0.5 mL, 0.5 mmol) to a solution of methyl 7H-indolo[2,1-a][2]benzazepine-10-carboxylate, 13-cyclohexyl-3-methoxy-6-[[[2-(methylamino)-2-oxoethyl]amino]carbonyl]- (140 mg, 0.27 mmol) in THF/MeOH (1:1, 3 mL) and heated the reaction mixture in a sealed tube with microwave irradiation at 80° C. for 20 min., then at 85° C. for 10 min. The reaction was cooled, neutralized with 1M HCl (aq.) (0.5 mL, 0.5 mmol) and concentrated to remove organic solvents. The residue was slurried with $H_2O$ and the solids were collected by filtration, flushed with $H_2O$ and dried to yield 7H-indolo[2,1-a][2]benzazepine-10-carboxylic acid, 13-cyclohexyl-3-methoxy-6-[[[2-(methylamino)-2-oxoethyl]amino]carbonyl]- (123 mg, 0.25 mmol, 90%) as a yellow solid. $^1$HNMR (500 MHz, $CD_3OD$) δ 8.30 (s. 1H), 7.87 (d, J=8.5 Hz, 1H), 7.70 (d, J=8.5 Hz, 1H), 7.62 (s, 1H), 7.60 (d, J=8.5 Hz, 1H), 7.20 (d, J=8.5 Hz, 1H), 7.15 (s, 1H), 5.74-5.60 (m, 1H), 4.24-4.11 (m, 1H), 4.02-3.88 (m, 2H), 3.95 (s, 3H), 2.95-2.84 (m, 1H), 2.75 (s, 3H), 2.22-1.17 (m, 10H). LCMS: m/e 500 (M–H)$^-$, ret time 1.38 min, column A, 3 minute gradient.

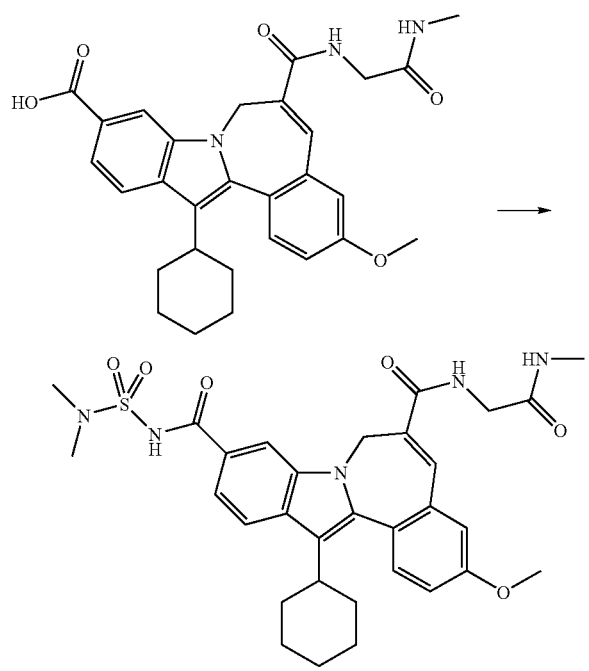

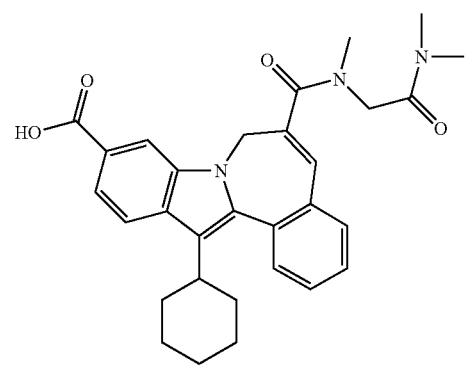

To a solution of 7H-indolo[2,1-a][2]benzazepine-10-carboxylic acid, 13-cyclohexyl-3-methoxy-6-[[[2-(methylamino)-2-oxoethyl]amino]carbonyl]- (110 mg, 0.22 mmol), N,N-dimethylsulfamide (136 mg, 1.10 mmol) and DMAP (134 mg, 1.10 mmol) in dimethylformamide (2 mL) was added PS-carbodiimide (576 mg, 1.3 mmol/g, 0.88 mmol). The reaction solution was shaken at rt overnight, filtered, concentrated and purified by preparative HPLC (MeOH/H$_2$O with an NH$_4$OAc buffer) to yield 7H-indolo[2,1-a][2]benzazepine-6,10-dicarboxamide, 13-cyclohexyl-N$^{10}$-[(dimethylamino)sulfonyl]-3-methoxy-N6-[2-(methylamino)-2-oxoethyl]- (40 mg, 0.07 mmol, 30%) as a yellow solid. $^1$HNMR (500 MHz, CD$_3$OD) δ 8.13 (s. 1H), 7.85 (d, J=8.6 Hz, 1H), 7.60-7.52 (m, 3H), 7.15 (dd, J=2.8, 8.8 Hz, 1H), 7.10 (d, J=2.8 Hz, 1H), 5.64-5.53 (m, 1H), 4.19-4.07 (m, 1H), 3.96-3.86 (m, 2H), 3.91 (s, 3H), 2.99 (s, 6H), 2.89-2.80 (m, 1H), 2.71 (s, 3H), 2.16-1.70 (m, 6H), 1.54-1.16 (m, 4H). LCMS: m/e 606 (M−H)$^−$, ret time 1.57 min, column A, 3 minute gradient.

-continued

To a stirred solution of methyl 7H-indolo[2,1-a][2]benzazepine-10-carboxylate, 13-cyclohexyl, 6-carboxylic acid (366 mg, 0.88 mmol), 2-N,N-dimethyl-2-(methylamino)acetamide (120 mg, 1.03 mmol) and triethylamine (0.37 mL) in DMF (6 mL) was added HATU (400 mg, 1.05 mmol). The reaction mixture was stirred at rt for 2 h, diluted with H$_2$O (~20 mL) and the resulting solids were collected by filtration, washed with H$_2$O and dried on the filter with aspirator vacuum for 1 h. The solids were dissolved into THF/MeOH (1:1, 6 mL) and 1M NaOH (aq.) (1.5 mL, 1.5 mmol). The reaction mixture was heated in a sealed tube with microwave irradiation at 85° C. for 20 min. The reaction was cooled, neutralized with 1M HCl (aq.) (1.5 mL, 1.5 mmol) and concentrated to remove organic solvents. The residue was slurried with H$_2$O and the solids were collected by filtration, flushed with H$_2$O and dried to yield 7H-indolo[2,1-a][2]benzazepine-10-carboxylic acid, 13-cyclohexyl-6-[[[2-(dimethylamino)-2-oxoethyl]methylamino]carbonyl]- (406 mg, 0.81 mmol, 92%) as a yellow solid. Mixture of amide rotamers: $^1$HNMR (300 MHz, DMSO-d$_6$) δ 12.58 (br s, 1H), 8.17 (br s, 0.5H), 8.13 (br s, 0.5H), 7.89 (d, J=8.8 Hz, 1H), 7.66-7.45 (m, 5H), 7.07 (br s, 0.5H), 6.90 (br s, 0.5H), 5.24-4.96 (m, 1H), 4.39-4.03 (m, 3H), 3.08-2.75 (m, 7H), 2.63 (s, 1.5H), 2.54 (s, 1.5H), 2.14-1.63 (m, 6H), 1.52-1.04 (m, 4H). LCMS: m/e 498 (M−H)$^−$, ret time 1.36 min, column A, 2 minute gradient.

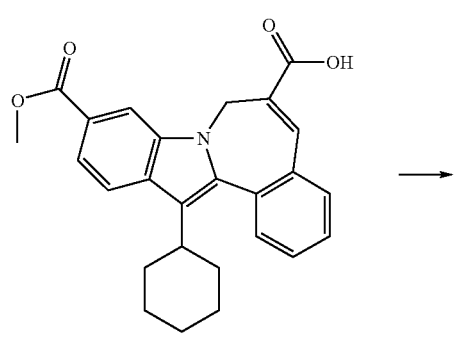

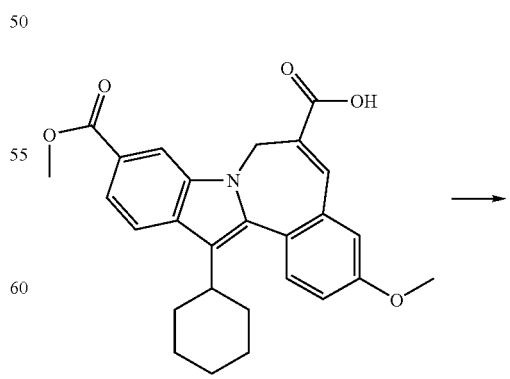

-continued

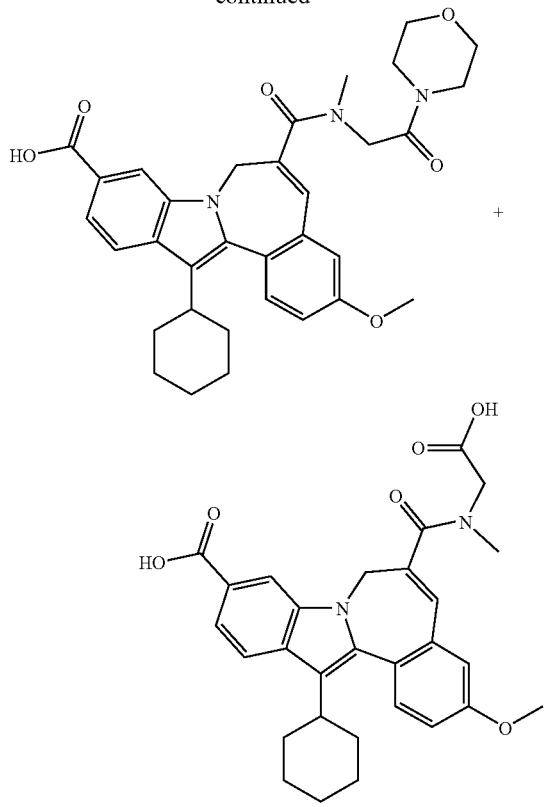

To a stirred solution of methyl 7H-indolo[2,1-a][2]benzazepine-10-carboxylate, 13-cyclohexyl, 6-carboxylic acid, 3-methoxy (200 mg, 0.45 mmol), 2-(methylamino)-1-morpholinoethanone (86 mg, 0.54 mmol) and triethylamine (0.19 mL) in DMF (3 mL) was added HATU (205 mg, 0.54 mmol). The reaction mixture was stirred at rt for 2 h, diluted with $H_2O$ (~12 mL) and the resulting solids were collected by filtration, washed with $H_2O$ and dried on the filter with aspirator vacuum for 1 h. The solids were dissolved into THF/MeOH (1:1, 4 mL) and 1M NaOH (aq.) (1.0 mL, 1.0 mmol). The reaction mixture was heated in a sealed tube with microwave irradiation at 85° C. for 20 min. The reaction was cooled, neutralized with 1M HCl (aq.) (1.0 mL, 1.0 mmol) and concentrated. The residue was slurried with $H_2O$ and the solids were collected by filtration, flushed with $H_2O$, dried and purified by preparative HPLC (MeOH/$H_2O$ with an $NH_4OAc$ buffer) to yield 7H-indolo[2,1-a][2]benzazepine-10-carboxylic acid, 13-cyclohexyl-3-methoxy-6-[[methyl[2-(4-morpholinyl)-2-oxoethyl]amino]carbonyl]- (163 mg, 0.29 mmol, 63%) as a yellow solid and 7H-indolo[2,1-a][2]benzazepine-10-carboxylic acid, 6-[[(carboxymethyl)methylamino]carbonyl]-13-cyclohexyl-3-methoxy- (13 mg, 0.03 mmol, 6%) as a yellow solid. Data for 7H-indolo[2,1-a][2]benzazepine-10-carboxylic acid, 13-cyclohexyl-3-methoxy-6-[[methyl[2-(4-morpholinyl)-2-oxoethyl]amino]carbonyl]-: $^1$HNMR (300 MHz, CDCl$_3$) δ 8.26 (br s, 1H), 7.85 (d, J=8.4 Hz, 1H), 7.74 (dd, J=1.1, 8.4 Hz, 1H), 7.48 (d, J=8.8 Hz, 1H), 7.03 (dd, J=2.7, 8.8 Hz, 1H), 7.00-6.92 (m, 1H), 6.89 (br s, 1H), 5.23-5.06 (m, 1H), 4.47-4.31 (m, 1H), 3.87 (s, 3H), 3.78-3.37 (m, 6H), 3.05-2.73 (m, 5H), 2.13-1.69 (m, 6H), 2.08 (s, 3H), 1.46-1.13 (m, 4H). LCMS: m/e 570 (M−H)⁻, ret time 1.38 min, column A, 2 minute gradient. Data for 7H-indolo[2,1-a][2]benzazepine-10-carboxylic acid, 6-[[(carboxymethyl)methylamino]carbonyl]-13-cyclohexyl-3-methoxy-. $^1$HNMR (300 MHz, DMSO-d$_6$) δ 8.09 (s, 1H), 7.82 (d, J=9.5 Hz, 1H), 7.57 (d, J=8.4 Hz, 1H), 7.47 (d, J=9.5 Hz, 1H), 7.24-6.95 (m, 3H), 5.20-5.02 (m, 1H), 4.23-4.04 (m, 1H), 3.86 (s, 3H), 3.86-3.74 (m, 2H), 2.85 (s, 3H), 2.82-2.71 (m, 1H), 2.12-1.12 (m, 10H). LCMS: m/e 503 (M+H)⁺, ret time 2.83 min, column B, 3 minute gradient.

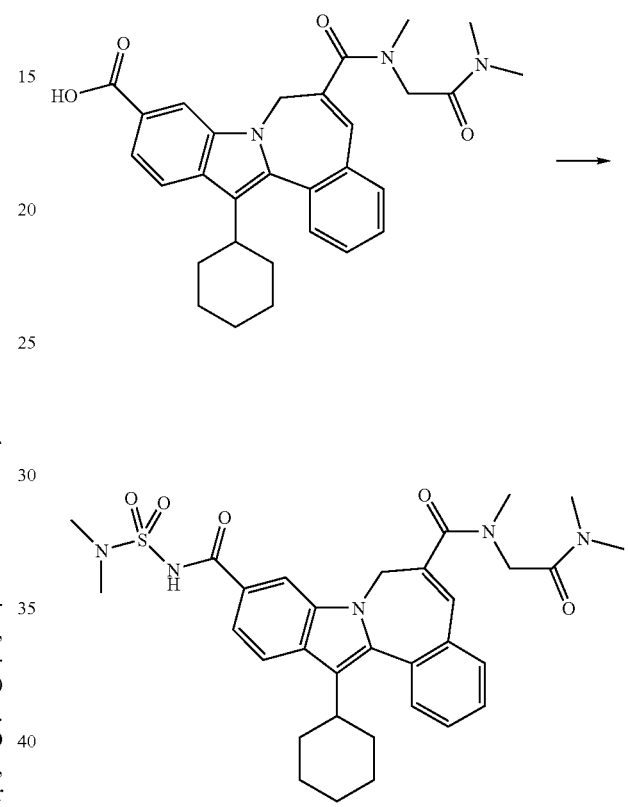

To a solution of 7H-indolo[2,1-a][2]benzazepine-10-carboxylic acid, 13-cyclohexyl-6-[[[2-(dimethylamino)-2-oxoethyl]methylamino]carbonyl]- (180 mg, 0.36 mmol), N,N-dimethylsulfamide (134 mg, 1.08 mmol) and DMAP (122 mg, 1.08 mmol) in dimethylformamide (2 mL) was added PS-carbodiimide (830 mg, 1.3 mmol/g, 1.08 mmol). The reaction solution was shaken at 45° C. overnight, filtered, concentrated and purified by preparative HPLC (MeOH/$H_2O$ with an $NH_4OAc$ buffer) to yield 7H-indolo[2,1-a][2]benzazepine-6,10-dicarboxamide, 13-cyclohexyl-N$^6$-[2-(dimethylamino)-2-oxoethyl]-N$^{10}$-[(dimethylamino)sulfonyl]-N$^6$-methyl- (90 mg, 0.15 mmol, 41%) as a yellow solid. $^1$HNMR (300 MHz, CDCl$_3$) δ 8.12 (br s, 1H), 7.88 (d, J=8.8 Hz, 1H), 7.71-7.52 (m, 2H), 7.50-7.35 (m, 3H), 6.86 (s, 1H), 5.15-5.01 (m, 1H), 4.67-4.51 (m, 1H), 3.79-3.62 (m, 1H), 3.14-2.92 (m, 12H), 2.88-2.75 (m, 1H), 2.48 (br s, 3H), 2.10-1.65 (m, 6H), 1.55-1.08 (m, 4H). LCMS: m/e 604 (M−H)⁻, ret time 2.57 min, column A, 4 minute gradient.

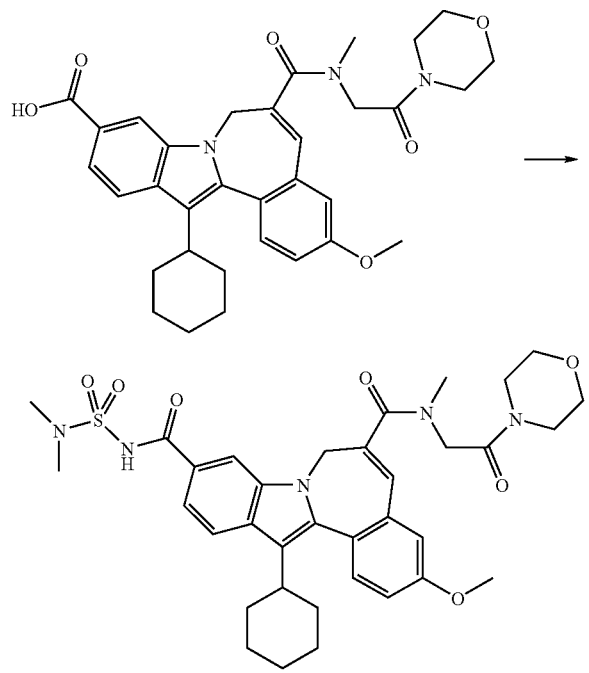

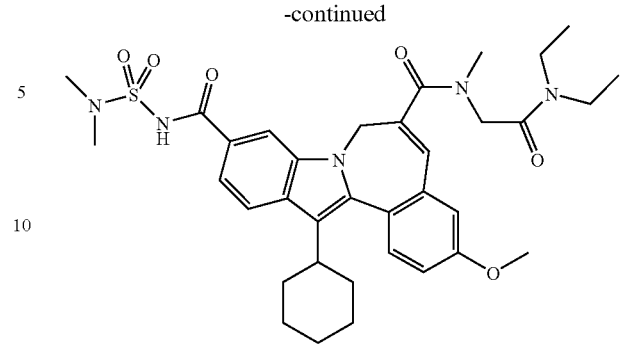

To a solution of 7H-indolo[2,1-a][2]benzazepine-10-carboxylic acid, 13-cyclohexyl-3-methoxy-6-[[methyl[2-(4-morpholinyl)-2-oxoethyl]amino]carbonyl]- (106 mg, 0.19 mmol), N,N-dimethylsulfamide (70 mg, 0.56 mmol) and DMAP (70 mg, 0.56 mmol) in dimethylformamide (1.2 mL) was added PS-carbodiimide (428 mg, 1.3 mmol/g, 0.56 mmol). The reaction solution was shaken at 45° C. for 6 h, filtered, concentrated and purified by preparative HPLC (MeOH/H$_2$O with an NH$_4$OAc buffer) to yield 7H-indolo[2,1-a][2]benzazepine-6,10-dicarboxamide, 13-cyclohexyl-N$^{10}$-[(dimethylamino)sulfonyl]-3-methoxy-N6-methyl-N$^6$-[2-(4-morpholinyl)-2-oxoethyl]- (26 mg, 0.04 mmol, 21%) as a yellow solid. Mixture of amide rotamers: $^1$HNMR (300 MHz, CD$_3$OD) δ 8.25-8.08 (m, 1H), 7.92 (d, J=8.4 Hz, 1H), 7.64-7.52 (m, 2H), 7.20-6.95 (m, 3H), 5.30-5.04 (m, 1H), 4.59-4.27 (m, 3H), 3.93 (s, 3H), 3.78-3.48 (m, 4H), 3.33 (s, 3H), 3.03 (s, 6H), 3.10-2.82 (m, 5H), 2.21-1.72 (m, 6H), 1.58-1.21 (m, 4H). LCMS: m/e 678 (M+H)$^+$, ret time 3.52 min, column B, 4 minute gradient.

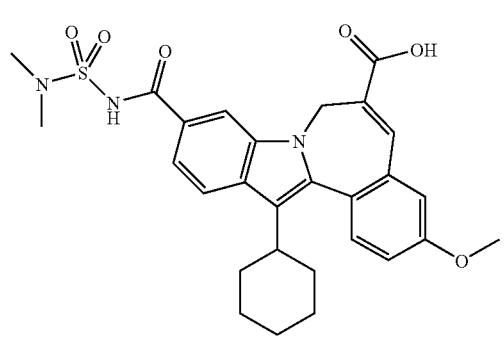

-continued

To a stirred solution of 13-cyclohexyl-N-[(dimethylamino)sulfonyl]-3-methoxy-7H-indolo[2,1-a][2]benzazepine-10-carboxamide-6-carboxylic acid (100 mg, 0.19 mmol), N,N-diethyl-2-(methylamino)acetamide hydrochloride (41 mg, 0.23 mmol) and triethylamine (0.11 mL) in DMF (2 mL) was added HATU (85 mg, 0.22 mmol). The reaction mixture was stirred at rt for 2 h, diluted with H$_2$O (~8 mL) and extracted with EtOAc (3×5 mL), the combined organics were concentrated and purified by preparative HPLC (MeOH/H$_2$O with an NH$_4$OAc buffer) to yield 7H-indolo[2,1-a][2]benzazepine-6,10-dicarboxamide, 13-cyclohexyl-N$^6$-[2-(diethylamino)-2-oxoethyl]-N$^{10}$-[(dimethylamino)sulfonyl]-3-methoxy-N$^6$-methyl- (68 mg, 0.10 mmol, 55%) as a yellow solid. $^1$HNMR (300 MHz, CDCl$_3$) δ 9.91 (br s, 1H), 8.06 (br s, 1H), 7.85 (d, J=8.4 Hz, 1H), 7.67-7.58 (m, 1H), 7.48 (d, J=8.4 Hz, 1H), 7.02 (dd, J=2.6, 8.4 Hz, 1H), 6.89 (br s, 1H), 6.83 (br s, 1H), 5.11-5.01 (m, 1H), 4.62-4.83 (m, 2H), 3.87 (s, 3H), 3.83-3.23 (m, 5H), 3.04 (s, 6H), 2.87-2.73 (m, 1H), 2.46 (s, 3H), 2.09-1.03 (m, 16H). LCMS: m/e 662 (M−H)$^−$, ret time 2.98 min, column A, 4 minute gradient.

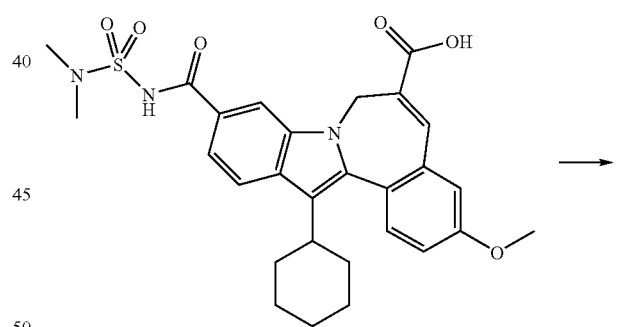

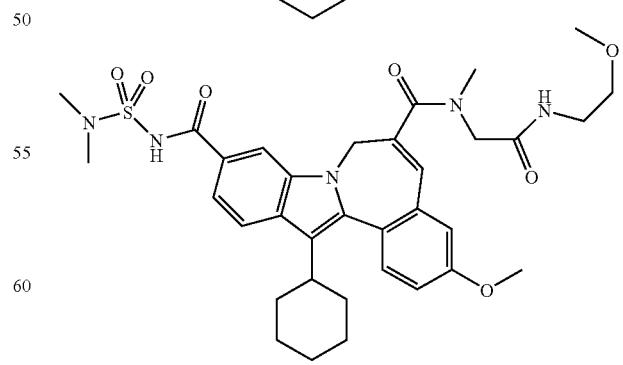

To a stirred solution of 13-cyclohexyl-N-[(dimethylamino)sulfonyl]-3-methoxy-7H-indolo[2,1-a][2]benzazepine-10-carboxamide-6-carboxylic acid (100 mg, 0.19 mmol), N,N- diethyl-2-(methylamino)acetamide hydrochloride (41 mg, 0.22 mmol) and triethylamine (0.11 mL) in DMF (2 mL) was added HATU (85 mg, 0.23 mmol). The reaction mixture was stirred at rt for 2 h, diluted with H₂O (~8 mL) and extracted with EtOAc (3×5 mL), the combined organics were concentrated and purified by preparative HPLC (MeOH/H₂O with an NH₄OAc buffer) to yield 7H-indolo[2,1-a][2]benzazepine-6,10-dicarboxamide, 13-cyclohexyl-$N^{10}$-[(dimethylamino)sulfonyl]-3-methoxy-$N^6$-[2-[(2-methoxyethyl)amino]-2-oxoethyl]-$N^6$-methyl- (58 mg, 0.09 mmol, 47%) as a yellow solid. Mixture of amide rotamers: ¹H-NMR (300 MHz, CDCl₃) δ 8.21 (s, 0.25H), 8.02 (s, 0.75H), 7.86 (d, J=8.8 Hz, 0.75H), 7.83 (d, J=8.8 Hz, 0.25H), 7.68-7.58 (m, 1H), 7.51 (d, J=7.8 Hz, 0.25H), 7.49 (d, J=7.8 Hz, 0.75H), 7.03 (dd, J=2.6, 8.8 Hz, 1H), 6.88 (d, J=2.6 Hz, 1H), 6.81 (s, 1H), 5.14-5.03 (m, 1H), 4.48-4.34 (m, 1H), 3.88 (s, 3H), 3.67-3.42 (m, 4H), 3.34 (s, 0.75H), 3.31 (s, 2.25H), 3.09-2.99 (m, 1H), 3.04 (s, 6H), 2.87-2.72 (m, 1H), 2.57-2.44 (m, 1H), 2.49 (s, 0.75H), 2.07 (s, 2.25H), 2.11-1.23 (m, 10H). LCMS: m/e 664 (M−H)⁻, ret time 2.69 min, column A, 4 minute gradient.

10% Palladium on carbon (38 mg, 0.04 mmol) was added to a solution of 7H-indolo[2,1-a][2]benzazepine-6,10-dicarboxamide, 13-cyclohexyl-$N^{10}$-[(dimethylamino)sulfonyl]-3-methoxy-$N^6$-[2-[(2-methoxyethyl)amino]-2-oxoethyl]-$N^6$-methyl- (40 mg, 0.06 mmol) in MeOH (2 mL) and the reaction mixture was vacuum flushed with nitrogen (3×) and then with hydrogen (3×). The reaction mixture was stirred under a balloon of hydrogen overnight, filtered through a pad of celite and concentrated to yield 5H-indolo[2,1-a][2]benzazepine-6,10-dicarboxamide, 13-cyclohexyl-$N^{10}$-[(dimethylamino)sulfonyl]-6,7-dihydro-3-methoxy-$N^6$-[2-[(2-methoxyethyl)amino]-2-oxoethyl]-$N^6$-methyl- (30 mg, 0.04 mmol, 75%) as a yellow solid. Diastereomeric mixture of atrope isomers with amide rotamers: Partial ¹HNMR (300 MHz, CDCl₃) δ 11.30 (br s, 0.2H), 11.00 (br s, 0.5H), 8.35 (br s, 90% H₂O0.1% TFA, Solvent B=90% MeOH10% H₂O0.1% TFA, Start % B=0, Final % B=100, Gradient time=2 min, Flow Rate=5 ml/min, Column: Xterra MS C18 S7 3.0×50 mm; LC/MS: (ES+) m/z (M+H)⁺=528.23, HPLC R$_f$=2.040 min. 0.2H), 7.98 (br s, 0.6H), 7.89-7.66 (m, 2H), 7.37-7.28 (m, 1H), 6.95-6.85 (m, 2H), 6.10-6.00 (m, 0.5H), 5.08-4.98 (m, 0.4H), 3.86 (s, 3H), 3.01 (s, 6H). LCMS: m/e 666 (M−H)⁻, ret time 2.74 min, column A, 4 minute gradient.

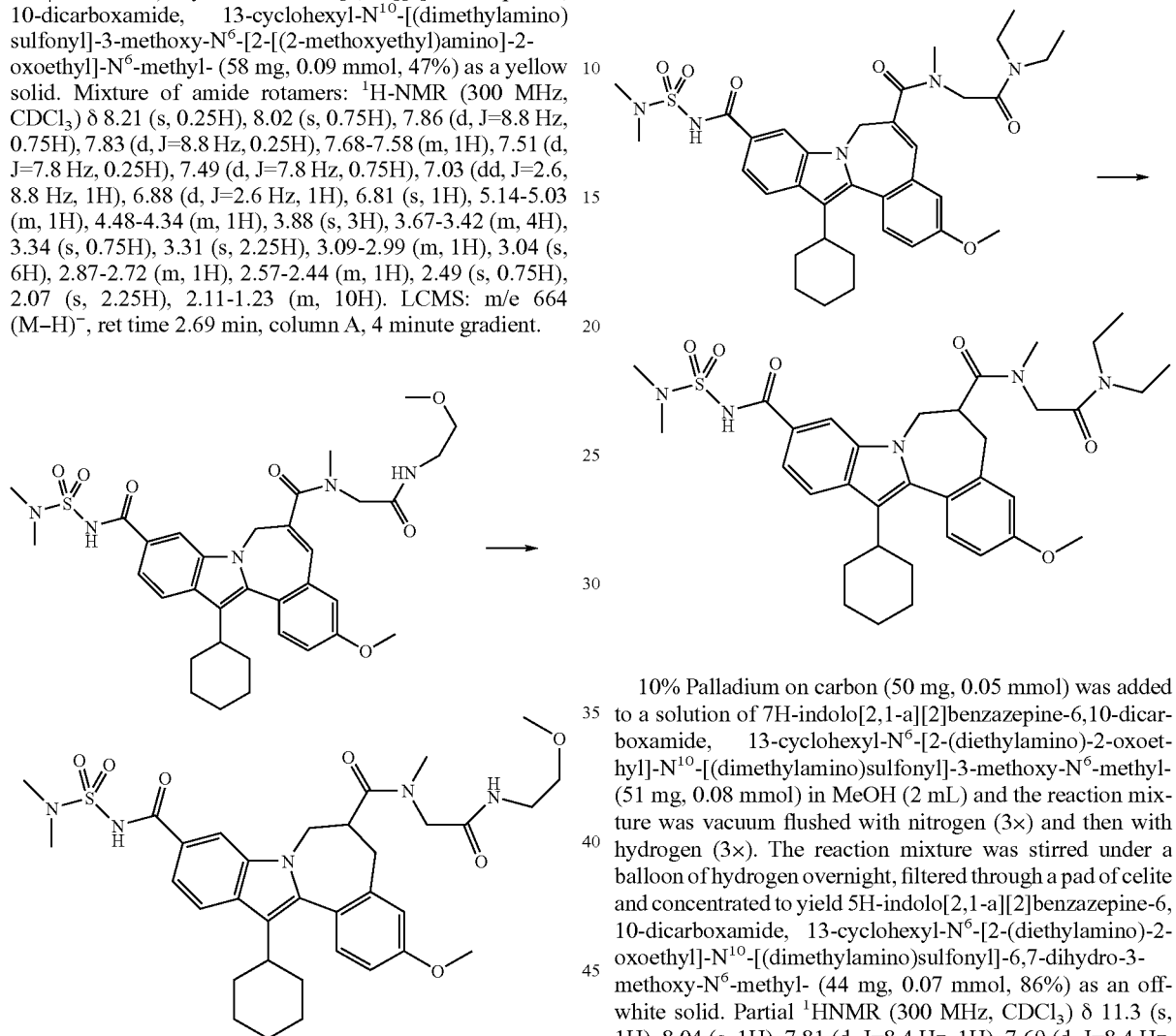

10% Palladium on carbon (50 mg, 0.05 mmol) was added to a solution of 7H-indolo[2,1-a][2]benzazepine-6,10-dicarboxamide, 13-cyclohexyl-$N^6$-[2-(diethylamino)-2-oxoethyl]-$N^{10}$-[(dimethylamino)sulfonyl]-3-methoxy-$N^6$-methyl- (51 mg, 0.08 mmol) in MeOH (2 mL) and the reaction mixture was vacuum flushed with nitrogen (3×) and then with hydrogen (3×). The reaction mixture was stirred under a balloon of hydrogen overnight, filtered through a pad of celite and concentrated to yield 5H-indolo[2,1-a][2]benzazepine-6,10-dicarboxamide, 13-cyclohexyl-$N^6$-[2-(diethylamino)-2-oxoethyl]-$N^{10}$-[(dimethylamino)sulfonyl]-6,7-dihydro-3-methoxy-$N^6$-methyl- (44 mg, 0.07 mmol, 86%) as an off-white solid. Partial ¹HNMR (300 MHz, CDCl₃) δ 11.3 (s, 1H), 8.04 (s, 1H), 7.81 (d, J=8.4 Hz, 1H), 7.69 (d, J=8.4 Hz, 1H), 7.31 (d, J=8.0 Hz, 1H), 6.94-6.86 (m, 2H), 4.80-4.71 (m, 1H), 4.60-4.52 (m, 1), 3.86 (s, 3H), 3.33 (s, 3H), 3.01 (s, 6H). LCMS: m/e 664 (M−H)⁻, ret time 3.12 min, column A, 4 minute gradient.

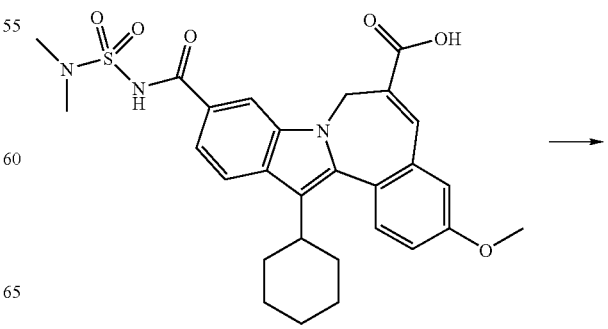

-continued

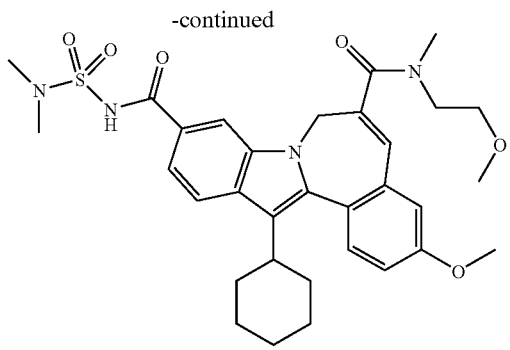

To a stirred solution of 13-cyclohexyl-N-[(dimethylamino)sulfonyl]-3-methoxy-7H-indolo[2,1-a][2]benzazepine-10-carboxamide-6-carboxylic acid (90 mg, 0.17 mmol), 2-methoxy-N-methylethanamine (22 mg, 0.25 mmol) and triethylamine (0.10 mL) in DMF (2 mL) was added HATU (82 mg, 0.22 mmol). The reaction mixture was stirred at rt for 1 h, diluted with H$_2$O (~5 mL), acidified with 1M HCl (aq.) (~0.75 mL) and the precipitate was collected by filtration. The solids were rinsed with water and dried to yield 7H-indolo[2,1-a][2]benzazepine-6,10-dicarboxamide, 13-cyclohexyl-N$^{10}$-[(dimethylamino)sulfonyl]-3-methoxy-N$^6$-(2-methoxyethyl)-N$^6$-methyl- (93 mg, 0.15 mmol, 91%) as a white solid. $^1$HNMR (300 MHz, DMSO-d$_6$) δ 11.59 (s, 1H), 8.34 (s, 1H), 7.87 (d, J=8.4 Hz, 1H), 7.63 (br d, J=8.4 Hz, 1H), 7.50 (d, J=9.2 Hz, 1H), 7.21-7.13 (m, 1H), 7.16 (s, 1H), 6.98 (s, 1H), 5.21-4.98 (m, 1H), 4.40-4.18 (m, 1H), 3.88 (s, 3H), 3.57-3.41 (m, 2H), 3.29 (s, 3H), 3.17-3.04 (m, 2H), 2.92 (s, 3H), 2.91 (s, 6H), 2.82-2.73 (m, 1H), 2.12-1.14 (m, 10H). LCMS: m/e 609 (M+H)$^+$, ret time 2.11 min, column C, 2 minute gradient.

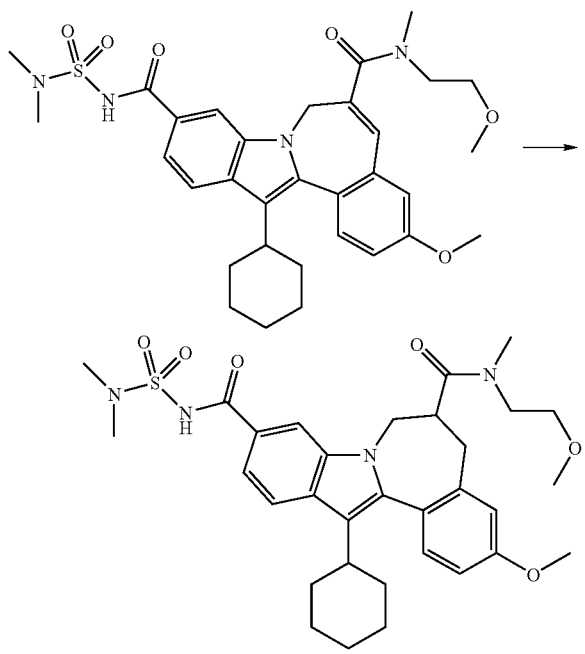

10% Palladium on carbon (77 mg, 0.07 mnol) was added to a solution of 7H-indolo[2,1-a][2]benzazepine-6,10-dicarboxamide, 13-cyclohexyl-N$^{10}$-[(dimethylamino)sulfonyl]-3-methoxy-N$^6$-(2-methoxyethyl)-N$^6$-methyl- (65 mg, 0.11 mmol) in MeOH/CH$_2$Cl$_2$ (1:1, 4 mL) and the reaction mixture was vacuum flushed with nitrogen (3×) and then with hydrogen (3×). The reaction was stirred under a balloon of hydrogen overnight, filtered through a pad of celite and concentrated to yield 5H-indolo[2,1-a][2]benzazepine-6,10-dicarboxamide, 13-cyclohexyl-N$^{10}$-[(dimethylamino)sulfonyl]-6,7-dihydro-3-methoxy-N$^6$-(2-methoxyethyl)-N$^6$-methyl- (60 mg, 0.10 mmol, 92%) as a light yellow solid. Mixture of atrope diastereomers. $^1$HNMR (300 MHz, CD$_3$OD) δ 8.10-7.92 (m, 1H), 7.91-7.83 (m, 1H), 7.62-7.51 (m, 1H), 7.42-7.33 (m, 1H), 7.10-6.84 (m, 2H), 4.67-4.44 (m, 1H), 3.93-3.86 (m, 3H), 3.84-3.21 (m, 1H), 3.06-2.86 (m, 8H), 2.83-2.64 (m, 2H), 2.18-1.19 (m, 10H). LCMS: m/e 611 (M+H)$^+$, ret time 2.12 min, column C, 2 minute gradient.

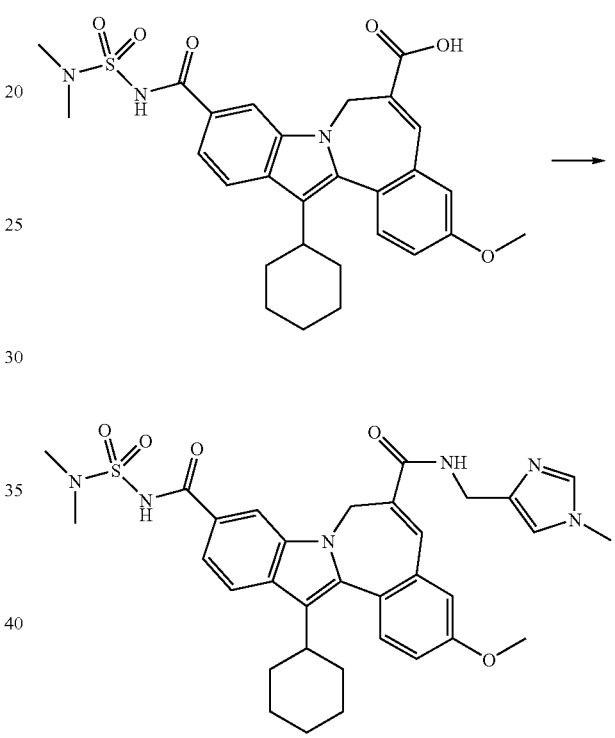

To a stirred solution of 13-cyclohexyl-N-[(dimethylamino)sulfonyl]-3-methoxy-7H-indolo[2,1-a][2]benzazepine-10-carboxamide-6-carboxylic acid (90 mg, 0.17 mmol), (1-methyl-1H-imidazol-4-yl)methanamine (28 mg, 0.25 mmol) and triethylamine (0.10 mL) in DMF (2 mL) was added HATU (82 mg, 0.22 mmol). The reaction mixture was stirred at rt for 1 h, diluted with H$_2$O (~5 mL), acidified with 1M HCl (aq.) (~0.75 mL) and the precipitate was collected by filtration. The solids were rinsed with water and dried to yield 7H-indolo[2,1-a][2]benzazepine-6,10-dicarboxamide, 13-cyclohexyl-N$^{10}$-[(dimethylamino)sulfonyl]-3-methoxy-N$^6$-[(1-methyl-1H-imidazol-4-yl)methyl]- (102 mg, 0.16 mmol, 96%) as a bright yellow solid. $^1$HNMR (300 MHz, CD$_3$OD) δ 8.46 (s, 1H), 8.14 (d, J=1.5 Hz, 1H), 7.90 (d, J=8.8 Hz, 1H), 7.62-7.54 (m, 3H), 7.33 (s, 1H), 7.20 (dd, J=2.9, 8.8 Hz, 1H), 7.13 (d, J=2.9 Hz, 1H), 5.70-5.55 (m, 1H), 4.50 (s, 2H), 4.29-4.11 (m, 1H), 3.94 (s, 3H), 3.83 (s, 3H), 3.04 (s, 6H), 2.89-2.80 (m, 1H), 2.23-1.16 (m, 10H). LCMS: m/e 632 (M+H)$^+$, ret time 1.81 min, column C, 2 minute gradient.

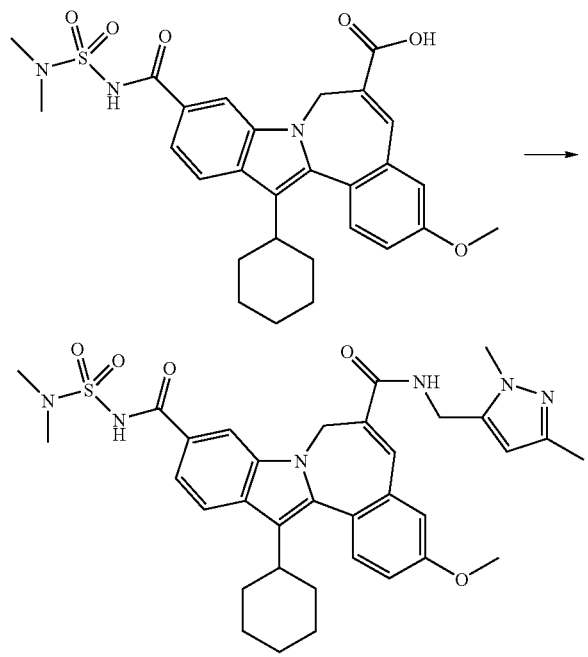

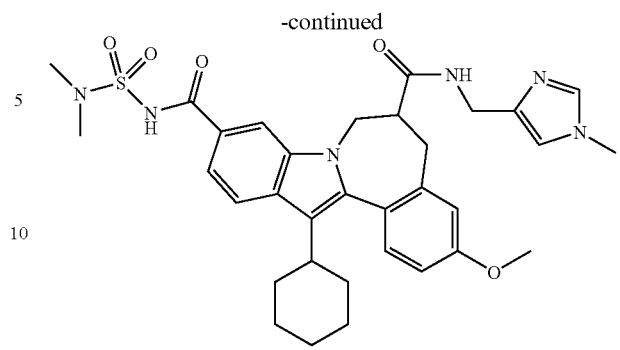

To a stirred solution of 13-cyclohexyl-N-[(dimethylamino)sulfonyl]-3-methoxy-7H-indolo[2,1-a][2]benzazepine-10-carboxamide-6-carboxylic acid (90 mg, 0.17 mmol), (1,3-dimethyl-1H-pyrazol-5-yl)methanamine (31 mg, 0.25 mmol) and triethylamine (0.10 mL) in DMF (2 mL) was added HATU (82 mg, 0.22 mmol). The reaction mixture was stirred at rt for 1 h, diluted with H$_2$O (~5 mL), acidified with 1M HCl (aq.) (~0.75 mL) and the precipitate was collected by filtration. The solids were rinsed with water and dried to yield 7H-indolo[2,1-a][2]benzazepine-6,10-dicarboxamide, 13-cyclohexyl-N$^{10}$-[(dimethylamino)sulfonyl]-N$^6$-[(1,3-dimethyl-1H-pyrazol-5-yl)methyl]-3-methoxy- (104 mg, 0.16 mmol, 96%) as a bright yellow solid. $^1$HNMR (300 MHz, CD$_3$OD) δ 8.15 (s, 1H), 7.91 (d, J=8.4 Hz, 1H), 7.62-7.54 (m, 2H), 7.52 (s, 1H), 7.18 (dd, J=8.8 Hz, 1H), 7.13 (br s, 1H), 6.06 (s, 1H), 5.72-5.52 (m, 1H), 4.50 (s, 2H), 4.27-4.10 (m, 1H), 3.93 (s, 3H), 3.80 (s, 3H), 3.03 (s, 6H), 2.95-2.80 (m, 1H), 2.23-1.15 (m, 10H), 2.18 (s, 3H). LCMS: m/e 645 (M+H)$^+$, ret time 2.09 min, column C, 2 minute gradient.

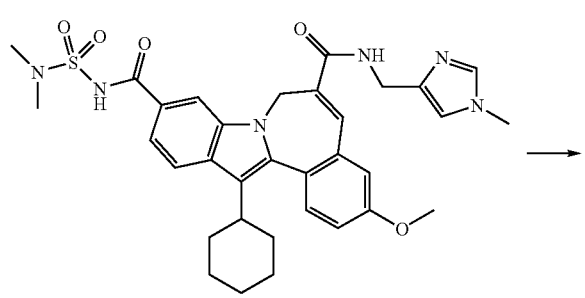

-continued

10% Palladium on carbon (75 mg, 0.07 mmol) was added to a solution of 7H-indolo[2,1-a][2]benzazepine-6,10-dicarboxamide, 13-cyclohexyl-N$^{10}$-[(dimethylamino)sulfonyl]-3-methoxy-N$^6$-[(1-methyl-1H-imidazol-4-yl)methyl]- (60 mg, 0.10 mmol) in MeOH/CH$_2$Cl$_2$ (1:1, 4 mL) and the reaction mixture was vacuum flushed with nitrogen (3×) and then with hydrogen (3×). The reaction was stirred under a balloon of hydrogen overnight, filtered through a pad of celite and concentrated to yield 5H-indolo[2,1-a][2]benzazepine-6,10-dicarboxamide, 13-cyclohexyl-N$^{10}$-[(dimethylamino)sulfonyl]-6,7-dihydro-3-methoxy-N$^6$-[(1-methyl-1H-imidazol-4-yl)methyl]- (60 mg, 0.09 mmol, 90%) as a bright yellow solid. Mixture of atrope diastereomers. LCMS: m/e 633 (M+H)$^+$, ret time 1.73 min, column C, 2 minute gradient.

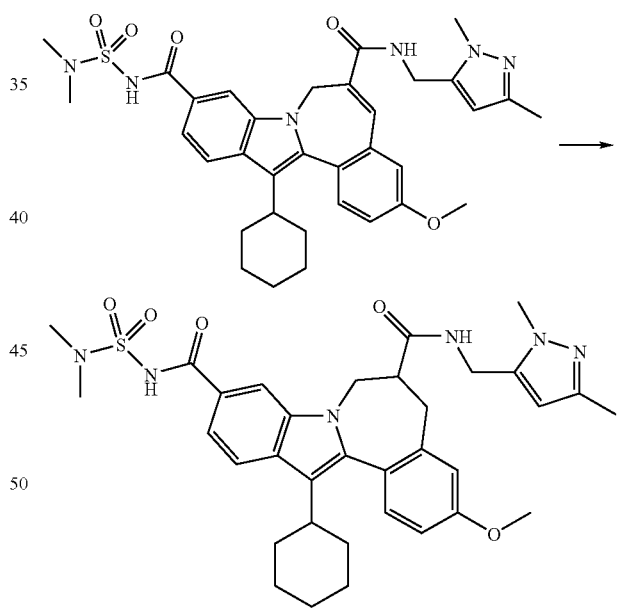

10% Palladium on carbon (75 mg, 0.07 mmol) was added to a solution of 7H-indolo[2,1-a][2]benzazepine-6,10-dicarboxamide, 13-cyclohexyl-N$^{10}$-[(dimethylamino)sulfonyl]-N$^6$-[(1,3-dimethyl-1H-pyrazol-5-yl)methyl]-3-methoxy- (60 mg, 0.09 mmol) in MeOH/CH$_2$Cl$_2$ (2:1, 3 mL) and the reaction mixture was vacuum flushed with nitrogen (3×) and then with hydrogen (3×). The reaction was stirred under a balloon of hydrogen overnight, filtered through a pad of celite and concentrated to yield 5H-indolo[2,1-a][2]benzazepine-6,10-dicarboxamide, 13-cyclohexyl-N$^{10}$-[(dimethylamino)sulfonyl]-6,7-dihydro-3-methoxy-N$^6$-(1,3-dimethyl-1H-pyrazol- 5-yl)methyl (51 mg, 0.08 mmol, 86%) as a bright yellow solid. Mixture of atrope diasteromers: ¹HNMR (300 MHz, CD₃OD) δ 8.09 (s, 0.3H), 7.98 (s, 0.7H), 7.90 (d, J=8.4 Hz, 0.3H), 7.88 (d, J=8.4 Hz, 0.7H), 7.61-7.53 (m, 1H), 7.42-7.34 (m, 1H), 7.07-6.98 (m, 1.7H), 6.86 (d, J=2.6 Hz, 0.3H), 6.23 (s, 0.3H), 6.15 (s, 0.7H), 4.87-4.57 (m, 2H), 4.54-4.34 (m, 2H), 3.90 (s, 2.1H), 3.89 (s, 0.9H), 3.87 (s, 0.9H), 3.84 (s, 2.1H), 3.26-3.07 (m, 1H) 3.03 (s, 6H), 2.99-2.67 (m, 3H), 2.29 (s, 0.9H), 2.26 (s, 2.1H), 2.21-1.20 (m, 10H). LCMS: m/e 647 (M+H)⁺, ret time 2.01 min, column C, 2 minute gradient.

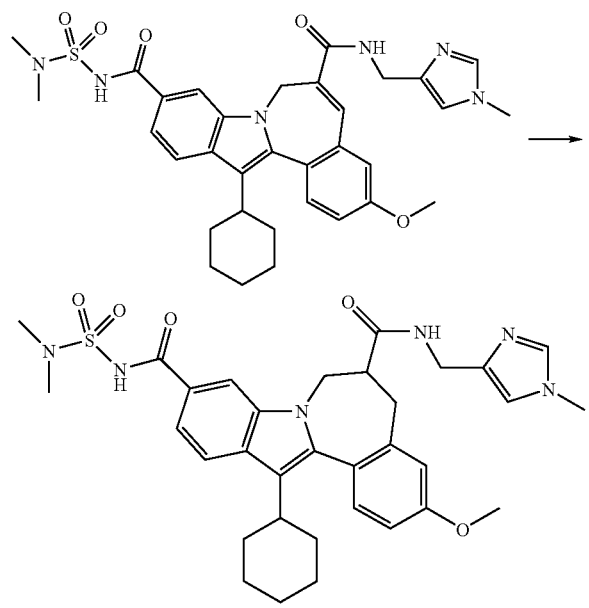

10% Palladium on carbon (75 mg, 0.07 mmol) was added to a solution of 7H-indolo[2,1-a][2]benzazepine-6,10-dicarboxamide, 13-cyclohexyl-N¹⁰-[(dimethylamino)sulfonyl]-3-methoxy-N⁶-[(1-methyl-1H-imidazol-4-yl)methyl]- (60 mg, 0.10 mmol) in MeOH/CH₂Cl₂ (1:1, 4 mL) and the reaction mixture was vacuum flushed with nitrogen (3×) and then with hydrogen (3×). The reaction was stirred under a balloon of hydrogen overnight, filtered through a pad of celite and concentrated to yield 5H-indolo[2,1-a][2]benzazepine-6,10-dicarboxamide, 13-cyclohexyl-N¹⁰-[(dimethylamino)sulfonyl]-6,7-dihydro-3-methoxy-N⁶-[(1-methyl-1H-imidazol-4-yl)methyl]- (60 mg, 0.09 mmol, 90%) as a bright yellow solid. Mixture of atrope diastereomers. LCMS: m/e 633 (M+H)⁺, ret time 1.73 min, column C, 2 minute gradient.

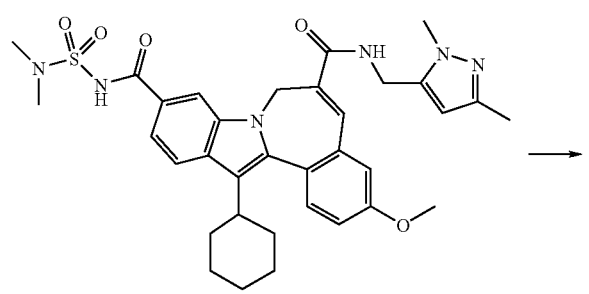

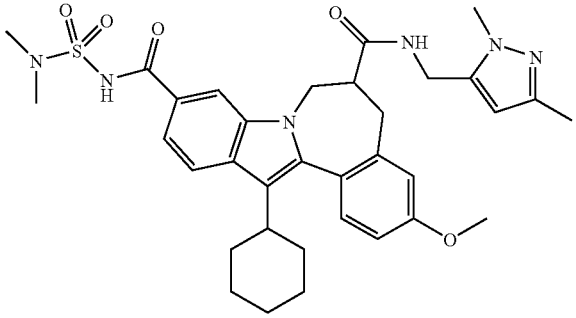

10% Palladium on carbon (75 mg, 0.07 mmol) was added to a solution of 7H-indolo[2,1-a][2]benzazepine-6,10-dicarboxamide, 13-cyclohexyl-N¹⁰-[(dimethylamino)sulfonyl]-N⁶-[(1,3-dimethyl-1H-pyrazol-5-yl)methyl]-3-methoxy- (60 mg, 0.09 mmol) in MeOH/CH₂Cl₂ (2:1, 3 mL) and the reaction mixture was vacuum flushed with nitrogen (3×) and then with hydrogen (3×). The reaction was stirred under a balloon of hydrogen overnight, filtered through a pad of celite and concentrated to yield 5H-indolo[2,1-a][2]benzazepine-6,10-dicarboxamide, 13-cyclohexyl-N¹⁰-[(dimethylamino)sulfonyl]-6,7-dihydro-3-methoxy-N⁶-(1,3-dimethyl-1H-pyrazol-5-yl)methyl (51 mg, 0.08 mmol, 86%) as a bright yellow solid. Mixture of atrope diastereomers: ¹HNMR (300 MHz, CD₃OD) δ 8.09 (s, 0.3H), 7.98 (s, 0.7H), 7.90 (d, J=8.4 Hz, 0.3H), 7.88 (d, J=8.4 Hz, 0.7H), 7.61-7.53 (m, 1H), 7.42-7.34 (m, 1H), 7.07-6.98 (m, 1.7H), 6.86 (d, J=2.6 Hz, 0.3H), 6.23 (s, 0.3H), 6.15 (s, 0.7H), 4.87-4.57 (m, 2H), 4.54-4.34 (m, 2H), 3.90 (s, 2.1H), 3.89 (s, 0.9H), 3.87 (s, 0.9H), 3.84 (s, 2.1H), 3.26-3.07 (m, 1H) 3.03 (s, 6H), 2.99-2.67 (m, 3H), 2.29 (s, 0.9H), 2.26 (s, 2.1 H), 2.21-1.20 (m, 10H). LCMS: m/e 647 (M+H)⁺, ret time 2.01 min, column C, 2 minute gradient.

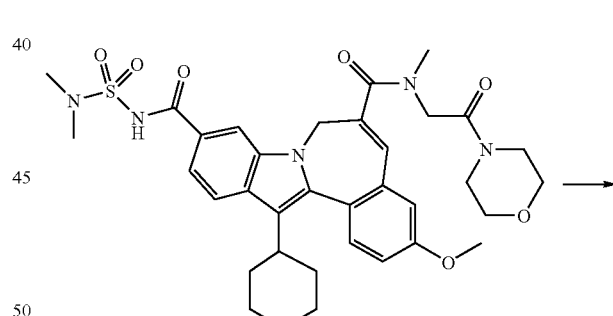

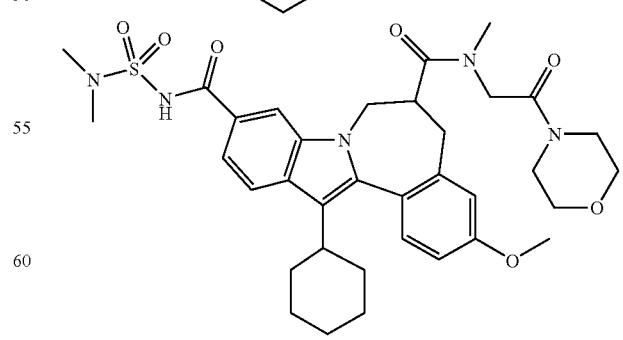

10% Palladium on carbon (60 mg, 0.06 mmol) was added to a solution of 7H-indolo[2,1-a][2]benzazepine-6,10-dicarboxamide, 13-cyclohexyl-N¹⁰-[(dimethylamino)sulfonyl]-

3-methoxy-N⁶-methyl-N⁶-[2-(4-morpholinyl)-2-oxoethyl]- (59 mg, 0.09 mmol) in MeOH (3 mL) and the reaction mixture was vacuum flushed with nitrogen (3×) and then with hydrogen (3×). The reaction mixture was stirred under a balloon of hydrogen overnight. The reaction mixture was once again vacuum flushed with nitrogen (3×) and then with hydrogen (3×) and stirred under a balloon of hydrogen overnight. The solution was filtered through a pad of celite and concentrated to yield 5H-indolo[2,1-a][2]benzazepine-6,10-dicarboxamide, 13-cyclohexyl-N¹⁰-[(dimethylamino)sulfonyl]-6,7-dihydro-3-methoxy-N⁶-methyl-N⁶-[2-(4-morpholinyl)-2-oxoethyl]- (31 mg, 0.05 mmol, 53%) as a yellow solid. Mixture of atrope diastereomers: ¹HNMR (500 MHz, CDCl₃) δ 10.85 (br s, 1H), 8.07 (s, 1H), 7.85 (d, J=8.5 Hz, 1H), 7.70 (d, J=8.5 Hz, 1H), 7.34 (d, J=8.2 Hz, 1H), 6.93 (d, J=8.2 Hz, 1H), 6.91 (s, 1H), 4.75-4.33 (m, 2H), 3.88 (s, 3H), 3.94-2.44 (m, 13H), 3.31 (s, 3H), 3.02 (s, 6H), 2.95-2.84 (m, 1H), 2.19-1.17 (m, 10H). LCMS: m/e 678 (M–H)⁻, ret time 2.77 min, column A, 4 minute gradient.

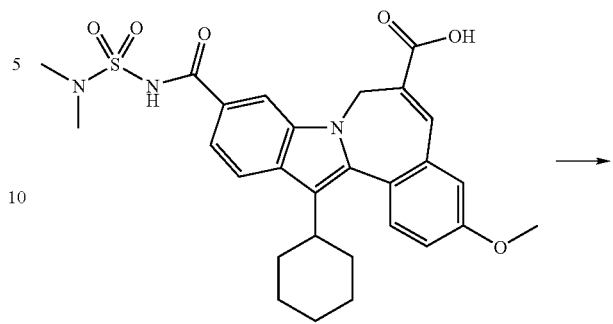

To a stirred solution of 13-cyclohexyl-N-[(dimethylamino)sulfonyl]-3-methoxy-7H-indolo[2,1-a][2]benzazepine-10-carboxamide-6-carboxylic acid (80 mg, 0.15 mmol), 3-methoxyazetidine hydrochloride (28 mg, 0.22 mmol) and triethylamine (0.09 mL) in DMF (1.5 mL) was added HATU (85 mg, 0.22 mmol). The reaction mixture was stirred at rt for 1.5 h, diluted with H₂O (~5 mL), acidified with 1M HCl (aq.) (~0.20 mL) and the precipitate was collected by filtration and flushed with H₂O to yield 7H-indolo[2,1-a][2]benzazepine-10-carboxamide, 3-methoxy, 13-cyclohexyl-N-[(dimethylamino)sulfonyl]-6-[[3-methoxyazetidinyl]carbonyl]- (57 mg, 0.09 mmol, 63%) as a yellow solid. ¹HNMR (500 MHz, CDCl₃) δ 9.68 (s, 1H), 8.10 (s, 1H), 15 7.88 (d, J=8.5 Hz, 1H), 7.57 (d, J=8.5 Hz, 1H), 7.52 (d, J=8.5 Hz, 1H), 7.11-7.05 (m, 2H), 6.09 (s, 1H), 5.59-5.47 (m, 1H), 4.39-3.95 (m, 6H), 3.91 (s, 3H), 3.28 (s, 3H), 3.06 (s, 6H), 2.86-2.77 (m, 1H), 2.14-1.14 (m 10H). LCMS: m/e 605 (M–H)⁻, ret time 3.07 min, column A, 4 minute gradient.

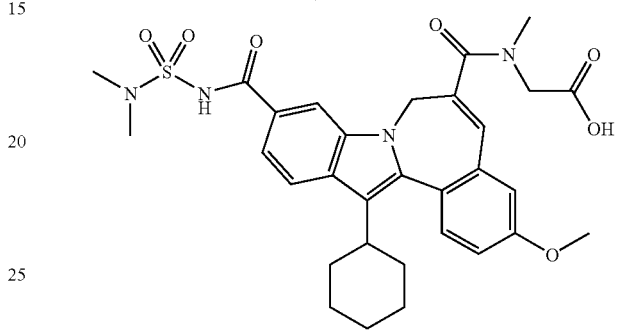

To a stirred solution of 13-cyclohexyl-N-[(dimethylamino)sulfonyl]-3-methoxy-7H-indolo[2,1-a][2]benzazepine-10-carboxamide-6-carboxylic acid (180 mg, 0.34 mmol), methyl 2-(methylamino)acetate hydrochloride (70 mg, 0.50 mmol) and triethylamine (0.19 mL) in DMF (2.5 mL) was added HATU (190 mg, 0.50 mmol). The reaction mixture was stirred at rt for 1.5 h, diluted with H₂O (~10 mL), acidified with 1M HCl (aq.) (~0.50 mL) and the precipitate was collected by filtration and flushed with H₂O. To a solution of the yellow solids in THF/MeOH (1:1, 3 mL) was added 1M NaOH (aq.) (0.75 mL, 0.75 mmol). The reaction solution was heated in a sealed tube with microwave irradiation at 85° C. for 30 min. The reaction was cooled, neutralized with 1M HCl (aq.) (0.75 mL, 0.75 mmol) and concentrated to remove organic solvents. The residue was slurried with H₂O and the solids were collected by filtration, flushed with H₂O and dried to yield 7H-indolo[2,1-a][2]benzazepine-6,10-dicarboxamide, 13-cyclohexyl-N¹⁰-[(dimethylamino)sulfonyl]-3-methoxy-N⁶-methyl-N⁶-acetic acid (148 mg, 0.24 mmol, 72%) as a yellow solid. LCMS: m/e 607 (M–H)⁻, ret time 2.05 min, column A, 4 minute gradient.

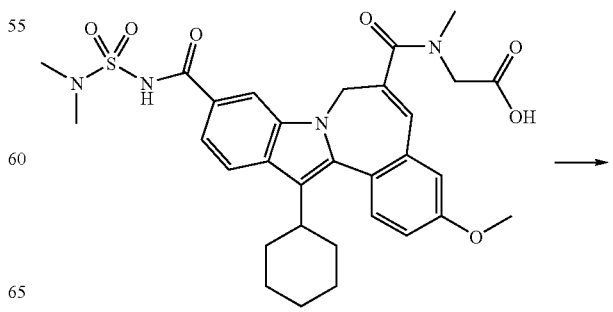

-continued

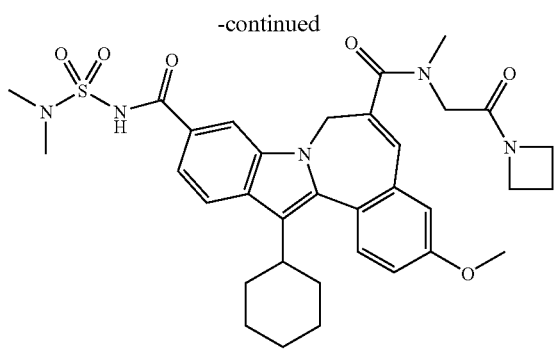

To a stirred solution of 7H-indolo[2,1-a][2]benzazepine-6,10-dicarboxamide, 13-cyclohexyl-N$^{10}$-[(dimethylamino)sulfonyl]-3-methoxy-N$^6$-methyl-N$^6$-acetic acid (45 mg, 0.074 mmol), azetidine hydrochloride (11 mg, 0.11 mmol) and triethylamine (0.05 mL) in DMF (1 mL) was added HATU (37 mg, 0.10 mmol). The reaction mixture was stirred at rt for 1.5 h, diluted with H$_2$O (~3 mL), acidified with 1N HCl(aq.) (~0.1 mL) and the precipitate was collected by filtration and flushed with H$_2$O. The solids were dissolved into MeOH and purified by preparative HPLC (MeOH/H$_2$O with an NH$_4$OAc buffer) to yield 7H-indolo[2,1-a][2]benzazepine-6,10-dicarboxamide, 13-cyclohexyl-N$^{10}$-[(dimethylamino)sulfonyl]-3-methoxy-N$^6$-methyl-N$^6$-[2-(azetidinyl)-2-oxoethyl]- (27 mg, 0.04 mmol, 56%) as a yellow solid. $^1$HNMR (500 MHz, CDCl$_3$) δ 10.65 (s, 1H), 8.13 (s, 1H), 7.87 (d, J=8.0 Hz, 1H), 7.68 (d, J=8.0 Hz, 1H), 7.51 (d, J=8.6 Hz, 1H), 7.05 (br d, J=8.6 Hz, 1H), 6.91 (br s, 1H), 6.81 (s, 1H), 5.04 (br d, J=13.7 Hz, 1H), 4.44 (br d, J=13.7 Hz, 1H), 4.40-4.11 (m, 4H), 3.89 (s, 3H), 3.48-3.40 (m, 1H), 3.10-3.02 (m, 1H), 3.06 (s, 6H), 2.86-2.76 (m, 1H), 2.48-1.14 (m, 15H). LCMS: m/e 648 (M+H)$^+$, ret time 3.55 min, column B, 4 minute gradient.

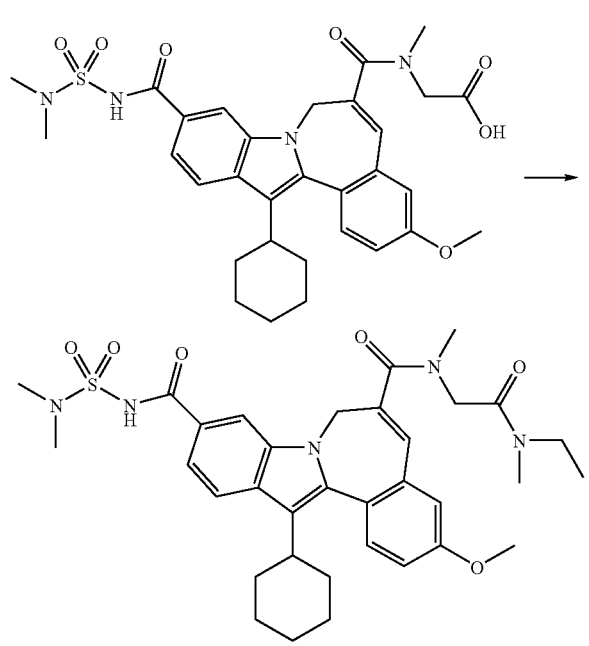

To a stirred solution of 7H-indolo[2,1-a][2]benzazepine-6,10-dicarboxamide, 13-cyclohexyl-N$^{10}$-[(dimethylamino)sulfonyl]-3-methoxy-N$^6$-methyl-N$^6$-acetic acid (45 mg, 0.074 mmol), ethylmethylamine (7 mg, 0.11 mmol) and triethylamine (0.05 mL) in DMF (1 mL) was added HATU (37 mg, 0.10 mmol). The reaction mixture was stirred at rt for 1.5 h, diluted with H$_2$O (~3 mL), acidified with 1N HCl(aq.) (~0.1 mL) and the precipitate was collected by filtration and flushed with H$_2$O. The solids were dissolved into MeOH and purified by preparative HPLC (MeOH/H$_2$O with an NH$_4$OAc buffer) to yield 7H-indolo[2,1-a][2]benzazepine-6,10-dicarboxamide, 13-cyclohexyl-N$^{10}$-[(dimethylamino)sulfonyl]-3-methoxy-N$^6$-methyl-N$^6$-[2-(methylethylamino)-2-oxoethyl]- (29 mg, 0.04 mmol, 60%) as a yellow solid. Mixture of rotamers. $^1$HNMR (500 MHz, CDCl$_3$) δ 10.06-9.89 (m, 1H), 8.14-8.06 (m, 1H), 7.87 (d, J=8.5 Hz, 1H), 7.69-7.62 (m, 1H), 7.51 (d, J=8.5 Hz, 1H), 7.05 (dd, J=2.4, 8.5 Hz, 1H), 6.94-6.88 (m, 1H), 6.85-6.81 (m, 1H), 5.12-5.01 (m, 1H), 4.69-4.54 (m, 1H), 4.47-4.38 (m, 1H), 3.90 (s, 3H), 3.87-3.50 (m, 2H), 3.38-3.27 (m, 1H), 3.09-2.95 (m, 3H), 3.06 (s, 6H), 2.87-2.77 (m, 1H), 2.52-1.07 (m, 16H). LCMS: m/e 650 (M+H)$^+$, ret time 3.60 min, column B, 4 minute gradient.

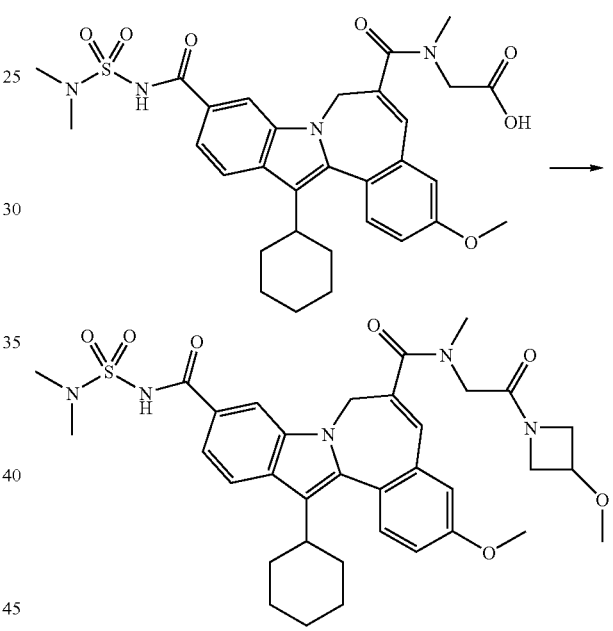

To a stirred solution of 7H-indolo[2,1-a][2]benzazepine-6,10-dicarboxamide, 13-cyclohexyl-N$^{10}$-[(dimethylamino)sulfonyl]-3-methoxy-N$^6$-methyl-N$^6$-acetic acid (45 mg, 0.074 mmol), 3-methoxyazetidine hydrochloride (14 mg, 0.11 mmol) and triethylamine (0.05 mL) in DMF (1 mL) was added HATU (37 mg, 0.10 mmol). The reaction mixture was stirred at rt for 1.5 h, diluted with H$_2$O (~3 mL), acidified with 1N HCl(aq.) (~0.1 mL) and the precipitate was collected by filtration and flushed with H$_2$O. The solids were dissolved into MeOH and purified by preparative HPLC (MeOH/H$_2$O with an NH$_4$OAc buffer) to yield 7H-indolo[2,1-a][2]benzazepine-6,10-dicarboxamide, 13-cyclohexyl-N$^{10}$-[(dimethylamino)sulfonyl]-3-methoxy-N$^6$-methyl-N$^6$-[2-(3-methoxyazetidinyl)-2-oxoethyl]- (41 mg, 0.06 mmol, 82%) as a yellow solid. Mixture of rotamers. $^1$HNMR (500 MHz, CDCl$_3$) δ 10.58-10.42 (m, 1H), 8.13-8.02 (m, 1H), 7.85 (d, J=8.4 Hz, 1H), 7.69-7.59 (m, 1H), 7.49 (d, J=8.4 Hz, 1H), 7.03 (dd, J=2.6, 8.4 Hz, 1H), 6.88 (d, J=2.6 Hz, 1H), 6.83-6.72 (m, 1H), 5.07-4.93 (m, 1H), 4.52-3.92 (m, 6H), 3.87 (s, 3H), 3.60-2.92 (m, 2H), 3.26 (s, 3H), 3.04 (s, 6H), 2.84-2.73 (m, 1H), 2.55-1.11 (m, 13H). LCMS: m/e 673 (M+H)+, ret time 3.57 min, column B, 4 minute gradient.

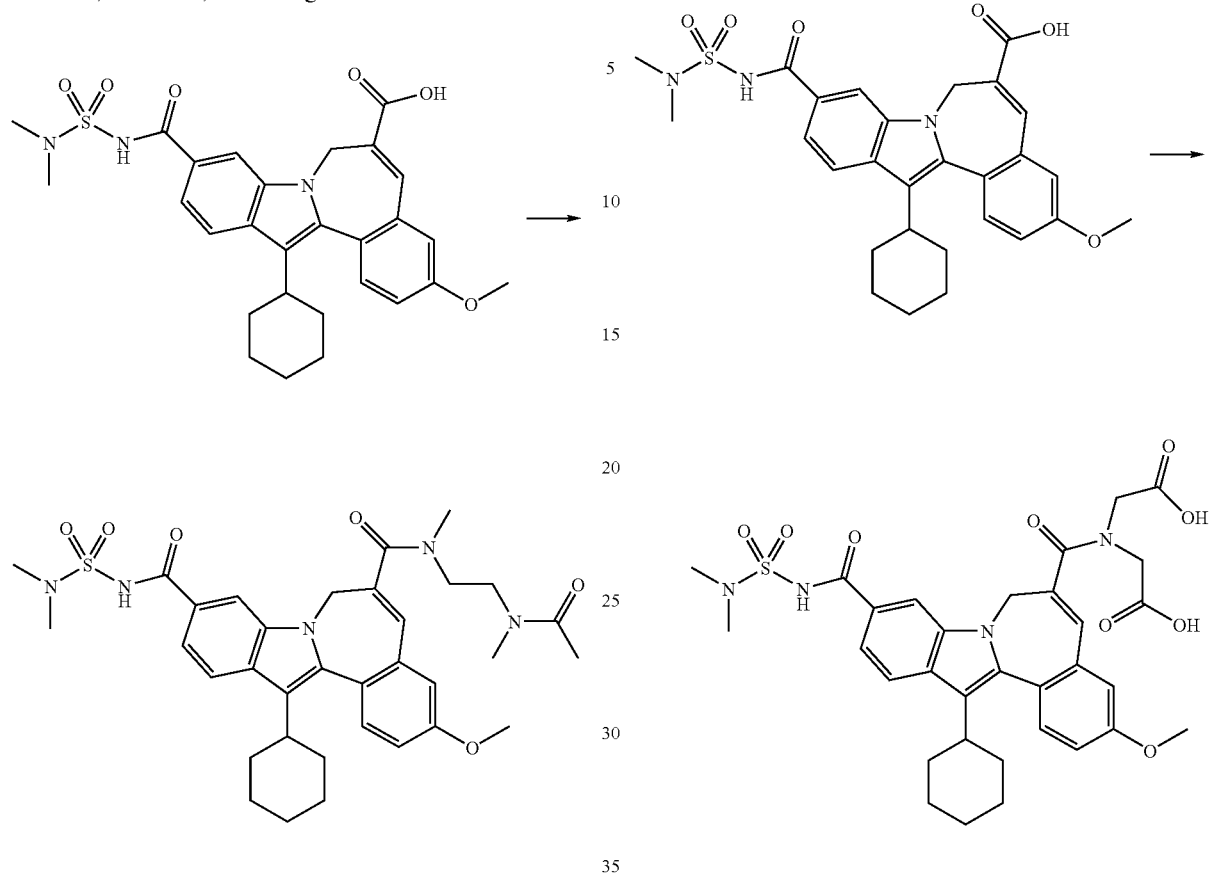

To a stirred solution of 13-cyclohexyl-N-[(dimethylamino)sulfonyl]-3-methoxy-7H-indolo[2,1-a][2]benzazepine-10-carboxamide-6-carboxylic acid (90 mg, 0.17 mmol), $N^1,N^2$-dimethylethane-1,2-diamine (150 mg, 1.7 mmol) and triethylamine (0.95 mL) in DMF (2 mL) was added HATU (82 mg, 0.22 mmol). The reaction mixture was stirred at rt overnight, diluted with H$_2$O (~3 mL), acidified with 1M HCl (aq.) and the precipitate was collected by filtration and flushed with H$_2$O. To a solution of the yellow solids in triethylamine (0.95 mL) and THF (1.5 mL) was added acetyl chloride (0.03 mL, 40 mmol). The reaction solution was stirred at rt for 30 min, quenched with MeOH and purified by preparative HPLC (MeOH/H$_2$O with a TFA buffer) to yield 7H-indolo[2,1-a][2]benzazepine-6,10-dicarboxamide, $N^6$-[2-(acetylmethylamino)ethyl]-13-cyclohexyl-$N^{10}$-[(dimethylamino)sulfonyl]-3-methoxy-$N^6$-methyl- (20 mg, 0.03 mmol, 18%) as a yellow solid. $^1$HNMR (500 MHz, CDCl$_3$) δ 11.55 (s, 1H), 8.42 (s, 1H), 7.87 (d, J=8.6 Hz, 1H), 7.75 (d, J=8.6 Hz, 1H), 7.46 (d, J=8.8 Hz, 1H), 7.01 (dd, J=2.6, 8.8 Hz, 1H), 6.86 (d, J=2.6 Hz, 1H), 6.77 (s, 1H), 4.76-4.29 (m, 2H), 3.86 (s, 3H), 3.16-2.69 (m, 5H), 3.11 (s, 3H), 3.01 (s, 6H), 2.52 (s, 3H), 2.24 (s, 3H), 2.84-2.73 (m, 1H), 2.16-1.14 (m, 10H). LCMS: m/e 673 (M+H)+, ret time 2.18 min, column C, 2 minute gradient.

To a stirred solution of 13-cyclohexyl-N-[(dimethylamino)sulfonyl]-3-methoxy-7H-indolo[2,1-a][2]benzazepine-10-carboxamide-6-carboxylic acid (150 mg, 0.28 mmol), dimethyl 2,2'-azanediyldiacetate hydrochloride (83 mg, 0.42 mmol) and triethylamine (0.16 mL) in DMF (2 mL) was added HATU (140 mg, 0.36 mmol). The reaction mixture was stirred at rt for 3 h, diluted with H$_2$O (~5 mL), acidified with 1M HCl (aq.) (~0.20 mL) and the precipitate was collected by filtration and flushed with H$_2$O. To a solution of the bright yellow solids in THF/MeOH (1:1, 3 mL) was added 1M NaOH (aq.) (1 mL, 1.0 mmol). The reaction solution was heated in a sealed tube with microwave irradiation at 65° C. for 20 min. The reaction was cooled, neutralized with 1M HCl (aq.) (1 mL, 1.0 mmol) and concentrated to remove organic solvents. The residue was slurried with H$_2$O and the solids were collected by filtration dissolved into MeOH and purified by preparative HPLC (CH$_3$CH/H$_2$O with an NH$_4$OAc buffer) to yield glycine, N-(carboxymethyl)-N-[[13-cyclohexyl-10-[[[(dimethylamino)sulfonyl]amino]carbonyl]-3-methoxy-7H-indolo[2,1-a][2]benzazepin-6-yl]carbonyl]- (88 mg, 0.13 mmol, 48%) as a yellow powder. Partial $^1$HNMR (300 MHz, DMSO-d$_6$) δ 8.04 (s, 1H), 7.71-7.65 (m, 2H), 7.46 (d, J=8.4 Hz, 1H), 7.14 (dd, J=2.6, 8.4 Hz, 1H), 6.98 (d, J=2.6 Hz, 1H), 6.89 (s, 1H), 3.86 (s, 3H), 2.67 (s, 6H). LCMS: m/e 651 (M−H)−, ret time 1.67 min, column A, 4 minute gradient.

433

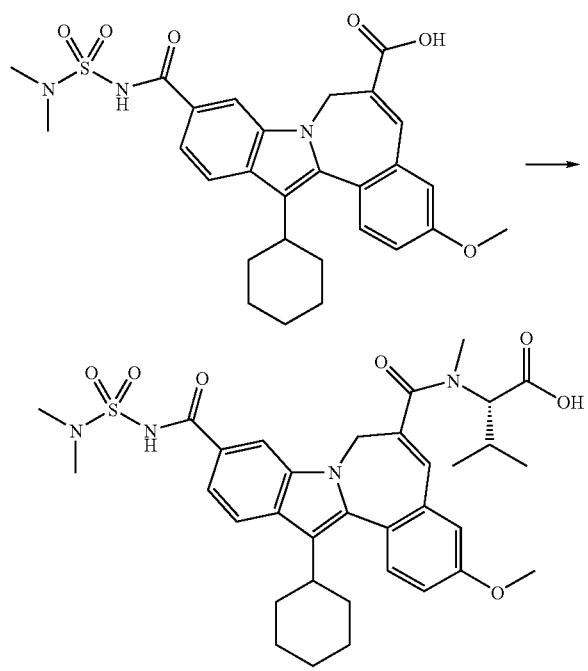

To a stirred solution of 13-cyclohexyl-N-[(dimethylamino)sulfonyl]-3-methoxy-7H-indolo[2,1-a][2]benzazepine-10-carboxamide-6-carboxylic acid (150 mg, 0.28 mmol), (S)-3-methyl-2-(methylamino)butanoic acid hydrochloride (77 mg, 0.42 mmol) and triethylamine (0.16 mL) in DMF (2 mL) was added HATU (140 mg, 0.36 mmol). The reaction mixture was stirred at rt for 3 h, diluted with $H_2O$ (~5 mL), acidified with 1M HCl (aq.) (~0.20 mL) and the precipitate was collected by filtration and flushed with $H_2O$. To a solution of the bright yellow solids in THF/MeOH (1:1, 3 mL) was added 1M NaOH (aq.) (0.6 mL, 0.6 mmol). The reaction solution was heated in a sealed tube with microwave irradiation at 65° C. for 20 min. The reaction was cooled, neutralized with 1M HCl (aq.) (0.6 mL, 0.6 mmol) and concentrated to remove organic solvents. The residue was slurried with $H_2O$ and the solids were collected by filtration dissolved into MeOH and purified by preparative HPLC ($CH_3CH/H_2O$ with an $NH_4OAc$ buffer) to yield L-valine, N-[[13-cyclohexyl-10-[[[(dimethylamino)sulfonyl]amino]carbonyl]-3-methoxy-7H-indolo[2,1-a][2]benzazepin-6-yl]carbonyl]-N-methyl- (155 mg, 0.24 mmol, 85%) as a yellow powder. LCMS: m/e 649 (M−H)⁻, ret time 2.25 min, column A, 4 minute gradient.

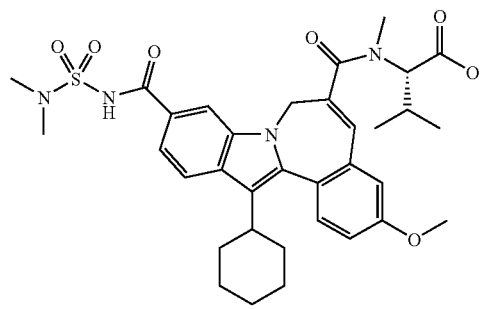

434

-continued

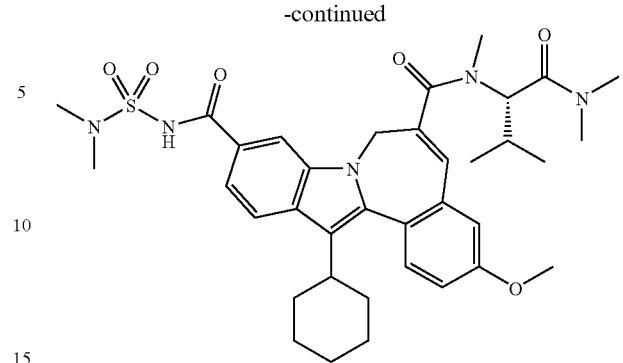

To a stirred solution of acid (50 mg, 0.077 mmol), dimethylamine (2M in THF, 0.80 mL, 0.16 mmol) and triethylamine (0.05 mL) in DMF (1.5 mL) was added HATU (40 mg, 0.10 mmol). The reaction mixture was stirred at rt for 1 h, diluted with $H_2O$ (~5 mL), acidified with 1M HCl (aq.) (~0.20 mL) and the precipitate was collected by filtration and flushed with $H_2O$. The solids were dissolved into MeOH and purified by preparative HPLC ($CH_3CH/H_2O$ with an $NH_4OAc$ buffer) to yield 7H-indolo[2,1-a][2]benzazepine-6,10-dicarboxamide, 13-cyclohexyl-$N^6$-[(1S)-1-[(dimethylamino)carbonyl]-2-methylpropyl]-$N^{10}$-[(dimethylamino)sulfonyl]-3-methoxy-$N^6$-methyl- (21 mg, 0.03 mmol, 40%) as a yellow powder. ¹HNMR (300 MHz, CDCl₃) δ 7.92 (s, 1H), 7.86 (d, J=8.4 Hz, 1H), 7.48 (d, J=8.4 Hz, 1H), 7.51-7.39 (m, 1H), 7.04 (dd, J=2.6, 8.8 Hz, 1H), 6.88 (d, J=2.6 Hz, 1H), 6.78 (s, 1H), 5.14-4.84 (m, 2H), 4.48-4.29 (m, 1H), 3.88 (s, 3H), 3.19 (s, 3H), 3.03 (s, 6H), 2.98 (s, 3H), 2.87-2.57 (m, 4H), 2.38-1.11 (m, 11H), 0.93 (br s, 6H). LCMS: m/e 676 (M−H)⁻, ret time 3.05 min, column A, 4 minute gradient.

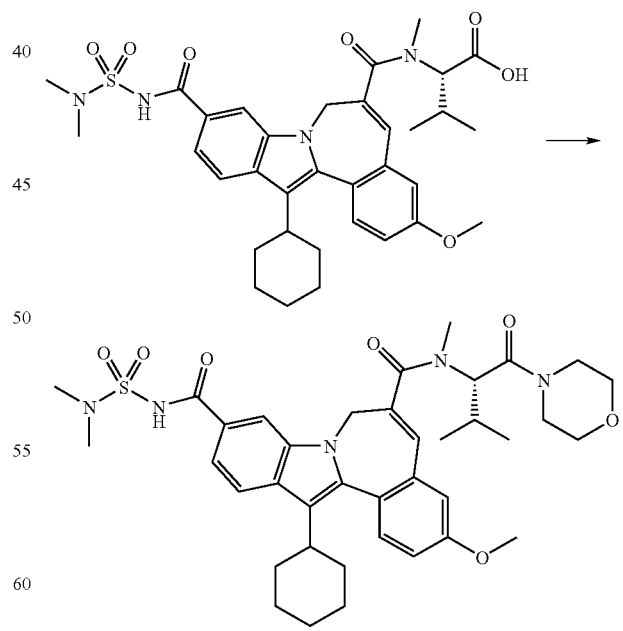

To a stirred solution of acid (50 mg, 0.077 mmol), morpholine (15 mg, 0.15 mmol) and triethylamine (0.05 mL) in DMF (1.5 mL) was added HATU (40 mg, 0.10 mmol). The reaction mixture was stirred at rt for 1 h, diluted with $H_2O$ (~5 mL), acidified with 1M HCl (aq.) (~0.20 mL) and the precipitate was collected by filtration and flushed with H$_2$O. The solids were dissolved into MeOH and purified by preparative HPLC (CH$_3$CH/H$_2$O with an NH$_4$OAc buffer) to yield 7H-indolo[2,1-a][2]benzazepine-6,10-dicarboxamide, 13-cyclohexyl-N$^{10}$-[(dimethylamino)sulfonyl]-3-methoxy-N$^6$-methyl-N$^6$-[(1S)-2-methyl-1-(4-morpholinylcarbonyl)propyl]- (28 mg, 0.04 mmol, 51%) as a yellow powder. $^1$HNMR (300 MHz, CDCl$_3$) δ 7.91 (s, 1H), 7.86 (d, J=8.4 Hz, 1H), 7.49 (d, J=8.8 Hz, 1H), 7.51-7.38 (m, 1H), 7.04 (dd, J=2.6, 8.8 Hz, 1H), 6.88 (d, J=2.6 Hz, 1H), 6.76 (s, 1H), 5.10-4.83 (m, 2H), 4.46-4.28 (m, 1H), 3.88 (s, 3H), 3.79-3.58 (m, 8H), 3.03 (s, 6H), 2.85-2.62 (m, 4H), 2.40-2.25 (m, 1H), 2.11-1.12 (m, 10H), 1.01-0.80 (m, 6H). LCMS: m/e 718 (M–H)$^-$, ret time 3.05 min, column A, 4 minute gradient.

The following HPLC methods and conditions apply to the experimental procedures below until otherwise noted:

Method 1: Analysis Conditions: Column: XTERRA 4.6×50 mm S5; Mobile Phase: (A) 10:90 methanol:water; (B) 90:10 methanol:water; Buffer: 0.1% TFA; Gradient Range: 0-100% B; Gradient Time: 3 min; Flow Rate: 4 mL/min; Analysis Time: 4 min; Detection: Detector 1: UV at 220 nm; Detector 2: MS (ESI+); Fraction Collection: WV-triggered; Fraction Drying.

Method 2: Analysis Conditions: Column: PHENOMENEX-LUNA 4.6×50 mm S10; Mobile Phase: (A) 10:90 methanol:water; (B) 90:10 methanol:water; Buffer: 0.1% TFA; Gradient Range:0-100% B; Gradient Time: 2 min; Flow Rate: 4 mL/min; Analysis Time: 3 min; Detection: Detector 1: UV at 254 nm; Detector 2: MS (ESI+); Fraction Collection: UV-triggered; Fraction Drying.

Method 3: Analysis Conditions: Column: PHENOMENEX-LUNA 4.6×50 mm s10; Mobile Phase: (A) 10:90 methanol:water; (B) 90:10 methanol:water; Buffer: 0.1% TFA; Gradient Range:0-100%; Gradient Time: 3 min; Flow Rate: 4 mL/min; Analysis Time: 4 min; Detection: Detector 1: UV at 254 run; Detector 2: MS (ESI+); Fraction Collection: UV-triggered; Fraction Drying.

Method 4: Analysis Conditions: Column: PHENOMENEX-LUNA 4.6×50 mm s10; Mobile Phase: (A) 10:90 methanol:water; (B) 90:10 methanol:water; Buffer: 0.1% TFA; Gradient Range:0-100% B; Gradient Time: 2 min; Flow Rate: 4 mL/min; Analysis Time: 3 min; Detection: Detector 1: UV at 220 nm; Detector 2: MS (ESI+); Fraction Collection: UV-triggered; Fraction Drying.

Method 5: Analysis Conditions: Column: PHENOMENEX-LUNA 3.0×50 mm S10; Mobile Phase: (A) 10:90 methanol:water; (B) 90:10 methanol:water; Buffer: 0.1% TFA; Gradient Range:0-100% B; Gradient Time: 2 min; Flow Rate: 4 mL/min; Analysis Time: 3 min; Detection: Detector 1: UV at 220 nm; Detector 2: MS (ESI+); Fraction Collection: UV-triggered; Fraction Drying.

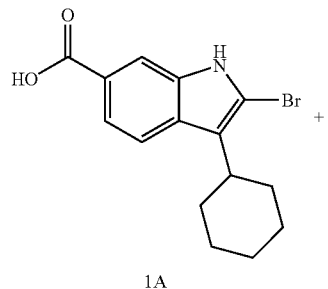

1A

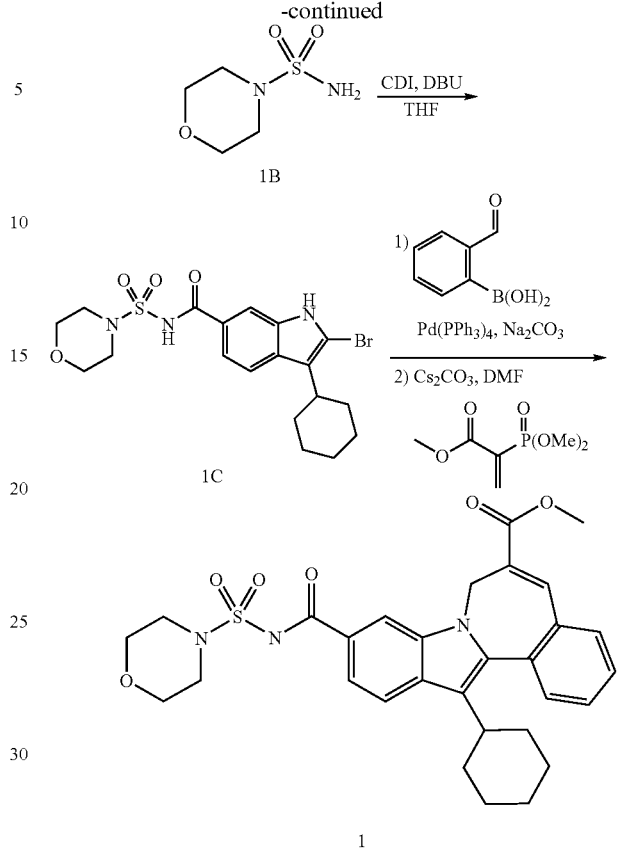

13-Cyclohexyl-N-[(morpholin-4-yl)sulfonyl]-6-methoxycarbonyl-7H-indolo[2,1-a][2]benzazepine-10-carboxamide. Step 1: Preparation of Compound 1A. A mixture of 2-bromo-3-cyclohexyl-1H-indole-6-carboxylic acid (1.0 g, 2.34 mmol) and CDI (0.492 g, 3.04 mmol) in THF (10 mL) was heated at 50° C. for 0.5 h, cooled down, added morpholine-4-sulfonamide (0.465 g, 2.8 mmol) and DBU (0.7 mL, 4.67 mmol). The generated brown solution was stirred for overnite. The reaction was worked up by diluting with EtOAc, washed by cold 1N HCl, brine, dried (MgSO$_4$), removed the solvent and purified by Biotage 40+M column [EtOAc/hexane (with 0.1% HOAc): 2% to 60%] to afford the product as a yellow solid (0.99 g, 90%). 1H NMR (400 MHz, MeOD) δ ppm 1.34-1.51 (m, 3 H) 1.70-1.81 (m, 3 H) 1.84-1.98 (m, 4 H) 2.79-2.93 (m, 1 H) 3.36-3.43 (m, 4 H) 3.67-3.74 (m, 4 H) 7.52 (dd, J=8.56, 1.76 Hz, 1 H) 7.73 (d, J=8.31 Hz, 1 H) 7.86 (d, J=1.76 Hz, 1 H). Step 2: Preparation of Compound 1. A mixture of Compound 1A (0.48 g, 1.02 mmol), Pd(PPh$_3$)$_4$ (0.076 g, 0.07 mmol), LiCl (0.129 g, 3.1 mmol) and aqueous Na$_2$CO$_3$ (1N, 3 mL, 3 mmol) in Toluene/EtOH (1/1, 10 mL) was degassed. The mixture was heated at 80° C. under N$_2$ for 3 h. The reaction mixture was cooled down, and removed the organic solvent in vacuo. The residue was acidified to pH 3 with cold 1N HCl, extracted with EtOAc/THF. The extraction was dried (Na$_2$SO$_4$), removed the solvents in vacuo to provide a brown tar. A mixture of Cs$_2$CO$_3$ (1.0 g, 3.06 mmol), methyl 2-(dimethoxyphosphoryl)acrylate (0.277 g, 1.43 mmol) and above product in DMF (5 mL) was stirred at 60° C. for 3 h and cooled down. The reaction mixture was acidified to pH 2, and extracted with EtOAc/ CH$_2$Cl$_2$. The extraction was washed with brine, dried (MgSO$_4$), removed the solvents and purified by Biotage 25+M column

[EtOAc/ hexane(with 0.1% HOAc): 2% to 55%) to afford a yellow solid. The solid was further purified by prep HPLC to afford compound 1 as a yellow solid (0.465 g, 81%). 1H NMR (400 MHz, MeOD) δ ppm 1.10-1.57 (m, 4 H) 1.77 (s, 2 H) 1.88-2.21 (m, 4 H) 2.80-2.93 (m, 1 H) 3.42-3.50 (m, 4 H) 3.71-3.78 (m, 4 H) 3.84 (s, 3 H) 4.12-4.28 (m, 1 H) 5.60-5.81 (m, 1 H) 7.59 (dd, 5 H) 7.89-7.97 (m, 2 H) 8.19 (s, 1 H), LC-MS (retention time: 3.61; MS m/z 564 M+H, Method 1).

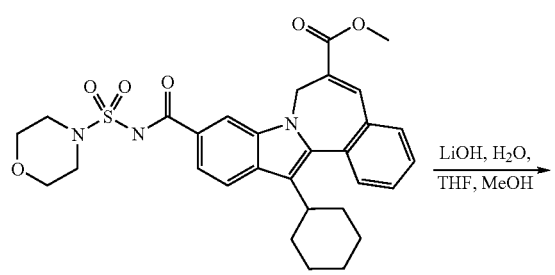

1

LiOH, H₂O,
THF, MeOH

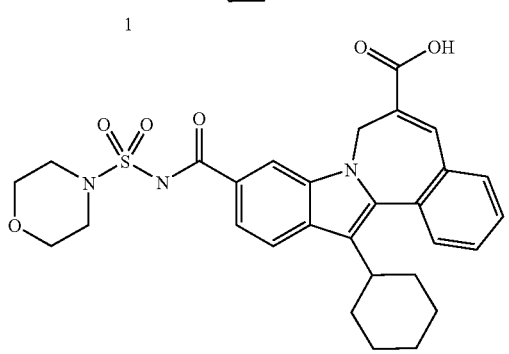

2

13-Cyclohexyl-N-[(morpholin-4-yl)sulfonyl]-6-carboxyl-7H-indolo[2,1-a][2]benzazepine-10-carboxamide. Step 1: Small amount of MeOH was added to a suspension of Compound 1 (0.46 g, 0.82) dispersed in THF (5 mL) and H₂O (2 mL) till no solid in the mixture. LiOH.H₂O (0.13 mmol 3.3 mmol)) was added. The mixture was stirred o/n, and removed the organic solvents in vacuo. The residue was acidified to pH 2, extracted with EtOAc/CH₂Cl₂. the extraction was washed with brine, dried (MgSO₄), removed the solvents to afford the compound 2 as a yellow foam (0.441 g, 98%). Analycal sample was further purified by Prep HPLC. 1H NMR (400 MHz, MeOD) δ ppm 1.15-1.58 (m, 4 H) 1.78 (s, 2 H) 1.88-2.20 (m, 4 H) 2.82-2.93(m, 1 H) 3.41-3.50(m, 4 H) 3.70-3.78 (m, 4 H) 4.08-4.27 (m, 1 H) 5.61-5.80 (m, 1 H) 7.49-7.69 (m, 5 H) 7.90-7.96 (m, 2 H) 8.18 (s, 1 H); LC-MS (retention time: 3.54; MS m/z 550 M+H, Method 1).

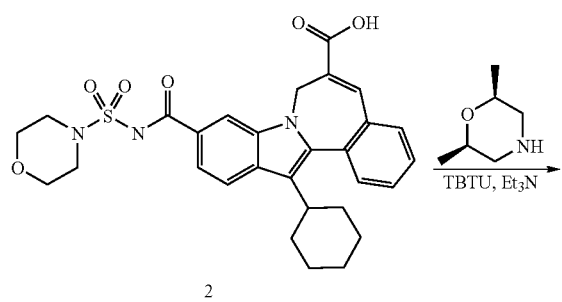

2

TBTU, Et₃N

-continued

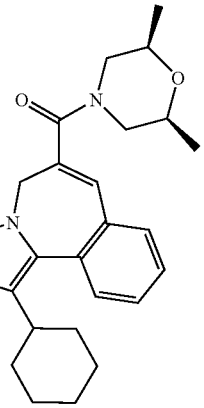

3

13-Cyclohexyl-N-[(morpholin-4-yl)sulfonyl]-6-[(cis-2,6-dimethylmorpholin-4-yl)carbonyl]piperidin-1-carbonyl]-7H-indolo[2,1-a][2]benzazepine-10-carboxamide. Step 1: A mixture of compound 2 (0.075 g, 0.16 mmol), triethyl amine (0.057 mL, 0.4 mmol), 2,6-dimethylmorpholine (0.043 g, 0.38 mmol) and TBTU (0.066 g, 0.20 mmol) in DMF (1.5 mL) was stirred for 2 h and purified by prep HPLC to afford compound 3 as a yellow solid (0.0427 g, 42%). LC-MS (retention time: 3.47; MS m/z 647 M+H, Method 1).

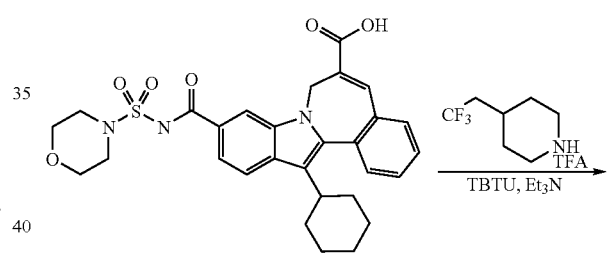

2

TBTU, Et₃N

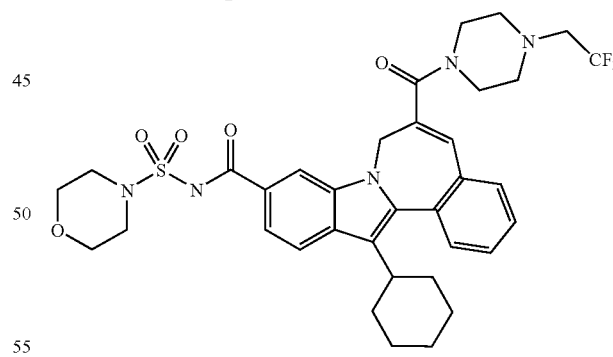

4

13-Cyclohexyl-N-[(morpholin-4-yl)sulfonyl]-6-[[(1-(2,2,2-trifloruoethyl)piperazin-4-yl)]carbonyl]-7H-indolo[2,1-a][2]benzazepine-10-carboxamide. Step 1: The trifluoroacetic acid salt of Compound 4 was obtained following the procedure described in preparation of compound 3 (44%). 1H NMR (400 MHz, CHLOROFORM-D) δ ppm 1.12-1.59 (m, 4 H) 1.77 (d, J=8.06 Hz, 2 H) 1.86-2.17 (m, 4 H) 2.69 (s, 3 H) 2.77-2.89 (m, 1 H) 3.14 (q, J=9.32 Hz, 2 H) 3.44-3.57 (m, 5 H) 3.62 (s, 3 H) 3.76 (t, J=4.28 Hz, 4 H) 4.15 (s, 2 H) 4.32 (d, J=13.09 Hz, 1 H) 5.25 (s, 1 H) 6.87 (s, 1 H) 7.38-7.44 (m, 1 H) 7.44-7.61 (m, 4 H) 8.22 (s, 1 H); LC-MS (retention time: 3.45; MS m/z 700 M+H, Method 1).

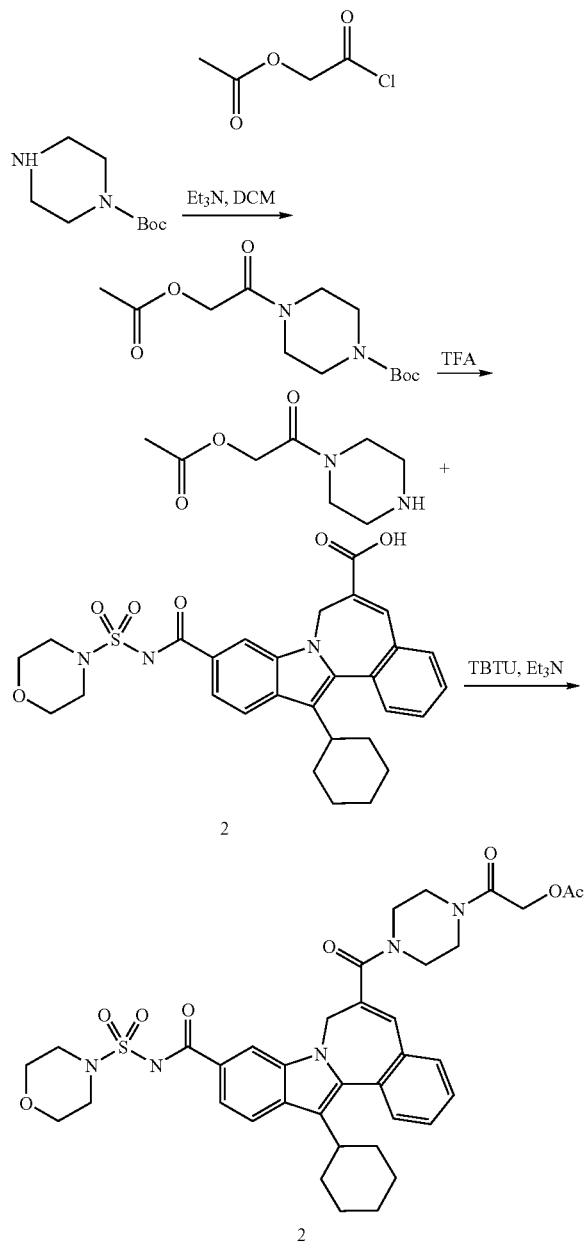

13-Cyclohexyl-N-[(morpholin-4-yl)sulfonyl]-6-[[1-(2-acetoxyacetyl)piperazin-4-yl]carbonyl]-7H-indolo[2,1-a][2]benzazepine-10-carboxamide. Step 1: 2-Chloro-2-oxoethyl acetate (1.5 mL, 14 mmol) was added to a solution of tert-butyl piperazine-1-carboxylate (2.0 g, 10.7 mmol), triethyl amine (2.2 mL, 16 mmoL) in dichloromethane (30 mL) at 0° C. The reaction mixture was stirred for 1.5 hr at r.t. removed the solvents in vacuo. The residue was taken up with dichloromethane/hexane and washed with cold 1 NHCl (2×), 1 N NaOH (2×), brine, dried (MgSO₄), removed the solvents in vacuo to afford the product as a white solid (2.8 g, 91%). 1H NMR (400 MHz, CHLOROFORM-D) δ ppm 1.46 (s, 9 H) 3.14-3.63 (m, J=50.11 Hz, 8 H). Step 2: A mixture of tert-butyl 4-(2-acetoxyacetyl)piperazine-1-carboxylate (0.073 g, 0.25 mmol) in trifluoroacetic acid/dichloromethane (1/1, 1.5 mL) was stirred for 0.5 h at r.t. The solvents were removed in vacuo to afford a brown residue. DMF (1.5 mL), Compound 2 (0.070 g, 0.13 mmol), Triethyl amine (0.089 mL 0.64 mmol), and TBTU (0.061 g, 0.19 mmol) were added to the residue. The reaction mixture was stirred for 1 h and purified by prep HPLC to afford compound 5 as a yellow solid (0.0552 g, 60%). 1H NMR (400 MHz, CHLOROFORM-D) δ ppm 1.31-1.59 (m, 4 H) 1.68-1.83 (m, 2 H) 1.84-2.13 (m, 4 H) 2.16 (s, 3 H) 2.75-2.88 (m, 1 H) 3.22-3.66 (m, 12 H) 3.73-3.81 (m, 4 H) 4.28-4.41 (m, J=6.55 Hz, 1 H) 4.67 (s, 2 H) 5.06-5.24 (m, 1 H) 6.88 (s, 1 H) 7.40 (d, J=7.05 Hz, 1 H) 7.45-7.55 (m, 3 H) 7.56-7.60 (m, 1 H) 7.91 (d, J=8.56 Hz, 1 H) 8.04 (s, 1 H); LC-MS (method 2, retention time: 2.13; MS m/z 718 M+H, Method 2).

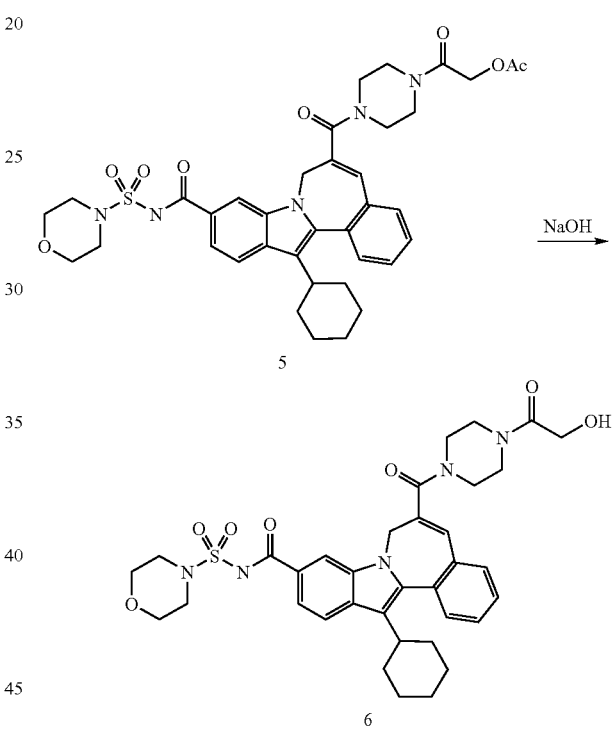

13-Cyclohexyl-N-[(morpholin-4-yl)sulfonyl]-6-[[-(hydroxy-acetyl)piperazin-4-yl]carbonyl]-7H-indolo[2,1-a][2]benzazepine-10-carboxamide. Step 1: A mixture of Compound 5 (0.047 g, 0.07 mmol) LiOH.H2O (0.040 g, 1 mmol), THF (6 mL) MeOH (3 mL), and H₂O (1 mL) was stirred for one day, acidified to pH 2 and extracted with Ethyl acetate/dicholoromethane (2×). The combined extracts were dried (MgSO₄), removed the solvents and purified by prep HPLC to afford the compound 6 as a pale yellow foam (0.0347 g, 78%) 1H NMR (400 MHz, CHLOROFORM-D) δ ppm 1.30-1.61 (m, 4 H) 1.70-1.82 (m, 2 H) 1.89-2.19 (m, 4 H) 2.77-2.87 (m, J=4.78 Hz, 1 H) 2.92-3.25 (m, 6 H) 3.35-3.62 (m, 6 H) 3.68-3.82 (m, 4 H) 4.16 (s, 2 H) 4.28-4.44 (m, 1 H) 5.07-5.23 (m, 1 H) 6.89 (s, 1 H) 7.40 (d, J=7.30 Hz, 1 H) 7.43-7.54 (m, 3 H) 7.56-7.61 (m, 1 H) 7.92 (d, J=8.31 Hz, 1 H) 8.10 (s, 1 H); LC-MS (retention time: 2.85; MS m/z 676 M+H, method 3).

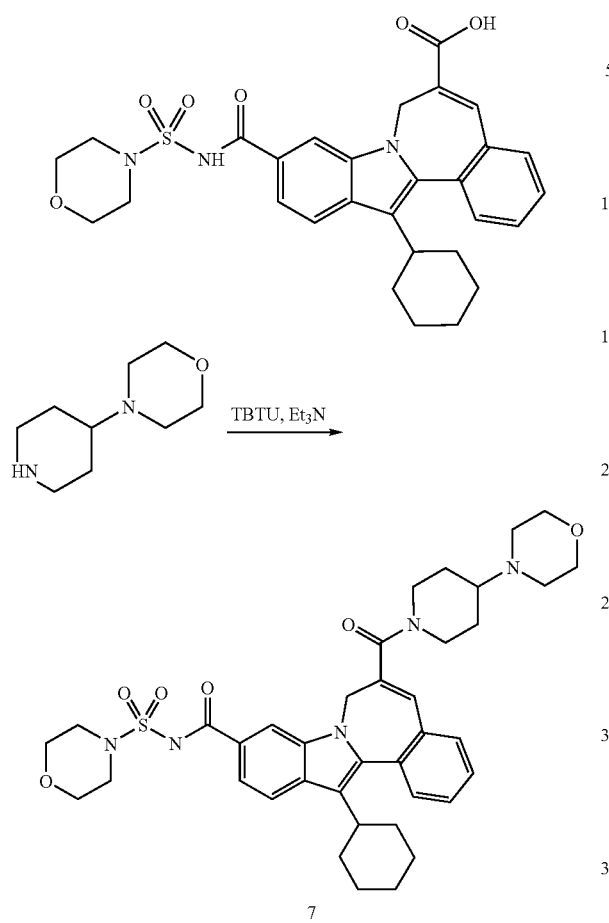

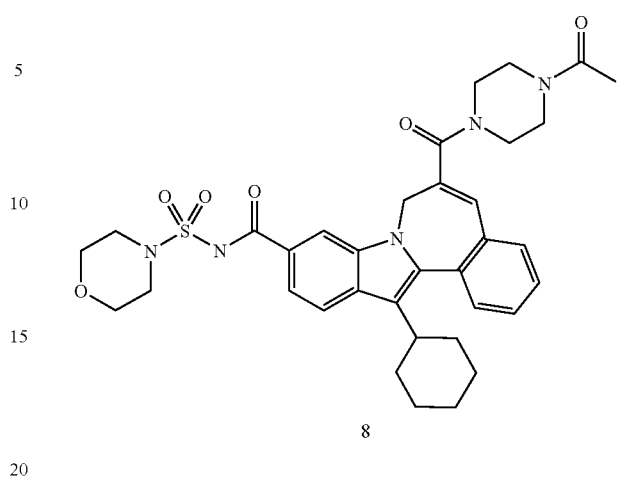

13-Cyclohexyl-N-[(morpholin-4-yl)sulfonyl]-6-[[4-(morpholin-4-yl)piperidin-1-yl]carbonyl]-7H-indolo[2,1-a][2]benzazepine-10-carboxamide. Step 1: Compound 7 was prepared from compound 2 by following the similar procedure of 3 in making compound 3 (47%). LC-MS (retention time: 2.09; MS m/z 702 M+H, Method 4).

13-Cyclohexyl-N-[(morpholin-4-yl)sulfonyl]-6-[(1-acetylpiperazin-4-yl)carbonyl]-7H-indolo[2,1-a][2]benzazepine-10-carboxamide. Step 1: Compound 8 was prepared from compound 2 by following the similar procedure of Step 1 of Scheme 3 in making Compound 3 (20%). 1H NMR (400 MHz, CHLOROFORM-D) δ ppm 1.29-1.56 (m, 4 H) 1.77 (s, 2 H) 1.88-2.13 (m, 4 H) 2.09 (s, 3 H) 2.77-2.88 (m, 1 H) 3.38-3.56 (m, 10 H) 3.60-3.69 (m, 2 H) 3.73-3.81 (m, 4 H) 4.27-4.40 (m, 1 H) 5.05-5.16 (m, 1 H) 6.89 (s, 1 H) 7.37-7.42 (m, 1 H) 7.45-7.61 (m, 4 H) 7.91 (d, J=8.56 Hz, 1 H) 7.99 (s, 1 H); LC-MS (retention time: 3.27, m/e 682 M+Na, Method 1).

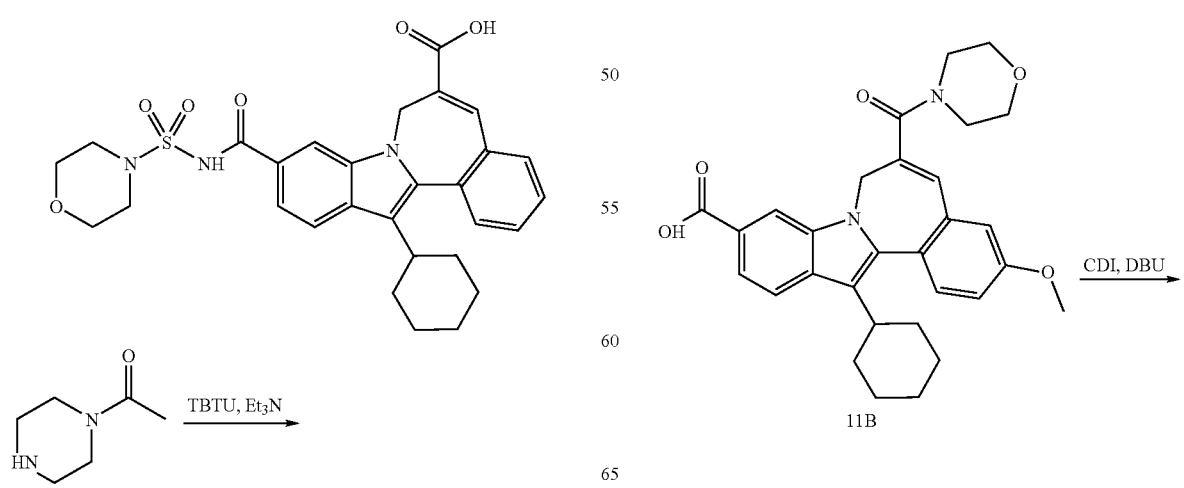

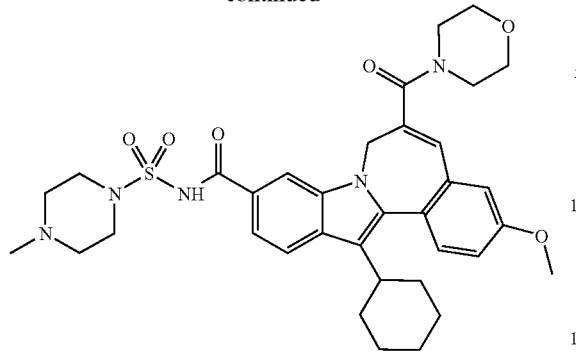

Cyclohexyl-N-[(4-methylpiperazin-1-yl)sulfonyl]-6-(morpholin-4-carbonyl)-3-methoxy-7H-indolo[2,1-a][2]benzazepine-10-carboxamide. Step 1: The trifluoroacetic acid salt of compound 11 was prepared from compound 11B and 11B by following the similar procedure of 10 in making compound 10 (18%). LC-MS (retention time: 3.00; MS m/z 662 M+H, Method 1).

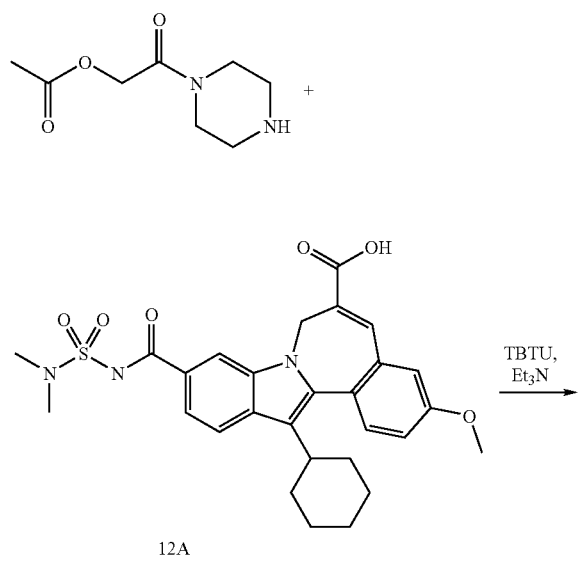

12A

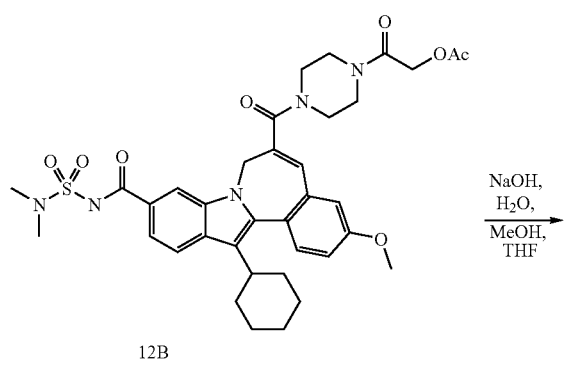

12B

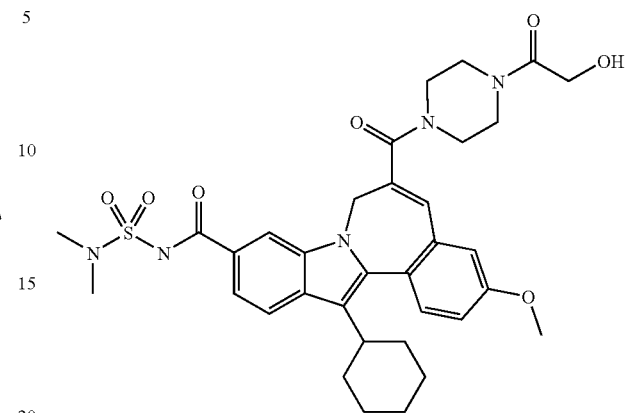

12

13-Cyclohexyl-N-[(dimethylamino)sulfonyl]-6-[[1-(hydroxy-acetyl)piperazin-4-yl)]carbonyl]-3-methoxy-7H-indolo[2,1-a][2]benzazepine-10-carboxamide. Step 1: Preparation of compound 12B. Compound 12B was prepared from compound 12A by following the similar procedure of Step 1 of scheme 3 in making Compound 3 (54%) 1H NMR (400 MHz, CHLOROFORM-D) δ ppm 1.15-1.62 (m, 4 H) 1.71-1.80 (m, 2 H) 1.81-2.09 (m, 4 H) 2.16 (s, 3 H) 2.74-2.87 (m, 1 H) 3.03 (s, 6 H) 3.24-3.74 (m, 8 H) 3.90 (s, 3 H) 4.23-4.38 (m, 1 H) 4.67 (s, 2 H) 5.13-5.33 (m, 1 H) 6.79 (s, 1 H) 6.89 (d, J=2.77 Hz, 1 H) 7.05 (dd, J=8.69, 2.64 Hz, 1 H) 7.49 (d, J=8.81 Hz, 1 H) 7.54 (dd, J=8.44, 1.39 Hz, 1 H) 7.87 (d, J=8.56 Hz, 1 H) 8.18 (s, 1 H). Step 2: Preparation of compound 12. A mixture of compound 12B (0.061 g, 0.09 mmol) and aqueous NaOH (1N 0.5 mL, 0.5 mmol)n and a few drops of MeOH was stirred at r.t. for 3 h. removed the organic solvent and the residue was partitioned between aqueous NaH2PO4 and EtOAc/THF. The organic solvent was washed with brine and dried (MgSO₄), removed the solvent and purified by prep HPLC to afford compound 12. (1H NMR (400 MHz, MeOD) δ ppm 1.13-1.53 (m, 4 H) 1.69-1.81 (m, 2 H) 1.86-2.21 (m, 4 H) 2.79-2.89 (m, 1 H) 2.98 (s, 6 H) 3.31-3.64 (m, 8 H) 3.89 (s, 3 H) 4.18 (s, 2 H) 4.29 (s, 1 H) 5.03-5.20 (m, 1 H) 6.96 (s, 1 H) 7.06 (d, J=2.52 Hz, 1 H) 7.12 (dd, J=8.56, 2.77 Hz, 1 H) 7.47-7.57 (m, 2 H) 7.87 (d, J=8.56 Hz, 1 H) 8.07 (s, 1 H).

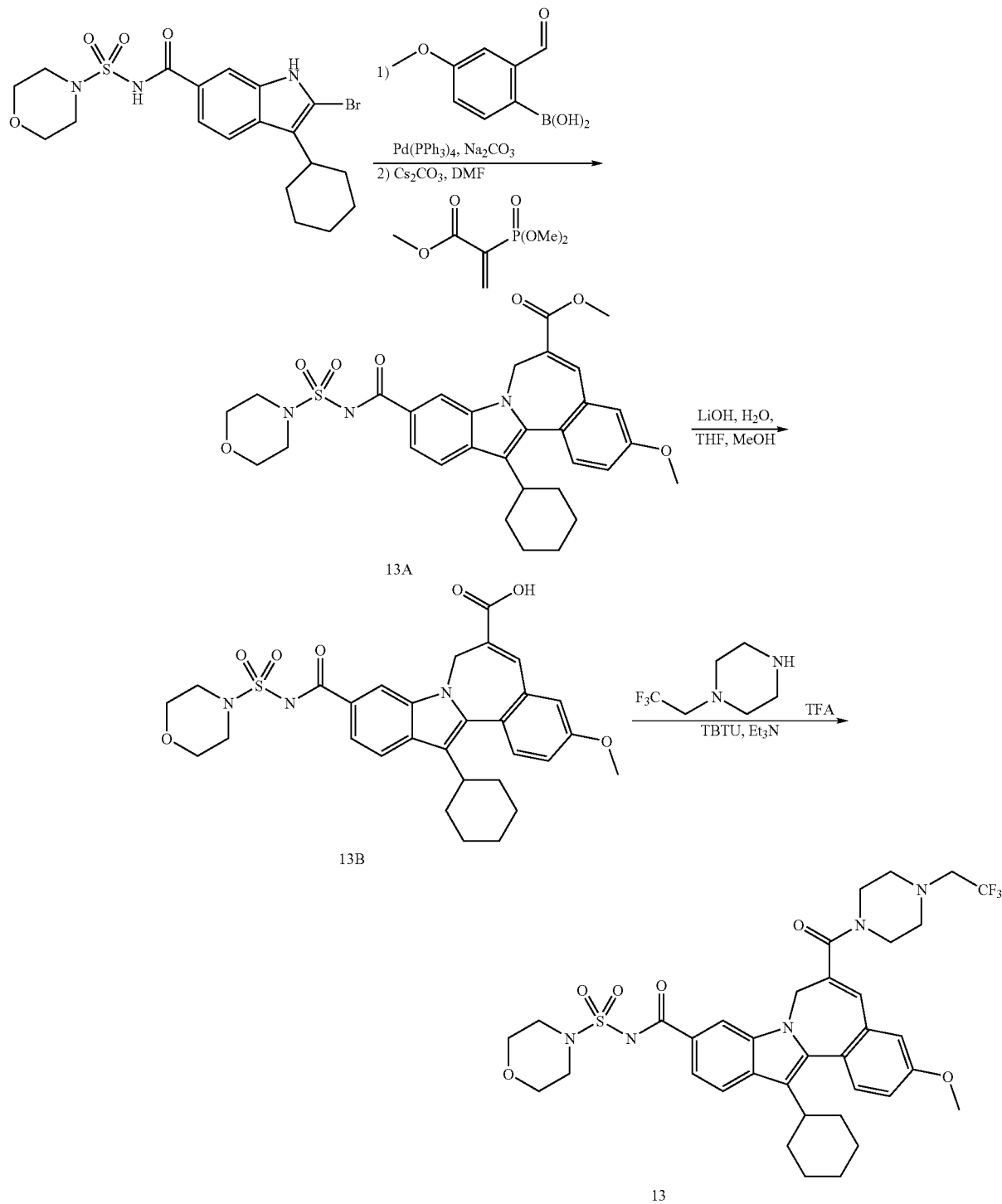

Cyclohexyl-N-[(morpholin-4-yl)sulfonyl]-6-[[1-(2,2,2-trifluoroethyl)piperazin-4-yl]carbonyl]-3-methoxy-7H-indolo[2,1-a][2]benzazepine-10-carboxamide. Step 1: Preparation of compound 13A. A mixture of 2-formyl-4-methoxylphenylboronic acid (0.264 g, 1.18 mmol), 2-bromo-3-cyclohexyl-N-(4-morpholin-4-yl)sulfonyl)-1H-indole-6-carboxamide (0.53 g, 1.13 mmol), Pd(PPh$_3$)$_4$ (0.078 g, 0.07mmol), LiCl (0.129 g, 3.1 mmol) and aq. Na$_2$CO$_3$ (1N, 3 mL, 3 mmol) in Toluene/EtOH (1/1, 10 mL) was degassed, filled with N2 and heated at 80° C. for 3 h. The reaction mixture was cooled down, and added saturated NaH2PO4, extracted with EtOAc. the extraction was dried (Na$_2$SO$_4$), removed the solvent in vacuo to provide a brown tar residue. The residue was dissolved in minimum amount of CH$_2$Cl$_2$ and hexane was added till no solid coming out, filtered to provide a yellow solid. A mixture of above solid, Cs$_2$CO$_3$ (1.1 g, 3.38 mmol), and methyl 2-(dimethoxyphosphoryl)acrylate (0.77 g, 1.43 mmol) in DMF ( 5 mL) was stirred at 60° C. for 3 h. The reaction mixture was cooled down and acidified to pH 2, extracted with EtOAc/CH$_2$Cl$_2$. The extraction was washed with brine, dried (MgSO$_4$), removed the solvent and purified by Biotage 40+M column[MeOH/dichloromethane: 0% to 20%) to afford compound 13A as a yellow solid. LC-MS (retention time: 3.53; MS m/z 594 M+H, Method 1). Step 2: Preparation of compound 13B. Compound 13B was prepared from Compound 13A by following the similar procedure of step 1 of Scheme 2 in making Compound 2 (100%) LC-MS (retention time: 3.50; MS m/z 580 M+H, Method 1). Step 3: Preparation of compound 13. Compound 13 was prepared from compound 13B by following the similar procedure of Step 1 of Scheme 3 in making compound 3 (100%). 1H NMR (400 MHz, CHLOROFORM-D) δ ppm 1.13-1.61 (m, 4 H) 1.70-1.83 (m, 2 H) 1.85-2.22 (m, 4 H) 2.75-2.88 (m, 1 H) 2.91-3.25 (m, 4 H) 3.40-3.65 (m, 6 H) 3.67-4.05 (m, 8 H) 3.91 (s, 3 H) 4.32 (d, J=14.35 Hz, 1 H) 5.38 (d, J=13.60 Hz, 1 H) 6.86 (s, 1 H) 6.91 (d, J=2.52 Hz, 1 H) 7.08 (dd, J=8.69, 2.64 Hz, 1 H) 7.51 (d, J=8.56 Hz, 1 H) 7.57 (dd, J=8.44, 1.13 Hz, 1 H) 7.92 (d, J=8.56 Hz, 1 H) 8.30 (s, 1 H); LC-MS (retention time: 3.46; MS m/z 730 M+H, Method 1).

J=8.56 Hz, 1 H) 7.55-7.67 (m, 1 H) 7.88 (d, J=8.31 Hz, 1 H) 8.17 (s, 1 H). LC-MS (retention time: 3.29; MS m/z 649 M+H, Method 1).

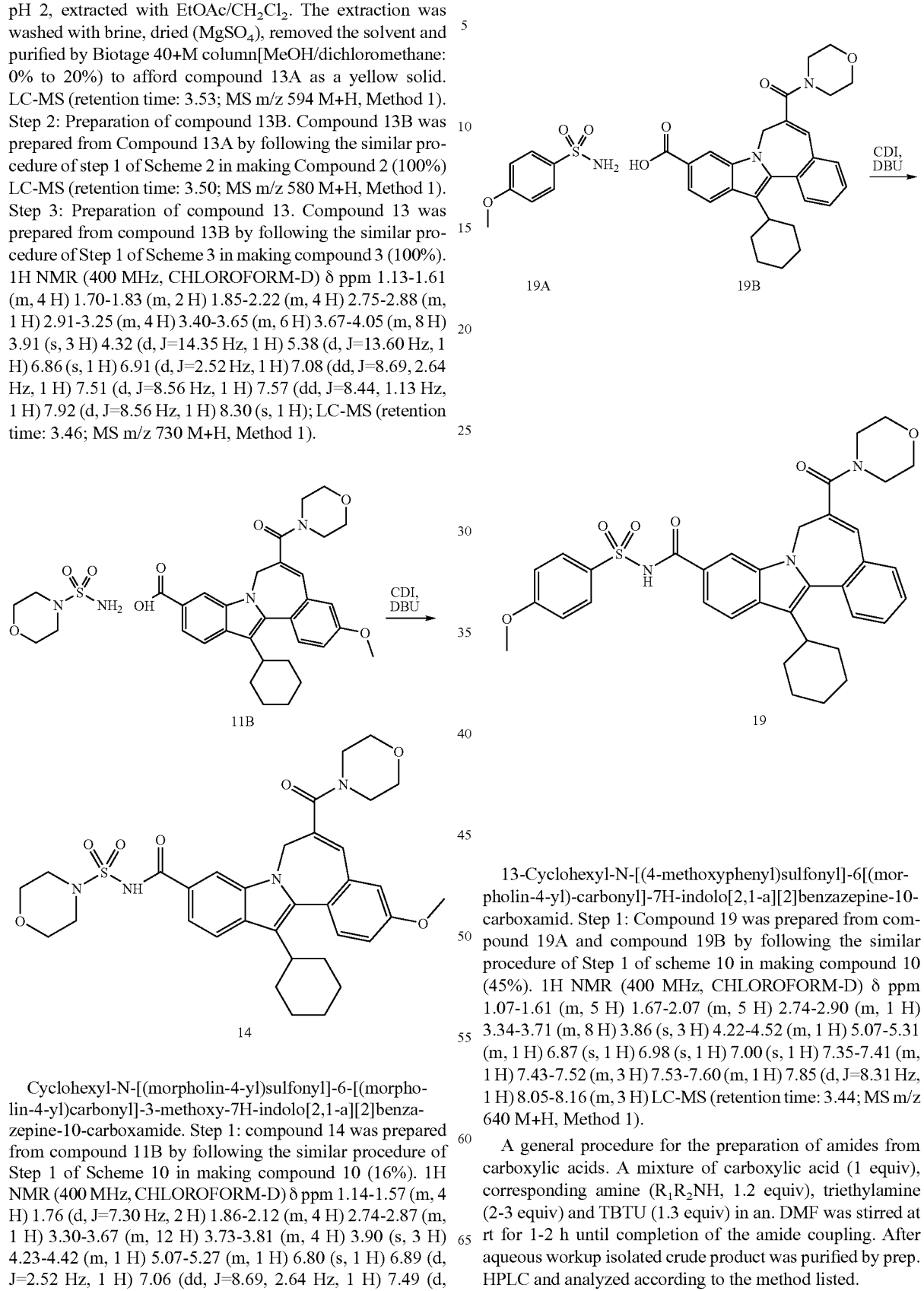

Cyclohexyl-N-[(morpholin-4-yl)sulfonyl]-6-[(morpholin-4-yl)carbonyl]-3-methoxy-7H-indolo[2,1-a][2]benzazepine-10-carboxamide. Step 1: compound 14 was prepared from compound 11B by following the similar procedure of Step 1 of Scheme 10 in making compound 10 (16%). 1H NMR (400 MHz, CHLOROFORM-D) δ ppm 1.14-1.57 (m, 4 H) 1.76 (d, J=7.30 Hz, 2 H) 1.86-2.12 (m, 4 H) 2.74-2.87 (m, 1 H) 3.30-3.67 (m, 12 H) 3.73-3.81 (m, 4 H) 3.90 (s, 3 H) 4.23-4.42 (m, 1 H) 5.07-5.27 (m, 1 H) 6.80 (s, 1 H) 6.89 (d, J=2.52 Hz, 1 H) 7.06 (dd, J=8.69, 2.64 Hz, 1 H) 7.49 (d, 13-Cyclohexyl-N-[(4-methoxyphenyl)sulfonyl]-6-[(morpholin-4-yl)-carbonyl]-7H-indolo[2,1-a][2]benzazepine-10-carboxamid. Step 1: Compound 19 was prepared from compound 19A and compound 19B by following the similar procedure of Step 1 of scheme 10 in making compound 10 (45%). 1H NMR (400 MHz, CHLOROFORM-D) δ ppm 1.07-1.61 (m, 5 H) 1.67-2.07 (m, 5 H) 2.74-2.90 (m, 1 H) 3.34-3.71 (m, 8 H) 3.86 (s, 3 H) 4.22-4.52 (m, 1 H) 5.07-5.31 (m, 1 H) 6.87 (s, 1 H) 6.98 (s, 1 H) 7.00 (s, 1 H) 7.35-7.41 (m, 1 H) 7.43-7.52 (m, 3 H) 7.53-7.60 (m, 1 H) 7.85 (d, J=8.31 Hz, 1 H) 8.05-8.16 (m, 3 H) LC-MS (retention time: 3.44; MS m/z 640 M+H, Method 1).

A general procedure for the preparation of amides from carboxylic acids. A mixture of carboxylic acid (1 equiv), corresponding amine (R$_1$R$_2$NH, 1.2 equiv), triethylamine (2-3 equiv) and TBTU (1.3 equiv) in an. DMF was stirred at rt for 1-2 h until completion of the amide coupling. After aqueous workup isolated crude product was purified by prep. HPLC and analyzed according to the method listed.

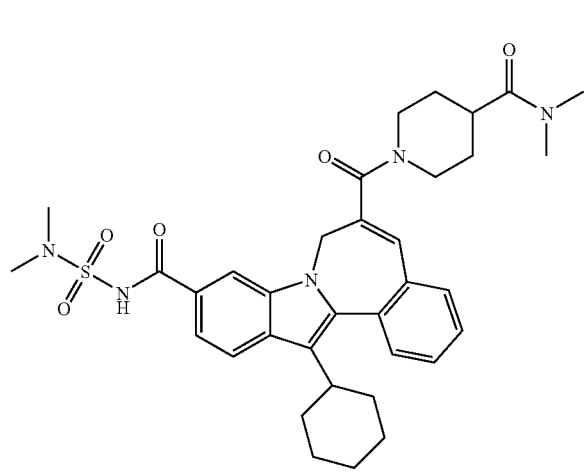

13-Cyclohexyl-N-[(dimethylamino)sulfonyl]-6-[4-[(dimethylamino)carbonyl]piperidin-1-carbonyl]-7H-indolo[2,1-a][2]benzazepine-10-carboxamide. LC/MS: Retention time: 1.937 min; m/e 646 (MH+, method 5).

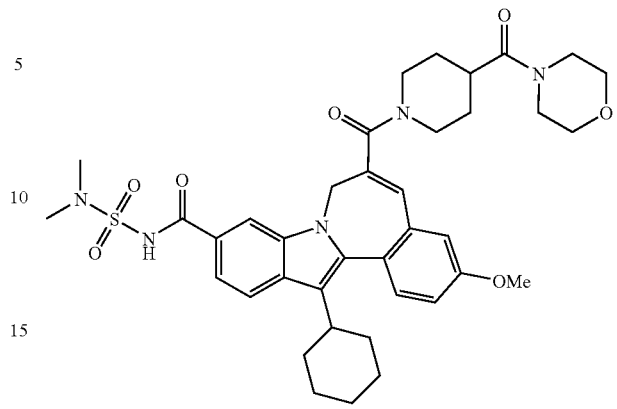

13-Cyclohexyl-N-[(dimethylamino)sulfonyl]-6-[4-[(morpholin-4-yl)carbonyl]piperidin-1-carbonyl]-3-methoxy-7H-indolo[2,1-a][2]benzazepine-10-carboxamide. LC/MS: Retention time: 1.953 min; m/e 718 (MH+, method 5); 1H NMR (400 MHz, CHLOROFORM-D) δ ppm 1.10-1.64 (m, 6 H) 1.75 (s, 2 H) 1.85-2.13 (m, 5 H) 2.51-2.88 (m, 3H) 2.88-3.17 (m, 10H) 3.38-3.49 (m, 2H) 3.51-3.77 (m, 6H) 3.90 (s, 3 H) 4.34-4.46 (m, 1 H) 4.96-5.12 (m, 1 H) 6.76 (s, 1 H) 6.90 (d, J=2.77 Hz, 1 H) 7.05 (dd, J=8.69, 2.64 Hz, 1 H) 7.44 (dd, J=8.44, 1.38 Hz, 1 H) 7.48 (d, J=8.56 Hz, 1 H) 7.87 (d, J=8.56 Hz, 1 H) 7.93 (s, 1 H).

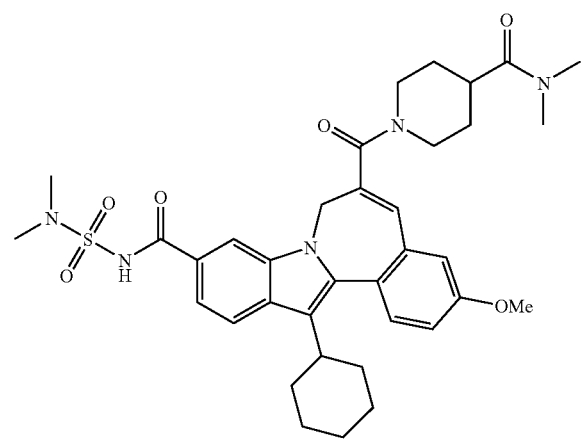

13-Cyclohexyl-N-[(dimethylamino)sulfonyl]-6-[4-[(dimethylamino)carbonyl]piperidin-1-carbonyl]-3-methoxy-7H-indolo[2,1-a][2]benzazepine-10-carboxamide. LC/MS: Retention time: 1.947 min; m/e 676 (MH+, method 5); 1H NMR (400 MHz, CHLOROFORM-D) δ ppm 1.14-1.68 (m, 6 H) 1.68-1.81 (m, 2 H) 1.84-2.15 (m, 4 H) 2.60-2.89 (m, 4 H) 2.94 (s, 3 H) 3.03 (s, 3 H) 3.05 (s, 6 H) 3.90 (s, 3 H) 4.27-4.59 (m, 5 H) 5.00-5.15 (m, 1 H) 6.81 (s, 1 H) 6.91 (d, J=2.27 Hz, 1 H) 7.05 (dd, J=8.69, 2.64 Hz, 1 H) 7.44-7.52 (m, 2 H) 7.87 (d, J=8.56 Hz, 1 H) 7.98 (s, 1 H).

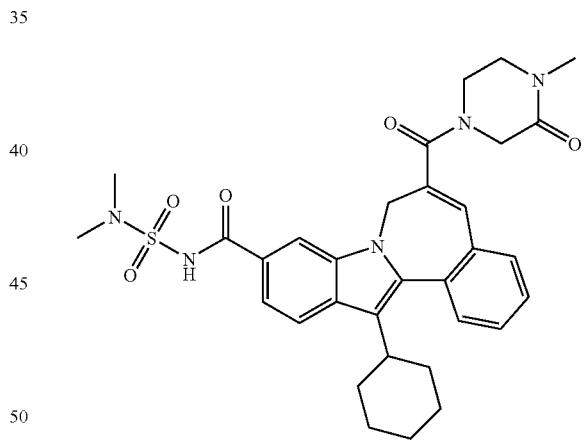

13-Cyclohexyl-N-[(dimethylamino)sulfonyl]-6-(1-methyl-2-oxo-piperazin-4-carbonyl)-7H-indolo[2,1-a][2]benzazepine-10-carboxamide. LS/MS: Retention time: 1.890 min; m/e 604 (MH+, method 5); 1H NMR (400 MHz, CHLOROFORM-D) δ ppm 1.13-1.27 (m, 1 H) 1.30-1.47 (m, 2 H) 1.48-1.60 (m, 1 H) 1.76 (d, J=9.06 Hz, 2 H) 1.87-2.13 (m, 4 H) 2.77-2.91 (m, 1 H) 3.02 (s, 3 H) 3.04 (s, 6 H) 3.07-3.44 (m, 2 H) 3.60-3.74 (m, 1 H) 3.84-4.00 (m, 1 H) 4.29 (d, J=2.52 Hz, 2 H) 4.36-4.49 (m, 1 H) 5.20-5.36 (m, 1 H) 6.96 (s, 1 H) 7.41-7.61 (m, 5 H) 7.91 (d, J=8.56 Hz, 1 H) 8.19 (s, 1 H).

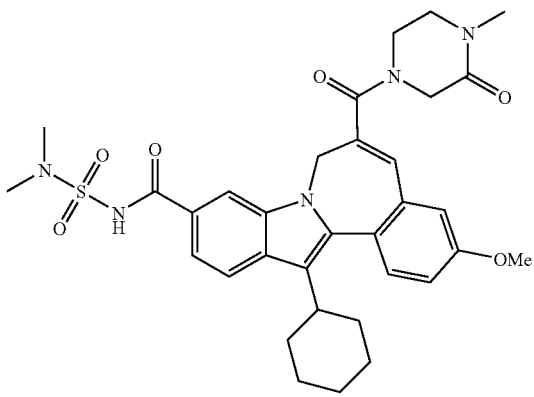

13-Cyclohexyl-N-[(dimethylamino)sulfonyl]-3-methoxy-6-(1-methyl-2-oxo-piperazin-4-carbonyl)-7H-indolo[2,1-a][2]benzazepine-10-carboxamide. LS/MS: Retention time: 1.920 min; m/e 634 (MH$^+$, method 5); 1H NMR (400 MHz, CHLOROFORM-D) δ ppm 1.12-1.64 (m, 5 H) 1.68-2.12 (m, 5 H) 2.76-2.85 (m, 1 H) 2.99 (s, 3 H) 3.05 (s, 6 H) 3.29-3.38 (m, 2 H) 3.67-3.87 (m, 2 H) 3.90 (s, 3 H) 4.12-4.40 (m, 3 H) 5.12-5.25 (m, 1 H) 6.92 (s, 2 H) 7.07 (dd, J=8.56,2.52 Hz, 1 H) 7.45-7.52 (m, 2 H) 7.88 (d, J=8.56 Hz, 1 H) 8.08 (s, 1 H) 9.26 (s, 1 H).

13-Cyclohexyl-N-[(4-methylpiperazin-1-yl)sulfonyl]-6-(2,6-dimethylmorpholin-4-carbonyl)-3-methoxy-7H-indolo[2,1-a][2]benzazepine-10-carboxamide. LS/MS: Retention time: 1.817 min; m/e 690 (MH$^+$, method 5); 1H NMR (400 MHz, CHLOROFORM-D) δ ppm 0.95-1.55 (m, 11 H) 1.70-1.81 (m, 2 H) 1.85-2.10 (m, 3 H) 2.42-3.21 (m, 11 H) 3.37-3.78 (m, 5 H) 3.90 (s, 3 H) 4.09 (s, 2 H) 4.23-4.40 (m, 1 H) 5.00-5.17 (m, 1 H) 6.78 (s, 1 H) 6.89 (d, J=2.27 Hz, 1 H) 7.06 (dd, J=8.81, 2.52 Hz, 1 H) 7.46-7.54 (m, 2 H) 7.87 (d, J=8.56 Hz, 1 H) 8.07 (s, 1 H).

The following general conditions for HPLC pertain to the following experimental procedures until otherwise noted: LC retention times refer to a Phenomenex-Luna 3.0×50 mm S10 column w/gradient elution (A: 10% MeOH-90% H$_2$O-0.1% TFA, B: 90% MeOH-10% H$_2$O-0.1% TFA; 0% B to 100% B over 2 min), 5 uL injection, w/ flow rate of 4 mL/min.

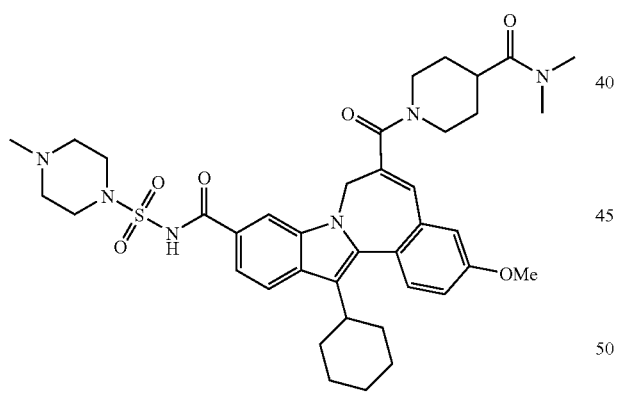

13-Cyclohexyl-N-[(4-methylpiperazin-1-yl)sulfonyl]-6-[4-[(dimethylamino)carbonyl]piperidin-1-carbonyl]-3-methoxy-7H-indolo[2,1-a][2]benzazepine-10-carboxamide. LS/MS: Retention time: 1.743 min; m/e 731 (MH$^+$, method 5); 1H NMR (400 MHz, CHLOROFORM-D) δ ppm 1.12-1.62 (m, 7 H) 1.75 (s, 3 H) 2.08 (s, 5 H) 2.83 (s, 3 H) 2.87-3.38 (m, 5 H) 2.90 (s, 3 H) 2.99 (s, 3 H) 3.42-3.75 (m, 6 H) 3.90 (s, 3 H) 4.15 (s, 2 H) 4.40 (s, 1 H) 5.00-5.12 (m, 1 H) 6.75 (s, 1 H) 6.89 (d, J=2.27 Hz, 1 H) 7.05 (dd, J=8.56, 2.52 Hz, 1 H) 7.40-7.52 (m, 2 H) 7.86 (d, J=8.31 Hz, 1 H) 7.94 (s, 1 H).

N-(1H-benzimidazol-2-ylmethyl)-13-cyclohexyl-6-[[4-(4-morpholinyl)-1-piperidinyl]carbonyl]-7H-indolo[2,1-a][2]benzazepine-10-carboxamide. To a stirred solution of 13-cyclohexyl-6-[[4-(4-morpholinyl)-1-piperidinyl]carbonyl]-7H-indolo[2,1-a][2]benzazepine-10-carboxylic acid (134 mg, 0.24 mmol) in DMF (500 μL) were added 2-aminomethyl benzimidazole dihydrochloride hydrate (75 mg, 0.32 mmol), N,N-diisopropylethylamine (165 μL, 0.95 mmol), N-(3-dimethylaminopropyl)-N'-ethylcarbodiimide hydrochloride (60 mg, 0.31 mmol), and 1-hydroxybenzotriazole (44 mg, 0.33 mmol). The suspension was allowed to stir at r.t. for 4 hr, at which point the solvent was removed under reduced pressure. CH$_2$Cl$_2$ (5 mL) was added, and the suspension filtered through Celite, and chromatographed on silica gel (gradient elution: 0%→10% MeOH in CH$_2$Cl$_2$) to afford the title compound as a pale yellow solid (24 mg, 14% yield). LC/MS (ESI) retention time: 1.57 min, m/z 683 (MH$^+$); $^1$H NMR (400 MHz, CDCl$_3$) δ 1.07-1.53 (m, 4 H) 1.63-1.78 (m, 3 H) 1.99 (s, 4 H) 2.25 (t, J=11.08 Hz, 1 H) 2.39 (s, 4 H) 2.59-2.87 (m, 3 H) 3.63 (s, 4 H) 4.14 (s, 1 H) 4.73-5.00 (m, 3 H) 6.78 (s, 1 H) 7.17 (ddd, J=9.63, 3.90, 3.59 Hz, 2 H) 7.34 (dd, J=7.05, 1.76 Hz, 1 H) 7.40-7.47 (m, 2 H) 7.50-7.58 (m, 4 H) 7.73 (d, J=8.31 Hz, 1 H) 8.16 (s, 1 H) 8.68 (s, 1 H).

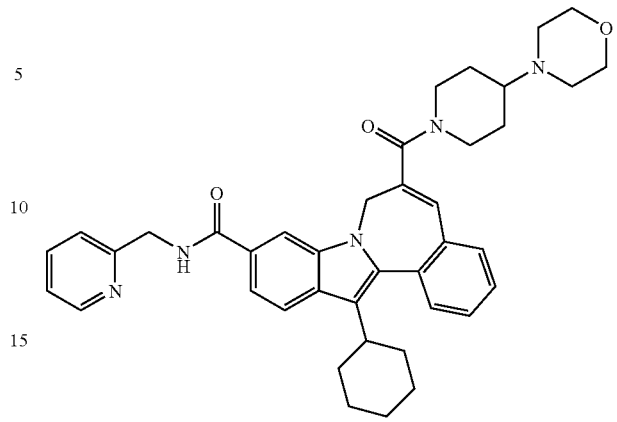

13-cyclohexyl-6-[[4-(4-morpholinyl)-1-piperidinyl]carbonyl]-N-(2-pyridinylmethyl)-7H-indolo[2,1-a][2]benzazepine-10-carboxamide. To a stirred solution of 13-cyclohexyl-6-[[4-(4-morpholinyl)-1 -piperidinyl]carbonyl]-7H-indolo[2,1-a][2]benzazepine-10-carboxylic acid (70 mg, 0.13 mmol) in CH$_2$Cl$_2$ (1 mL) were added N,N-diisopropylethylamine (85 μL, 0.49 mmol), 2-(aminomethyl)pyridine (17 mg, 0.16 mmol), N-(3-dimethylaminopropyl)-N'-ethylcarbodiimide hydrochloride (34 mg, 0.18 mmol), and 1 -hydroxybenzotriazole (24 mg, 0.18 mmol). The suspension was allowed to stir at r.t. for 22 hr, filtered through Celite, and chromatographed on silica gel (gradient elution: 0%→15% MeOH in CH$_2$Cl$_2$) to afford the title compound as a yellow solid (43 mg, 51% yield). LC/MS (ESI) retention time: 1.57 min, m/z 643 (MH$^+$); $^1$H NMR (400 MHz, CDCl$_3$) δ 1.15-1.27 (m, 3 H) 1.29-1.45 (m, 3 H) 1.48-1.58 (m, 1 H) 1.61-1.70 (m, 1 H) 1.71-1.81 (m, 2 H) 1.86-1.97 (m, 1 H) 1.98-2.15 (m, 3 H) 2.27 (t, J=11.08 Hz, 1 H) 2.38 (s, 4 H) 2.60-2.77 (m, 2 H) 2.78-2.89 (m, 1 H) 3.61 (s, 4 H) 4.40 (s, 1 H) 4.79 (d, J=4.53 Hz, 2 H) 5.09 (s, 1 H) 6.81 (s, 1 H) 7.18-7.22 (m, 1 H) 7.36 (t, J=8.18 Hz, 2 H) 7.41-7.49 (m, 2 H) 7.50-7.59 (m, 2 H) 7.62-7.73 (m, 2 H) 7.89 (d, J=8.56 Hz, 1 H) 8.05 (s, 1 H) 8.56 (d, J=4.53 Hz, 1 H).

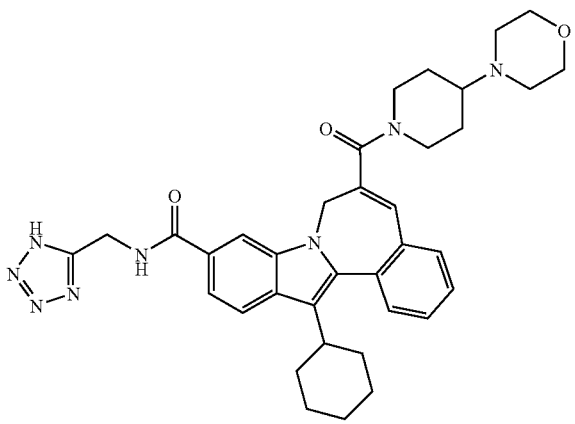

13-cyclohexyl-6-[[4-(4-morpholinyl)-1-piperidinyl]carbonyl]-N-(1H-tetrazol-5-ylmethyl)-7H-indolo[2,1-a][2]benzazepine-10-carboxamide. To a stirred solution of 13-cyclohexyl-6-[[4-(4-morpholinyl)-1-piperidinyl]carbonyl]-7H-indolo[2,1-a][2]benzazepine-10-carboxylic acid (135 mg, 0.24 mmol) in CH$_2$Cl$_2$ (1 mL) were added N,N-diisopropylethylamine (170 μL, 0.98 mmol), N-(3-dimethylaminopropyl)-N'-ethylcarbodiimide hydrochloride (64 mg, 0.33 mmol), 1-hydroxybenzotriazole (47 mg, 0.35 mmol), and 5-(aminomethyl)tetrazole (33 mg, 0.33 mmol). The suspension was allowed to stir at r.t. for 23 hr, filtered through Celite, and chromatographed on silica gel (gradient elution: 0%→30% MeOH in CH$_2$Cl$_2$) to afford the title compound as a yellow solid (70 mg, 46% yield). LC/MS (ESI) retention time: 1.61 min, m/z 635 (MH$^+$); $^1$H NMR (400 MHz, CD$_3$OD) δ 1.08-1.23 (m, 1 H) 1.35-1.48 (m, 4 H) 1.66 -1.79 (m, 3 H) 1.86 -1.92 (m, 1 H) 1.96 -2.14 (m, 3 H) 2.44-2.60 (m, 5 H) 2.74 -2.89 (m, 2 H) 3.16 (dd, J=7.55 Hz, 1 H) 3.57 -3.73 (m, 5 H) 4.25 (s, 1 H) 4.94-5.08 (m, 1 H) 6.87 (s, 1 H) 7.43-7.51 (m, 3 H) 7.52-7.59 (m, 2 H) 7.83 (d, J=8.56 Hz, 1 H) 8.11 (s, 1 H).

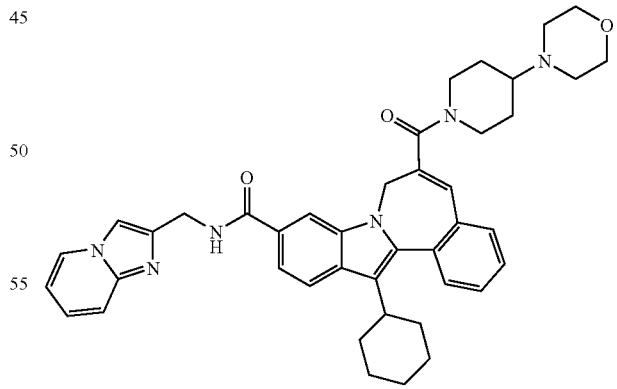

13-cyclohexyl-N-(imidazo[1,2-a]pyridin-2-ylmethyl)-6-[[4-(4-morpholinyl)-1-piperidinyl]carbonyl]-7H-indolo[2,1-a][2]benzazepine-10-carboxamide. To a stirred solution of 13-cyclohexyl-6-[[4-(4-morpholinyl)-1-piperidinyl]carbonyl]-7H-indolo[2,1-a][2]benzazepine-10-carboxylic acid (70 mg, 0.13 mmol) in CH$_2$Cl$_2$ (1 mL) were added N,N-diisopropylethylamine (85 μL, 0.49 mmol), 2-aminomethylimidazo[1,2-a]pyridine dihydrochloride (36 mg, 0.16 mmol), N-(3-dimethylaminopropyl)-N'-ethylcarbodiimide hydrochloride (34 mg, 0.18 mmol), and 1-hydroxybenzotriazole (24 mg, 0.18 mmol). The suspension was allowed to stir at r.t. for 17 hr, and the solvent was removed under reduced pressure. The resulting solid was suspended in DMF (1 mL) and stirred for an additional 4 hr before being concentrated under reduced pressure, dissolved in CH$_2$Cl$_2$, filtered through Celite, and chromatographed on silica gel (gradient elution: 0%→20% MeOH in CH$_2$Cl$_2$) to afford the title compound as a yellow solid (22 mg, 35% yield). LC/MS (ESI) retention time: 1.53 min, m/z 683 (MH$^+$); $^1$H NMR (400 MHz, CDCl$_3$) δ 1.13-1.21 (m, 1 H) 1.29-1.45 (m, 4 H) 1.57-1.67 (m, 1 H) 1.69-1.79 (m, 2 H) 1.84-1.95 (m, 1 H) 1.96-2.12 (m, 3 H) 2.30-2.31 (m, 4 H) 2.57-2.75 (m, 2 H) 2.80-2.81 (m, 1 H) 3.60 (s, 4 H) 4.36 (s, 1 H) 4.80 (s, 2 H) 5.06 (s, 1 H) 6.74 (t, J=6.42 Hz, 1 H) 6.79 (s, 1 H) 7.07-7.18 (m, 1 H) 7.32-7.37 (m, 2 H) 7.39-7.46 (m, 2 H) 7.47-7.56 (m, 3 H) 7.60 (s, 1 H) 7.84 (d, J=8.56 Hz, 1 H) 7.99-8.10 (m, 2 H).

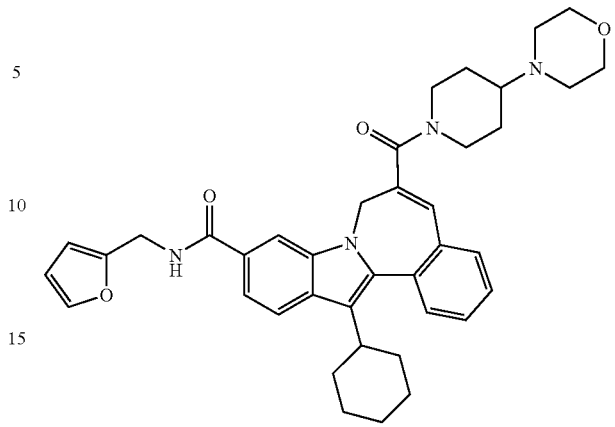

13-cyclohexyl-N-(2-furanylmethyl)-6-[[4-(4-morpholinyl)-1-piperidinyl]carbonyl]-7H-indolo[2,1-a][2]benzazepine-10-carboxamide. A solution of 13-cyclohexyl-6-[[4-(4-morpholinyl)-1-piperidinyl]carbonyl]-7H-indolo[2,1-a][2]benzazepine-10-carboxylic acid (40 mg, 0.07 mmol), N,N-diisopropylethylamine (60 μL, 0.34 mmol), N-(3-dimethylaminopropyl)-N'-ethylcarbodiimide hydrochloride (19 mg, 0.1 mmol), 1-hydroxybenzotriazole (14 mg, 0.1 mmol), and furfuryl amine (10 mg, 0.1 mmol) in CH$_2$Cl$_2$ (1.5 mL) was stirred at r.t. overnight, diluted with CH$_2$Cl$_2$ (3 mL), and chromatographed on silica gel (gradient elution: 0%→10% MeOH in CH$_2$Cl$_2$) to afford a yellow oil. Et$_2$O (5 mL) was added to dissolve the oil, and concentration afforded the title compound as a pale yellow solid (42 mg, 95% yield). LC/MS (ESI) retention time: 1.74 min, m/z 633 (MH$^+$); $^1$H NMR (400 MHz, CDCl$_3$) δ 1.29-1.44 (m, 3 H) 1.46-1.57 (m, 1 H) 1.69-1.81 (m, 3 H) 1.86-1.97 (m, 1 H) 1.98-2.11 (m, 3 H) 2.27-2.37 (m, 1 H) 2.38-2.49 (m, 4 H) 2.61-2.78 (m, 2 H) 2.78-2.89 (m, 1 H) 3.66 (s, 4 H) 4.38 (s, 1 H) 4.66 (d, J=5.29 Hz, 2 H) 5.06 (s, 1 H) 6.22-6.41 (m, 2 H) 6.64 (t, J=5.04 Hz, 1 H) 6.81 (s, 1 H) 7.33-7.50 (m, 5 H) 7.51-7.61 (m, 1 H) 7.85 (d, J=8.31 Hz, 1 H) 7.97 (s, 1 H); $^{13}$C NMR (101 MHz, CDCl$_3$) δ 26.20, 27.02, 33.27, 36.73, 37.04, 41.92, 49.45, 61.67, 66.94, 107.54, 108.90, 110.48, 116.84, 120.05, 121.19, 127.05, 127.95, 128.21, 129.24, 130.08, 130.96, 131.24, 133.24, 134.00, 135.18, 136.39, 142.15, 151.57, 167.74, 168.88.

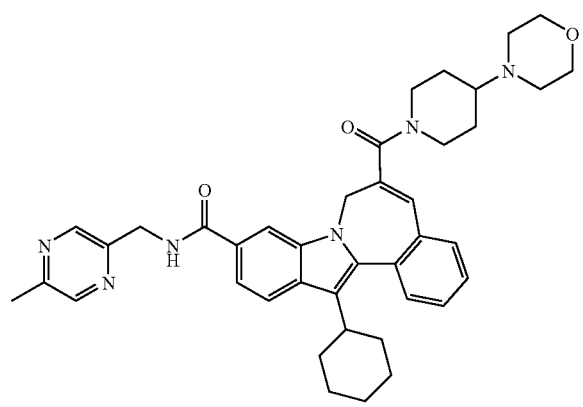

13-cyclohexyl-N-[(5-methylpyrazinyl)methyl]-6-[[4-(4-morpholinyl)-1-piperidinyl]carbonyl]-7H-indolo[2,1-a][2]benzazepine-10-carboxamide. A solution of 13-cyclohexyl-6-[[4-(4-morpholinyl)-1-piperidinyl]carbonyl]-7H-indolo[2,1-a][2]benzazepine-10-carboxylic acid (40 mg, 0.07 mmol), 2-(aminomethyl)-5-methylpyrazine (12 mg, 0.1 mmol), N,N-diisopropylethylamine (60 μL, 0.34 mmol), N-(3-dimethylaminopropyl)-N'-ethylcarbodiimide hydrochloride (19 mg, 0.1 mmol), and 1-hydroxybenzotriazole (14 mg, 0.1 mmol) in CH$_2$Cl$_2$ (1.5 mL) was stirred at r.t. for 20 h, at which point it was introduced directly to silica gel and chromatographed (gradient elution: 0%→10% MeOH in CH$_2$Cl$_2$) to afford a yellow foam, which was triturated with Et$_2$O and dried to give the title compound as a pale yellow solid (43 mg, 90% yield). LC/MS (ESI) retention time: 1.69 min, m/z 659 (MH$^+$); $^1$H NMR (400 MHz, CDCl$_3$) δ 1.28-1.44 (m, 3 H) 1.46-1.59 (m, 1 H) 1.61-1.70 (m, 1 H) 1.71-1.81 (m, 2 H) 1.85-1.96 (m, 1 H) 1.97-2.13 (m, 3 H) 2.29 (t, J=10.45 Hz, 1 H) 2.35-2.46 (m, 4 H) 2.55 (s, 3 H) 2.61-2.77 (m, 2 H) 2.77-2.89 (m, 2 H) 3.62 (s, 4 H) 4.38 (s, 1 H) 4.78 (d, J=5.04 Hz, 2 H) 5.00-5.18 (m, 1 H) 6.81 (s, 1 H) 7.32-7.40 (m, 2 H) 7.40-7.50 (m, 3 H) 7.51-7.59 (m, 1 H) 7.88 (d, J=8.56 Hz, 1 H) 8.01 (s, 1 H) 8.39 (s, 1 H) 8.56 (d, J=1.01 Hz, 1 H); $^{13}$C NMR (101 MHz, CDCl$_3$) δ 21.18, 26.21, 27.03, 28.08, 33.26, 36.73, 41.91, 42.60, 49.52, 61.59, 67.07, 108.98, 116.90, 120.03, 121.21, 126.98, 127.94, 128.21, 129.27, 130.96, 131.23, 133.27, 134.01, 135.18, 135.25, 136.39, 142.94, 143.40, 149.41, 152.50, 168.10, 168.87.

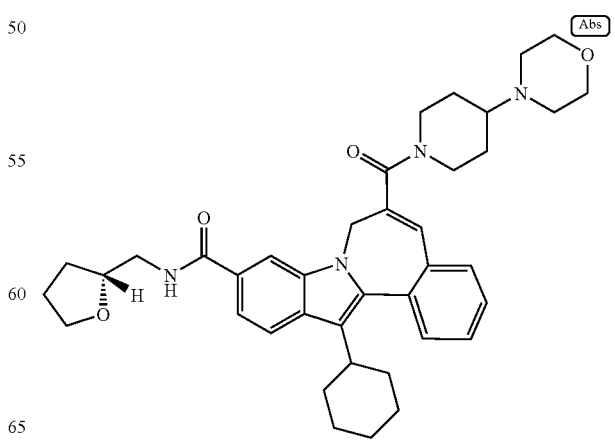

13-cyclohexyl-6-[[4-(4-morpholinyl)-1-piperidinyl]carbonyl]-N-[[(2R)-tetrahydro-2-furanyl]methyl]-7H-indolo[2,1-a][2]benzazepine-10-carboxamide. A solution of 13-cyclohexyl-6-[[4-(4-morpholinyl)-1-piperidinyl]carbonyl]-7H-indolo[2,1-a][2]benzazepine-10-carboxylic acid (40 mg, 0.07 mmol), N,N-diisopropylethylamine (60 μL, 0.34 mmol), N-(3-dimethylaminopropyl)-N'-ethylcarbodiimide hydrochloride (19 mg, 0.1 mmol), 1-hydroxybenzotriazole (14 mg, 0.1 mmol), and (R)-(−)-tetrahydrofurfurylamine (10 mg, 0.1 mmol) in CH$_2$Cl$_2$ (1.5 mL) was stirred at r.t. overnight, diluted with CH$_2$Cl$_2$ (5 mL), and chromatographed on silica gel (gradient elution: 0%→10% MeOH in CH$_2$Cl$_2$) to afford a yellow oil. Et$_2$O (5 mL) was added to dissolve the oil, and concentration afforded the title compound as an off-white solid (32 mg, 72% yield). LC/MS (ESI) retention time: 1.75 min, m/z 637 (MH$^+$); $^1$H NMR (400 MHz, CDCl$_3$) δ 1.31-1.44 (m, 3 H) 1.48-1.57 (m, 1 H) 1.58-1.69 (m, 2 H) 1.72-1.80 (m, 2 H) 1.87-1.96 (m, 3 H) 1.98-2.11 (m, 4 H) 2.25-2.36 (m, 1 H) 2.42 (s, 3 H) 2.62-2.78 (m, 1 H) 2.78-2.89 (m, 1 H) 3.39 (ddd, J=12.53, 6.20 Hz, 1 H) 3.66 (s, 4 H) 3.74-3.85 (m, 2 H) 3.86-3.95 (m, 1 H) 4.40 (s, 1 H) 5.07 (s, 1 H) 6.60 (t, J=5.29 Hz, 1 H) 6.82 (s, 1 H) 7.34-7.50 (m, 4 H) 7.52-7.59 (m, 1 H) 7.86 (d, J=8.56 Hz, 1 H) 7.97 (s, 1 H).

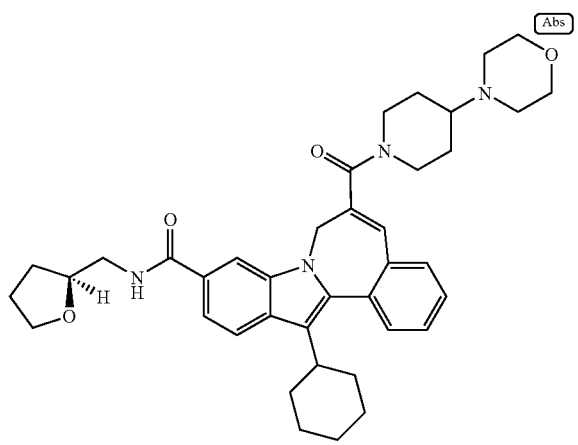

13-cyclohexyl-6-[[4-(4-morpholinyl)-1-piperidinyl]carbonyl]-N-[[(2S)-tetrahydro-2-furanyl]methyl-7H-indolo[2,1-a][2]benzazepine-10-carboxamide. A solution of 13-cyclohexyl-6-[[4-(4-morpholinyl)-1-piperidinyl]carbonyl]-7H-indolo[2,1-a][2]benzazepine-10-carboxylic acid (40 mg, 0.07 mmol), N,N-diisopropylethylamine (60 μL, 0.34 mmol), N-(3-dimethylaminopropyl)-N'-ethylcarbodiimide hydrochloride (19 mg, 0.1 mmol), 1-hydroxybenzotriazole (14 mg, 0.1 mmol), and (S)-(+)-tetrahydrofurfurylamine (10 mg, 0.1 mmol) in CH$_2$Cl$_2$ (1.5 mL) was stirred at r.t. overnight, diluted with CH$_2$Cl$_2$ (5 mL), and chromatographed on silica gel (gradient elution: 0%→10% MeOH in CH$_2$Cl$_2$) to afford a yellow oil. Et$_2$O (5 mL) was added to dissolve the oil, and concentration afforded the title compound as an off-white solid (32 mg, 72% yield). LC/MS (ESI) retention time: 1.73 min, m/z 637 (MH$^+$); $^1$H NMR (400 MHz, CDCl$_3$) δ 1.27-1.43 (m, 3 H) 1.47-1.57 (m, 1 H) 1.58-1.70 (m, 2 H) 1.70-1.81 (m, 2 H) 1.86-1.97 (m, 3 H) 1.98-2.12 (m, 4 H) 2.25-2.35 (m, 1 H) 2.42 (s, 3 H) 2.63-2.77 (m, 1 H) 2.78-2.89 (m, 1 H) 3.29-3.46 (m, 1 H) 3.65 (s, 4 H) 3.74-3.85 (m, 2 H) 3.85-3.98 (m, 1 H) 4.09 (ddd, J=14.16, 7.11, 3.40 Hz, 1 H) 4.39 (s, 1 H) 5.08 (s, 1 H) 6.67-6.75 (m, 1 H) 6.82 (s, 1 H) 7.34-7.39 (m, 1 H) 7.40-7.50 (m, 3 H) 7.52-7.59 (m, 1 H) 7.86 (d, J=8.56 Hz, 1 H) 7.99 (s, 1 H).

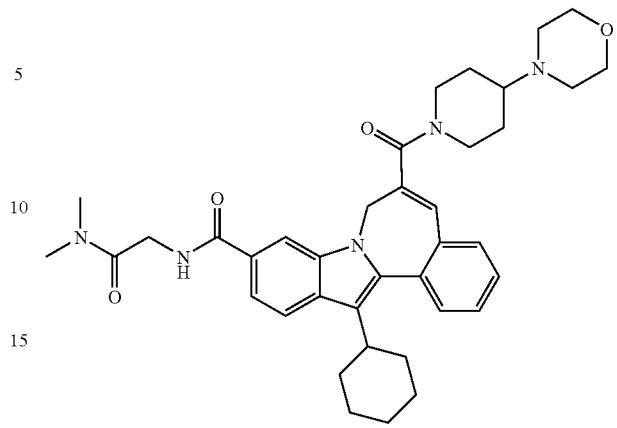

13-cyclohexyl-N-[2-(dimethylamino)-2-oxoethyl]-6-[[4-(4-morpholinyl)-1-piperidinyl]carbonyl]-7H-indolo[2,1-a][2]benzazepine-10-carboxamide. To a stirred solution of 13-cyclohexyl-6-[[4-(4-morpholinyl)-1-piperidinyl]carbonyl]-7H-indolo[2,1-a][2]benzazepine-10-carboxylic acid (40 mg, 0.07 mmol) in CH$_2$Cl$_2$ (1.5 mL) were added N,N-diisopropylethylamine (60 μL, 0.34 mmol), 2-amino-N,N-dimethylacetamide monoacetate (16 mg, 0.1 mmol), N-(3-dimethylaminopropyl)-N'-ethylcarbodiimide hydrochloride (19 mg, 0.1 mmol), and 1-hydroxybenzotriazole (14 mg, 0.1 mmol). The suspension was allowed to stir at r.t. for 2 days, then diluted with CH$_2$Cl$_2$, filtered through Celite, and chromatographed on silica gel (gradient elution: 0%→10% MeOH in CH$_2$Cl$_2$) to give the title compound as a yellow solid (22 mg, 48% yield). LC/MS (ESI) retention time: 1.66 min, m/z 638 (MH$^+$); $^1$H NMR (400 MHz, CDCl$_3$) δ 1.29-1.43 (m, 2 H) 1.47-1.59 (m, 1 H) 1.71-1.80 (m, 2 H) 1.87-1.96 (m, 1 H) 2.34-2.35 (m, 1 H) 2.40-2.51 (m, 3 H) 2.60-2.76 (m, 2 H) 2.77-2.89 (m, 1 H) 3.02 (s, 3 H) 3.04 (s, 3 H) 3.66 (s, 4 H) 4.25 (d, J=3.78 Hz, 2 H) 4.39 (s, 1 H) 5.07-5.08 (m, 1 H) 6.61 (s, 1 H) 6.81 (s, 1 H) 7.33-7.49 (m, 5 H) 7.51-7.59 (m, 1 H) 7.86 (d, J=8.56 Hz, 1 H) 8.02 (s, 1 H).

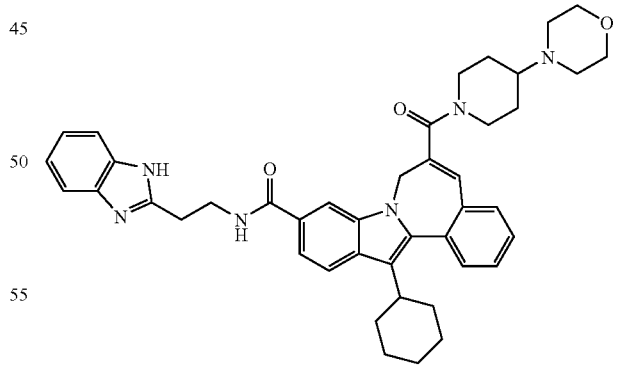

N-[2-(]H-benzimidazol-2-yl)ethyl]-13-cyclohexyl-6-[[4-(4-morpholinyl)-1-piperidinyl]carbonyl]-7H-indolo[2,1-a][2]benzazepine-10-carboxamide. A solution of 13-cyclohexyl-6-[[4-(4-morpholinyl)-1-piperidinyl]carbonyl]-7H-indolo[2,1-a][2]benzazepine-10-carboxylic acid (47 mg, 0.085 mmol), N,N-diisopropylethylamine (60 μL, 0.34 mmol), 2-(2-aminoethyl)benzimidazole dihydrochloride (23 mg, 0.1 mmol), N-(3-dimethylaminopropyl)-N'-ethylcarbodiimide hydrochloride (23 mg, 0.12 mmol), and 1-hydroxybenzotriazole (16 mg, 0.12 mmol) in CH$_2$Cl$_2$ (3.1 mL) was stirred at r.t. overnight, then introduced directly to silica gel. Elution (gradient: 0%→5% MeOH in CH$_2$Cl$_2$) gave the title compound as a yellow powder (20 mg, 34% yield). LC/MS (ESI) retention time: 1.57 min, m/z 697 (MH$^+$); $^1$H NMR (400 MHz, CDCl3) δ 1.09-1.21 (m, 1 H) 1.22-1.37 (m, 3 H) 1.38-1.48 (m, 1 H) 1.58-1.68 (m, 1 H) 1.69-1.76 (m, 2 H) 1.87 (t, 1 H) 1.97 (t, 2 H) 2.27 (t, J=10.95 Hz, 1 H) 2.39 (s, 3 H) 2.61-2.72 (m, 1 H) 2.72-2.82 (m, 1 H) 3.26 (t, J=6.04 Hz, 2 H) 3.61-3.70 (m, 4 H) 3.98 (s, 2 H) 4.18 (s, 1 H) 4.86 (s, 1 H) 6.80 (s, 1 H) 7.13 (dd, J=6.04, 3.27 Hz, 2 H) 7.33-7.38 (m, 2 H) 7.40-7.46 (m, 2 H) 7.46-7.53 (m, 3 H) 7.73 (d, J=8.56 Hz, 1 H) 7.77-7.85 (m, 1 H) 8.04 (s, 1 H).

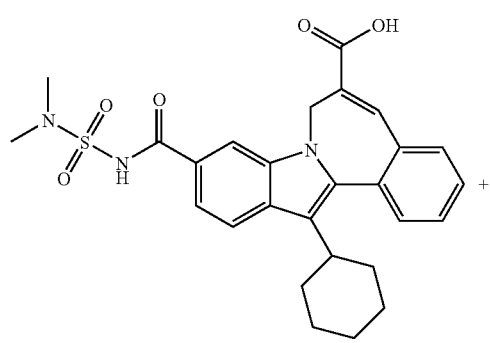

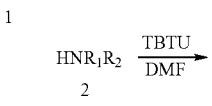

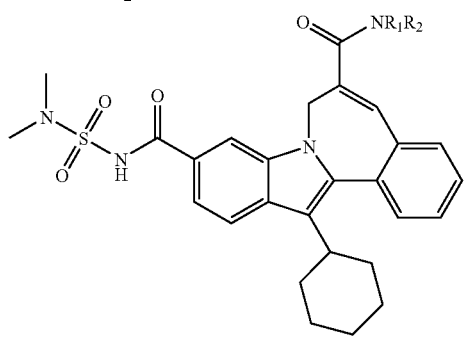

To 0.05 mmol of 1 in 1.0 mL of anhydrous N,N-Dimethylformamide (DMF) in a 3 dram vial equipped with a teflon lined screw cap was added 0.15 mmol (3 eq.) of 2-(1H-Benzotriazole-1-yl)-1,1,3,3,-Tetramethyluronium Tetrafluoroborate (TBTU) in 1.0 mL of anhydrous DMF followed by the addition of 0.1 mmol (2 eq.) of amine 2 in 1.0 mL of anhydrous DMF and 0.1 mmol (2 eq.) of triethylamine (neat). The reaction was shaken on an Innova 2000 orbital shaker at 240 rpm overnight, at room temperature. The reaction volume was then reduced to a total volume of 2.0 mL in a Savant Speedvac and the crude product was purified using a Shimadzu preparative HPLC employing acetonitrile/water and 10 mM trifluoroacetic acid buffer with a Waters Sunfire, C18, 19 mm×100 mm, 5 μm column at a focused gradient of 50-100% B (B=90% acetonitrile/HPLC water, 0.1% TFA) and a flow rate of 25 mL/min. Postpurification LC/MS data was obtained on a Shimadzu analytical LC/Micromass Platform LC (ESI+) at 220 nm using the following set of conditions: Phenomenex 10 μm C18, 4.6×30mm column, with a gradient of 0-100% B (B=90% HPLC grade methanol/0.1% trifluoroacetic acid/10% HPLC grade water), (A=90% HPLC grade water /0.1% trifluoroacetic acid/10% HPLC grade methanol), in 2 minutes with a 1 minute hold at a rate of 5 mL/minute.

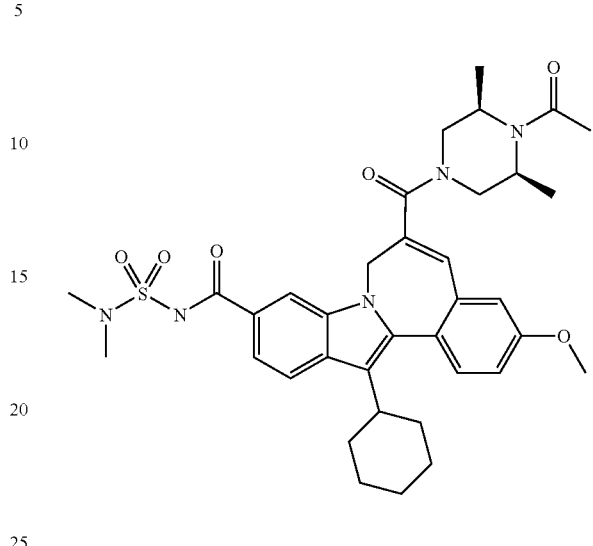

6-(((3S,5R)-4-Acetyl-3,5-dimethylpiperazin-1-yl)carbonyl)-13-cyclohexyl-N-((dimethylamino)sulfonyl)-3-methoxy-7H-indolo[2,1-a][2]benzazepine-10-carboxamide. $^1$H NMR: δ (500 MHz, CDCl$_3$) δ ppm 0.80 (m, 1H), 1.15 (m, 4 H), 1.39 (m, 4 H), 1.79 (m, 3 H), 1.99 (m, 3 H), 2.06 (s, 3 H), 2.82 (m, 4 H), 3.04 (s, 6 H), 3.17 (m, 1 H), 3.90 (s, 3 H), 4.14 (m, 2 H), 4.38 (m, 1 H) 5.19 (m, 1 H), 6.89 (m, 2 H), 7.07 (dd, J=8.78, 2.74 Hz, 1 H), 7.46-7.54 (m, 2 H), 7.87 (d, J=8.78 Hz, 1 H), 8.09 (s, 1 H), 9.28 (br s, 1 H). LC/MS: m/z 676.26, Rf 2.04 min., 97.3% purity.

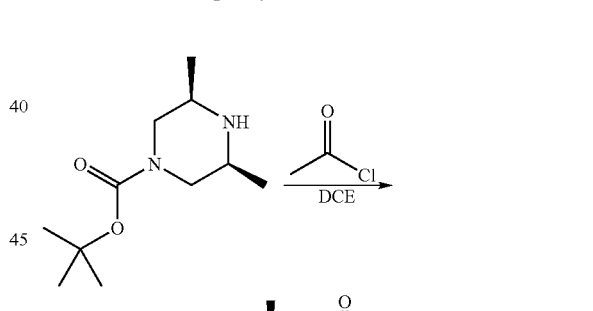

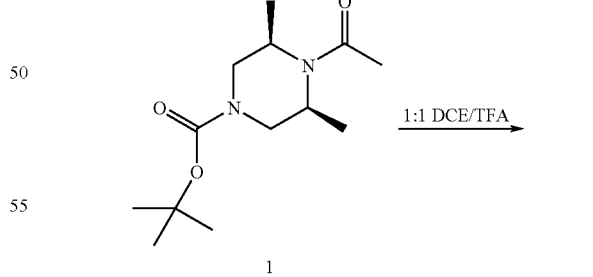

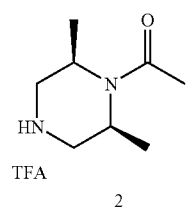

1-((2S,6R)-2,6-Dimethylpiperazin-1-yl)ethanone. To 1.0 g (4.67 mmol) of commercially available (3S,5R)-tert-butyl 3,5-dimethylpiperazine-1-carboxylate was added 5 mL of dry dichloroethane in a 100 mL round bottom flask equipped with a loose fitting septa. To this mixture was added 2.0 equivalents (9.33 mmol, 1.63 mL) of redistilled N,N-diisopropylethylamine and the flask was cooled to 0° C. To this solution was added 2.0 equivalents (9.33 mmol, 663.0 µL) of acetyl chloride portionwise. The ice bath was then removed and the solution was stirred at room temperature overnight. The crude product was taken up in a separatory funnel, washed with 5 mL of a saturated sodium bicarbonate solution, 5 mL of a brine solution and dried over magnesium sulfate. Evacuation of solvent gave a quantitative yield (1.2 g) of 1, (3S,5R)-tert-butyl 4-acetyl-3,5-dimethylpiperazine-1-carboxylate, as brown oily solid. LC/MS: m/z 257.25, Rf 1.35 min., 90.0% purity. To 75 mgs (0.29 mmmol) of 1 was added 2 mL of 1:1 solution of dichloroethane and trifluoroacetic acid in a 25 mL round bottom flask equipped with a loose fitting septa. The solution was stirred for about 1 hour at room temperature then evacuated to near dryness on a rotary evaporator to give a brown oil. The resulting oil was triturated with diethyl ether to give 65 mg (82% yield) of 2, 1-((2S,6R)-2,6-dimethylpiperazin-1-yl)ethanone, as a tan amorphous solid. ¹H NMR (300 MHz, Tetrahydrofurn-d8): δ ppm 1.40 (d, J=7.32 Hz, 6 H), 2.07 (s, 3 H), 3.13 (dd, J=12.99, 5.31 Hz, 2 H), 3.28-3.38 (m, 2 H), 4.56 (br s, 1 H).

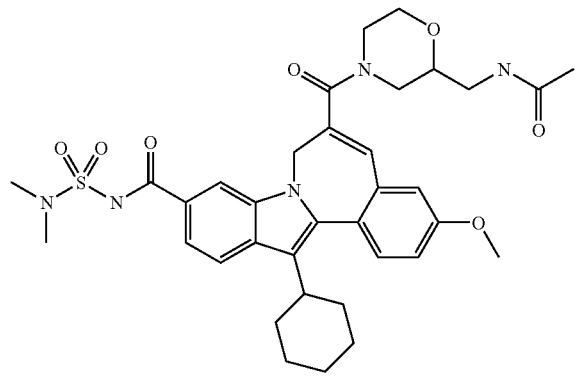

6-((2-(Acetamidomethyl)morpholin-4-yl)carbonyl)-13-cyclohexyl-N-((dimethylamino)sulfonyl)-3-methoxy-7H-indolo[2,1-a][2]benzazepine-10-carboxamide. ¹H NMR: (500 MHz, MeOD) δ ppm 1.21 (m, 1 H), 1.40-1.49 (m, 4 H), 1.76 (d, J=9.16 Hz, 2 H), 1.83 (m, 1 H), 1.90 (s, 3 H), 1.93-1.99 (m, 1 H), 2.00-2.10 (m, 3 H), 2.81 (m, 1 H), 2.84 (dd, J=10.65, 3.32Hz, 2 H), 3.00-3.06 (m, 6 H), 3.11-3.18(m, 1 H), 3.19-3.28 (m, 1 H), 3.41-3.51 (m,2H), 3.80-3.88(m, 1 H), 3.90 (s, 3 H), 4.31 (m, 1 H), 5.06-5.15 (m, 1 H), 6.93 (br s, 1 H), 7.08 (s, 1 H), 7.12 (dd, J=8.71, 2.63 Hz, 1 H), 7.51 (d, J=8.71 Hz, 1 H), 7.55 (dd, J=8.48, 1.60 Hz, 1 H), 7.88 (d, J=8.48 Hz, 1 H), 8.09 (s, 1 H). LC/MS: m/z 678.23, Rf 2.04 min., 95.0% purity.

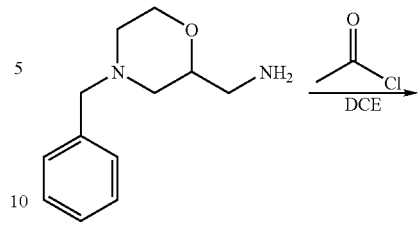

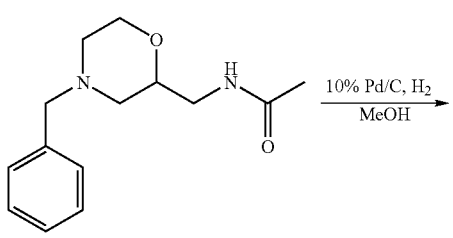

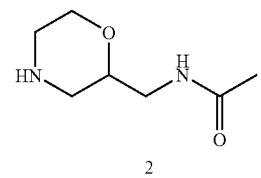

N-(morpholin-2-ylmethyl)acetamide. To 136 mg (0.66 mmol) of commercially available (4-benzylmorpholin-2-yl)methanamine was added 4 mL of dry dichloroethane in a 10 mL sealed tube. To this solution was added 2.0 equivalents (1.32 mmol) of cold acetyl chloride drop-wise followed by 2.0 equivalents of redistilled N,N-diisopropylethylamine. The tube was sealed and the solution was stirred at 60° C. overnight. The crude product was returned to room temperature, evaporated to dryness, re-dissolved in N,N-dimethylformamide and purified using a Shimadzu preparative HPLC employing methanol/water and 10 mM trifluoroacetic acid buffer with a Phenomenex-Luna, C18, 30 mm×100 mm, 5 µm column with 0-100% B at a flow rate of 40 mL/min. Evacuation of solvent gave 230 mgs (96% yield) of 1, N-((4-benzylmorpholin-2-yl)methyl)acetamide, as the trifluoroacetic acid salt. LC/MS: m/z 249.21, Rf 0.41 min., 100% purity. To 0.63 mmol of 1 in a 25 mL round bottom flask was added approximately 5 mL of methanol and 100 mgs of 10% palladium on carbon. The round bottom flask was fitted with a septa, and a needle attached to balloon of hydrogen was inserted. The mixture was stirred at room temperature overnight. The crude product was then filtered through a pad of celite and the solvent evaporated to yield 170 mgs (99% yield) of 2, N-(morpholin-2-ylmethyl)acetamide, as a clear colorless viscous oil. ¹H NMR: δ (300 MHz, DMF-d7) ppm 1.89 (s, 3 H), 2.97 (m, 2 H), 3.37 (m, 1 H), 3.45 (m, 1 H), 3.74 (m, 1 H), 3.90 (m, 2 H) 4.05 (m, 1 H), 4.63-4.76 (m, 1 H).

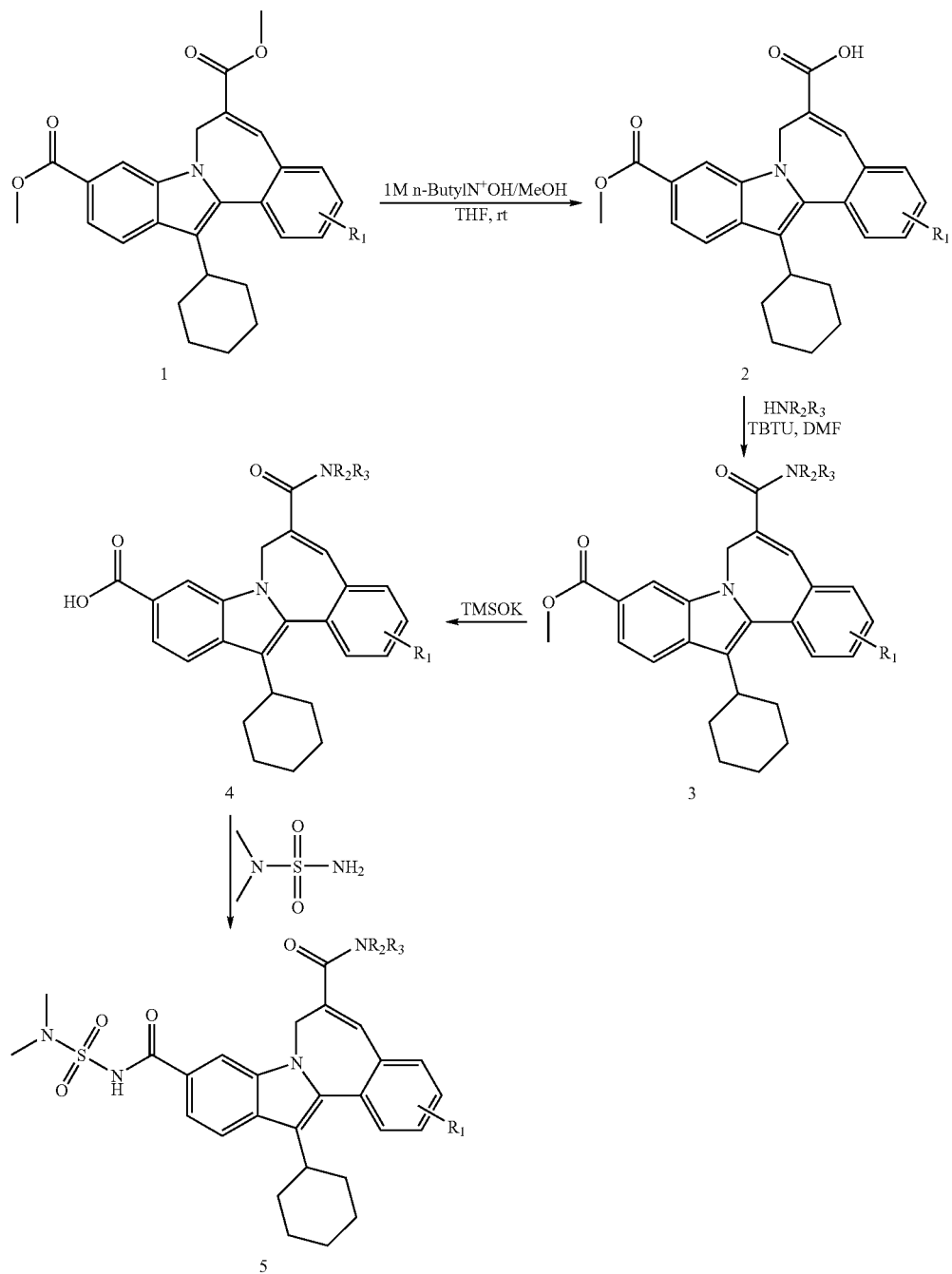

To 1.0 g of dimethyl ester 1 was added 1.0 equivalent of 1M n-Butyl ammonium hydroxide in methanol along with 75 mL of tetrahydrofuran. The mixture was stirred for 8 hours at room temperature. The crude product was concentrated en-vacuo, taken up in ethyl acetate and made slightly acidic (pH=5) by the addition of 1 M HCl. The organic layers were washed with brine, and the product dried over magnesium sulfate. The carboxylic acid 2 was evacuated to dryness to give a light yellow foam (yields 94-99%) which was used without further purification. To 0.2 mmol of carboxylic acid 2 in 3 mL of N,N-dimethylformamide in a 2 dram vial was added 2 equivalents of amine and 2 equivalents of 2-(1H-Benzotriazole-1-yl)-1,1,3,3,-Tetramethyluronium Tetrafluoroborate (TBTU). The vial was capped and shaken over night at room temperature. The reaction volume was then reduced to a total volume of 2.0 mL in a Savant Speedvac and the crude product was purified using a Shimadzu preparative HPLC employing acetonitrile/water and 10 mM trifluoroacetic acid buffer with a Waters Sunfire, C18, 19 mm×100 mm, 5 μm column at a focused gradient of 50-100% B and a flow rate of 25 mL/min. Postpurification LC/MS data was obtained on a Shimadzu analytical LC/Micromass Platform LC (ESI+) at 220 nm using the following set of conditions: Phenomenex 10 μm C18, 4.6×30 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 2 minutes with a 1 minute hold at a rate of 5 mL/minute. To 0.15 mmol of methyl ester 3 was added 3 equivalents of Potassium trimethylsilanolate (TMSOK) and 3 mL of dry tetrahydrofuran. The mixture was stirred at room temperature overnight. After the overnight reaction, the crude product was evacuated to near dryness, taken up in ethyl acetate, and neutralized with 0.5 M HCl. After extraction the solvent was removed to give a near quantitative yield of carboxylic acid 4 (purity>90%) which was used without further purification. To 0.14 mmol of carboxylic acid 4 in 1 mL of dry tetrahydrofuran was added 3 equivalents of carbonyldiimidazole. The solution was heated for 2-3 hours at 70° C. in a 1 dram vial equipped with a screw cap. At this point, 1.4 equivalents of neat 1,8-Diazabicyclo[5.4.0]undec-7-ene (DBU) was dripped into the mixture followed by the addition of N,N-Dimethylsulfamide (as a solid). The vial was returned to the heating bath and shaken overnight. The crude product 5 was then evacuated to dryness and purified using a Shimadzu preparative HPLC to give dimethylamino sulfonylindole 5 as a yellow amorphous solid (35-50% yield).

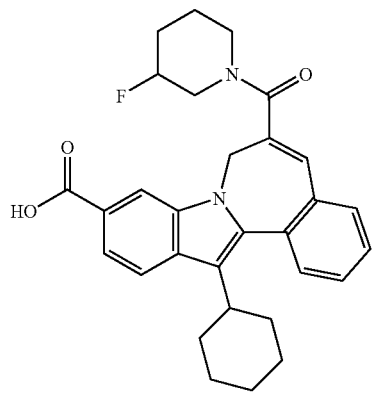

13-Cyclohexyl-6-((3-fluoropiperidin-1-yl)carbonyl)-7H-indolo[2,1-a][2]benzazepine-10-carboxylic acid. LC/MS: m/z 487.28, Rf 2.13 min., 90% purity.

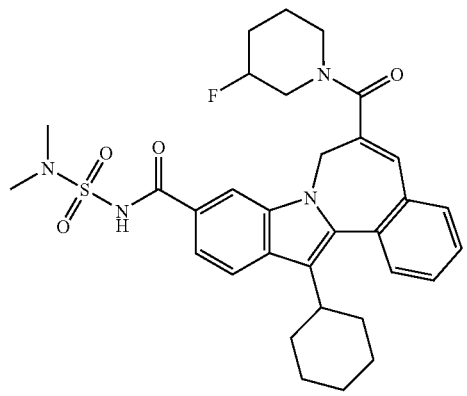

13-Cyclohexyl-N-((dimethylamino)sulfonyl)-6-((3-fluoropiperidin-1-yl)carbonyl)-7H-indolo[2,1-a][2]benzazepine-10-carboxamide. $^1$H NMR: (300 MHz, CHLOROFORM-D) δ ppm 1.21-1.44 (m, 6 H), 1.76 (m, 4 H), 1.94 (m, 1 H), 2.06 (s, 3 H), 2.83 (d, J=2.93 Hz, 2 H), 3.06 (m, 3 H), 3.30 (s, 6 H), 3.97 (s, 1 H), 4.48 (m, 1 H), 6.96 (s, 1 H), 7.38-7.44 (m, 1 H), 7.44-7.53 (m, 2 H) 7.54-7.61 (m, 1 H), 7.79 (d, J=8.42 Hz, 1 H), 7.91 (d, J=8.78 Hz, 1 H), 8.28 (s, 1 H). LC/MS: m/z 593.36, Rf 2.15 min., 100% purity.

Methyl 13-cyclohexyl-6-((3-fluoropiperidin-1-yl)carbonyl)-7H-indolo[2,1-a][2]benzazepine-10-carboxylate. LC/MS: m/z 501.28, Rf 2.24 min., 100% purity.

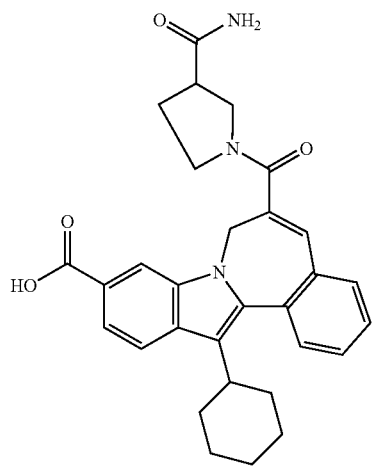

6-((3-carbamoylpyrrolidin-1-yl)carbonyl)-1 3-cyclohexyl-7H-indolo[2,1-a][2]benzazepine-10-carboxylic acid. LC/MS: m/z 498.25, Rf 2.05 min., 100% purity.

467

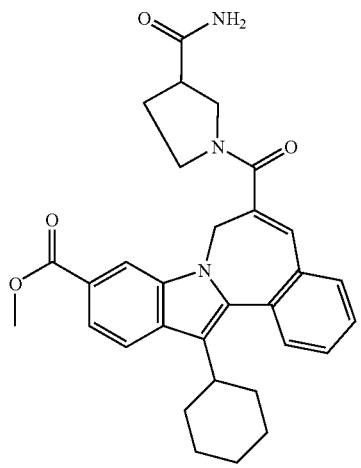

Methyl 6-((3-carbamoylpyrrolidin-1-yl)carbonyl)-13-cyclohexyl-7H-indolo[2,1-a][2]benzazepine-10-carboxylate. LC/MS: m/z 512.29, Rf 2.15 min., 100% purity.

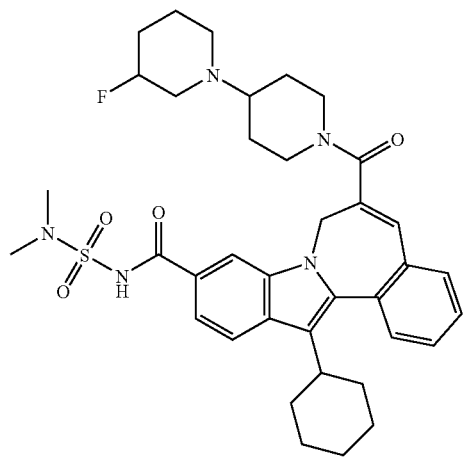

13-Cyclohexyl-N-((dimethylamino)sulfonyl)-6-((3-fluoro-1,4'-bipiperidin-1'-yl)carbonyl)-7H-indolo[2,1-a][2]benzazepine-10-carboxamide. $^1$H NMR: (300 MHz, CHLOROFORM-D) δ ppm 1.21 (m, 2 H), 1.30-1.44 (m, 4 H), 1.52 (m, 1 H), 1.66 (m, 1 H), 1.77 (m, 5 H), 2.04 (m, 6 H), 2.82 (m, 5 H) 2.89 (m, 1 H), 2.94-3.08 (m, 2 H), 3.12 (m, 1 H), 3.48 (m, 3 H), 3.68 (m, 1 H), 4.42 (m, 1 H), 4.57 (m, 1 H), 4.88 (m, 1 H), 5.05 (m, 1 H), 5.17 (m, 1 H), 6.84 (s, 1 H), 7.37-7.43 (m, 1 H), 7.45-7.52 (m, 2 H), 7.54-7.60 (m, 1 H), 7.76 (d, J=8.78 Hz, 1 H), 7.92 (d, J=8.78 Hz, 1 H), 8.39 (s, 1 H). LC/MS: m/z 676.43, Rf 1.86 min., 91.2% purity.

468

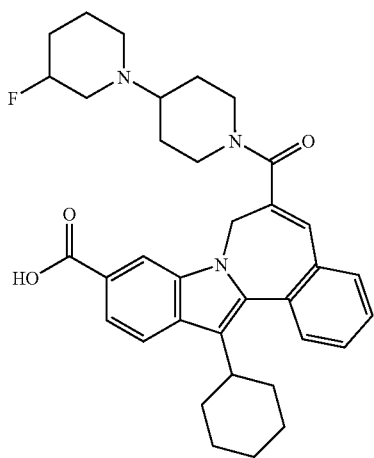

13-Cyclohexyl-N-((dimethylamino)sulfonyl)-6-((3-fluoro-1,4'-bipiperidin-1'-yl)carbonyl)-7H-indolo[2,1-a][2]benzazepine-10-carboxamide. LC/MS: m/z 570.40, Rf 1.86 min., 86.1% purity.

Methyl 13-cyclohexyl-6-((3-fluoro-1,4'-bipiperidin-1'-yl)carbonyl)-7H-indolo[2,1-a][2]benzazepine-10-carboxylate. LC/MS: m/z 584.39, Rf 1.88 min., 95.0% purity.

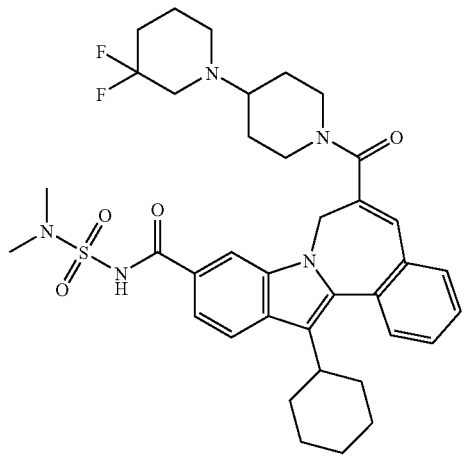

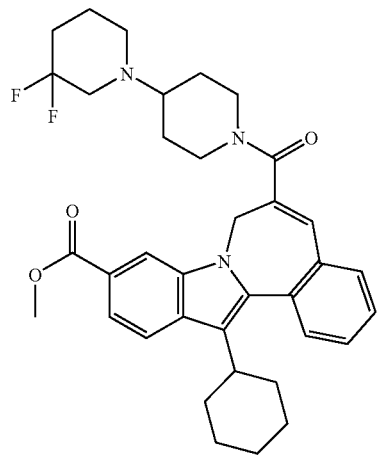

13-Cyclohexyl-6-((3,3-difluoro-1,4'-bipiperidin-1'-yl)carbonyl)-N-((dimethylamino)sulfonyl)-7H-indolo[2,1-a][2]benzazepine-10-carboxamide. ¹H NMR: (300 MHz, CHLOROFORM-D) δ ppm 1.21 (m, 2 H), 1.32-1.45 (m, 4 H), 1.78 (m, 3 H), 1.94-2.10 (m, 9 H), 2.55-2.68 (m, 2 H), 2.69 (m, 6 H), 2.85 (m, 3 H), 2.89 (m, 2 H), 2.97-3.15 (m, 2 H), 3.48 (m, 1 H), 4.44 (m, 1 H), 5.19 (m, 1H), 6.86 (s, 1 H) 7.42 (m, 1 H), 7.46-7.53 (m, 2 H), 7.55-7.60 (m, 1 H), 7.78 (d, J=8.42 Hz, 1 H), 7.94 (d, J=8.42 Hz, 1 H), 8.40 (s, 1 H). LC/MS: m/z 694.46, Rf 1.88 min., 96.5% purity.

Methyl 13-cyclohexyl-6-((3,3-difluoro-1,4'-bipiperidin-1'-yl)carbonyl)-7H-indolo[2,1-a][2]benzazepine-10-carboxylate. LC/MS: m/z 602.38, Rf 1.97 min., 100% purity.

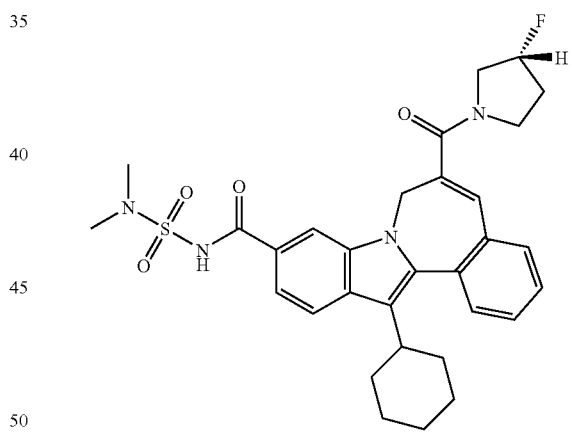

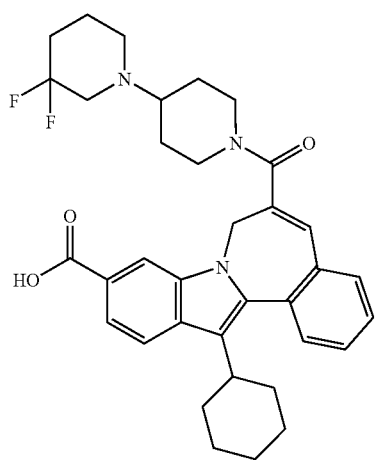

13-Cyclohexyl-6-((3,3-difluoro-1,4'-bipiperidin-1'-yl)carbonyl)-7H-indolo[2,1-a][2]benzazepine-10-carboxylic acid. LC/MS: m/z 588.43, Rf 1.88 min., 85.0% purity.

13-Cyclohexyl-N-((dimethylamino)sulfonyl)-6-(((3R)-3-fluoropyrrolidin-1-yl)carbonyl)-7H-indolo[2,1-a][2]benzazepine-10-carboxamide. ¹H NMR: (300 MHz, CHLOROFORM-D) δ ppm 1.27 (m, 1 H), 1.38 (m, 3H), 1.60 (m, 1 H), 1.77 (m, 3 H), 1.92 (m, 1 H), 2.08 (m, 4 H), 2.80-2.93 (m, 1 H), 3.49 (s, 1 H), 3.75 (m, 2 H) 3.86-4.00 (m, 2 H), 4.33 (m, 1 H), 5.18 (m, 4 H), 5.31 (m, 2 H), 7.11 (s, 1 H), 7.40-7.54 (m, 3 H), 7.56-7.63 (m, 1 H), 7.80 (d, J=8.78Hz, 1 H), 7.90 (d, J=8.78 Hz, 1 H), 8.36 (s, 1 H). LC/MS: m/z 579.26, Rf 2.13 min., 100% purity.

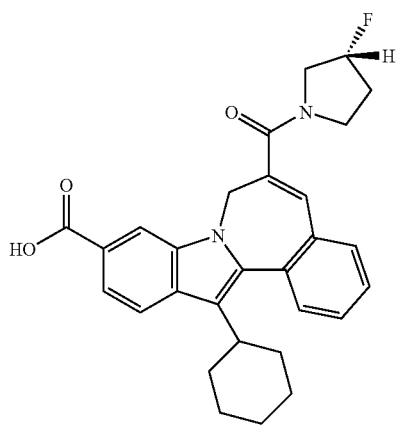

13-Cyclohexyl-6-(((3R)-3-fluoropyrrolidin-1-yl)carbonyl)-7H-indolo[2,1-a][2]benzazepine-10-carboxylic acid. LC/MS: m/z 473.28, Rf 2.11 min., 90.0% purity.

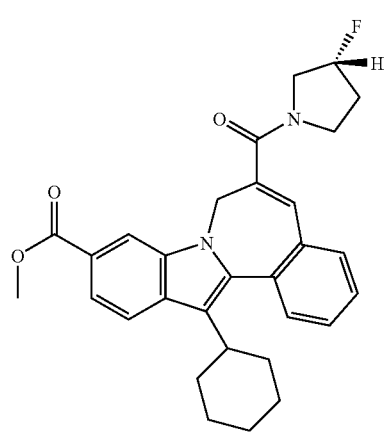

Methyl-13-cyclohexyl-6-(((3R)-3-fluoropyrrolidin-1-yl)carbonyl)-7H-indolo[2,1-a][2]benzazepine-10-carboxylate. LC/MS: m/z 487.25, Rf 2.22 min., 100% purity.

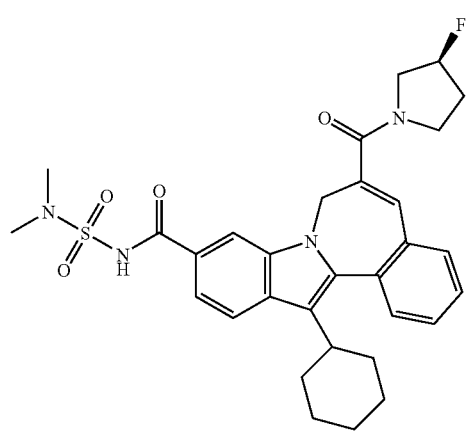

13-Cyclohexyl-N-((dimethylamino)sulfonyl)-6-(((3S)-3-fluoropyrrolidin-1-yl)carbonyl)-7H-indolo[2,1-a][2]benzazepine-10-carboxamide. ¹H NMR: (300 MHz, CHLOROFORM-D) δ ppm 1.26 (m, 1 H), 1.37 (m, 3H), 1.60 (m, 1 H), 1.77 (m, 3 H), 1.92 (m, 1 H), 2.08 (m, 4 H), 2.80-2.93 (m, 1 H), 3.49 (s, 1 H), 3.74 (m, 2 H) 3.86-4.00 (m, 2 H), 4.34 (m, 1 H), 4.57(m, 4 H), 5.33 (m, 2 H), 7.11 (s, 1 H), 7.40-7.61 (m, 4 H), 7.79 (d, J=8.42 Hz, 1 H), 7.91 (d, J=8.42 Hz, 1 H), 8.35 (s, 1 H). LC/MS: m/z 579.17, Rf 2.11 min., 97.2% purity.

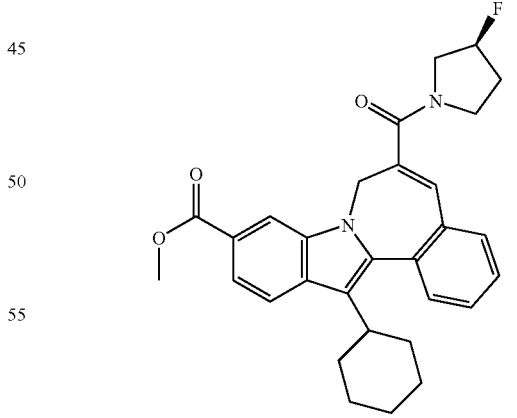

13-Cyclohexyl-6-(((3S)-3-fluoropyrrolidin-1-yl)carbonyl)-7H-indolo[2,1-a][2]benzazepine-10-carboxylic acid. LC/MS: m/z 473.26, Rf 2.12 min., 90.0% purity.

Methyl 13-cyclohexyl-6-(((3S)-3-fluoropyrrolidin-1-yl)carbonyl)-7H-indolo[2,1-a][2]benzazepine-10-carboxylate. LC/MS: m/z 487.24, Rf 2.21 min., 100% purity.

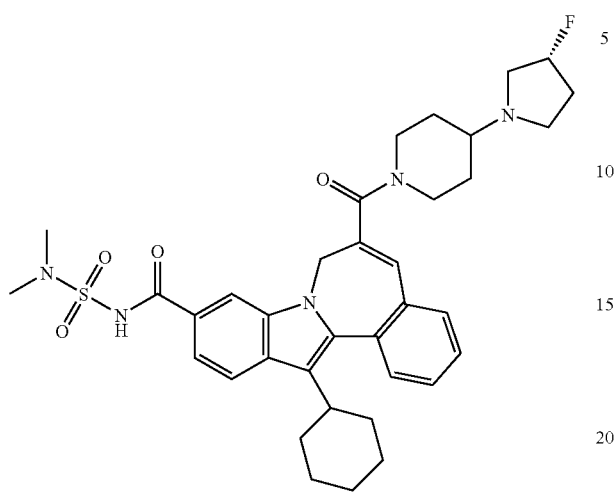

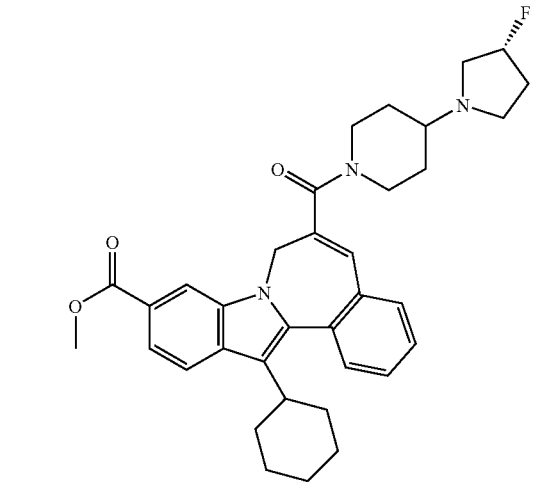

13-Cyclohexyl-N-((dimethylamino)sulfonyl)-6-((4-((3R)-3-fluoropyrrolidin-1-yl)piperidin-1-yl)carbonyl)-7H-indolo[2,1-a][2]benzazepine-10-carboxamide. $^1$H NMR: (300 MHz, CHLOROFORM-D) δ ppm 1.21 (m, 1 H), 1.35 (m, 4 H), 1.79 (m, 3 H), 2.01 (m, 4 H), 2.28-2.35 (m, 2 H), 2.65-2.79 (m, 8 H), 3.04 (m, 5 H), 3.11 (m, 3 H), 3.47 (m, 1 H), 3.83 (m, 1H), 4.43 (m, 1 H), 5.24 (m, 1 H), 5.40 (m, 1 H), 6.90 (s, 1 H), 7.44 (m, 1 H), 7.50 (m, 2 H), 7.57 (m, 1 H), 7.79 (d, J=8.78 Hz, 1 H), 7.93 (d, J=8.78 Hz, 1 H), 8.36 (s, 1 H). LC/MS: m/z 662.45, Rf 1.86 min., 100% purity.

Methyl 13-cyclohexyl-6-((4-((3R)-3-fluoropyrrolidin-1-yl)piperidin-1-yl)carbonyl)-7H-indolo[2,1-a][2]benzazepine-10-carboxylate. LC/MS: m/z 570.32, Rf 1.95 min., 100% purity.

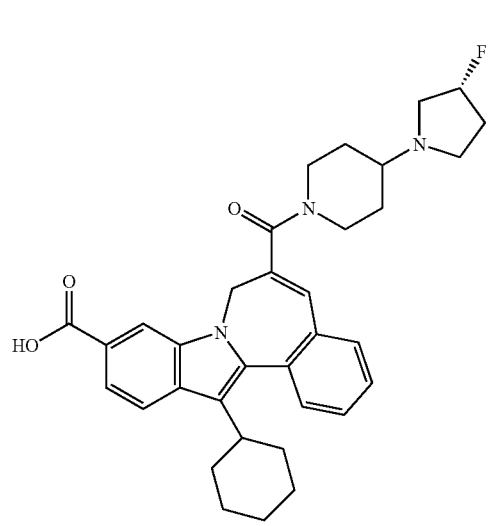

13-Cyclohexyl-6-((4-((3R) -3-fluoropyrrolidin-1-yl)piperidin-1-yl) carbonyl)-7H-indolo[2,1-a][2]benzazepine-10-carboxylic acid. LC/MS: m/z 556.38, Rf 1.86 min., 85.0% purity.

13-Cyclohexyl-N-((dimethylamino)sulfonyl)-6-((4-((3S)-3-fluoropyrrolidin-1-yl)piperidin-1-yl)carbonyl)-7H-indolo[2,1-a][2]benzazepine-10-carboxamide. $^1$H NMR: (300 MHz, CHLOROFORM-D) δ ppm 1.20 (m, 1 H), 1.27-1.43 (m, 4 H), 1.75 (m, 3 H), 2.05 (m, 3 H), 2.32 (m, 3 H), 2.55 (m, 8 H), 2.80 (m, 5 H), 3.11 (m, 3 H), 3.47 (m, 1 H), 3.83 (m, 1H), 4.32-4.44 (m, 1 H), 5.20 (m, 1 H), 5.39 (m, 1 H), 6.89 (s, 1 H), 7.39-7.58 (m, 4 H), 7.79 (d, J=8.78 Hz, 1 H), 7.91 (d, J=8.78 Hz, 1 H) 8.36 (s, 1 H). LC/MS: m/z 662.39, Rf 1.86 min., 100% purity.

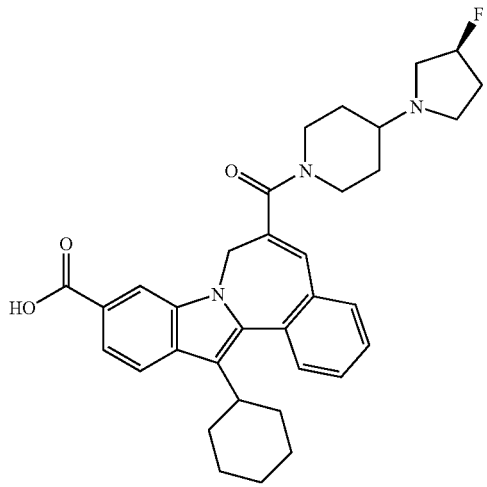

13-cyclohexyl-6-((4-((3S)-3-fluoropyrrolidin-1-yl)piperidin-1-yl)carbonyl)-7H-indolo[2,1-a][2]benzazepine-10-carboxylic acid. LC/MS: m/z 556.38, Rf 1.86 min., 85.0% purity.

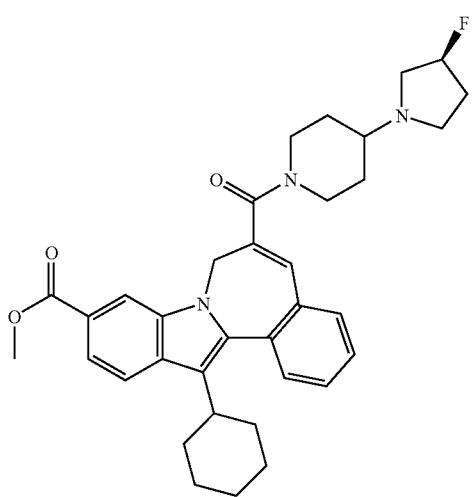

Methyl 13-cyclohexyl-6-((4-((3S)-3-fluoropyrrolidin-1-yl)piperidin-1-yl)carbonyl)-7H-indolo[2,1-a][2]benzazepine-10-carboxylate. LC/MS: m/z 570.32, Rf 1.94 min., 94.2% purity.

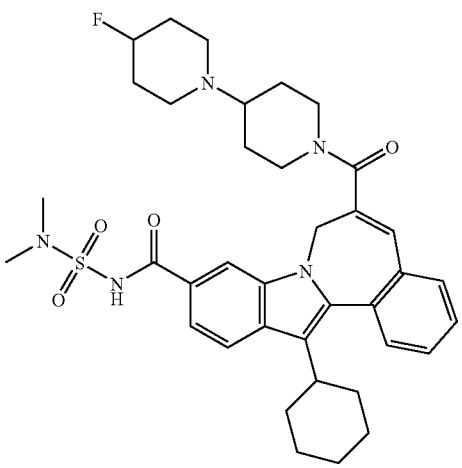

13-Cyclohexyl-N-((dimethylamino)sulfonyl)-6-((4-fluoro-1,4'-bipiperidin-1'-yl)carbonyl)-7H-indolo[2,1-a][2]benzazepine-10-carboxamide. $^1$H NMR: (300 MHz, CHLOROFORM-D) δ ppm 1.24 (m, 1 H), 1.37 (m, 3 H), 1.49 (m, 1 H), 1.67 (m, 1 H), 1.76 (m, 2 H), 1.95 (m, 1 H), 2.04 (m, 3 H), 2.13 (m, 4 H), 2.23 (m, 1 H), 2.31 (m, 1 H), 2.82 (m, 3 H), 2.89 (m, 2 H), 3.04-3.20 (m, 7 H), 3.34 (m, 2 H), 4.42 (m, 1 H), 4.59 (m, 1 H), 4.82 (m, 1 H), 5.00 (m, 1 H), 5.23 (m, 1 H), 6.84 (s, 1 H), 7.38-7.44 (m, 1 H), 7.50 (m, 2 H), 7.58 (m, 1 H), 7.79 (d, J=8.42 Hz, 1 H), 7.94 (d, J=8.42 Hz, 1 H), 8.43 (s, 1 H). LC/MS: m/z 676.46, Rf 1.87 min., 100% purity.

13-Cyclohexyl-6-((4-fluoro-1,4'-bipiperidin-1'-yl)carbonyl)-7H-indolo[2,1-a][2]benzazepine-10-carboxylic acid. LC/MS: m/z 570.42, Rf 1.87 min., 85.0% purity.

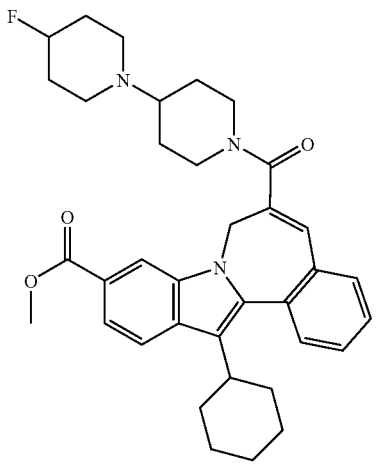

Methyl 13-cyclohexyl-6-((4-fluoro-1,4'-bipiperidin-1'yl)carbonyl)-7H-indolo[2,1-a][2]benzazepine-10-carboxylate. LC/MS: m/z 584.32, Rf 1.94 min., 100% purity.

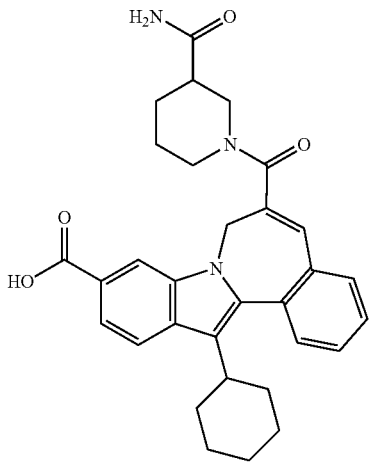

6-((3-carbamoylpiperidin-1-yl)carbonyl)-13-cyclohexyl-7H-indolo[2,1-a][2]benzazepine-10-carboxylic acid. LC/MS: m/z 512.31, Rf 2.05 min., 99.0% purity.

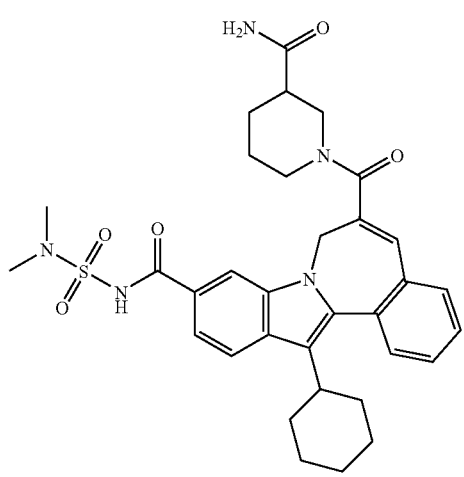

6-((3-Carbamoylpiperidin-1-yl)carbonyl)-13-cyclohexyl-N-((dimethylamino)sulfonyl)-7H-indolo[2,1-a][2]benzazepine-10-carboxamide. $^1$H NMR: (300 MHz, MeOD) δ ppm 1.19 (m, 3 H) 1.37-1.46 (m, 5 H), 1.65 (m, 2 H), 1.75 (m, 2 H), 1.86 (m, 2 H), 2.05 (m, 3 H), 2.83 (m, 2 H), 2.99 (m, 1 H), 3.28 (s, 6 H), 4.37 (m, 1 H), 5.11 (m, 1 H), 6.95 (s, 1 H), 7.47-7.53 (m, 3 H), 7.57-7.61 (m, 1 H), 7.69 (dd, J=8.42, 1.46 Hz, 1 H), 7.87 (d, J=8.42 Hz, 1 H), 8.18 (s, 1 H). LC/MS: m/z 618.36, Rf 2.05 min., 100% purity.

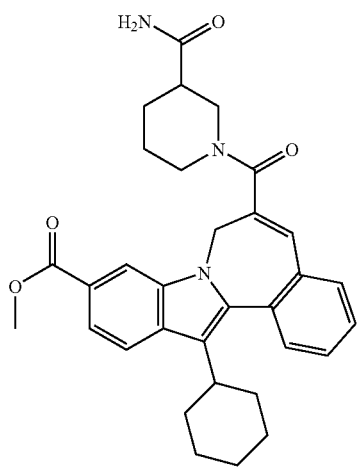

Methyl 6-((3-carbamoylpiperidin-1-yl)carbonyl)-13-cyclohexyl-7H-indolo[2, ]-a][2]benzazepine-10-carboxylate. LC/MS: m/z 526.26, Rf 2.17 min., 100% purity.

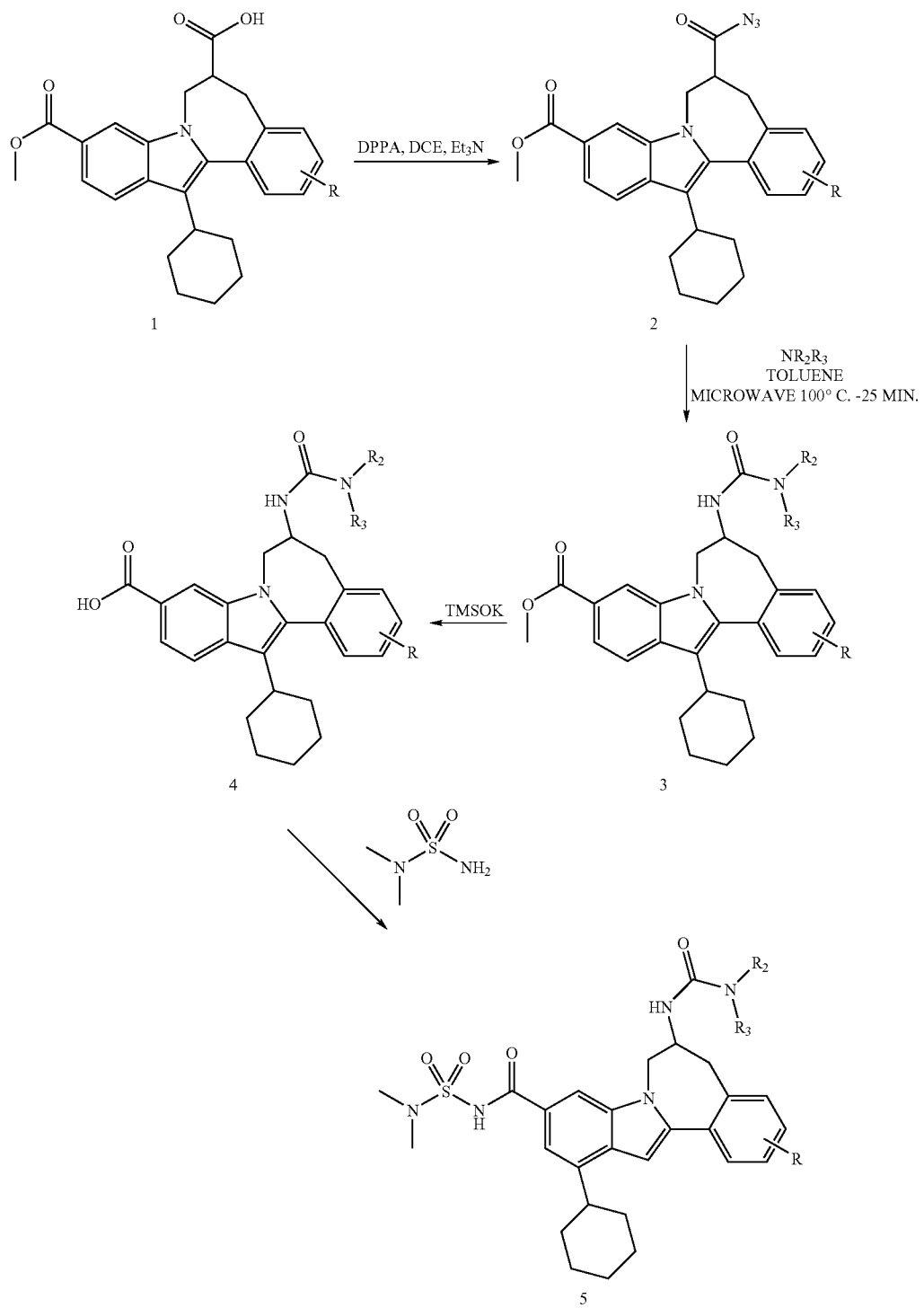

To 1.0 g of carboxylic acid 1 in a 100 mL round bottom flask equipped with a septa under nitrogen, was added 20 mL of dry dichloroethane (DCE). To this solution was then added 1.2 equivalents of Diphenylphosphorylazide (DPPA) in one portion followed by 3 equivalents of triethylamine. The solution was stirred overnight at room temperature. The reaction progress was followed by an analytical Shimadzu LC/MS. The crude mixture was passed through a 24 g SiliCycle/Isco silica gel cartridge with DCE to give acyl azide 2 as a light yellow foam after solvent evacuation (50-65% yield). The acyl azide was found to be stable at room temperature in a vacuum desiccator for up to one month. To 0.3 mmol of acyl azide 2 in 2 mL of dry toluene was added 1.2 equivalents of amine in a Biotage/Personal Chemistry microwave vial. The vial was capped and heated to 100° C. in a Biotage/Personal Chemistry Emrys Optomizer microwave for 25 minutes. The crude reaction mixture was then evacuated to near dryness, taken up in a 1:1 ethyl acetate/hexane mixture and purified by flash chromatography to yield urea 3 (50-55% yield). To 0.15 mmol of intermediate 3 was added 10 equivalents of potassium trimethylsilanolate (TMSOK) and 3 mL of dry tetrahydrofuran. The mixture was stirred at room temperature overnight. After the overnight treatment, the crude product was evacuated to near dryness, taken up in ethyl acetate, and neutralized with 0.5 M HCl. After extraction the solvent was removed to give a near quantitative yield of carboxylic acid 4 (purity >90%) which was used without further purification. To 0.14 mmol of carboxylic acid 4 in 1 mL of dry tetrahydrofuran was added 3 equivalents of carbonyldiimidazole. The solution was heated for 2-3 hours at 70° C. in a one dram vial equipped with a screw cap. At this point, 1.4 equivalents of neat 1,8-Diazabicyclo[5.4.0]undec-7-ene (DBU) was dripped into the mixture followed by the addition of N,N-Dimethylsulfamide (as a solid). The vial was returned to the heating bath and shaken overnight. The crude reaction mixture was then evacuated to dryness and purified using a Shimadzu preparative HPLC to give dimethylamino sulfamide 5 as a yellow amorphous solid (35-50% yield).

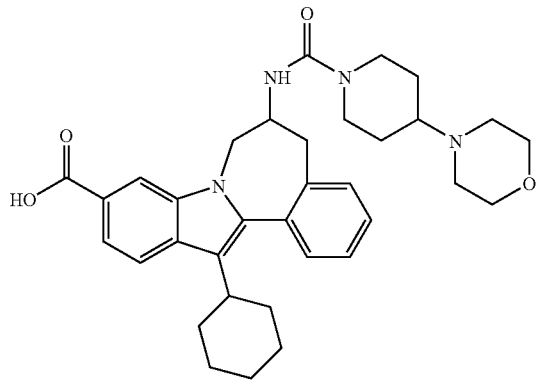

13-Cyclohexyl-6-(((4-morpholin-4-ylpiperidin-1-yl)carbonyl)amino)-6,7-dihydro-5H-indolo[2,1-a][2]benzazepine-10-carboxylic acid. ¹H NMR: (500 MHz, BENZENE-D6) δ ppm 1.07-1.15 (m, 1 H), 1.15-1.23 (m, 1 H), 1.24-1.32 (m, 1 H), 1.41 (m, 1 H), 1.57 (m, 2 H), 1.65 (m, 3 H), 1.86 (m, 1 H), 2.06-2.13 (m, 4 H), 2.24 (m, 2 H), 2.60 (m, 1 H), 2.69 (m, 2 H), 2.84 (m, 1 H), 3.09 (m, 1 H), 3.21 (m, 1 H), 3.29-3.37 (m, 1 H), 3.41 (m, 2 H), 3.57 (m, 2 H), 3.69 (m, 1 H), 3.86 (m, 1 H), 4.03 (m, 1 H), 4.22 (m,1 H), 4.35 (m, 1 H), 4.64 (m, 1H), 7.01 (d, J=7.02 Hz, 1 H), 7.09-7.13 (m, 1 H), 7.20 (m, 1 H), 7.44 (d, J=7.63 Hz, 1 H), 7.97 (d, J=8.55 Hz, 1 H), 8.24 (d, J=8.24 Hz, 1 H), 8.29 (s, 1 H). LC/MS: m/z 571.30, Rf 1.95 min., 98.0% purity.

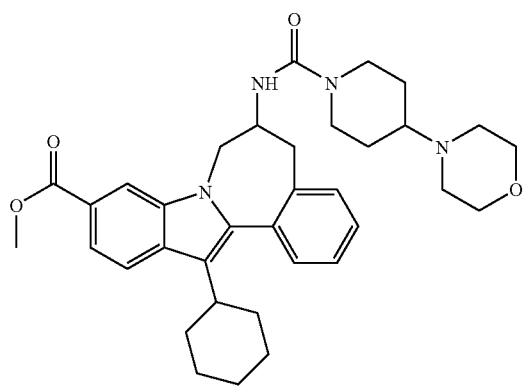

Methyl 13-cyclohexyl-6-(((4-morpholin-4-ylpiperidin-1-yl)carbonyl)amino)-6,7-dihydro-5H-indolo[2,1-a][2]benzazepine-10-carboxylate. ¹H NMR: (500 MHz, CHLOROFORM-D) δ ppm 1.38 (m, 2 H), 1.69 (m, 1 H), 1.75-1.81 (m, 3 H), 1.83 (m, 2 H), 2.05-2.12 (m, 1 H), 2.19-2.26 (m, 1 H), 2.72 (m, 1 H), 2.92-2.99 (m, 4 H), 3.15 (m, 2 H), 3.34-3.43 (m, 3 H), 3.52 (m, 1 H), 3.75-3.82 (m, 2 H), 3.90 (s, 3 H), 4.02 (d, J=2.44 Hz, 4 H), 4.32 (m, 1 H), 4.41-4.49 (m, 2 H), 4.60 (m, 1 H), 7.35-7.45 (m, 4 H), 7.72 (dd, J=8.55, 1.53 Hz, 1 H), 7.88 (d, J=8.55 Hz, 1 H), 8.01 (s, 1 H). LC/MS: m/z 585.36, Rf 1.98 min., 94.8% purity.

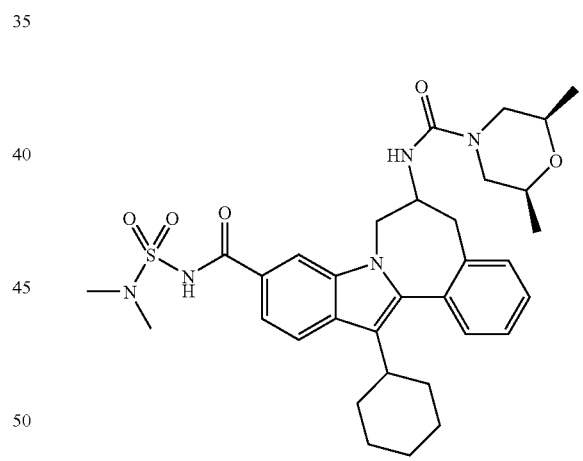

13-Cyclohexyl-N-((dimethylamino)sulfonyl)-6-((((2R,6S)-2,6-dimethylmorpholin-4-yl)carbonyl)amino)-6,7-dihydro-5H-indolo[2,-a][2]benzazepine-10-carboxamide. ¹H NMR: (500 MHz, CHLOROFORM-D) δ ppm 1.04 (d, J=6.41 Hz, 3 H), 1.10 (d, J=6.41 Hz, 3 H), 1.15 (m,1 H), 1.27 (d,1 H), 1.39-1.49 (m, 2 H), 1.63 (d, J=11.60 Hz, 1 H), 1.78 (m, 2 H), 1.89-1.99 (m, 1 H), 2.01-2.10 (m, 3 H), 2.32-2.40 )m, 1 H), 2.43-2.52 (m, 2 H), 2.83-2.92 (m, 1 H), 3.00 (s, 6 H), 3.46 (m, 1 H), 3.62-3.71 (m, 3 H) 3.92 (m,1 H), 4.39 (m, 1 H), 4.59 (m,1 H), 7.38-7.46 (m, 4 H), 7.54-7.61 (m, 1 H), 7.89-7.92 (m, 2 H). LC/MS: m/z 622.25, Rf2.12 min., 100% purity.

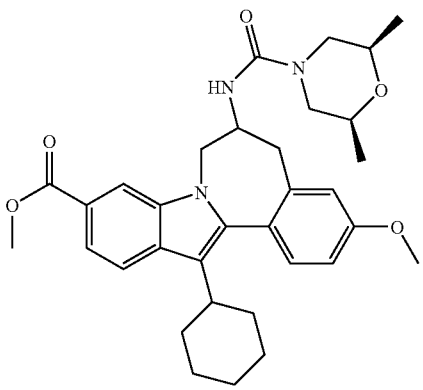

Methyl 13-cyclohexyl-6-((((2R,6S)-2,6-dimethylmorpholin-4-yl)carbonyl)amino)-3-methoxy-6,7-dihydro-5H-indolo[2,1-a][2]benzazepine-10-carboxylate. $^1$H NMR: (500 MHz, CHLOROFORM-D) δ ppm 1.11 (d, J=6.10 Hz, 3 H), 1.15 (d, J=6.10 Hz, 3 H), 1.19-1.29 (m, 3 H), 1.36-1.44 (m, 1 H), 1.69 (m,1 H), 1.78 (m, 2 H), 1.92-2.06 (m, 2 H), 2.19 (t, J=1.6 Hz, 1 H), 2.48-2.56 (m, 2 H), 2.96 (m, 2 H), 3.50 (d, J=12.82 Hz, 1 H), 3.54-3.63 (m, 2 H), 3.71 (d, J=12.21 Hz, 1 H), 3.81 (dd, J=15.11, 3.81 Hz, 1 H), 3.87 (s, 3 H), 3.91 (s, 3 H), 4.36 (d, J=8.24 Hz, 1 H), 4.43 (d, J=14.95 Hz, 1 H), 4.60-4.68 (m, 1 H), 6.91-6.98 (m, 2 H), 7.37 (d, J=8.24 Hz, 1 H), 7.76 (dd, J=8.55, 1.53 Hz, 1 H), 7.87 (d, J=8.24 Hz, 1 H), 8.01 (s, 1 H). LC/MS: m/z 560.33, Rf 2.27 min., 100% purity.

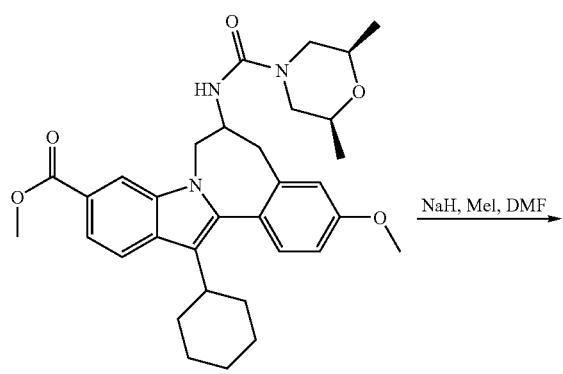

NaH, MeI, DMF

To 64.8 mgs (0.11 mmol) of urea was added 4 mL of dry N,N-dimethylformamide and 1.2 equivalents (3.6 mgs) of 95% NaH under nitrogen in a 25 mL round bottom flask equipped with a septa. To this mixture was then added 2.0 equivalents (0.22 mmol, 13.6 µL) of methyl iodide. The mixture was stirred overnight at room temperature at which point another 2.0 equivalents of methyl iodide was added. The mixture was stirred for an additional 48 hours. The product was purified by flash chromatography (20-50% ethyl acetate in hexane) to give 50.5 mgs (80.0% yield) of the desired N-methyl urea (Intermediate A) as an amorphous yellow solid. $^1$H NMR: (500 MHz, CHLOROFORM-D) δ ppm 1.20 (m, 6 H), 1.24-1.31 (m, 1 H), 1.36-1.44 (m, 2 H), 1.62 (d, J=12.51 Hz, 0.2 H), 1.69 (d, J=12.51 Hz, 0.8 H), 1.78 (m, 2 H), 1.91-2.10 (m, 4 H), 2.63-2.71 (m, 4 H), 2.74 (dd, J=12.51, 5.49 Hz, 1 H), 2.82-3.04 (m, 3 H), 3.50-3.59 (m, 2 H), 3.66 (m, 2 H), 3.88 (s, 3 H), 3.92-3.97 (m, 3 H), 4.00 (m,1 H), 4.43-4.50 (m, 1 H), 4.57 (m, 0.3 H), 4.63 (m, 0.7 H), 6.92-6.99 (m, 2 H), 7.32 (d, J=8.24 Hz, 0.8 H), 7.36 (d, J=8.24 Hz, 0.2 H), 7.75 (d, J=8.55 Hz, 1 H), 7.86 (m, 1 H), 8.03 (s, 0.7 H), 8.09 (s, 0.3 H). LC/MS: m/z 574.13, Rf 2.42 min., 100% purity.

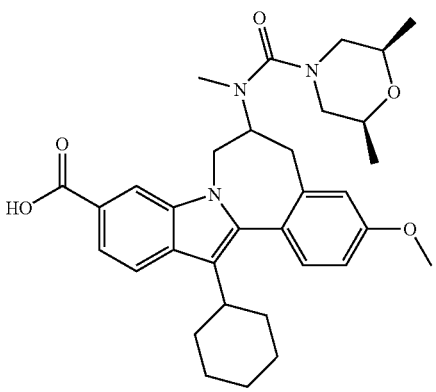

13-Cyclohexyl-6-((((2R,6S)-2,6-dimethylmorpholin-4-yl)carbonyl)(methyl)amino)-3-methoxy-6,7-dihydro-5H-indolo[2,1-a][2]benzazepine-10-carboxylic acid. $^1$H NMR: (500 MHz, CHLOROFORM-D) δ ppm 1.25 (m, 6 H), 1.27-1.47 (m, 1 H), 1.36-1.44 (m, 2 H), 1.60-1.78 (m, 3 H), 2.04 (m, 4 H), 2.58-2.94 (m, 8 H), 3.49-3.70 (m, 4 H), 3.88 (s, 3 H), 4.00 (m,1 H), 4.50-4.68 (m, 2 H), 6.97 (m, 2 H), 7.34 (m,1 H), 7.88 (m, 2 H), 8.15 (s, 0.7 H), 8.23 (s, 0.3 H). LC/MS: m/z 560.31, Rf 2.27 min., 91.8% purity.

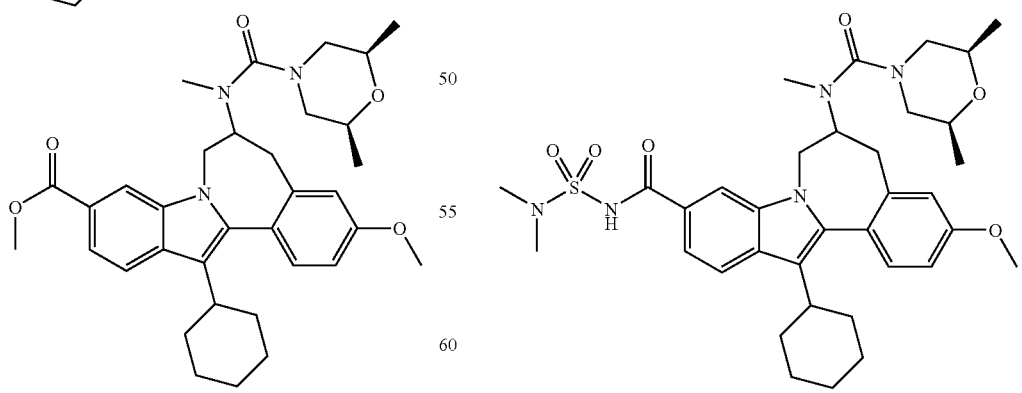

13-Cyclohexyl-N-((dimethylamino)sulfonyl)-6-((((2R,6S)-2,6-dimethylmorpholin-4-yl)carbonyl)(methyl)amino)-3-methoxy-6,7-dihydro-5H-indolo[2,1-a][2]benzazepine-10-carboxamide. $^1$H NMR: (500 MHz, CHLOROFORM-D)

δ ppm 1.19 (m, 6 H), 1.25 (m, 1 H), 1.36-1.42 (m, 2 H), 1.58-1.71 (m, 1 H), 1.79 (m, 2 H), 1.91-2.05 (m, 4 H), 2.57-2.64 (m, 3 H), 2.67 (s, 3H), 2.74 (m, 1 H), 2.82-3.99 (m, 3 H), 3.02-3.14 (m, 6 H), 3.50 (m, 2 H), 3.66 (m, 2 H), 3.88 (s, 3 H), 3.97-4.12 (m,2 H), 4.47-4.62 (m, 2 H), 6.96 (m, 2 H), 7.31 (d, J=8.55 Hz, 0.7 H), 7.36 (d, J=8.55 Hz, 0.3 H), 7.44 (d, J=8.55 Hz, 0.7 H), 7.57 (d, J=8.55 Hz, 0.3 H), 7.89 (m, 1 H), 7.99 (s, 0.7 H), 8.04 (s, 0.3 H). LC/MS: m/z 666.33, Rf 2.20 min., 97.0% purity.

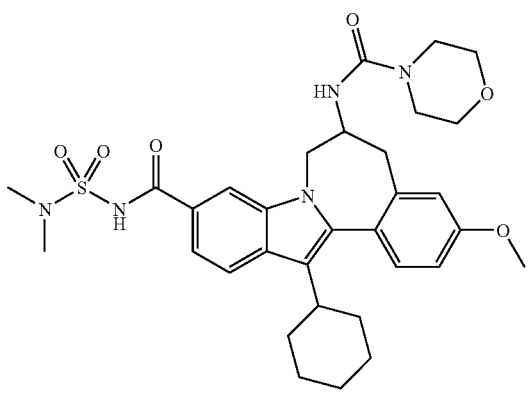

13-Cyclohexyl-N-((dimethylamino)sulfonyl)-3-methoxy-6-((morpholin-4-ylcarbonyl)amino)-6,7-dihydro-5H-indolo[2,1-a][2]benzazepine-10-carboxamide. $^1$H NMR: (500 MHz, CHLOROFORM-D) δ ppm 1.37 (m, 1 H), 1.36-1.44 (m, 2 H), 1.67 (d, J=12.51 Hz, 1 H), 1.79 (m, 2 H), 1.93 (d, J=12.82 Hz, 2 H), 1.96-2.05 (m, 3 H), 2.04 (m, 1 H), 2.97 (m, 1 H), 3.04 (s, 6 H), 3.19-3.28 (m, 2 H), 3.33-3.40 (m, 3 H), 3.62-3.71 (m, 4 H), 3.84 (m, 1 H), 3.88 (m, 3 H), 4.44 (d, J=7.32 Hz, 1 H), 4.51 (d, J=14.95 Hz, 1 H), 4.55-4.63 (m, 1 H), 6.88-6.98 (m, 2 H), 7.35-7.41 (m, 1 H), 7.54 (dd, J=8.39, 1.37 Hz, 0.8 H), 7.60 (dd, J=8.39, 1.37 Hz, 0.2 H), 7.88 (m, 1 H), 7.98 (s, 0.8 H), 8.11 (s, 0.2 H). LC/MS: m/z 624.37, Rf 2.08 min., 100% purity.

(6R)-13-Cyclohexyl-6-((morpholin-4-ylcarbonyl)amino)-6, 7-dihydro-5H-indolo[2,1a][2]benzazepine-10-carboxylic acid and (6S)-13-Cyclohexyl-6-((morpholin-4-ylcarbonyl)amino)-6,7-dihydro-5H-indolo[2, 1a][2]benzazepine-10-carboxylic acid. The chiral separation was accomplished using preparative chiral supercritical fluid chromatography (SFC) employing a Chiralpak AS-H, 30×250 mm, 5 μm column. The mixture of enantiomers was taken up in methanol (10 mg/2 mL), injected onto the column and eluted with 85% CO$_2$ and 15% methanol with 0.1% trifluoroacetic acid buffer at a flow rate of 70 mL/minute. The temperature was maintained at 35° C. and the pressure at 150 bar throughout the experiment and the elution of the products was monitored by a UV detector at a wave length of 210 nm. Isomer A eluted 9.5-13.0 minutes. Isomer B eluted 27.5-32.0 minutes. The samples were concentrated en-vacuo to give enantiomerically pure ivory colored amorphous solids. Isomer A $^1$H NMR: (500 MHz, MeOD) δ ppm 1.20-1.30 (m, 2 H), 1.40-1.45 (m, 2 H), 1.59 (m, 1 H), 1.72-1.80 (m, 2 H), 1.91 (d, J=10.68 Hz, 1 H), 1.98-2.04 (m, 2 H), 2.05-2.11 (m, 1 H), 2.41-2.48 (m, 1 H), 2.86 (dd, J=13.28, 6.87 Hz, 1 H), 2.96 (m, 1 H), 3.34-3.42 (m, 3 H), 3.56-3.65 (m, 5 H), 4.37 (m, 1 H), 4.55 (d, J=14.65 Hz, 1 H), 7.37-7.46 (m, 4 H), 7.67 (dd, J=8.39, 1.37 Hz, 1 H), 7.84 (d, J=8.39 Hz, 1 H), 7.99 (s, 1 H). LC/MS: m/z 488.22, Rf2.14 min., 100% purity. Isomer B $^1$H NMR: (500 MHz, MeOD) δ ppm 1.20-1.29 (m, 2 H), 1.37-1.45 (m, 2 H), 1.60 (d, J=11.60 Hz, 1 H), 1.76 (m, 2 H), 1.91 (d, J=11.29 Hz, 1 H), 1.99-2.04 (m, 2 H), 2.07 (m, 1 H), 2.40-2.47 (m, 1 H), 2.86 (dd, J=13.12, 6.71 Hz, 1 H), 2.92-3.01 (m, 1 H), 3.34-3.42 (m, 3 H), 3.56-3.65 (m, 5 H), 4.34-4.40 (m, 1 H), 4.56 (d, J=14.95 Hz, 1 H), 7.36-7.46 (m, 4 H), 7.67 (dd, J=8.39, 1.37 Hz, 1 H), 7.84 (d, J=8.39 Hz, 1 H) 7.99 (s, 1 H). LC/MS: m/z 488.22, Rf 2.14 min., 100% purity.

(6R)-13-cyclohexyl-N-((dimethylamino)sulfonyl)-6-((morpholin-4-ylcarbonyl)amino)-6,7-dihydro-5H-indolo[2,1-a][2]benzazepine-10-carboxamide and (6S)-13-cyclohexyl-N-((dimethylamino)sulfonyl)-6-((morpholin-4-ylcarbonyl)amino)-6,7-dihydro-5H-indolo[2,1-a][2]benzazepine-10-carboxamide. The chiral separation was accomplished using preparative chiral supercritical fluid chromatography (SFC) employing a Chiralpak OD-H, 30×250 mm, 5 μm column. The mixture of enantiomers was taken up in methanol (10 mg/2 mL), injected onto the column and eluted with 80% CO$_2$ and 20% methanol with 0.1% trifluoroacetic acid buffer at a flow rate of 70 mL/minute. The temperature was maintained at 35° C. and the pressure at 150 bar throughout the experiment and the elution of the products was monitored by a UV detector at a wave length of 210 nm. Isomer A eluted at 10.7-12.5 minutes. Isomer B eluted at 15.8-19.5 minutes. The samples were concentrated en-vacuo to give enantiomerically pure yellow amorphous solids.

Isomer A $^1$H NMR: (500 MHz, MeOD) δ ppm 1.23-1.32 (m, 1 H), 1.45 (m, 2 H), 1.61 (m, 1 H), 1.78 (m, 2 H), 1.92-2.03 (m, 1 H), 2.03-2.12 (m, 3 H), 2.42-2.49 (m, 1 H), 2.88 (ddd, J=13.35, 7.02,6.79 Hz, 1 H), 2.96 (m, 1 H), 3.00 (s, 6 H), 3.36-3.44 (m, 3 H), 3.54-3.61 (m, 2 H), 3.61-3.69 (m, 3 H), 4.39 (m, 1 H), 4.61 (d, J=14.95 Hz, 1 H), 4.83-4.88 (m, 1 H), 7.39-7.48 (m, 4 H), 7.58 (dd, J=8.55, 1.53 Hz, 1 H), 7.90 (d, J=8.55, 1 H), 7.94 (s, 1 H). LC/MS: m/z 594.19, Rf2.06 min., 100% purity. Isomer B $^1$H NMR: (500 MHz, MeOD) δ ppm 1.24-1.33 (m, 1 H), 1.45 (m, 2 H), 1.61 (m, 1 H), 1.74-1.82 (m, 2 H), 1.92 (m, 1 H), 2.03-2.12 (m, 3 H), 2.42-2.49 (m, 1 H), 2.88 (ddd, J=13.58, 7.02, 6.87 Hz, 1 H), 3.00 (m, 7 H), 3.36-3.44 (m, 3 H), 3.54-3.61 (m, 2 H), 3.61-3.69 (m, 3 H), 4.39 (m, 1 H), 4.61 (d, J=14.95 Hz, 1 H), 4.83-4.88 (m, 1 H), 7.41-7.47 (m, 4 H), 7.57 (dd, J=8.55, 1.53 Hz, 1 H), 7.89 (d, J=8.55, 1 H), 7.94 (s, 1 H). LC/MS: m/z 594.21, Rf2.06 min., 100% purity.

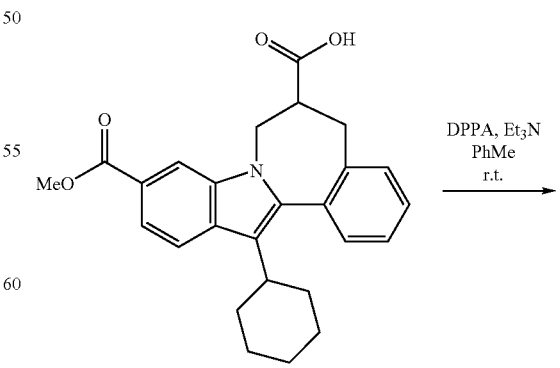

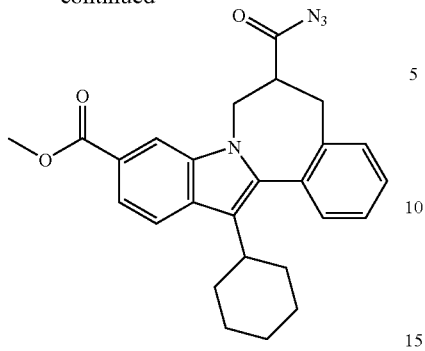

5H-indolo[2,1-a][2]benzazepine-10-carboxylic acid, 6-(azidocarbonyl)-13-cyclohexyl-6,7-dihydro-, methyl ester. To a mixture of the acid (5H-indolo[2,1-a][2]benzazepine-6,10-dicarboxylic acid, 13-cyclohexyl-6,7-dihydro-, 10-methyl ester) (989.2 mg, 2.37 mmol) in PhMe (15 ml) at r.t. under $N_2$ was added triethylamine (304 mg, 3.0 mmol), followed by diphenylphosphoryl azide (DPPA) (845 mg, 3.07 mmol). The mixture was stirred at r.t. for 3.5 hr. The volatiles were then evaporated and the residue purified by Biotage flash chromatography (gradient elution, 0 to 30% EtOAc/Hexane) to gave the acyl azide (5H-indolo[2,1-a][2]benzazepine-10-carboxylic acid, 6-(azidocarbonyl)-13-cyclohexyl-6,7-dihydro-, methyl ester) (532 mg); Analytical HPLC method: Solvent A=10% MeOH 90% $H_2O$ 0.1% TFA, Solvent B=90% MeOH 10% $H_2O$ 0.1% TFA, Start % B=0, Final % B=100, Gradient time=2 min, Flow Rate=5 ml/min, Column: Xterra MS C18 S7 3.0×50 mm; LC/MS: (ES+) m/z $(M+H)^+$=443.16, HPLC $R_t$=2.197 min.

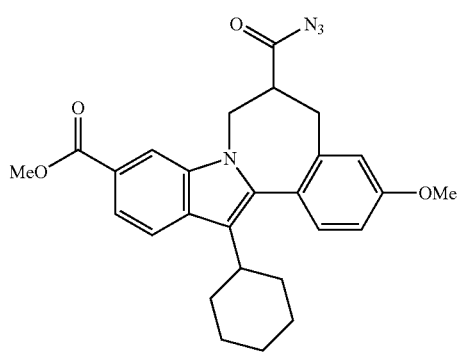

5H-indolo[2,1-a][2]benzazepine-10-carboxylic acid, 6-(azidocarbonyl)-13-cyclohexyl-6,7-dihydro-3-methoxy-, methyl ester. This methoxyphenyl analog (5H-indolo[2,1-a][2]benzazepine-10-carboxylic acid, 6-(azidocarbonyl)-13-cyclohexyl-6,7-dihydro-3-methoxy-, methyl ester) was prepared in a similar manner; Analytical HPLC method: Solvent A=10% MeOH 90% $H_2O$ 0.1% TFA, Solvent B=90% MeOH 10% $H_2O$ 0.1% TFA, Start % B=0, Final % B=100, Gradient time=2 min, Flow Rate=5 ml/min, Column: Xterra MS C18 S7 3.0×50 mm; LC/MS: (ES+) m/z $(M+H)^+$=473.22, HPLC $R_t$=2.183 min.

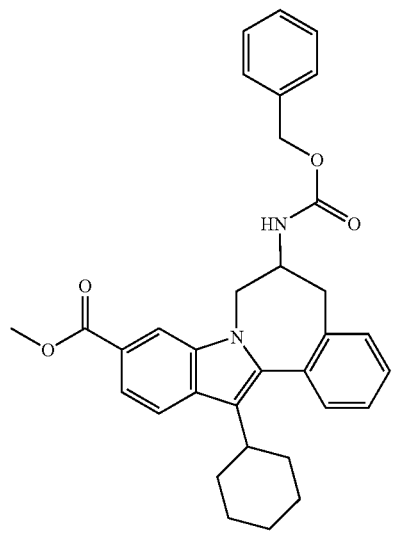

5H-indolo[2,1-a][2]benzazepine-10-carboxylic acid, 13-cyclohexyl-6,7-dihydro-6-[[(phenylmethoxy)carbonyl]amino]-, methyl ester. To a mixture of the acyl azide (5H-indolo[2,1-a][2]benzazepine-10-carboxylic acid, 6-(azidocarbonyl)-13-cyclohexyl-6,7-dihydro-, methyl ester) (57.4 mg, 0.13 mM) under $N_2$ at r.t. in a microwave reaction tube was added a solution of benzyl alcohol (28 mg, 0.26 mmol) in PhMe (1 ml). The reaction mixture was then placed under microwave irradiation in an Emrys Optimizer (Personal Chemistry) at 100° C. and with the absorption level set to normal for 15 min. More benzyl alcohol (0.28 mg, 2.6 mmol) was then added to the reaction mixture, which was then placed under microwave irradiation under the same conditions for 45 min. The volatiles were then evaporated and the residue purified by Biotage flash chromatography (gradient elution, 0 to 20% EtOAc/Hexane) to gave the carbamate (5H-indolo[2,1-a][2]benzazepine-10-carboxylic acid, 13-cyclohexyl-6,7-dihydro-6-[[(phenylmethoxy)carbonyl]amino]-, methyl ester); Analytical HPLC method: Solvent A=10% MeOH 90% $H_2O$ 0.1% TFA, Solvent B=90% MeOH 10% $H_2O$ 0.1% TFA, Start % B=0, Final % B=100, Gradient time=2 min, Flow Rate=5 ml/min, Column: Xterra MS C18 S7 3.0×50 mm; LC/MS: (ES+) m/z $(M+H)^+$=523.18, HPLC $R_t$=2.185 min.

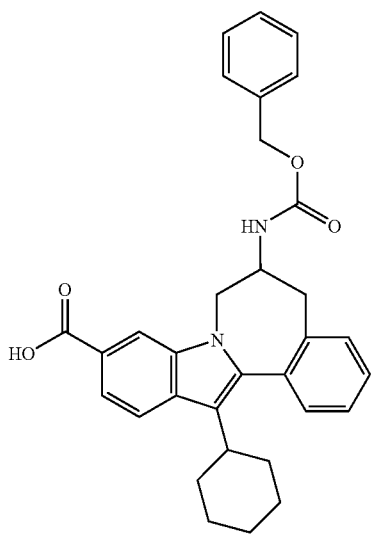

13-cyclohexyl-6,7-dihydro-6-[[(phenylmethoxy)carbonyl]amino]-5H-indolo[2,1-a][2]benzazepine-10-carboxylic acid. (5H-indolo[2,1-a][2]benzazepine-10-carboxylic acid, 13-cyclohexyl-6,7-dihydro-6-[[(phenylmethoxy)carbonyl]amino]-) was prepared from (5H-indolo[2,1-a][2]benzazepine-10-carboxylic acid, 13-cyclohexyl-6,7-dihydro-6-[[(phenylmethoxy)carbonyl]amino]-, methyl ester) using TMSOK in THF in a similar manner as described before; Analytical HPLC method: Solvent A=10% MeOH 90% $H_2O$ 0.1% TFA, Solvent B=90% MeOH 10% $H_2O$ 0.1% TFA, Start % B=0, Final % B=100, Gradient time=2 min, Flow Rate=5 ml/min, Column: Xterra MS C18 S7 3.0×50 mm; LC/MS: (ES+) m/z $(M+H)^+$=509.21, HPLC $R_t$=2.082 min.

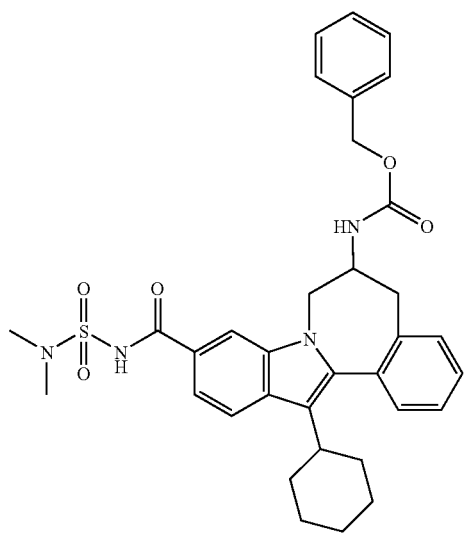

[13-cyclohexyl-10-[[[(dimethylamino)sulfonyl]amino]carbonyl]-6,7-dihydro-5H-indolo[2,1-a][2]benzazepin-6-yl]-carbamic acid, phenylmethyl ester. Carbamic acid, [13-cyclohexyl-10-[[[(dimethylamino)sulfonyl]amino]carbonyl]-6,7-dihydro-5H-indolo[2,1-a][2]benzazepin-6-yl]-, phenylmethyl ester) was prepared from (5H-indolo[2,1-a][2]benzazepine-10-carboxylic acid, 13-cyclohexyl-6,7-dihydro-6-[[(phenylmethoxy)carbonyl]amino]-) using 1,1'-carbonyldiimidazole (CDI) as a coupling reagent in a similar manner as described before; Analytical HPLC method: Solvent A=10% MeOH 90% $H_2O$ 0.1% TFA, Solvent B 90% MeOH 10% $H_2O$ 0.1% TFA, Start % B=0, Final % B=100, Gradient time=2 min, Flow Rate=5 ml/min, Column: Xterra MS C18 S7 3.0×50 mm; LC/MS: (ES+) m/z $(M+H)^+$=615.20, HPLC $R_t$=2.048 min.

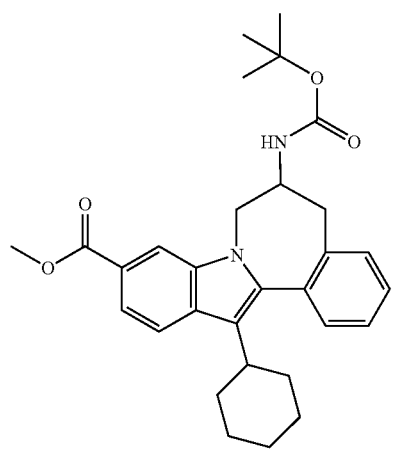

13-cyclohexyl-6-[[(1,1-dimethylethoxy)carbonyl]amino]-6,7-dihydro-5H-indolo[2,1-a][2]benzazepine-10-carboxylic acid, methyl ester. To a mixture of the acyl azide (5H-indolo[2,1-a][2]benzazepine-10-carboxylic acid, 6-(azidocarbonyl)-13-cyclohexyl-6,7-dihydro-, methyl ester) (532 mg, 1.2 mmol) under $N_2$ at r.t. in a microwave reaction tube was added tert-butyl alcohol (10 ml). The reaction mixture was then placed under microwave irradiation in an Emrys Optimizer (Personal Chemistry) at 100° C. and with the absorption level set to normal for 15 min. The mixture was then added with excess water. The white precipitates were filtered, washed with water twice and purified by Biotage flash chromatography (gradient elution, 0 to 40% EtOAc/Hexane) to gave the carbamate (5H-indolo[2,1-a][2]benzazepine-10-carboxylic acid, 13-cyclohexyl-6-[[(1,1-dimethylethoxy)carbonyl]amino]-6,7-dihydro-, methyl ester) (179.3 mg); Analytical HPLC method: Solvent A=10% MeOH 90% $H_2O$ 0.1% TFA, Solvent B=90% MeOH 10% $H_2O$ 0.1% TFA, Start % B=0, Final % B=100, Gradient time=2 min, Flow Rate=5 ml/min, Column: Xterra MS C18 S7 3.0×50 mm; LC/MS: (ES+) m/z $(M+H)^+$=489.21, HPLC $R_t$=2.183 min.

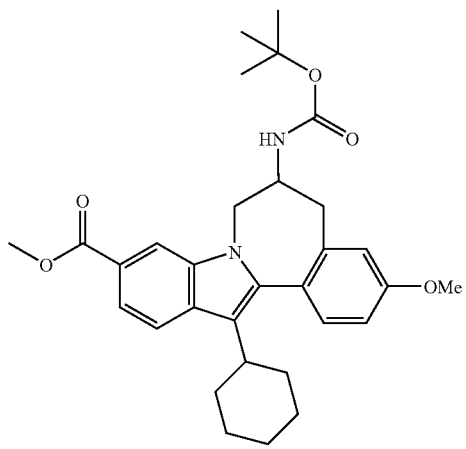

13-cyclohexyl-6-[[(1,1-dimethylethoxy)carbonyl]amino]-6,7-dihydro-3-methoxy-5H-indolo[2,1-a][2]benzazepine-10-carboxylic acid, methyl ester. This methoxyphenyl analog (5H-indolo[2,1 -a][2]benzazepine-10-carboxylic acid, 13-cyclohexyl-6-[[(1,1-dimethylethoxy)carbonyl]amino]-6,7-dihydro-3-methoxy-, methyl ester) was prepared from the acyl azide (5H-indolo[2,1-a][2]benzazepine-10-carboxylic acid, 6-(azidocarbonyl)-13-cyclohexyl-6,7-dihydro-3-methoxy-, methyl ester) in a similar manner; Analytical HPLC method: Solvent A=10% MeOH90% H$_2$O0.1% TFA, Solvent B=90% MeOH10% H$_2$O0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=519.30, HPLC R$_t$=2.165 min.

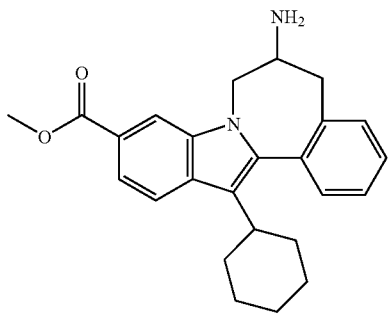

6-amino-13-cyclohexyl-6,7-dihydro-5H-indolo[2,1-a][2]benzazepine-10-carboxylic acid, methyl ester. To (5H-indolo[2,1-a][2]benzazepine-10-carboxylic acid, 13-cyclohexyl-6-[[(1,1-dimethylethoxy)carbonyl]amino]-6,7-dihydro-, methyl ester) (179.3 mg) as obtained above at r.t. under N$_2$ was added a solution of HCl in 1,4-dioxane (2 ml, 4M). The mixture was stirred at r.t. for 3 hr. 20 min. and then evaporated to dryness to give the hydrochloride salt of (5H-indolo[2,1-a][2]benzazepine-10-carboxylic acid, 6-amino-13-cyclohexyl-6,7-dihydro-, methyl ester); Analytical HPLC method: Solvent A=10% MeOH90% H$_2$O0.1% TFA, Solvent B=90% MeOH10% H$_2$O0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=389.24, HPLC R$_t$=1.790 min.

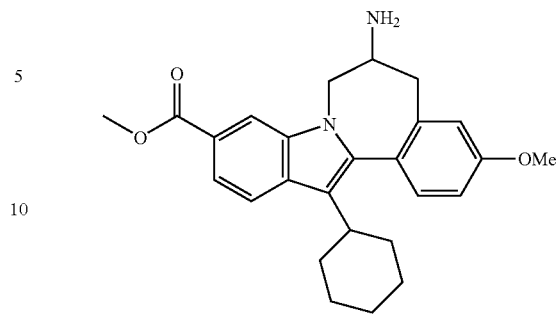

6-amino-13-cyclohexyl-6,7-dihydro-3-methoxy-5H-indolo[2,1-a][2]benzazepine-10-carboxylic acid, methyl ester. The hydrochloride salt of this methoxyphenyl analog (5H-indolo[2,1-a][2]benzazepine-10-carboxylic acid, 6-amino-13-cyclohexyl-6,7-dihydro-3-methoxy-, methyl ester) was prepared from 5H-indolo[2,1-a][2]benzazepine-10-carboxylic acid, 13-cyclohexyl-6-[[( 1,1-dimethylethoxy)carbonyl]amino]-6,7-dihydro-3-methoxy-, methyl ester in a similar manner; Analytical HPLC method: Solvent A=10% MeOH90% H$_2$O0.1% TFA, Solvent B=90% MeOH10% H$_2$O0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=419.27, HPLC R$_t$=1.80 min.

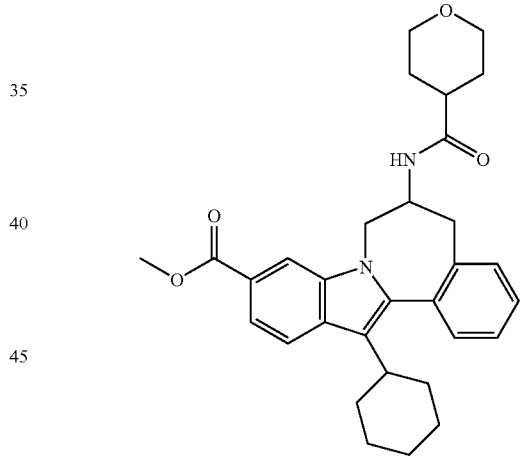

13-cyclohexyl-6,7-dihydro-6-[[(tetrahydro-2H-pyran-4-yl)carbonyl]amino]-5H-indolo[2,1 -a][2]benzazepine-10-carboxylic acid, methyl ester. To the hydrochloride salt of (5H-indolo[2,1-a][2]benzazepine-10-carboxylic acid, 6-amino-13-cyclohexyl-6,7-dihydro-, methyl ester) (equivalent to 54.4 mg (0.1 1 mmol) of the Boc-amine (5H-indolo[2,1-a][2]benzazepine-10-carboxylic acid, 13-cyclohexyl-6-[[(1,1-dimethylethoxy)carbonyl]amino]-6,7-dihydro-, methyl ester)) at r.t. under N$_2$ was added a solution of the acid chloride (32.7 mg, 0.22 mmol) in THF (1 ml), and then triethylamine (77 µl, 0.55 mmol). The mixture was stirred at r.t. for 1 hr, evaporated, and the residue obtained purified by Biotage flash chromatography (gradient elution, 0 to 100% EtOAc/Hexane) to gave the amide (5H-indolo[2,1-a][2]benzazepine-10-carboxylic acid, 13-cyclohexyl-6,7-dihydro-6-[[(tetrahydro-2H-pyran-4-yl)carbonyl]amino]-, methyl ester) (45 mg); Analytical HPLC method: Solvent A=10%

MeOH 90% H₂O 0.1% TFA, Solvent B=90% MeOH 10% H₂O 0.1% TFA, Start % B=0, Final % B=100, Gradient time=2 min, Flow Rate=5 ml/min, Column: Xterra MS C18 S7 3.0×50 mm; LC/MS: (ES+) m/z (M+H)⁺=501.23, HPLC $R_t$=2.073 min.

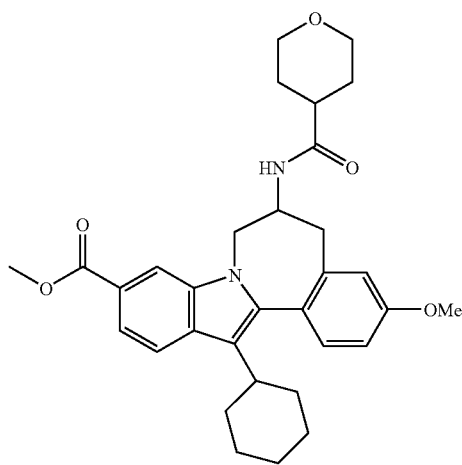

13-cyclohexyl-6,7-dihydro-3-methoxy-6-[[(tetrahydro-2H-pyran-4-yl)carbonyl]amino]-5H-indolo[2,1-a][2]benzazepine-10-carboxylic acid, methyl ester. This methoxyphenyl analog (5H-indolo[2,1-a][2]benzazepine-10-carboxylic acid, 13-cyclohexyl-6,7-dihydro-3-methoxy-6-[[(tetrahydro-2H-pyran-4-yl)carbonyl]amino]-, methyl ester) was prepared from 5H-indolo[2,1-a][2]benzazepine-10-carboxylic acid, 6-amino-13-cyclohexyl-6,7-dihydro-3-methoxy-, methyl ester in a similar manner; Analytical thin layer chromatography (5% MeOH/CH₂Cl₂) $R_f$=0.5; Analytical HPLC method: Solvent A=10% MeOH 90% H₂O 0.1% TFA, Solvent B=90% MeOH 10% H₂O 0.1% TFA, Start % B=0, Final % B=100, Gradient time=2 min, Flow Rate=5 ml/min, Column: Xterra MS C18 S7 3.0×50 mm; LC/MS: (ES+) m/z (M+H)⁺=531.29, HPLC $R_t$=2.028 min.

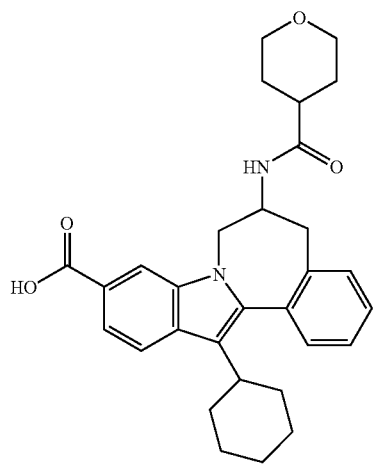

13-cyclohexyl-6,7-dihydro-6-[[(tetrahydro-2H-pyran-4-yl)carbonylyamino]-5H-indolo[2,1-a][2]benzazepine-10-carboxylic acid. (5H-indolo[2,1-a][2]benzazepine-10-carboxylic acid, 13-cyclohexyl-6,7-dihydro-6-[[(tetrahydro-2H-pyran-4-yl)carbonyl]amino]-) was prepared from (5H-indolo[2,1-a][2]benzazepine-10-carboxylic acid, 13-cyclohexyl-6,7-dihydro-6-[[(tetrahydro-2H-pyran-4-yl)carbonyl]amino]-, methyl ester) using TMSOK in THF in a similar manner as described before; Analytical HPLC method: Solvent A=10% MeOH 90% H₂O 0.1% TFA, Solvent B=90% MeOH 10% H₂O 0.1% TFA, Start % B=0, Final % B=100, Gradient time=2 min, Flow Rate=5 ml/min, Column: Xterra MS C18 S7 3.0×50 mm; LC/MS: (ES+) m/z (M+H)⁺=487.19, HPLC $R_t$=1.978 min.

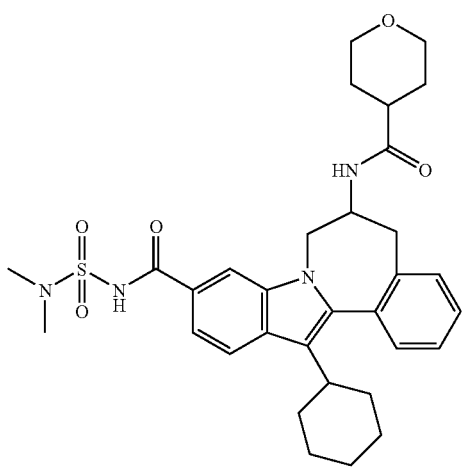

13-cyclohexyl-N-[(dimethylamino)sulfonyl]-6,7-dihydro-6-[[(tetrahydro-2H-pyran-4-yl)carbonyl]amino]-5H-indolo[2,1-a][2]benzazepine-10-carboxamide. (5H-indolo[2,1-a][2]benzazepine-10-carboxamide, 13-cyclohexyl-N-[(dimethylamino)sulfonyl]-6,7-dihydro-6-[[(tetrahydro-2H-pyran-4-yl)carbonyl]amino]-) was prepared from (5H-indolo[2,1-a][2]benzazepine-10-carboxylic acid, 13-cyclohexyl-6,7-dihydro-6-[[(tetrahydro-2H-pyran-4-yl)carbonyl]amino]-) using CDI as a coupling reagent in a similar manner as described before; Analytical HPLC method: Solvent A=10% MeOH 90% H₂O 0.1% TFA, Solvent B=90% MeO H 10% H₂O 0.1% TFA, Start % B=0, Final % B=100, Gradient time=2 min, Flow Rate=5 ml/min, Column: Xterra MS C18 S7 3.0×50 mm; LC/MS: (ES+) m/z (M+H)⁺=593.23, HPLC $R_t$=1.928 min.

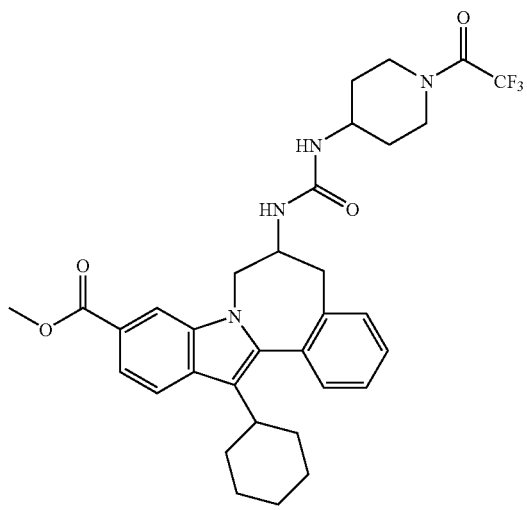

13-cyclohexyl-6,7-dihydro-6-[[[[1-(trifluoroacetyl)-4-piperidinyl]amino]carbonyl]amino]-5H-indolo[2,1-a][2]benzazepine-10-carboxylic acid, methyl ester. (5H-indolo[2,1-a][2]benzazepine-10-carboxylic acid, 13-cyclohexyl-6,7-dihydro-6-[[[[1-(trifluoroacetyl)-4-piperidinyl]amino]carbonyl]amino]-, methyl ester) was prepared from (5H-indolo[2,1-a][2]benzazepine-10-carboxylic acid, 6-amino-13-cyclohexyl-6,7-dihydro-, methyl ester) and the corresponding isocyanate under microwave conditions (PhMe, 100° C., normal absorption level); Analytical HPLC method: Solvent A=10% MeOH90% H$_2$O0.1% TFA, Solvent B=90% MeOH10% H$_2$O0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=611.32, HPLC R$_t$=2.100 min.

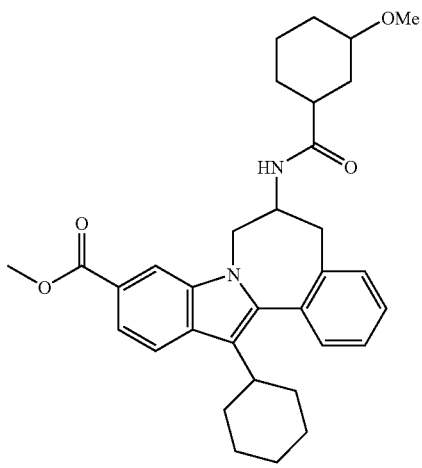

13-cyclohexyl-6,7-dihydro-6-[[(3-methoxycyclohexyl)carbonyl]amino]-5H-indolo[2,1-a][2]benzazepine-10-carboxylic acid, methyl ester. (5H-indolo[2,1-a][2]benzazepine-10-carboxylic acid, 13-cyclohexyl-6,7-dihydro-6-[[(3-methoxycyclohexyl)carbonyl]amino]-, methyl ester) was prepared from (5H-indolo[2,1-a][2]benzazepine-10-carboxylic acid, 6-amino-13-cyclohexyl-6,7-dihydro-, methyl ester) and the corresponding acid chloride in a similar manner as described before; Analytical thin layer chromatography (5% MeOH/CH$_2$Cl$_2$) R$_f$=0.6; Analytical HPLC method: Solvent A=10% MeOH90% H$_2$O0.1% TFA, Solvent B=90% MeOH10% H$_2$O0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=529.31, HPLC R$_t$=2.100 min.

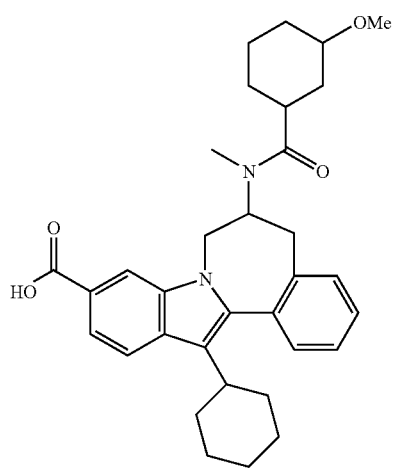

13-cyclohexyl-6,7-dihydro-6-[[(3-methoxycyclohexyl)carbonyl]methylamino]-5H-indolo[2,1-a][2]benzazepine-10-carboxylic acid. To a mixture of the methyl ester (5H-indolo[2,1-a][2]benzazepine-10-carboxylic acid, 13-cyclohexyl-6,7-dihydro-6-[[(3-methoxycyclohexyl)carbonyl]amino]-, methyl ester) (47 mg, 88.9 µmol)) in DMF (1.5 ml) at r.t. under N$_2$ was added NaH (107 mg, 2.68 mmol, 60% in oil), and the reaction mixture stirred for about 10 min. MeI (23 µl, 0.37 mmol) was then added to the mixture, which was stirred at r.t. for 18.5 hr. The reaction mixture was diluted with water (2 ml), and acidified with hydrochloric acid (1N). The precipitates were filtered, washed with water (3×1 ml), and dried under high vacuum to give the acid (5H-indolo[2,1-a][2]benzazepine-10-carboxylic acid, 13-cyclohexyl-6,7-dihydro-6-[[(3-methoxycyclohexyl)carbonyl]methylamino]-); Analytical thin layer chromatography (5% MeOH/CH$_2$Cl$_2$) R$_f$=0.4; Analytical HPLC method: Solvent A=10% MeOH90% H$_2$O0.1% TFA, Solvent B=90% MeOH10% H$_2$O0.1% TFA, Start % B=0, Final % B=100, Gradient time=2 min, Flow Rate=5 ml/min, Column: Xterra MS C18 S7 3.0×50mm; LC/MS: (ES+) m/z (M+H)$^+$=529.34, HPLC R$_t$=2.085 min.

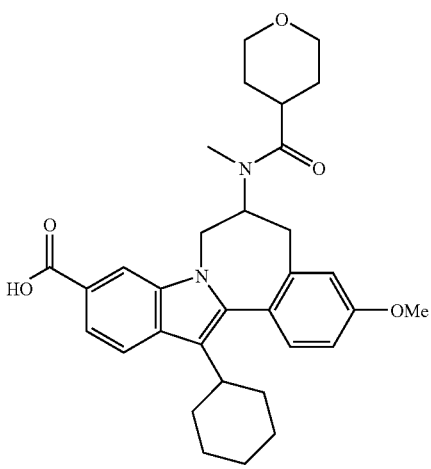

13-cyclohexyl-6,7-dihydro-3-methoxy-6-[methyl[(tetrahydro-2H-pyran-4-yl)carbonyl]amino]-5H-indolo[2,1-a][2]benzazepine-10-carboxylic acid. (5H-indolo[2,1-a][2]benzazepine-10-carboxylic acid, 13-cyclohexyl-6,7-dihydro-3-methoxy-6-[methyl[(tetrahydro-2H-pyran-4-yl)carbonyl]amino]-) was prepared from (5H-indolo[2,1-a][2]benzazepine-10-carboxylic acid, 13-cyclohexyl-6,7-dihydro-3-methoxy-6-[[(tetrahydro-2H-pyran-4-yl)carbonyl]amino]-, methyl ester) in a similar manner; Analytical thin layer chromatography (5% MeOH/CH$_2$Cl$_2$) R$_f$=0.3; Analytical HPLC method: Solvent A=10% MeOH90% H$_2$O0.1% TFA, Solvent B=90% MeOH10% H$_2$O0.1% TFA, Start % B=0, Final % B=100, Gradient time=2 min, Flow Rate=5 ml/min, Column: Xterra MS C18 S7 3.0×50mm; LC/MS: (ES+) m/z (M+H)$^+$=531.27, HPLC R$_t$=2.020 min.

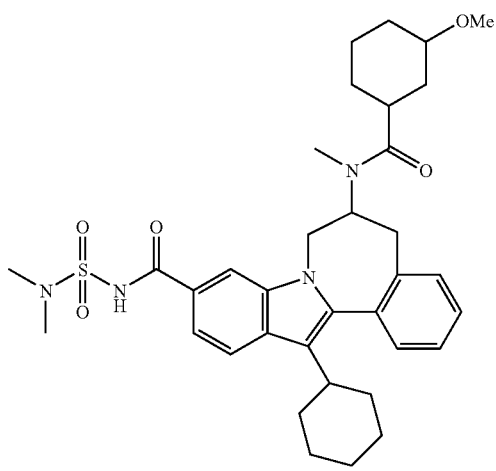

13-cyclohexyl-N-[(dimethylamino)sulfonyl]-6,7-dihydro-6-[[(3-methoxycyclohexyl)carbonyl]methylamino]-5H-indolo[2,1-a][2]benzazepine-10-carboxamide. (5H-indolo[2,1-a][2]benzazepine-10-carboxamide, 13-cyclohexyl-N-[(dimethylamino)sulfonyl]-6,7-dihydro-6-[[(3-methoxycyclohexyl)carbonyl]methylamino]-) was prepared from (5H-indolo[2,1-a][2]benzazepine-10-carboxylic acid, 13-cyclohexyl-6,7-dihydro-6-[[(3-methoxycyclohexyl)carbonyl]methylamino]-) using CDI as a coupling reagent in a similar manner as described before; Analytical HPLC method: Solvent A=10% MeOH90% H$_2$O0.1% TFA, Solvent B=90% MeOH10% H$_2$O0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=635.32, HPLC R$_t$=2.042 min.

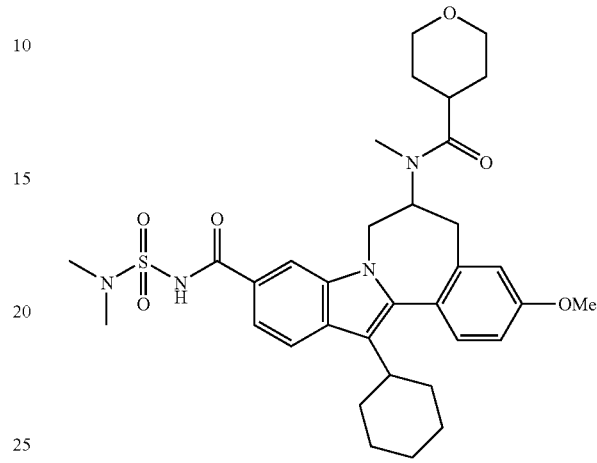

13-cyclohexyl-N-[(dimethylamino)sulfonyl]-6,7-dihydro-3-methoxy-6-[methyl[(tetrahydro-2H-pyran-4-yl)carbonyl]amino]-5H-indolo[2,1-a][2]benzazepine-10-carboxamide. (5H-indolo[2,1-a][2]benzazepine-10-carboxamide, 13-cyclohexyl-N-[(dimethylamino)sulfonyl]-6,7-dihydro-3-methoxy-6-[methyl[(tetrahydro-2H-pyran-4-yl)carbonyl]amino]-) was prepared from (5H-indolo[2,1-a][2]benzazepine-10-carboxylic acid, 13-cyclohexyl-6,7-dihydro-3-methoxy-6-[methyl[(tetrahydro-2H-pyran-4-yl)carbonyl]amino]-) using CDI as a coupling reagent in a similar manner as described before; Analytical HPLC method: Solvent A=10% MeOH90% H$_2$O0.1% TFA, Solvent B=90% MeOH10% H$_2$O0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=637.27, HPLC R$_t$=1.958 min.

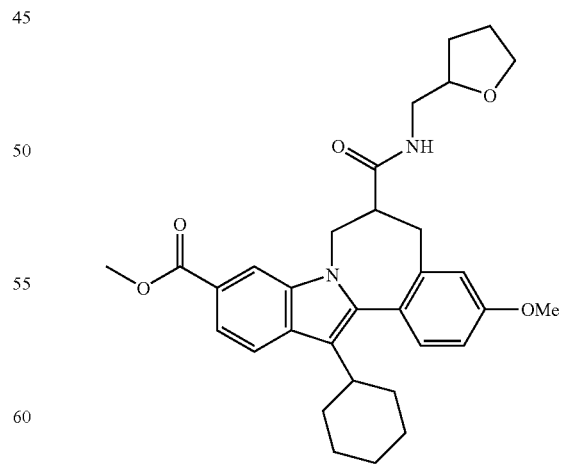

13-cyclohexyl-6,7-dihydro-3-methoxy-6-[[[(tetrahydro-2-furanyl)methyl]amino]carbonyl]-5H-indolo[2,1-a][2]benzazepine-10-carboxylic acid, methyl ester. To a mixture of the acid (5H-indolo[2,1-a][2]benzazepine-6,10-dicarboxylic acid, 13-cyclohexyl-6,7-dihydro-3-methoxy-, 10-methyl ester) (100 mg, 0.22 mmol) in $CH_2Cl_2$ (1 ml) at r.t. under $N_2$ was added a solution of oxalyl chloride in $CH_2Cl_2$ (0.45 ml, 0.9 mmol, 2M ). 2 drops of DMF was then added using a syringe with a G21 needle. The mixture was stirred at r.t. for 1 hr, and then evaporated and dried under high vacuum. A solution of the tetrahydrofurfurylamine (0.14 ml, 1.36 mmol) in $CH_2Cl_2$ (1 ml) was then added to the residue. The reaction mixture was stirred for 1 hr, evaporated and purified by Biotage flash chromatography (gradient elution, 0 to 50% EtOAc/Hexane) to gave the amide (5H-indolo[2,1-a][2]benzazepine-10-carboxylic acid, 13-cyclohexyl-6,7-dihydro-3-methoxy-6-[[[(tetrahydro-2-furanyl)methyl]amino]carbonyl]-, methyl ester); Analytical thin layer chromatography (5% $MeOH/CH_2Cl_2$) $R_f$=0.45; Analytical HPLC method: Solvent A=10% MeOH 90% $H_2O$ 0.1% TFA, Solvent B=90% MeOH 10% $H_2O$ 0.1% TFA, Start % B=0, Final % B=100, Gradient time=2 min, Flow Rate=5 ml/min, Column: Xterra MS C18 S7 3.0×50 mm; LC/MS: (ES+) m/z $(M+H)^+$=531.26, HPLC $R_t$=2.070 min.

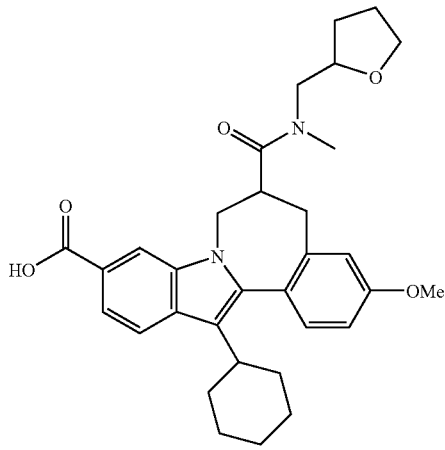

13-cyclohexyl-6,7-dihydro-3-methoxy-6-[[methyl[(tetrahydro-2-furanyl)methyl]amino]carbonyl]-5H-indolo[2,1-a][2]benzazepine-10-carboxylic acid. (5H-indolo[2,1-a][2]benzazepine-10-carboxylic acid, 13-cyclohexyl-6,7-dihydro-3-methoxy-6-[[methyl[(tetrahydro-2-furanyl)methyl]amino]carbonyl]-) was prepared from (5H-indolo[2,1-a][2]benzazepine-10-carboxylic acid, 13-cyclohexyl-6,7-dihydro-3-methoxy-6-[[[(tetrahydro-2-furanyl)methyl]amino]carbonyl]-, methyl ester) by methylation using MeI and NaH in DMF in a similar manner as described before; Analytical thin layer chromatography (5% $MeOH/CH_2Cl_2$) $R_f$=0.35; Analytical HPLC method: Solvent A=10% MeOH 90% $H_2O$ 0.1% TFA, Solvent B=90% MeOH 10% $H_2O$ 0.1% TFA, Start % B=0, Final % B=100, Gradient time=2 min, Flow Rate=5 ml/min, Column: Xterra MS C18 S7 3.0×50 mm; LC/MS: (ES+) m/z $(M+H)^+$=531.22, HPLC $R_t$=2.003 min.

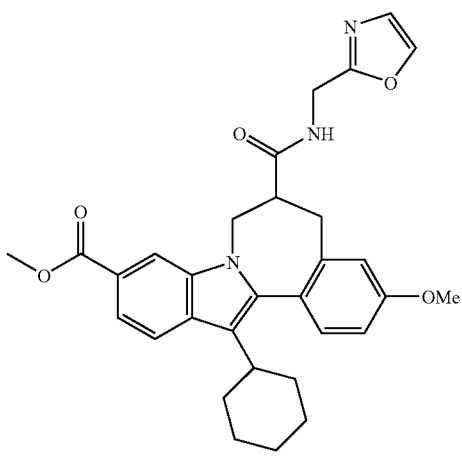

13-cyclohexyl-6,7-dihydro-3-methoxy-6-[[(2-oxazolylmethyl)amino]carbonyl]-5H-indolo[2,1-a][2]benzazepine-10-carboxylic acid, methyl ester. (5H-indolo[2,1-a][2]benzazepine-10-carboxylic acid, 13-cyclohexyl-6,7-dihydro-3-methoxy-6-[[(2-oxazolylmethyl)amino]carbonyl]-, methyl ester) was prepared from 5H-indolo[2,1-a][2]benzazepine-6,10-dicarboxylic acid, 13-cyclohexyl-6,7-dihydro-3-methoxy-, 10-methyl ester and 2-aminomethyloxazole in a similar manner as described; Analytical thin layer chromatography (5% $MeOH/CH_2Cl_2$) $R_f$=0.40; Analytical HPLC method: Solvent A=10% MeOH 90% $H_2O$ 0.1% TFA, Solvent B=90% MeOH 10% $H_2O$ 0.1% TFA, Start % B=0, Final % B=100, Gradient time=2 min, Flow Rate=5 ml/min, Column: Xterra MS C18 S7 3.0×50 mm; LC/MS: (ES+) m/z $(M+H)^+$=528.23, HPLC $R_t$=2.040 min.

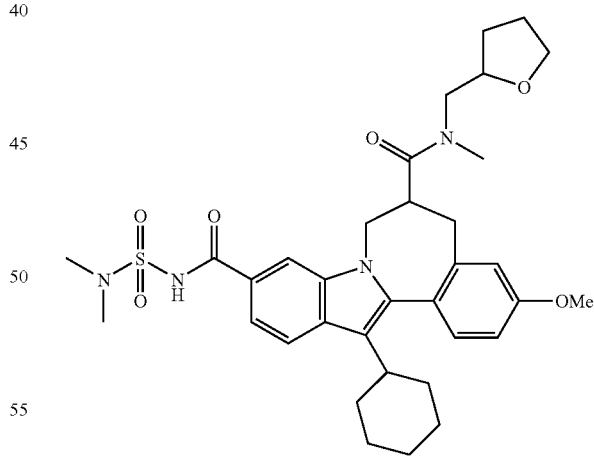

13-cyclohexyl-N~10~-[(dimethylamino)sulfonyl]-6,7-dihydro-3-methoxy-N~6~-methyl-N~6~-[(tetrahydro-2-furanyl)methyl]-5H-indolo[2,1-a][2]benzazepine-6,10-dicarboxamide. (5H-indolo[2,1-a][2]benzazepine-6,10-dicarboxamide, 13-cyclohexyl-N~10~-[(dimethylamino)sulfonyl]-6,7-dihydro-3-methoxy-N~6~-methyl-N~6~-[(tetrahydro-2-furanyl)methyl]-) was prepared from (5H-indolo[2,1-a][2]benzazepine-10-carboxylic acid, 13-cyclohexyl-6,7-dihydro-3-methoxy-6-[[methyl[(tetrahydro-2-furanyl)methyl]amino]carbonyl]-) using CDI as a coupling reagent in a similar manner as described before; Analytical HPLC method: Solvent A=10% MeOH90% H₂O0.1% TFA, Solvent B=90% MeOH10% H₂O0.1% TFA, Start % B=0, Final % B=100, Gradient time=2 min, Flow Rate=5 ml/min, Column: Xterra MS C18 S7 3.0×50 mm; LC/MS: (ES+) m/z (M+H)⁺=637.27, HPLC R$_t$=1.953 min.

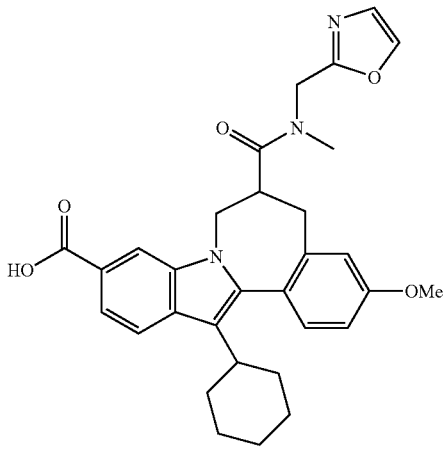

13-cyclohexyl-6,7-dihydro-3-methoxy-6-[[methyl(2-oxazolylmethyl)amino]carbonyl]-5H-indolo[2,1-a][2]benzazepine-10-carboxylic acid. 5H-indolo[2,1-a][2]benzazepine-10-carboxylic acid, 13-cyclohexyl-6,7-dihydro-3-methoxy-6-[[methyl(2-oxazolylmethyl)amino]carbonyl]-) was prepared from (5H-indolo[2,1-a][2]benzazepine-10-carboxylic acid, 13-cyclohexyl-6,7-dihydro-3-methoxy-6-[[(2-oxazolylmethyl)amino]carbonyl]-, methyl ester) by methylation using MeI and NaH in DMF in a similar manner as described before; Analytical thin layer chromatography (5% MeOH/CH₂Cl₂) R$_f$=0.30; Analytical HPLC method: Solvent A=10% MeOH90% H₂O0.1% TFA, Solvent B=90% MeOH10% H₂O0.1% TFA, Start % B=0, Final % B=100, Gradient time=2 min, Flow Rate=5 ml/min, Column: Xterra MS C18 S7 3.0×50 mm; LC/MS: (ES+) m/z (M+H)⁺=531.31, HPLC R$_t$=1.970 min.

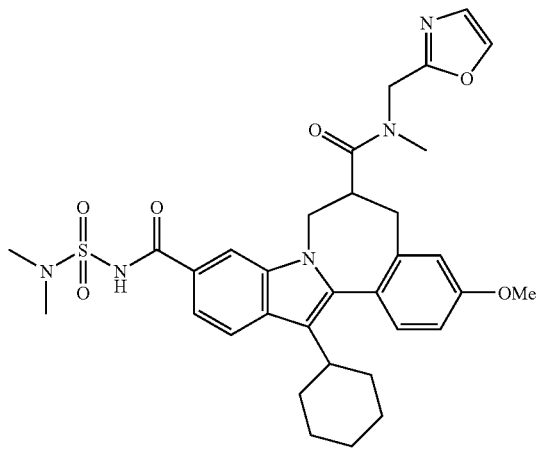

13-cyclohexyl-N~10~-[(dimethylamino)sulfonyl]-6,7-dihydro-3-methoxy-N~6~-methyl-N~6~-(2-oxazolylmethyl)-5H-indolo[2,1-a][2]benzazepine-6,10-dicarboxamide.

5H-indolo[2,1-a][2]benzazepine-6,10-dicarboxamide, 13-cyclohexyl-N~10~-[(dimethylamino)sulfonyl]-6,7-dihydro-3-methoxy-N~6~-methyl-N~6~-(2-oxazolylmethyl)-) was prepared from (5H-indolo[2,1-a][2]benzazepine-10-carboxylic acid, 13-cyclohexyl-6,7-dihydro-3-methoxy-6-[[methyl(2-oxazolylmethyl)amino]carbonyl]-) using CDI as a coupling reagent in a similar manner as described before; Analytical HPLC method: Solvent A=10% MeOH90% H₂O0.1% TFA, Solvent B=90% MeOH20% H₂O0.1% TFA, Start % B=0, Final % B=100, Gradient time=2 min, Flow Rate=5 ml/min, Column: Xterra MS C18 S7 3.0×50 mm; LC/MS: (ES+) m/z (M+H)⁺=634.22, HPLC R$_t$=1.937 min.

The Liquid chromatography and Mass spectrometry conditions which follow pertain to the following procedures until noted: LCMS data: Gradient time: 2 min; Flow rate: 4 mL/min;, Stop time: Gradient time: +1 minute; Starting conc: 0% B; Eluent A: 10% MeOH/90% H₂O with 0.1% TFA; Eluent B: 90% MeOH /10% H₂O with 0.1% TFA; Column 6: Phenomenex-luna 10 μ C18 4.6×50 mm S10.

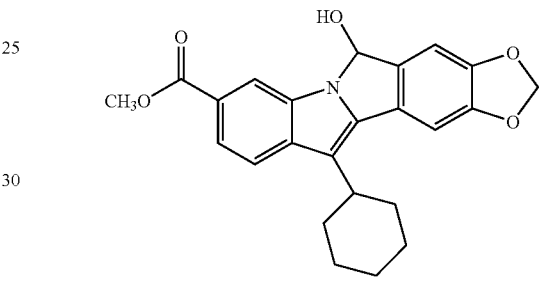

ESI-MS m/z 388(M-17, positive ion mode); 1H NMR (300 MHz, CHLOROFORM-D) δ ppm 1.29-1.62 (m, 3 H) 1.70-2.09 (m, 7 H) 2.95-3.17 (m, 1 H) 3.90 (d, J=2.20 Hz, 3 H) 6.38 (d, J=23.05 Hz, 1 H) 7.03 (d, 1 H) 7.18 (s, 1 H) 7.21 (s, 1 H) 7.66-7.73 (m, 2 H) 8.12 (d, J=15.00 Hz, 1 H).

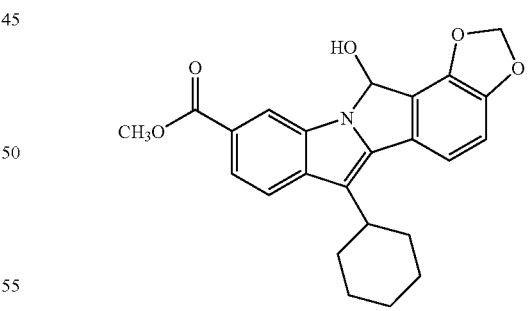

ESI-MS m/z 388(M-17, positive ion mode), m/z 405(M): 1H NMR (500 MHz, Acetone) δ ppm 1.80-2.13 (m, 3 H) 2.23-2.53 (m, 7 H) 3.62-3.79 (m, 1 H) 4.38 (s, 3 H) 6.64 (d, J=2.14 Hz, 2 H) 6.66 (d, J=9.46 Hz, 1 H) 7.31 (d, J=9.16 Hz, 1 H) 7.47 (d, J=7.93 Hz, 1 H) 7.87 (d, J=7.93 Hz, 1 H) 8.17 (d, J=8.24 Hz, 1 H) 8.28 (d, J=8.54 Hz, 1 H) 8.67 (s, 1 H).

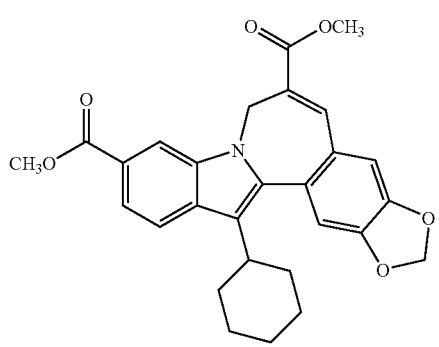

ESI-MS m/z 474(MH+); 1H NMR (300 MHz, 1H NMR (300 MHz, CHLOROFORM-D) δ ppm 1.14-1.47 (m, 3 H) 1.88 (d, J=75.75 Hz, 7 H) 2.73-2.82 (m, 1 H) 6.10 (d, J=10.61 Hz, 2 H) 6.89 (s, 1 H) 6.95-6.98 (m, 1 H) 7.60-7.77 (m, 2 H) 7.77-7.86 (m, 1 H) 8.25 (s, 1 H).

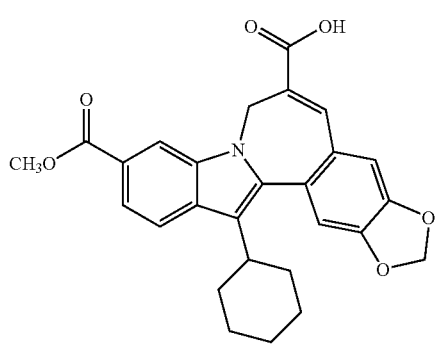

ESI-MS m/z 538(MH+); 1H NMR (300 MHz, DMSO-D6) δ ppm 1.02-1.51 (m, 4 H) 1.61-2.14 (m, 6 H) 2.40-2.59 (m, 6 H) 2.69-2.89 (m, 1 H) 3.89 (s, 3 H) 4.07-4.26 (m, 1 H) 5.45-5.67 (m, 1 H) 7.53-7.74 (m, 5 H) 7.88 (s, 1 H) 7.94 (d, J=8.42 Hz, 1 H) 8.18 (s, 1 H).

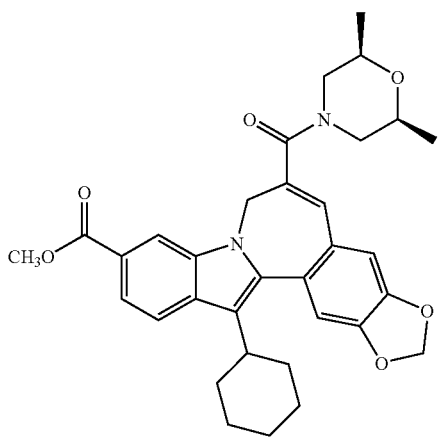

ESI-MS m/z 557(MH+); 1H NMR (300 MHz, CHLOROFORM-D) δ ppm 0.75-2.49 (m, 21 H) 2.71-2.97 (m, 2 H) 3.24-3.47 (m, 1 H) 3.88-3.99 (m, 3 H) 4.39 (s, 1 H) 5.02 (d, J=13.17 Hz, 1 H) 6.08 (d, J=13.54 Hz, 2 H) 6.60 (s, 1 H) 6.80 (s, 1 H) 6.94 (s, 1 H) 7.71 (d, J=8.05 Hz, 1 H) 7.83 (d, 1 H) 8.08 (s, 1 H).

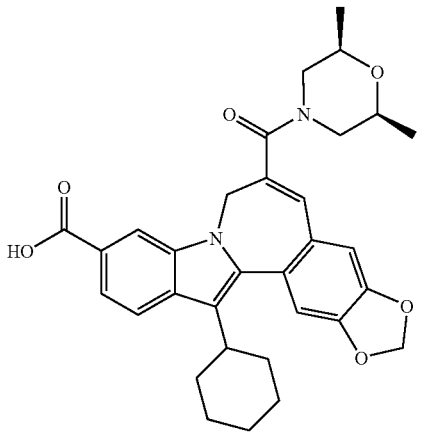

ESI-MS m/z 543(MH+); 1 H NMR (300 MHz, CHLOROFORM-D) δ ppm 0.62-2.17 (m, 19 H) 2.21-2.46 (m, 2 H) 2.68-2.93 (m, 1 H) 3.25-3.46 (m, 1 H) 4.39 (d, 1 H) 5.20 (d, 1 H) 6.08 (d, J=14.64 Hz, 2 H) 6.61 (s, 1 H) 6.81 (s, 1 H) 6.96 (s, 1 H) 7.75-7.89 (m, 2 H) 8.42 (s, 1 H).

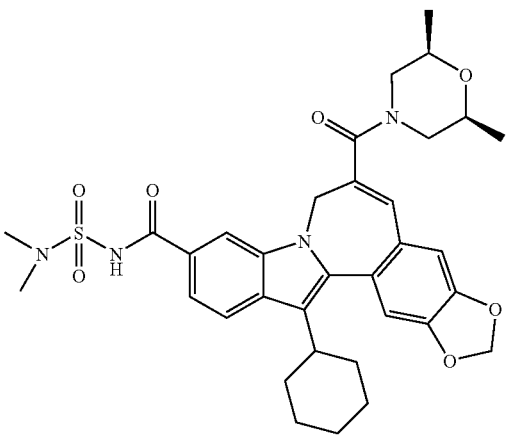

ESI-MS m/z 649(MH+); 1H NMR (300 MHz, DMSO-D6) δ ppm 2.72-2.83 (m, 2 H) 2.85-2.92 (m, J=4.39 Hz, 6 H) 4.34 (d, 1 H) 5.09 (d, J=1.83 Hz, 1 H) 6.20 (d, J=21.59 Hz, 2 H) 6.76 (s, 1 H) 7.03 (s, 1 H) 7.15 (s, 1 H) 7.65 (d, J=8.78 Hz, 1 H) 7.89 (d, J=8.78 Hz, 1 H) 8.51 (s, 1 H).

505
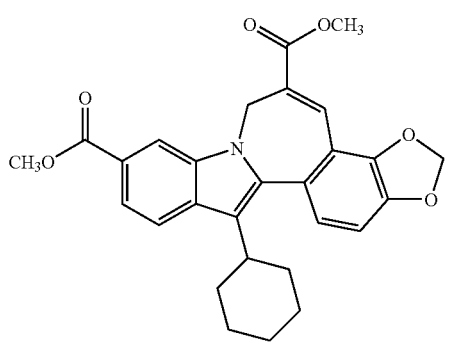
1H NMR (500 MHz, CHLOROFORM-D) δ ppm 1.07-2.17 (m, 10 H) 2.68-2.91 (m, 1 H) 3.83 (s, 3 H) 3.95 (s, 3 H) 4.17-4.41 (m, 1 H) 5.60-5.79 (m, 1 H) 5.99-6.23 (m, 1 H) 7.00 (d, 1 H) 7.07 (d, 1 H) 7.74 (dd, 1 H) 7.85 (d, J=8.55 Hz, 1 H) 7.88 (s, 1 H) 8.28 (s, 1 H).
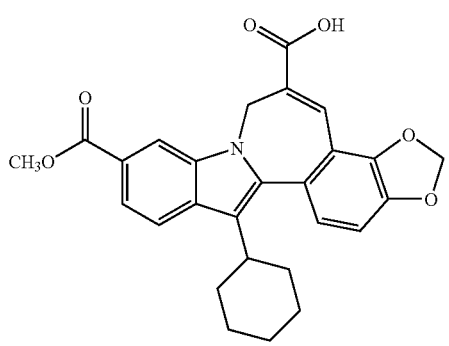
ESI-MS m/z 460(MH+); 1H NMR (500 MHz, Acetone) δ ppm 1.35-2.26 (m, 10 H) 2.86-3.01 (m, 1 H) 3.91 (s, 3 H) 4.33 (s, 1 H) 5.73 (s, 1 H) 6.07-6.38 (m, 2 H) 7.13-7.17 (m, 1 H) 7.18-7.22 (m, 1 H) 7.67-7.72 (m, 1 H) 7.89 (s, 1 H) 7.93 (d, J=8.55 Hz, 1 H) 8.29 (s, 1 H).
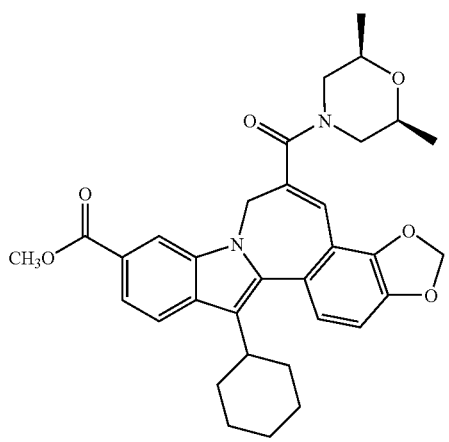
ESI-MS m/z 557(MH+); 1H NMR (300 MHz, CHLOROFORM-D) δ ppm 0.78-2.16 (m, 16 H) 2.40 (s, 2 H) 2.72-2.87 (m, 2 H) 2.90-3.08 (m, 1 H) 3.24-3.52 (m, 1 H) 3.86-3.89 (m, 1 H) 3.92 (s, 3 H) 4.35-4.59 (m, 1 H) 4.92-5.18 (m, 1 H)
506
5.97-6.18 (m, 2 H) 6.75 (s, 1 H) 6.94 (d, 1 H) 7.01 (d, 1 H) 7.71 (dd, 1 H) 7.83 (q, 1 H) 8.11 (s, 1 H).
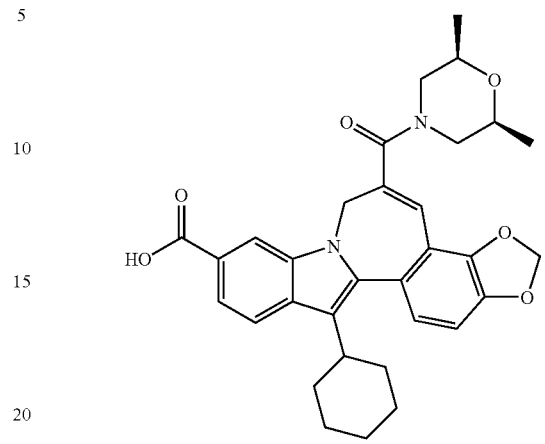
ESI-MS m/z 543(MH+); 1H NMR (300 MHz, CHLOROFORM-D) δ ppm 0.73-2.16 (m, 16 H) 2.26-2.53 (m, 2 H) 2.56-2.93 (m, 2 H) 3.26-3.67 (m, 2 H) 4.35-4.62 (m, 1 H) 5.09-5.41 (m, 1 H) 5.92-6.18 (m, 2 H) 6.74-6.80 (m, 1 H) 6.95 (d, 1 H) 7.03 (d, 1 H) 7.79 (d, 1 H) 7.86 (d, 1 H) 8.41-8.45 (m, 1 H).
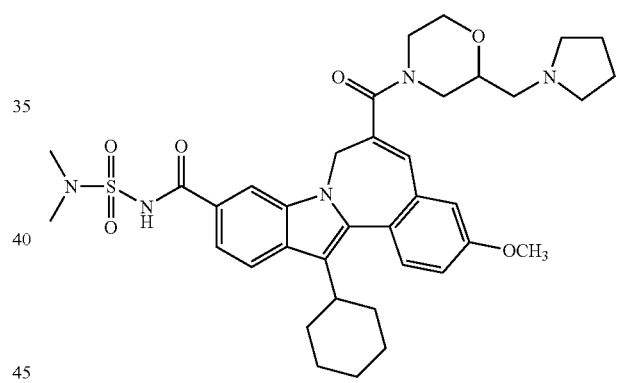
LCMS: m/z 690(MH+), ret time 1.88 min.
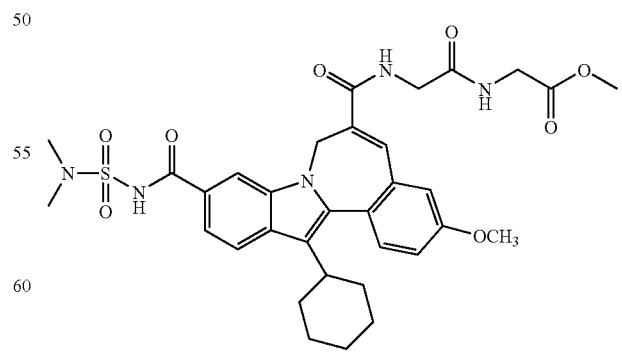
1H NMR (500 MHz, CHLOROFORM-D) δ ppm 1.10-1.57 (m, 3 H) 1.89 (s, 7 H) 2.72-2.83 (m, 1 H) 2.92-3.05 (m, 6 H) 3.64-3.69 (m, 3 H) 3.87-3.91 (m, 3 H) 4.02-4.16 (m, 5 H)

5.12-5.53 (m, 1 H) 6.95-6.99 (m, 1 H) 7.05 (d, 1 H) 7.27-7.36 (m, 2 H) 7.44-7.52 (m, 2 H) 7.67 (d, 1 H) 7.83 (d, 1 H) 8.11-8.14 (m, 1 H).

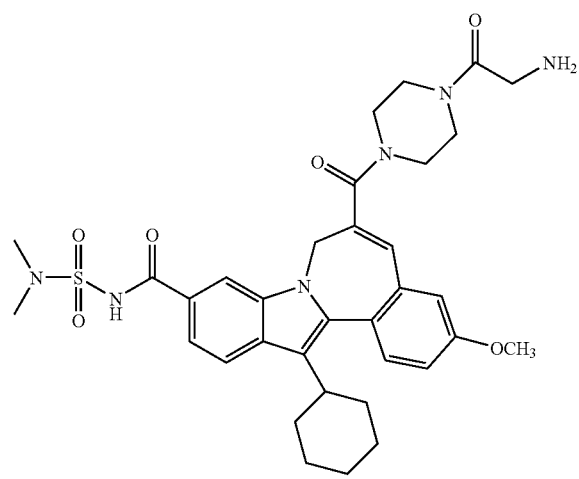

Step 1. A solution of tert-butyl piperazine-1-carboxylate (372.5 mg, 2.0 mmol) and N,N-diisopropylethylamine (517 mg, 4 mmol) in DMSO (2 mL) was rapidly added to a stirred solution of Fmoc-Gly OH (594.6 mg, 2 mmol) and TBTU (707 mg, 2.2 mmol) in DMSO (2 mL) at 10° C. The cooling bath was removed and stirred continued for 30 min at 22° C. The mixture was poured into water and the precipitated solid extracted into ethyl acetate. The organic solution was washed (water(2×), dilute HCl, brine), dried (sodium sulfate) and concentrated to leave the product as a yellow froth. A portion (140 mg) was purified on a silicic acid thick layer plate. The plate was eluted with methylene chloride:ethyl acetate (4:1). The band containing the product was extracted. The extract was concentrated and the residue crystallized form methanol to leave the titled compound. LC/MS m/z 466(MH$^+$); 1H NMR (300 MHz, CHLOROFORM-D) δ ppm 1.44 (s, 9 H) 3.31-3.38 (m, J=5.49 Hz, 2 H) 3.38-3.48 (m, 4 H) 3.55-3.65 (m, J=5.49 Hz, 2 H) 4.02 (d, J=4.03 Hz, 2 H) 4.20 (t, J=7.14 Hz, 1 H) 4.35 (d, J=7.32 Hz, 2 H) 5.79 (s, 1 H) 7.28 (t, J=7.50 Hz, 2 H) 7.37 (t, J=7.14 Hz, 2 H) 7.58 (d, J=6.95 Hz, 2 H) 7.73 (d, J=7.32 Hz, 2 H). Step 2. A solution of tert-butyl 4-(2-(((9H-fluren-9-yl)methoxy)carbonyl)acetyl)piperazine-1-carboxylate in TFA and methylene chloride (1:1) was stirred for 1 hr at 22° C. The solution was concentrated and the residue diluted with hexanes. Removal of the hexanes left the titled compound as a hygroscopic colorless foam. LCMS: m/z 366(MH$^+$), ret time 2.06 min. 13-cyclohexyl-N-[(dimethylamino)sulfonyl]-3-methoxy-6-[[4-(2-aminoacetyl)-1-piperazinyl]carbonyl-7H-indolo[2,1-a][2]benzazepine-10-carboxamide trifluoroacetate. Diisopropylethylamine (55 mL, 0.315 mmol) was added to a stirred solution at 22° C. of 6-carboxy-13-cyclohexyl-N-[(dimethylamino)sulfonyl]-3-methoxy-5H-indolo[2,1-a][2]benzaepine-10-carboxamide (50 mg, 0.0788 mmol), (9H-fluoren-9-yl)methyl 2-oxo-2-(piperazin-1-yl)ethylcarbamate trifluoroacetate (83 mg, 0.173 mmol), and TBTU (56 mg, 0.173 mmol) in DMSO (0.3 mL). The solution was stirred for 30 min and then diluted with water to precipitate the Fmoc protected product. This product was dried in a desicator charged with phosphorous pentoxide. Piperidine (0.4 mL) was added to a solution of the dried solid in DMF (1 mL). After 30 min the solution was injected on a Shimadzu preparative liquid chromatograph fitted with a reverse phase column. The column was eluted with methanol, water containing 0.1% TFA. The methanol was removed on a rotary evaporator. The solution was lyophilized to leave the product as a TFA salt (12.8 mg, 16.5% yield). ESI-MS m/z 663(MH$^+$); 1H NMR (500 MHz, CHLOROFORM-D) δ ppm 1.05-1.49 (m, 3 H) 1.59-2.09 (m, 10 H) 2.71-3.04 (m, 6 H) 3.27-3.63 (m, 8 H) 3.80-3.83 (m, 3 H) 3.92-4.17 (m, 3 H) 4.96-5.12 (m, 1 H) 6.80 (d, 1 H) 6.88 (d, 1 H) 6.97 (d, 1 H) 7.41 (d, 1 H) 7.52 (d, 1 H) 7.75 (d, 1 H) 7.97-8.16 (m, 2 H) 8.18-8.21 (m, 1 H).

The Liquid chromatography and Mass spectrometry conditions which follow pertain to the following procedures until noted: LCMS data: Gradient time: 2 min; Flow rate: 4 mL/min; Stop time: Gradient time +2 minute; Starting conc: 0% B; Eluent A: 10% MeOH/90% H$_2$O with 0.1% TFA; Eluent B: 90% MeOH/10% H$_2$O with 0.1% TFA; Column 1: Phenomenex 10 µ C18 4.6×50 mm.

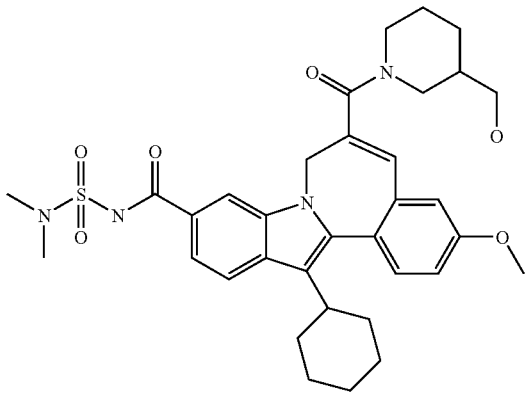

LCMS: m/z 635 (MH$^+$), ret time 2.89 min.

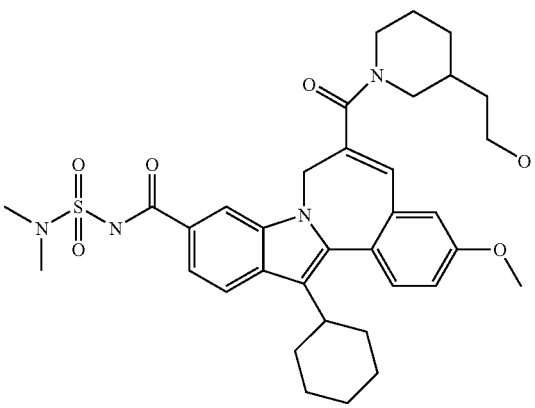

LCMS: m/z 649 (MH$^+$), ret time 2.88 min.

509
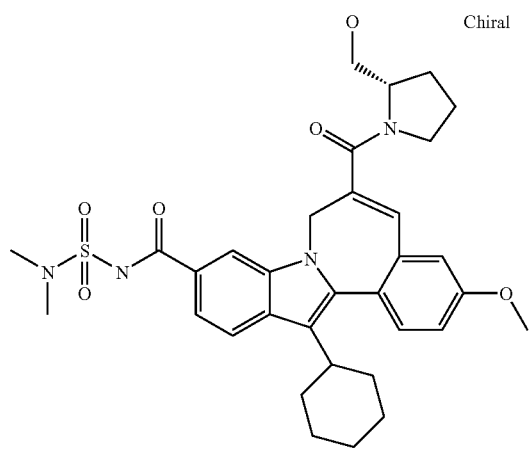
LCMS: m/z 621 (MH+), ret time 2.86 min.
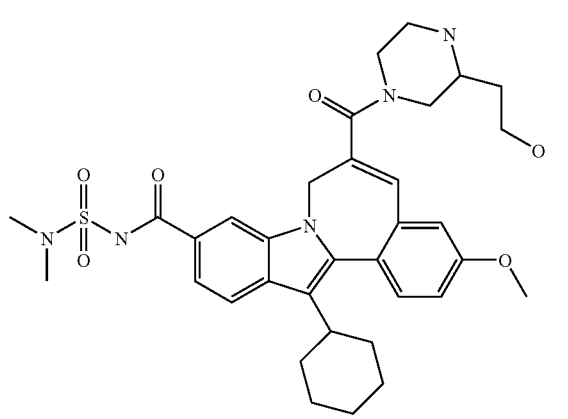
LCMS: m/z 650 (MH+), ret time 2.59 min.
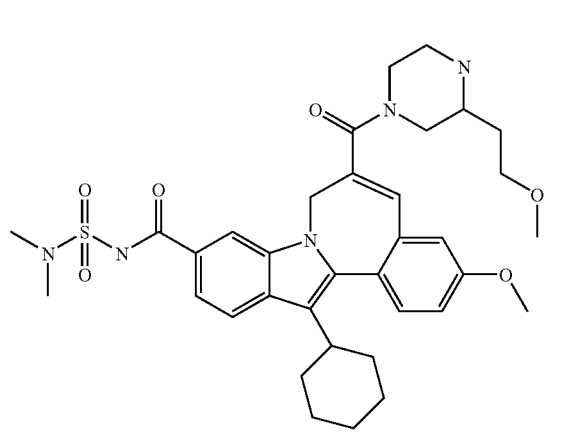
LCMS: m/z 664 (MH+), ret time 2.51 min.
510
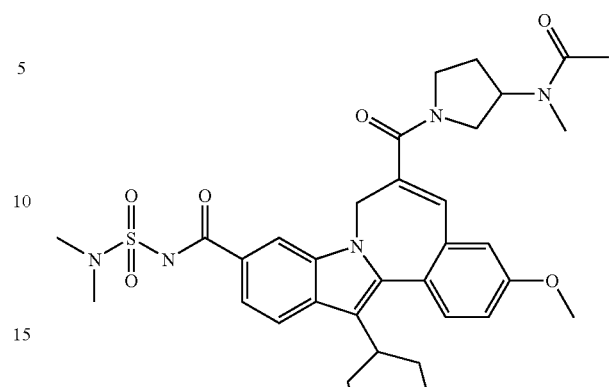
LCMS: m/z 662 (MH+), ret time 2.03 min.
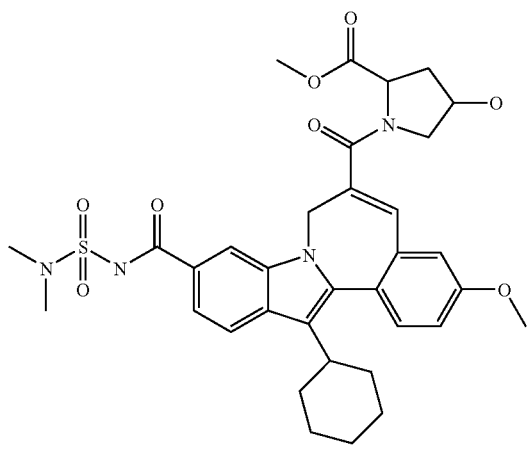
LCMS: m/z 665 (MH+), ret time 2.03 min.
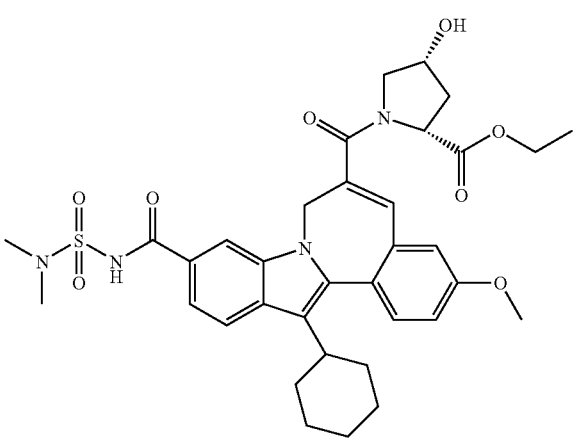
LCMS: m/z 679 (MH+), ret time 2.06 min.

511
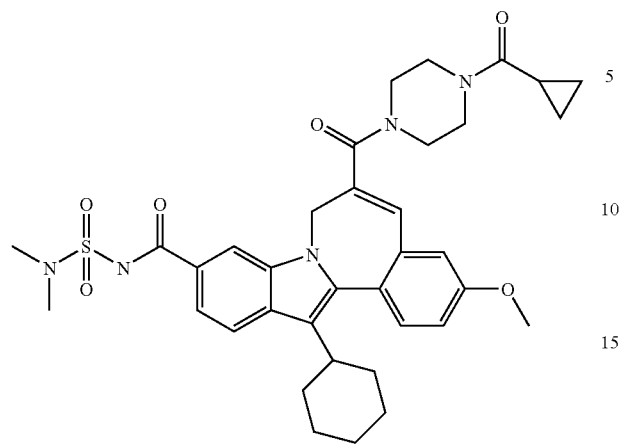
LCMS: m/z 674 (MH+), ret time 2.06 min.
512
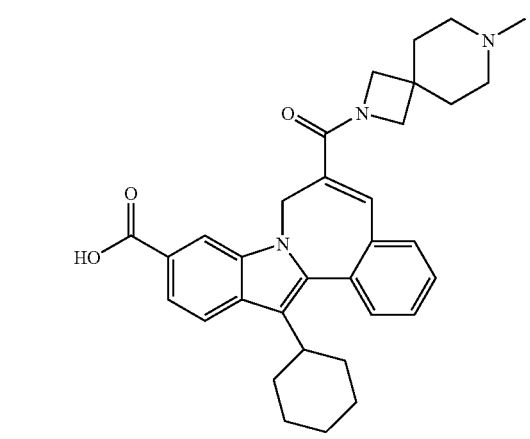
LCMS: m/z 524 (MH+), ret time 2.23 min.
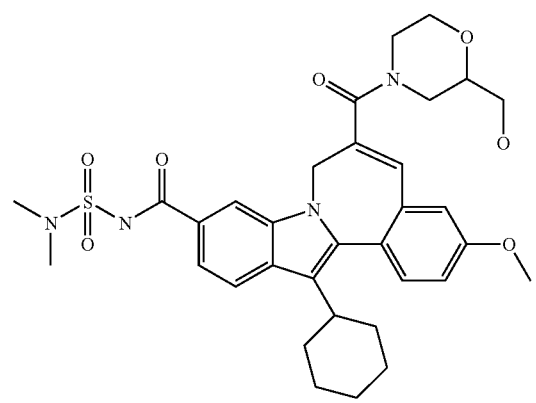
ESI-MS m/z 637 (MH+); 1H NMR (500 MHz, MeOD) δ ppm 1.38-1.82 (m, 4 H) 1.95-2.42 (m, 6 H) 3.04-3.52 (m, 5 H) 3.24-3.27 (m, 6 H) 3.60-3.85 (m, 3 H) 4.15 (s, 3 H) 4.21-4.71 (m, 2 H) 4.54-4.71 (m, 1 H) 5.30-5.46 (m, 1 H) 7.20 (s, 1 H) 7.33 (s, 1 H) 7.38 (dd, J=8.55, 2.44 Hz, 1 H) 7.80 (dd, J=19.84, 8.55 Hz, 2 H) 8.14 (d, J=8.55 Hz, 1 H) 8.35 (s, 1 H).
LCMS: m/z 561 (MH+), ret time 2.64 min.
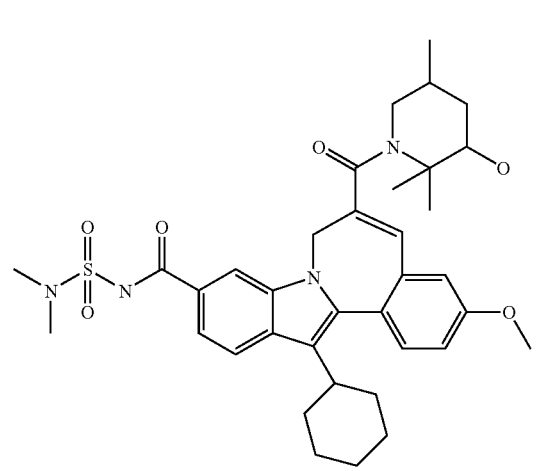
LCMS: m/z 663 (MH+), ret time 2.72 min.
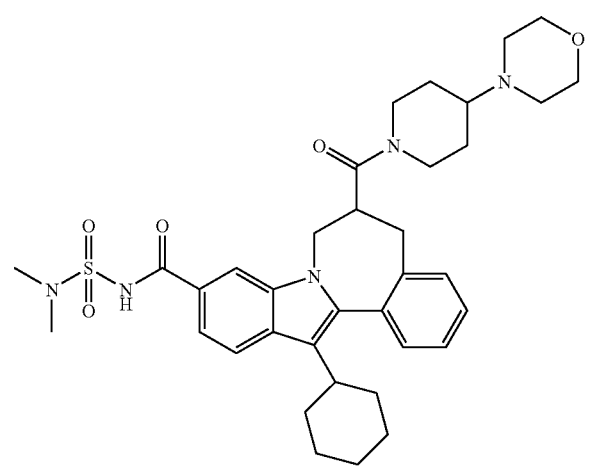
LCMS: m/z 662 (MH+), ret time 1.75 min.

513 514
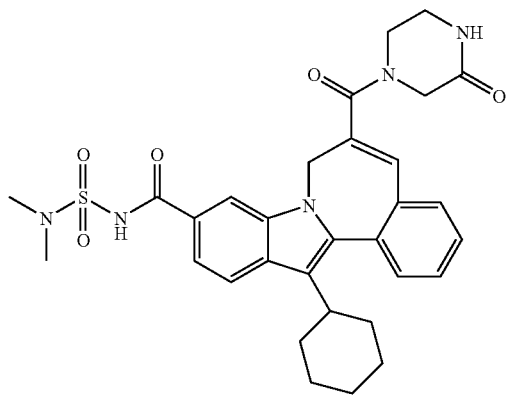
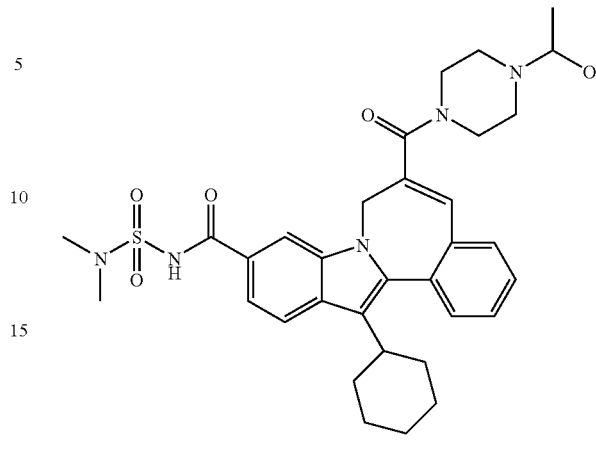
LCMS: m/z 590 (MH+), ret time 2.50 min.
LCMS: m/z 618 (MH+), ret time 2.52 min.
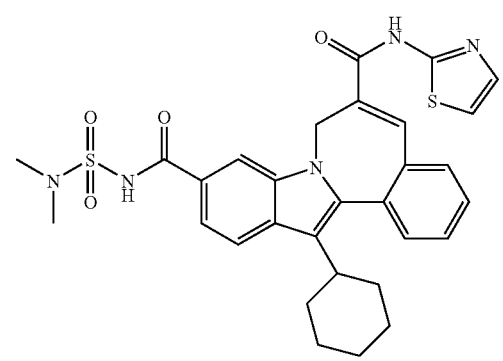
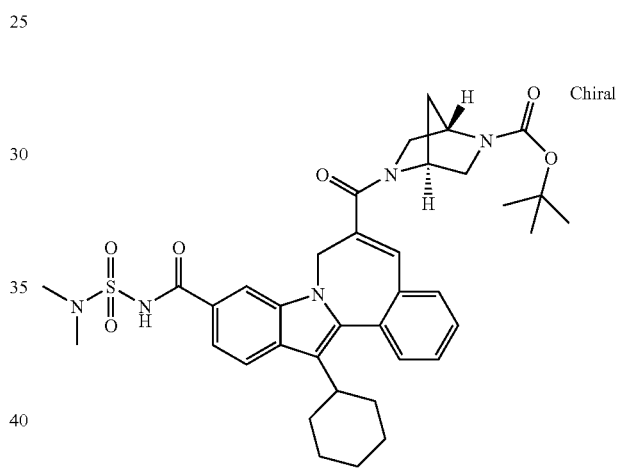
LCMS: m/z 590 (MH+), ret time 2.66 min.
LCMS: m/z 688 (MH+), ret time 2.68 min.
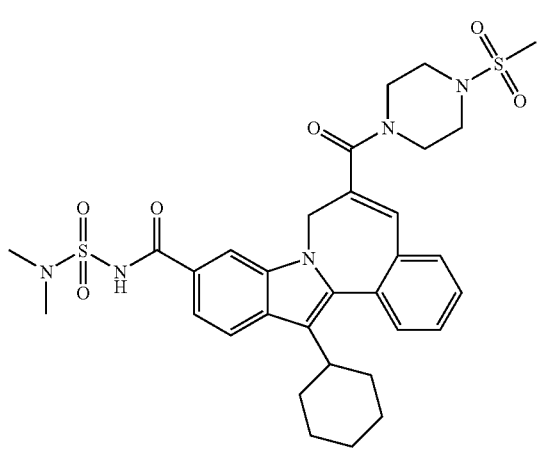
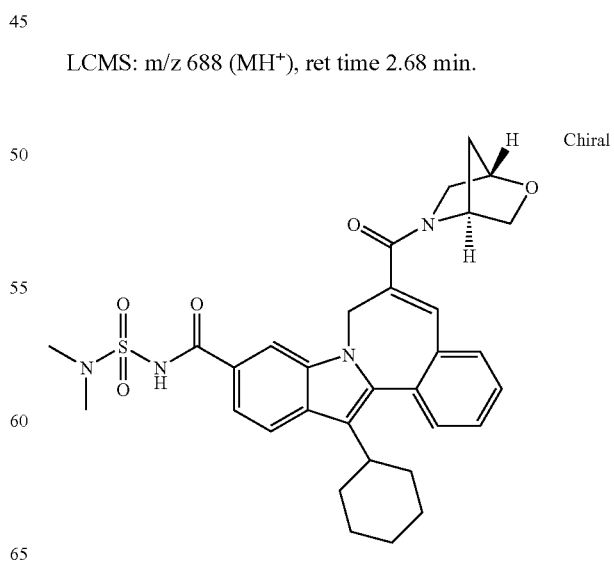
LCMS: m/z 654 (MH+), ret time 2.53 min.
LCMS: m/z 589 (MH+), ret time 2.56 min.

515
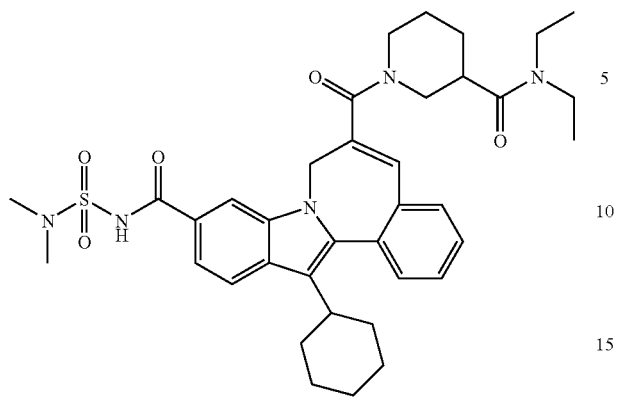
LCMS: m/z 674 (MH+), ret time 2.64 min.
516
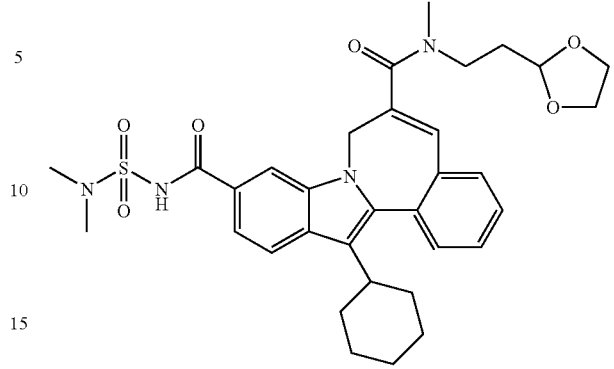
LCMS: m/z 621 (MH+), ret time 2.62 min.
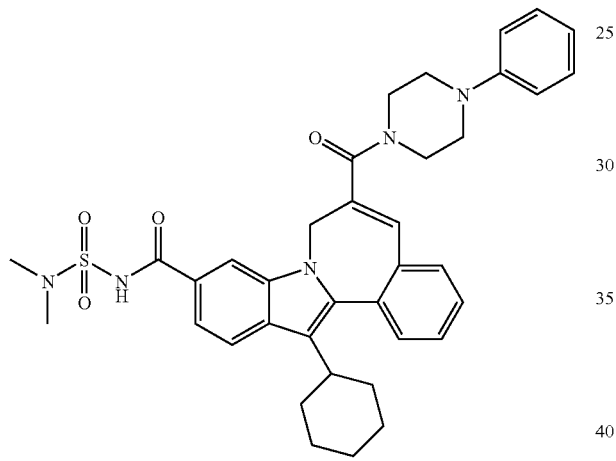
LCMS: m/z 652 (MH+), ret time 2.72 min.
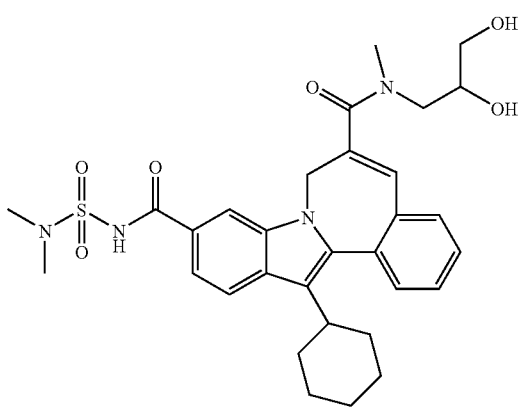
LCMS: m/z 595 (MH+), ret time 2.52 min.
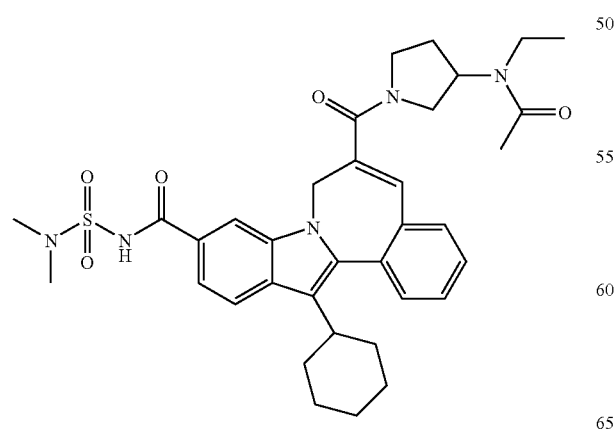
LCMS: m/z 646 (MH+), ret time 2.59 min.
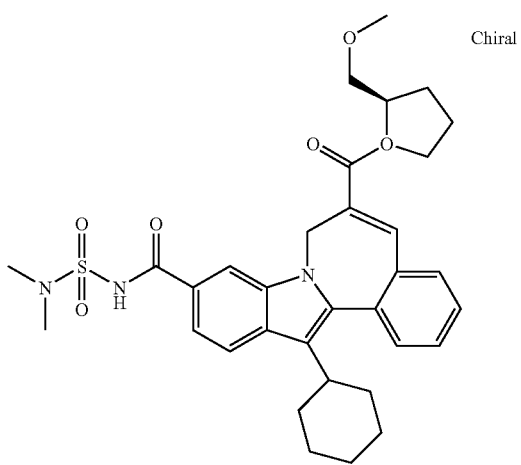
LCMS: m/z 605 (MH+), ret time 2.65 min.

517                                   518
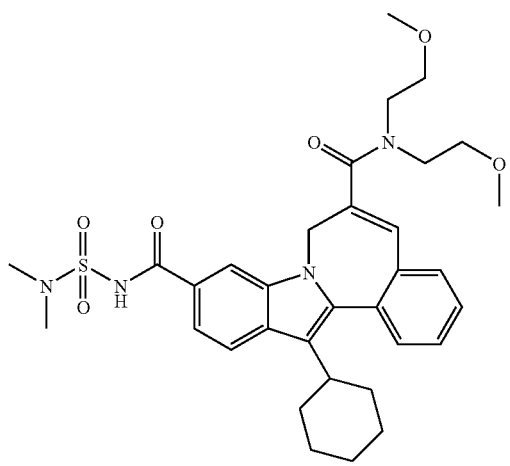
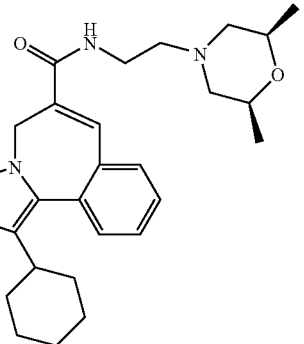
LCMS: m/z 648 (MH+), ret time 2.46 min.
LCMS: m/z 623 (MH+), ret time 2.64 min.
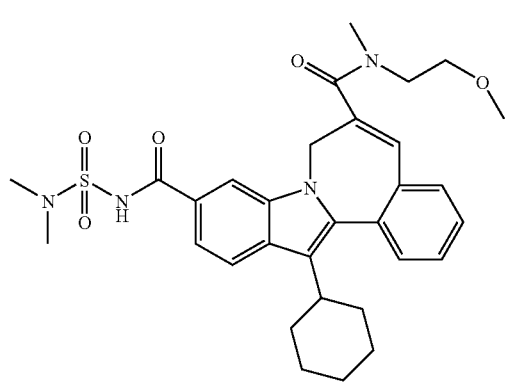
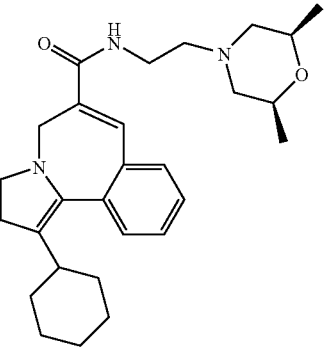
LCMS: m/z 589 (MH+), ret time 2.55 min.
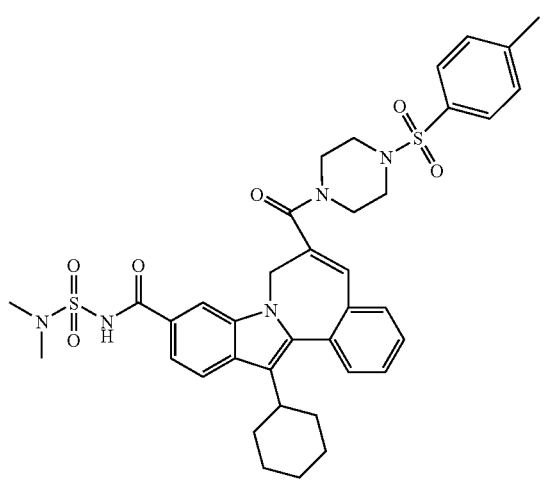
LCMS: m/z 730 (MH+), ret time 2.68 min.     LCMS: m/z 584 (MH+), ret time 2.47 min.

519 520
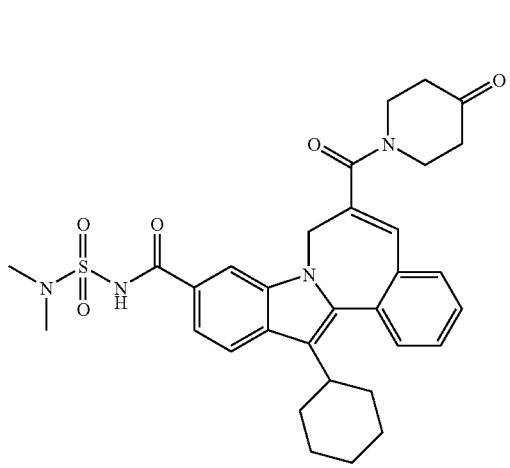
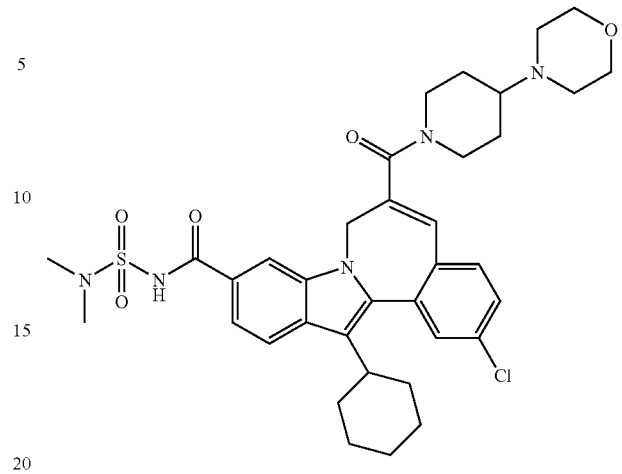
LCMS: m/z 589 (MH+), ret time 1.91 min.
ESI-MS m/z 695 (MH+); 1H NMR (500 MHz, MeOD) δ ppm 1.27-1.58 (m, 6 H) 1.61-1.73 (m, 1 H) 1.78-2.23 (m, 8 H) 2.83-2.92 (m, 2 H) 2.93-3.01 (m, 2 H) 3.04 (s, 6 H) 3.14-3.30 (m, 6 H) 3.36-3.48 (m, 1 H) 3.72-3.84 (m, 1 H) 4.08-4.19 (m, 1 H) 4.49 (s, 1 H) 5.22 (s, 1 H) 7.02 (s, 1 H) 7.54-7.61 (m, 2 H) 7.62-7.66 (m, 2 H) 8.02 (d, J=8.85 Hz, 1 H) 8.18 (s, 1 H).
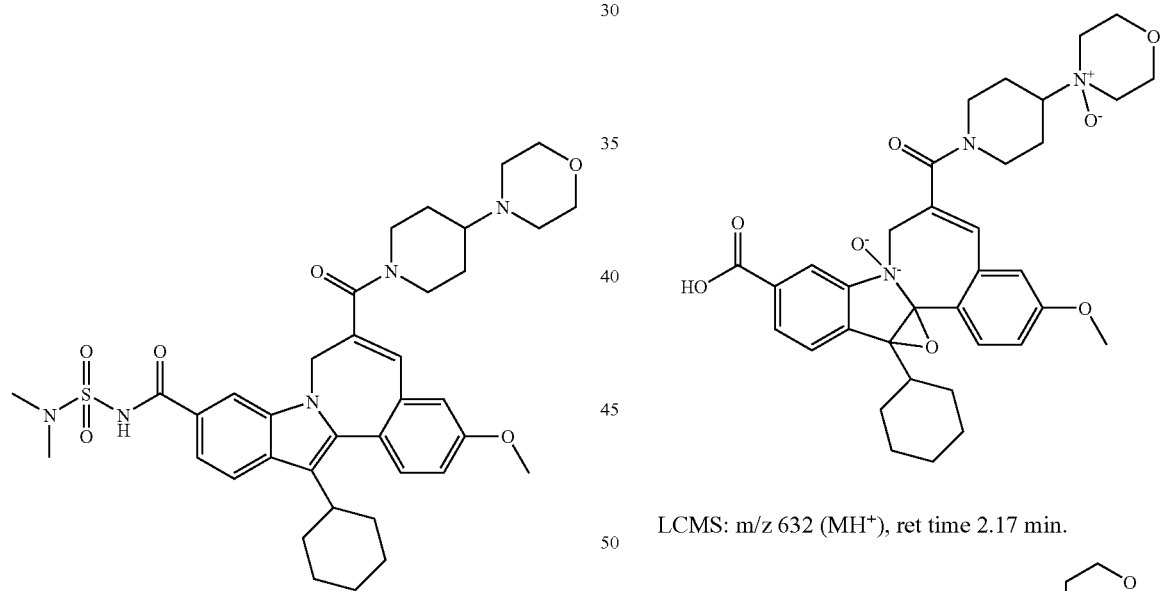
LCMS: m/z 632 (MH+), ret time 2.17 min.
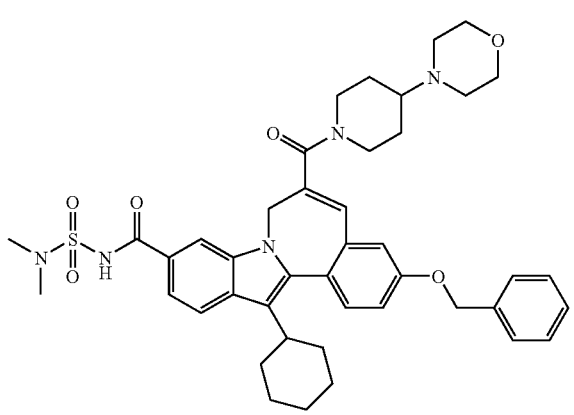
ESI-MS m/z 690 (MH+); 1H NMR (500 MHz, MeOD) δ ppm 1.19-1.56 (m, 6 H) 1.59-1.72 (m, 1 H) 1.75-2.20 (m, 8 H) 2.84-3.00 (m, 3 H) 3.03 (s, 6 H) 3.07-3.31 (m, 5 H) 3.36-3.49 (m, 1 H) 3.67-3.85 (m, 2 H) 3.94 (s, 3 H) 4.04-4.20 (m, 2 H) 4.42-4.51 (m, 1 H) 5.13-5.24 (m, 1 H) 6.99 (s, 1 H) 7.05-7.11 (m, 1 H) 7.16-7.22 (m, 1 H) 7.57-7.63 (m, 2 H) 7.97 (d, J=8.55 Hz, 1 H) 8.15 (s, 1 H).
LCMS: m/z 766 (MH+), ret time 2.03 min.

521
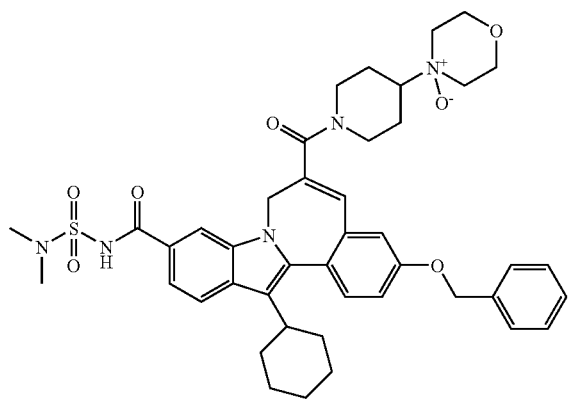
LCMS: m/z 782 (MH⁺), ret time 1.99 min.
522
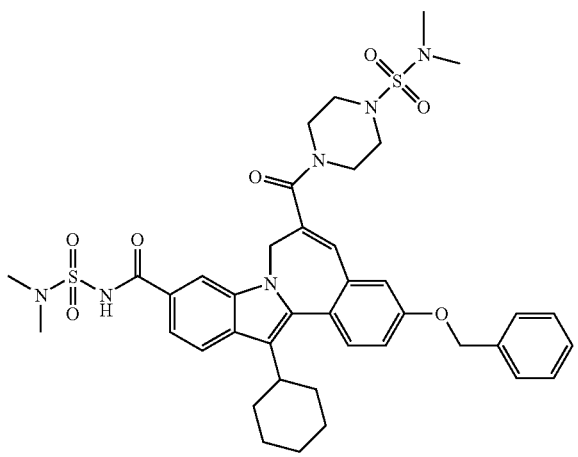
LCMS: m/z 789 (MH⁺), ret time 2.23 min.
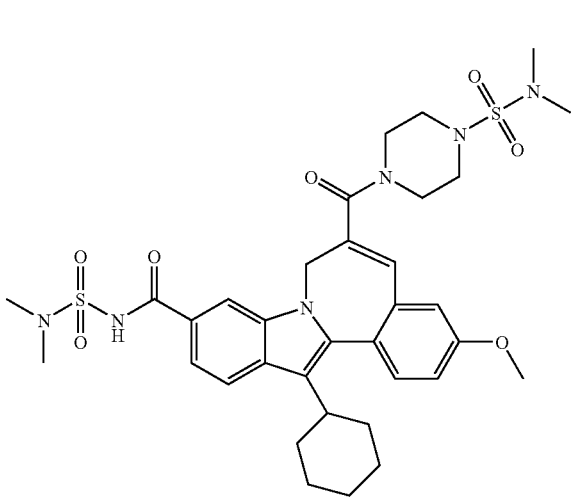
LCMS: m/z 713 (MH⁺), ret time 2.07 min.
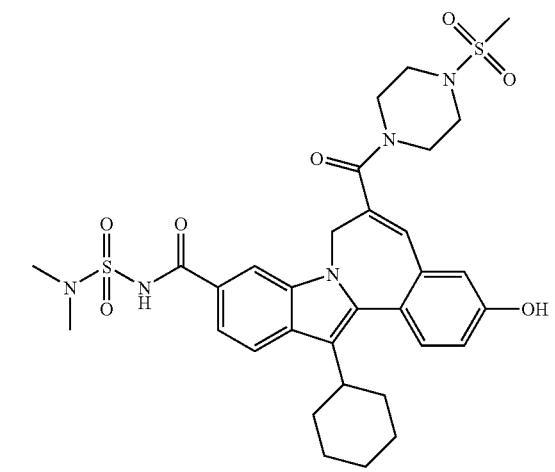
LCMS: m/z 670 (MH⁺), ret time 1.86 min.
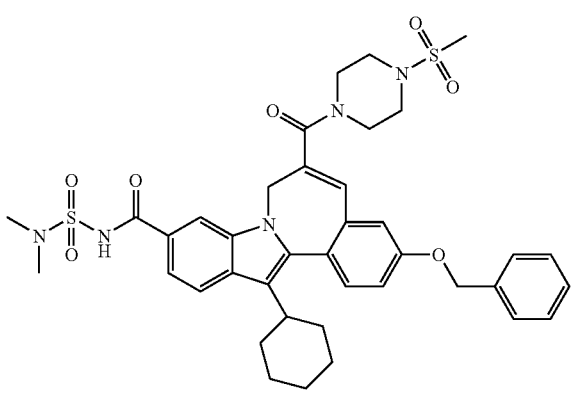
LCMS: m/z 760 (MH⁺), ret time 2.21 mm
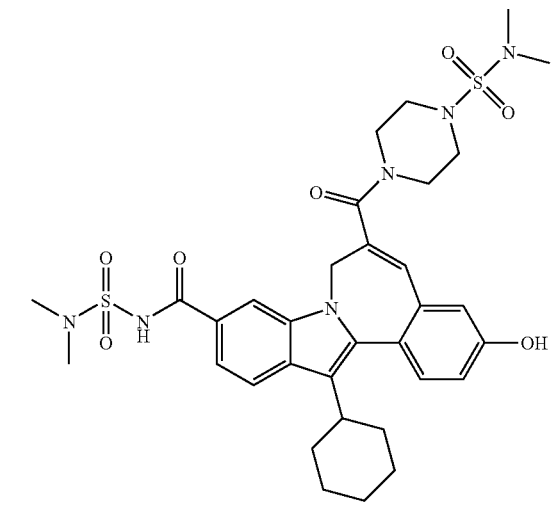
LCMS: m/z 699 (MH⁺), ret time 1.91 min.

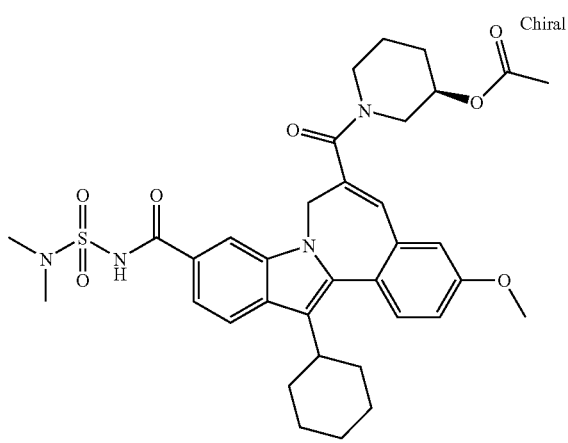

LCMS: m/z 663 (MH⁺), ret time 2.07 min.

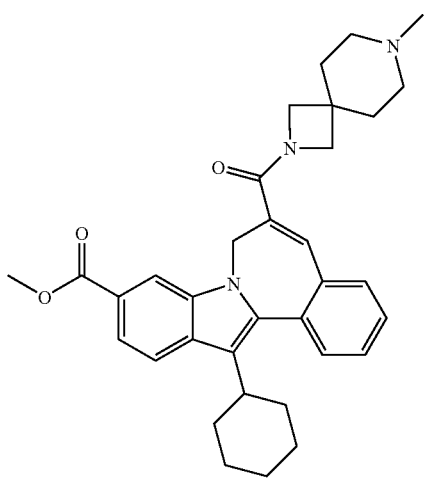

LCMS: m/z 538 (MH⁺), ret time 2.41 min.

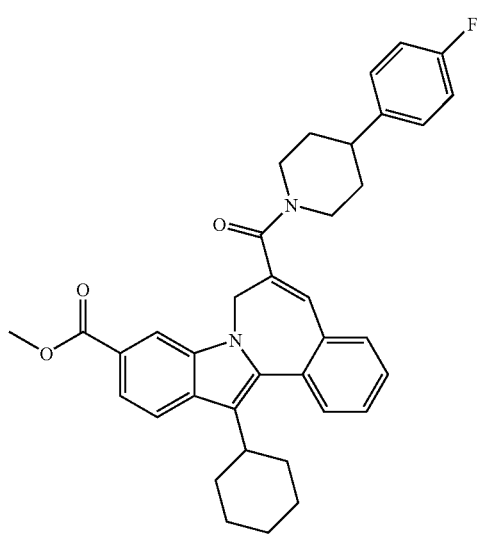

The Liquid chromatography and Mass spectrometry conditions which follow pertain to the following procedures until noted: LCMS: m/z 575 (MH⁺), ret time 2.73 min LCMS data: Gradient time: 2 min; Flow rate: 4 mL/min; Stop time: Gradient time+1 minute; Starting conc: 0% B; Eluent A: 10% MeOH/90% H₂O with 0.1% TFA; Eluent B: 90% MeOH/10% H₂O with 0.1% TFA; Column 3: Phenomenex-luna 10 4.6×50 mm S10.

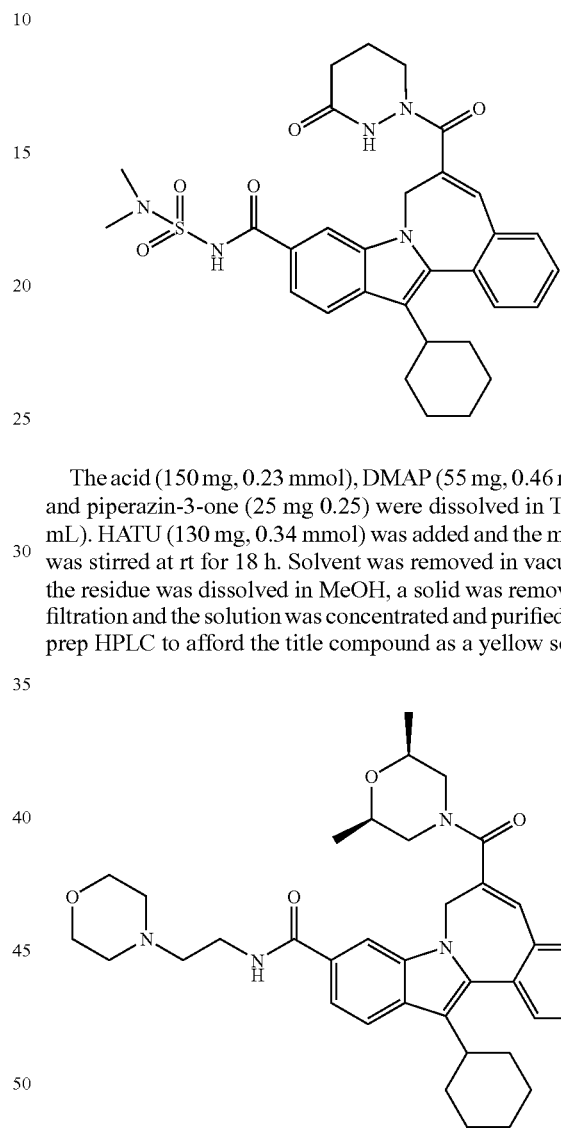

The acid (150 mg, 0.23 mmol), DMAP (55 mg, 0.46 mmol) and piperazin-3-one (25 mg 0.25) were dissolved in THF (3 mL). HATU (130 mg, 0.34 mmol) was added and the mixture was stirred at rt for 18 h. Solvent was removed in vacuo and the residue was dissolved in MeOH, a solid was removed by filtration and the solution was concentrated and purified using prep HPLC to afford the title compound as a yellow solid.

13-cyclohexyl-6-[[(2R,6S)-2,6-dimethyl-4-morpholinyl] carbonyl]-N-[2-(4-morpholinyl)ethyl]-7H-indolo[2,-a][2] benzazepine-10-carboxamide. The title compound was prepared as described above for 13-Cyclohexyl-6-(2,6-dimethyl-4-morpholinylcarbonyl)-5H-indolo[2,1-a][2] benzazepine-N-(2-hydroxyethyl)-10-carboxamide using aminoethylmorpholino as the amine counterpart. After prep HPLC the title compound was obtained as a yellow solid. ¹HNMR (500 MHz, DMSO) δ 9.74 (bs, 1H), 8.70 (m, 1H), 8.17 (s, 1H), 7.91 (d, J=8.5 Hz, 1H), 7.57 (m, 4H), 6.96 (s, 1H), 5.08 (br s, 1H), 4.37 (br s, 1H), 4.03 (m, 2H), 3.78-3.58 (m, 8H), 3.19 (m, 2H), 2.77 (m, 1H), 2.54 (m, 6H), 2.10-1.0 (m, 16 H). LCMS: m/e 611 (M+H)⁺, ret time 2.00 min, column 3, 2 minute gradient.

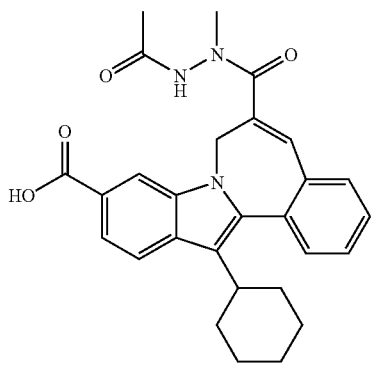

13-cyclohexyl-7H-indolo[2,1-a][2]benzazepine-6,10-dicarboxylic acid, 6-(2-acetyl-1-methylhydrazide). A mixute of 13-cyclohexyl-6-(carboxy)-5H-indolo[2,1-a][2]benzazepine-10-carboxylate (200 mg, 0.48 mmol), DMAP (117 mg, 0.96 mmol) and N'-methylacetohydrazide (84 mg, 0.96 mmol) in THF (10 mL) was treated with HATU (366 mg, 0.96 mmol) and stirred at rt for 1 h. Solvent was removed in vacuo and AcOEt (25 mL) and H$_2$O (25 mL) were added. The organic layer was separated and dried over Na$_2$SO$_4$. The residue was dissolved in 5 mL of MeOH and 5 mL of THF. NaOH (1N, 1.44 mL) was added and the mixture was heated at 70° C. for 18 h, then NaOH (1N, 2 mL) was added and the temperature was raised to 80° C. After 1 h, the reaction was cooled to rt and quenched with HCl (1N). Volatiles were removed in vacuo, the solid was dissolved in DMF/MeOH and purified using prep HPLC to afford the title compound as a yellow solid (83 mg). $^1$HNMR (500 MHz, DMSO) δ 8.20 (s, 1H), 7.94 (d, J=8.5 Hz, 1H), 7.65-7.52 (m, 5H), 7.21 (br s, 1H), 5.15 (br s, 1H), 4.37 (br s, 1H), 3.05 (s, 6H), 2.75 (m, 1H), 2.10-1.15 (m, 10H). LCMS: m/e 472 (M+H)$^+$, ret time 2.23 min, column 3, 2 minute gradient.

solid (20 mg). $^1$HNMR (500 MHz, DMSO) δ 8.43 (br s, 1H), 7.95 (d, J=8.5 Hz, 1H), 7.70-7.60 (m, 5H), 7.18 (br s, 1H), 5.23 (br s, 1H), 4.25 (br s, 1H), 3.05 (s, 3H), 2.97 (s, 6H), 2.75 (m, 1H), 2.10-1.15 (m, 10H). LCMS: m/e 578 (M+H)$^+$, ret time 2.18 min, column 3, 2 minute gradient.

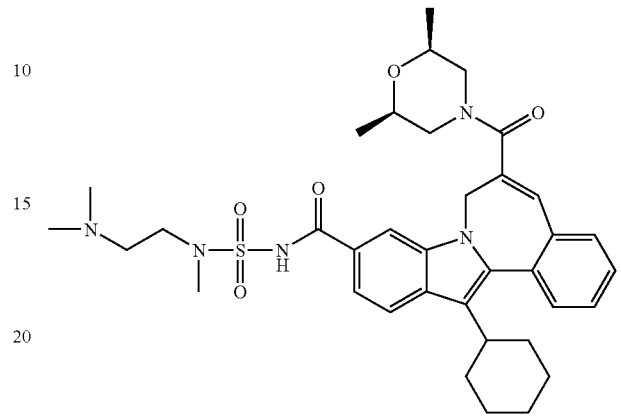

13-cyclohexyl-N-[[[2-(dimethylamino)ethyl]methylamino]sulfonyl]-6-[[(2R,6S)-2,6-dimethyl-4-morpholinyl]carbonyl]-7H-indolo[2,1-a][2]benzazepine-10-carboxamide. The title compound was prepared as described above for 7H-indolo[2,1-a][2]benzazepine-10-carboxamide, 13-cyclohexyl-6-[[(2R,6S)-2,6-dimethyl-4-morpholinyl]carbonyl]-N-[(methylamino)sulfonyl]-, using N,N-dimethylethane-1,2-diamine sulfonylurea. $^1$HNMR (500 MHz, DMSO) δ 9.43 (br s, 1H), 8.51 (br s, 1H), 7.95 (d, J=8.5 Hz, 1H), 7.70-7.60 (m, 5H), 6.95 (br s, 1H), 5.13 (br s, 1H), 4.39 (br s, 1H), 3.38-2.80 (m, 10H), 2.75 (m, 1H), 2.70-1.00 (m, 16H). LCMS: m/e 662 (M+H)$^+$, ret time 2.09 min, column 3, 2 minute gradient.

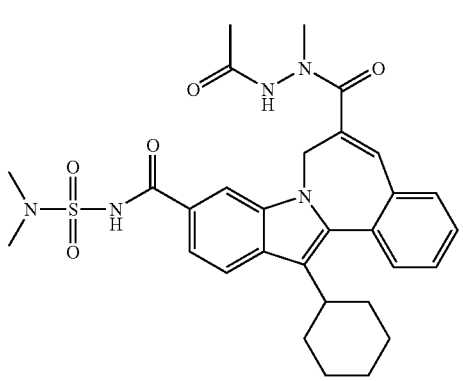

13-cyclohexyl-10-[[[(dimethylamino)sulfonyl]amino]carbonyl]-7H-indolo[2,1-a][2]benzazepine-6-carboxylic acid, 2-acetyl-1-methylhydrazide. 7H-indolo[2,1-a][2]benzazepine-6,10-dicarboxylic acid, 13-cyclohexyl-, 6-(2-acetyl-1-methylhydrazide) (95 mg, 0.2 mmol) was dissolved in THF (2mL), CDI (39 mg, 0.24 mmol) was added and the mixture was heated at 50° C. for 2 h, then cooled at rt. A solution of DBU (42 uL, 0.28 mmol) in THF (0.5 mL) was added dropwise, followed by dimethylsulfonyl amide (30 mg, 0.24 mmol). The mixture was heated at 50° C. for 18 h. Volatiles were removed in vacuo and the residue was purified using prep HPLC to afford the title compound as a yellow

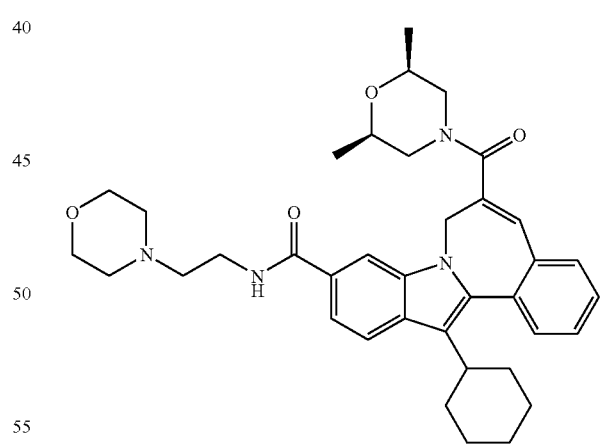

7H-indolo[2,1-a][2]benzazepine-10-carboxamide, 13-cyclohexyl-6-[[(2R,6S)-2,6-dimethyl-4-morpholinyl]carbonyl]-N-[2-(4-morpholinyl)ethyl]-. The title compound was prepared as described above for 13-Cyclohexyl-6-(2,6-dimethyl-4-morpholinylcarbonyl)-5H-indolo[2,1-a][2]benzazepine-N-(2-hydroxyethyl)-10-carboxamide using aminoethylmorpholino as the amine counterpart. After prep HPLC the title compound was obtained as a yellow solid. $^1$HNMR (500 MHz, DMSO) δ 9.74 (bs, 1H), 8.70 (m, 1H), 8.17 (s, 1H), 7.91 (d, J=8.5 Hz, 1H), 7.57 (m, 4H), 6.96 (s, 1H), 5.08

(br s, 1H), 4.37 (br s, 1H), 4.03 (m, 2H), 3.78-3.58 (m, 8H), 3.19 (m, 2H), 2.77 (m, 1H), 2.54 (m, 6H), 2. 10-1.0 (m, 16H). LCMS: m/e 611 (M+H)⁺, ret time 2.00 min, column 3, 2 minute gradient.

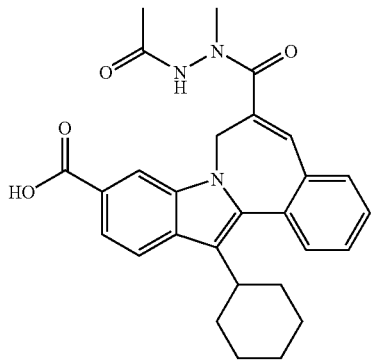

7H-indolo[2,1-a][2]benzazepine-6,10-dicarboxylic acid, 13-cyclohexyl-, 6-(2-acetyl-1-methylhydrazide). A mixute of 13-cyclohexyl-6-(carboxy)-5H-indolo[2,1-a][2]benzazepine-10-carboxylate (200 mg, 0.48 mmol), DMAP (117 mg, 0.96 mmol) and N'-methylacetohydrazide (84 mg, 0.96 mmol) in THF (10 mL) was treated with HATU (366 mg, 0.96 mmol) and stirred at rt for 1 h. Solvent was removed in vacuo and AcOEt (25 mL) and H₂O (25 mL) were added. The organic layer was separated and dried over Na₂SO₄. The residue was dissolved in 5 mL of MeOH and 5 mL of THF. NaOH (1N, 1.44 mL) was added and the mixture was heated at 70° C. for 18 h, then NaOH (1N, 2 mL) was added and the temperature was raised to 80° C. After 1 h, the reaction was cooled to rt and quenched with HCl (1N). Volatiles were removed in vacuo, the solid was dissolved in DMF/MeOH and purified using prep HPLC to afford the title compound as a yellow solid (83 mg). ¹HNMR (500 MHz, DMSO) δ 8.20 (s, 1H), 7.94 (d, J=8.5 Hz, 1H), 7.65-7.52 (m, 5H), 7.21 (br s, 1H), 5.15 (br s, 1H), 4.37 (br s, 1H), 3.05 (s, 6H), 2.75 (m, 1H), 2.10-1.15 (m, 10H). LCMS: m/e 472 (M+H)⁺, ret time 2.23 min, column 3, 2 minute gradient.

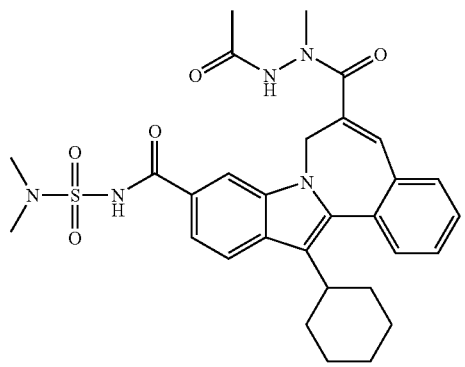

7H-indolo[2,1-a][2]benzazepine-6-carboxylic acid, 13-cyclohexyl-10-[[[(dimethylamino)sulfonyl]amino]carbonyl]-, 2-acetyl-1-methylhydrazide. 7H-indolo[2,1-a][2]benzazepine-6,10-dicarboxylic acid, 13-cyclohexyl-, 6-(2-acetyl-1-methylhydrazide) (95 mg, 0.2 mmol) was dissolved in THF (2mL), CDI (39 mg, 0.24 mmol) was added and the mixture was heated at 50° C. for 2 h, then cooled at rt. A solution of DBU (42 uL, 0.28 mmol) in THF (0.5 mL) was added dropwise, followed by dimethylsulfonyl amide (30 mg, 0.24 mmol). The mixture was heated at 50° C. for 18 h. Volatiles were removed in vacuo and the residue was purified using prep HPLC to afford the title compound as a yellow solid (20 mg). ¹HNMR (500 MHz, DMSO) δ 8.43 (br s, 1H), 7.95 (d, J=8.5 Hz, 1H), 7.70-7.60 (m, 5H), 7.18 (br s, 1H), 5.23 (br s, 1H), 4.25 (br s, 1H), 3.05 (s, 3H), 2.97 (s, 6H), 2.75 (m, 1H), 2.10-1.15 (m, 10H). LCMS: m/e 578 (M+H)⁺, ret time 2.18 min, column 3, 2 minute gradient.

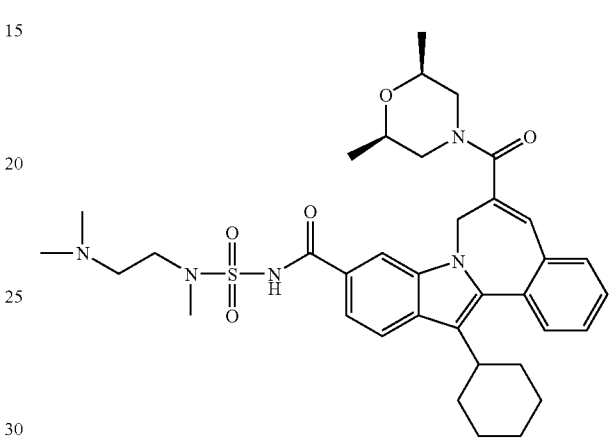

7H-indolo[2,1-a][2]benzazepine-10-carboxamide, 13-cyclohexyl-N-[[[2-(dimethylamino)ethyl]methylamino]sulfonyl]-6-[[(2R, 6S)-2,6-dimethyl-4-morpholinyl]carbonyl]-. The title compound was prepared as described above for 7H-indolo[2,1-a][2]benzazepine-10-carboxamide, 13-cyclohexyl-6-[[(2R,6S)-2,6-dimethyl-4-morpholinyl]carbonyl]-N-[(methylamino)sulfonyl]-, using N,N-dimethylethane-1, 2-diamine sulfonylurea. ¹HNMR (500 MHz, DMSO) δ 9.43 (br s, 1H), 8.51 (br s, 1H), 7.95 (d, J=8.5 Hz, 1H), 7.70-7.60 (m, 5H), 6.95 (br s, 1H), 5.13 (br s, 1H), 4.39 (br s, 1H), 3.38-2.80 (m, 10H), 2.75 (m, 1H), 2.70-1.00 (m, 16H). LCMS: mile 662 (M+H)⁺, ret time 2.09 min, column 3, 2 minute gradient.

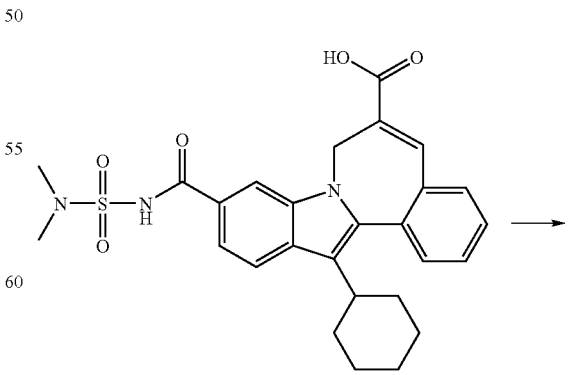

A

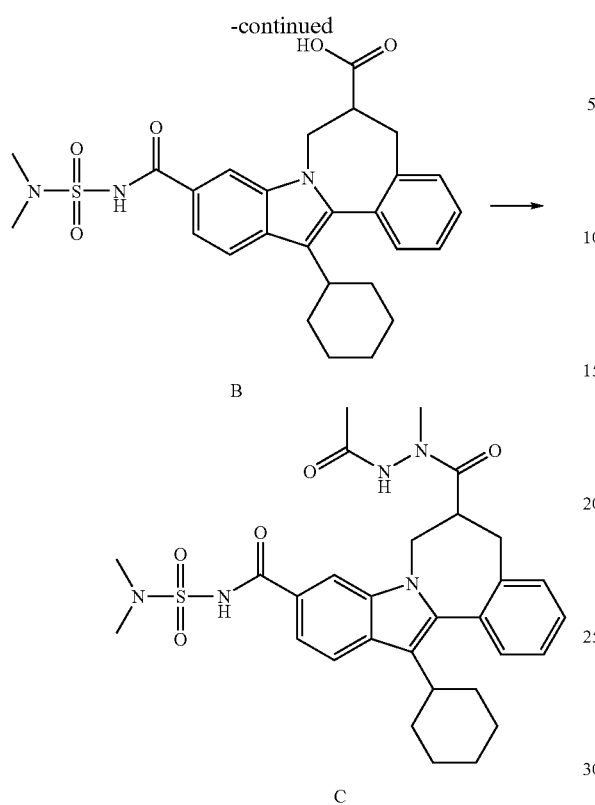

B

C

To a flask containing a solution of compound A (1.2 g, xx mmol) in MeOH (20 mL) was added a catalytic amount of Pd (10% in C) and a balloom filled with H2 was placed on top. The mixture was stirred at rt for 24 h. The catalyst was removed by filtration and the solution was concentrated to afford a pale yellow solid containing compound B (~70% pure) which was used in the next step without further purification. This solid (200 mg, 0.39 mmol) was dissolved in THF (4 mL) and treated with DMAP (143 mg, 1.17 mmol), hydrazine (34 mg, 0.39 mmol) and HATU (222 mg, 0.58 mmol). The mixture was stirred at rt for 18 h. Solvent was removed in vacuo and H2O was added. The solid was collected by filtration and purified using reverse phase prep HPLC to afford the title compound C as a pale yellow solid (28 mg). $^1$HNMR (500 MHz, DMSO) δ 8.45 (br s, 1H), 8.09 (m, 1H), 7.95 (d, J=8.5 Hz, 1H), 7.70-7.40 (m, 5H), 4.7 (m, 1H), 3.05 (d, J=12.0 Hz, 3H), 3.05 (s, 6H), 2.97 (m, 1H), 2.1(s, 3H), 2.10-1.15 (m, 10H). LCMS: m/e 580 (M+H)$^+$, ret time 2.25 min, column 3, 2 minute gradient.

The general methods described below pertain to the experimental procedures below until further noted: LCMS data: Stop time: Gradient time+1 minute; Starting conc: 0% B unless otherwise noted; Eluent A: 5% CH$_3$CN/95% H$_2$O with 10 mM NH$_4$OAc (for columns A, D and E); 10% MeOH/90% H$_2$O with 0.1% TFA (for columns B and C); Eluent B: 95% CH$_3$CN/5% H$_2$O with 10 mM NH$_4$OAc (for columns A, D and E); 90% MeOH/10% H$_2$O with 0.1% TFA (for columns B and C); Column A: Phenomenex 10 μ 4.6×50 mm C18; Column B: Phenomenex C18 10 μ 3.0×50 mm; Column C: Phenomenex 4.6×50 mm C18 10; Column D: Phenomenex Lina C18 513.0×50 mm; Column E:Phenomenex 5μ 4.6×50 mm C18.

Preparative HPLC data: Gradient: Linear over 20 min. unless otherwise noted; Starting conc: 15% B unless otherwise noted; Ending conc: 100% B; Eluent A: 5% CH3CN/ 95% H2O with 10 mM NH4OAc; Eluent B: 95% CH3CN/5% H2O with 10 mM NH4OAc; Column: Sunfire Prep C18 OBD 5130×100 mm.

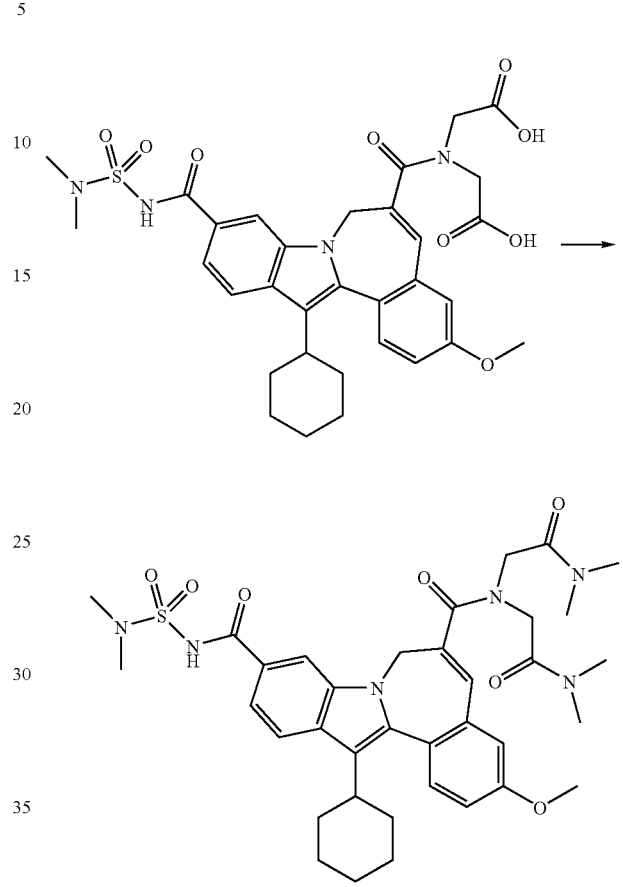

7H-Indolo[2,1-a][2]benzazepine-6,10-dicarboxamide, 13-cyclohexyl-N6,N6-bis[2-(dimethylamino)-2-oxoethyl]-N10-[(dimethylamino)sulfonyl]-3-methoxy-. To a stirred solution of glycine, N-(carboxymethyl)-N-[[13-cyclohexyl-10-[[[(dimethylamino)sulfonyl]amino]carbonyl]-3-methoxy-7H-indolo[2,1-a][2]benzazepin-6-yl]carbonyl]- (43 mg, 0.066 mmol), dimethylamine (2M in THF, 0.13 mL, 0.26 mmol) and triethylamine (0.037 mL) in DMF (1 mL) was added HATU (75 mg, 0.20 mmol). The reaction mixture was stirred at rt for 2 h, and additional dimethylamine (2M in THF, 0.10 mL, 0.20 mmol) and HATU (70 mg, 0.18 mmol) were added. The reaction was stirred at rt overnight, diluted with H2O (~10 mL), acidified with 1N HCl(aq.) (~0.25 mL) and the precipitate was collected by filtration and flushed with H2O to yield 7H-indolo[2,1-a][2]benzazepine-6,10-dicarboxamide, 13-cyclohexyl-N6,N6-bis[2-(dimethylamino)-2-oxoethyl]-N10-[(dimethylamino)sulfonyl]-3-methoxy- (31 mg, 0.044 mmol, 67%) as a yellow solid. 1HNMR (300 MHz, CD3OD) δ 8.22 (d, J=1.5 Hz, 1H), 7.93 (d, J=8.8 Hz, 1H), 7.62 (dd, J=1.5, 8.8 Hz, 1H), 7.56 (d, J=8.8 Hz, 1H), 7.16 (dd, J=2.6, 8.8 Hz, 1H), 7.03 (br s, 1H), 7.02 (d, J=2.6 Hz, 1H), 5.27-5.09 (m, 1H), 4.49-4.28 (m, 3H), 4.15-4.02 (m, 1H), 3.93 (s, 3H), 3.90-3.77 (m, 1H), 3.07 (s, 3H), 3.04 (s, 6H), 2.98-2.83 (m, 1H), 2.54 (s, 3H), 2.37 (s, 3H), 2.20-1.19 (m, 10H). LCMS: m/e 705 (M–H)–, ret time 2.67 min, column A, 4 minute gradient.

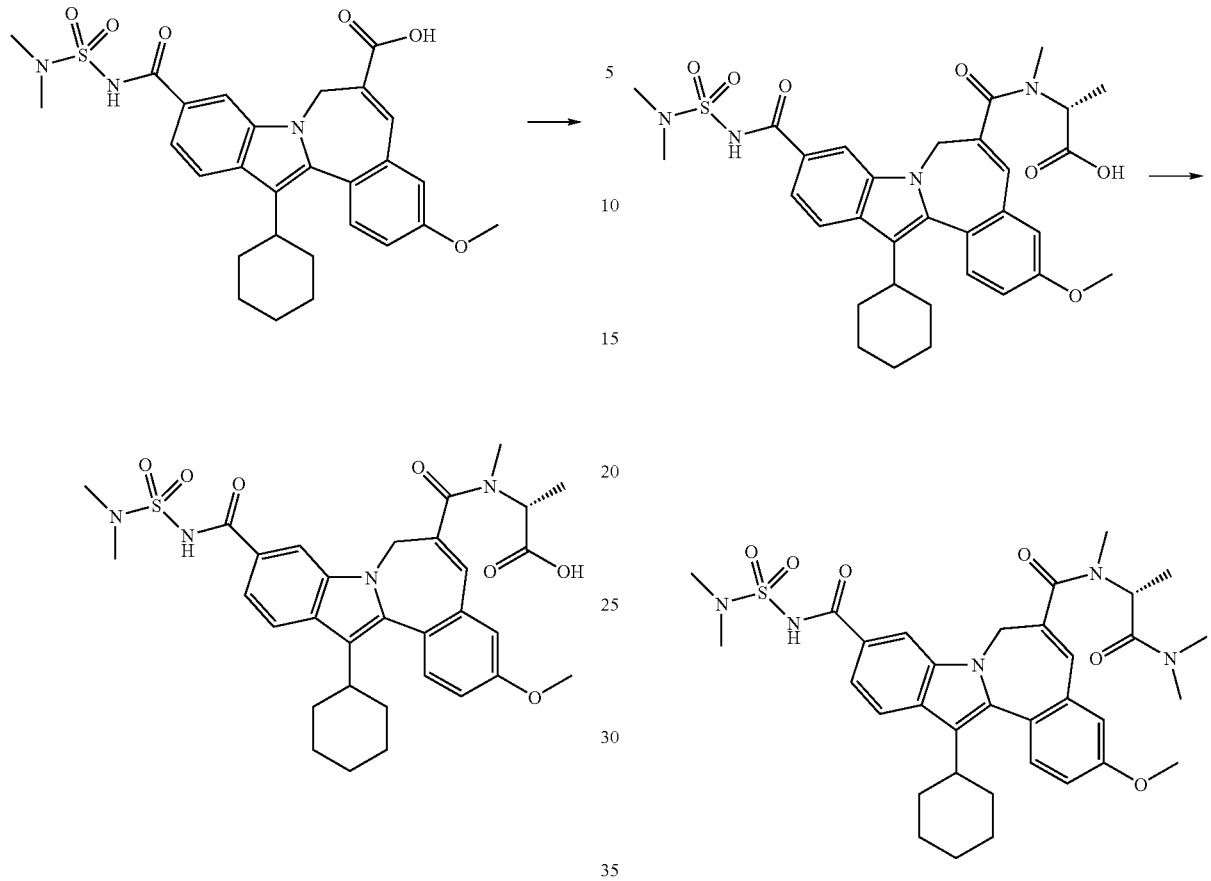

D-alanine, N-[[13-cyclohexyl-10-[[[(dimethylamino)sulfonyl]amino]carbonyl]-3-methoxy-7H-indolo[2,1-a][2]benzazepin-6-yl]carbonyl]-N-methyl-. To a stirred solution of 13-cyclohexyl-N-[(dimethylamino)sulfonyl]-3-methoxy-7H-indolo[2,1-a][2]benzazepine-10-carboxamide-6-carboxylic acid (150 mg, 0.28 mmol), (R)-methyl 2-(methylamino)propanoate hydrochloride (64 mg, 0.42 mmol) and triethylamine (0.16 mL) in DMF (2 mL) was added HATU (137 mg, 0.36 mmol). The reaction mixture was stirred at rt for 2.5 h, diluted with $H_2O$ (~10 mL), acidified with 1M HCl (aq.). (~0.5 mL) and the precipitate was collected by filtration and flushed with $H_2O$. To a solution of the yellow solids in THF/MeOH (1:1, 3 mL) was added 1M NaOH (aq.) (0.6 mL, 0.6 mmol). The reaction solution was heated in a sealed tube with microwave irradiation at 70° C. for 20 min. The reaction was cooled, neutralized with 1M HCl (aq.) (0.6 mL, 0.6 mmol) and concentrated to remove organic solvents. The residue was slurried with $H_2O$ and the solids were collected by filtration and washed with $H_2O$ to yield D-alanine, N-[[13-cyclohexyl-10-[[[(dimethylamino)sulfonyl]amino]carbonyl]-3-methoxy-7H-indolo[2,1-a][2]benzazepin-6-yl]carbonyl]-N-methyl- (154 mg, 0.25 mmol, 89%) as a yellow solid. $^1$HNMR (300 MHz, $CD_3OD$) δ 8.12 (s, 1H), 7.93 (d, J=8.4 Hz, 1H), 7.63-7.54 (m, 2H), 7.16 (dd, J=2.7, 8.6 Hz, 1H), 7.14-6.99 (m, 2H), 5.25-5.02 (m, 1H), 4.62-4.33 (m, 2H), 3.93 (s, 3H), 3.03 (s, 6H), 3.01-2.82 (m, 4H), 2.21-1.20 (m, 10H). LCMS: m/e 621 (M–H)$^-$, ret time 2.07 min, column A, 4 minute gradient.

7H-Indolo[2,1-a][2]benzazepine-6,10-dicarboxamide, 13-cyclohexyl-$N^6$-[(1R)-2-(dimethylamino)-1-methyl-2-oxoethyl]-$N^{10}$-[(dimethylamino)sulfonyl]-3-methoxy-$N^6$-methyl-. To a stirred solution of D-alanine, N-[[13-cyclohexyl-10-[[[(dimethylamino)sulfonyl]amino]carbonyl]-3-methoxy-7H-indolo[2,1-a][2]benzazepin-6-yl]carbonyl]-N-methyl- (50 mg, 0.08 mmol), dimethylamine (2M in THF, 0.080 mL, 0.16 mmol) and triethylamine (0.05 mL) in DMF (1.5 mL) was added HATU (46 mg, 0.12 mmol). The reaction mixture was stirred at rt for 2 h, diluted with $H_2O$ (~10mL), acidified with 1M HCl (aq.) (~0.50 mL), stirred 30 min. and the precipitate was collected by filtration and flushed with $H_2O$. The solids were dissolved into MeOH and purified by preparative HPLC ($CH_3CN/H_2O$ with 10 mM $NH_4OAc$) to yield 7H-indolo[2,1-a][2]benzazepine-6,10-dicarboxamide, 13-cyclohexyl-$N^6$-[(1R)-2-(dimethylamino)-1-methyl-2-oxoethyl]-$N^{10}$-[(dimethylamino)sulfonyl]-3-methoxy-$N^6$-methyl- (28 mg, 0.043 mmol, 54%) as a yellow solid. $^1$HNMR (300 MHz, $CDCl_3$) δ 10.10-9.41 (m, 1H), 8.07 (s, 1H), 7.86 (d, J=8.8 Hz, 1H), 7.71-7.55 (m, 1H), 7.49 (d, J=8.4 Hz, 1H), 7.03 (dd, J=2.6, 8.4 Hz, 1H), 6.89 (d, J=2.6 Hz, 1H), 6.78-6.61 (m, 1H), 5.37-5.02 (m, 1H), 4.96-4.79 (m, 1H), 4.46-4.27 (m, 1H), 3.88 (s, 3H), 3.19-2.71 (m, 7H), 3.02 (s, 6H), 2.49-1.09 (m, 16H). LCMS: m/e 648 (M–H)$^-$, ret time 2.82 min, column A, 4 minute gradient.

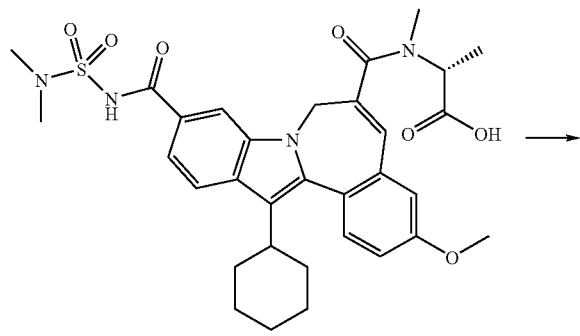

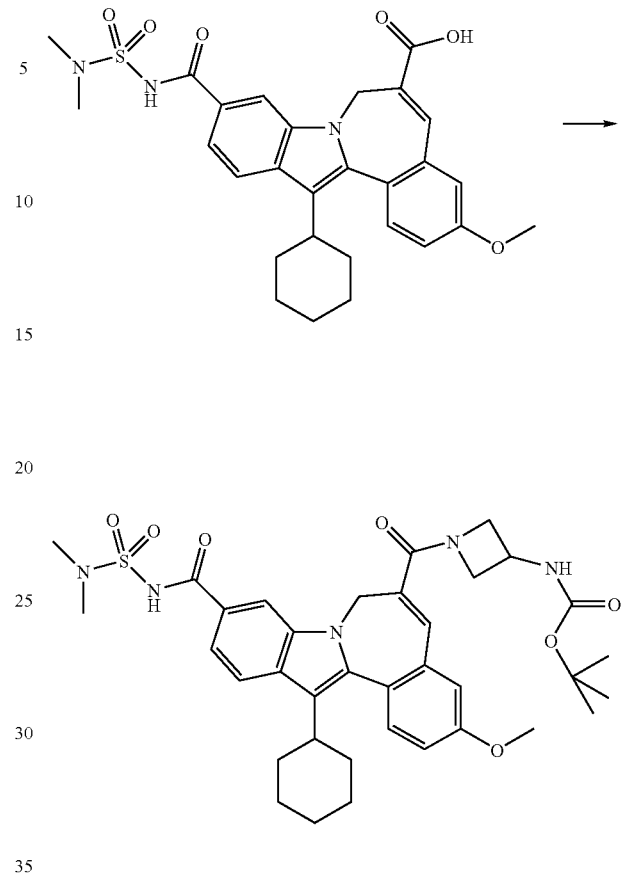

7H-Indolo[2,1-a][2]benzazepine-6,10-dicarboxamide, 13-cyclohexyl-N[10]-[(dimethylamino)sulfonyl]-3-methoxy-N[6]-methyl-N[6]-[(1R)-1-methyl-2-(4-morpholinyl)-2-oxoethyl]-. To a stirred solution of D-alanine, N-[[13-cyclohexyl-10-[[[(dimethylamino)sulfonyl]amino]carbonyl]-3-methoxy-7H-indolo[2,1-a][2]benzazepin-6-yl]carbonyl]-N-methyl- (50 mg, 0.08 mmol), morpholine (14 mg, 0.16 mmol) and triethylamine (0.05 mL) in DMF (1.5 mL) was added HATU (46 mg, 0.12 mmol). The reaction mixture was stirred at rt for 2 h, diluted with $H_2O$ (~10 mL), acidified with 1M HCl (aq.) (~0.50 mL), stirred 30 min. and the precipitate was collected by filtration and flushed with $H_2O$. The solids were dissolved into MeOH and purified by preparative HPLC ($CH_3CN/H_2O$ with 10 mM $NH_4OAc$) to yield 7H-indolo[2,1-a][2]benzazepine-6,10-dicarboxamide, 13-cyclohexyl-N[10]-[(dimethylamino)sulfonyl]-3-methoxy-N[6]-methyl-N[6]-[(1R)-1-methyl-2-(4-morpholinyl)-2-oxoethyl]- (26 mg, 0.038 mmol, 47%) as a yellow solid. $^1$HNMR (300 MHz, $CDCl_3$) δ 8.07 (br s, 1H), 7.87 (d, J=8.8 Hz, 1H), 7.70-7.57 (m, 1H), 7.50 (d, J=8.8 Hz, 1H), 7.03 (dd, J=2.6, 8.8 Hz, 1H), 6.88 (d, J=2.6 Hz, 1H), 6.74-6.62 (m, 1H), 5.32-5.12 (m, 1H), 4.97-4.82 (m, 1H), 4.47-4.29 (m, 1H), 3.88 (s, 3H), 3.90-2.72 (m, 9H), 3.02 (s, 6H), 2.52-1.10 (m, 16H). LCMS: m/e 690 (M−H)$^-$, ret time 2.82 min, column A, 4 minute gradient.

Carbamic acid, [1-[[13-cyclohexyl-10-[[[(dimethylamino)sulfonyl]amino]carbonyl]-3-methoxy-7H-indolo[2,1-a][2]benzazepin-6-yl]carbonyl]-3-azetidinyl]-, 1,1-dimethylethyl ester. To a stirred solution of 13-cyclohexyl-N-[(dimethylamino)sulfonyl]-3-methoxy-7H-indolo[2,1-a][2]benzazepine-10-carboxamide-6-carboxylic acid (300 mg, 0.56 mmol), tert-butyl azetidin-3-ylcarbamate (192 mg, 1.2 mmol) and triethylamine (0.33 mL) in DMF (3 mL) was added HATU (320 mg, 0.84 mmol). The reaction mixture was stirred at rt for 3 h, additional tert-butyl azetidin-3-ylcarbamate (100 mg, 0.58 mmol) and HATU (120 mg, 0.32 mmol) were added and the reaction mixture was stirred at rt for 2 h and then diluted with $H_2O$ and stirred. The resulting precipitate was collected by filtration, flushed with $H_2O$, dissolved into MeOH and purified by preparative HPLC ($CH_3CN/H_2O$ with 10 mM $NH_4OAc$) to yield carbamic acid, [1-[[13-cyclohexyl-10-[[[(dimethylamino)sulfonyl]amino]carbonyl]-3-methoxy-7H-indolo[2,1-a][2]benzazepin-6-yl]carbonyl]-3-azetidinyl]-, 1,1-dimethylethyl ester (282 mg, 0.041 mmol, 73%) as a yellow solid. $^1$HNMR (300 MHz, $CDCl_3$) δ 8.23 (br s, 1H), 7.84 (d, J=8.8 Hz, 1H), 7.54 (d, J=8.4 Hz, 1H), 7.47 (d, J=8.4 Hz, 1H), 7.04 (dd, J=2.6, 8.8 Hz, 1H), 6.97 (br s, 1H), 6.86 (d, J=2.6 Hz, 1H), 5.66-5.42 (m, 1H), 4.56-3.83 (m, 6H), 3.89 (s, 3H), 3.01 (s, 6H), 2.87-2.72 (m, 1H), 2.12-1.08 (mm, 11H), 1.40 (s, 9H). LCMS: m/e 690 (M−H)$^-$, ret time 3.26 min, column A, 4 minute gradient.

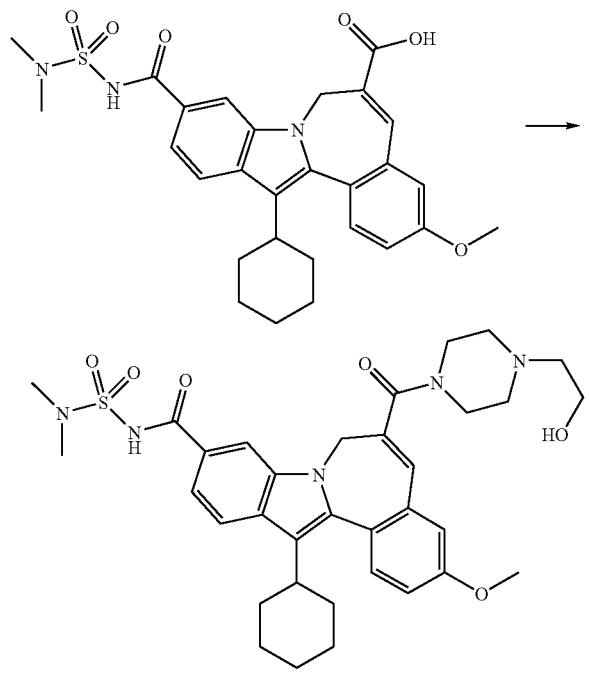

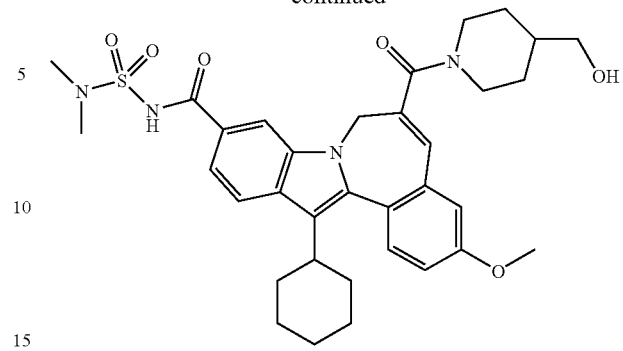

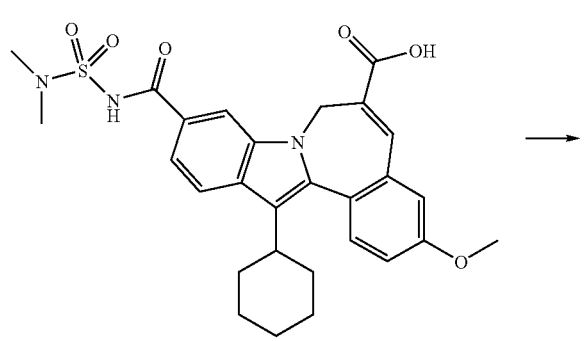

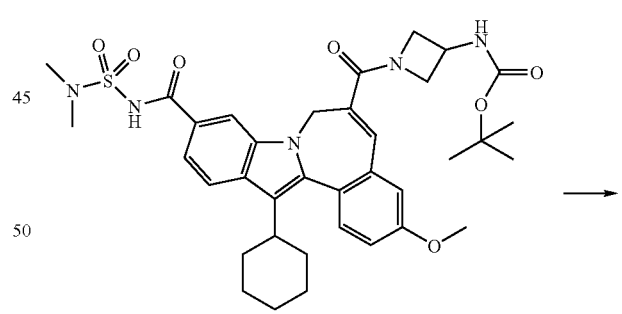

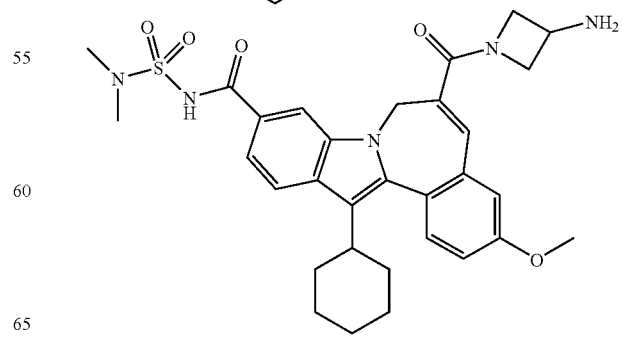

7H-Indolo[2,1-a][2]benzazepine-10-carboxamide, 13-cyclohexyl-N-[(dimethylamino)sulfonyl]-6-[[4-(2-hydroxyethyl)-1-piperazinyl]carbonyl]-3-methoxy-. To a stirred solution of 13-cyclohexyl-N-[(dimethylamino)sulfonyl]-3-methoxy-7H-indolo[2,1-a][2]benzazepine-10-carboxamide-6-carboxylic acid (100 mg, 0.19 mmol), 2-(piperazin-1-yl)ethanol (44 mg, 0.34 mmol) and triethylamine (0.12 mL) in DMF (1.0 mL) was added HATU (99 mg, 0.26 mmol). The reaction mixture was stirred at rt for 2 h, diluted with $H_2O$ and concentrated. The residue was dissolved into MeOH and purified by preparative HPLC ($CH_3CN/H_2O$ with 10 mM $NH_4OAc$) to yield 7H-indolo[2,1-a][2]benzazepine-10-carboxamide, 13-cyclohexyl-N-[(dimethylamino)sulfonyl]-6-[[4-(2-hydroxyethyl)-1-piperazinyl]carbonyl]-3-methoxy- (108 mg, 0.17 mmol, 88%) as a yellow solid. $^1$HNMR (300 MHz, $CD_3OD$) δ 8.14 (s, 1H), 7.90 (d, J=8.8 Hz, 1H), 7.64 (d, J=8.8 Hz, 1H), 7.56 (d, J=8.4 Hz, 1H), 7.15 (dd, J=2.6, 8.4 Hz, 1H), 7.09 (d, J=2.6 Hz, 1H), 6.96 (s, 1H), 5.21-5.03 (m, 1H), 4.51-4.29 (m, 1H), 3.93 (s, 3H), 3.66-3.59 (m, 2H), 3.59-3.36 (m 2H), 3.00 (s, 6H), 2.94-2.80 (m, 1H), 2.54-1.08 (m, 18H). LCMS: m/e 648 (M–H)$^-$, ret time 2.52 min, column A, 4 minute gradient.

7H-Indolo[2,1-a][2]benzazepine-10-carboxamide, 13-cyclohexyl-N-[(dimethylamino)sulfonyl]-6-[[4-(hydroxymethyl)-1-piperidinyl]carbonyl]-3-methoxy-. To a stirred solution of 13-cyclohexyl-N-[(dimethylamino)sulfonyl]-3-methoxy-7H-indolo[2,1-a][2]benzazepine-10-carboxamide-6-carboxylic acid (100 mg, 0.19 mmol), piperidin-4-ylmethanol (39 mg, 0.34 mmol) and triethylamine (0.12 mL) in DMF (1.0 mL) was added HATU (99 mg, 0.26 mmol). The reaction mixture was stirred at rt for 2 h, diluted with $H_2O$ and concentrated. The residue was dissolved into MeOH and purified by preparative HPLC ($CH_3CN/H_2O$ with 10 mM $NH_4OAc$) to yield 7H-indolo[2,1-a][2]benzazepine-10-carboxamide, 13-cyclohexyl-N-[(dimethylamino)sulfonyl]-6-[[4-(hydroxymethyl)-1-piperidinyl]carbonyl]-3-methoxy- (103 mg, 0.16 mmol, 86%) as a yellow solid. $^1$HNMR (300 MHz, $CD_3OD$) δ 8.09 (s, 1H), 7.87 (d, J=8.4 Hz, 1H), 7.59 (dd, J=1.2, 8.4 Hz, 1H), 7.52 (d, J=8.8 Hz, 1H), 7.09 (dd, J=2.6, 8.8 Hz, 1H), 7.05 (d, J=2.6 Hz, 1H), 6.90 (s, 1H), 5.17-4.97 (m, 1H), 4.46-4.24 (m, 1H), 3.90 (s, 3H), 3.37-3.26 (m, 2H), 2.98 (s, 6H), 2.95-2.74 (m, 3H), 2.19-1.01 (m, 17H). LCMS: m/e 633 (M–H)$^-$, ret time 2.74 min, column A, 4 minute gradient.

7H-Indolo[2,1-a][2]benzazepine-10-carboxamide, 6-[(3-amino-1-azetidinyl)carbonyl]-13-cyclohexyl-N-[(dimethylamino)sulfonyl]-3-methoxy-. To a solution of carbamic acid, [1-[[13-cyclohexyl-10-[[[(dimethylamino)sulfonyl]amino]carbonyl]-3-methoxy-7H-indolo[2,1-a][2]benzazepin-6-yl]carbonyl]-3-azetidinyl]-, 1,1-dimethylethyl ester (60 mg, 0.087 mmol) in CH₂Cl₂ (1.5 mL) was added trifluoroacetic acid (1.5 mL). The reaction mixture was stirred at rt for 2 h, concentrated and the residue was dissolved into MeOH and purified by preparative HPLC (CH₃CN/H₂O with 10 mM NH₄OAc) to yield 7H-indolo[2,1-a][2]benzazepine-10-carboxamide, 6-[(3-amino-1-azetidinyl)carbonyl]-13-cyclohexyl-N-[(dimethylamino)sulfonyl]-3-methoxy- (31 mg, 0.05 mmol, 60%) as a fluffy yellow solid. ¹HNMR (300 MHz, d₆-DMSO) δ 8.16 (s, 1H), 7.74 (d, J=8.4 Hz, 1H), 7.64 (d, J=8.4 Hz, 1H), 7.48 (d, J=8.0 Hz, 1H), 7.28-7.17 (m, 3H) 5.57-5.26 (m, 1H), 4.72-4.46 (m, 1H), 3.98-3.08 (m, 5H), 3.87 (s, 3H), 2.75 (s, 6H), 2.83-2.68 (m, 1H), 2.12-0.96 (m, 12H). LCMS: m/e 592 (M+H)⁺, ret time 3.14 min, column B, 4 minute gradient.

δ 8.22-7.98 (m, 1H), 7.90-7.79 (m, 1H), 7.58-7.48 (m, 1H), 7.35-7.26 (m, 1H), 7.07-6.74 (m, 2H), 4.80-3.34 (m, 12H), 3.11-2.43 (m, 14H), 2.11-1.12 (m, 11H). LCMS: m/e 650 (M−H)⁻, ret time 2.54 min, column A, 4 minute gradient.

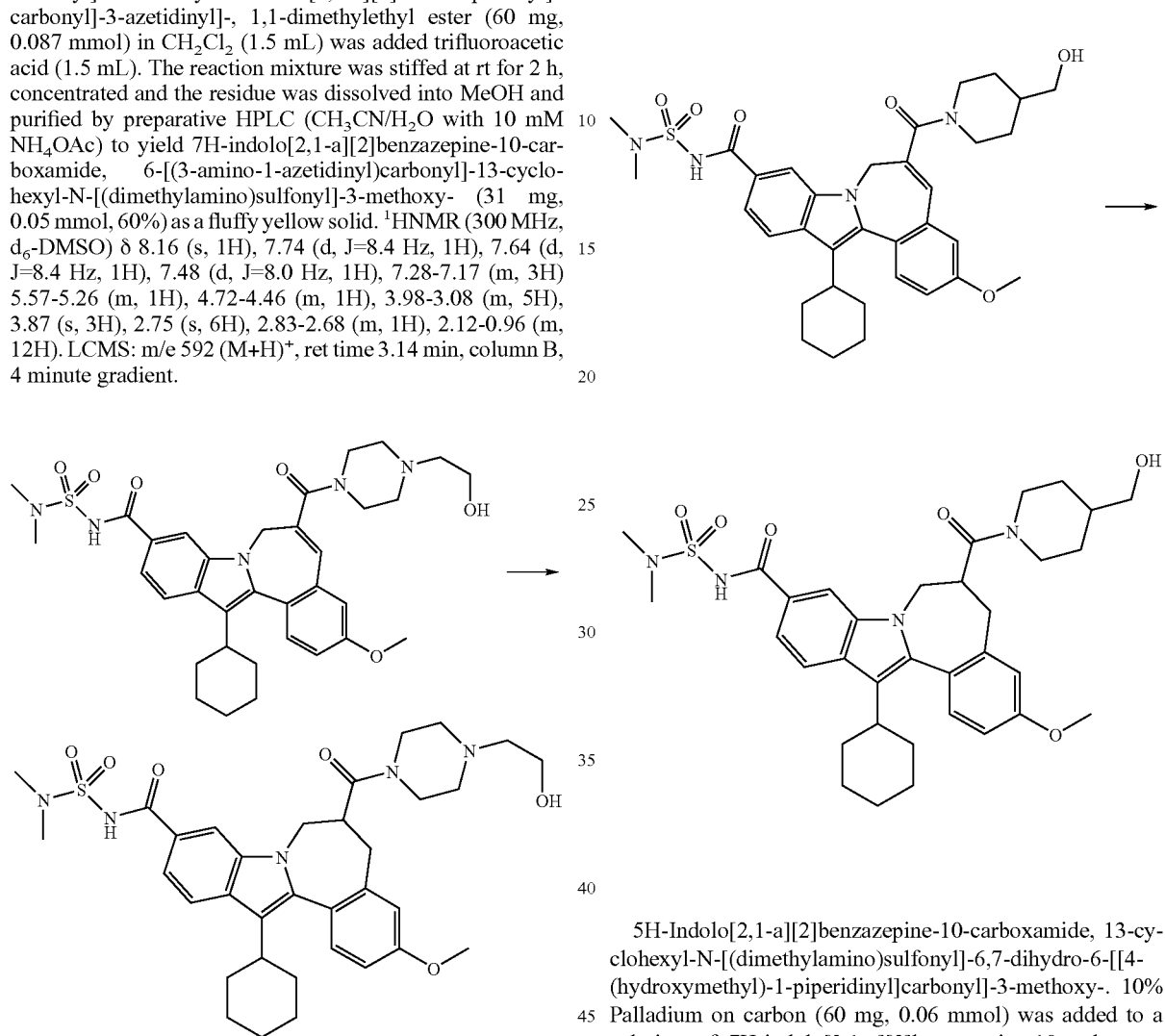

5H-Indolo[2,1-a][2]benzazepine-10-carboxamide, 13-cyclohexyl-N-[(dimethylamino)sulfonyl]-6,7-dihydro-6-[[4-(2-hydroxyethyl)-1-piperazinyl]carbonyl]-3-methoxy-. 10% Palladium on carbon (60 mg, 0.06 mmol) was added to a solution of 7H-indolo[2,1-a][2]benzazepine-10-carboxamide, 13-cyclohexyl-N-[(dimethylamino)sulfonyl]-6-[[4-(2-hydroxyethyl)-1-piperazinyl]carbonyl]-3-methoxy- (67 mg, 0.10 mMol) in MeOH (3 mL) and the reaction mixture was vacuum flushed with nitrogen (3×) and then with hydrogen (4×). The reaction was stirred under a balloon of hydrogen overnight and again vacuum flushed with nitrogen (3×) and then with hydrogen (4×). The reaction was stirred under a balloon of hydrogen overnight, filtered through a pad of celite and concentrated. The residue was dissolved into MeOH and purified by preparative HPLC (CH₃CN/H₂O with 10 mM NH₄OAc) to yield 5H-indolo[2,1-a][2]benzazepine-10-carboxamide, 13-cyclohexyl-N-[(dimethylamino)sulfonyl]-6,7-dihydro-6-[[4-(2-hydroxyethyl)-1-piperazinyl]carbonyl]-3-methoxy- (24 mg, 0.037 mmol, 36%) as a yellow solid. Mixture of atrope diastereomers. ¹HNMR (300 MHz, CDCl₃)

5H-Indolo[2,1-a][2]benzazepine-10-carboxamide, 13-cyclohexyl-N-[(dimethylamino)sulfonyl]-6,7-dihydro-6-[[4-(hydroxymethyl)-1-piperidinyl]carbonyl]-3-methoxy-. 10% Palladium on carbon (60 mg, 0.06 mmol) was added to a solution of 7H-indolo[2,1-a][2]benzazepine-10-carboxamide, 13-cyclohexyl-N-[(dimethylamino)sulfonyl]-6-[[4-(hydroxymethyl)-1-piperidinyl]carbonyl]-3-methoxy- (71 mg, 0.11 mmol) in MeOH (3 mL) and the reaction mixture was vacuum flushed with nitrogen (3×) and then with hydrogen (4×). The reaction was stirred under a balloon of hydrogen overnight and again vacuum flushed with nitrogen (3×) and then with hydrogen (4×). The reaction was stirred under a balloon of hydrogen overnight, filtered through a pad of celite and concentrated. The residue was dissolved into MeOH and purified by preparative HPLC (CH₃CN/H₂O with 10 mM NH₄OAc) to yield 5H-indolo[2,1-a][2]benzazepine-10-carboxamide, 13-cyclohexyl-N-[(dimethylamino)sulfonyl]-6,7-dihydro-6-[[4-(hydroxymethyl)-1-piperidinyl]carbonyl]-3-methoxy- (49 mg, 0.077 mmol, 69%) as a yellow solid. Mixture of atrope diastereomers. ¹HNMR (300 MHz, CDCl₃) δ 10.12-8.98 (m, 1H), 8.10-7.90 (m, 1H), 7.88-7.76 (m, 1H), 7.55-7.42 (m, 1H), 7.36-7.25 (m, 1H), 6.97-6.75 (m, 2H), 4.69-2.40 (m, 22H), 2.11-0.90 (m, 15H). LCMS: m/e 635 (M−H)⁻, ret time 2.75 min, column A, 4 minute gradient.

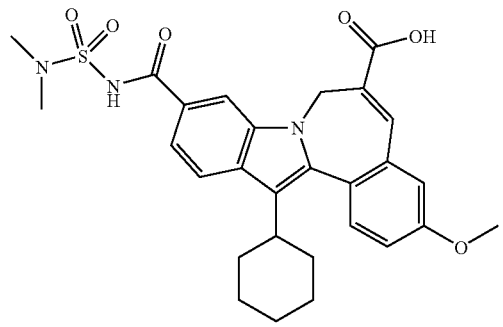

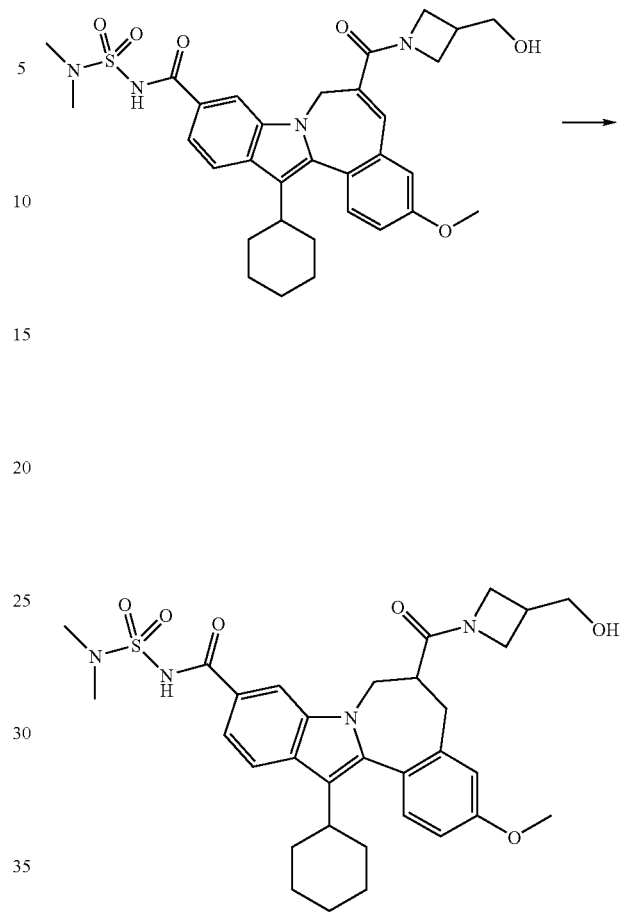

7H-Indolo[2,1-a][2]benzazepine-10-carboxamide, 13-cyclohexyl-N-[(dimethylamino)sulfonyl]-6-[[3-(hydroxymethyl)-1-azetidinyl]carbonyl]-3-methoxy. To a solution of tert-butyl 3-(hydroxymethyl)azetidine-1-carboxylate (70 mg, 0.37 mmol) in CH$_2$Cl$_2$ (1 mL) was added trifluoroacetic acid (1 mL). The reaction mixture was stirred at rt for 2 h, concentrated, and the residue was combined with 13-cyclohexyl-N-[(dimethylamino)sulfonyl]-3-methoxy-7H-indolo [2,1-a][2]benzazepine-10-carboxamide-6-carboxylic acid (72 mg, 0.13 mmol), triethylamine (0.10 mL), DMF (2.5 mL) and HATU (72 mg, 0.19 mmol). The reaction mixture was stirred at rt for 2 h and then additional azetidin-3-ylmethanol (prepared by stirring tert-butyl 3-(hydroxymethyl)azetidine-1-carboxylate (70 mg, 0.37 mmol) with trifluoroacetic acid (1 mL) for 10 min, and then concentrating to dryness) in DMF (0.5 mL) and HATU (70 mg, 0.18 mmol) were added. The reaction mixture was stirred 0.5 h, diluted with MeOH (0.5 mL) and purified by preparative HPLC (CH$_3$CN/H$_2$O with 10 mM NH$_4$OAc) to yield 7H-indolo[2,1-a][2]benzazepine-10-carboxamide, 13-cyclohexyl-N-[(dimethylamino)sulfonyl]-6-[[3-(hydroxymethyl)-1-azetidinyl]carbonyl]-3-methoxy- (67 mg, 0.11 mmol, 85%) as a yellow solid. $^1$HNMR (300 MHz, CDCl$_3$) δ 8.08 (br s, 1H), 7.85 (d, J=8.4 Hz, 1H), 7.63 (br d, J=8.4 Hz, 1H), 7.47 (d, J=8.8 Hz, 1H), 7.11(s, 1H), 7.04 (dd, J=8.8 Hz, 1H), 6.90 (d, J=2.6 Hz, 1H), 5.50-5.33 (m, 1H), 4.49-3.52 (m, 7H), 3.89 (s, 3H), 3.01 (s, 6H), 2.93-2.70 (m, 1H), 2.17-1.06 (m, 11H). LCMS: m/e 605 (M−H)$^-$, ret time 2.63 min, column A, 4 minute gradient.

5H-Indolo[2,1-a][2]benzazepine-10-carboxamide, 13-cyclohexyl-N-[(dimethylamino)sulfonyl]-6,7-dihydro-6-[[3-(hydroxymethyl)-1-azetidinyl]carbonyl]-3-methoxy-. 10% Palladium on carbon (70 mg, 0.07 mmol) was added to a solution of 7H-indolo[2,1-a][2]benzazepine-10-carboxamide, 13-cyclohexyl-N-[(dimethylamino)sulfonyl]-6-[[3-(hydroxymethyl)-1-azetidinyl]carbonyl]-3-methoxy- (52 mg, 0.086 mmol) in MeOH/CH$_2$Cl$_2$ (6:1, 3.5 mL) and the reaction mixture was vacuum flushed with nitrogen (3×) and then with hydrogen (4×). The reaction was stirred under a balloon of hydrogen overnight, filtered through a pad of celite and concentrated. The residue was passed through a plug of silica gel (flushing with 10% MeOH/EtOAc) and concentrated to dryness to yield 5H-indolo[2,1-a][2]benzazepine-10-carboxamide, 13-cyclohexyl-N-[(dimethylamino)sulfonyl]-6,7-dihydro-6-[[3-(hydroxymethyl)-1-azetidinyl]carbonyl]-3-methoxy- (47 mg, 0.077 mmol, 90%) as a yellow solid. Mixture of atrope diastereomers. $^1$HNMR (300 MHz, CDCl$_3$) δ 10.36-9.70 (m, 1H), 8.01-7.91 (m, 1H), 7.86-7.75 (m, 1H), 7.59-7.43 (m, 1H), 7.33-7.26 (m, 1H), 6.94-6.82 (m, 2H), 4.61-3.58 (m, 9H), 3.46-2.53 (m, 10H), 2.11-0.76 (m, 14H). LCMS: m/e 607 (M−H)$^-$, ret time 2.56 min, column A, 4 minute gradient.

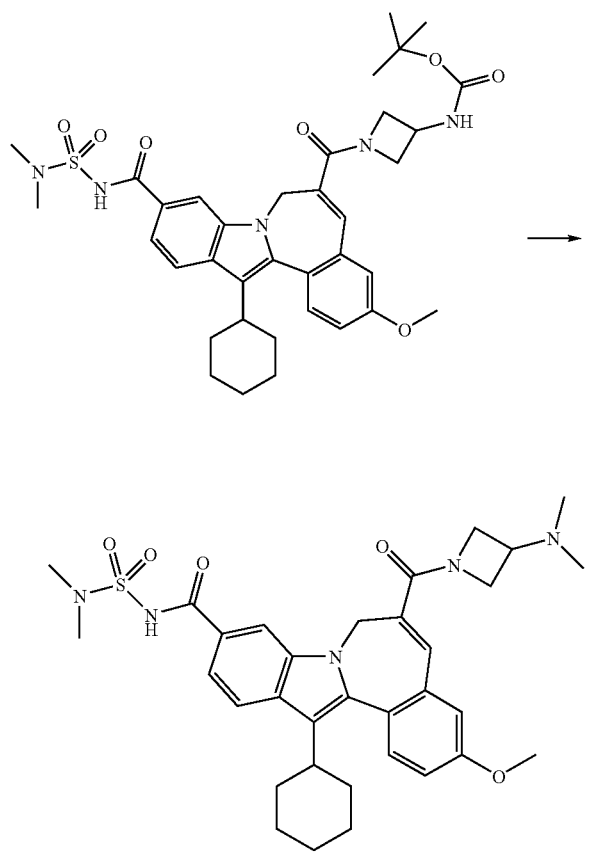

7H-Indolo[2,1-a][2]benzazepine-10-carboxamide, 13-cyclohexyl-6-[[3-(dimethylamino)-1-azetidinyl]carbonyl]-N-[(dimethylamino)sulfonyl]-3-methoxy-. To a solution of carbamic acid, [1-[[[13-cyclohexyl-10-[[[(dimethylamino)sulfonyl]amino]carbonyl]-3-methoxy-7H-indolo[2,1-a][2]benzazepin-6-yl]carbonyl]-3-azetidinyl]-, 1,1-dimethylethyl ester (136 mg, 0.20 mmol) in ClCH$_2$CH$_2$Cl (3 mL) was added trifluoroacetic acid (3 mL). The reaction mixture was stirred at rt for 2 h, concentrated and 60% of the residue was dissolved into MeOH. To this stirring solution at rt was added NaCNBH$_3$ (90 mg 1.5 mmol) and then formaldehyde (37 wt % in H$_2$O, 0.15 mL, 5.4 mmol). The reaction mixture was stirred for 2 h, diluted with MeOH and purified by preparative HPLC (CH$_3$CN/H$_2$O with 10 mM NH$_4$OAc) to yield 7H-indolo[2,1-a][2]benzazepine-10-carboxamide, 13-cyclohexyl-6-[[3-(dimethylamino)-1-azetidinyl]carbonyl]-N-[(dimethylamino)sulfonyl]-3-methoxy- (52 mg, 0.084 mmol, 72% over two steps) as a yellow solid. $^1$HNMR (300 MHz, CDCl$_3$) δ 8.07 (d, J=1.4 Hz, 1H), 7.85 (d, J=8.8 Hz, 1H), 7.50 (dd, J=1.4, 8.8 Hz, 1H), 7.49 (d, J=8.8 Hz, 1H), 7.05 (dd, J=2.6, 8.6 Hz, 1H), 7.04 (s, 1H), 6.88 (d, J=2.6 Hz, 1H), 5.59-5.36 (m, 1H), 4.27-3.85 (m, 5H), 3.89 (s, 3H), 3.46 (s, 3H), 3.03 (s, 6H), 2.86-2.72 (m, 1H), 2.11 (s, 3H), 2.14-1.11 (m, 10H). LCMS: m/e 618 (M−H)$^-$, ret time 2.81 min, column A, 4 minute gradient.

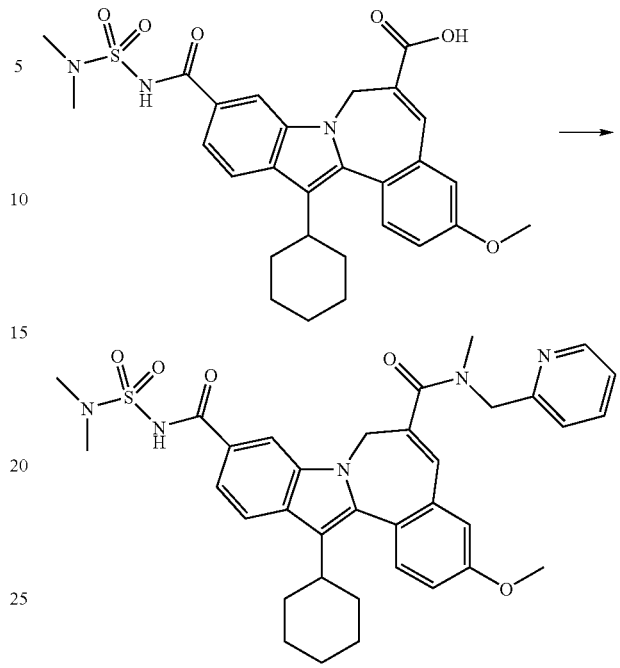

7H-Indolo[2,1-a][2]benzazepine-6,10-dicarboxamide, 13-cyclohexyl-N$^{10}$-[(dimethylamino)sulfonyl]-3-methoxy-N$^6$-methyl-N$^6$-(2-pyridinylmethyl)-. To a stirred solution of 13-cyclohexyl-N-[(dimethylamino)sulfonyl]-3-methoxy-7H-indolo[2,1-a][2]benzazepine-10-carboxamide-6-carboxylic acid (80 mg, 0.15 mmol), N-methyl-1-(pyridin-2-yl)methanamine hydrochloride (33 mg, 0.27 mmol) and triethylamine (0.085 mL, 0.60 mmol) in DMF (1 mL) was added HATU (80 mg, 0.21 mmol). The reaction mixture was stirred at rt for 30 min., diluted with MeOH (~1 mL) and purified by preparative HPLC (CH$_3$CN/H$_2$O with 10 mM NH$_4$OAc) to yield 7H-indolo[2,1-a][2]benzazepine-6,10-dicarboxamide, 13-cyclohexyl-N$^{10}$-[(dimethylamino)sulfonyl]-3-methoxy-N$^6$-methyl-N$^6$-(2-pyridinylmethyl)- (74 mg, 0.12 mmol, 77%) as a yellow solid. $^1$HNMR (300 MHz, CDCl$_3$) δ 8.49 (br s, 1H), 8.09 (s, 1H), 7.85 (d, J=8.4 Hz, 1H), 7.56 (d, J=8.4 Hz, 1H), 7.51 (d, J=8.4 Hz, 1H), 7.75-6.79 (m, 6H), 5.33-5.03 (m, 1H), 4.73-4.50 (m, 2H), 4.45-4.18 (m, 1H), 3.86 (s, 3H), 3.05 (s, 6H), 2.92 (s, 3H), 2.87-2.71 (m, 1H), 2.12-1.06 (m, 10H). LCMS: m/e 640 (M−H)$^-$, ret time 2.90 min, column A, 4 minute gradient.

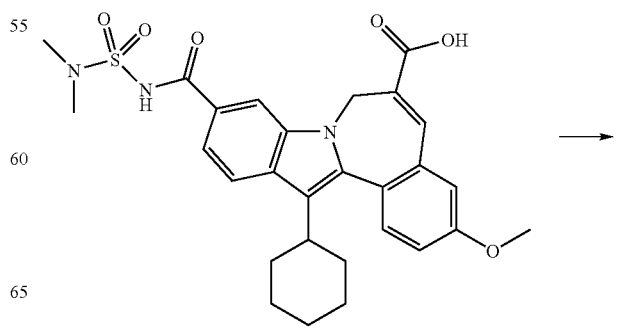

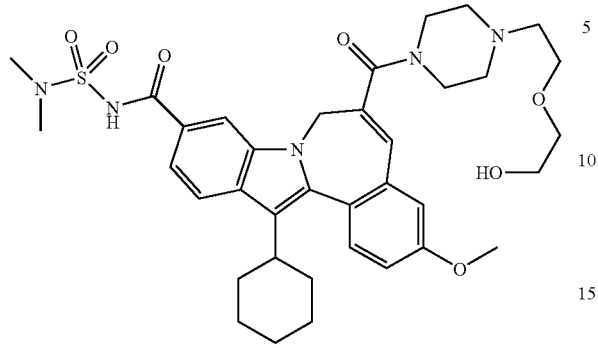

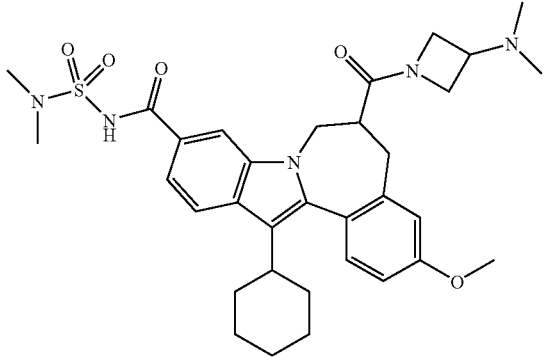

7H-Indolo[2,1-a][2]benzazepine-10-carboxamide, 13-cyclohexyl-N-[(dimethylamino)sulfonyl]-6-[[4-[2-(2-hydroxyethoxy)ethyl]-1-piperazinyl]carbonyl]-3-methoxy-. To a stirred solution of 13-cyclohexyl-N-[(dimethylamino)sulfonyl]-3-methoxy-7H-indolo[2,1-a][2]benzazepine-10-carboxamide-6-carboxylic acid (80 mg, 0.15 mmol), 2-(2-(piperazin-1-yl)ethoxy)ethanol (50 mg, 0.29 mmol) and triethylamine (0.10 mL) in DMF (1 mL) was added HATU (80 mg, 0.21 mmol). The reaction mixture was stirred at rt for 1 h diluted with MeOH (~1 mL) and purified by preparative HPLC (CH$_3$CN/H$_2$O with 10 mM NH$_4$OAc) to yield 7H-Indolo[2,1-a][2]benzazepine-10-carboxamide, 13-cyclohexyl-N-[(dimethylamino)sulfonyl]-6-[[4-[2-(2-hydroxyethoxy)ethyl]-1-piperazinyl]carbonyl]-3-methoxy- (90 mg, 0.13 mmol, 87%) as a yellow solid. $^1$HNMR (300 MHz, CD$_3$OD) δ 8.11 (d, J=1.5 Hz, 1H), 7.86 (d, J=8.4 Hz, 1H), 7.60 (dd, J=1.5, 8.4 Hz, 1H), 7.51 (d, J=8.8 Hz, 1H), 7.11 (dd, J=2.6, 8.8 Hz, 1H), 7.05 (d, J=2.6 Hz, 1H), 6.91 (s, 1H), 5.17-4.99 (m, 1H), 4.44-4.23 (m, 1H), 3.89 (s, 3H), 3.73-3.25 (m, 10H), 2.97 (s, 6H), 2.90-2.77 (m, 1H), 2.58-2.50 (m, 2H), 2.46-1.12 (m, 14H). LCMS: m/e 692 (M−H)$^-$, ret time 2.45 min, column A, 4 minute gradient.

5H-Indolo[2,1-a][2]benzazepine-10-carboxamide, 13-cyclohexyl-6-[[3-(dimethylamino)-1-azetidinyl]carbonyl]-N-[(dimethylamino)sulfonyl]-6,7-dihydro-3-methoxy-. 10% Palladium on carbon (50 mg, 0.05 mmol) was added to a solution of 7H-indolo[2,1-a][2]benzazepine-10-carboxamide, 13-cyclohexyl-6-[[3-(dimethylamino)-1-azetidinyl]carbonyl]-N-[(dimethylamino)sulfonyl]-3-methoxy- (32 mg, 0.052 mmol) in MeOH/CH$_2$Cl$_2$ (1:1, 3 mL) and the reaction mixture was vacuum flushed with nitrogen (3×) and then with hydrogen (4×). The reaction was stirred under a balloon of hydrogen overnight, filtered through a pad of celite and concentrated to yield 5H-indolo[2,1-a][2]benzazepine-10-carboxamide, 13-cyclohexyl-6-[[3-(dimethylamino)-1-azetidinyl]carbonyl]-N-[(dimethylamino)sulfonyl]-6,7-dihydro-3-methoxy- (30 mg, 0.048 mmol, 93%) as a tan solid. Mixture of atrope diastereomers and amide rotamers. $^1$HNMR (300 MHz, CD$_3$OD) δ 8.15-7.94 (m, 1H), 7.89-7.80 (m, 1H), 7.60-7.48 (m, 1H), 7.39-7.30 (m, 1H), 7.09-6.84 (m, 2H), 4.74-2.50 (m, 24H), 2.16-1.08 (m, 12H). LCMS: m/e 622 (M+H)$^+$, ret time 3.15 min, column B, 4 minute gradient.

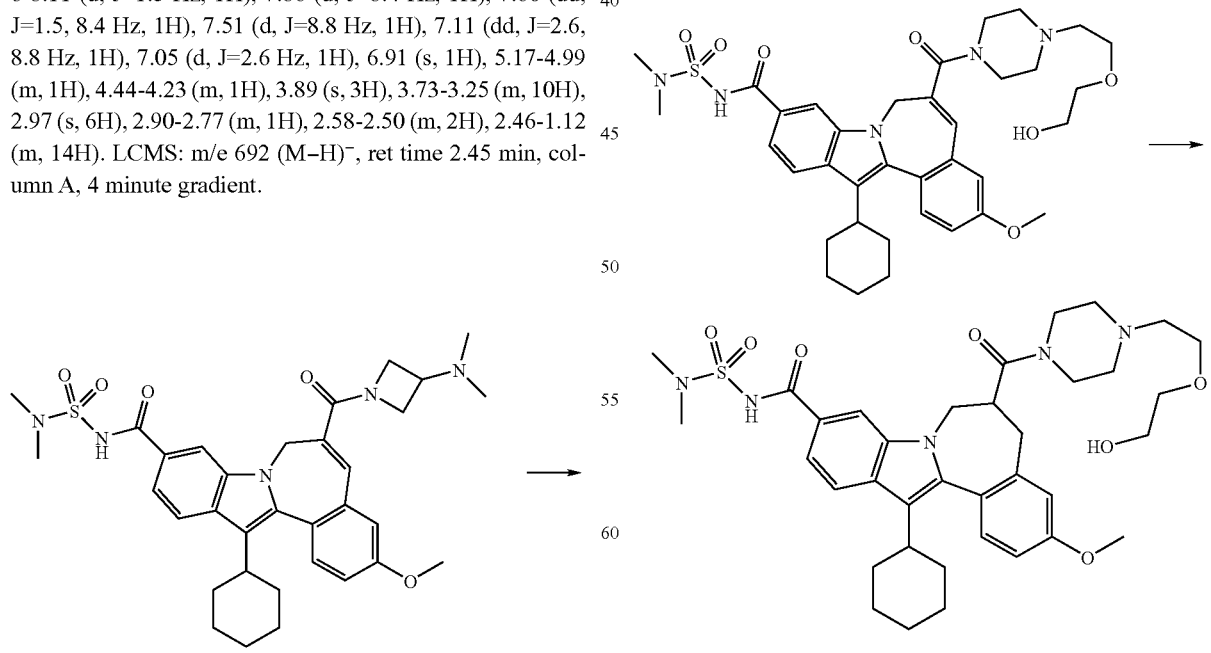

5H-Indolo[2,1-a][2]benzazepine-10-carboxamide, 13-cyclohexyl-N-[(dimethylamino)sulfonyl]-6,7-dihydro-6-[[4-

[2-(2-hydroxyethoxy)ethyl]-1-piperazinyl]carbonyl]-3-methoxy-. 10% Palladium on carbon (40 mg, 0.04 mmol) was added to a solution of 7H-indolo[2,1-a][2]benzazepine-10-carboxamide, 13-cyclohexyl-N-[(dimethylamino)sulfonyl]-6-[[4-[2-(2-hydroxyethoxy)ethyl]-1-piperazinyl]carbonyl]-3-methoxy- (48 mg, 0.069 mmol) in MeOH/CH$_2$Cl$_2$ (2:1, 3 mL) and the reaction mixture was vacuum flushed with nitrogen (3×) and then with hydrogen (4×). The reaction was stirred under a balloon of hydrogen overnight and again vacuum flushed with nitrogen (3×) and then with hydrogen (4×) and stirred under a balloon of hydrogen for 3 d. The reaction was treated with additional 10% palladium on carbon (40 mg, 0.04 mmol), vacuum flushed with nitrogen (3×) and then with hydrogen (4×) and stirred under a balloon of hydrogen overnight. The reaction was filtered through a pad of celite and concentrated. The residue was dissolved into MeOH and purified by preparative HPLC (CH$_3$CN/H$_2$O with 10 mM NH$_4$OAc) to yield 5H-indolo[2,1-a][2]benzazepine-10-carboxamide, 13-cyclohexyl-N-[(dimethylamino)sulfonyl]-6,7-dihydro-6-[[4-[2-(2-hydroxyethoxy)ethyl]-1-piperazinyl]carbonyl]-3-methoxy- (23 mg, 0.033 mmol, 48%) as a yellow solid. Mixture of atrope diastereomers. $^1$HNMR (300 MHz, CD$_3$OD) δ 8.17-7.97 (m, 1H), 7.90-7.82 (m, 1H), 7.67-7.53 (m, 1H), 7.41-7.33 (m, 1H), 7.11-6.86 (m, 2H), 4.61-4.41 (m, 1H), 4.14-3.26 (m, 16H), 3.05-2.88 (m, 7H), 2.84-2.59 (m, 8H), 2.20-1.18 (m 10H). LCMS: m/e 694 (M−H)$^-$, ret time 2.54 min, column A, 4 minute gradient.

mixture was stirred at rt for 2 h and concentrated to dryness. The residue was dissolved into MeOH, loaded onto an SCX cartridge, flushed with MeOH, eluted with 2M NH$_3$ in MeOH and concentrated to dryness. To a stirred solution of the residue (45 mg), 13-cyclohexyl-N-[(dimethylamino)sulfonyl]-3-methoxy-7H-indolo[2,1-a][2]benzazepine-10-carboxamide-6-carboxylic acid (60 mg, 0.11 mmol), and triethylamine (0.15 mL) in DMF (1.5 mL) was added HATU (60 mg, 0.16 mmol). The reaction mixture was stirred at rt for 2 h, treated with additional HATU (60 mg, 0.16 mmol) and stirred 3 H. The reaction mixture was diluted with MeOH and purified by preparative HPLC (CH$_3$CN/H$_2$O with 10 mM NH$_4$OAc) to yield 7H-indolo[2,1-a][2]benzazepine-10-carboxamide, 13-cyclohexyl-6-[[3-[(dimethylamino)carbonyl]-1-azetidinyl]carbonyl]-N-[(dimethylamino)sulfonyl]-3-methoxy- (19 mg, 0.029 mmol, 27%) as a yellow solid. $^1$HNMR (300 MHz, CD$_3$OD) δ 8.15 (s 1H), 7.88 (d, J=8.4 Hz, 1H), 7.61 (d, J=8.4 Hz, 1H), 7.56 (d, J=8.4 Hz, 1H), 7.27 (s, 1H), 7.16 (dd, J=2.6, 8.4 Hz, 1H), 7.12 (d, J=2.6 Hz, 1H), 5.60-5.32 (m, 1H), 4.68-4.06 (m, 5H), 3.93 (s, 3H), 3.84-3.68 (m, 1H), 3.01 (s, 6H), 2.95 (s, 3H), 2.93 (s, 3H), 2.94-2.82 (m, 1H), 2.21-1.12 (m, 10H). LCMS: m/e 646 (M−H)$^-$, ret time 2.70 min, column A, 4 minute gradient.

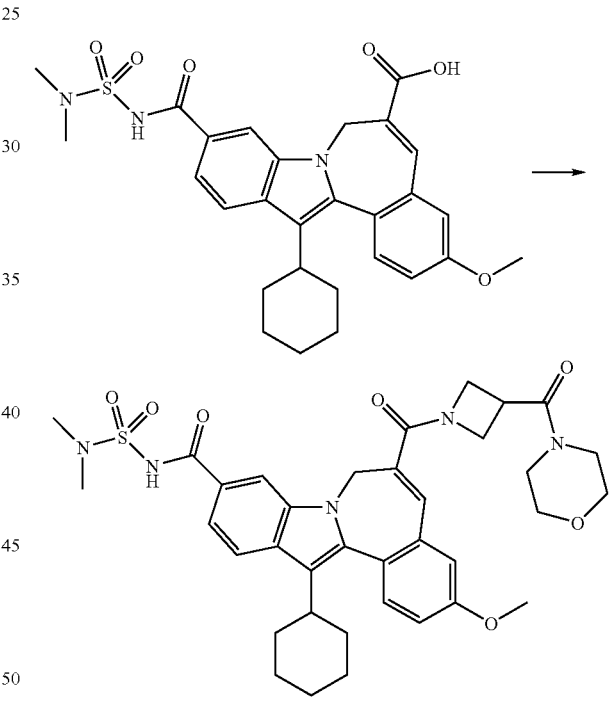

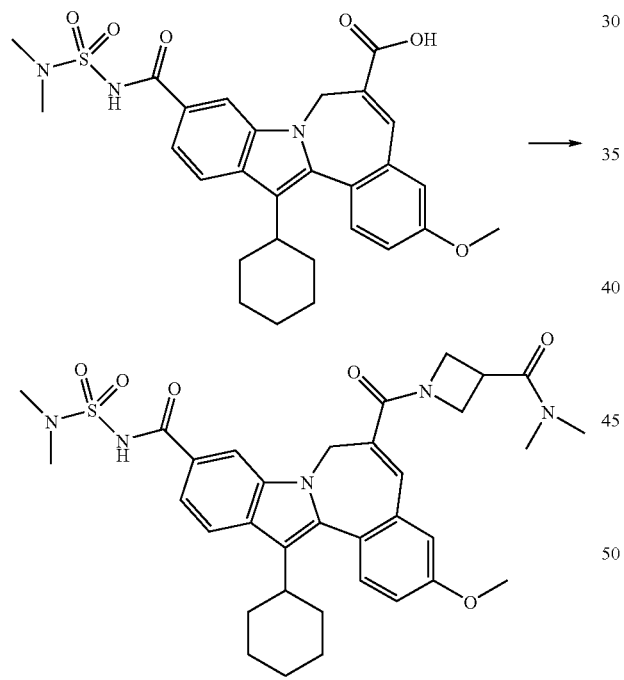

7H-Indolo[2,1a][2]benzazepine-10-carboxamide, 13-cyclohexyl-6-[[3-[(dimethylamino)carbonyl]-1-azetidinyl]carbonyl]-N-[(dimethylamino)sulfonyl]-3-methoxy-. To a stirred solution of 1-(tert-butoxycarbonyl)azetidine-3-carboxylic acid (75 mg, 0.37 mmol), dimethylamine (2M in THF, 0.37 mL, 0.74 mmol) and triethylamine (0.20 mL) in DMF (2.0 mL) was added HATU (213 mg, 0.66 mmol). The reaction mixture was stirred at rt for 0.5 h, diluted with H$_2$O (10 mL) and extracted with CH$_2$Cl$_2$ (3×5 mL). The combine organics were concentrated, dissolved into ClCH$_2$CH$_2$Cl (6 mL) and treated with trifluoroacetic acid (4 mL). The reaction 7H-Indolo[2,1-a][2]benzazepine-10-carboxamide, 13-cyclohexyl-N-[(dimethylamino)sulfonyl]-3-methoxy-6-[[3-(4-morpholinylcarbonyl)-1-azetidinyl]carbonyl]-. To a stirred solution of 1-(tert-butoxycarbonyl)azetidine-3-carboxylic acid (75 mg, 0.37 mmol), morpholine (0.065 mL, 0.74 mmol) and triethylamine (0.20 mL) in DMF (2.0 mL) was added HATU (213 mg, 0.66 mmol). The reaction mixture was stirred at rt for 0.5 h, diluted with H$_2$O (10 mL) and extracted with CH$_2$Cl$_2$ (3×5 mL). The combine organics were concentrated, dissolved into ClCH$_2$CH$_2$Cl (6 mL) and treated with trifluoroacetic acid (4 mL). The reaction mixture was stirred at rt for 2 h and concentrated to dryness. The residue was dissolved into MeOH, loaded onto an SCX cartridge, flushed with MeOH, eluted with 2M NH$_3$ in MeOH and concentrated to dryness. To a stirred solution of the residue (38 mg), 13-cyclohexyl-N-[(dimethylamino)sulfonyl]-3-methoxy-7H-indolo[2,1-a][2]benzazepine-10-carboxamide-6-carboxylic acid (60 mg, 0.11 mmol), and triethylamine (0.15 mL) in DMF (1.5 mL) was added HATU (60 mg, 0.16 mmol). The reaction mixture was stirred at rt for 2 h, treated with additional HATU (60 mg, 0.16 mmol) and stirred 3 h. The reaction mixture was diluted with MeOH and purified by preparative HPLC (CH$_3$CN/H$_2$O with 10 mM NH$_4$OAc) to yield 7H-indolo[2,1-a][2]benzazepine-10-carboxamide, 13-cyclohexyl-N-[(dimethylamino)sulfonyl]-3-methoxy-6-[[3-(4-morpholinylcarbonyl)-1-azetidinyl]carbonyl]- (19 mg, 0.028 mmol, 25%) as a yellow solid. $^1$HNMR (300 MHz, CD$_3$OD) δ 8.16 (s 1H), 7.88 (d, J=8.4 Hz, 1H), 7.63 (d, J=8.4 Hz, 1H), 7.56 (d, J=8.4 Hz, 1H), 7.27 (s, 1H), 7.17 (dd, J=2.6, 8.4 Hz, 1H), 7.13 (d, J=2.6 Hz, 1H), 5.60-5.32 (m, 1H), 4.67-4.05 (m, 5H), 3.94 (s, 3H), 3.83-3.52 (m, 7H), 3.41-3.21 (m, 2H), 3.07 (s, 6H), 2.95-2.82 (m, 1H), 2.20-1.16 (m, 10H). LCMS: m/e 688 (M−H)$^-$, ret time 2.67 min, column A, 4 minute gradient.

To a solution of 13-cyclohexyl-N-[(dimethylamino)sulfonyl]-3-methoxy-7H-indolo[2,1-a][2]benzazepine-10-carboxamide-6-carboxylic acid (90 mg, 0.17 mmol), 2-hydroxy-2-methyl-1-(piperazin-1-yl)propan-1-one (150 mg, 0.87 mmol) and triethylamine (0.20 mL, 1.4 mmol) in DMF (2 mL) was added HATU (120 mg, 0.31 mmol). The reaction mixture was stirred at rt for 2 h, then diluted with MeOH and purified by prep HPLC (CH$_3$CN/H$_2$O with 10 mM NH$_4$OAc) to yield 7H-indolo[2,1-a][2]benzazepine-10-carboxamide, 13-cyclohexyl-N-[(dimethylamino)sulfonyl]-6-[[4-(2-hydroxy-2-methyl-1-oxopropyl)-1-piperazinyl]carbonyl]-3-methoxy- (78 mg, 0.11 mmol, 67%) as a yellow solid. $^1$HNMR (300 MHz, MeOD) δ 8.16 (s, 1H), 7.89 (d, J=8.4 Hz, 1H), 7.65 (dd, J=1.5, 8.4 Hz, 1H), 7.56 (d, J=8.4 Hz, 1H), 7.15 (dd, J=2.6, 8.4 Hz, 1H), 7.10 (d, J=2.6 Hz, 1H), 6.98 (s, 1H), 5.24-5.03 (m, 1H), 4.50-4.31 (m, 1H), 3.93 (s, 3H), 3.87-3.26 (m, 8H), 2.98 (s, 6H), 2.95-2.80 (m, 1H), 2.24-1.16 (m, 10H), 1.40 (s, 6H). LCMS: m/e 692 (M+H)$^+$, ret time 2.14 min, column B, 2 minute gradient.

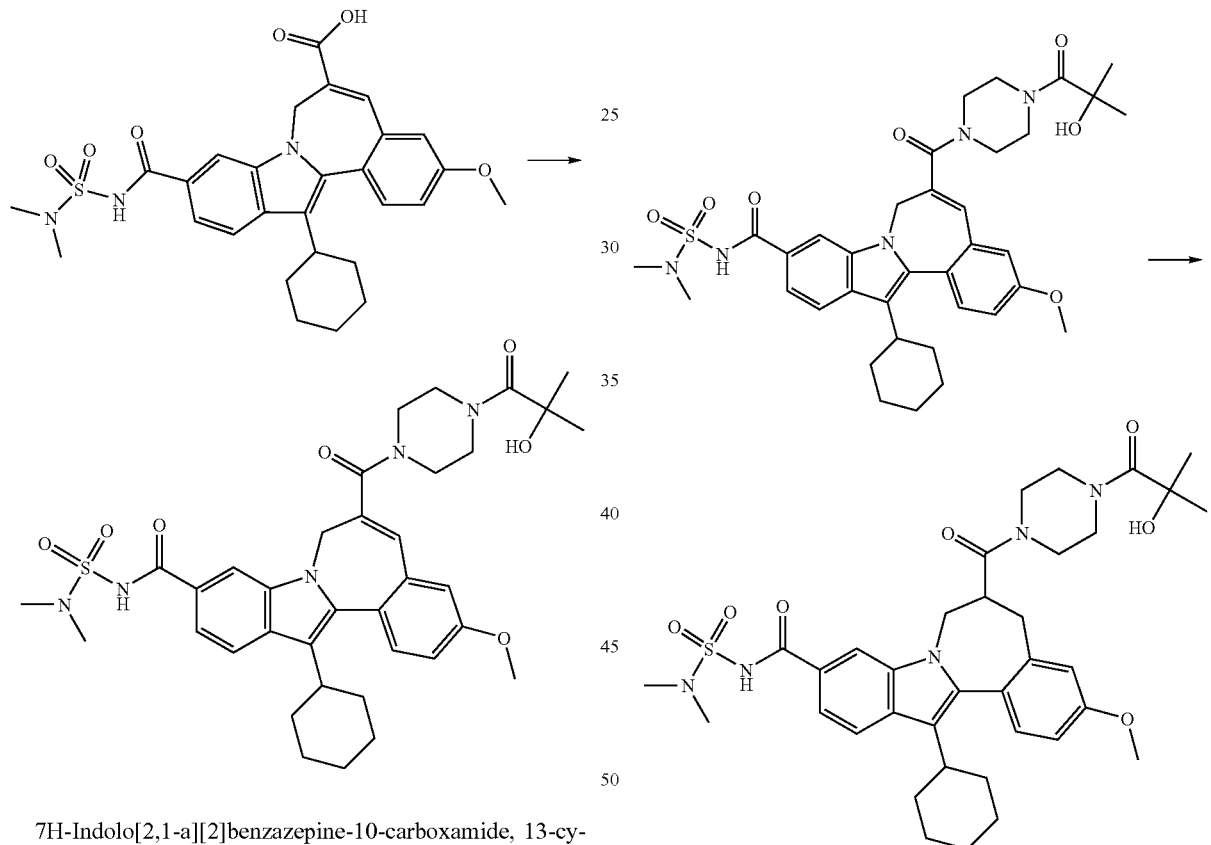

7H-Indolo[2,1-a][2]benzazepine-10-carboxamide, 13-cyclohexyl-N-[(dimethylamino)sulfonyl]-6-[[4-(2-hydroxy-2-methyl-1-oxopropyl)-1-piperazinyl]carbonyl]-3-methoxy-. To a solution of tert-butyl piperazine-1-carboxylate (372 mg, 2.0 mmol), 2-hydroxy-2-methylpropanoic acid (229 mg, 2.2 mmol) and triethylamine (1.1 mL) in DMF (7 mL) was added HATU (988 mg, 2.6 mmol). The reaction mixture was stirred at rt for 2 h, then diluted with H$_2$O, neutralized with 1N aqueous HCl (8 mL), concentrated, and the residue was partitioned between EtOAc and H$_2$O. The organic phase was separated, washed with brine and concentrated to a white solid (1.1 g). The solid was dissolved into ClCH$_2$CH$_2$Cl (10 mL) and treated with trifluoroacetic acid (5 mL). The reaction mixture was stirred at rt for 2 h, and concentrated to yield crude 2-hydroxy-2-methyl-1-(piperazin-1-yl)propan-1-one (1.1 g) as yellow semi-solid.

5H-Indolo[2,1-a][2]benzazepine-10-carboxamide, 13-cyclohexyl-N-[(dimethylamino)sulfonyl]-6,7-dihydro-6-[[4-(2-hydroxy-2-methyl-1-oxopropyl)-1-piperazinyl]carbonyl]-3-methoxy-. 10% Palladium on carbon (40 mg, 0.04 mmol) was added to a solution of 7H-indolo[2,1-a][2]benzazepine-10-carboxamide, 13-cyclohexyl-N-[(dimethylamino)sulfonyl]-6-[[4-(2-hydroxy-2-methyl-1-oxopropyl)-1-piperazinyl]carbonyl]-3-methoxy- (39 mg, 0.056 mmol) in MeOH/CH$_2$Cl$_2$ (1:1, 2 mL) and the reaction mixture was vacuum flushed with nitrogen (3×) and then with hydrogen (4×). The reaction was stirred under a balloon of hydrogen overnight and again vacuum flushed with nitrogen (3×) and then with hydrogen (4×). The reaction was stirred under a balloon of hydrogen for 1 d, filtered through a pad of celite and concentrated to give a light yellow solid (31 mg). Part of the residue (20 mg) was dissolved MeOH/CH$_2$Cl$_2$ (1:1, 2 mL) treated with 10% palladium on carbon (40 mg, 0.04 mmol), vacuum flushed with nitrogen (3×) and then with hydrogen (4×) and stirred under a balloon of hydrogen overnight. The reaction was filtered through a pad of celite, concentrated and purified by preparative HPLC (MeOH/H$_2$O/0.1% TFA) to yield 5H-Indolo[2,1-a][2]benzazepine-10-carboxamide, 13-cyclohexyl-N-[(dimethylamino)sulfonyl]-6,7-dihydro-6-[[4-(2-hydroxy-2-methyl-1-oxopropyl)-1-piperazinyl]carbonyl]-3-methoxy- (5.6 mg, 0.008 mmol, 22%) as a yellow solid. Mixture of atrope diastereomers. $^1$HNMR (300 MHz, MeOD) δ 8.16 (s, 0.3H), 7.99 (s, 0.7H), 7.90 (d, J=8.4 Hz, 0.3H), 7.87 (d, J=8.4 Hz, 0.7H), 7.65-7.52 (m, 1H), 7.39 (d, J=8.4 Hz, 0.7H), 7.39 (d, J=8.4 Hz, 0.3H), 7.15-6.88 (m, 2H), 4.67-3.46 (m, 10H), 3.91 (s, 2.1H), 3.88 (s, 0.9H), 3.03 (s, 6H), 2.99-2.65 (m, 4H), 2.20-1.21 (m, 10H), 1.49 (s, 1.8H), 1.48 (s, 4.2H). LCMS: m/e 694(M+H)$^+$, ret time 2.14 min, column B, 2 minute gradient.

stirred at rt for 2 h, and concentrated under vacuum to a crude yellow oil. Part of this material (~0.18 mmol) was added to a solution of 1-hydroxycyclopropanecarboxylic acid (24 mg, 0.23 mmol), HATU (89 mg, 0.23 mmol) and triethylamine (0.13 mL) in DMF (2 mL). The reaction mixture was stirred at rt for 2 h, and additional 1-hydroxycyclopropanecarboxylic acid (30 mg, 0.29 mmol), HATU (100 mg, 0.26 mmol) and triethylamine (0.10 mL) were added. The reaction was stirred at rt overnight and half of the mixture was diluted with MeOH/DMSO and purified by prep HPLC (MeOH/H$_2$O/ 0.1% TFA) to yield 7H-indolo[2,1-a][2]benzazepine-10-carboxamide, 13-cyclohexyl-N-[(dimethylamino)sulfonyl]-6-[[4-[(1-hydroxycyclopropyl)carbonyl]-1-piperazinyl] carbonyl]-3-methoxy- (51 mg, 0.074 mmol, 81%) as a yellow solid. $^1$HNMR (300 MHz, MeOD) δ 8.13 (d, J=1.5, 1H), 7.93 (d, J=8.4 Hz, 1H), 7.60 (dd, J=1.5, 8.4 Hz, 1H), 7.57 (d, J=8.4 Hz, 1H), 7.16 (dd, J=2.6, 8.4 Hz, 1H), 7.13 (d, J=2.6 Hz, 1H), 7.02 (s, 1H), 5.26-5.06 (m, 1H), 4.49-4.28 (m, 1H), 3.93 (s, 3H), 3.87-3.42 (m, 8H), 3.02 (s, 6H), 2.95-2.82 (m, 1H), 2.24-1.14 (m, 10H), 1.08-1.00 (m, 2H), 0.92-0.84 (m, 2H). LCMS: m/e 690 (M+H)$^+$, ret time 2.13 min, column B, 2 minute gradient.

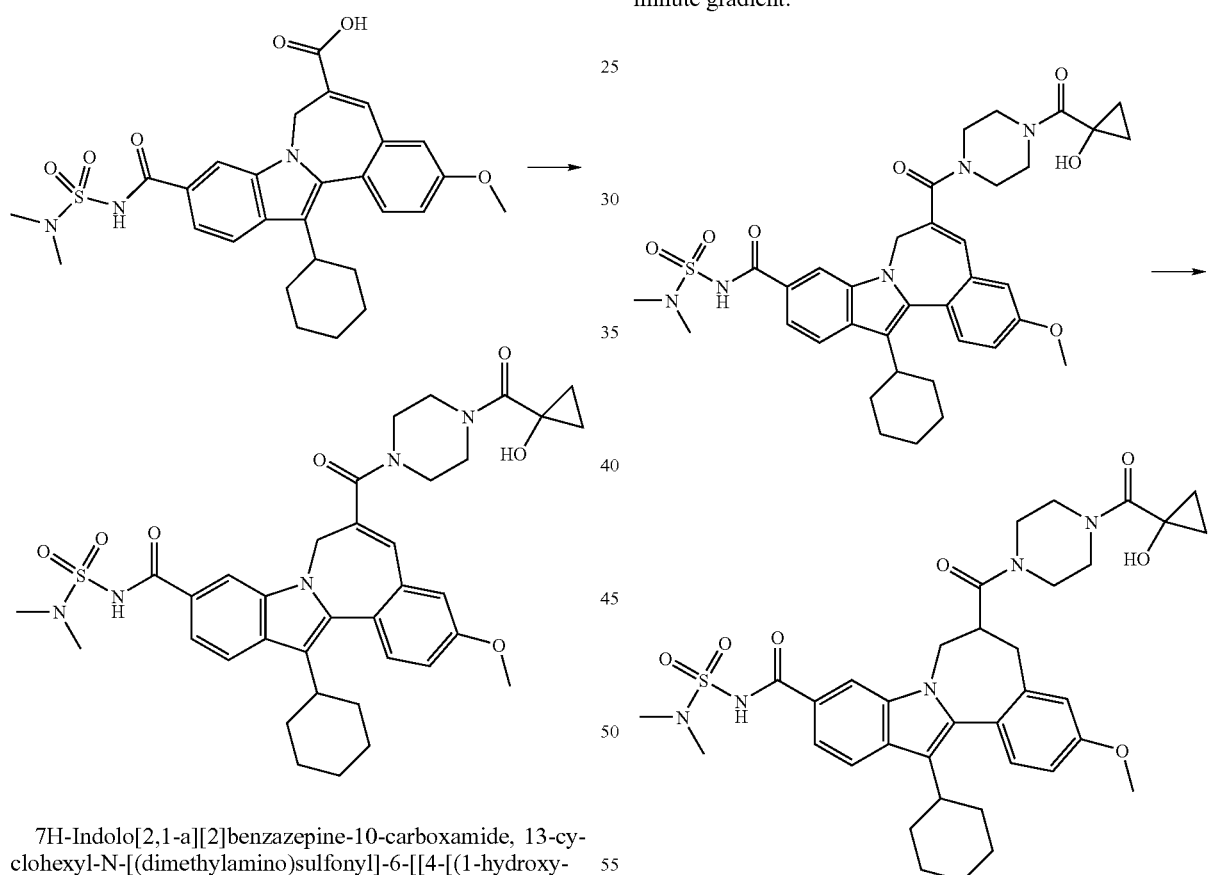

7H-Indolo[2,1-a][2]benzazepine-10-carboxamide, 13-cyclohexyl-N-[(dimethylamino)sulfonyl]-6-[[4-[(1-hydroxycyclopropyl)carbonyl]-1-piperazinyl]carbonyl]-3-methoxy-. To a solution of 13-cyclohexyl-N-[(dimethylamino)sulfonyl]-3-methoxy-7H-indolo[2,1-a][2]benzazepine-10-carboxamide-6-carboxylic acid (150 mg, 0.28 mmol), tert-butyl piperazine-1-carboxylate (68 mg, 0.36 mmol) and triethylamine (0.16 mL) in DMF (3 mL) was added HATU (138 mg, 0.36 mmol). The reaction mixture was stirred at rt for 1.5 h, diluted with H$_2$O (5 mL) and neutralized with 1N aqueous HCl (1.1 mL). The resulting precipitate was collected by filtration, washed with H$_2$O and dried under nitrogen. The solid was dissolved into ClCH$_2$CH$_2$Cl (2 mL) and treated with trifluoroacetic acid (2 mL). The reaction mixture was 5H-Indolo[2,1-a][2]benzazepine-10-carboxamide, 13-cyclohexyl-N-[(dimethylamino)sulfonyl]-6,7-dihydro-6-[[4-[(1-hydroxycyclopropyl)carbonyl]-1-piperazinyl]carbonyl]-3-methoxy-. 10% Palladium on carbon (60 mg, 0.06 mmol) was added to a solution of 7H-indolo[2,1-a][2]benzazepine-10-carboxamide, 13-cyclohexyl-N-[(dimethylamino)sulfonyl]-6-[[4-[(1-hydroxycyclopropyl)carbonyl]-1-piperazinyl] carbonyl]-3-methoxy- (58 mg, 0.084 mmol) in MeOH/ CH$_2$Cl$_2$ (2:1, 3 mL) and the reaction mixture was vacuum flushed with nitrogen (3×) and then with hydrogen (4×). The reaction was stirred under a balloon of hydrogen overnight and again vacuum flushed with nitrogen (3×) and then with hydrogen (4×). The reaction was stirred under a balloon of hydrogen for 1 d, treated with trifluoroacetic acid (2 drops), vacuum flushed with nitrogen (3×) and then with hydrogen (4×) and stirred 3 h. The reaction mixture was filtered through a pad of celite and concentrated. The residue was dissolved MeOH (2 mL) treated with 10% palladium on carbon (70 mg, 0.07 mmol), vacuum flushed with nitrogen (3×) and then with hydrogen (4×) and stirred under a balloon of hydrogen for 2 d. The reaction was filtered through a pad of celite, concentrated and purified by preparative HPLC (CH$_3$CN/H$_2$O with 10 mM NH$_4$OAc) to yield 5H-indolo[2,1-a][2]benzazepine-10-carboxamide, 13-cyclohexyl-N-[(dimethylamino)sulfonyl]-6,7-dihydro-6-[[4-[(1-hydroxycyclopropyl)carbonyl]-1-piperazinyl]carbonyl]-3-methoxy- (8.3 mg, 0.012 mmol, 14%) as a white solid. Mixture of atrope diastereomers. $^1$HNMR (300 MHz, MeOD) δ 8.11-7.96 (m, 1H), 7.89-7.81 (m, 1H), 7.67-7.54 (m, 1H), 7.42-7.33 (m, 1H), 7.13-6.87 (m, 2H), 4.63-4.43 (m, 1H), 4.43-3.39 (m, 12 H)), 3.02-2.97 (m, 6H), 2.96-2.66 (m, 4H), 2.21-1.10 (m, 14H). LCMS: m/e 692 (M+H)$^+$, ret time 2.17 min, column B, 2 minute gradient.

7H-Indolo[2,1-a][2]benzazepine-6,10-dicarboxamide, 13-cyclohexyl-N$^6$-[(1S)-2-(dimethylamino)-1-(hydroxymethyl)-1-methyl-2-oxoethyl]-N$^{10}$-[(dimethylamino)sulfonyl]-3-methoxy-. To a solution of 13-cyclohexyl-N-[(dimethylamino)sulfonyl]-3-methoxy-7H-indolo[2,1-a][2]benzazepine-10-carboxamide-6-carboxylic acid (90 mg, 0.17 mmol), (S)-2-amino-3-hydroxy-N,N,2-trimethylpropanamide (61 mg, 0.42 mmol) and triethylamine (0.12 mL) in DMF (2 mL) was added HATU (160 mg, 0.42 mmol). The reaction mixture was stirred at rt for 16 h, then diluted with MeOH/DMSO and purified by prep HPLC (MeOH/H$_2$O/ 0.1% TFA) to yield an orange solid, which was further purified by prep HPLC (CH$_3$CN/H$_2$O with 10 mM NH$_4$OAc) to yield 7H-indolo[2,1-a][2]benzazepine-6,10-dicarboxamide, 13-cyclohexyl-N$^6$-[(1S)-2-(dimethylamino)-1-(hydroxymethyl)-1-methyl-2-oxoethyl]-N$^{10}$-[(dimethylamino)sulfonyl]-3-methoxy- (14 mg, 0.021 mmol, 12%) as a bright yellow solid. $^1$HNMR (300 MHz, MeOD) δ 8.15 (s, 1H), 7.90 (d, J=8.8 Hz, 1H), 7.66-7.53 (m, 3H), 7.22-7.12 (m, 2H), 5.67-5.47 (m, 1H), 4.27-4.09 (m, 1H), 4.07-3.77 (m, 2H), 3.95 (s, 3H), 3.10-2.68 (m, 6H), 3.02 (s, 6H), 2.97-2.83 (m, 1H), 2.21-1.13 (m, 13H). LCMS: m/e 666 (M+H)$^+$, ret time 1.94 min, column B, 2 minute gradient.

The following general procedures pertain to the following examples until further noted.

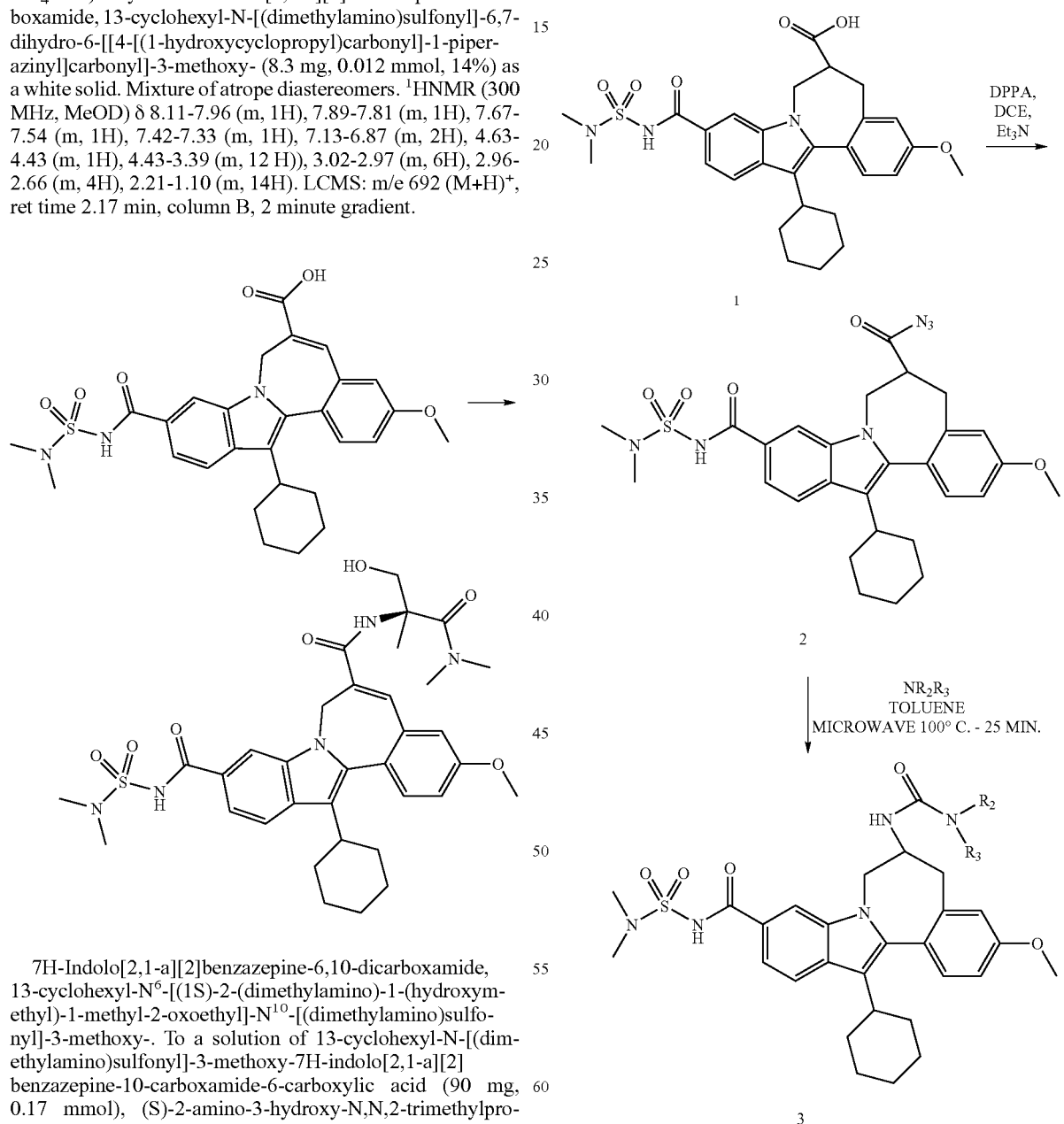

To 1.0 g of carboxylic acid 1 in a 100 mL round bottom flask equipped with a septa under nitrogen, was added 20 mL of dry dichloroethane (DCE). To this solution was then added 1.2 equivalents of Diphenylphosphorylazide (DPPA) in one portion followed by 3 equivalents of triethylamine. The solution was stirred overnight at room temperature. The reaction progress was followed by an analytical Shimadzu LC/MS. The crude mixture was passed through a 24 g SiliCycle/Isco silica gel cartridge with DCE to give acyl azide 2 as a light yellow foam after solvent evacuation (50-65% yield). The acyl azide was found to be stable at room temperature in a vacuum desiccator for up to one month. To 0.2 mmol of acyl azide 2 in 1.5 mL of dry toluene was added 1.2 equivalents of amine in a Biotage/Personal Chemistry microwave vial. The vial was capped and heated to 100° C. in a Biotage/Personal Chemistry Emrys Optomizer microwave for 25 minutes. The crude reaction mixture was then evacuated to near dryness, taken up in 2 mL acetonitrile and purified using a Shimadzu preparative HPLC employing acetonitrile/water and 10 mM trifluoroacetic acid buffer with a Waters Sunfire, C18, 19 mm×100 mm, 5 μm column at a focused gradient of 50-100% B and a flow rate of 25 mL/min., to give dimethylamino sulfamide ureas 3 as yellow amorphous solids (35-50% yield). Postpurification LC/MS data was obtained on a Shimadzu analytical LC/Micromass Platform LC (ESI+) at 220 nm using the following set of conditions: Phenomenex 10 μm C18, 4.6×30 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 2 minutes with a 1 minute hold at a rate of 5 mL/minute.

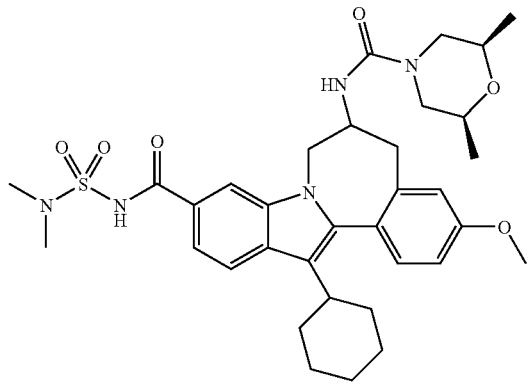

5H-Indolo[2,1-a][2]benzazepine-10-carboxamide, 13-cyclohexyl-N-[(dimethylamino)sulfonyl]-6-[[[(2R,6S)-2,6-dimethyl-4 morpholinyl]carbonyl]amino]-6,7-dihydro-3-methoxy-. $^1$H NMR (500 MHz, CHLOROFORM-D) δ ppm: 1.11-1.19 (m, 5 H), 1.27 (m, 1 H), 1.36-1.45 (m, 2 H), 1.68 (m, 1 H), 1.79 (m, 2 H), 1.92-2.04 (m, 4 H), 2.23 (t, J=12.05 Hz, 1 H), 2.50-2.58 (m, 2 H), 2.97 (m, 2 H), 3.04-3.08 (m, 6 H), 3.47 (d, J=12.51 Hz, 1 H), 3.55-3.60 (m, 1 H), 3.61-3.70 (m, 2 H), 3.79 (dd, J=15.26, 2.44 Hz, 1 H), 3.88 (m, 3 H), 4.43 (m, 1 H), 4.48 (d, J=15.26 Hz, 1 H), 4.61 (m, 1 H), 6.92-7.00 (m, 2 H), 7.34-7.41 (m, 1 H), 7.50-7.58 (m, 1 H), 7.89 (m, 1 H), 7.98 (s, 1 H). LC/MS: m/z 652.38 (MH$^+$), Rf 2.11 min., 98.0% purity.

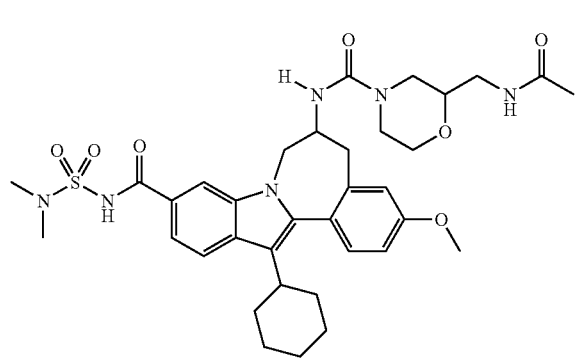

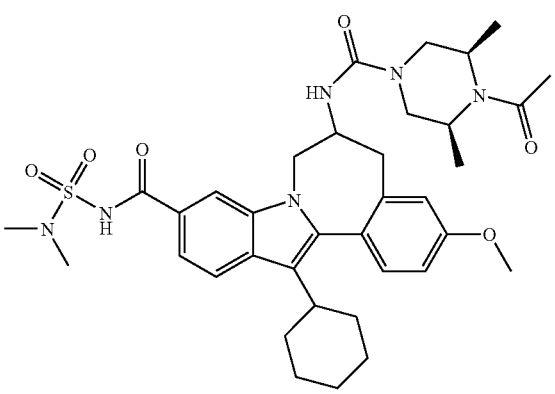

5H-Indolo[2,1-a][2]benzazepine-10-carboxamide, 6-[[[2-[(acetylamino)methyl]-4-morpholinyl]carbonyl]amino]-13-cyclohexyl-N-[(dimethylamino)sulfonyl]-6,7-dihydro-3-methoxy-. $^1$H NMR (500 MHz, CHLOROFORM-D) δ ppm: 1.23-1.31 (m, 1 H), 1.40-1.46 (m, 2 H), 1.70 (m, 1 H), 1.75-1.83 (m, 2H), 1.85-1.94 (m, 3H), 1.98-2.03 (m, 2 H), 2.21-2.34 (m, 1 H), 2.71-2.81 (m, 1 H), 2.87-2.97 (m, 3 H), 3.01-3.06 (m, 6 H), 3.07-3.16 (m, 1 H), 3.20-3.29 (m, 1 H), 3.30-3.38 (m, 1 H), 3.41-3.49 (m, 1 H), 3.52 (m, 1 H), 3.56-3.64 (m, 1 H), 3.76 (m, 2 H), 3.88 (s, 3 H), 4.00 (m, 1 H), 4.46 (m, 1 H), 4.55 (m, 1 H), 4.63 (m, 1 H), 6.93-6.97 (m, 2 H), 7.38 (m, 1 H), 7.49 (m, 1 H), 7.85-7.90 (m, 1 H), 7.96 (s, 1 H). LC/MS: m/z 695.44 (MH$^+$), Rf 2.15 min., 98.9% purity.

5H-Indolo[2,1-a][2]benzazepine-10-carboxamide, 6-[[[(3R, 5S)-4-acetyl-3,5-dimethyl-1-piperazinyl]carbonyl]amino]-13-cyclohexyl-N-[(dimethylamino)sulfonyl]-6,7-dihydro-3-methoxy-, rel-. $^1$H NMR (500 MHz, CHLOROFORM-D) δ ppm: 1.26 (m, 4 H), 1.37 (m, 5 H), 1.44 (m, 2 H), 1.70 (m, 1 H) 1.77-1.82 (m, 2 H), 1.94 (m, 1 H), 1.99 (m, 3 H), 2.14-2.22 (m, 3 H), 2.26 (m, 1 H), 2.90-2.95 (m, 1 H), 2.98-3.07 (m, 7 H), 3.17 (m, 2 H), 3.83 (d, J=15.56 Hz, 1 H), 3.88 (s, 3 H), 4.48 (d, J=14.95 Hz, 1 H), 4.61 (m, 2 H), 4.70 (m, 1 H), 6.94 (s, 1 H), 6.97 (m, 1 H), 7.38 (m, 1 H), 7.46-7.55 (m, 1 H), 7.89 (m, 1 H), 7.95 (m, 1 H). LC/MS: m/z 693.47 (MH$^+$), Rf 2.07 min., 94.8% purity.

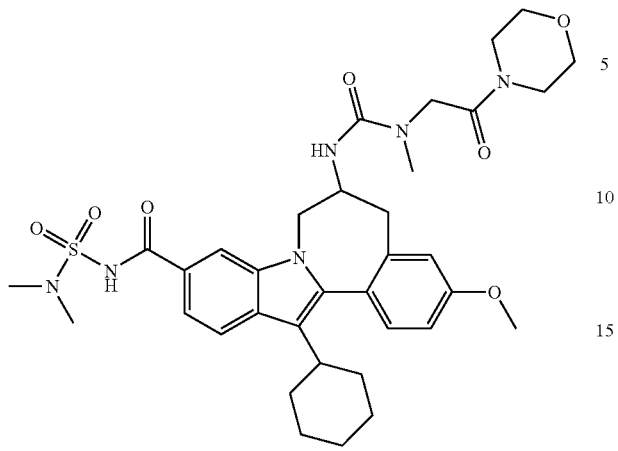

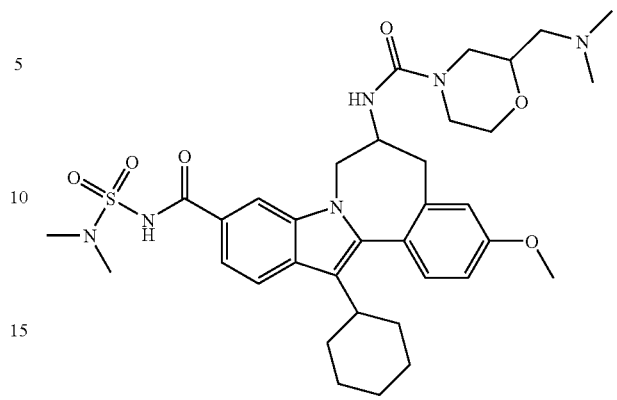

5H-Indolo[2,1-a][2]benzazepine-10-carboxamide, 13-cyclohexyl-N-[(dimethylamino)sulfonyl]-6,7-dihydro-3-methoxy-6-[[[methyl[2-(4-morpholinyl)-2-oxoethyl]amino]carbonyl]amino]-. $^1$H NMR (500 MHz, CHLOROFORM-D) δ ppm: 1.21-1.30 (m, 1 H), 1.36-1.44 (m, 1 H), 1.65 (d, J=11.90 Hz, 1 H), 1.78 (d, J=9.46 Hz, 2 H), 1.96 (d, J=11.90 Hz, 1 H), 1.98-2.07 (m, 3 H), 2.25 (t, J=12.21 Hz, 1 H), 2.87-2.95 (m, 5 H), 2.96-3.01 (m, 6 H), 3.02-3.06 (m, 1 H), 3.43-3.52 (m, 2 H), 3.60-3.69 (m, 2 H), 3.72-3.81 (m, 5 H), 3.84-3.90 (m, 3 H), 4.37 (d, J=14.95 Hz, 1 H), 4.56-4.65 (m, 1 H), 4.71-4.80 (m, 2 H), 6.92-6.99 (m, 2 H), 7.39 (d, J=8.55 Hz, 1 H), 7.86-7.94 (m, 2 H), 8.50 (s, 1 H). LC/MS: m/z 695.85 (MH$^+$), Rf 2.14 min., 100.0% purity.

5H-Indolo[2,1-a][2]benzazepine-10-carboxamide, 13-cyclohexyl-6-[[[2-[(dimethylamino)methyl]-4-morpholinyl]carbonyl]amino]-N-[(dimethylamino)sulfonyl]-6,7-dihydro-3-methoxy-. $^1$H NMR (500 MHz, CHLOROFORM-D) δ ppm: 1.27 (m, 1 H), 1.35-1.41 (m, 1 H), 1.69 (m, 1 H), 1.77 (m, 2 H), 1.92 (m, 1 H), 1.96-2.04 (m, 2 H), 2.23-2.31 (m, 1 H), 2.78-2.88 (m, 4 H), 2.88-2.97 (m, 4 H), 2.98-3.06 (m, 6 H), 3.09 (d, J=1.53 Hz, 2 H), 3.22 (m, 1 H), 3.34 (m, 1 H), 3.44 (m, 1 H), 3.44-3.49 (m, 2 H), 3.49-3.58 (m, 1 H), 3.62 (m, 1 H), 3.78 (m, 1 H), 3.79-3.85 (m, 1 H), 3.85-3.90 (m, 3 H), 3.90-3.99 (m, 1 H), 4.44-4.52 (m, 1 H), 4.54 (m, 1 H), 6.90-6.99 (m, 2 H), 7.32-7.39 (m, 1 H), 7.54 (m, 1 H), 7.89 (d, J=8.55 Hz, 1 H), 7.98 (s, 1 H). LC/MS: m/z 681.49 (MH$^+$), Rf 1.89 min., 93.1% purity.

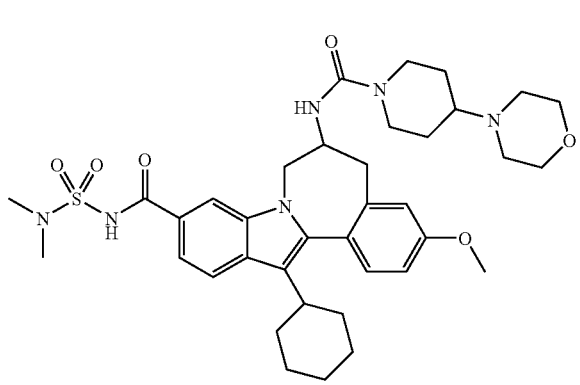

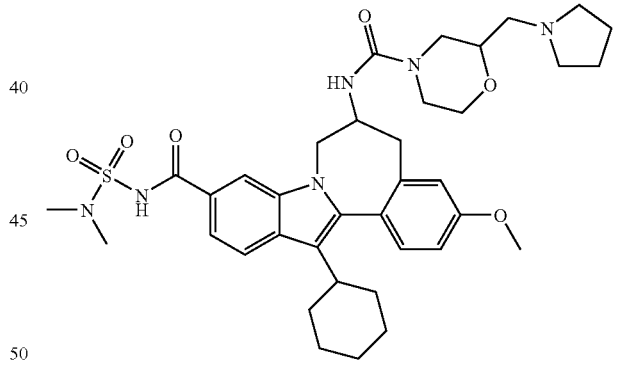

5H-Indolo[2,1-a][2]benzazepine-10-carboxamide, 13-cyclohexyl-N-[(dimethylamino)sulfonyl]-6,7-dihydro-3-methoxy-6-[[[4-(4-morpholinyl)-1-piperidinyl]carbonyl]amino]-. $^1$H NMR (500 MHz, CHLOROFORM-D) δ ppm: 1.28 (m, 1 H), 1.34-1.48 (m, 2 H), 1.70 (m, 1 H), 1.78 (m, 2 H), 1.94 (m, 1 H), 1.98-2.04 (m, 4 H), 2.19 (t, J=11.75 Hz, 1 H), 2.68 (t, J=11.75 Hz, 1 H), 2.89-2.98 (m, 3 H), 3.00 (s, 6 H), 3.03-3.07 (m, 1 H), 3.14 (m, 1 H), 3.26 (m, 2 H), 3.44 (m, 1 H), 3.48 (m, 2 H), 3.58 (m, 1 H), 3.62 (m, 1 H), 3.73-3.82 (m, 1 H), 3.88 (s, 3 H), 3.92-4.07 (m, 3 H), 4.32 (m, 1 H), 4.47-4.55 (m, 2 H), 4.55-4.62 (m, 1 H), 6.91-6.97 (m, 2 H), 7.36 (d, J=8.24 Hz, 1 H), 7.50-7.55 (m, 1 H), 7.89 (d, J=8.24 Hz, 1 H), 8.04 (s, 1 H). LC/MS: m/z 707.50 (MH$^+$), Rf 1.89 min., 99.0% purity.

5H-Indolo[2,1a][2]benzazepine-10-carboxamide, 13-cyclohexyl-N-[(dimethylamino)sulfonyl]-6,7-dihydro-3-methoxy-6-[[[2-(1-pyrrolidinylmethyl)-4-morpholinyl]carbonyl]amino]-. $^1$H NMR (500 MHz, CHLOROFORM-D) δ ppm: 1.26 (m, 1 H), 1.35-1.48 (m, 2 H), 1.67 (m, 1 H), 1.78 (m, 2 H), 1.90 (m, 1 H), 1.98-2.07 (m, 6 H), 2.25-2.34 (m, 1 H), 2.77-2.83 (m, 1 H), 2.87-2.95 (m, 2 H), 2.96-3.05 (m, 6 H), 3.06-3.12 (m, 1 H), 3.17 (m, 1 H), 3.31-3.35 (m, 1 H), 3.47-3.50 (m, 1 H), 3.53 (m, 1 H), 3.64-3.70 (m, 2 H), 3.77-3.86 (m, 2 H), 3.87-3.88 (m, 3 H), 3.91-3.93 (m, 2 H), 3.95-4.04 (m, 1 H), 4.19 (d, J=13.73 Hz, 1 H), 4.36 (m, 1 H), 4.41-4.48 (m, 1 H), 4.50 (m, 1 H), 6.91-6.99 (m, 2 H), 7.32-7.38 (m, 1 H), 7.55-7.76 (m, 1 H), 7.86-7.93 (m, 1 H), 8.02-8.53 (m, 1 H). LC/MS: m/z 707.5 (MH$^+$), Rf 1.90 min., 94.1% purity.

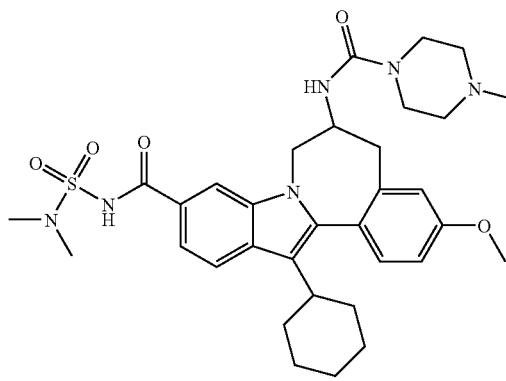

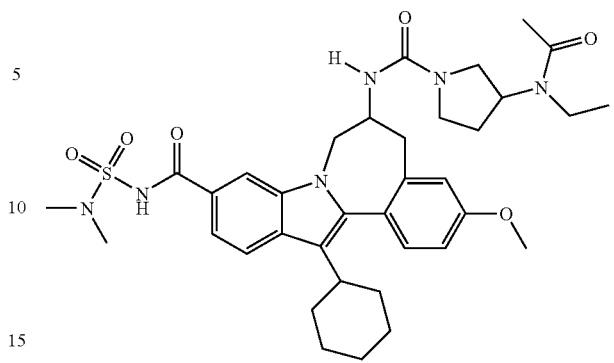

1,4-Piperazinedicarboxamide, N-[13-cyclohexyl-10-[[[(dimethylamino)sulfonyl]amino]carbonyl]-6,7-dihydro-3-methoxy-5H-indolo[2,1-a][2]benzazepin-6-yl]-. ¹H NMR (500 MHz, CHLOROFORM-D) δ ppm: 1.23-1.31 (m, 1 H), 1.34-1.44 (m, 2 H), 1.66 (m, 1 H), 1.78 (m, 2 H), 1.94 (m, 1 H), 1.99 (m, 2 H), 2.15 (m, 1 H), 2.90-2.99 (m, 2 H), 3.00-3.06 (m, 6 H), 3.23-3.31 (m, 2 H), 3.46-3.56 (m, 6 H), 3.77-3.86 (m, 1 H), 3.88 (s, 3 H), 4.39 (d, J=7.63 Hz, 1 H), 4.51 (d, J=14.95 Hz, 1 H), 4.61 (m, 1 H), 6.90-6.98 (m, 2 H), 7.38 (d, J=8.55 Hz, 1 H), 7.44 (d, J=8.55 Hz, 1 H), 7.89 (d, J=8.55 Hz, 1 H), 7.96 (s, 1 H). LC/MS: m/z 666.42 (MH⁺), Rf 2.02 min., 92.7% purity.

5H-Indolo[2,1-a][2]benzazepine-10-carboxamide, 6-[[[3-(acetylethylamino)-1-pyrrolidinyl]carbonyl]amino]-13-cyclohexyl-N-[(dimethylamino)sulfonyl]-6,7-dihydro-3-methoxy-. ¹H NMR (500 MHz, CHLOROFORM-D) δ ppm: 1.09-1.18 (m, 3 H), 1.20-1.29 (m, 2 H), 1.35-1.44 (m, 2 H), 1.68 (m, 1 H), 1.78 (m, 2 H), 1.91 (m, 2 H), 1.98 (m, 1 H), 2.01 (m, 1 H), 2.08 (m, 3 H), 2.14 (m, 1 H), 2.16-2.23 (m, 1 H), 2.29-2.33 (m, 1 H), 2.89-2.97 (m, 2 H), 2.99-3.07 (m, 7 H), 3.24-3.33 (m, 2 H), 3.35 (m, 1 H), 3.41 (m, 1 H), 3.74 (dd, J=14.95, 3.05 Hz, 1 H), 3.85-3.90 (s, 3 H), 4.26 (m, 1 H), 4.50 (d, J=15.26 Hz, 1 H), 4.57 (m, 1 H), 6.93 (m, 1 H), 6.96 (m, 1 H), 7.37 (m, 1 H), 7.56-7.66 (m, 1 H), 7.89 (m, 1 H), 7.95-8.02 (m, 1 H). LC/MS: m/z 693.46 (MH⁺), Rf 2.11 min., 100.0% purity.

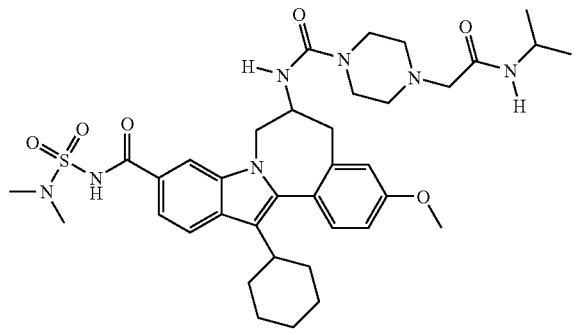

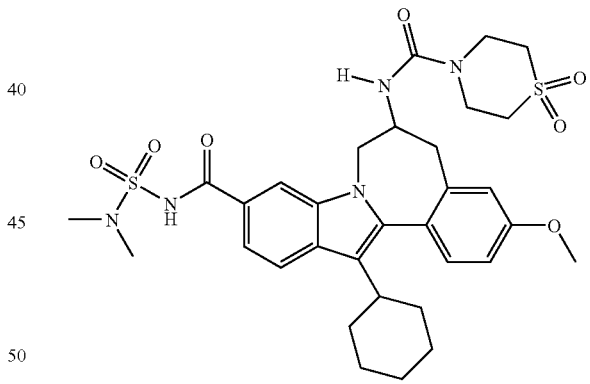

5H-Indolo[2,1-a][2]benzazepine-10-carboxamide, 13-cyclohexyl-N-[(dimethylamino)sulfonyl]-6,7-dihydro-3-methoxy-6-[[[4-[2-[(1-methylethyl)amino]-2-oxoethyl]-1-piperazinyl]carbonyl]amino]-. ¹H NMR (500 MHz, CHLOROFORM-D) δ ppm: 1.10-1.14 (m, 6 H), 1.26 (m, 1 H), 1.35-1.39 (m, 1 H), 1.42 (m, 1 H), 1.70 (m, 1 H), 1.78 (d, J=11.60 Hz, 2 H), 1.93-2.00 (m, 4 H), 2.26 (t, J=12.05 Hz, 1 H), 2.88-2.98 (m, 3 H), 2.99-3.05 (m, 6 H), 3.42 (m, 4 H), 3.68 (dd, J=15.26, 3.05 Hz, 1 H), 3.85-3.89 (m, 4 H), 3.90-3.94 (m, 1 H), 3.95-4.04 (m, 3 H), 4.45 (m, 1 H), 4.66 (d, J=14.95 Hz, 1 H), 4.78 (m, 1 H), 6.81 (d, J=7.63 Hz, 1 H), 6.91-6.99 (m, 2 H), 7.33-7.40 (m, 2 H), 7.87 (d, J=8.24 Hz, 1 H). LC/MS: m/z 722.56 (MH⁺), Rf 1.91 min., 96.4% purity.

5H-Indolo[2,1-a][2]benzazepine-10-carboxamide, 13-cyclohexyl-N-[(dimethylamino)sulfonyl]-6-[[[(1,1-dioxido-4-thiomorpholinyl)carbonyl]amino]-6,7-dihydro-3-methoxy-. ¹H NMR (500 MHz, CHLOROFORM-D) δ ppm: 1.27 (m, 1 H), 1.36-1.48 (m, 2 H), 1.65-1.68 (m, 1 H), 1.78-1.80 (m, 2 H), 1.92-2.00 (m, 3 H), 2.21 (m, 1 H), 2.99-3.00 (m, 3 H), 3.04 (s, 6 H), 3.08-3.13 (m, 3 H), 3.71 (m, 2 H), 3.79-3.86 (m, 1 H), 3.88 (s, 3 H) 3.95 (m, 2H), 4.50 (d, J=15.26 Hz, 1 H), 4.58 (m, 1 H), 4.63 (m, 1 H), 6.92-7.00 (m, 2 H), 7.33-7.42 (m, 2 H), 7.85-7.91 (m, 1 H), 7.94 (s, 1 H). LC/MS: m/z 672.35 (MH⁺), Rf 2.02 min., 96.8% purity.

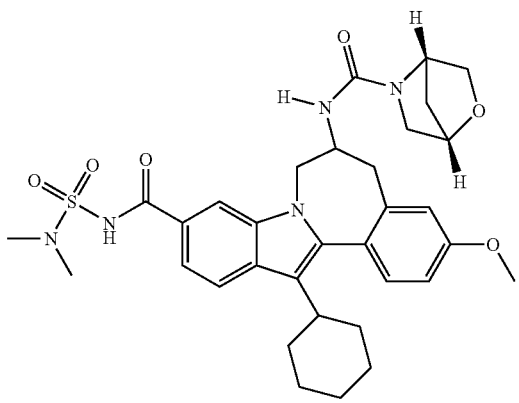

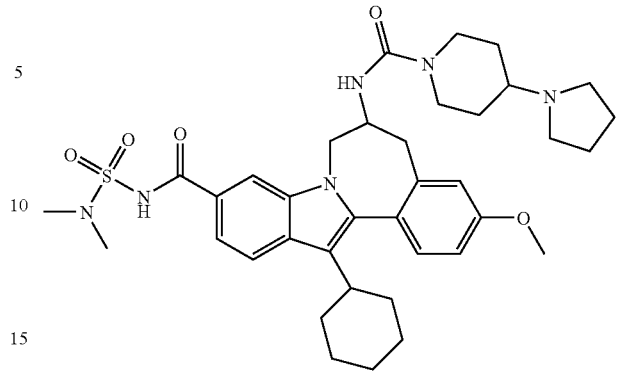

5H-Indolo[2,1-a][2]benzazepine-10-carboxamide, 13-cyclohexyl-N-[(dimethylamino)sulfonyl]-6,7-dihydro-3-methoxy-6-[[[(1S,4S)-2-oxa-5-azabicyclo[2.2.1]hept-5-ylcarbonyl]amino]-. ¹H NMR (500 MHz, CHLOROFORM-D) δ ppm: 1.27 (m, 1 H), 1.36-1.46 (m, 2 H), 1.68 (m, 1 H), 1.78 (m, 2 H), 1.90-1.96 (m, 3 H), 1.97-2.07 (m, 3 H), 2.08-2.26 (m, 1 H), 2.92-3.00 (m, 2 H), 3.02-3.07 (m, 6 H), 3.08-3.17 (m, 1 H), 3.31 (m, 1 H), 3.78-3.82 (m, 1 H), 3.88 (s, 3 H), 3.92-4.02 (m, 1H), 4.23 (m, 1 H), 4.46-4.63 (m, 3 H), 4.74 (m, 1 H), 6.92-7.00 (m, 2 H), 7.35-7.42 (m, 1 H), 7.52-7.62 (m, 1 H), 7.86-7.96 (m, 2 H). LC/MS: m/z 636.40 (MH⁺), Rf 2.06 min., 97.9% purity.

5H-Indolo[2,1-a][2]benzazepine-10-carboxamide, 13-cyclohexyl-N-[(dimethylamino)sulfonyl]-6,7-dihydro-3-methoxy-6-[[[4-(1-pyrrolidinyl)-1-piperidinyl]carbonyl]amino]-. ¹H NMR (500 MHz, CHLOROFORM-D) δ ppm: 1.24-1.31 (m, 1 H), 1.35-1.43 (m, 2 H), 1.68 (m, 1 H,) 1.78 (m, 2 H), 1.92 (m, 2 H), 1.97-2.14 (m, 10 H), 2.19-2.24 (m, 1 H), 2.70 (m, 1 H), 2.86-2.97 (m, 4 ), 2.98-3.02(m, 6H), 3.16(m, 1 H), 3.71-3.81 (m,3 H) 3.87-3.91 (m, 4H), 4.02 (m, 1 H), 4.51 (d, J=14.95 Hz, 1 H), 4.59 (m, 1 H), 4.69 (m, 1 H), 6.92-6.96 (m, 2 H), 7.35 (d, J=8.24 Hz, 1 H), 7.62 (m, 1 H), 7.89 (d, J=8.54 Hz, 1 H), 8.10 (s, 1 H). LC/MS: m/z 691.48 (MH⁺), Rf 1.89 min., 98.0% purity.

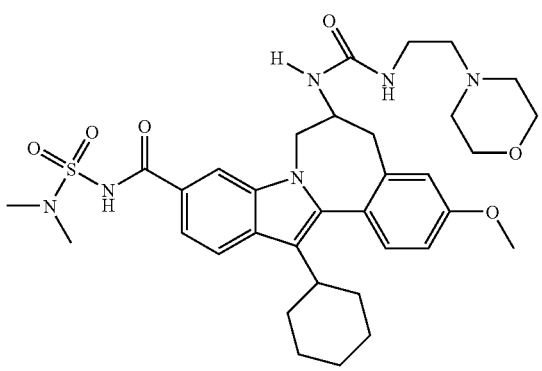

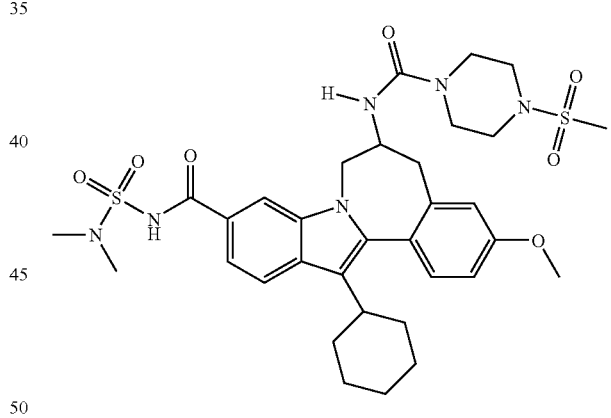

5H-Indolo[2,1-a][2]benzazepine-10-carboxamide, 13-cyclohexyl-N-[(dimethylamino)sulfonyl]-6,7-dihydro-3-methoxy-6-[[[[2-(4-morpholinyl)ethyl]amino]carbonyl]amino]-. ¹H NMR (500 MHz, CHLOROFORM-D) δ ppm: 1.22-1.29 (m, 1 H), 1.34-1.45 (m, 2 H), 1.64 (m, 1 H), 1.77 (m, 2 H), 1.91 (m, 1 H), 1.95-2.03 (m, 2 H), 2.23 (t, J=12.05 Hz, 1 H), 2.88-2.97 (m, 4 H), 2.99-3.06 (m, 6 H), 3.20 (m, 1 H), 3.34 (m, 1 H), 3.48 (m, 2 H), 3.59 (m, 1 H), 3.65 (m, 1 H), 3.75 (dd, J=15.11, 3.36 Hz, 1 H), 3.83 (m, 1 H), 3.87 (m, 3 H), 3.89 (m, 1 H), 3.92 (m, 1 H), 3.96-4.03 (m, 2 H), 4.43 (m, 2 H), 6.92 (m, 2 H), 7.35 (m, 1 H), 7.47 (m,1 H), 7.84-7.88 (m, 2 H). LC/MS: m/z 667.45 (MH⁺), Rf 1.88 min., 98.0% purity.

5H-Indolo[2,1-a][2]benzazepine-10-carboxamide, 13-cyclohexyl-N-[(dimethylamino)sulfonyl]-6,7-dihydro-3-methoxy-6-[[[4-(methylsulfonyl)-1-piperazinyl]carbonyl]amino]-. ¹H NMR (500 MHz, CHLOROFORM-D) δ ppm: 1.23-1.32 (m, 1 H), 1.38-1.47 (m, 2 H), 1.67 (m, 1 H), 1.79 (m, 2 H), 1.93 (m, 1 H), 1.96-2.06 (m, 2 H), 2.24-2.32 (m, 1 H), 2.77-2.84 (m, 1 H), 2.85 (s, 3 H), 2.93-2.96 (m, 2 H), 3.00 (s, 3 H), 3.05 (m, 3 H), 3.18-3.28 (m, 5 H), 3.64-3.67 (m, 2 H), 3.74-3.78 (m, 1 H), 3.89 (s, 3 H), 4.50 (d, J=15.26 Hz, 1 H), 4.58 (m, 2 H), 6.93 (d, J=2.44 Hz, 1 H), 6.98 (dd, J=8.55, 2.44 Hz, 1 H), 7.38 (d, J=8.24 Hz, 1 H), 7.49 (dd, J=8.54, 1.53 Hz, 1 H), 7.86-7.93 (m, 2 H). LC/MS: m/z 701.39 (MH⁺), Rf 2.05 min., 100.0% purity.

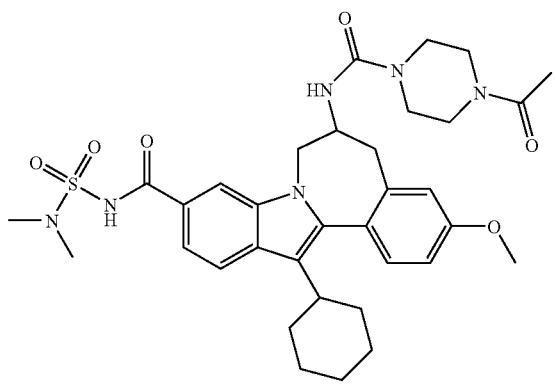

5H-Indolo[2,1-a][2]benzazepine-10-carboxamide, 6-[[[(4-acetyl-1-piperazinyl)carbonyl]amino]-13-cyclohexyl-N-[(dimethylamino)sulfonyl]-6,7-dihydro-3-methoxy-. $^1$H NMR (500 MHz, CHLOROFORM-D) δ ppm: 1.22-1.32 (m, 1 H), 1.36-1.47 (m, 2 H), 1.66 (m, 1 H), 1.79 (m, 2 H), 1.93 (m, 1 H), 1.97-2.06 (m, 3 H), 2.10-2.16 (s, 3 H), 2.14-2.24 (m, 1 H), 2.83-2.98 (m, 2 H), 300-3.09 (m, 6 H), 3.22 (m, 1 H), 3.31-3.41 (m, 2 H), 3.51-3.61 (m, 4 H), 3.64-3.71 (m, 1 H), 3.73-3.82 (m, 1 H), 3.88 (s, 3 H), 4.50 (m, 1 H), 4.55-4.64 (m, 1 H), 6.93 (m, 1 H), 6.95-6.99 (m, 1 H), 7.38 (d, J=8.24 Hz, 1 H), 7.47 (dd, J=8.55, 1.53 Hz, 1 H), 7.86-7.92 (m, 1 H), 7.94 (s, 1 H). LC/MS: m/z 665.45 (MH$^+$), Rf 2.05 min., 97.4% purity.

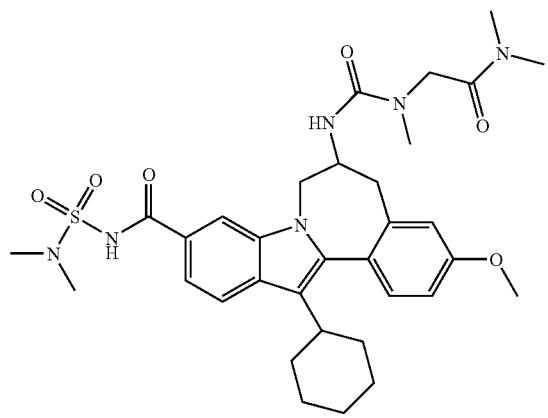

5H-Indolo[2,1-a][2]benzazepine-10-carboxamide, 13-cyclohexyl-6-[[[[2-(dimethylamino)-2-oxoethyl]methylamino]carbonyl]amino]-N-[(dimethylamino)sulfonyl]-6,7-dihydro-3-methoxy-. $^1$H NMR (500 MHz, CHLOROFORM-D) δ ppm: 1.22-1.33 (m, 1 H), 1.34-1.46 (m, 2 H), 1.65 (m, 1 H), 1.78 (m, 2 H), 1.93 (m, 1 H), 1.98-2.08 (m, 3 H), 2.26 (m, 1 H), 2.82-3.04 (m, 16 H), 3.55 (m, 1 H), 3.75 (m, 1 H), 3.88 (m, 3 H), 4.39 (m, 1 H), 4.58-4.63 (m, 1 H), 4.69-4.75 (m, 2 H), 6.91-6.96 (m, 2 H), 7.35-7.40 (m, 1 H), 7.87-7.89 (m, 2 H), 8.64-8.66 (m, 1 H). LC/MS: m/z 653.42 (MH$^+$), Rf 2.10 min., 100.0% purity.

(6R)-5H-Indolo[2,1-a][2]benzazepine-10-carboxamide, 13-cyclohexyl-6-[[[[2-(dimethylamino)-2-oxoethyl]methylamino]carbonyl]amino]-N-[(dimethylamino)sulfonyl]-6,7-dihydro-3-methoxy- and (6S)-5H-Indolo[2,1-a][2]benzazepine-10-carboxamide, 13-cyclohexyl-6-[[[[2-(dimethylamino)-2-oxoethyl]methylamino]carbonyl] amino]-N-[(dimethylamino)sulfonyl]-6,7-dihydro-3-methoxy-. The chiral separation the R & S enantiomers was accomplished using preparative chiral supercritical fluid chromatography (SFC) employing a ChiralCel OD-H, 30×250 mm, 5 μm column. The mixture of enantiomers was taken up in isopropanol (4 mg/1 mL), injected onto the column and eluted with 80% $CO_2$ and 20% methanol with 0.1% trifluoroacetic acid buffer at a flow rate of 70 mL/minute. The temperature was maintained at 35° C. and the pressure at 150 bar throughout the experiment and the elution of the products was monitored by a UV detector at a wave length of 210 nm. Isomer A eluted at 13.92 minutes. Isomer B eluted at 17.93 minutes. The samples were concentrated en-vacuo to give enantiomerically pure yellow amorphous solids. Isomer A: $^1$H NMR (500 MHz, CHLOROFORM-D): δ ppm 1.20-1.29 (m, 1 H), 1.33-1.43 (m, 2 H), 1.65 (d, J=11.12 Hz, 1 H), 1.77 (m, 2 H), 1.92 (d, J=11.12 Hz, 1 H), 1.98-2.08 (m, 3 H), 2.26 (t, J=12.21 Hz, 1 H), 2.82 (br s, 3 H), 2.85-2.89 (m, 1 H), 2.93 (s, 3 H), 3.00 (s, 6 H) 3.03 (s, 3 H), 3.04 (s, 3H), 3.54 (d, J=14.95 Hz, 1 H), 3.75 (dd, J=14.95, 2.75 Hz, 1 H), 3.88 (s, 3 H), 4.39 (d, J=14.95 Hz, 1 H), 4.59 (m, 1 H), 4.71 (m, 2 H), 6.93 (s, 1 H), 6.95 (d, J=8.55 Hz, 1 H), 7.39 (d, J=8.55 Hz, 1 H), 7.89 (m, 2 H), 8.64 (s, 1 H). LC/MS: m/z 653.41 (MH$^+$), Rf 2.08 min., 99.0% purity. Isomer B: $^1$H NMR (500 MHz, CHLOROFORM-D): δ ppm 1.18-1.29 (m, 1 H), 1.37-1.44 (m, 2 H), 1.65 (d, J=12.51 Hz, 1 H), 1.78 (m, 2 H), 1.93 (d, J=12.51 Hz, 1 H), 1.98-2.07 (m, 3 H), 2.26 (t, J=12.21 Hz, 1 H), 2.83 (br s, 3 H), 2.85-2.89 (m, 1 H), 2.92 (s, 3 H), 3.00 (s, 6 H) 3.03 (s, 3 H), 3.04 (s, 3H), 3.57 (d, J=15.26 Hz, 1 H), 3.75 (dd, J=14.95, 2.75 Hz, 1 H), 3.88 (s, 3 H), 4.40 (d, J=15.26 Hz, 1 H), 4.59 (m, 1 H), 4.73 (m, 2 H), 6.93 (s, 1 H), 6.96 (d, J=8.24 Hz, 1 H), 7.39 (d, J=8.24 Hz, 1 H), 7.89 (m, 2 H), 8.62 (s, 1 H). LC/MS: m/z 653.46 (MH$^+$), Rf 2.09 min., 95.3% purity.

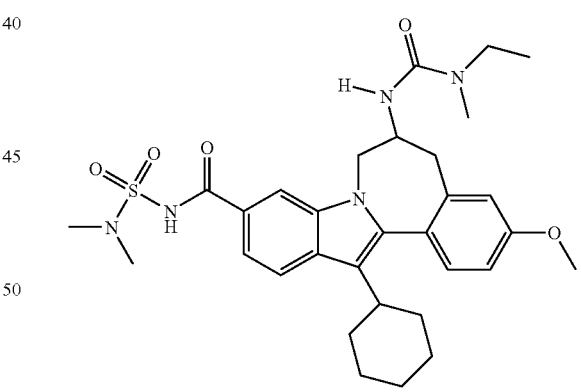

5H-Indolo[2,1-a][2]benzazepine-10-carboxamide, 13-cyclohexyl-N-[(dimethylamino)sulfonyl]-6-[[(ethylmethylamino)carbonyl]amino]-6,7-dihydro-3-methoxy-. $^1$H NMR (500 MHz, Acetone-D6) δ ppm: 1.09-1.18 (m, 3 H), 1.36 (m, 1 H), 1.51 (m, 2 H), 1.68 (m, 1 H), 1.84 (m, 2 H), 1.99 (m, 1 H), 2.08-2.20 (m, 3 H), 2.57 (t, J=12.20 Hz, 1 H), 2.88 (s, 3 H), 2.94-3.02 (m, 2 H), 3.04-3.10 (m, 6 H), 3.32-3.41 (m, 1 H), 3.72 (m, 1 H), 3.97 (m, 3 H), 4.55 (m, 1 H), 4.68 (m, 1 H), 4.76 (m, 1 H), 7.05-7.12 (m, 1 H), 7.18 (s, 1 H), 7.48-7.51 (m, 1H), 7.74-7.79 (m, 1 H), 7.96-8.02 (m, 1H), 8.17 (s, 1 H). LC/MS: m/z 596.35 (MH$^+$), Rf 2.08 min., 99.4% purity.

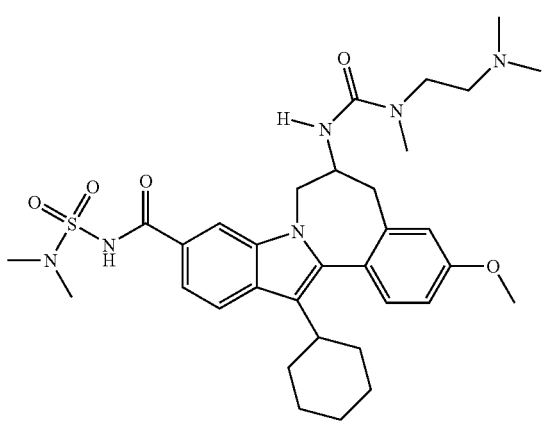
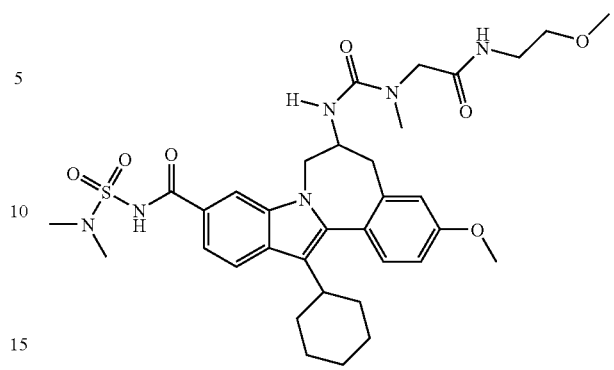

5H-Indolo[2,1-a][2]benzazepine-10-carboxamide, 13-cyclohexyl-6-[[[[2-(dimethylamino)ethyl]methylamino]carbonyl]amino]-N-[(dimethylamino)sulfonyl]-6,7-dihydro-3-methoxy-. $^1$H NMR (500 MHz, Acetone-D6) δ ppm: 1.27 (m, 1 H), 1.44 (m, 2 H), 1.60 (m, 1 H), 1.76 (m, 2 H), 1.90 (m, 1 H), 2.49 (m, 1 H), 2.84-2.91 (m, 3 H), 2.93-3.01 (m, 8 H), 3.02-3.05 (m, 1 H), 3.10 (m, 4H), 3.30 (m, 1 H), 3.47 (m, 1 H) 3.60 (m, 1 H), 3.68 (m, 1 H,) 3.88 (s, 3 H), 3.96 (m, 1 H), 4.02 (m, 2 H), 4.10 (m, 1 H), 4.54 (m, 1 H), 4.61 (d, J=14.95 Hz, 1 H), 4.67 (m, 1H), 7.02-7.07 (m, 2 H), 7.41-7.45 (m, 1 H), 7.70 (d, J=8.55 Hz, 1 H), 7.89 (d, J=8.55 Hz, 1 H), 8.30 (s, 1 H). LC/MS: m/z 639.58 (MH$^+$), Rf 1.87 min., 100.0% purity.

5H-Indolo[2,1-a][2]benzazepine-10-carboxamide, 13-cyclohexyl-N-[(dimethylamino)sulfonyl]-6,7-dihydro-3-methoxy-6-[[[[2-[(2-methoxyethyl)amino]-2-oxoethyl]methylamino]carbonyl]amino]-. $^1$H NMR (500 MHz, Acetone-D6) δ ppm: 1.26 (m, 1 H), 1.45 (m, 2 H), 1.61 (m, 1 H), 1.76 (m, 2 H), 1.92 (m, 1 H), 2.08 (m, 3 H), 2.44-2.52 (m, 1 H), 2.86 (m, 4 H), 2.96 (m, 6 H), 3.22 (s, 2 H), 3.30 (m, 2 H), 3.37 (m, 4 H), 3.65 (m, 1 H), 3.84 (m, 1 H), 3.89 (s, 3 H), 4.09 (m, 1 H), 4.44 (m, 1 H), 4.51 (m, 1 H), 7.02 (d, J=7.93 Hz, 1 H), 7.06-7.10 (m, 1 H), 7.42-7.45 (m, 1 H), 7.72 (d, J=8.24 Hz, 1 H), 7.91 (m, 1 H), 8.34 (s, 1 H). LC/MS: m/z 683.40 (MH$^+$), Rf 2.08 min., 98.4% purity.

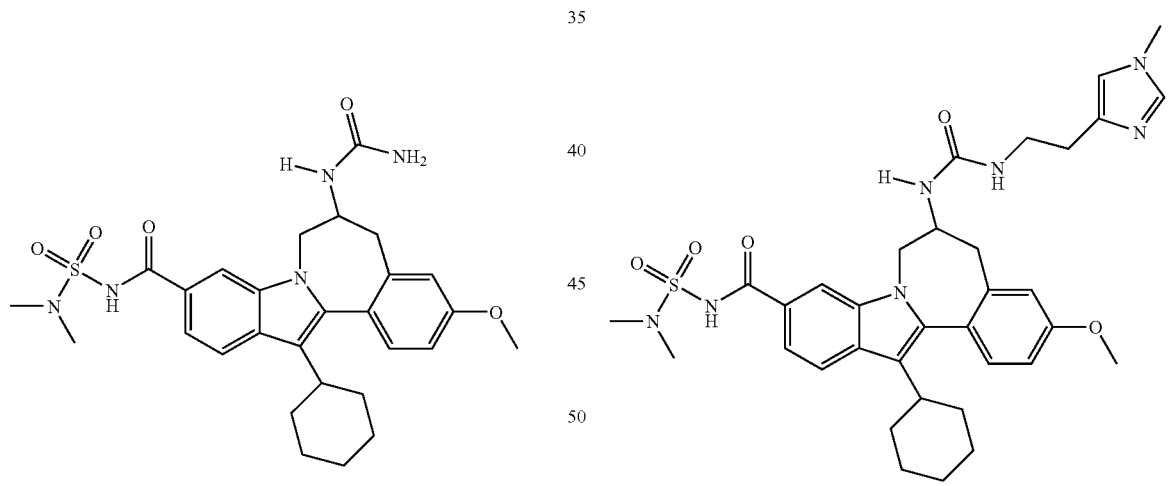

5H-Indolo[2,1-a][2]benzazepine-10-carboxamide, 6-[(aminocarbonyl)amino]-13-cyclohexyl-N-[(dimethylamino)sulfonyl]-6,7-dihydro-3-methoxy-. $^1$H NMR (500 MHz, Acetone-D6) δ ppm: 1.27 (m, 1 H), 1.44 (m, 2 H), 1.60 (m, 1 H), 1.76 (m, 2 H), 1.92 (m, 3 H), 2.22 (m, 1 H), 2.63-2.73 (m, 1 H), 2.98 (m, 6 H), 3.23-3.30 (m, 1 H), 3.71 (m, 1 H), 3.89 (s, 3 H), 4.43 (m, 1 H), 4.54 (m, 1 H), 4.59-4.69 (m, 1 H), 6.96-7.10 (m, 2 H), 7.41 (m, 1 H), 7.68-7.74 (m, 1 H), 7.93 (m, 1 H), 8.17-8.34 (m, 1 H). LC/MS: m/z 554.21 (MH$^+$), Rf 2.02 min., 100.0% purity.

5H-Indolo[2,1-a][2]benzazepine-10-carboxamide, 13-cyclohexyl-N-[(dimethylamino) sulfonyl]-6,7-dihydro-3-methoxy-6-[[[[2-(1-methyl-1H-imidazol-4-yl)ethyl]amino]carbonyl]amino]-. $^1$H NMR (500 MHz, Acetone-D6) δ ppm: 1.26 (m, 1 H) 1.43 (m, 2 H), 1.59 (m, 1 H), 1.71-1.80 (m, 2 H), 1.90 (m, 1 H), 1.99 (m, 2 H), 2.24 (m, 1 H), 2.64 (m, 1 H), 2.90-3.01 (m, 9 H), 3.44 (m, 1 H), 3.50 (m, 1 H), 3.61 (m, 1 H), 3.67 (m, 1 H), 3.84-3.92 (m, 3 H), 3.95-4.02 (m, 4 H), 4.40 (m, 1 H), 4.50 (m, 1 H), 4.59 (m, 1H), 6.98-7.03 (m, 1 H), 7.08 (s, 1 H), 7.21-7.24 (m, 1 H), 7.41 (m, 1 H), 7.63-7.71 (m, 1 H), 7.86-7.93 (m, 1 H), 8.04-8.28 (m, 1 H), 8.71-8.79 (m, 1 H). LC/MS: m/z 662.44 (MH$^+$), Rf 1.85 min., 95.0% purity.

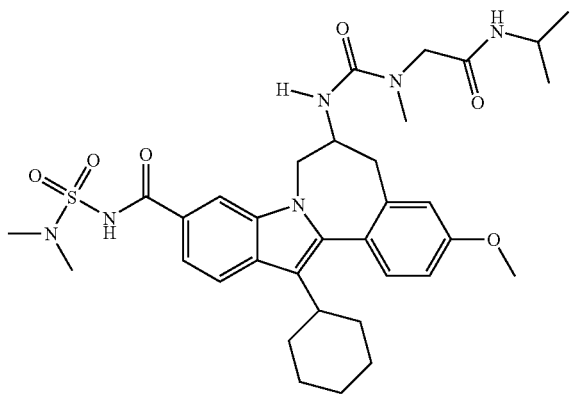

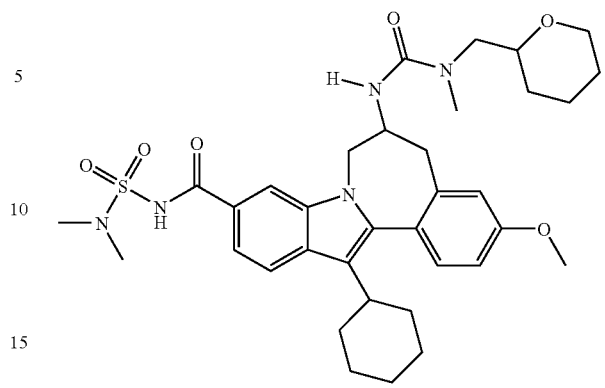

5H-Indolo[2,1-a][2]benzazepine-10-carboxamide, 13-cyclohexyl-N-[(dimethylamino)sulfonyl]-6,7-dihydro-3-methoxy-6-[[[methyl[2-[(1-methylethyl)amino]-2-oxoethyl]amino]carbonyl]amino]-. $^1$H NMR (500 MHz, Acetone-D6) δ ppm: 0.99 (d, J=6.41 Hz, 3 H), 1.07-1.16 (m, 3 H), 1.21-1.30 (m, 1 H), 1.44 (m, 2 H), 1.60 (m, 1 H), 1.76 (m, 2 H), 1.93 (m, 2 H), 2.45 (m, 1 H), 2.85-2.90 (m, 1 H), 2.92-3.00 (m, 10 H), 3.30 (m, 1 H), 3.48 (m, 1 H), 3.65 (d, J=14.95 Hz, 1 H), 3.81 (m, 1 H), 3.89 (s, 3 H), 3.96-4.02 (m, 2 H), 4.44 (m, 1 H), 4.51 (d, J=14.95 Hz, 1 H), 7.02 (d, J=8.24 Hz, 1 H), 7.07-7.10 (m, 1 H), 7.43 (m, 1 H), 7.72 (m, 1 H), 7.91 (m, 1 H), 8.35 (s, 1 H). LC/MS: m/z 667.44 (MH$^+$), Rf 2.09 min., 99.5% purity.

5H-Indolo[2,1-a][2]benzazepine-10-carboxamide, 13-cyclohexyl-N-[(dimethylamino)sulfonyl]-6,7-dihydro-3-methoxy-6-[[[methyl[(tetrahydro-2H-pyran-2-yl)methyl]amino]carbonyl]amino]-. $^1$H NMR (500 MHz, Acetone-D6) δ ppm: 0.99-1.12 (m, 1 H), 1.26 (m, 2 H), 1.40 (m, 1 H), 1.44 (m, 3 H), 1.58 (m, 2 H), 1.66 (m, 1 H), 1.76 (m, 2 H), 1.92 (m, 1 H), 2.68 (m, 1 H), 2.87 (m, 2 H), 2.92-3.02 (m, 9 H), 3.11 (m, 1 H), 3.20-3.30 (m, 3 H), 3.51 (m, 1 H), 3.65 (m, 1 H), 3.74 (m, 1 H), 3.86-3.92 (m, 4 H), 4.27 (m, 1 H), 4.50 (m, 1 H), 4.61-4.77 (m, 1 H), 6.98-7.10 (m, 2 H), 7.42 (m, 1 H), 7.68-7.75 (m, 1 H), 7.90-7.95 (m, 1 H), 8.06-8.25 (m, 1 H). LC/MS: m/z 666.47 (MH$^+$), Rf 2.26 min., 100.0% purity.

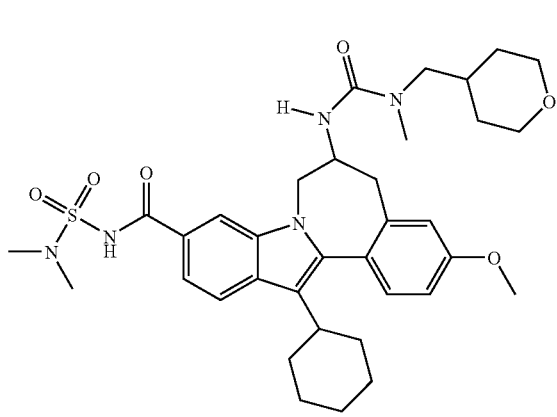

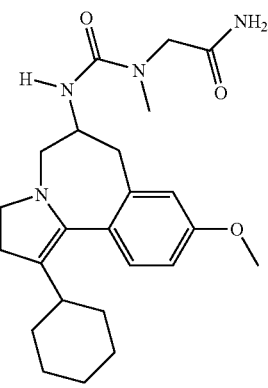

5H-Indolo[2,1-a][2]benzazepine-10-carboxamide, 13-cyclohexyl-N-[(dimethylamino)sulfonyl]-6,7-dihydro-3-methoxy-6-[[[methyl[(tetrahydro-2H-pyran-4-yl)methyl]amino]carbonyl]amino]-. $^1$H NMR (500 MHz, Acetone-D6) δ ppm: 1.04-1.13 (m, 1 H), 1.16-1.26 (m, 2 H), 1.42 (m, 2 H), 1.50 (m, 2 H), 1.57 (m, 1 H), 1.73 (m, 2 H), 1.81 (m, 1 H), 1.87 (m, 2 H), 2.41-2.49 (m, 1 H), 2.79 (m, 2 H), 2.87-2.99 (m, 9 H), 3.05 (m, 1 H), 3.15-3.26 (m, 3 H), 3.48 (m, 1 H), 3.63 (m, 1 H), 3.77 (m, 1 H), 3.80-3.87 (m, 4 H), 4.44 (m, 1 H), 4.57 (m, 1 H), 4.64 (m, 1 H), 6.93-7.00 (m, 1 H), 7.06 (s, 1 H), 7.38 (m, 1 H), 7.65 (m, 1 H), 7.88 (m, 1 H), 8.05-8.30 (m, 1 H). LC/MS: m/z 666.42 (MH$^+$), Rf 2.10 min., 100.0% purity.

5H-Indolo[2,1-a][2]benzazepine-10-carboxamide, 6-[[[(2-amino-2-oxoethyl)methylamino]carbonyl]amino]-13-cyclohexyl-N-[(dimethylamino)sulfonyl]-6,7-dihydro-3-methoxy-. $^1$H NMR (500 MHz, Acetone-D6) δ ppm: 1.29 (m, 1 H), 1.46 (m, 2 H), 1.65 (m, 1 H), 1.77 (m, 2 H), 1.92 (m, 1 H), 2.01 (m, 2 H), 2.13 (m, 1 H), 2.67 (t, J=12.51 Hz, 1 H), 2.84 (s, 3 H), 2.87-2.96 (m, 3 H), 2.98-3.01 (s, 6 H), 3.55-3.64 (m, 2 H), 3.88-3.95 (s, 3 H), 4.42 (m, 1 H), 4.57-4.65 (m, 1 H), 7.12 (m, 1 H) 7.31 (m, 1 H), 7.39 (m, 1 H), 7.76-7.83 (m, 1 H), 7.94 (m, 1 H), 8.20 (s, 1 H). LC/MS: m/z 625.35 (MH$^+$), Rf 2.06 min., 97.8% purity.

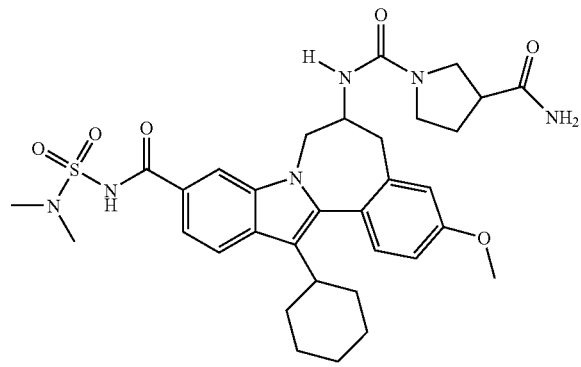

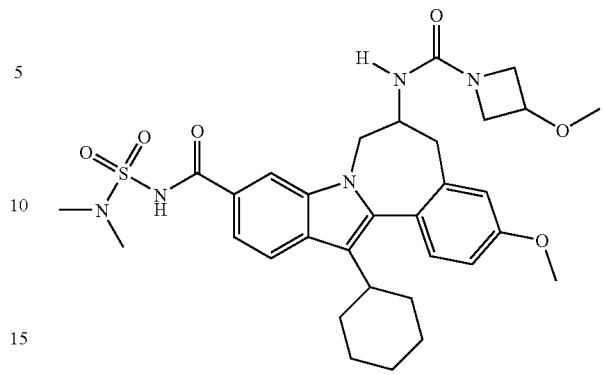

1,3-Pyrrolidinedicarboxamide, N~1~-[13-cyclohexyl-10-[[[(dimethylamino)sulfonyl]amino]carbonyl]-6,7-dihydro-3-methoxy-5H-indolo[2,1-a][2]benzazepin-6-yl]-. ¹H NMR (500 MHz, Acetone-D6) δ ppm: 1.27 (m, 1 H), 1.43 (m, 2 H), 1.60 (m, 1 H), 1.76 (m, 2 H) 1.89 (m, 1 H), 2.01 (m, 2 H), 2.12 (m, 1 H), 2.51 (m, 1 H), 2.90-2.95 (m, 2 H), 2.98 (s, 6 H), 3.02-3.12 (m, 2 H), 3.29-3.45 (m, 4 H), 3.53 (m, 1 H), 3.65 (m, 1 H), 3.89 (s, 3 H), 4.48-4.67 (m, 2 H), 7.01 (m, 1 H), 7.10 (m, 1 H), 7.41 (m, 1 H), 7.69 (m, 1 H), 7.91 (m, 1 H), 8.04-8.08 (m, 1 H). LC/MS: m/z 651.38 (MH⁺), Rf 2.01 min., 95.0% purity.

5H-Indolo[2,1-a][2]benzazepine-10-carboxamide, 13-cyclohexyl-N-[(dimethylamino)sulfonyl]-6,7-dihydro-3-methoxy-6-[[(3-methoxy-1-azetidinyl)carbonyl]amino]-. ¹H NMR (500 MHz, Acetone-D6) δ ppm 1.26 (m, 1 H), 1.44 (m, 2 H), 1.62 (m, 1 H), 1.76 (m, 2 H), 1.91 (m, 1 H), 2.01 (m, 1 H), 2.41 (t, J=12.21 Hz, 1 H), 2.64-2.72 (m, 1 H), 2.85-2.93 (m, 1 H), 2.96 (m, 1 H), 2.97-3.01 (m, 6 H), 3.20-3.25 (m, 3 H), 3.67 (m, 2 H), 3.71-3.78 (m, 1 H), 3.89 (s, 3 H), 3.93 (m, 1 H), 4.05-4.18 (m, 1 H), 4.19-4.24 (m, 1 H), 4.42 (m, 1 H), 4.57 (d, J=14.95 Hz, 1 H), 4.61-4.67 (m, 1H), 6.99-7.10 (m, 2 H), 7.39-7.44 (m, 1 H), 7.66-7.71 (m, 1 H), 7.90-7.95 (m, 1 H), 8.16-8.35 (m, 1 H). LC/MS: m/z 624.37 (MH⁺), Rf 2.07 min., 100.0% purity.

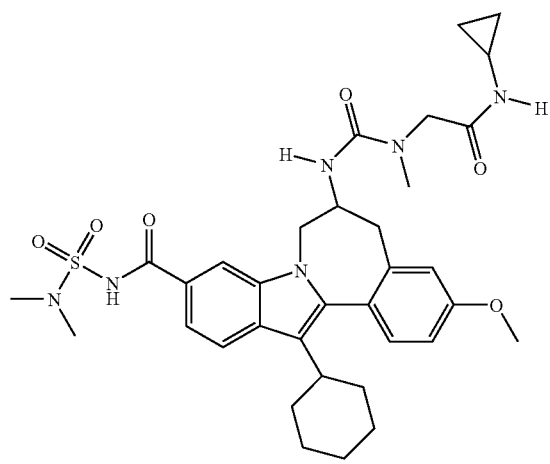

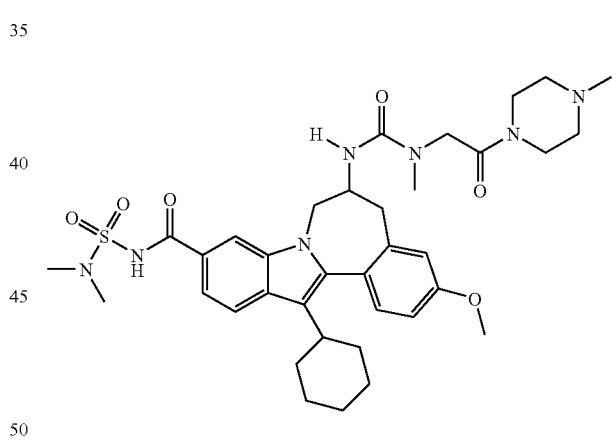

5H-Indolo[2,1-a][2]benzazepine-10-carboxamide, 13-cyclohexyl-6-[[[[2-(cyclopropylamino)-2-oxoethyl]methylamino]carbonyl]amino]-N-[(dimethylamino)sulfonyl]-6,7-dihydro-3-methoxy-. ¹H NMR (500 MHz, Acetone-D6) δ ppm: 0.34-0.48 (m, 2 H), 0.55-0.71 (m, 2 H), 1.28 (m, 1 H), 1.45 (m, 2 H), 1.61 (m, 1 H), 1.76 (m, 2 H), 1.92 (m, 1 H), 2.01 (m, 1 H), 2.13 (m, 1 H), 2.48 (m, 1 H), 2.67-2.80 (m, 2 H), 2.81-2.90 (m, 3 H), 2.92-3.01 (m, 9 H), 3.57-3.68 (m, 1 H), 3.75-3.97 (m, 4 H), 4.38-4.48 (m, 1 H), 4.50-4.60 (m, 1 H), 7.01-7.05 (m, 1 H), 7.06-7.14 (m, 1 H), 7.38-7.47 (m, 1 H), 7.71-7.81 (m, 1 H), 7.91-7.94 (m, 1 H), 8.20-8.37 (m, 1 H). LC/MS: m/z 665.38 (MH⁺), Rf 2.08 min., 95.0% purity.

5H-Indolo[2,1-a][2]benzazepine-10-carboxamide, 13-cyclohexyl-N-[(dimethylamino)sulfonyl]-6,7-dihydro-3-methoxy-6-[[[methyl[2-(4-methyl-1-piperazinyl)-2-oxoethyl]amino]carbonyl]amino]-. ¹H NMR (500 MHz, Acetone-D6) δ ppm: 1.29 (m, 1 H), 1.44-1.54 (m, 2 H), 1.63 (m, 1 H), 1.80 (m, 2 H), 1.95 (m, 1 H), 2.00 (m, 1 H), 2.49 (t, J=12.81 Hz, 1 H), 2.85-2.94 (m, 2 H), 2.95-3.04 (m, 12 H), 3.59 (m, 1 H), 3.69 (m, 2 H), 3.79 (m, 1 H), 3.87-3.95 (m, 4 H), 3.95-4.03 (m, 2 H), 4.45-4.53 (m, 2 H), 4.67-4.71 (m, 1 H), 7.06 (m, 1 H), 7.14 (m, 1 H), 7.41-7.49 (m, 1 H), 7.72-7.81 (m, 1 H), 7.96 (dd, J=8.55, 1.53 Hz, 1 H), 8.37-8.46 (m, 1 H). LC/MS: m/z 708.50 (MH⁺), Rf 1.87 min., 96.9% purity.

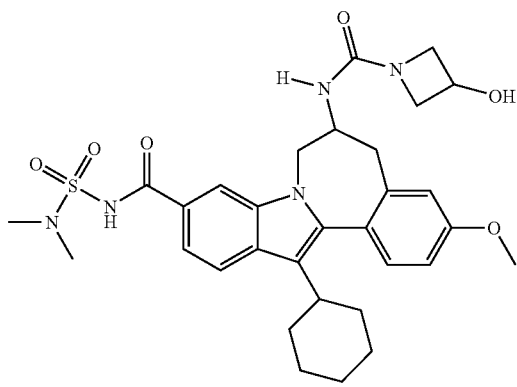

5H-Indolo[2,1-a][2]benzazepine-10-carboxamide, 13-cyclohexyl-N-[(dimethylamino)sulfonyl]-6,7-dihydro-6-[[(3-hydroxy-1-azetidinyl)carbonyl]amino]-3-methoxy-. $^1$H NMR (500 MHz, Acetone-D6) δ ppm 1.30 (m, 1 H), 1.47 (m, 2 H), 1.64 (m, 1 H), 1.80 (m, 2 H), 1.95 (m, 1 H), 2.04 (m, 1 H), 2.43 (t, J=11.90 Hz, 1 H), 2.71 (m, 1 H), 2.92 (m, 2 H), 2.99 (m, 1 H), 3.02 (m, 6 H), 3.64 (m, 2 H), 3.70 (m, 1 H), 3.93 (s, 3 H), 4.00 (m, 1 H), 4.13 (m, 1 H), 4.44 (m, 1 H), 4.57-4.68 (m, 2 H), 7.02-7.13 (m, 2 H), 7.42-7.46 (m, 1 H), 7.72-7.74 (m, 1 H), 7.94-7.97 (m, 1 H), 8.16-8.38 (m, 1 H). LC/MS: m/z 610.33 (MH$^+$), Rf 2.01 min., 95.0% purity.

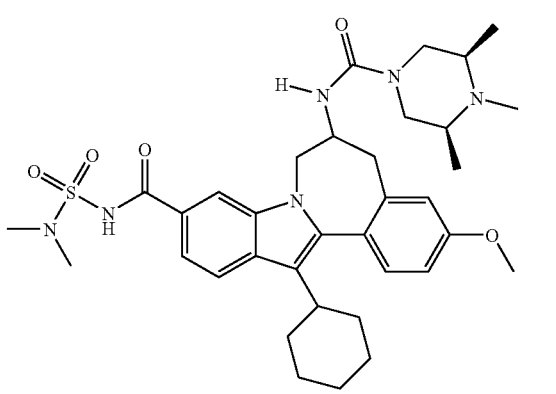

5H-Indolo[2,1-a][2]benzazepine-10-carboxamide, 13-cyclohexyl-N-[(dimethylamino)sulfonyl]-6,7-dihydro-3-methoxy-6-[[[(3R,5S)-3,4,5-trimethyl-1-piperazinyl]carbonyl]amino]-, rel-. $^1$H NMR (500 MHz, Acetone-D6) δ ppm: 1.28 (m, 4 H), 1.45-1.54 (m, 5 H), 1.66 (m, 1 H), 1.78-1.88 (m, 2 H), 1.95 (m, 2 H), 2.43 (t, J=11.90 Hz, 1 H), 2.96-3.01 (m, 2 H), 3.03-3.05 (m, 9 H), 3.19 (m, 1 H), 3.37 (m, 1 H), 3.55 (m, 1 H), 3.68-3.77 (m, 1 H), 3.93 (m, 3 H), 3.96-4.02 (m, 4 H), 4.49 (m, 2 H), 4.69 (m, 1 H), 7.15 (m, 1 H), 7.25-7.29 (m, 1 H), 7.47-7.50 (m, 1 H), 7.76 (m, 1 H), 7.93-7.99 (m, 1 H), 8.10 (m, 1H). LC/MS: m/z 665.54 (MH$^+$), Rf 1.85 min., 95.0% purity.

General LC/MS conditions as shown below were utilized for the procedures below until further noted: LCMS data: Gradient time: 2 min; Flow rate: 4 mL/min; Stop time: Gradient time +2 minute; Starting conc: 0% B; Eluent A: 10% MeOH/90% H$_2$O with 0.1% TFA; Eluent B: 90% MeOH/10% H$_2$O with 0.1% TFA; Column 1: Phenomenex 10 μ C18 4.6×50 mm.

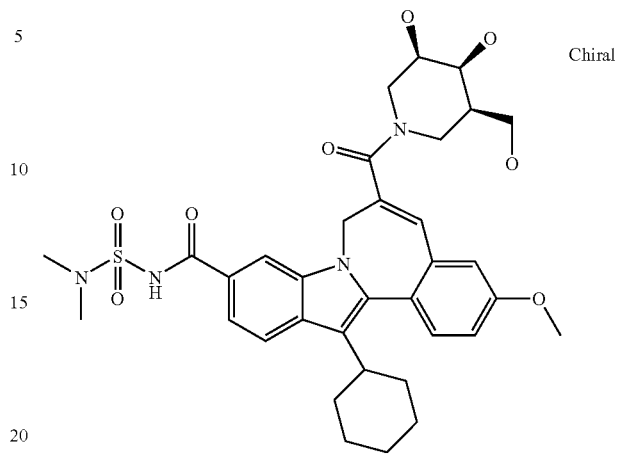

ESI-MS m/e 667 (MH$^+$), 1H NMR (500 MHz, MeOD) δ 1.12-2.23 (m, 11 H) 2.82-2.96 (m, 2 H) 3.01-3.07 (m, 6 H) 3.28-3.46 (m, 5 H) 3.71-3.87 (m, 1 H) 3.93 (s, 3 H) 4.27-4.46 (m, 1 H) 4.43-4.68 (m, 1 H) 5.17 (m, 1 H) 7.03 (s, 1 H) 7.08-7.22 (m, 2 H) 7.58 (dd, J=14.80, 8.39 Hz, 2 H) 7.92 (d, J=8.54 Hz, 1 H) 8.11 (s, 1 H).

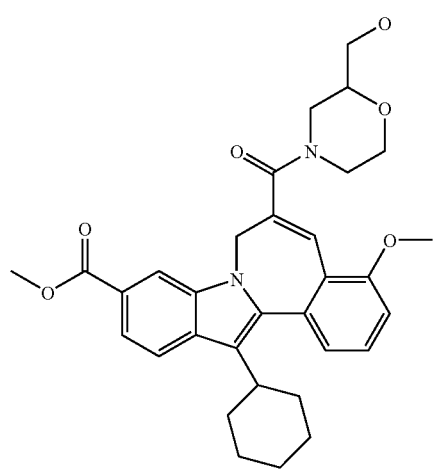

ESI-MS m/e 545 (MH$^+$), 1H NMR (500 MHz, MeOD) δ 1.14-2.23 (m, 11 H) 2.67-3.03 (m, 4H) 3.35-3.59 (m, 3 H) 3.69-3.92 (m, 2 H) 3.92-3.99 (m, 6 H) 4.32-4.45 (m, 1 H) 5.12-5.26 (m, 1 H) 7.03-7.26 (m, 3 H) 7.48-7.60 (m, 1 H) 7.66-7.76 (m, 1 H) 7.86-7.95 (m, 1 H) 8.19-8.31 (m, 1 H).

571
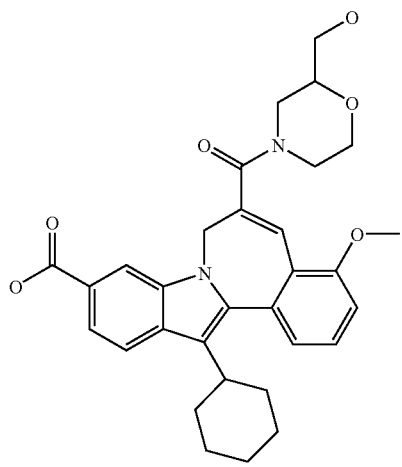
ESI-MS m/e 531 (MH+), 1 H NMR (500 MHz, MeOD) δ 1.17-2.23 (m, 11 H) 2.68-3.00 (m, 4 H) 3.36-3.60 (m, 3 H) 3.65-3.93 (m, 2 H) 3.95-4.00 (m, 3 H) 4.35-4.46 (m, 1 H) 5.13-5.24(m, 1 H) 7.05-7.27 (m, 3 H) 7.50-7.59 (m, 1 H) 7.70-7.78 (m, 1 H) 7.87-7.95 (m, 1 H) 8.21-8.32 (m, 1 H).
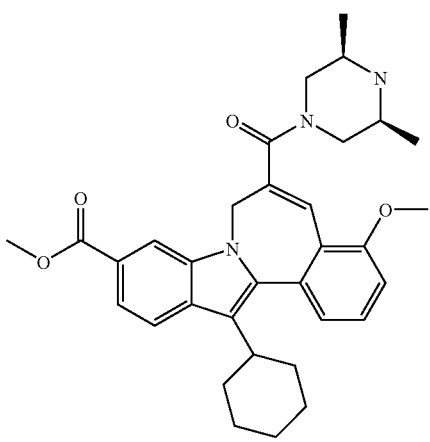
ESI-MS m/e 542 (MH+), 1H NMR (500 MHz, MeOD) δ ppm 0.84-1.55 (m, 10 H) 1.80 (d, J=10.99 Hz, 2 H) 1.94-2.21 (m, 4 H) 2.70-3.00 (m, 4 H) 3.23-3.39 (m, 2 H) 3.96 (s, 3 H) 3.98 (s, 3 H) 4.29-4.51 (m, 2 H) 5.21 (d, J=14.95 Hz, 1 H) 7.16-7.27 (m, 3 H) 7.58 (t, J=8.09 Hz, 1 H) 7.75 (dd, J=8.39, 1.37 Hz, 1 H) 7.95 (d, J=8.55 Hz, 1 H) 8.28 (s, 1 H).
572
ESI-MS m/e 528 (MH+), 1H NMR (500 MHz, MeOD) δ 0.70-1.56 (m, 10 H) 1.72-1.85 (m, 2 H) 1.92-2.23 (m, 4 H) 2.62-3.03 (m, 4 H) 3.17-3.40 (m, 2 H) 3.96-4.00 (m, 3 H) 4.26-4.54 (m, 2 H) 5.21 (d, J=14.65 Hz, 1 H) 7.09-7.30 (m, 3 H) 7.52-7.64 (m, 1 H) 7.71-7.83 (m, 1 H) 7.90-8.00 (m, 1 H) 8.28 (s, 1 H).
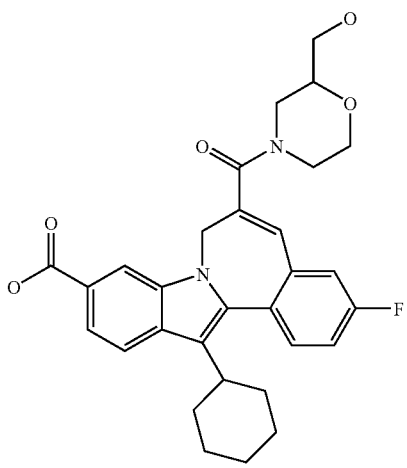
ESI-MS m/e 519 (MH+), 1H NMR (500 MHz, MeOD) δ 1.17-2.24 (m, 11 H) 2.72-3.25 (m, 5 H) 3.35-3.96 (m, 4 H) 4.43 (s, 1 H) 5.18 (s, 1 H) 6.97 (s, 1 H) 7.25-7.41 (m, 2 H) 7.59-7.79 (m, 2 H) 7.86-7.96 (m, 1 H) 8.25 (s, 1 H).

573
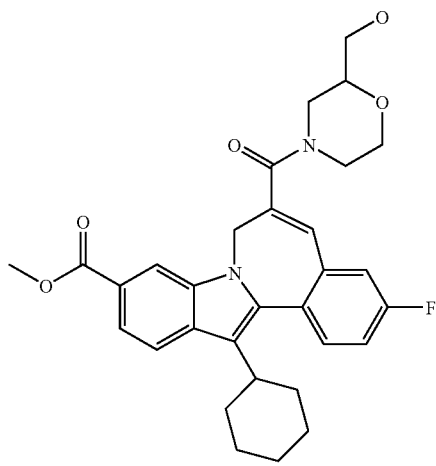
ESI-MS m/e 533 (MH+), 1H NMR (500 MHz, MeOD) δ ppm 1.16-2.25 (m, 11 H) 2.76-2.93 (m, 2 H) 2.92-3.26 (m, 3 H) 3.34-3.65 (m, 4 H) 3.91-3.99 (m, 3 H) 4.42 (s, 1 H) 5.18 (s, 1 H) 6.97 (s, 1 H) 7.27-7.42 (m, 2 H) 7.60-7.69 (m, 1 H) 7.69-7.78 (m, 1 H) 7.85-7.99 (m, 1 H) 8.19-8.28 (m, 1 H).
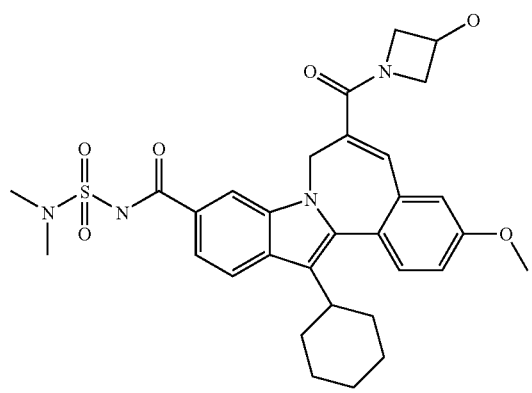
ESI-MS m/e 593 (MH+).
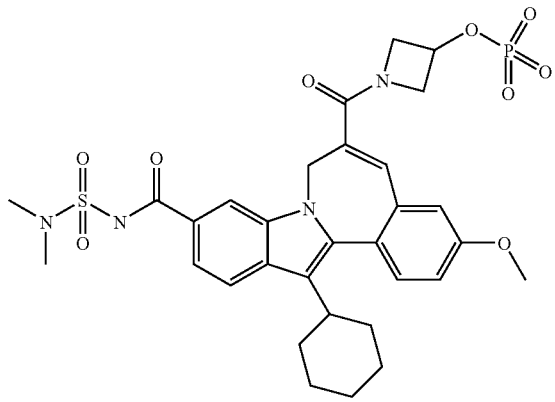
ESI-MS m/e 673 (MH+), 1H NMR (500 MHz, MeOD) δ 1.18-1.34 (m, 1 H) 1.38-1.58 (m, 3 H) 1.75-1.86 (m, 2 H) 1.98-2.21 (m, 4 H) 2.83-2.95 (m, 2 H) 3.04 (d, J=1.53 Hz, 6 H) 3.95 (s, 3 H) 4.11-4.28 (m, 2 H) 4.36-4.64 (m, 2 H) 4.97-5.10
574
(m, 1 H) 5.42-5.58 (m, 1 H) 7.15-7.22 (m, 2 H) 7.31 (s, 1 H) 7.55-7.63 (m, 2 H) 7.92 (d, J=8.24 Hz, 1 H) 8.14 (s, 1 H).
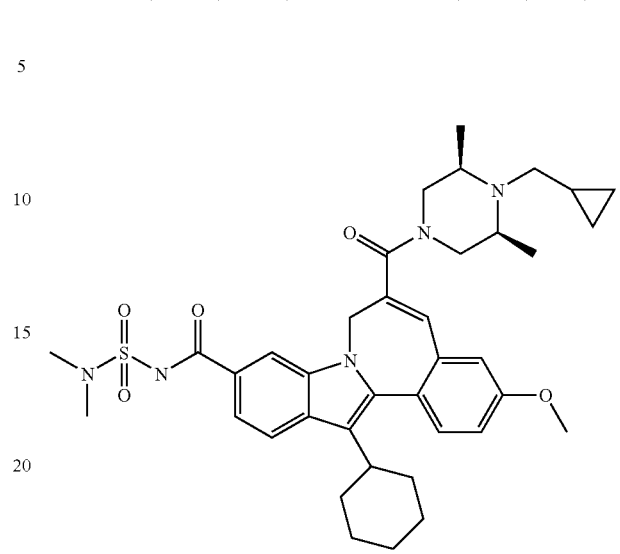
ESI-MS m/e 688 (MH+), 1H NMR (500 MHz, MeOD) δ 0.34-0.51 (m, 2 H) 0.69-1.04 (m, 6 H) 1.21-1.59 (m, 7 H) 1.75-2.20 (m, 6 H) 2.85-3.14 (m, 5 H) 3.02 (s, 6 H) 3.38-3.72 (m, 3 H) 3.94 (d, J=1.22 Hz, 3 H) 4.07-4.55 (m, 2 H) 5.16-5.28 (m, 1 H) 7.04 (s, 1 H) 7.12 (s, 1 H) 7.18-7.23 (m, 1 H) 7.56-7.66 (m, 2 H) 7.99 (d, J=8.54 Hz, 1 H) 8.18 (s, 1 H).
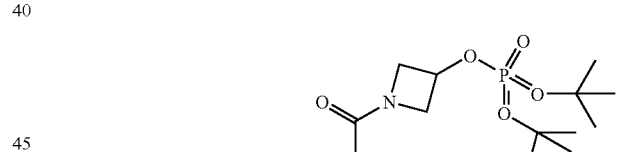
ESI-MS m/e 785 (MH+), 1H NMR (500 MHz, MeOD) δ 1.22-1.61 (m, 22 H) 1.75-1.85 (m, 2 H) 1.93-2.19 (m, 4 H) 2.81-2.97 (m, 2 H) 3.04 (d, J=1.22 Hz, 6 H) 3.95 (d, J=1.22 Hz, 3 H) 4.07-4.30 (m, 2 H) 4.38-4.63 (m, 2 H) 4.94-5.08 (m, 1 H) 5.43-5.56 (m, 1 H) 7.15-7.22 (m, 2 H) 7.31 (s, 1 H) 7.59 (t, J=9.00 Hz, 3 H) 7.92 (d, J=8.54 Hz, 1 H) 8.14 (s, 1 H).

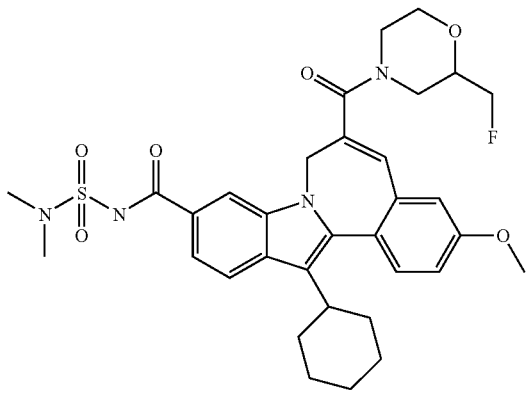

ESI-MS m/e 639 (MH+), 1 H NMR (500 MHz, MeOD) δ 1.22-1.32 (m, 1 H) 1.40-1.58 (m, 3 H) 1.76-1.86 (m, 2 H) 1.94-2.19 (m, 4 H) 2.84-2.99 (m, 2 H) 3.03 (s, 6 H) 3.08-3.24 (m, 1 H) 3.40-3.55 (m, 2 H) 3.57-3.71 (m, 2 H) 3.85-3.91 (m, 1 H) 3.94 (s, 3 H) 4.19-4.53 (m, 3 H) 5.12-5.25 (m, 1 H) 6.95-7.04 (m, 1 H) 7.12 (s, 1 H) 7.18 (dd, J=8.55, 2.75 Hz, 1 H) 7.53-7.65 (m, 2 H) 7.94 (d, J=8.55 Hz, 1 H) 8.16 (s, 1 H).

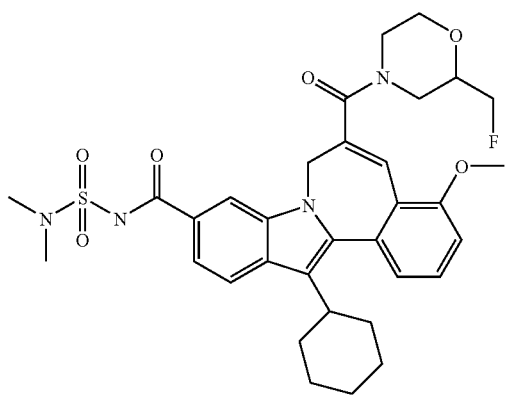

ESI-MS m/e 639 (MH+), 1H NMR (500 MHz, MeOD) δ 1.17-1.34 (m, 1 H) 1.38-1.56(m,3H) 1.75-1.86 (m, 2 H) 1.93-2.21 (m, 4 H) 2.87-3.01 (m, 2 H) 3.04 (s, 6 H) 3.10-3.24 (m, 1 H) 3.38-3.77 (m, 3 H) 3.82-3.95 (m, 1 H) 3.97 (s, 3 H) 4.00-4.23 (m, 1 H) 4.24-4.55 (m, 3 H) 5.20 (d, J=14.34 Hz, 1 H) 7.21 (dd, J=17.24, 8.09 Hz, 3 H) 7.56 (t, J=8.09 Hz, 1 H) 7.62 (d, J=8.24 Hz, 1 H) 7.96 (d, J=8.85 Hz, 1 H) 8.17 (d, J=8.85 Hz, 1 H).

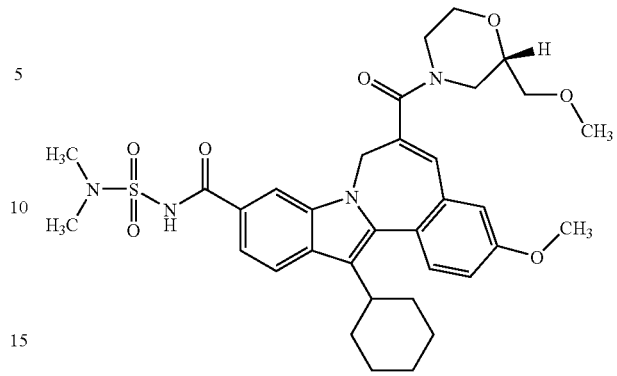

13-Cyclohexyl-N-[(dimethylamino)sulfonyl]-6-[(2S-2-(methoxymethyl)-4-morpholinyl)carbonyl]-5H-indolo[2,1-a][2]benzazepine-10-carboxamide. TBTU (32 mg, 0.10 mmol) was added to a stirred solution at 22° C. of 13-cyclohexyl-N-[(dimethylamino)sulfonyl]-3-methoxy-7H-indolo[2,1-a][2]benzazepine-10-carboxamide-6-carboxylic acid (40.5 mg, 0.075 mmol), (2S)-2-(methoxymethyl)morpholine hydrochloride (17 mg, 0.01 mmol), and TEA (37.9 mg, 0.375 mmol) in DMSO (0.30 mL). After stirring for 1 hr the solution was diluted with water and acidified with dilute HCl to precipitate the titled compound as a gel. The mixture was extracted with ethyl acetate. The extract was washed (water (2×), brine), dried (sodium sulfate), and concentrated to leave a foam. A solution of the foam in methylene chloride was applied to a silicic acid thick layer plate. The plate was developed with methylene chloride –3% acetic acid. The band containing the product was removed and extracted with methylene chloride –10% methanol. Removal of the solvents left the product (22.2 mg, 45 % yield) as a yellow solid. 1H NMR (500 MHz, CHLOROFORM-D) δ ppm 0.85-2.04(m, 10 H) 3.06 (s, 6 H) 3.11-3.82 (m, 8 H) 3.90 (s, 3 H) 4.35 (s, 1 H) 5.11 (s, 1 H) 6.75-6.84 (m, 1 H) 6.91 (d, J=2.44 Hz, 1 H) 7.06 (dd, J=8.55, 2.75 Hz, 1 H) 7.49 (d, J=8.55 Hz, 1 H) 7.55 (d, J=8.24 Hz, 1 H) 7.88 (d, J=8.54 Hz, 1 H) 8.16 (s, 1 H) 9.45 (s, 1 H).

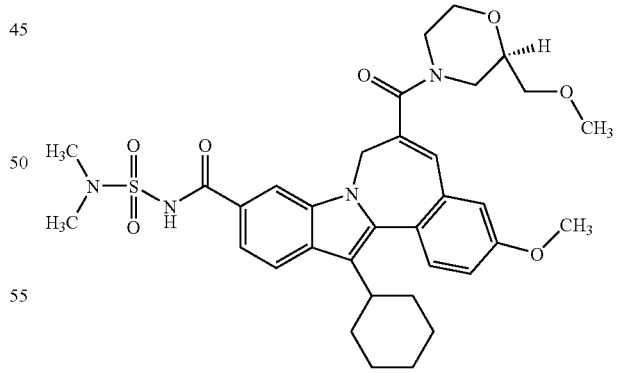

13-Cyclohexyl-N-[(dimethylamino)sulfonyl]-6-[(2R-2-(methoxymethyl)-4-morpholinyl)carbonyl]-5H-indolo[2,1-a][2]benzazepine-10-carboxamide. TBTU (89 mg, 0.276 mmol) was added to a stirred solution at 22° C. of 13-cyclohexyl-N-[(dimethylamino)sulfonyl]-3-methoxy-7H-indolo[2,1-a][2]benzazepine-10-carboxamide-6-carboxylic acid (123.5 mg, 0.230 mmol), (2R)-2-(methoxymethyl)morpholine hydrochloride (54 mg, 0.322 mmol), and TEA (93 mg, 0.92 mmol) in DMSO (1.2 mL). After stirring for 2 hr the solution was diluted with water and acidified with dilute HCl to precipitate the titled compound as a gel. The mixture was extracted with chloroform. The extract was washed (water (2×), brine), dried (magnesium sulfate), and concentrated to leave a froth. A solution of the froth in methylene chloride was applied to a silicic acid thick layer plate. The plate was developed with methylene chloride –2% acetic acid. The band containing the product was removed and extracted with methylene chloride –10% methanol. Removal of the solvents left the product as a yellow solid. 1H NMR (500 MHz, CHLOROFORM-D) δ ppm 0.85-2.05 (m, 10 H) 3.06 (s, 6 H) 3.14-3.33 (m, 5 H) 3.80-3.88 (m, 1 H) 3.90 (s, 3 H) 4.35 (s, 1 H) 5.13 (s, 1 H) 6.76-6.83 (m, 1 H) 6.90 (d, J=2.14 Hz, 1 H) 7.06 (dd, J=8.70, 2.59 Hz, 1 H) 7.48 (d, 1 H) 7.54 (d, J=8.24 Hz, 1 H) 7.88 (d, J=8.55 Hz, 1 H) 8.14 (s, 1 H) 9.54 (s, 1 H).

The following general HPLC method applies to the procedures that follow until otherwise noted:

Shimadzu LC-MS discovery software; % A=10% methanol, 90% water, 0.1% TFA; % B=90% methanol, 10% water, 0.1% TFA;Initial % B=50; Final % B=100; Gradient=5 min; Runtime=6 min; Flow rate=5 ml/min; UV@ 220 nm; Column=Phenomenex Luna C18, 10u, 3.0 mm×50 mm; Product Retention time=4.2 min. MS m/z 487(MH⁺).

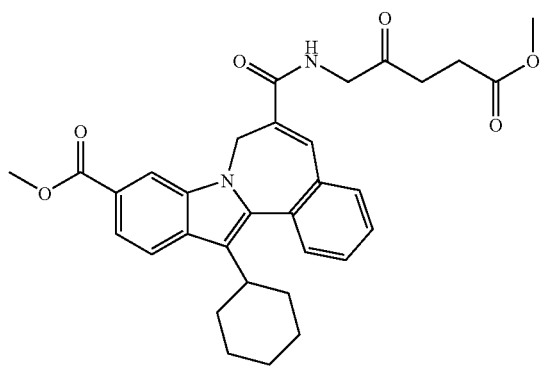

7H-indolo[2,1-a][2]benzazepine-10-carboxylic acid, 13-cyclohexyl-6-[[(5-methoxy-2,5-dioxopentyl)amino]carbonyl]-, methyl ester. 7H-indolo[2,1-a][2]benzazepine-10-carboxylic acid, 6-(chlorocarbonyl)-13-cyclohexyl-, methyl ester (499 mg, 1.15 mMol) was dissolved in 10 ml of anhydrous dichloromethane and methyl 5-aminolevulinate hydrochloride (244 mg, 1.34 mMol) was added to the reaction mixture followed by 0.5 ml of pyridine (6.2 mMol). The reaction was stirred under nitrogen at room temperature for 40 hours. Volatiles were removed in vacuuo and the residue was partitioned between ethyl acetate and 0.1 N hydrochloric acid. The organic phase was washed with brine, dried over magnesium sulfate to yield 603 mg of crude product. The product was combined with 433 mg of a previous reaction run under the same conditions. The mixture was purified by silica column chromatography eluting with a gradient of 20% ethyl acetate in dichloromethane to 20% ethyl acetate in dichloromethane to yield 0.56 g (45%) of product. 1H NMR (500 MHz, CHLOROFORM-D) δ ppm 8.28 (s, 1 H) 7.87 (d, J=8.55 Hz, 1 H) 7.74 (dd, J=8.55, 1.22 Hz, 1 H) 7.59 (d, J=7.93 Hz, 1 H) 7.43-7.56 (m, 3 H) 7.38 (s, 1 H) 6.71 (t, J=4.12 Hz, 1 H) 5.65 (d, J=10.99 Hz, 1 H) 4.31 (d, J=27.16 Hz, 2 H) 4.14-4.23 (m, 1 H) 3.94 (s, 3 H) 3.67 (s, 3 H) 2.80-2.91 (m, 1 H) 2.01-2.16 (m, 3 H) 1.70-2.00 (m, 3 H) 1.29-1.70 (m, 6 H) 1.14-1.31 (m, 2 H).

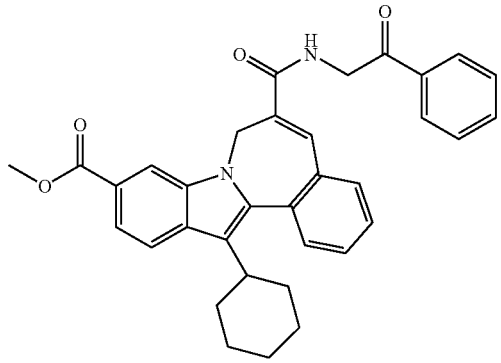

Methyl 13-cyclohexyl-6-(((2-(4-(methyloxy)phenyl)-2-oxoethyl)amino)carbonyl)-7H-indolo[2,1-a][2]benzazepine-10-carboxylate. 7H-indolo[2,1-a][2]benzazepine-10-carboxylic acid, 6-(chlorocarbonyl)-13-cyclohexyl-, methyl ester (500 mg, 1.15 mMol) was dissolved in 10 ml of anhydrous dichloromethane and 2-amino-4-methoxyacetophenone hydrochloride (280 mg, 1.39 mMol) was added to the reaction mixture followed by 0.3 ml of diisopropylethyl amine(1.72 mMol). The reaction was stirred under nitrogen for 23.5 hrs. Volatiles were removed in vacuuo and the residue was partitioned between ethyl acetate and 1.0 N hydrochloric acid. The organic phase was washed with brine, dried over magnesium sulfate to yield 648 mg of crude product. The crude product was adsorbed onto 1.65 g of silica gel and chromatographed on 20 g of silica gel using a gradient of dichloromethane to 5% ethyl acetate in dichloromethane. Trailing product was removed from the column using 10% ethyl acetate in dichloromethane. 1H NMR (500 MHz, CHLOROFORM-D) δ ppm 1.17-1.50 (m, 5 H) 1.52-1.84 (m, 6 H) 1.85-1.98 (m, 1 H) 2.00-2.15 (m, 3 H) 2.78-2.92 (m, 1 H) 3.88 (s, 3 H) 3.94 (s, 3 H) 4.19 (d, J=11.60 Hz, 1 H) 4.79 (d, J=25.64 Hz, 2 H) 5.71 (d, J=9.16 Hz, 1 H) 6.97 (d, J=8.85 Hz, 2 H) 7.13 (s, 1 H) 7.43-7.56 (m, 4 H) 7.60 (d, J=7.32 Hz, 1 H) 7.71-7.79 (m, 1 H) 7.87 (d, J=8.55 Hz, 1 H) 7.96 (d, J=8.85 Hz, 2 H) 8.32 (s, 1 H); MS m/z 563(MH⁺).

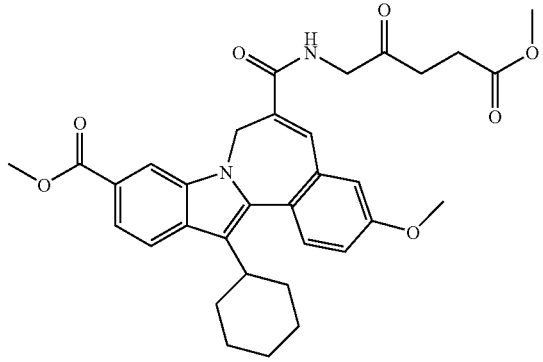

Methyl 13-cyclohexyl-3-(methyloxy)-6-(((5-(methyloxy)-2,5-dioxopentyl)amino)carbonyl)-7H-indolo[2,1-a][2]benzazepine-10-carboxylate. 13-cyclohexyl-3-(methyloxy)-10-((methyloxy)carbonyl)-7H-indolo[2,1-a][2]benzazepine-6-carboxylic acid (1.00 g, 2.24 mMol) was dissolved in 20 ml of DMF along with 1-hydroxy-7-azabenzotriazole (483 mg, 3.5 mMol). The reaction was placed under nitrogen and 1-[3-(dimethylamino)propyl]-3-ethylcarbodiimide hydrochloride (663 mg, 3.5 mMol) was added and the reaction stirred for 1 hr at room temperature. 5-aminolevleunic acid hydrochloride (608 mg, 3.35 mMol) was added to the reaction followed by diisopropylethyl amine (0.44 mL, 2.5 mMol). The reaction was stirred overnight under nitrogen at room temperature. Volatiles were removed in vacuuo and the residue was partitioned between ethyl acetate and 0.1 N hydrochloric acid. The aqueous phase was extracted with ethyl acetate and the organic phases combined, washed with brine and dried over magnesium sulfate. Volatiles were removed in vacuuo to yield 1.47 g of crude product which was combined with 698 mg of a previous experiment. The crude product was purified by silica gel chromatography eluting with a gradient of 10% ethyl acetate/dichloromethane to 25% ethyl acetate/dichloromethane to yield 1.64 g (84%) of product as a yellow solid. 1H NMR (500 MHz, CHLOROFORM-D) δ ppm 1.12-1.30 (m, 1 H) 1.32-1.50 (m, 2 H) 1.77 (d, J=9.16 Hz, 2 H) 1.89-1.99 (m, 1 H) 1.99-2.18 (m, 3 H) 2.67 (t, J=6.10 Hz, 2 H) 2.72-2.87 (m, 3 H) 3.67 (s, 3 H) 3.91 (s, 3 H) 3.94 (s, 3 H) 4.15 (d, J=19.23 Hz, 1 H) 4.31 (d, J=34.79 Hz, 2 H) 5.62 (d, J=12.82 Hz, 1 H) 6.70 (t, J=4.12 Hz, 1 H) 6.96 (d, J=2.44 Hz, 1 H) 7.08 (dd, J=8.55, 2.75 Hz, 1 H) 7.33 (s, 1 H) 7.51 (d, J=8.55 Hz, 1 H) 7.73 (d, J=8.24 Hz, 1 H) 7.84 (d, J=8.24 Hz, 1 H) 8.26 (s, 1 H); MS m/z 573(MH$^+$); MS m/z 571(M−H)$^-$.

additional 1.5 hrs. 1N hydrochloric acid (200 mL) was added to the reaction and a precipitate filtered off and rinsed with water and dried in vacuuo, to yield 1.14 g (87%) of crude product. The product was purified by silica gel chromatography eluting with a gradient of 15% ethyl acetate in hexanes to 25% ethyl acetate in hexanes to yield 0.81 g (62%) of product as a yellow solid. 1H NMR (500 MHz, CHLOROFORM-D) δ ppm 1.25 (t, J=7.17 Hz, 1 H) 1.31-1.48 (m, 2 H) 1.48-1.63 (m, 3 H) 1.77 (d, J=9.46 Hz, 2 H) 1.86-1.98 (m, 1 H) 1.98-2.16 (m, 3 H) 2.77-2.89 (m, 1 H) 3.91 (s, 3 H) 3.94 (s, 3 H) 4.18 (d, J=14.04 Hz, 1 H) 4.32 (d, J=34.79 Hz, 2 H) 5.62 (d, J=11.29 Hz, 1 H) 6.65 (s, 1 H) 6.97 (d, J=2.75 Hz, 1 H) 7.09 (dd, J=8.55, 2.75 Hz, 1 H) 7.35 (s, 1 H) 7.52 (d, J=8.85 Hz, 1 H) 7.73 (d, J=8.55 Hz, 1 H) 7.84 (d, J=8.54 Hz, 1 H) 8.26 (s, 1 H) 9.71 (s, 1 H).

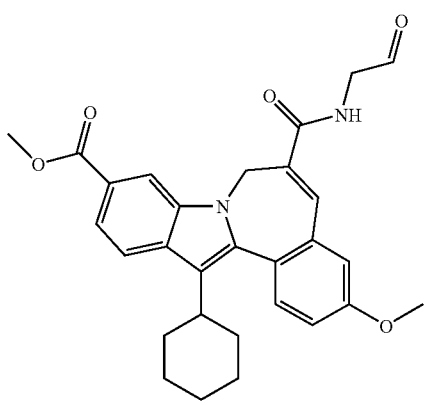

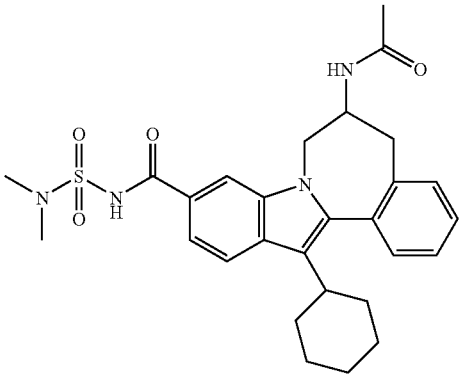

Methyl 13-cyclohexyl-3-(methyloxy)-6-(((2-oxoethyl)amino)carbonyl)-7H-indolo[2,1-a][2]benzazepine-10-carboxylate. 13-cyclohexyl-3-(methyloxy)-10-((methyloxy)carbonyl)-7H-indolo[2,1-a][2]benzazepine-6-carboxylic acid (1.50 g, 3.37 mMol) was dissolved in 32 ml of DMF along with 1-hydroxy-7-azabenzotriazole (697 mg, 5.1 mMol). The reaction was placed under nitrogen and 1-[3-(dimethylamino)propyl]-3-ethylcarbodiimide hydrochloride (967 mg, 5.04 mMol) was added and the reaction stirred for 1.5 hr at room temperature. Aminoacetaldehyde dimethylacetal (0.44 mL, 4.1 mMol) was added to the reaction and the reaction stirred at room temperature under nitrogen for 16 hrs. Volatiles were removed in vacuuo and the residue was partitioned between ethyl acetate and 0.1 N hydrochloric acid. The aqueous phase was extracted with ethyl acetate and the organic phases combined, washed with 0.1N hydrochloric acid then brine and dried over magnesium sulfate. Volatiles were removed in vacuuo to yield 1.98 g of crude product which was used in the next reaction without purification. The crude acetal (1.4 g, 2.7 mMol) was dissolved in 30 mL of acetone and 2M hydrochloric acid (1.6 mL, 3.2 mMol) and briefly heated to reflux then allow to stir for 2.5 hrs before being briefly heated to reflux again and allowed to stir an 5H-indolo[2,1-a][2]benzazepine-10-carboxylic acid, 13-cyclohexyl-6,7-dihydro-6-[(methylcarbonyl)amino]-, methyl ester. Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=523.30, HPLC R$_t$=1.853 min.

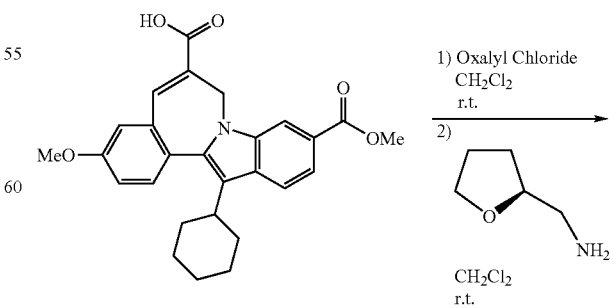

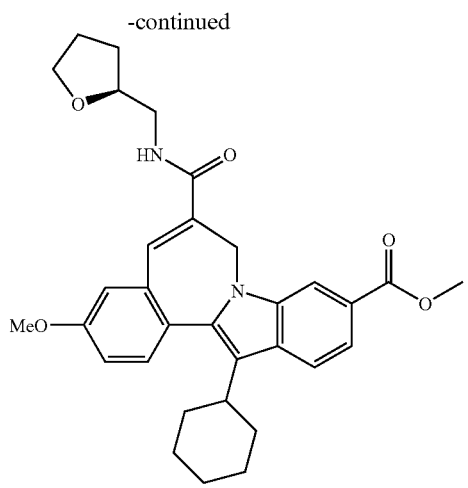

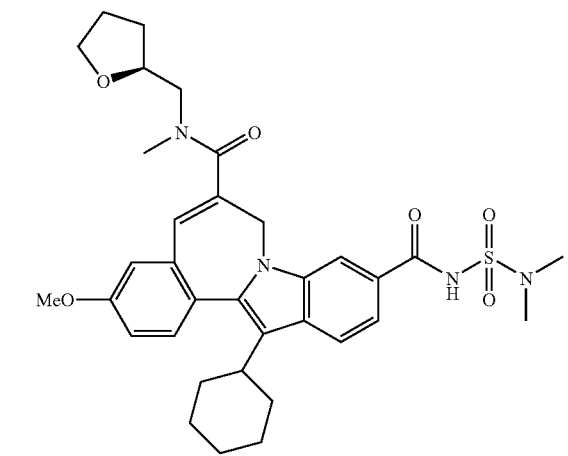

Methyl 13-cyclohexyl-3-(methyloxy)-6-(((((2S)-tetrahydro-2-furanylmethyl)amino)carbonyl)-7H-indolo[2,1-a][2]benzazepine-10-carboxylate. Prepared from 13-cyclohexyl-3-(methyloxy)-10-((methyloxy)carbonyl)-7H-indolo[2,1-a][2]benzazepine-6-carboxylic acid in a similar manner as described before. Analytical thin layer chromatography (5% MeOH/CH$_2$Cl$_2$) R$_f$=0.65; Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=529.27, HPLC R$_t$=2.115 min.

13-Cyclohexyl-N$^{10}$-((dimethylamino)sulfonyl)-N$^6$-methyl-3-(methyloxy)-N$^6$-((2S)-tetrahydro-2-furanylmethyl)-7H-indolo[2,1-a][2]benzazepine-6,10-dicarboxamide. Prepared from 13-Cyclohexyl-3-(methyloxy)-6-((methyl((2S)-tetrahydro-2-furanylmethyl)amino)carbonyl)-7H-indolo[2,1-a][2]benzazepine-10-carboxylic acid using CDI as a coupling reagent in a similar manner as described before; Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=635.28, HPLC R$_t$=1.978 min.

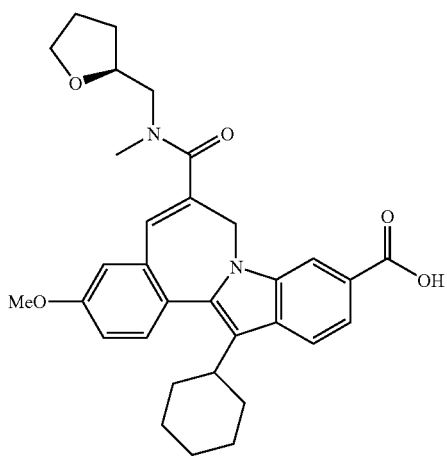

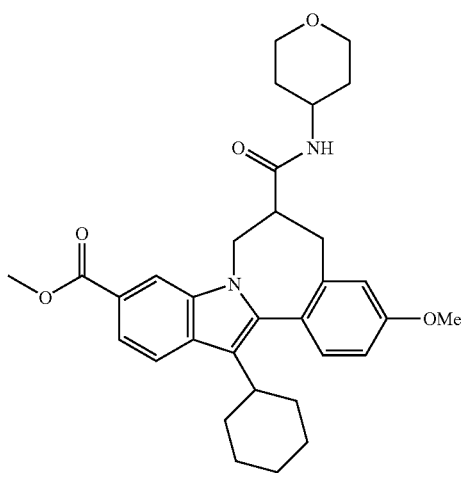

13-Cyclohexyl-3-(methyloxy)-6-((methyl((2S)-tetrahydro-2-furanylmethyl)amino)carbonyl)-7H-indolo[2,1-a][2]benzazepine-10-carboxylic acid. Prepared from methyl 13-cyclohexyl-3-(methyloxy)-6-(((((2S)-tetrahydro-2-furanylmethyl)amino)carbonyl)-7H-indolo[2,1-a][2]benzazepine-10-carboxylate by methylation using MeI and NaH in DMF in a similar manner as described before; Analytical thin layer chromatography (5% MeOH/CH$_2$Cl$_2$) R$_f$=0.45; Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=529.21, HPLC R$_t$=2.035 min.

Methyl 13-cyclohexyl-3-(methyloxy)-6-((tetrahydro-2H-pyran-4-ylamino)carbonyl)-6,7-dihydro-5H-indolo[2,1-a][2]benzazepine-10-carboxylate. Prepared in a similar manner as described before. Analytical thin layer chromatography (5% MeOH/CH$_2$Cl$_2$) R$_f$=0.50; Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=531.40, HPLC R$_t$=2.072 min.

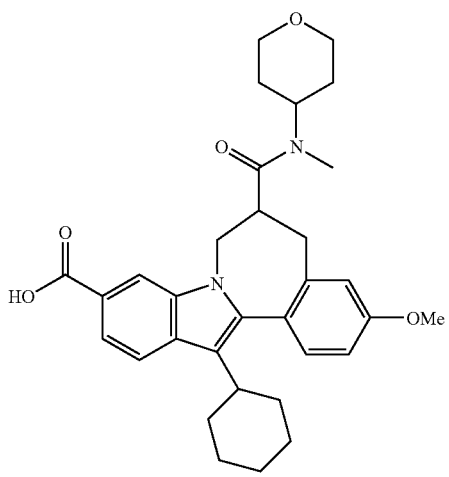

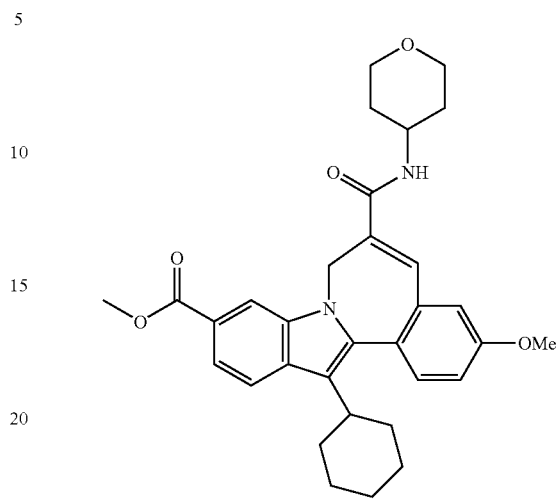

time=2 min, Flow Rate=5 ml/min, Column: Xterra MS C18 S7 3.0×50 mm; LC/MS: (ES+) m/z (M+H)$^+$=637.20, HPLC R$_t$=1.937 min.

13-Cyclohexyl-3-(methyloxy)-6-((methyl(tetrahydro-2H-pyran-4-yl)amino)carbonyl)-6,7-dihydro-5H-indolo[2,1-a] [2]benzazepine-10-carboxylic acid. Prepared from Methyl 13-cyclohexyl-3-(methyloxy)-6-((tetrahydro-2H-pyran-4-ylamino)carbonyl)-6,7-dihydro-5H-indolo[2,1-a][2]benzazepine-10-carboxylate by methylation using MeI and NaH in DMF in a similar manner as described before; Analytical thin layer chromatography (5% MeOH/CH$_2$Cl$_2$) R$_f$=0.30; Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=531.21, HPLC R$_t$=1.998 min.

Methyl 13-Cyclohexyl-3-(methyloxy)-6-((tetrahydro-2H-pyran-4-ylamino)carbonyl)-7H-indolo[2,1-a][2]benzazepine-10-carboxylate. Prepared in a similar manner as described before. Analytical thin layer chromatography (5% MeOH/CH$_2$Cl$_2$) R$_f$=0.70; Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=529.15, HPLC R$_t$=2.092 min.

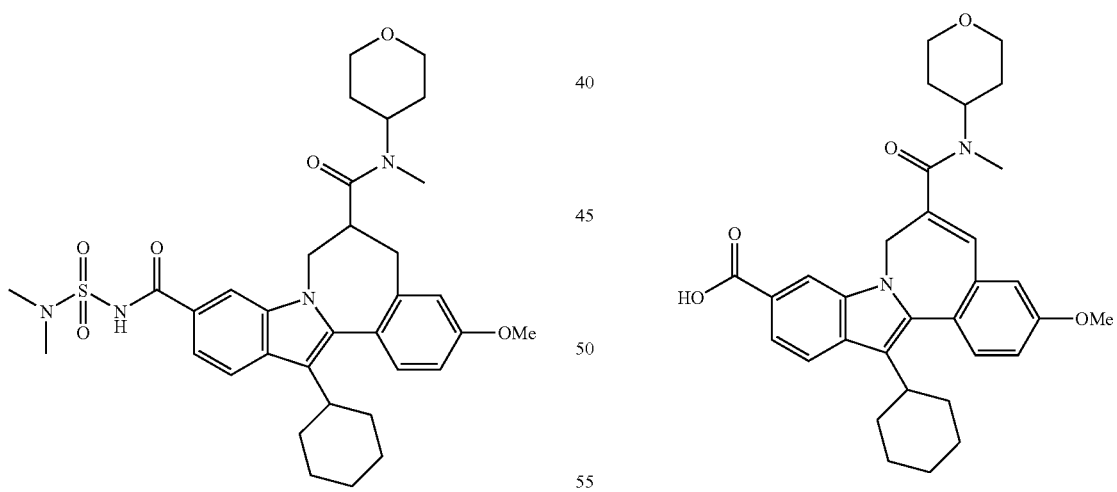

13-Cyclohexyl-N$^{10}$-((dimethylamino)sulfonyl)-N$^6$-methyl-3-(methyloxy)-N$^6$-(tetrahydro-2H-pyran-4-yl)-6,7-dihydro-5H-indolo[2,1-a][2]benzazepine-6,10-dicarboxamide. Prepared from 13-Cyclohexyl-3-(methyloxy)-6-((methyl(tetrahydro-2H-pyran-4-yl)amino)carbonyl)-6,7-dihydro-5H-indolo[2,1-a][2]benzazepine-10-carboxylic acid using CDI as a coupling reagent in a similar manner as described before; Analytical HPLC method: Solvent A=10% MeOH-90% H$_2$O-0.1% TFA, Solvent B=90% MeOH-10% H$_2$O-0.1% TFA, Start % B=0, Final % B=100, Gradient 13-Cyclohexyl-3-(methyloxy)-6-((methyl(tetrahydro-2H-pyran-4-yl)amino)carbonyl)-7H-indolo[2,1-a][2]benzazepine-10-carboxylic acid. Prepared from methyl 13-Cyclohexyl-3-(methyloxy)-6-((tetrahydro-2H-pyran-4-ylamino) carbonyl)-7H-indolo[2,1-a][2]benzazepine-10-carboxylate by methylation using MeI and NaH in DMF in a similar manner as described before; Analytical thin layer chromatography (5% MeOH/CH$_2$Cl$_2$) R$_f$=0.50; Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)⁺=529.32, HPLC $R_t$=1.995 min.

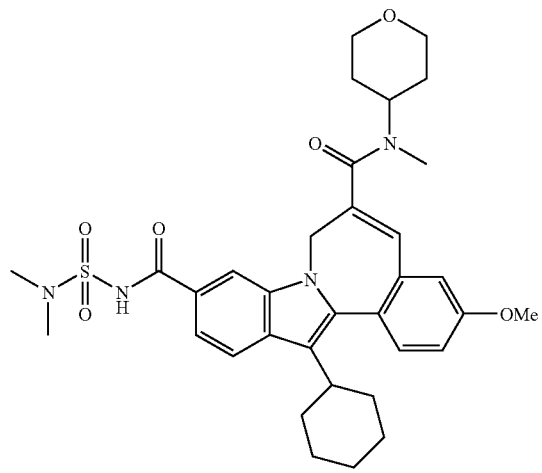

13-Cyclohexyl-$N^{10}$-((dimethylamino)sulfonyl)-$N^6$-methyl-3-(methyloxy)-$N^6$-(tetrahydro-2H-pyran-4-yl)-7H-indolo[2,1-a][2]benzazepine-6,10-dicarboxamide. Prepared from 13-cyclohexyl-3-(methyloxy)-6-((methyl(tetrahydro-2H-pyran-4-yl)amino)carbonyl)-7H-indolo[2,1-a][2]benzazepine-10-carboxylic acid using CDI as a coupling reagent in a similar manner as described before; Analytical HPLC method: Solvent A=10% MeOH-90% H₂O-0.1% TFA, Solvent B=90% MeOH-10% H₂O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)⁺=635.46, HPLC $R_t$=1.937 min.

To a stirred solution of methyl 7H-indolo[2,1-a][2]benzazepine-10-carboxylate, 13-cyclohexyl, 6-carboxylic acid (830 mg, 2.0 mmol), 1-(piperazin-1-yl)ethanone (310 mg, 2.4 mmol) and triethylamine (0.85 mL) in DMF (8 mL) was added HATU (910 mg, 2.4 mmol). The reaction mixture was stirred at rt for 2 h, diluted with H₂O (~15 mL) and the solids were collected by filtration washed with H₂O and dried under vacuum overnight to yield 7H-indolo[2,1-a][2]benzazepine-10-carboxylic acid, 13-cyclohexyl-6-[[4-(acetyl)-1-piperazinyl]carbonyl]-, methyl ester (1.19 g, 2.3 mmol, quant.) as a yellow solid. LCMS: m/e 526 (M+H)⁺, ret time 2.96 min, column B, 3 minute gradient.

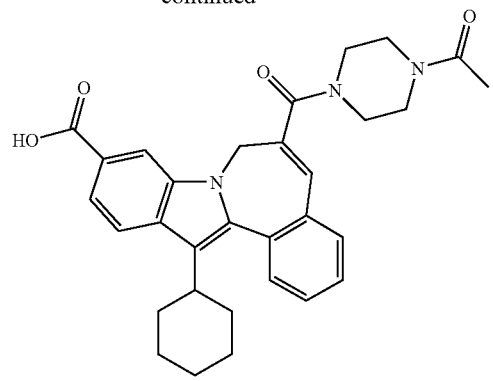

7H-indolo[2,1-a][2]benzazepine-10-carboxylic acid, 13-cyclohexyl-6-[[4-(acetyl)-1-piperazinyl]carbonyl]-, methyl ester (1.14 g, 2.2 mmol) was dissolved into MeOH// THF (1:1, 10 mL) and treated with 1M aqueous NaOH (3 mL). The reaction mixture was stirred and heated at 85° C. with microwave irradiation for 30 min in a sealed tube. The clear solution was neutralized with 1M aqueous HCl (3 mL) and concentrated to remove organic solvents. The resultant solids were collected by filtration, washed with H₂O and dried under vacuum to yield 7H-indolo[2,1-a][2]benzazepine-10-carboxylic acid, 13-cyclohexyl-6-[[4-(acetyl)-1-piperazinyl]carbonyl] (1.09 g, 0.21 mmol, 97%) as a yellow solid which was used without further purification. LCMS: m/e 512 (M+H)⁺, ret time 2.80 min, column B, 3 minute gradient.

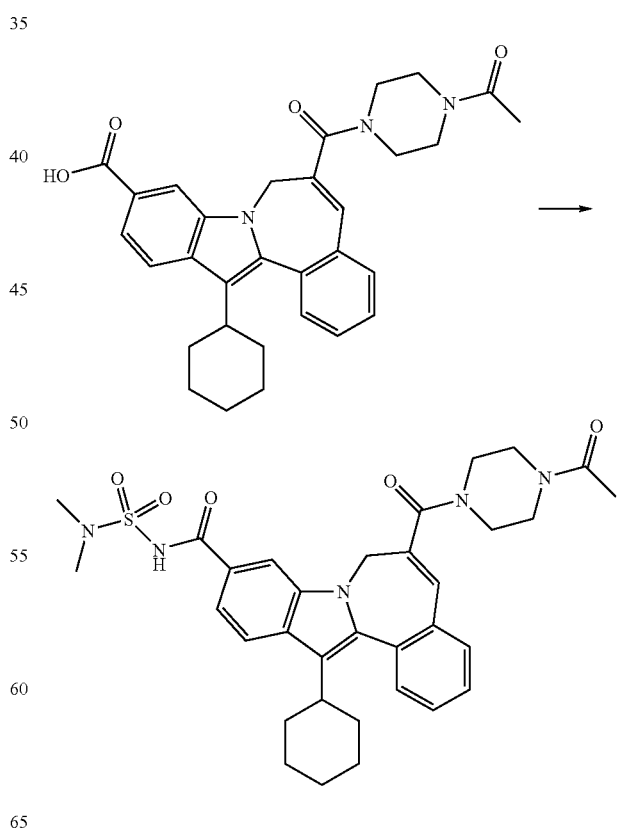

To a stirred solution of 7H-indolo[2,1-a][2]benzazepine-10-carboxylic acid, 13-cyclohexyl-6-[[4-(acetyl)-1-piperazinyl]carbonyl] (400 mg, 0.78 mmol), N,N-dimethylsulfamide (390 mg, 3.13 mmol) and DMAP (380 mg, 3.13 mmol) in dimethylacetamide (6 mL) was added 1-(3-dimethylaminopropyl)-3-ethylcarbodiimide hydrochloride (450 mg, 2.34 mmol). The reaction solution was stirred at 50° C. for 3 h, concentrated, purified by preparative HPLC (CH$_3$CN/H$_2$O with NH$_4$OAc buffer) to yield 7H-indolo[2,1-a][2]benzazepine-10-carboxamide, 13-cyclohexyl-N-[(dimethylamino)sulfonyl]-6-[[4-(acetyl)-1-piperazinyl]carbonyl] (135 mg, 0.22 mol, 28%) as a yellow powder. $^1$HNMR (500 MHz, DMSO-d$_6$) δ 11.62 (s, 1H), 8.44 (s, 1H), 7.93 (d, J=8.5 Hz, 1H), 7.65 (d, J=8.5 Hz, 1H), 7.62-7.55 (m, 4H), 7.04 (s, 1H), 5.19 (br s, 1H), 4.34 (br s, 1H), 3.59-3.30 (m, 8H), 2.91 (s, 6H), 2.85-2.75 (m, 1H), 2.10-1.36 (m, 10H), 1.99 (s, 3H). LCMS: m/e 616 (M−H)$^−$, ret time 1.57 min, column A, 2 minute gradient.

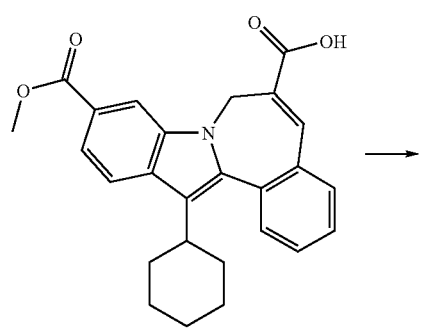

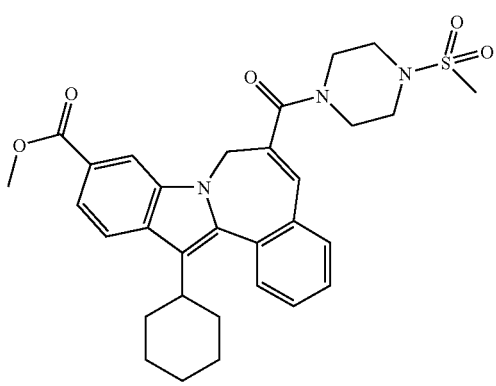

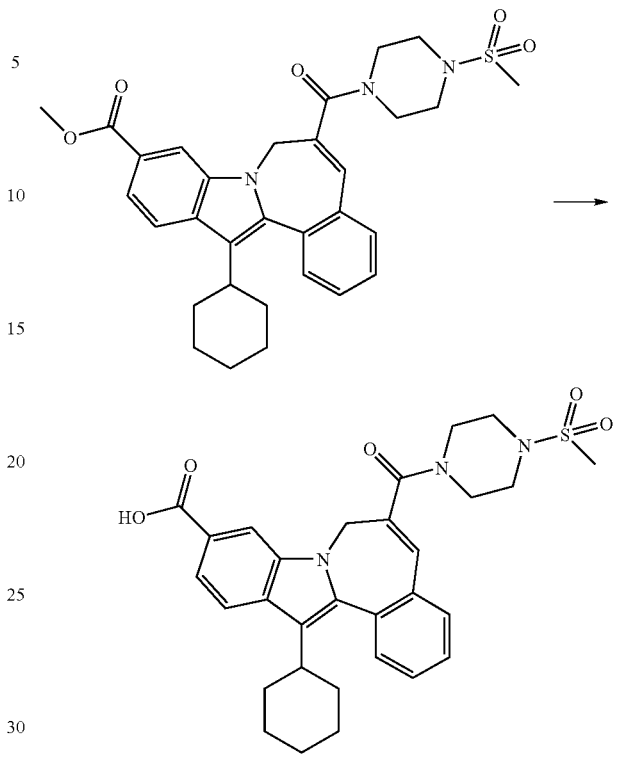

7H-indolo[2,1-a][2]benzazepine-10-carboxylic acid, 13-cyclohexyl-6-[[4-(methylsulfonyl)-1-piperazinyl]carbonyl]-, methyl ester (1.04 g, 1.9 mmol) was dissolved into MeOH//THF (1:1, 10 mL) and treated with 1M aqueous NaOH (2.5 mL). The reaction mixture was stirred and heated at 80° C. with microwave irradiation for 15 min in a sealed tube. The clear solution was neutralized with 1M aqueous HCl (3 mL) and concentrated to remove organic solvents. The resultant solids were collected by filtration, washed with H$_2$O and dried under vacuum to yield 7H-indolo[2,1-a][2]benzazepine-10-carboxylic acid, 13-cyclohexyl-6-[[4-(methylsulfonyl)-1-piperazinyl]carbonyl] (0.93 g, 0.17 mmol, 92%) as a yellow solid which was used without further purification. LCMS: m/e 548 (M+H)$^+$, ret time 2.88 min, column B, 3 minute gradient.

To a stirred solution of methyl 7H-indolo[2,1-a][2]benzazepine-10-carboxylate, 13-cyclohexyl, 6-carboxylic acid (830 mg, 2.0 mmol), 1-(methylsulfonyl)piperazine (394 mg, 2.4 mmol) and triethylamine (0.85 mL) in DMF (10 mL) was added HATU (910 mg, 2.4 mmol). The reaction mixture was stirred at rt for 2 h, diluted with H$_2$O (~15 mL) and the solids were collected by filtration, washed with H$_2$O and dried under vacuum overnight to yield 7H-indolo[2,1-a][2]benzazepine-10-carboxylic acid, 13-cyclohexyl-6-[[4-(methylsulfonyl)-1-piperazinyl]carbonyl]-, methyl ester (1.08 g, 1.9 mmol, 96%) as a yellow solid. LCMS: m/e 562 (M+H)$^+$, ret time 2.85 min, column B, 3 minute gradient.

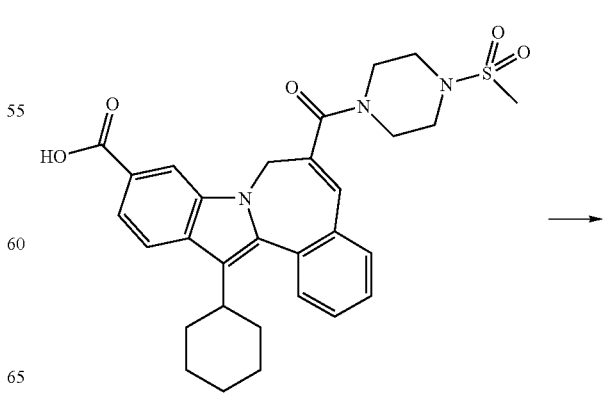

589

-continued

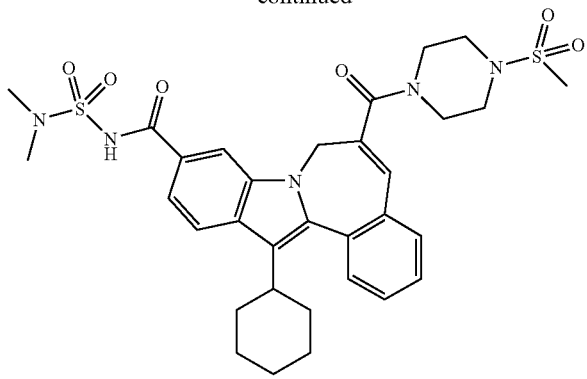

To a stirred solution of 7H-indolo[2,1-a][2]benzazepine-10-carboxylic acid, 13-cyclohexyl-6-[[4-(methylsulfonyl)-1-piperazinyl]carbonyl] (430 mg, 0.79 mmol), N,N-dimethylsulfamide (390 mg, 3.13 mmol) and DMAP (380 mg, 3.13 mmol) in dimethylacetamide (6 mL) was added 1-(3-dimethylaminopropyl)-3-ethylcarbodiimide hydrochloride (450 mg, 2.34 mmol). The reaction solution was stirred at 50° C. for 3 h, concentrated, purified by preparative HPLC (CH$_3$CN/H$_2$O with NH$_4$OAc buffer) to yield 7H-indolo[2,1-a][2]benzazepine-10-carboxamide, 13-cyclohexyl-N-[(dimethylamino)sulfonyl]-6-[[4-(methylsulfonyl)-1-piperazinyl carbonyl] (135 mg, 0.22 mol, 28%) as a yellow powder. $^1$HNMR (500 MHz, DMSO-d$_6$) δ 11.65 (s, 1H), 8.41 (br s, 1H), 7.94 (d, J=8.5 Hz, 1H), 7.65 (dd, J=1.5, 8.5 Hz, 1H), 7.63-7.55 (m, 4H), 7.04 (s, 1H), 5.19 (br s, 1H), 4.34 (br s, 1H), 3.66-3.31 (m, 8H), 2.92 (s, 6H), 2.84 (s, 3H), 2.82-2.75 (m, 1H), 2.11-1.06 (m, 10H). LCMS: m/e 652(M–H)$^1$, ret time 1.63 min, column A, 2 minute gradient.

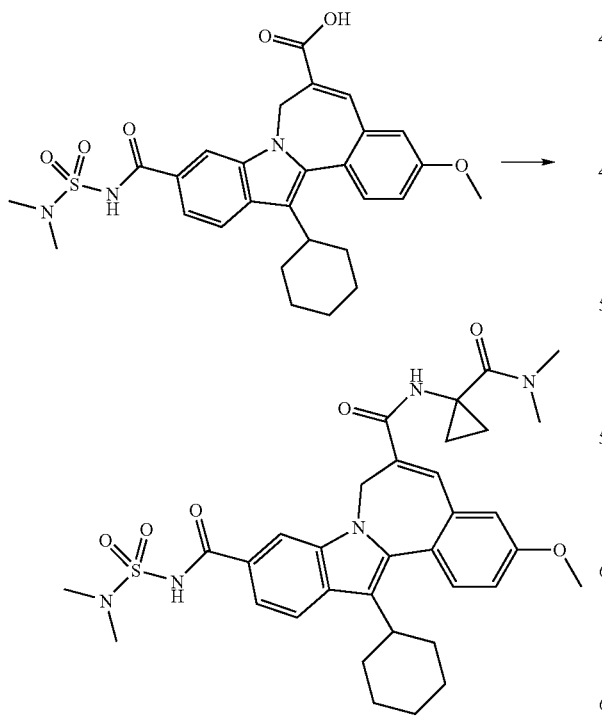

590

HATU (36 mg, 0.093 mmol) and triethylamine (19 mg, 0.19 mmol) were added to a solution of 13-cyclohexyl-N-[(dimethylamino)sulfonyl]-3-methoxy-7H-indolo[2,1-a][2]benzazepine-10-carboxamide-6-carboxylic acid (50 mg, 0.093 mmol) in DMF (1 mL). The mixture was stirred at rt for 1 h, and then 1-methylaminocyclopropane-1 carboxylic acid hydrochloride (14 mg, 0.093 mmol) and TEA (19 mg, 0.19 mmol) in H$_2$O (0.3 ml) were added and the mixture was stirred at rt for 1 h. To this mixture HATU (150 mg, 0.40 mmol) and triethylamine (19 mg, 0.19 mmol) were added, followed by 2.0 M dimethylamine in methanol solution (0.20 ml, 0.40 mmol). The reaction was stirred at rt overnight, diluted with methanol and purified by prep HPLC (MeCN/H$_2$O 10 mM NH$_4$OAc system) to yield 7H-indolo[2,1-a][2]benzazepine-6,10-dicarboxamide, 13-cyclohexyl-N$^6$-[1'-(dimethylcarbamoyl)cyclopropyl]-N$^{10}$-[(dimethylamino)sulfonyl]-3-methoxy- as yellow solid (23 mg, 0.035 mmol, 38%). 1H NMR (300 MHz, MeOD) δ ppm 1.10-2.20 (m, 14 H), 2.80-3.10 (m, 16 H), 3.93 (s, 3 H), 4.32 (br s, 1 H), 5.13 (br s, 1 H), 7.00-7.10 (m, 2 H), 7.15 (dd, J=8.8, 2.6 Hz, 1 H), 7.55 (d, J=8.8 Hz, 1 H), 7.63 (d, J=8.4 Hz, 1 H), 7.90 (d, J=8.4 Hz, 1 H), 8.10 (s, 1H). LCMS: M-1/e 660, ret time 1.51 min, column D, 2 minute gradient.

We claim:
1. A compound of formula I

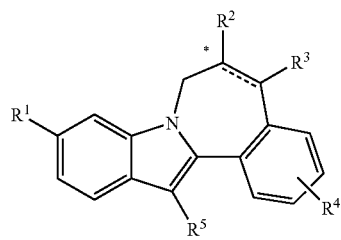

wherein:
R$^1$ is CO$_2$R$^6$ or CONR$^7$R$^8$;
R$^2$ is CONR$^9$R$^{10}$, CO$_2$benzyl, NHCO$_2$(alkyl), NHCO$_2$benzyl, NHCO(alkyl), NHCO(cycloalkyl), NHCOR$^{14}$, NHCO((R$^{15}$)alkyl), NHCO((R$^{16}$)alkyl), NHCO(tetrahydropyranyl), NHCO(methoxycycloalkyl), NHCON(R$^6$)$_2$, NHCON(R$^6$)((N(R$^6$)$_2$)alkyl), NHCON(R$^6$)((CO$_2$R$^6$)alkyl), NHCON(R$^6$)((CON(R$^6$)$_2$)alkyl), NHCON(R$^6$)((COR$^{15}$)alkyl), NHCON(R$^6$)((tetrahydropyranyl)alkyl),

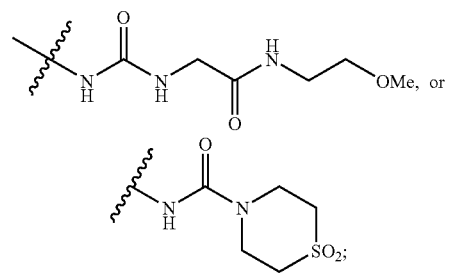

R$^3$ is hydrogen or alkyl;
R$^4$ is hydrogen, halo, alkyl, alkoxy, or benzyloxy;
R$^5$ is C$_{5-7}$cycloalkyl;
R$^6$ is hydrogen, alkyl, or cycloalkyl;

$R^7$ is hydrogen, alkyl, cycloalkyl, alkoxy, aminoalkyl, (alkylamino)alkyl, (dialkylamino)alkyl, $(CO_2R^6)$alkyl, $(CON(R^6)(R^6))$alkyl, (alkyl)CONH, tetrazolyl, tetrahydropyranyl, sulfolanyl, $SO_2R^{11}$, $SO_2R^{12}$, or $(R^{13})$alkyl;

$R^8$ is hydrogen, alkyl, or cycloalkyl;

or $NR^7R^8$ taken together is pyrrolidinyl, piperidinyl, piperazinyl, homomorpholinyl, homopiperidinyl, morpholinyl, or thiomorpholinyl, and is substituted with 0-2 substituents selected from halo, alkyl, and haloalkyl;

$R^9$ is cycloalkyl, dihydroxyalkyl, (alkoxy)alkyl, $(R^{12})$alkyl, (CHO)alkyl, $(CO_2R^6)$alkyl, $(CON(R^6)_2)$alkyl, $(COR^{12})$alkyl, $(COR^{15})$alkyl, ((alkoxyalkyl)amido)alkyl, (alkylamido)alkyl, (tetrahydrofuranyl)alkyl, (dioxolanyl)alkyl, $(alkylCO)(R^6)$amino, $((alkylCO)(R^6)$amino)alkyl, tetrahydropyranyl, or sulfolanyl;

$R^{10}$ is hydrogen, alkyl, cycloalkyl, hydroxyalkyl, dihydroxyalkyl, (alkoxy)alkyl, aminoalkyl, (alkylamino)alkyl, (dialkylamino)alkyl, $(R^{12})$alkyl, (CHO)alkyl, $(CO_2R^6)$alkyl, $(CON(R^6)_2)$alkyl, $(COR^{12})$alkyl, $(COR^{15})$alkyl, $(R^{16})$alkyl, ((alkoxyalkyl)amido)alkyl, (alkylamido)alkyl, (tetrahydrofuranyl)alkyl, (dioxolanyl)alkyl, $(alkylCO)(R^6)$amino, $((alkylCO)(R^6)$amino)alkyl, tetrahydropyranyl, or sulfolanyl;

or $NR^9R^{10}$ taken together is azetidinyl, pyrrolidinyl, piperidinyl, piperazinyl, homomorpholinyl, homopiperidinyl, morpholinyl, or thiomorpholinyl, and is substituted with 0-4 substituents selected from the group consisting of halo, hydroxy, $OPO(OR^6)_2$, alkoxy, alkyl, cycloalkyl, (cycloalkyl)alkyl, haloalkyl, hydroxyalkyl, alkoxyalkyl, (hydroxy)alkoxyalkyl, (alkoxy)alkyl, amino, alkylamino, dialkylamino, $(alkylCO)(R^6)$amino, $(alkoxyCO)(R^6)$amino, $(alkoxyalkylCO)(R^6)$amino, (alkylCO)alkylamino, $(cycloalkyl)(PhSO_2)$amino, $CO_2R^6$, $CON(R^6)_2$, CONH(alkenyl), $(R^{12})CO$, (alkyl)CO, (cycloalkyl)CO, (hydroxyalkyl)CO, ((hydroxy)cycloalkyl)CO, (aminoalkyl)CO, (acetoxyalkyl)CO, PhCO, (furanyl)CO, (benzodioxanyl)CO, $(alkyl)CO_2$, $SO_2R^{11}$, $SO_2R^{12}$, $(CO_2R^6)$alkyl, $(CON(R^6)_2)$alkyl, $(COR^{12})$alkyl, $(alkylCO)(R^6)$aminoalkyl, (PhCONH)alkyl, $(R^{12})$alkyl, $R^{12}$, phenyl, methoxyphenyl, pyrrolyl, furanyl, thienyl, imidazolyl, isoxazolyl, oxazolyl, thiazolyl, triazolyl, oxadiazolyl, pyridinyl, pyrimidinyl, pyrazinyl, triazinyl, pyrazolyl,

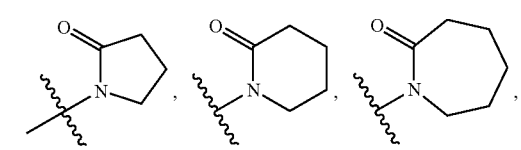, 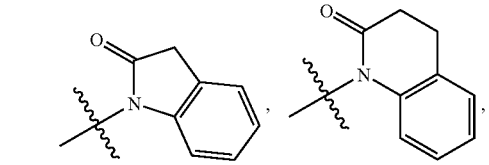,

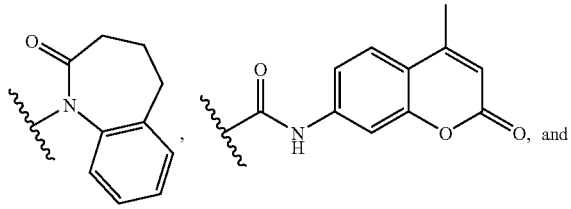, and

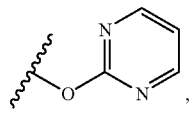, provided that if $NR^9R^{10}$ is pyrrolidinyl, piperidinyl, piperazinyl, homomorpholinyl, homopiperidinyl, morpholinyl, or thiomorpholinyl it cannot be substituted with 0-2 substituents selected from alkyl, hydroxy, amino, alkylamino, dialkylamino, or pyridinyl;

or $NR^9R^{10}$ taken together is

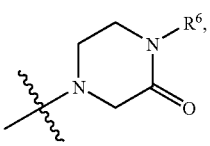, 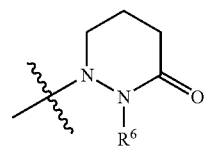,

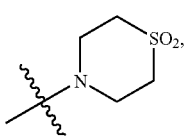, 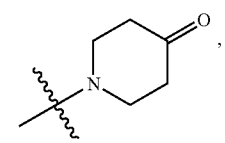,

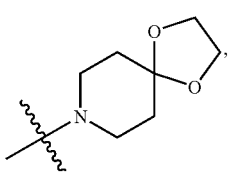, 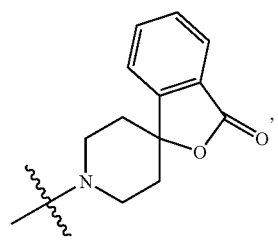,

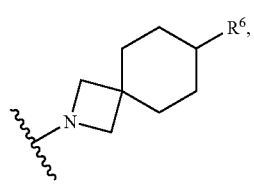, 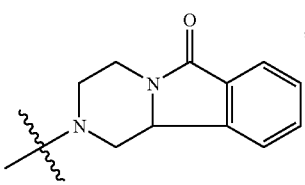,

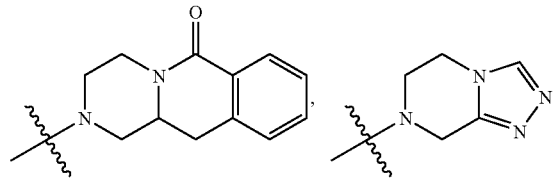,

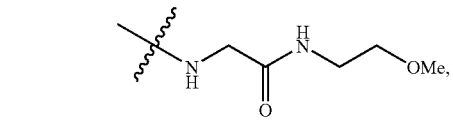,

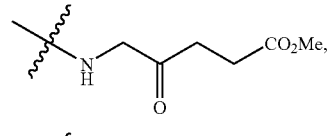,

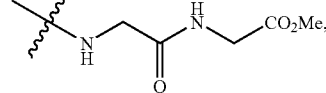,

-continued

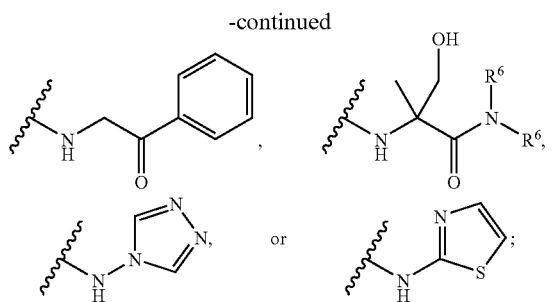

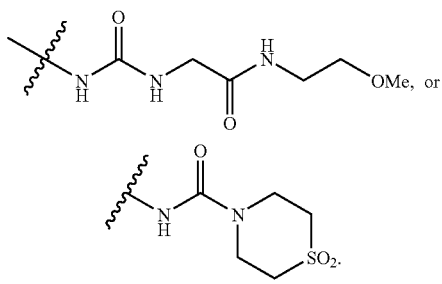

or NR⁹R¹⁰ taken together is a [2.2.1] or [2.2.2] bridged bicyclic amine wherein the bicycle contains 0-1 NR⁶, NCO₂R⁶, or O;

R¹¹ is alkyl, haloalkyl, cycloalkyl, alkoxy, amino, alkylamino, dialkylamino, ((R⁶)(R⁶)N)alkylamino, (((R⁶)(R⁶)N)alkyl)₂amino, N,O-dimethylhydroxylamino, or phenyl, wherein the phenyl is substituted with 0-2 substituents selected from the group consisting of halo, alkyl, haloalkyl, and alkoxy;

R¹² is pyrrolidinyl, piperidinyl, piperazinyl, homomorpholinyl, homopiperidinyl, morpholinyl, or thiomorpholinyl, and is substituted with 0-2 substituents selected from halo, alkyl, haloalkyl, and alkoxy;

R¹³ is pyrrolidinyl, piperidinyl, piperazinyl, homomorpholinyl, homopiperidinyl, morpholinyl, thiomorpholinyl, tetrahydrofuranyl, furanyl, thienyl, pyrrolyl, pyrazolyl, imidazolyl, isoxazolyl, oxazolyl, triazolyl, oxadiazolyl, tetrazolyl, pyridinyl, pyrazinyl, pyrimidinyl, imidazopyridinyl, or benzimidazole, and is substituted with 0-2 alkyl substituents;

R¹⁴ is azetidine, pyrrolidinyl, piperidinyl, piperazinyl, homomorpholinyl, homopiperidinyl, morpholinyl, thiomorpholinyl, or S,S-dioxothiomorpholinyl, and is substituted with 0-3 substituents selected from halo, alkyl, hydroxy, alkoxy, aminoalkyl, (alkylamino)alkyl, (dialkylamino)alkyl, (CO₂R⁶)alkyl, (CON(R⁶)₂)alkyl, ((R⁶CO)(R⁶)amino)alkyl, (R¹⁵)alkyl, (R⁶CO)(R⁶)amino, R¹⁵, alkylCO, CF₃CO, CO₂R⁶, CON(R⁶)₂, or SO₂R⁶;

or R¹⁴ is a [2.2.1] or [2.2.2] bridged bicyclic amine wherein the bicycle contains 0-1 O;

R¹⁵ is azetidinyl, pyrrolidinyl, piperidinyl, piperazinyl, homomorpholinyl, homopiperidinyl, morpholinyl, or thiomorpholinyl, and is substituted with 0-2 halo, alkyl, or alkoxy substituents;

R¹⁶ is pyrazolyl, imidazolyl, isoxazolyl, oxazolyl, thiazolyl, triazolyl, oxadiazolyl, tetrazolyl, or pyridinyl, and is substituted with 0-2 substituents; and the dashed line is either a single bond or a double bond, provided that if the dashed line is a single bond, the carbon bearing the asterisk is either of the R configuration, the S configuration, or a mixture of R and S configurations;

or a pharmaceutically acceptable salt thereof.

2. A compound of claim 1 where R² is NHCO₂(alkyl), NHCO₂benzyl, NHCO(alkyl), NHCO(cycloalkyl), NHCOR¹⁴, NHCO((R¹⁵)alkyl), NHCO((R¹⁶)alkyl), NHCO(tetrahydropyranyl), NHCO(methoxycycloalkyl), NHCON(R⁶)₂, NHCON(R⁶)((N(R⁶)₂)alkyl), NHCON(R⁶)((CO₂R⁶)alkyl), NHCON(R⁶)((CON(R⁶)₂)alkyl), NHCON(R⁶)((COR¹⁵)alkyl), NHCON(R⁶)((tetrahydropyranyl)alkyl), 3. A compound of claim 1 where R² is CONR⁹R¹⁰.

4. A compound of claim 1 where NR⁹R¹⁰ taken together is azetidinyl, pyrrolidinyl, piperidinyl, piperazinyl, homomorpholinyl, homopiperidinyl, morpholinyl, or thiomorpholinyl, and is substituted with 1-4 substituents selected from the group consisting of halo, OPO(OR⁶)₂, alkoxy, cycloalkyl, (cycloalkyl)alkyl, haloalkyl, hydroxyalkyl, alkoxyalkyl, (hydroxy)alkoxyalkyl, (alkoxy)alkyl, (alkylCO)(R⁶)amino, (alkoxyCO)(R⁶)amino, (alkoxyalkylCO)(R⁶)amino, (alkylCO)alkylamino, (cycloalkyl)(PhSO₂)amino, CO₂R⁶, CON(R⁶)₂, CONH(alkenyl), (R¹²)CO, (alkyl)CO, (cycloalkyl)CO, (hydroxyalkyl)CO, ((hydroxy)cycloalkyl)CO, (aminoalkyl)CO, (acetoxyalkyl)CO, PhCO, (furanyl)CO, (benzodioxanyl)CO, (alkyl)CO₂, SO₂R¹¹, SO₂R¹², (CO₂R⁶)alkyl, (CON(R⁶)₂)alkyl, (COR¹²)alkyl, (alkylCO)(R⁶)aminoalkyl, (PhCONH)alkyl, (R¹²)alkyl, phenyl, methoxyphenyl, pyrrolyl, furanyl, thienyl, imidazolyl, isoxazolyl, oxazolyl, thiazolyl, triazolyl, oxadiazolyl, pyrimidinyl, pyrazinyl, triazinyl, pyrazolyl,

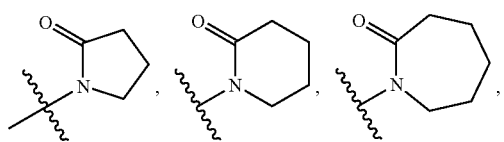

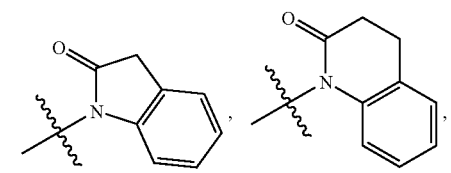

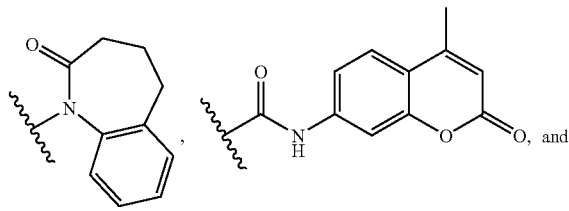, and

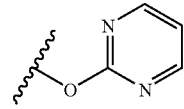.

5. A compound of claim 1 where $NR^9R^{10}$ taken together is

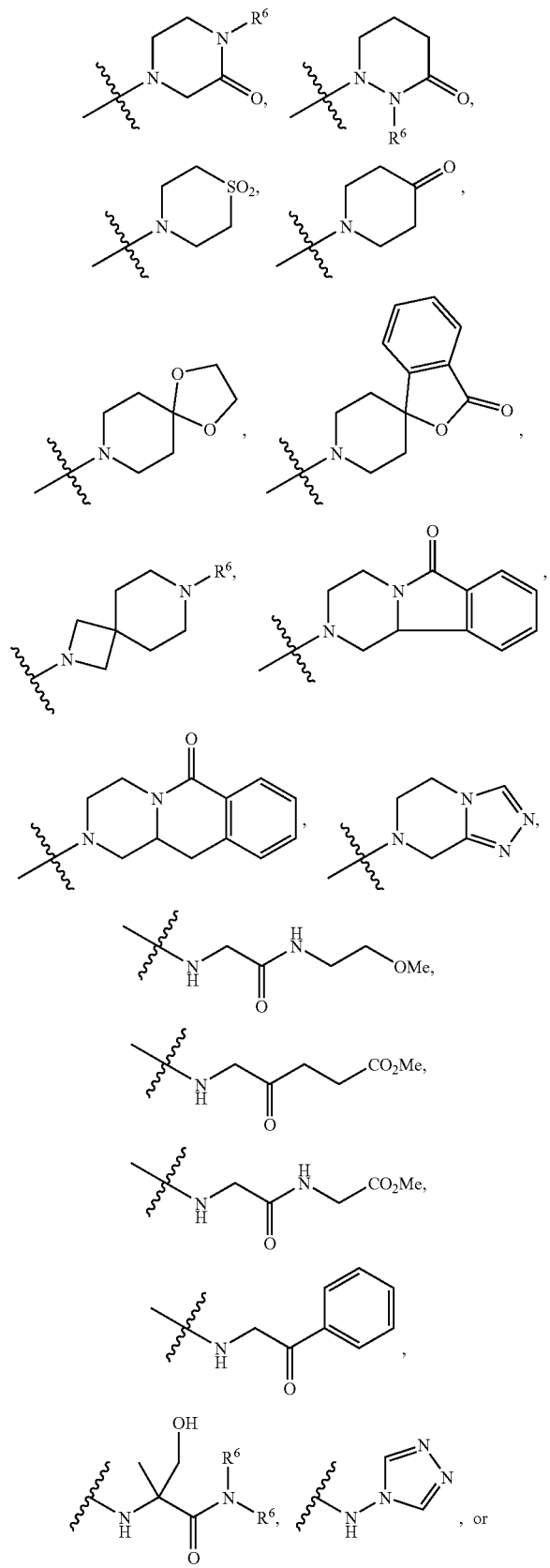

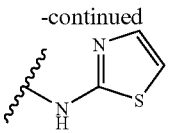

6. A compound of claim 1 where $NR^9R^{10}$ taken together is a [2.2.1] or [2.2.2] bridged bicyclic amine wherein the bicycle contains 0-1 $NR^6$, $NCO_2R^6$, or O.

7. A compound of claim 1 where the dashed line is a single bond and the carbon bearing the asterisk is of the R configuration.

8. A compound of claim 1 where the dashed line is a single bond and the carbon bearing the asterisk is of the S configuration.

9. A compound of formula I

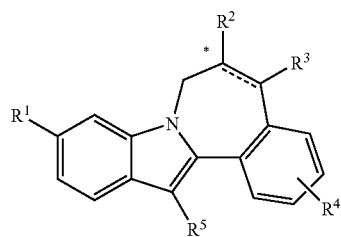

wherein:

$R^1$ is $CONR^7R^8$;

$R^2$ is $CO_2R^6$, $CO_2$benzyl, $CONR^9R^{10}$, $NHCO_2$(alkyl), $NHCO_2$benzyl, NHCO(alkyl), NHCO(cycloalkyl), $NHCOR^{14}$, $NHCO((R^{15})$alkyl), $NHCO((R^{16})$alkyl), NHCO(tetrahydropyranyl), NHCO(methoxycycloalkyl), $NHCON(R^6)_2$, $NHCON(R^6)((N(R^6)_2)$alkyl), $NHCON(R^6)((CO_2R^6)$alkyl), $NHCON(R^6)((CON(R^6)_2)$alkyl), $NHCON(R^6)((COR^{15})$alkyl), $NHCON(R^6)$((tetrahydropyranyl)alkyl),

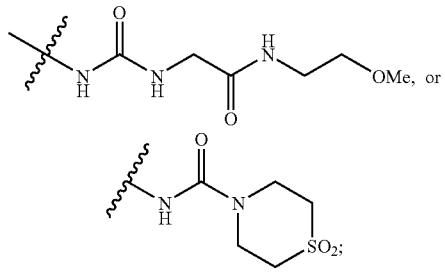

$R^3$ is hydrogen or alkyl;

$R^4$ is hydrogen, halo, alkyl, alkoxy, or benzyloxy;

$R^5$ is $C_{5-7}$cycloalkyl;

$R^6$ is hydrogen, alkyl, or cycloalkyl;

$R^7$ is $(CO_2R^6)$alkyl, $(CON(R^6)(R^6))$alkyl, (alkyl)CONH, tetrazolyl, tetrahydropyranyl, sulfolanyl, $SO_2R^{11}$, $SO_2R^{12}$, or $(R^{13})$alkyl;

$R^8$ is hydrogen, alkyl, or cycloalkyl;

or $NR^7R^8$ taken together is pyrrolidinyl, piperidinyl, piperazinyl, homomorpholinyl, homopiperidinyl, morpholinyl, or thiomorpholinyl, and is substituted with 0-2 substituents selected from halo, alkyl, and haloalkyl;

R⁹ is hydrogen, alkyl, cycloalkyl, hydroxyalkyl, dihydroxyalkyl, (alkoxy)alkyl, aminoalkyl, (alkylamino)alkyl, (dialkylamino)alkyl, ($R^{12}$)alkyl, (CHO)alkyl, ($CO_2R^6$)alkyl, ($CON(R^6)_2$)alkyl, ($COR^{12}$)alkyl, ($COR^{15}$)alkyl, ($R^{16}$)alkyl, ((alkoxyalkyl)amido)alkyl, (alkylamido)alkyl, (tetrahydrofuranyl)alkyl, (dioxolanyl)alkyl, (alkylCO)($R^6$)amino, ((alkylCO)($R^6$)amino)alkyl, tetrahydropyranyl, or sulfolanyl;

$R^{10}$ is hydrogen, alkyl, cycloalkyl, hydroxyalkyl, dihydroxyalkyl, (alkoxy)alkyl, aminoalkyl, (alkylamino)alkyl, (dialkylamino)alkyl, ($R^{12}$)alkyl, (CHO)alkyl, ($CO_2R^6$)alkyl, ($CON(R^6)_2$)alkyl, ($COR^{12}$)alkyl, ($COR^{15}$)alkyl, ($R^{16}$)alkyl, ((alkoxyalkyl)amido)alkyl, (alkylamido)alkyl, (tetrahydrofuranyl)alkyl, (dioxolanyl)alkyl, (alkylCO)($R^6$)amino, ((alkylCO)($R^6$)amino)alkyl, tetrahydropyranyl, or sulfolanyl;

or $NR^9R^{10}$ taken together is azetidinyl, pyrrolidinyl, piperidinyl, piperazinyl, homomorpholinyl, homopiperidinyl, morpholinyl, or thiomorpholinyl, and is substituted with 0-4 substituents selected from the group consisting of halo, hydroxy, $OPO(OR^6)_2$, alkoxy, alkyl, cycloalkyl, (cycloalkyl)alkyl, haloalkyl, hydroxyalkyl, alkoxyalkyl, (hydroxy)alkoxyalkyl, (alkoxy)alkyl, amino, alkylamino, dialkylamino, (alkylCO)($R^6$)amino, (alkoxyCO)($R^6$)amino, (alkoxyalkylCO)($R^6$)amino, (alkylCO)alkylamino, (cycloalkyl)($PhSO_2$)amino, $CO_2R^6$, $CON(R^6)_2$, CONH(alkenyl), ($R^{12}$)CO, (alkyl)CO, (cycloalkyl)CO, (hydroxyalkyl)CO, ((hydroxy)cycloalkyl)CO, (aminoalkyl)CO, (acetoxyalkyl)CO, PhCO, (furanyl)CO, (benzodioxanyl)CO, (alkyl)$CO_2$, $SO_2R^{11}$, $SO_2R^{12}$, ($CO_2R^6$)alkyl, ($CON(R^6)_2$)alkyl, ($COR^{12}$)alkyl, (alkylCO)($R^6$)aminoalkyl, (PhCONH)alkyl, ($R^{12}$)alkyl, $R^{12}$, phenyl, methoxyphenyl, pyrrolyl, furanyl, thienyl, imidazolyl, isoxazolyl, oxazolyl, thiazolyl, triazolyl, oxadiazolyl, pyridinyl, pyrimidinyl, pyrazinyl, triazinyl, pyrazolyl,

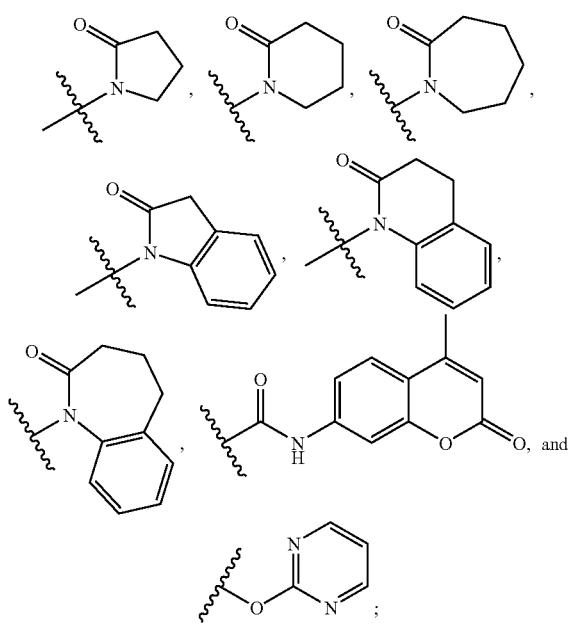

or $NR^9R^{10}$ taken together is

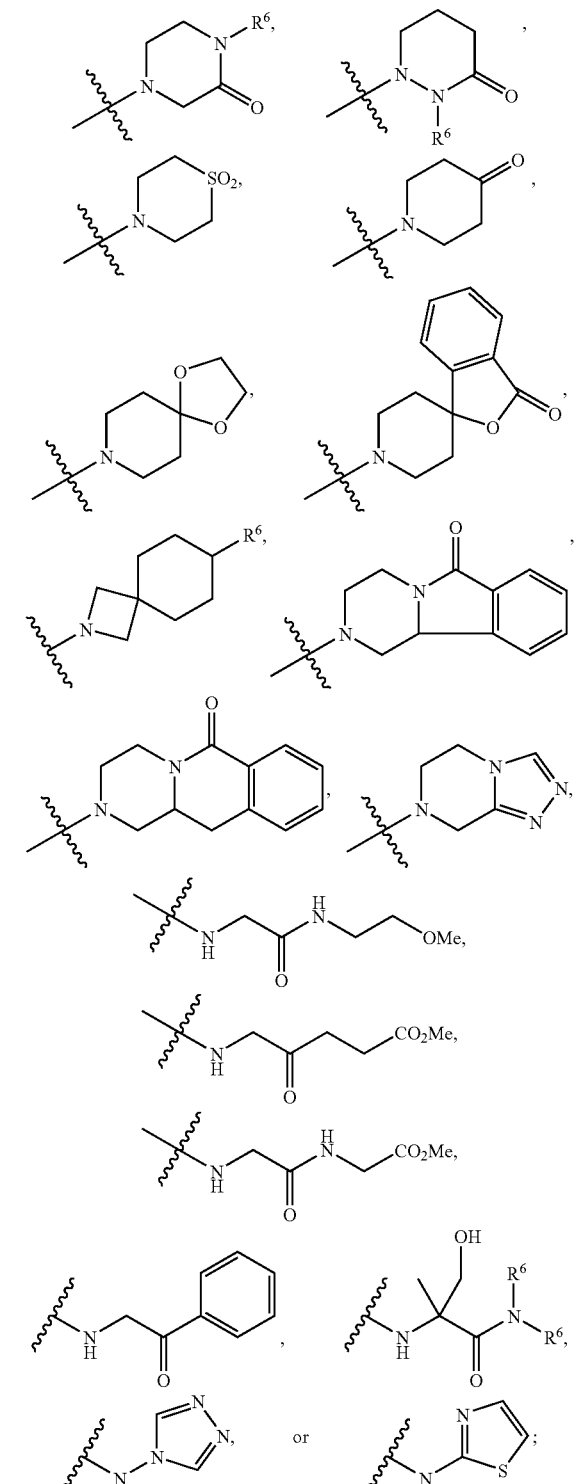

or $NR^9R^{10}$ taken together is a [2.2.1] or [2.2.2] bridged bicyclic amine wherein the bicycle contains 0-1 NR, $NCO_2R^6$, or O;

$R^{11}$ is haloalkyl, alkoxy, (($R^6$)($R^6$)N)alkylamino, ((($R^6$)($R^6$)N)alkyl)₂ amino, N,O-dimethylhydroxylamino;

$R^{12}$ is pyrrolidinyl, piperidinyl, piperazinyl, homomorpholinyl, homopiperidinyl, morpholinyl, or thiomorpholinyl, and is substituted with 0-2 substituents selected from halo, alkyl, haloalkyl, and alkoxy;

R¹³ is pyrrolidinyl, piperidinyl, piperazinyl, homomorpholinyl, homopiperidinyl, morpholinyl, thiomorpholinyl, or tetrahydrofuranyl, and is substituted with 0-2 alkyl substituents;

R¹⁴ is azetidine, pyrrolidinyl, piperidinyl, piperazinyl, homomorpholinyl, homopiperidinyl, morpholinyl, thiomorpholinyl, or S,S-dioxothiomorpholinyl, and is substituted with 0-3 substituents selected from halo, alkyl, hydroxy, alkoxy, aminoalkyl, (alkylamino)alkyl, (dialkylamino)alkyl, (CO₂R⁶)alkyl, (CON(R⁶)₂)alkyl, ((R⁶CO)(R⁶)amino)alkyl, (R¹⁵)alkyl, (R⁶CO)(R⁶)amino, R¹⁵, alkylCO, CF₃CO, CO₂R⁶, CON(R⁶)₂, or SO₂R⁶;

or R¹⁴ is a [2.2.1] or [2.2.2] bridged bicyclic amine wherein the bicycle contains 0-1 O;

R¹⁵ is azetidinyl, pyrrolidinyl, piperidinyl, piperazinyl, homomorpholinyl, homopiperidinyl, morpholinyl, or thiomorpholinyl, and is substituted with 0-2 halo, alkyl, or alkoxy substituents;

R¹⁶ is pyrazolyl, imidazolyl, isoxazolyl, oxazolyl, thiazolyl, triazolyl, oxadiazolyl, tetrazolyl, or pyridinyl, and is substituted with 0-2 alkyl substituents; and the dashed line is either a single bond or a double bond, provided that if the dashed line is a single bond, the carbon bearing the asterisk is either of the R configuration, the S configuration, or a mixture of R and S;

or a pharmaceutically acceptable salt thereof.

10. A compound of formula II

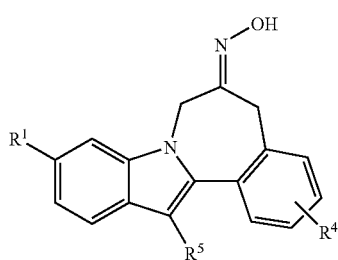

wherein:

R¹ is CO₂R⁶ or CONR⁷R⁸;

R⁴ is hydrogen, halo, alkyl, alkoxy, or benzyloxy;

R⁵ is C₅₋₇cycloalkyl;

R⁶ is hydrogen, alkyl, or cycloalkyl;

R⁷ is hydrogen, alkyl, cycloalkyl, alkoxy, aminoalkyl, (alkylamino)alkyl, (dialkylamino)alkyl, (CO₂R⁶)alkyl, (CON(R⁶)(R⁶))alkyl, (alkyl)CONH, tetrazolyl, tetrahydropyranyl, sulfolanyl, SO₂R¹¹, SO₂R¹², or (R¹³)alkyl;

R⁸ is hydrogen, alkyl, or cycloalkyl;

or NR⁷R⁸ taken together is pyrrolidinyl, piperidinyl, piperazinyl, homomorpholinyl, homopiperidinyl, morpholinyl, or thiomorpholinyl, and is substituted with 0-2 substituents selected from halo, alkyl, and haloalkyl;

R¹¹ is alkyl, haloalkyl, cycloalkyl, alkoxy, amino, alkylamino, dialkylamino, ((R⁶)(R⁶)N)alkylamino, (((R⁶)(R⁶)N)alkyl)₂amino, N,O-dimethylhydroxylamino, or phenyl, wherein the phenyl is substituted with 0-2 substituents selected from the group consisting of halo, alkyl, haloalkyl, and alkoxy;

R¹² is pyrrolidinyl, piperidinyl, piperazinyl, homomorpholinyl, homopiperidinyl, morpholinyl, or thiomorpholinyl, and is substituted with 0-2 substituents selected from halo, alkyl, haloalkyl, and alkoxy; and R¹³ is pyrrolidinyl, piperidinyl, piperazinyl, homomorpholinyl, homopiperidinyl, morpholinyl, thiomorpholinyl, tetrahydrofuranyl, furanyl, thienyl, pyrrolyl, pyrazolyl, imidazolyl, isoxazolyl, oxazolyl, triazolyl, oxadiazolyl, tetrazolyl, pyridinyl, pyrazinyl, pyrimidinyl, imidazopyridinyl, or benzimidazole, and is substituted with 0-2 alkyl substituents;

or a pharmaceutically acceptable salt thereof.

11. A compound of formula III

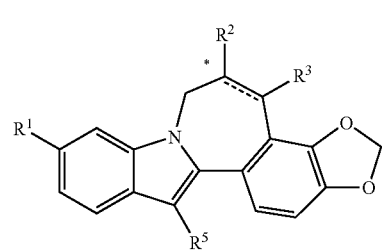

wherein:

R¹ is CO₂R⁶ or CONR⁷R⁸;

R² is CO₂R⁶, CO₂benzyl, CONR⁹R¹⁰, NHCO₂(alkyl), NHCO₂benzyl, NHCO(alkyl), NHCO(cycloalkyl), NHCOR¹⁴, NHCO((R¹⁵)alkyl), NHCO((R¹⁶)alkyl), NHCO(tetrahydropyranyl), NHCO(methoxycycloalkyl), NHCON(R⁶)₂, NHCON(R⁶)((N(R⁶)₂)alkyl), NHCON(R⁶)((CO₂R⁶)alkyl), NHCON(R⁶)((CON(R⁶)₂)alkyl), NHCON(R⁶)((COR¹⁵)alkyl), NHCON(R⁶)((tetrahydropyranyl)alkyl),

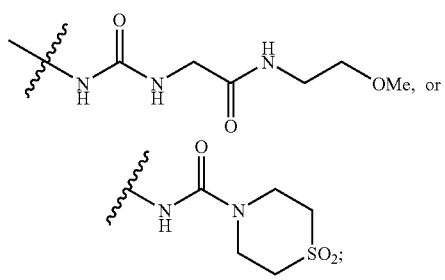

R³ is hydrogen or alkyl;

R⁵ is C₅₋₇cycloalkyl;

R⁶ is hydrogen, alkyl, or cycloalkyl;

R⁷ is hydrogen, alkyl, cycloalkyl, alkoxy, aminoalkyl, (alkylamino)alkyl, (dialkylamino)alkyl, (CO₂R⁶)alkyl, (CON(R⁶)(R⁶))alkyl, (alkyl)CONH, tetrazolyl, tetrahydropyranyl, sulfolanyl, SO₂R¹¹, SO₂R¹², or (R¹³)alkyl;

R⁸ is hydrogen, alkyl, or cycloalkyl;

or NR⁷R⁸ taken together is pyrrolidinyl, piperidinyl, piperazinyl, homomorpholinyl, homopiperidinyl, morpholinyl, or thiomorpholinyl, and is substituted with 0-2 substituents selected from halo, alkyl, and haloalkyl;

R⁹ is hydrogen, alkyl, cycloalkyl, hydroxyalkyl, dihydroxyalkyl, (alkoxy)alkyl, aminoalkyl, (alkylamino)alkyl, (dialkylamino)alkyl, (R¹²)alkyl, (CHO)alkyl, (CO₂R⁶)alkyl, (CON(R⁶)₂)alkyl, (COR¹²)alkyl, (COR¹⁵)alkyl, (R¹⁶)alkyl, ((alkoxyalkyl)amido)alkyl, (alkylamido)alkyl, (tetrahydrofuranyl)alkyl, (dioxolanyl)alkyl, (alkylCO)(R⁶)amino, ((alkylCO)(R⁶)amino)alkyl, tetrahydropyranyl, or sulfolanyl;

R¹⁰ is hydrogen, alkyl, cycloalkyl, hydroxyalkyl, dihydroxyalkyl, (alkoxy)alkyl, aminoalkyl, (alkylamino)alkyl, (dialkylamino)alkyl, (R¹¹²)alkyl, (CHO)alkyl, (CO₂R⁶)alkyl, (CON(R⁶)₂)alkyl, (COR¹²)alkyl, (COR¹⁵)alkyl, (R¹⁶)alkyl, ((alkoxyalkyl)amido)alkyl, (alkylamido)alkyl, (tetrahydrofuranyl)alkyl, (dioxolanyl)alkyl, (alkylCO)(R⁶)amino, ((alkylCO)(R⁶)amino)alkyl, tetrahydropyranyl, or sulfolanyl;

or NR⁹R¹⁰ taken together is azetidinyl, pyrrolidinyl, piperidinyl, piperazinyl, homomorpholinyl, homopiperidinyl, morpholinyl, or thiomorpholinyl, and is substituted with 0-4 substituents selected from the group consisting of halo, hydroxy, OPO(OR⁶)₂, alkoxy, alkyl, cycloalkyl, (cycloalkyl)alkyl, haloalkyl, hydroxyalkyl, alkoxyalkyl, (hydroxy)alkoxyalkyl, (alkoxy)alkyl, amino, alkylamino, dialkylamino, (alkylCO)(R⁶)amino, (alkoxyCO)(R⁶)amino, (alkoxyalkylCO)(R⁶)amino, (alkylCO)alkylamino, (cycloalkyl)(PhSO₂)amino, CO₂R⁶, CON(R⁶)₂, CONH(alkenyl), (R¹²)CO, (alkyl)CO, (cycloalkyl)CO, (hydroxyalkyl)CO, ((hydroxy)cycloalkyl)CO, (aminoalkyl)CO, (acetoxyalkyl)CO, PhCO, (furanyl)CO, (benzodioxanyl)CO, (alkyl)CO₂, SO₂R¹¹, SO₂R¹², (CO₂R⁶)alkyl, (CON(R⁶)₂)alkyl, (COR¹²)alkyl, (alkylCO)(R⁶)aminoalkyl, (PhCONH)alkyl, (R¹²)alkyl, R¹², phenyl, methoxyphenyl, pyrrolyl, furanyl, thienyl, imidazolyl, isoxazolyl, oxazolyl, thiazolyl, triazolyl, oxadiazolyl, pyridinyl, pyrimidinyl, pyrazinyl, triazinyl, pyrazolyl,

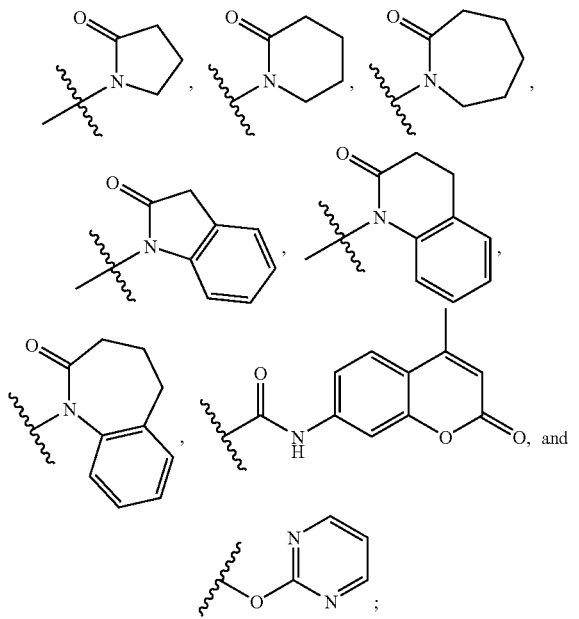

or NR⁹R¹⁰ taken together is

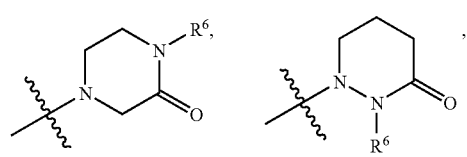

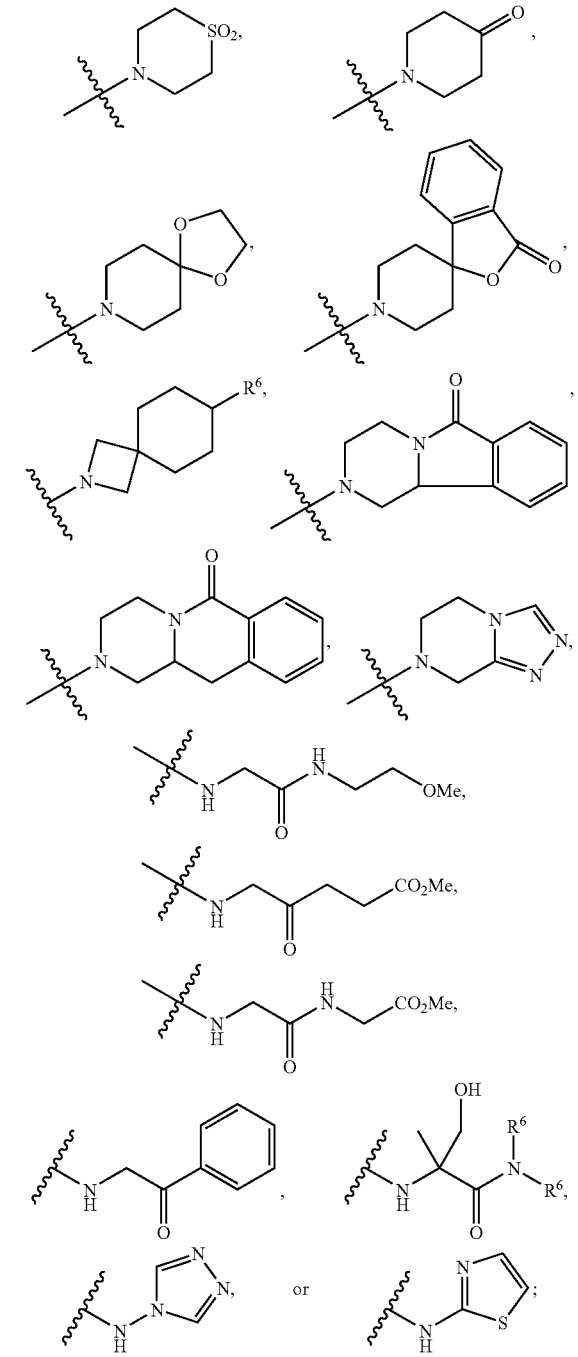

or NR⁹R¹⁰ taken together is a [2.2.1] or [2.2.2] bridged bicyclic amine wherein the bicycle contains 0-1 NR⁶, NCO₂R⁶, or O;

R¹¹ is alkyl, haloalkyl, cycloalkyl, alkoxy, amino, alkylamino, dialkylamino, ((R⁶)(R⁶)N)alkylamino, (((R⁶)(R⁶)N)alkyl)₂amino, N,O-dimethylhydroxylamino, or phenyl, wherein the phenyl is substituted with 0-2 substituents selected from the group consisting of halo, alkyl, haloalkyl, and alkoxy;

R¹² is pyrrolidinyl, piperidinyl, piperazinyl, homomorpholinyl, homopiperidinyl, morpholinyl, or thiomorpholinyl, and is substituted with 0-2 substituents selected from halo, alkyl, haloalkyl, and alkoxy;

$R^{13}$ is pyrrolidinyl, piperidinyl, piperazinyl, homomorpholinyl, homopiperidinyl, morpholinyl, thiomorpholinyl, tetrahydrofuranyl, furanyl, thienyl, pyrrolyl, pyrazolyl, imidazolyl, isoxazolyl, oxazolyl, triazolyl, oxadiazolyl, tetrazolyl, pyridinyl, pyrazinyl, pyrimidinyl, imidazopyridinyl, or benzimidazole, and is substituted with 0-2 alkyl substituents;

$R^{14}$ is azetidine, pyrrolidinyl, piperidinyl, piperazinyl, homomorpholinyl, homopiperidinyl, morpholinyl, thiomorpholinyl, or S,S-dioxothiomorpholinyl, and is substituted with 0-3 substituents selected from halo, alkyl, hydroxy, alkoxy, aminoalkyl, (alkylamino)alkyl, (dialkylamino)alkyl, $(CO_2R^6)$alkyl, $(CON(R^6)_2)$alkyl, $((R^6CO)(R^6)amino)$alkyl, $(R^{15})$alkyl, $(R^6CO)(R^6)$amino, $R^{15}$, alkylCO, $CF_3CO$, $CO_2R^6$, $CON(R^6)_2$, or $SO_2R^6$;

or $R^{14}$ is a [2.2.1] or [2.2.2] bridged bicyclic amine wherein the bicycle contains 0-1 O;

$R^{15}$ is azetidinyl, pyrrolidinyl, piperidinyl, piperazinyl, homomorpholinyl, homopiperidinyl, morpholinyl, or thiomorpholinyl, and is substituted with 0-2 halo, alkyl, or alkoxy substituents;

$R^{16}$ is pyrazolyl, imidazolyl, isoxazolyl, oxazolyl, thiazolyl, triazolyl, oxadiazolyl, tetrazolyl, or pyridinyl, and is substituted with 0-2 alkyl substituents; and the dashed line is either a single bond or a double bond, provided that if the dashed line is a single bond, the carbon bearing the asterisk is either of the R configuration, the S configuration, or a mixture of R and S;

or a pharmaceutically acceptable salt thereof.

12. A compound of formula IV

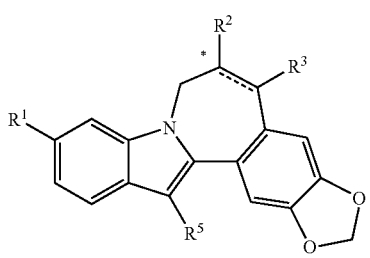

IV wherein:

$R^1$ is $CO_2R^6$ or $CONR^7R^8$;

$R^2$ is $CO_2R^6$, $CO_2$benzyl, $CONR^9R^{10}$, $NHCO_2$(alkyl), $NHCO_2$benzyl, NHCO(alkyl), NHCO(cycloalkyl), $NHCOR^{14}$, $NHCO((R^{15})$alkyl), $NHCO((R^{16})$alkyl), NHCO(tetrahydropyranyl), NHCO(methoxycycloalkyl), $NHCON(R^6)_2$, $NHCON(R^6)((N(R^6)_2)$alkyl), $NHCON(R^6)((CO_2R^6)$alkyl), $NHCON(R^6)((CON(R^6)_2)$alkyl), $NHCON(R^6)((COR^{15})$alkyl), $NHCON(R^6)((tetrahydropyranyl)$alkyl), -continued $R^3$ is hydrogen or alkyl;

$R^5$ is $C_{5-7}$cycloalkyl;

$R^6$ is hydrogen, alkyl, or cycloalkyl;

$R^7$ is hydrogen, alkyl, cycloalkyl, alkoxy, aminoalkyl, (alkylamino)alkyl, (dialkylamino)alkyl, $(CO_2R^6)$alkyl, $(CON(R^6)(R^6))$alkyl, (alkyl)CONH, tetrazolyl, tetrahydropyranyl, sulfolanyl, $SO_2R^{11}$, $SO_2R^{12}$, or $(R^{13})$alkyl;

$R^8$ is hydrogen, alkyl, or cycloalkyl;

or $NR^7R^8$ taken together is pyrrolidinyl, piperidinyl, piperazinyl, homomorpholinyl, homopiperidinyl, morpholinyl, or thiomorpholinyl, and is substituted with 0-2 substituents selected from halo, alkyl, and haloalkyl;

$R^9$ is hydrogen, alkyl, cycloalkyl, hydroxyalkyl, dihydroxyalkyl, (alkoxy)alkyl, aminoalkyl, (alkylamino)alkyl, (dialkylamino)alkyl, $(R^{12})$alkyl, (CHO)alkyl, $(CO_2R^6)$alkyl, $(CON(R^6)_2)$alkyl, $(COR^{12})$alkyl, $(COR^{15})$alkyl, $(R^{16})$alkyl, ((alkoxyalkyl)amido)alkyl, (alkylamido)alkyl, (tetrahydrofuranyl)alkyl, (dioxolanyl)alkyl, $(alkylCO)(R^6)amino$, $((alkylCO)(R^6)amino)$alkyl, tetrahydropyranyl, or sulfolanyl;

$R^{10}$ is hydrogen, alkyl, cycloalkyl, hydroxyalkyl, dihydroxyalkyl, (alkoxy)alkyl, aminoalkyl, (alkylamino)alkyl, (dialkylamino)alkyl, $(R^{12})$alkyl, (CHO)alkyl, $(CO_2R^6)$alkyl, $(CON(R^6)_2)$alkyl, $(COR^{12})$alkyl, $(COR^{15})$alkyl, $(R^{16})$alkyl, ((alkoxyalkyl)amido)alkyl, (alkylamido)alkyl, (tetrahydrofuranyl)alkyl, (dioxolanyl)alkyl, $(alkylCO)(R^6)amino$, $((alkylCO)(R^6)amino)$alkyl, tetrahydropyranyl, or sulfolanyl;

or $NR^9R^{10}$ taken together is azetidinyl, pyrrolidinyl, piperidinyl, piperazinyl, homomorpholinyl, homopiperidinyl, morpholinyl, or thiomorpholinyl, and is substituted with 0-4 substituents selected from the group consisting of halo, hydroxy, $OPO(OR^6)_2$, alkoxy, alkyl, cycloalkyl, (cycloalkyl)alkyl, haloalkyl, hydroxyalkyl, alkoxyalkyl, (hydroxy)alkoxyalkyl, (alkoxy)alkyl, amino, alkylamino, dialkylamino, $(alkylCO)(R^6)amino$, $(alkoxyCO)(R^6)amino$, $(alkoxyalkylCO)(R^6)amino$, (alkylCO)alkylamino, $(cycloalkyl)(PhSO_2)amino$, $CO_2R^6$, $CON(R^6)_2$, CONH(alkenyl), $(R^{12})CO$, (alkyl)CO, (cycloalkyl)CO, (hydroxyalkyl)CO, ((hydroxy)cycloalkyl)CO, (aminoalkyl)CO, (acetoxyalkyl)CO, PhCO, (furanyl)CO, (benzodioxanyl)CO, (alkyl)$CO_2$, $SO_2R^{11}$, $SO_2R^{12}$, $(CO_2R^6)$alkyl, $(CON(R^6)_2)$alkyl, $(COR^{12})$alkyl, $(alkylCO)(R^6)aminoalkyl$, (PhCONH)alkyl, $(R^{12})$alkyl, $R^{12}$, phenyl, methoxyphenyl, pyrrolyl, furanyl, thienyl, imidazolyl, isoxazolyl, oxazolyl, thiazolyl, triazolyl, oxadiazolyl, pyridinyl, pyrimidinyl, pyrazinyl, triazinyl, pyrazolyl,

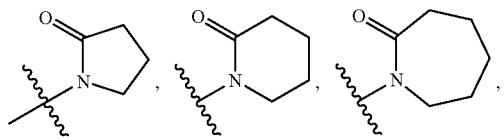

-continued

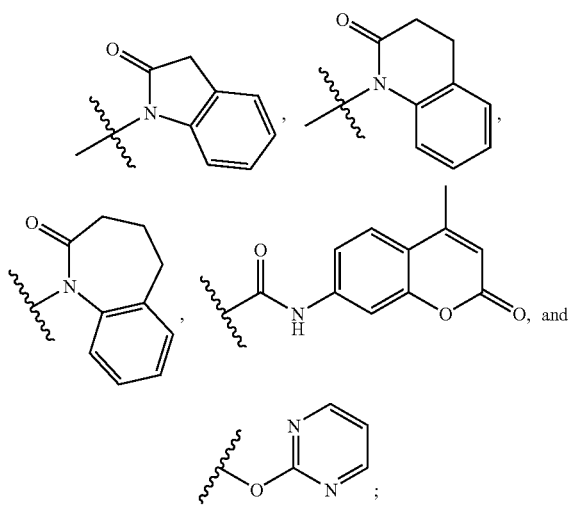

or NR⁹R¹⁰ take together is

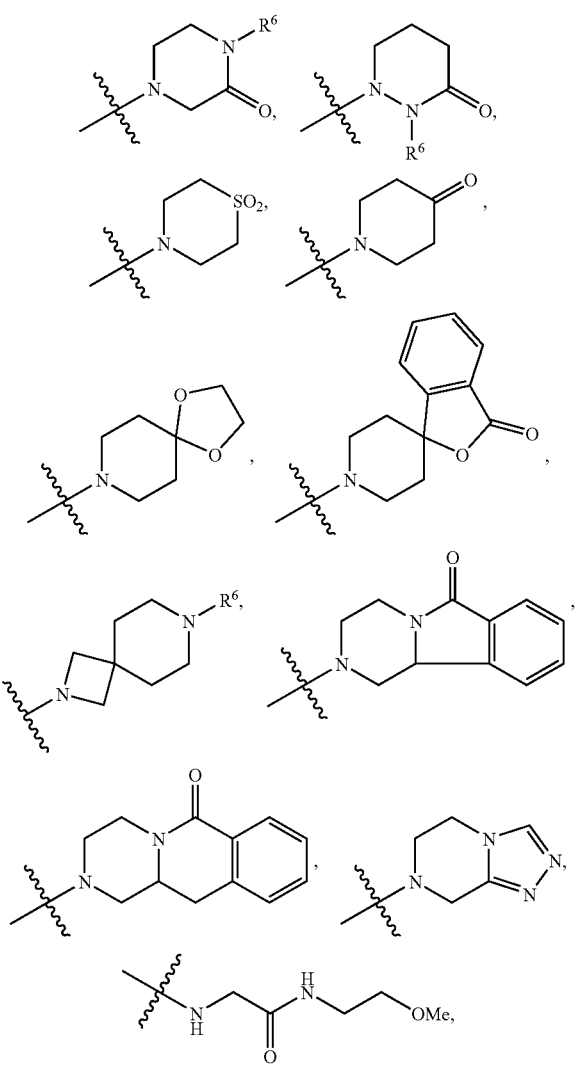

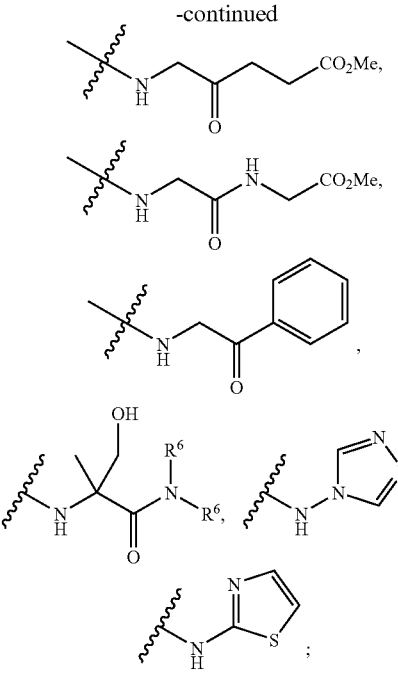

or NR⁹R¹⁰ taken together is a [2.2.1] or [2.2.2] bridged bicyclic amine wherein the bicycle contains 0-1 NR⁶, NCO₂R⁶, or O;

R¹¹ is alkyl, haloalkyl, cycloalkyl, alkoxy, amino, alkylamino, dialkylamino, ((R⁶)(R⁶)N)alkylamino, (((R⁶)(R⁶)N)alkyl)₂amino, N,O-dimethylhydroxylamino, or phenyl, wherein the phenyl is substituted with 0-2 substituents selected from the group consisting of halo, alkyl, haloalkyl, and alkoxy;

R¹² is pyrrolidinyl, piperidinyl, piperazinyl, homomorpholinyl, homopiperidinyl, morpholinyl, or thiomorpholinyl, and is substituted with 0-2 substituents selected from halo, alkyl, haloalkyl, and alkoxy;

R¹³ is pyrrolidinyl, piperidinyl, piperazinyl, homomorpholinyl, homopiperidinyl, morpholinyl, thiomorpholinyl, tetrahydrofuranyl, furanyl, thienyl, pyrrolyl, pyrazolyl, imidazolyl, isoxazolyl, oxazolyl, triazolyl, oxadiazolyl, tetrazolyl, pyridinyl, pyrazinyl, pyrimidinyl, imidazopyridinyl, or benzimidazole, and is substituted with 0-2 alkyl substituents;

R¹⁴ is azetidine, pyrrolidinyl, piperidinyl, piperazinyl, homomorpholinyl, homopiperidinyl, morpholinyl, thiomorpholinyl, or S,S-dioxothiomorpholinyl, and is substituted with 0-3 substituents selected from halo, alkyl, hydroxy, alkoxy, aminoalkyl, (alkylamino)alkyl, (dialkylamino)alkyl, (CO₂R⁶)alkyl, (CON(R⁶)₂)alkyl, ((R⁶CO)(R⁶)amino)alkyl, (R¹⁵)alkyl, (R⁶CO)(R⁶)amino, R¹⁵, alkylCO, CF₃CO, CO₂R⁶, CON(R⁶)₂, or SO₂R⁶;

or R¹⁴ is a [2.2.1] or [2.2.2] bridged bicyclic amine wherein the bicycle contains 0-1 O;

R¹⁵ is azetidinyl, pyrrolidinyl, piperidinyl, piperazinyl, homomorpholinyl, homopiperidinyl, morpholinyl, or thiomorpholinyl, and is substituted with 0-2 halo, alkyl, or alkoxy substituents;

R¹⁶ is pyrazolyl, imidazolyl, isoxazolyl, oxazolyl, thiazolyl, triazolyl, oxadiazolyl, tetrazolyl, or pyridinyl, and is substituted with 0-2 alkyl substituents; and the dashed line is either a single bond or a double bond, provided that if the dashed line is a single bond, the carbon bearing the asterisk is either of the R configuration, the S configuration, or a mixture of R and S;
or a pharmaceutically acceptable salt thereof.
13. A compound of claim 1 or 9 selected from the group consisting of
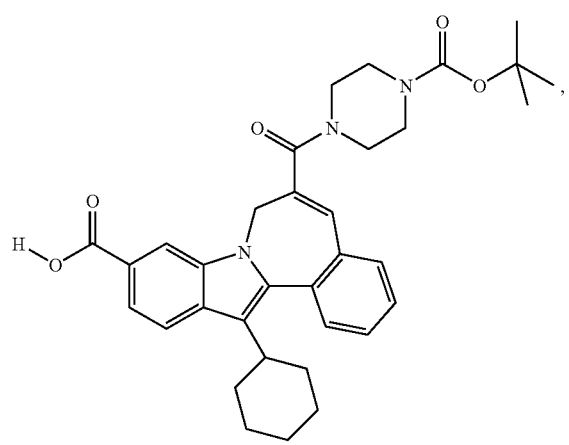
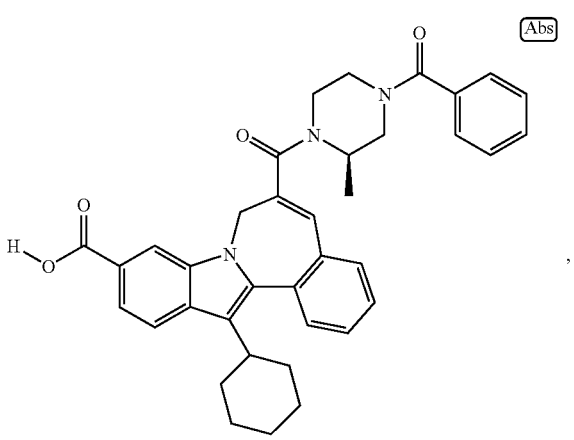
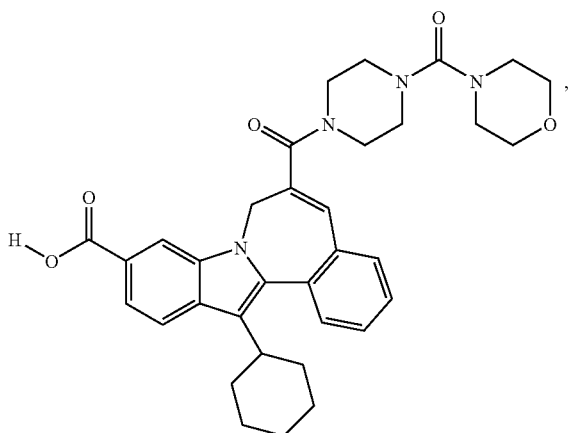
-continued
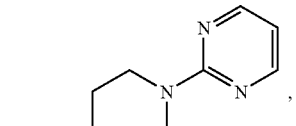
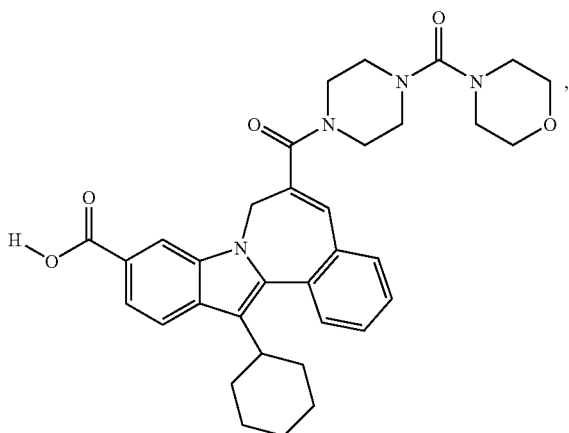

609
-continued
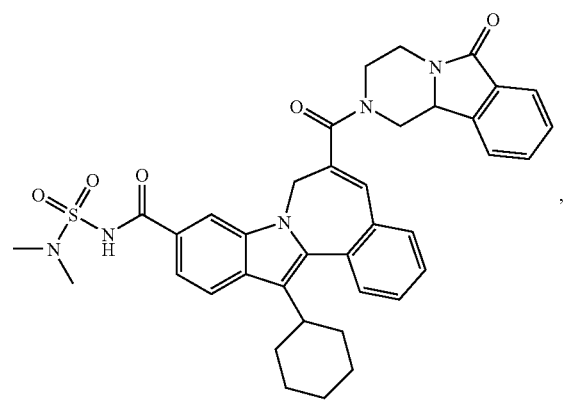
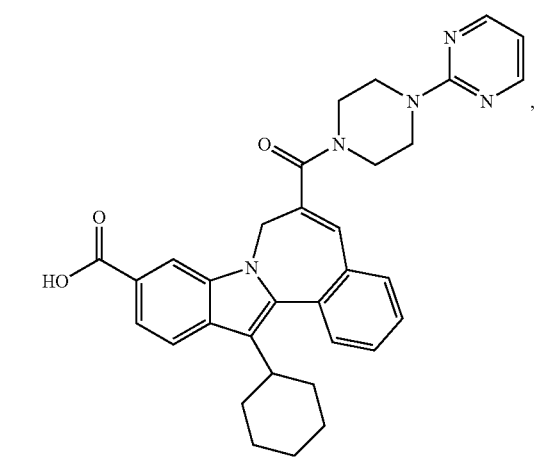
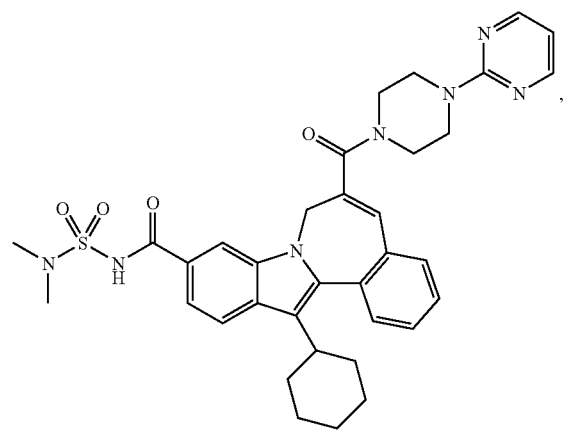
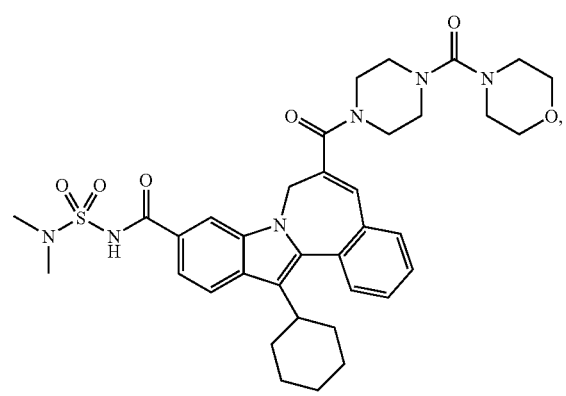
610
-continued
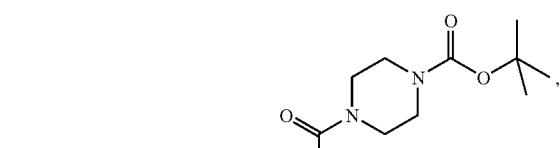
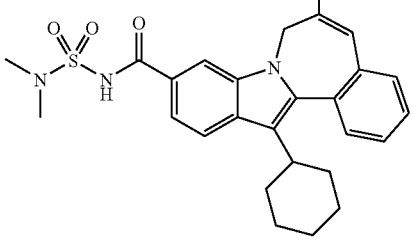
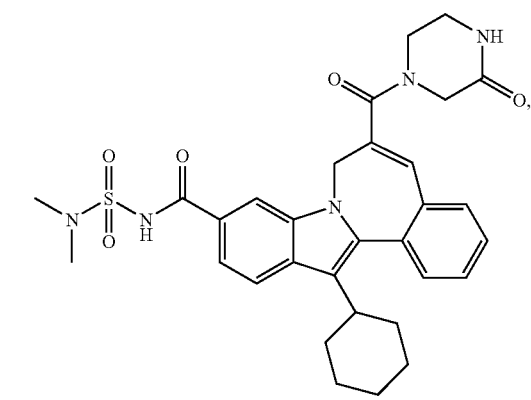
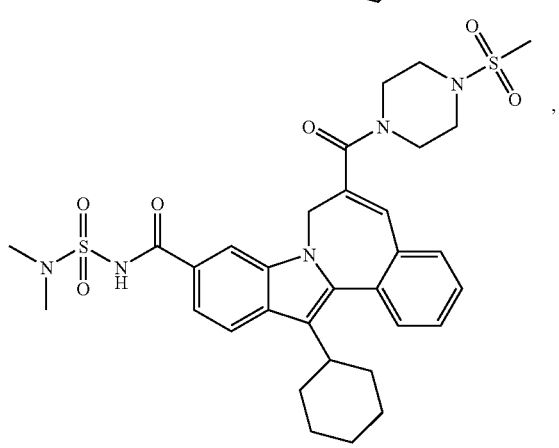

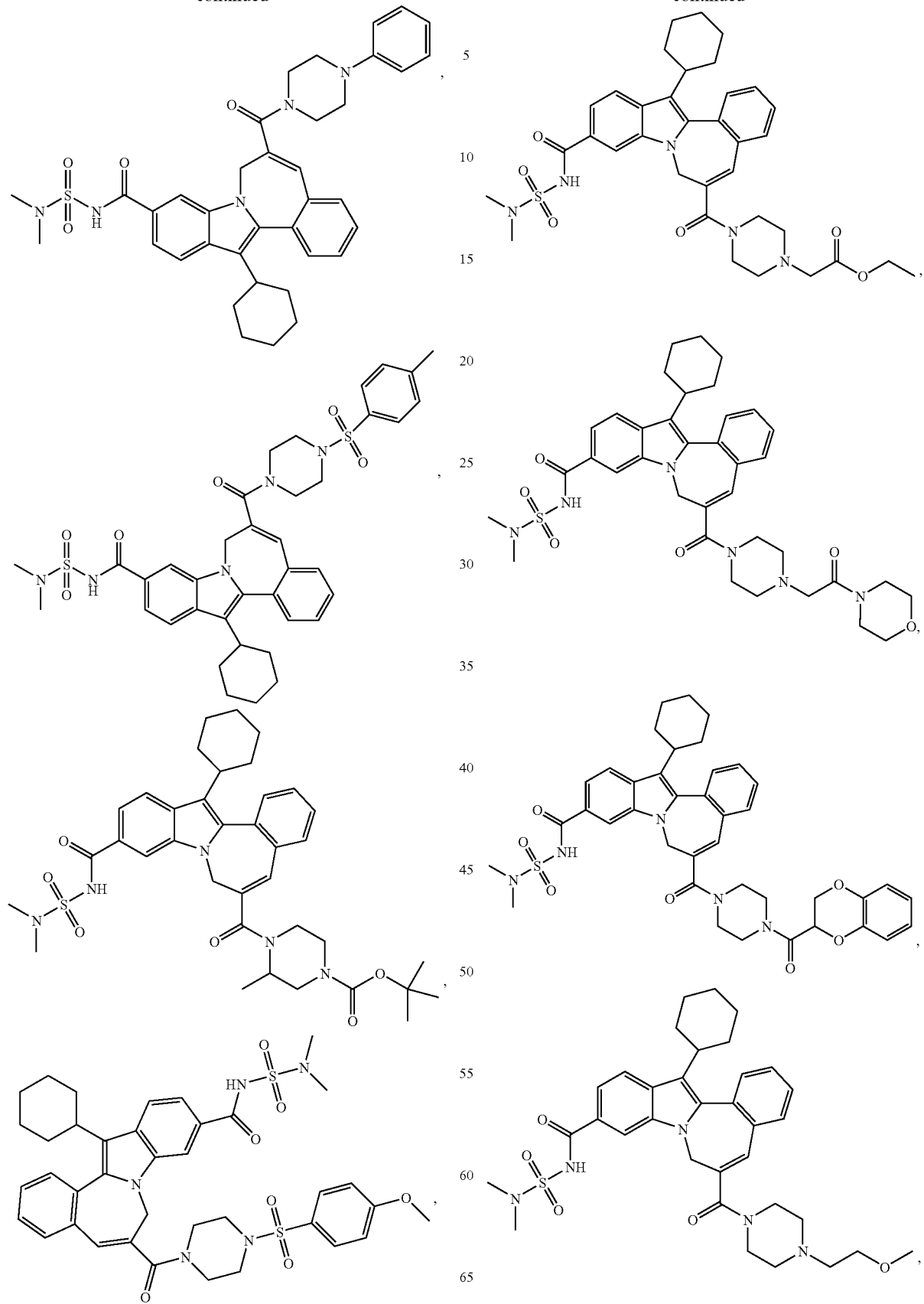

613
-continued
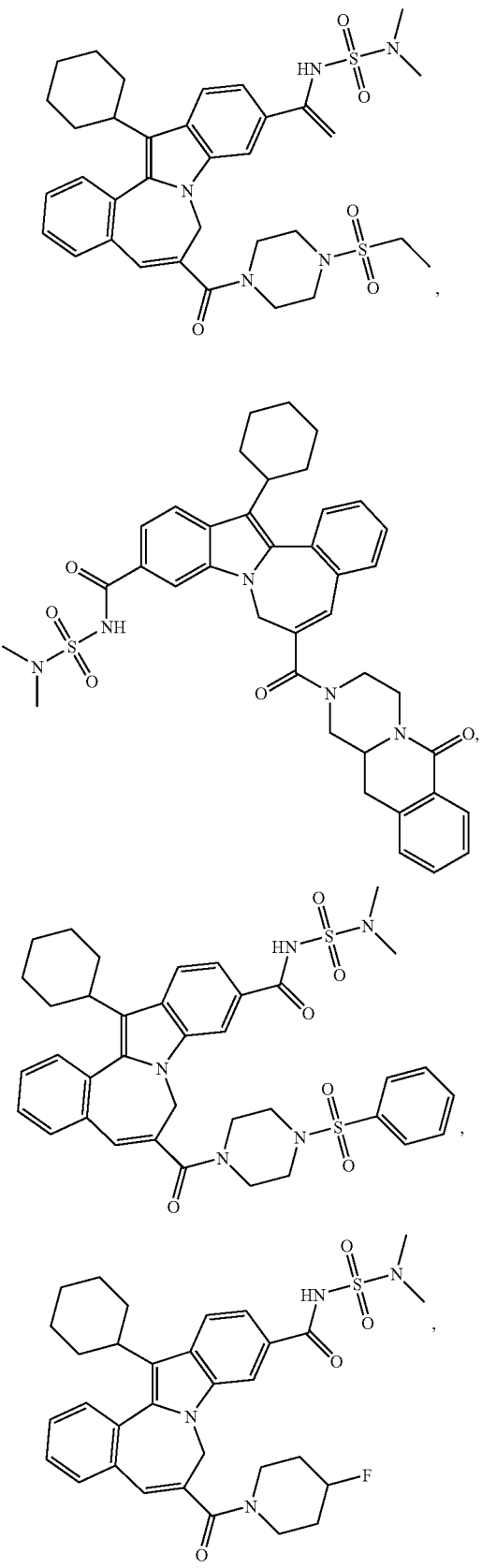
614
-continued
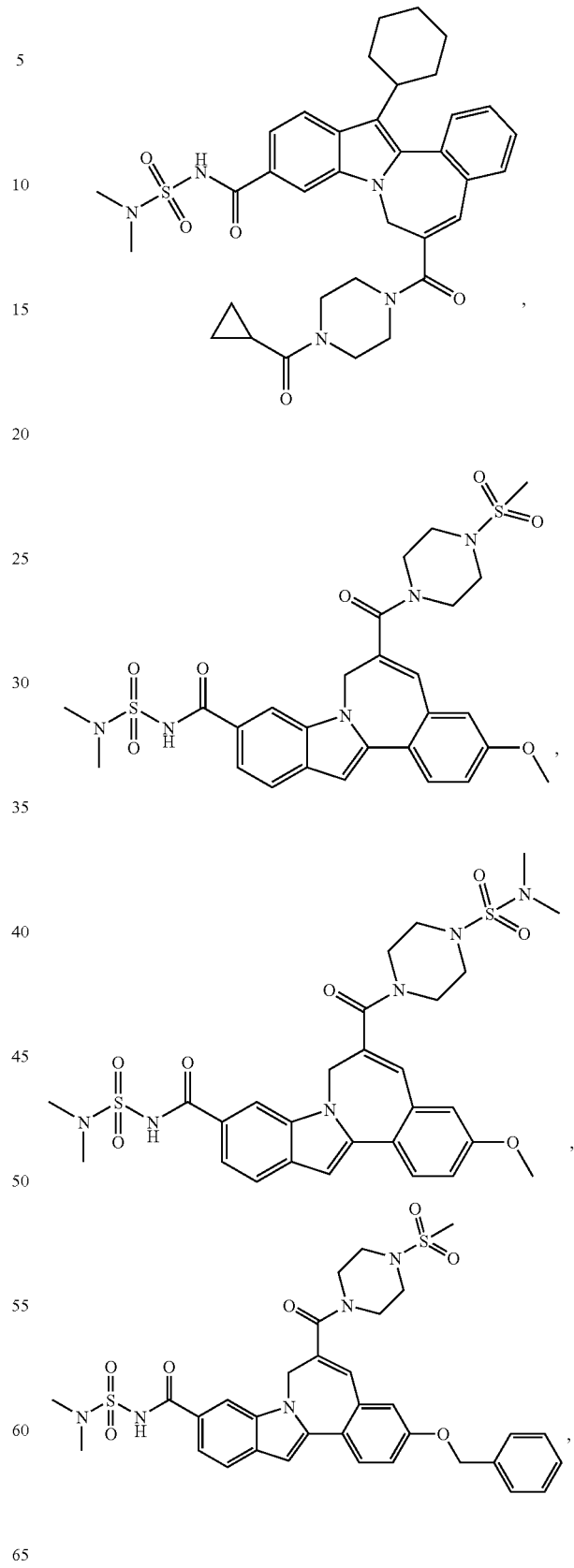

615
-continued
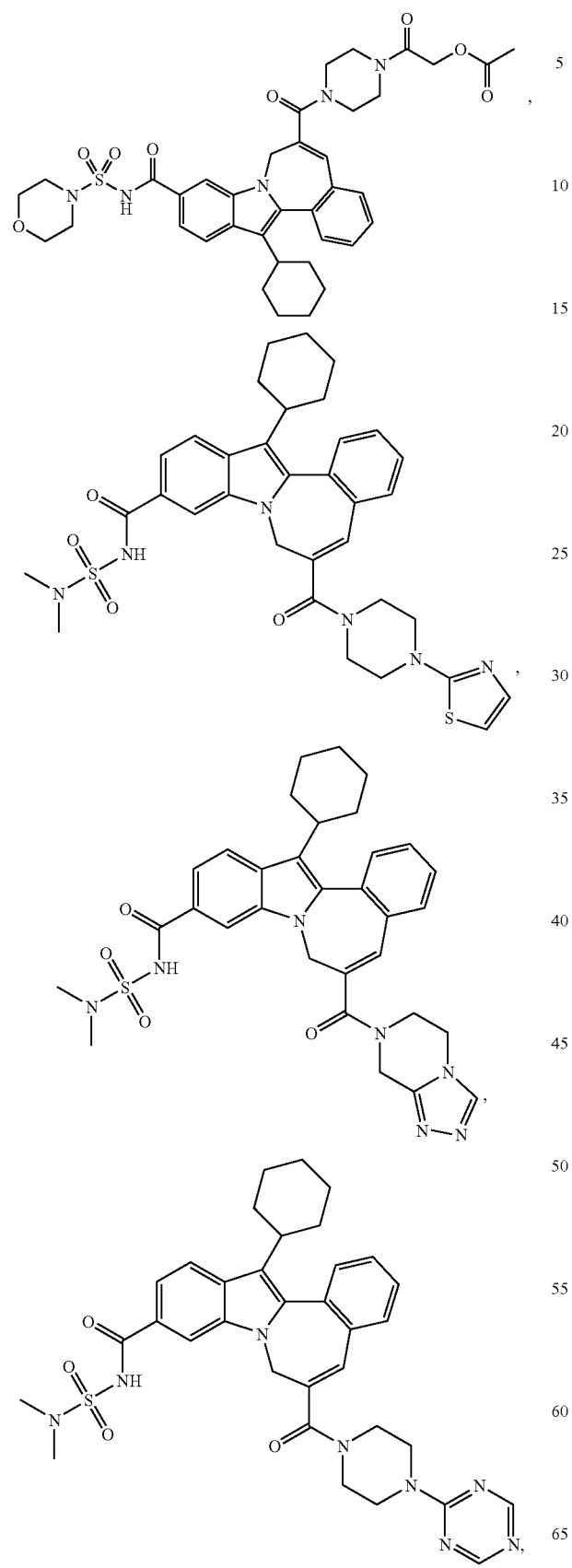
616
-continued
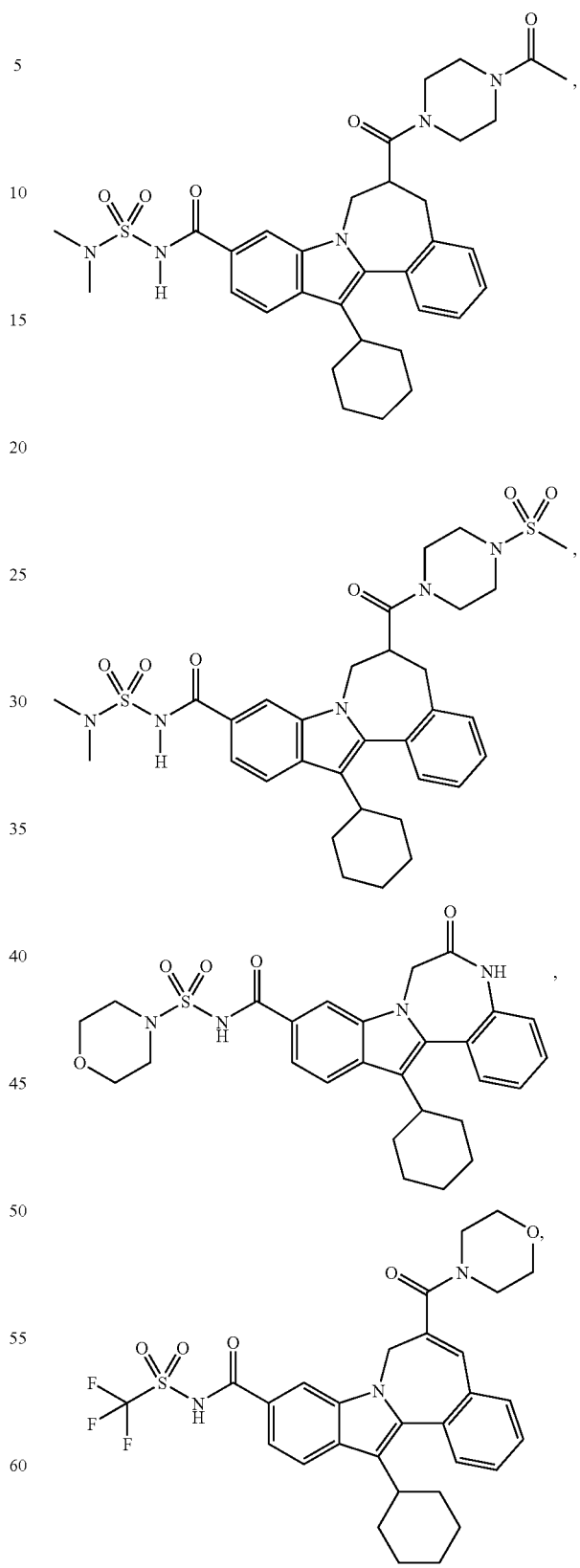

-continued
617
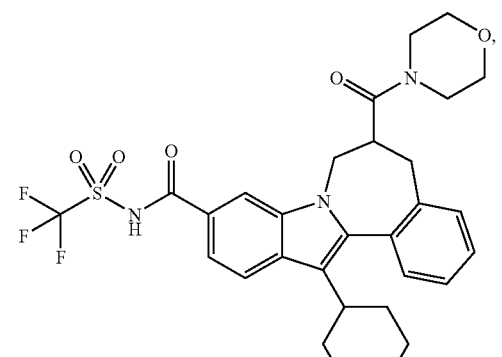
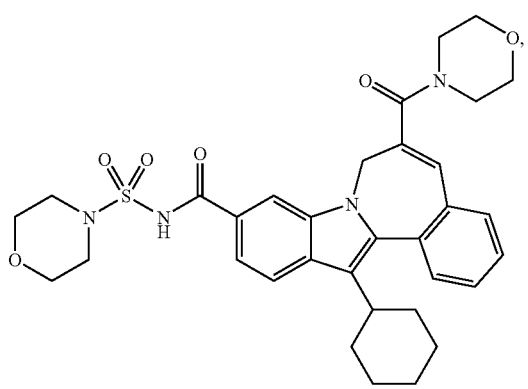
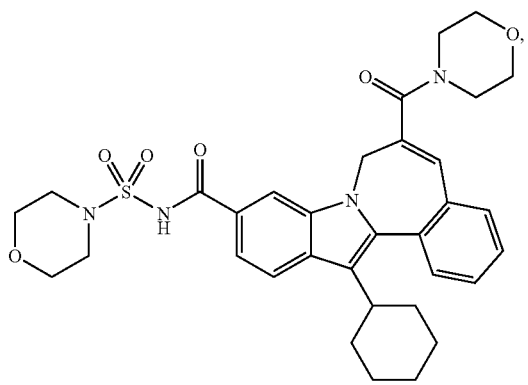
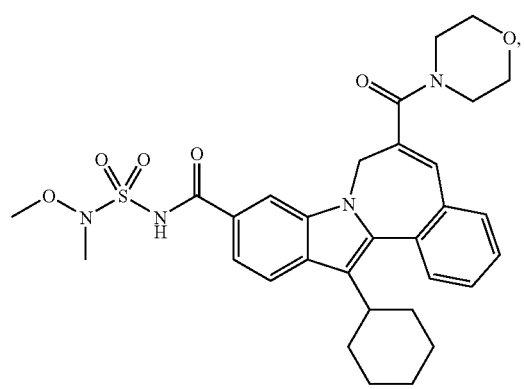
618
-continued
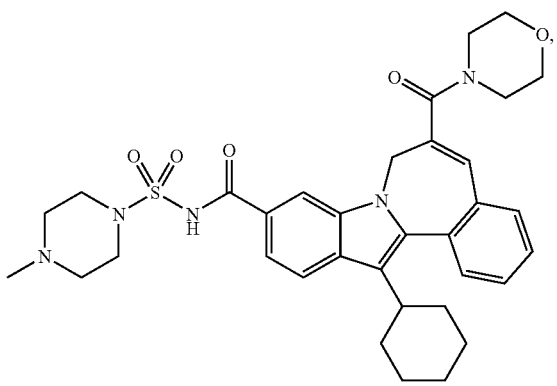
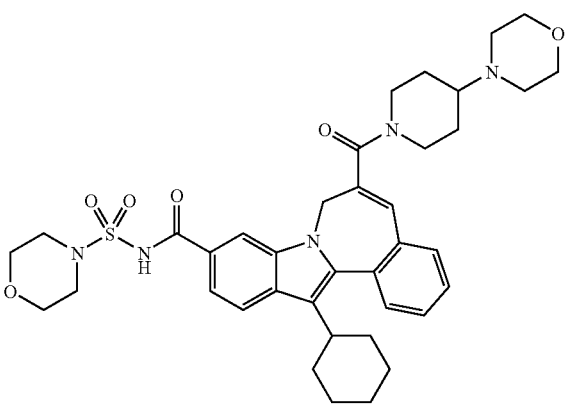
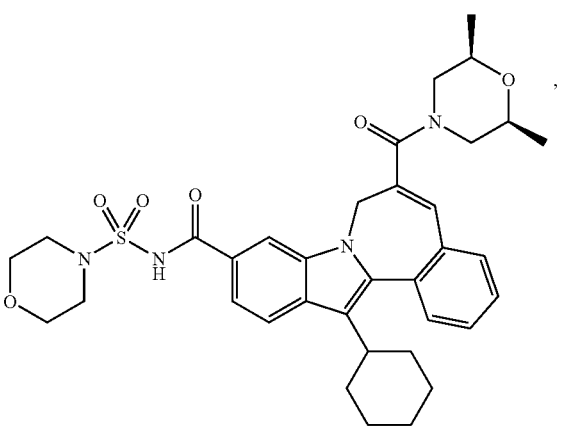
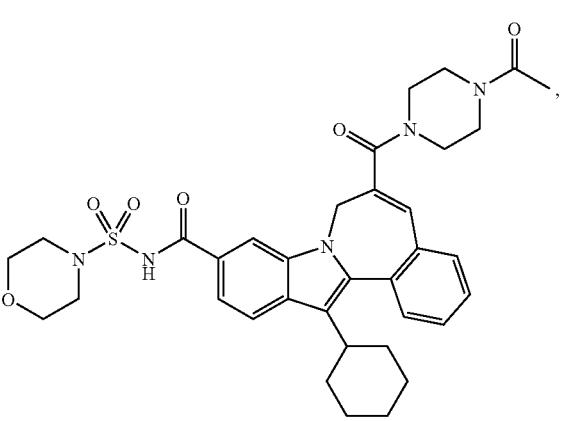

619
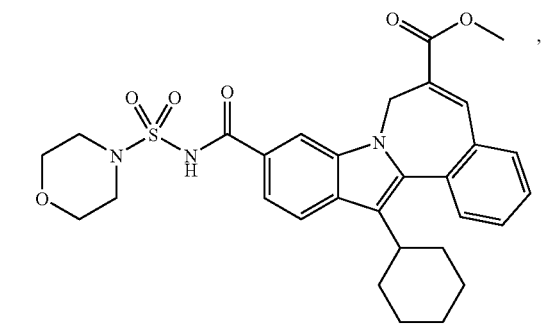
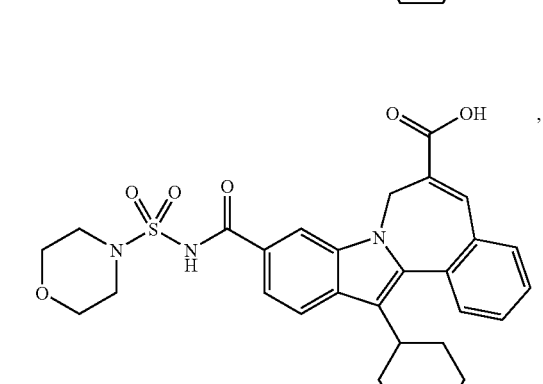
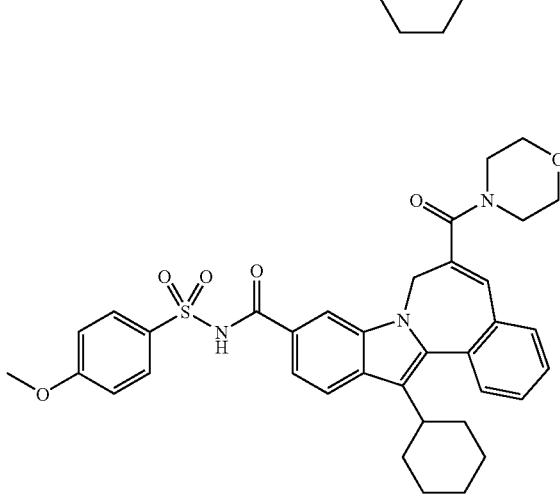
620
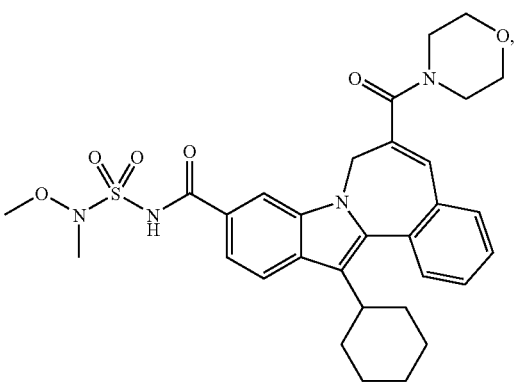
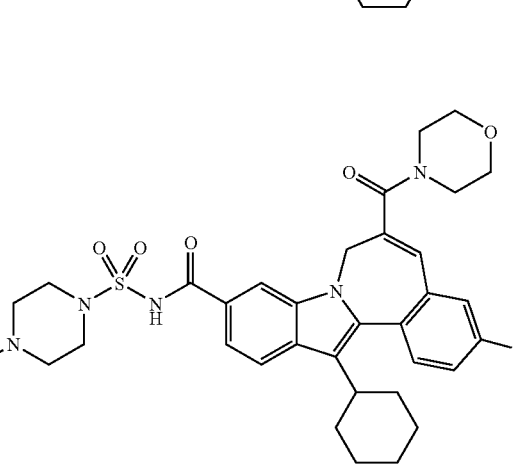
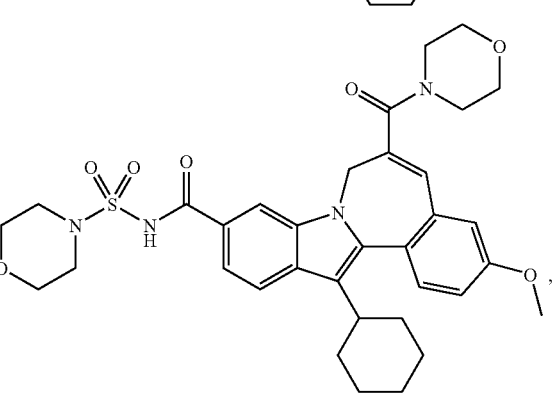

621
-continued
622
-continued
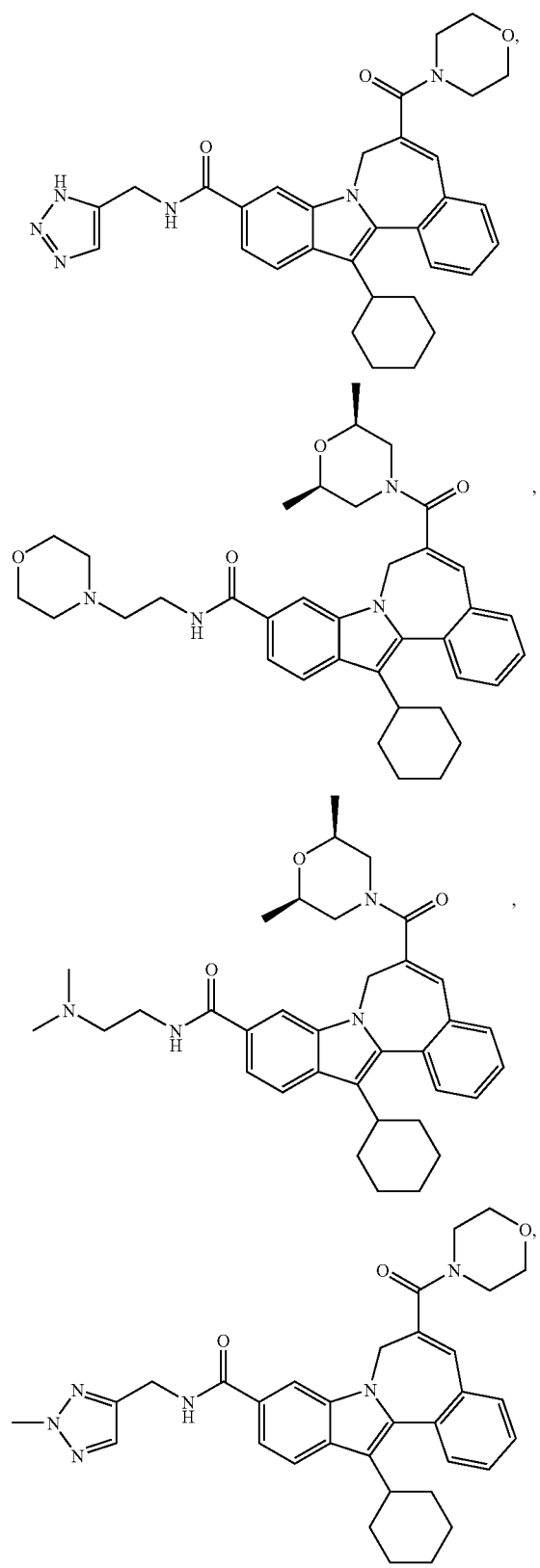
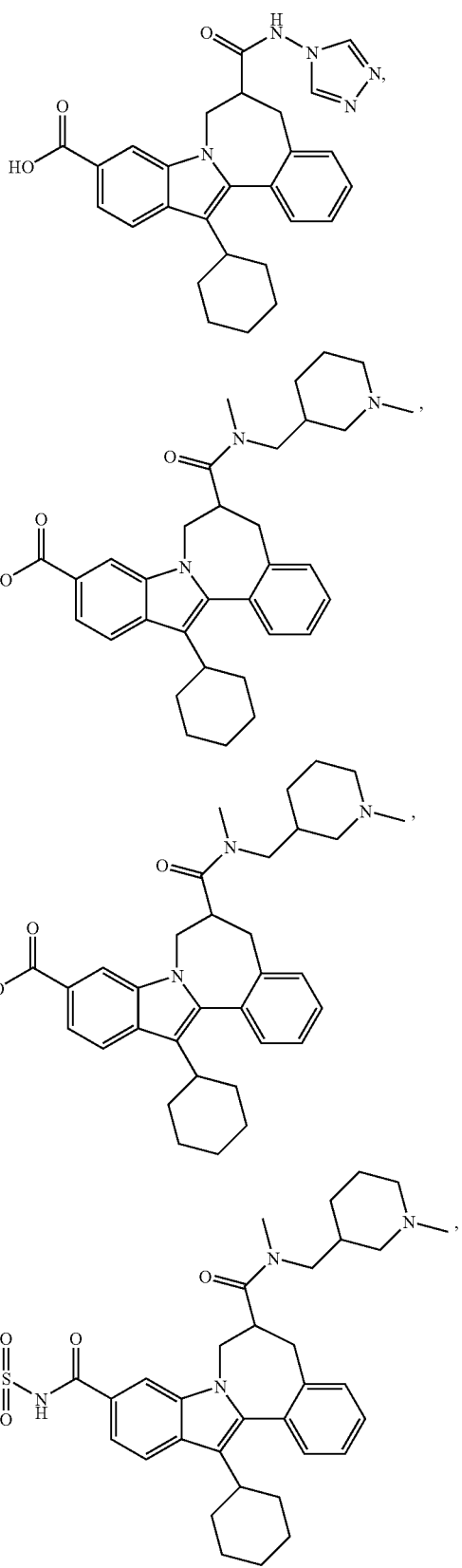

-continued
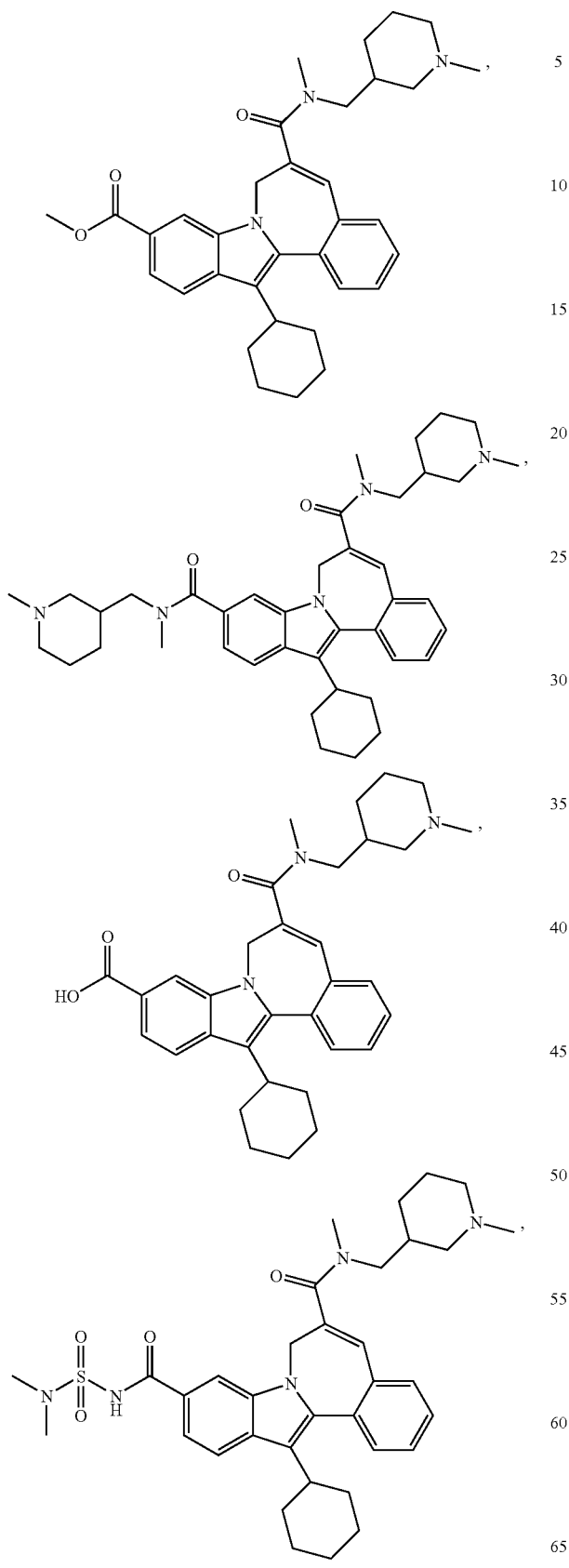
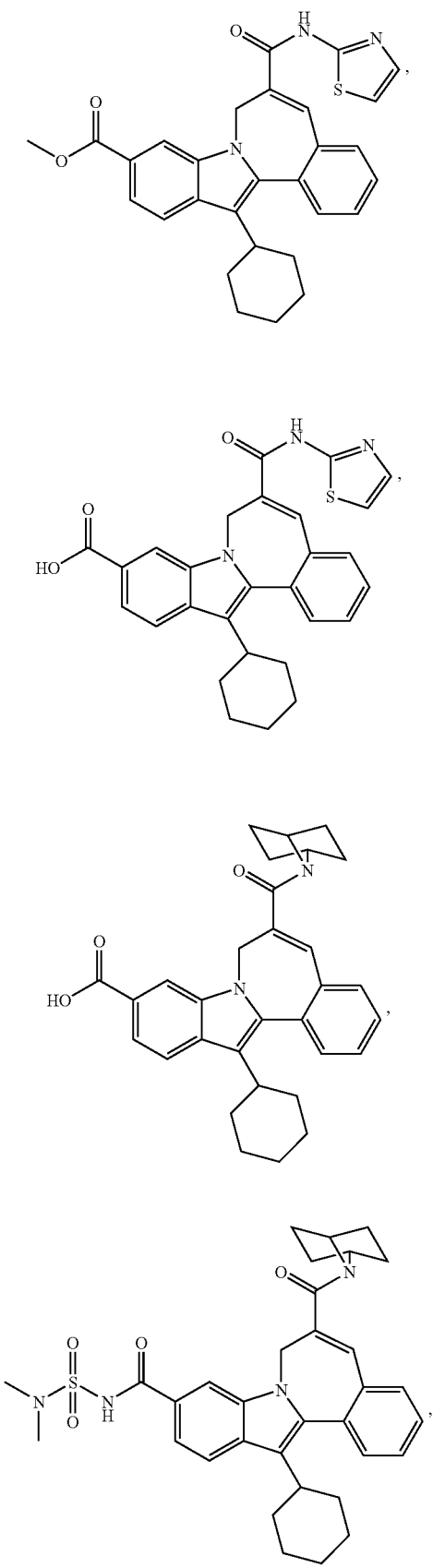

625
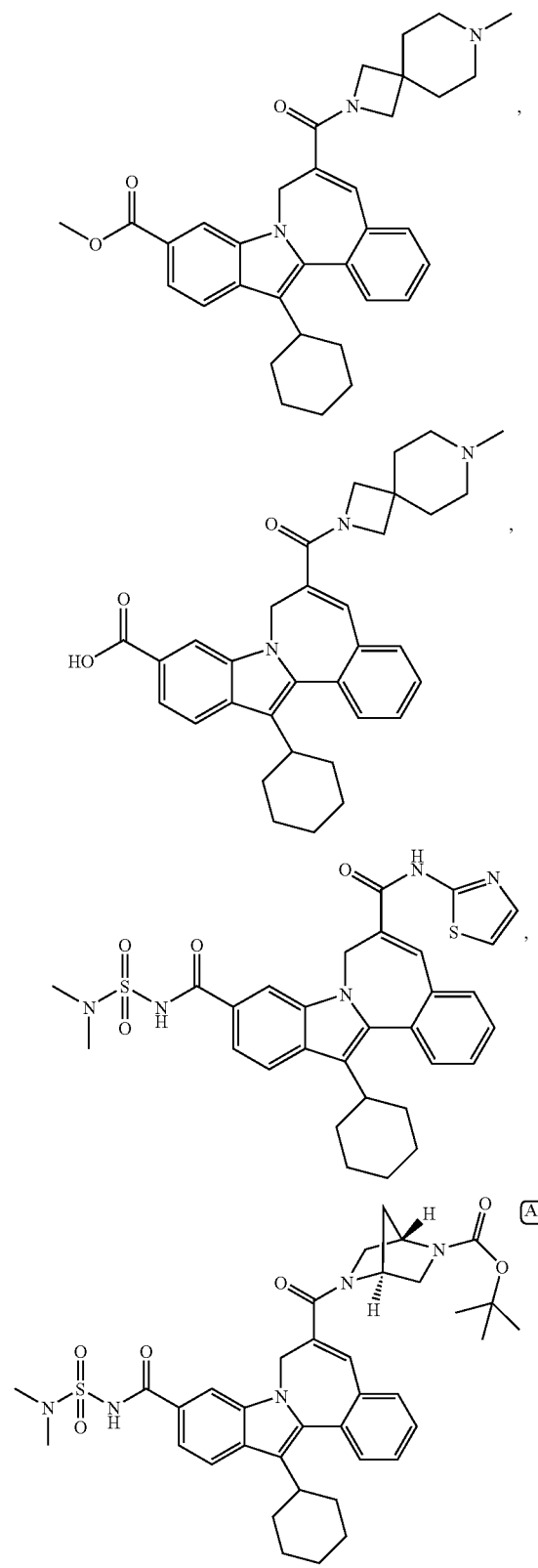
626
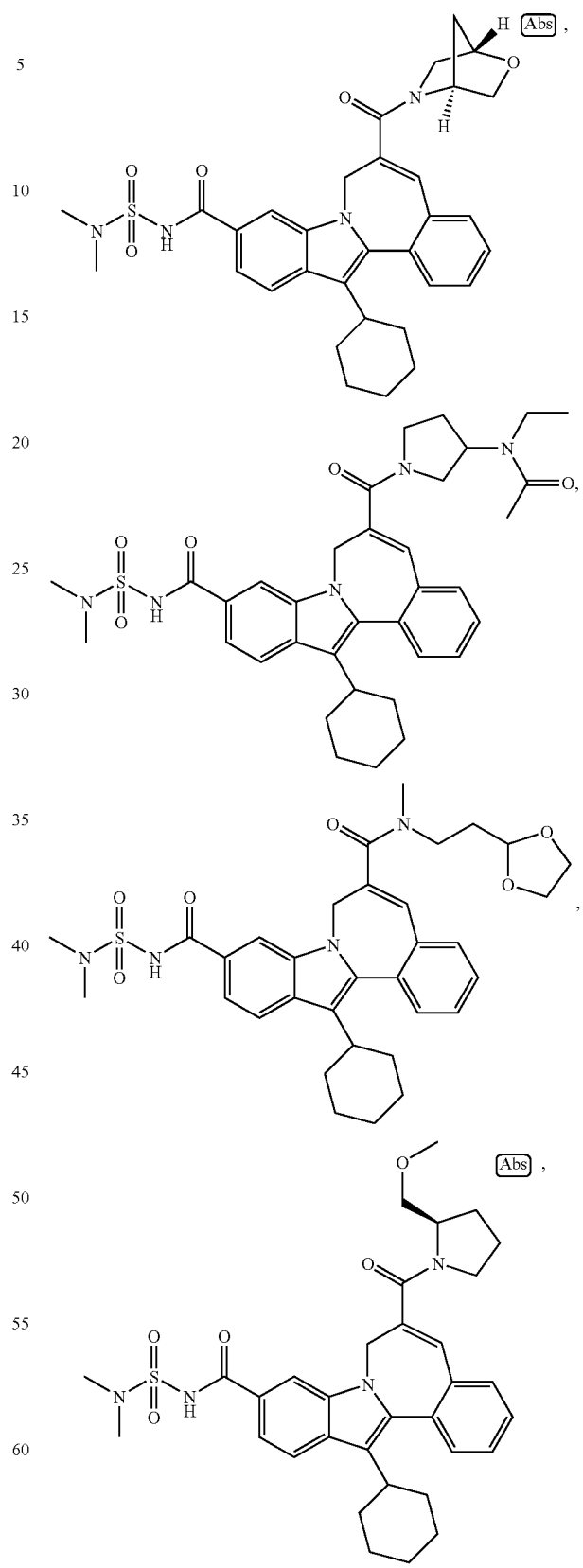

627
-continued
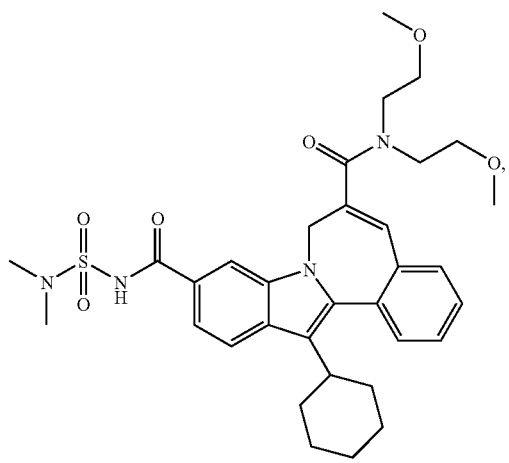
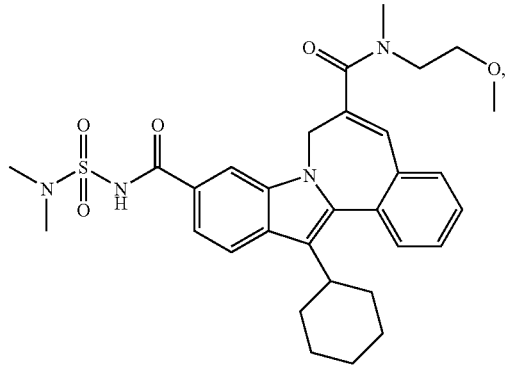
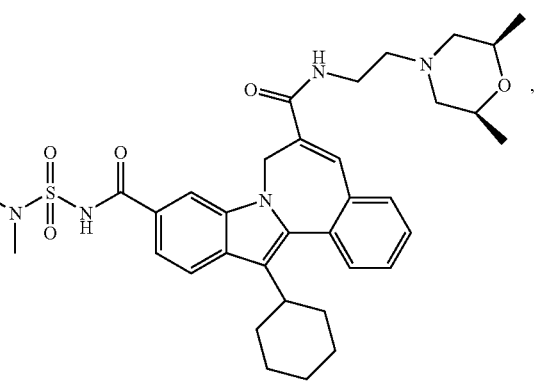
628
-continued
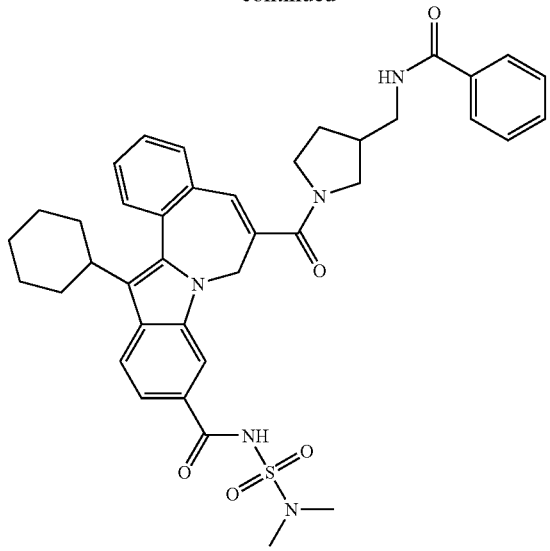
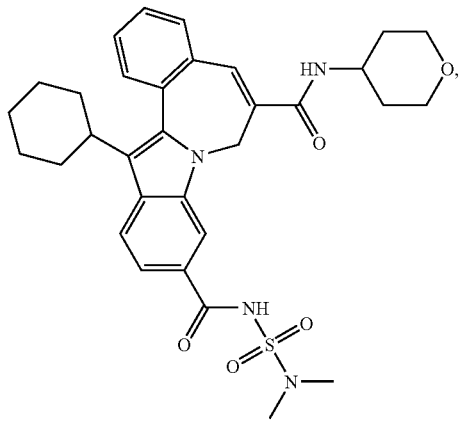
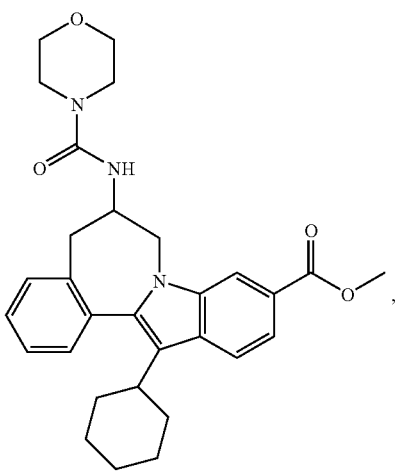

629
-continued
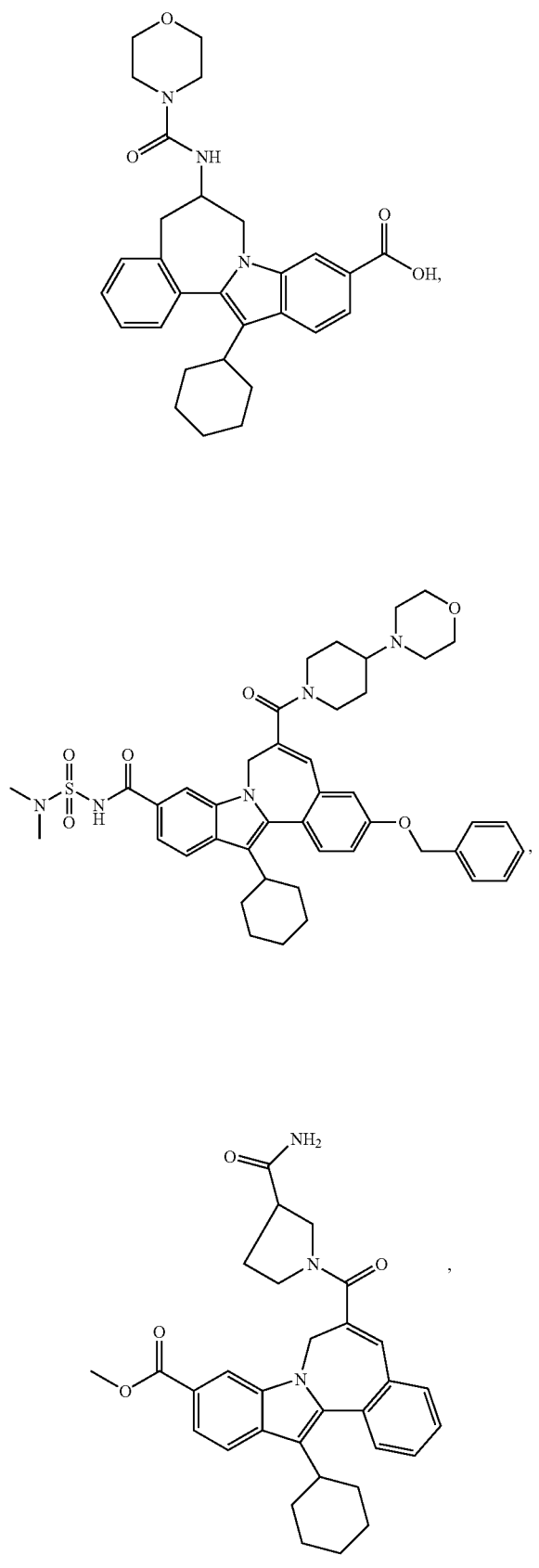
630
-continued
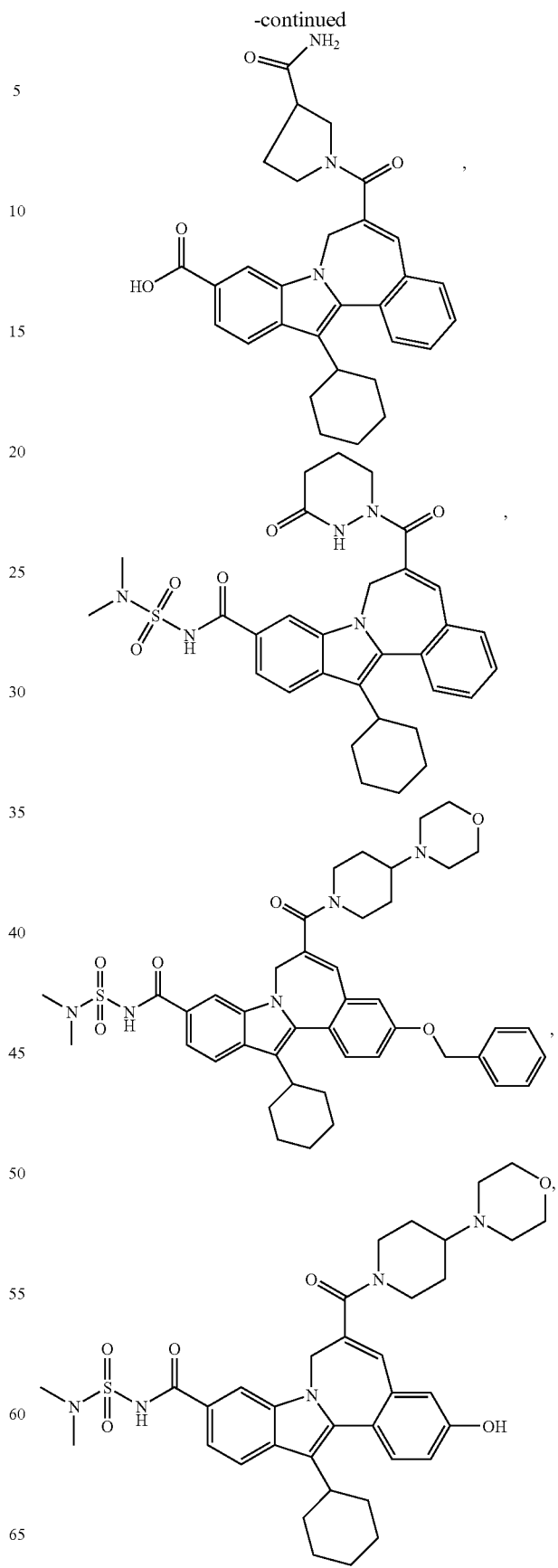

631                                      632
-continued                               -continued
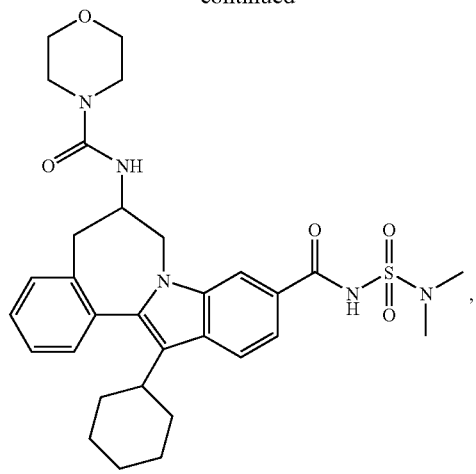
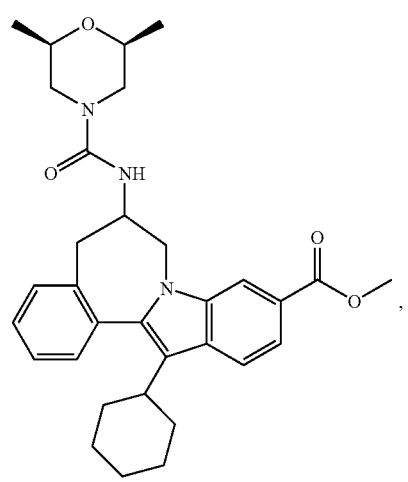
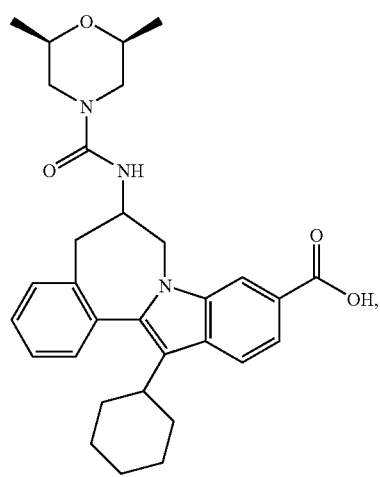
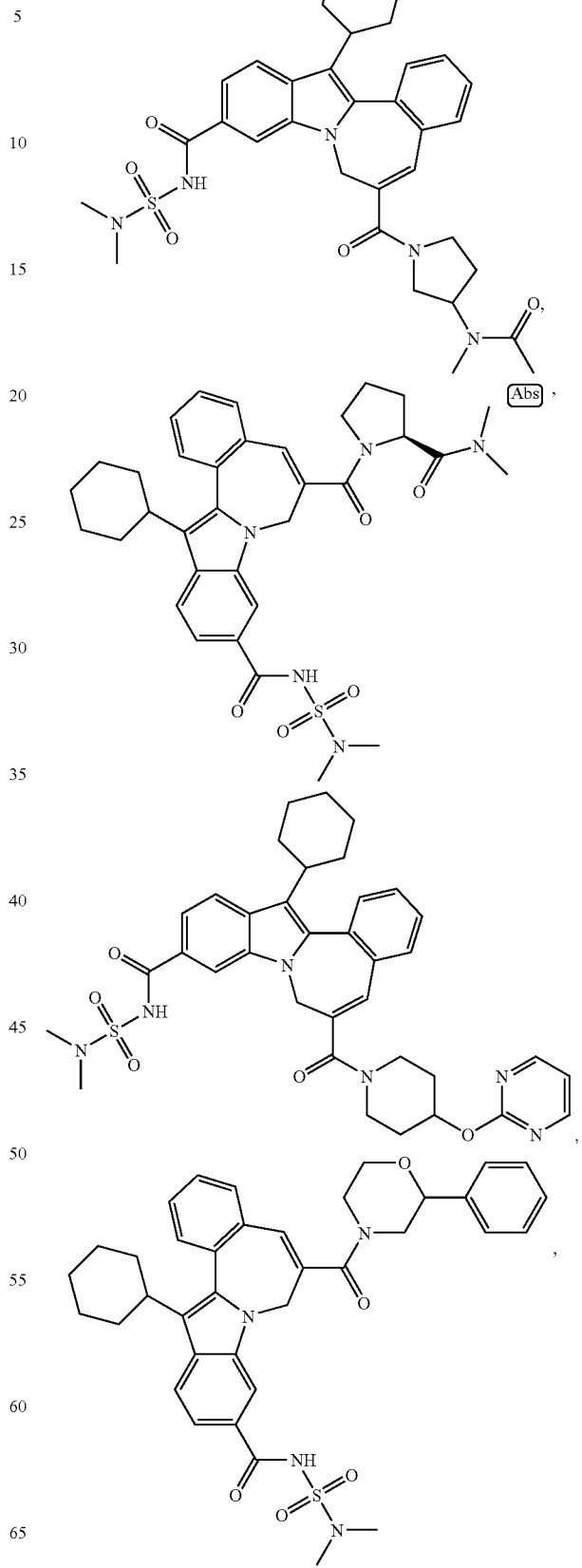

633
-continued
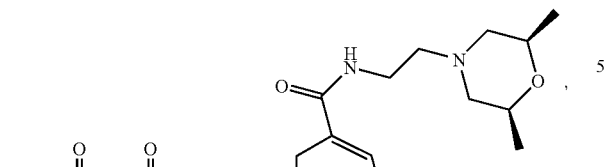
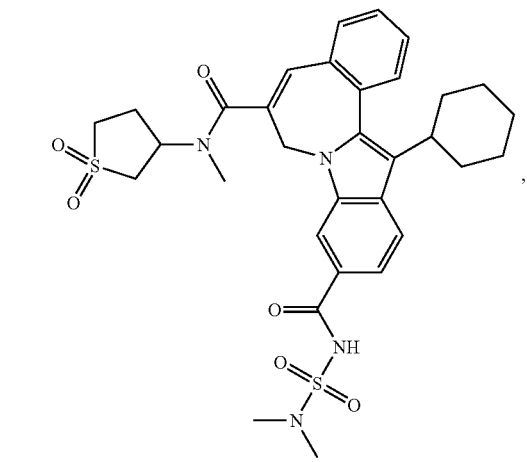
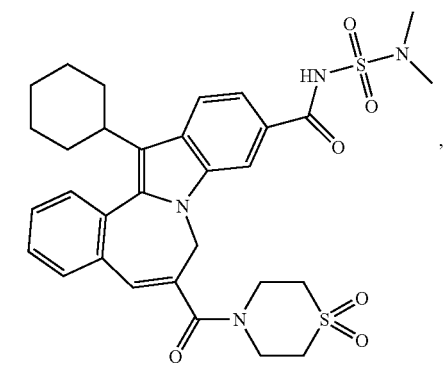
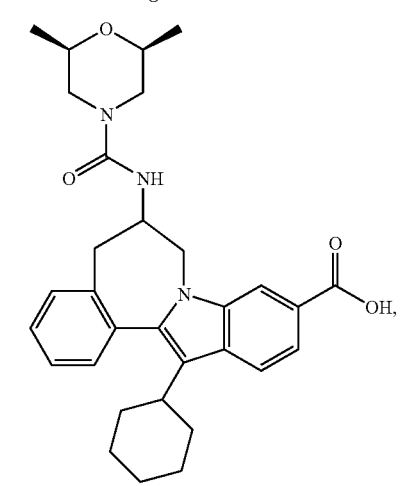
634
-continued
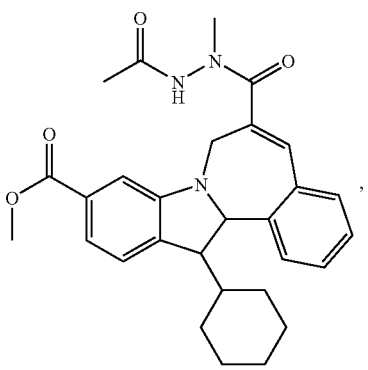
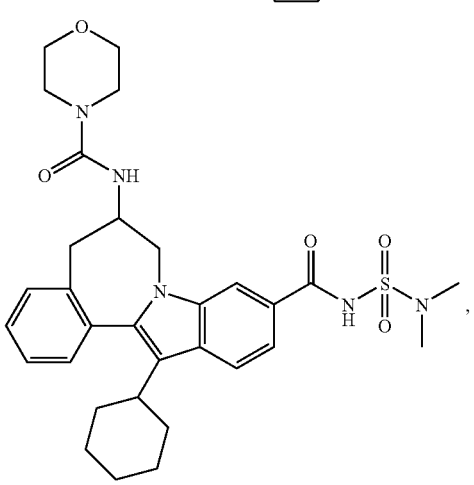
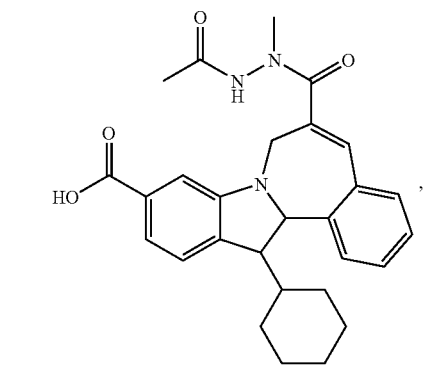
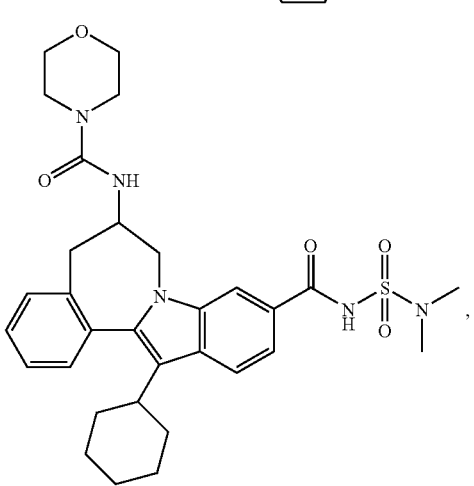

-continued
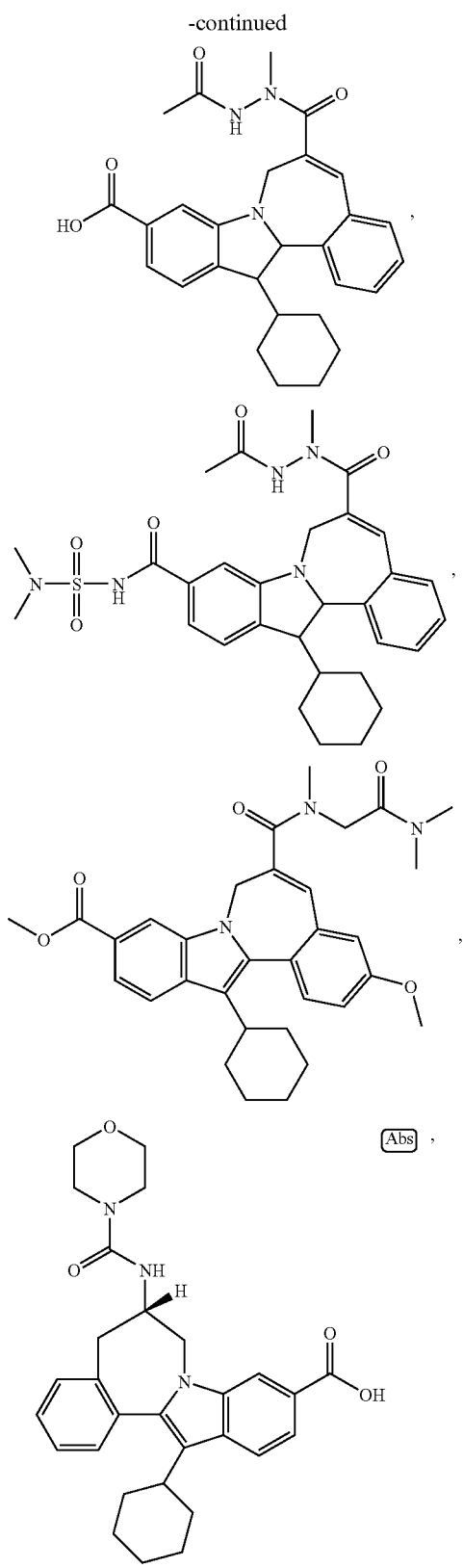

637
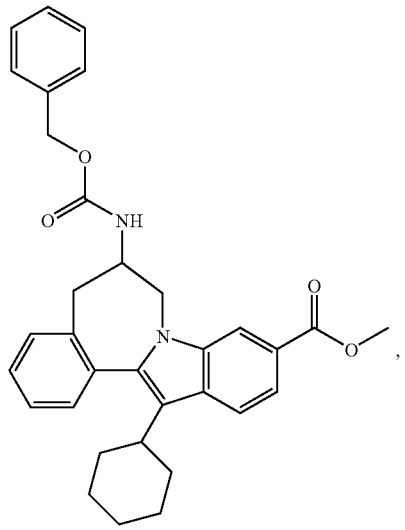
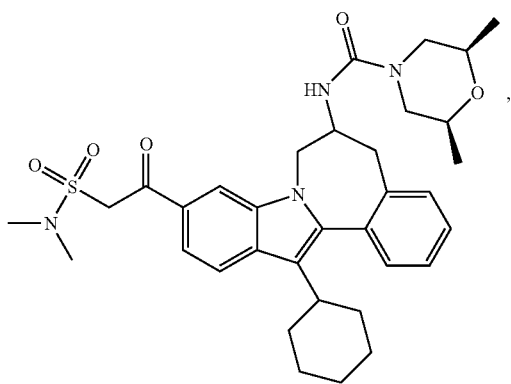
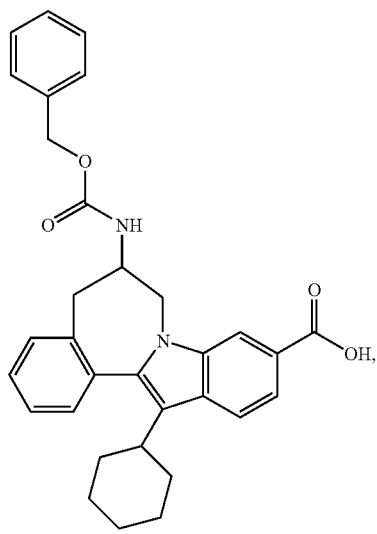
638
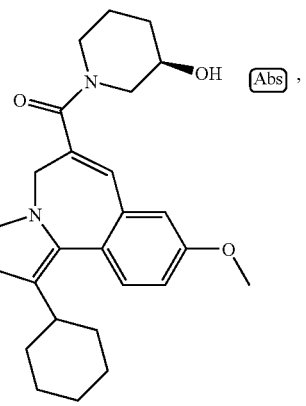
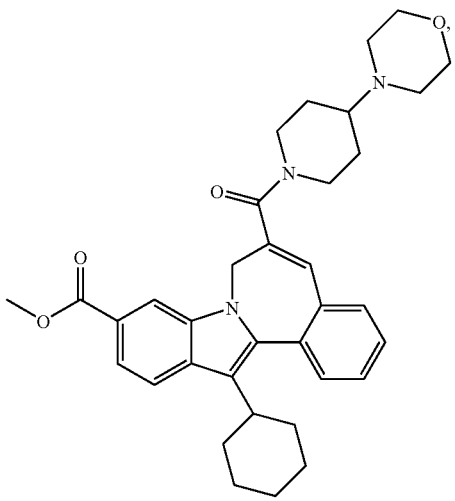

639
-continued
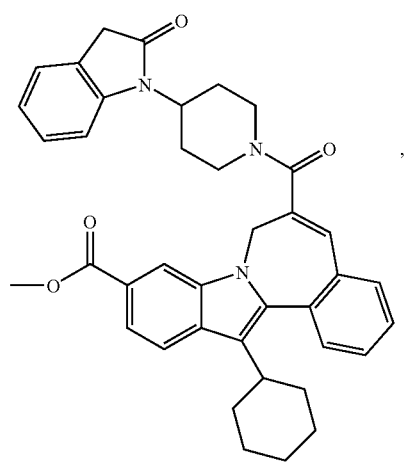
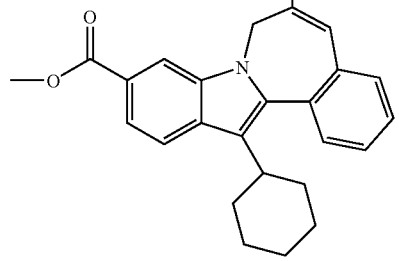
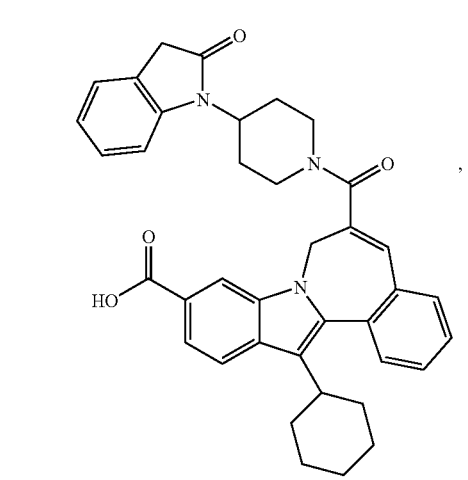
640
-continued
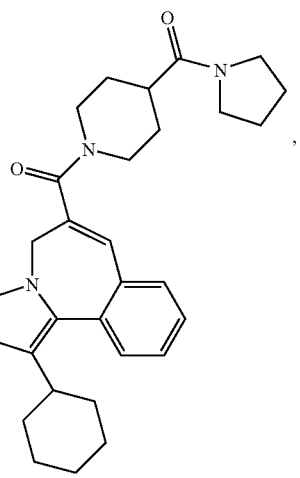
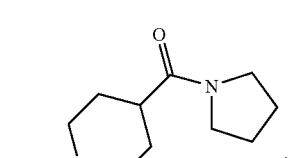
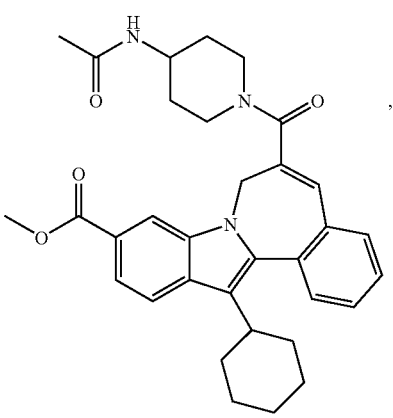

641
-continued
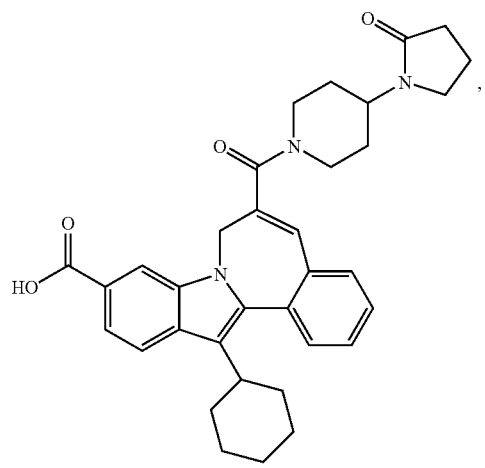
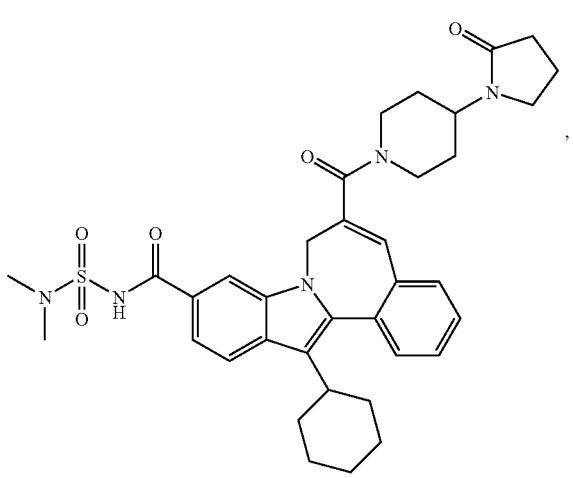
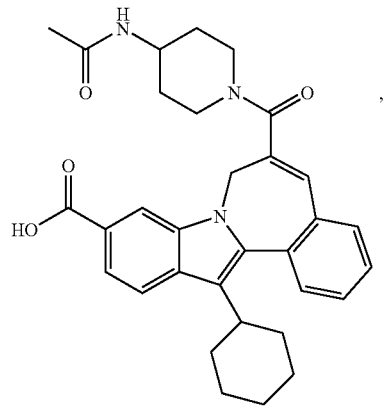
642
-continued
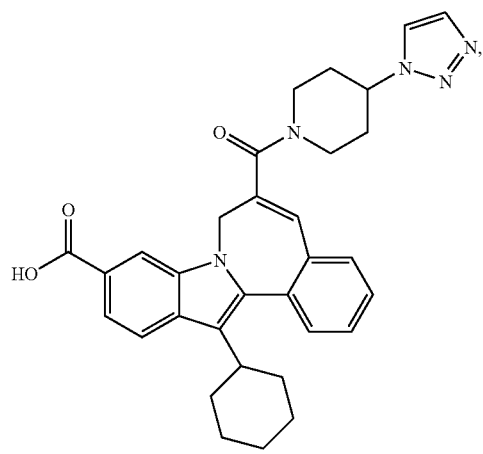
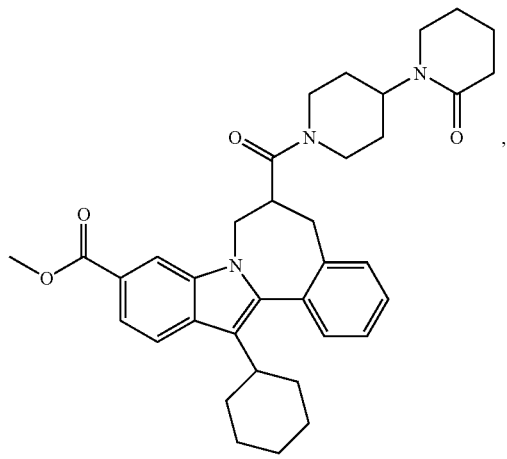
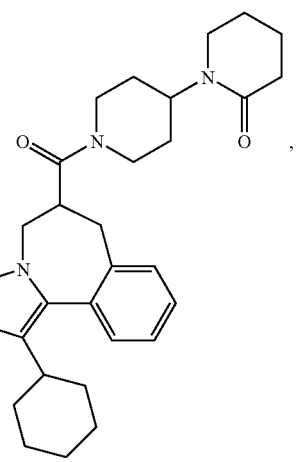

643
-continued
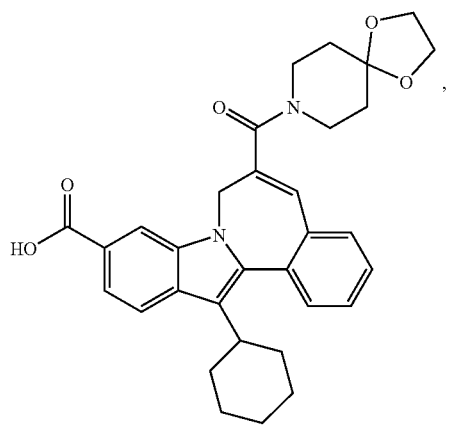
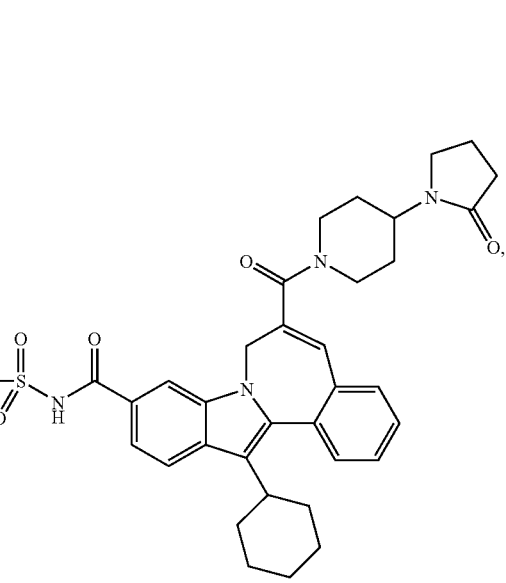
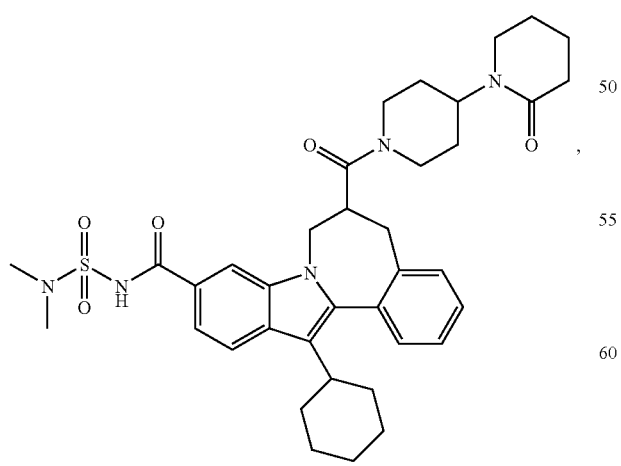
644
-continued
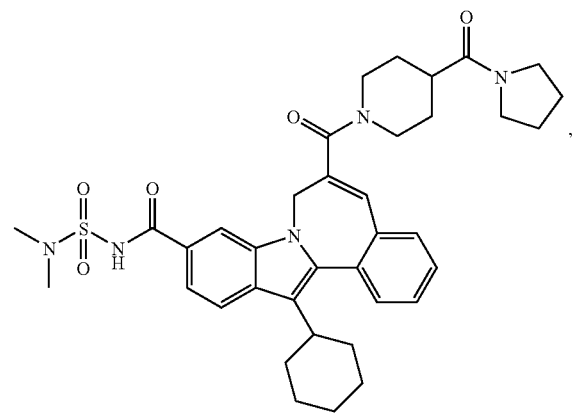
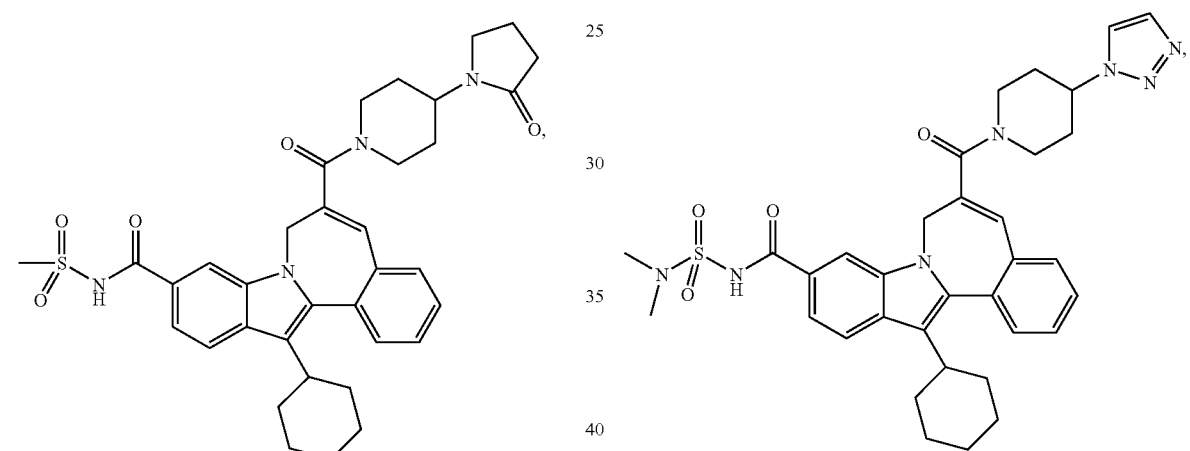
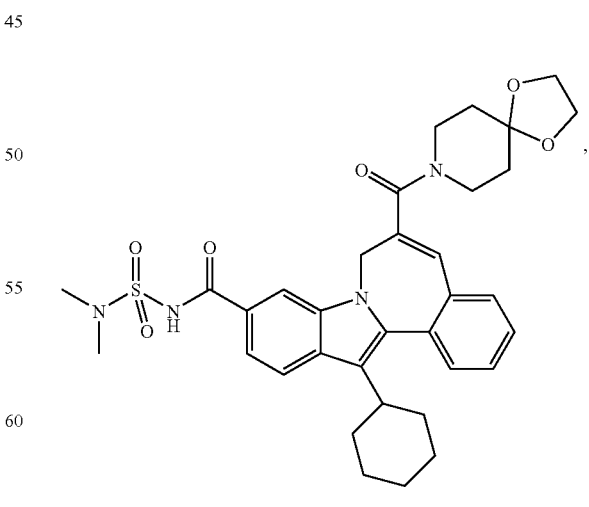

645
-continued
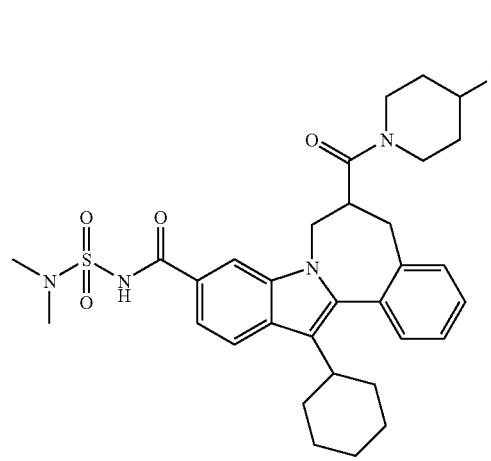
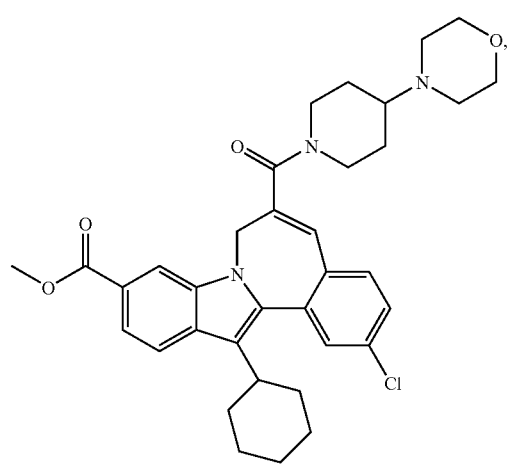
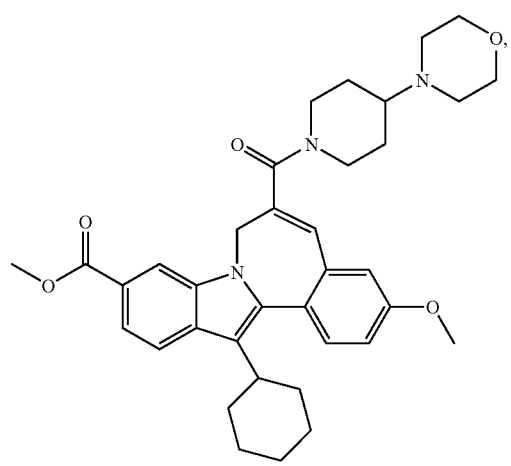
646
-continued
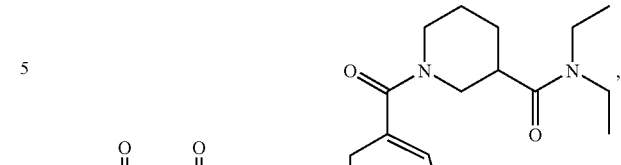
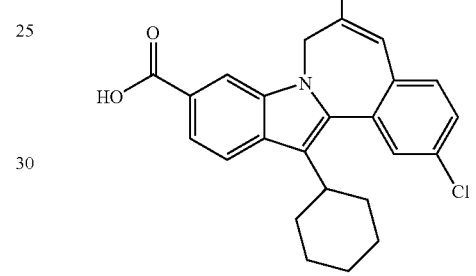
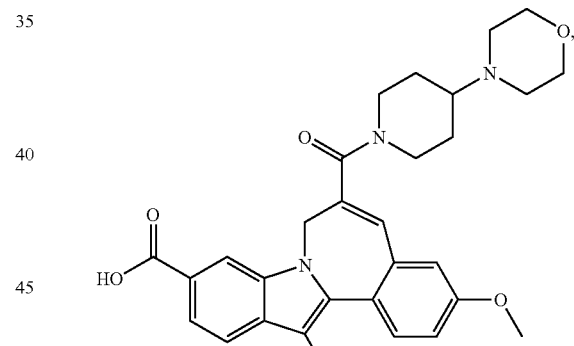
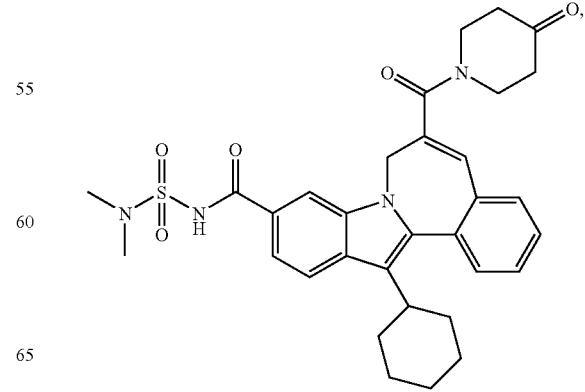

-continued
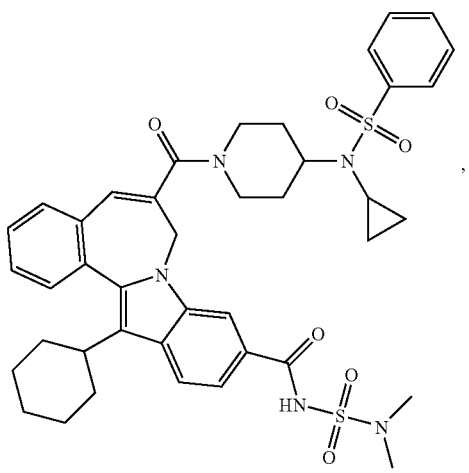
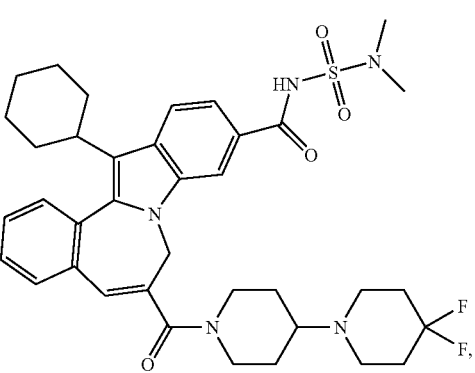
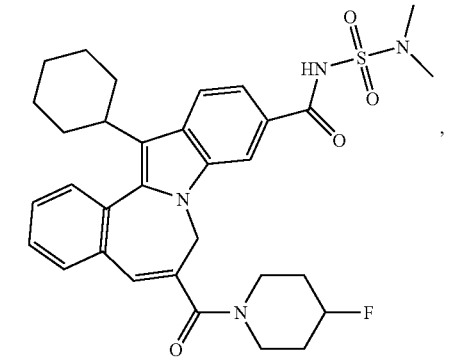
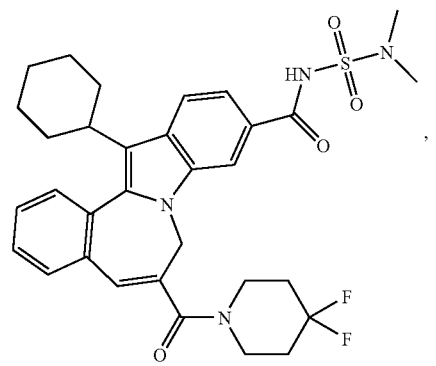
-continued
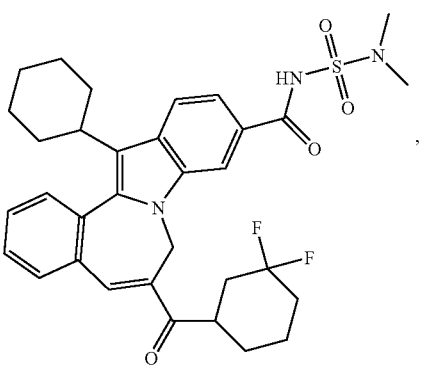
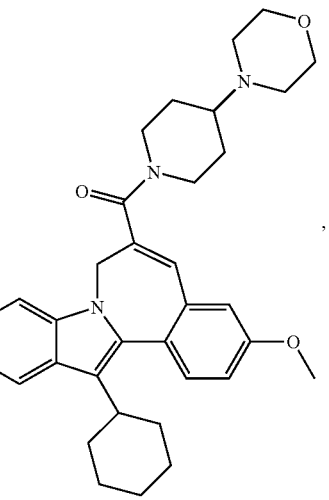
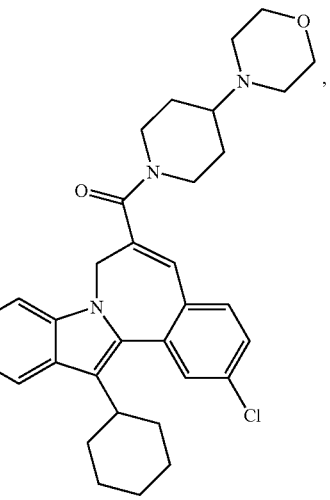

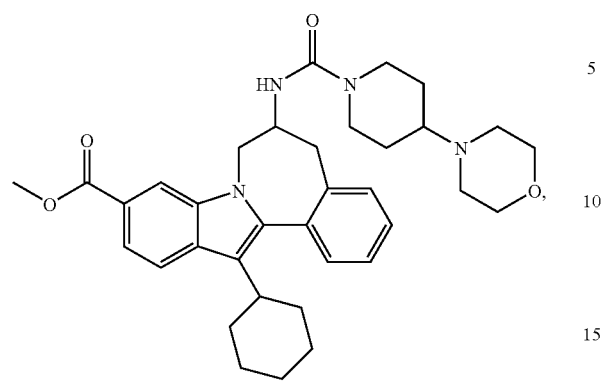
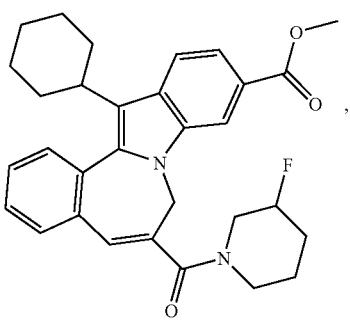

-continued
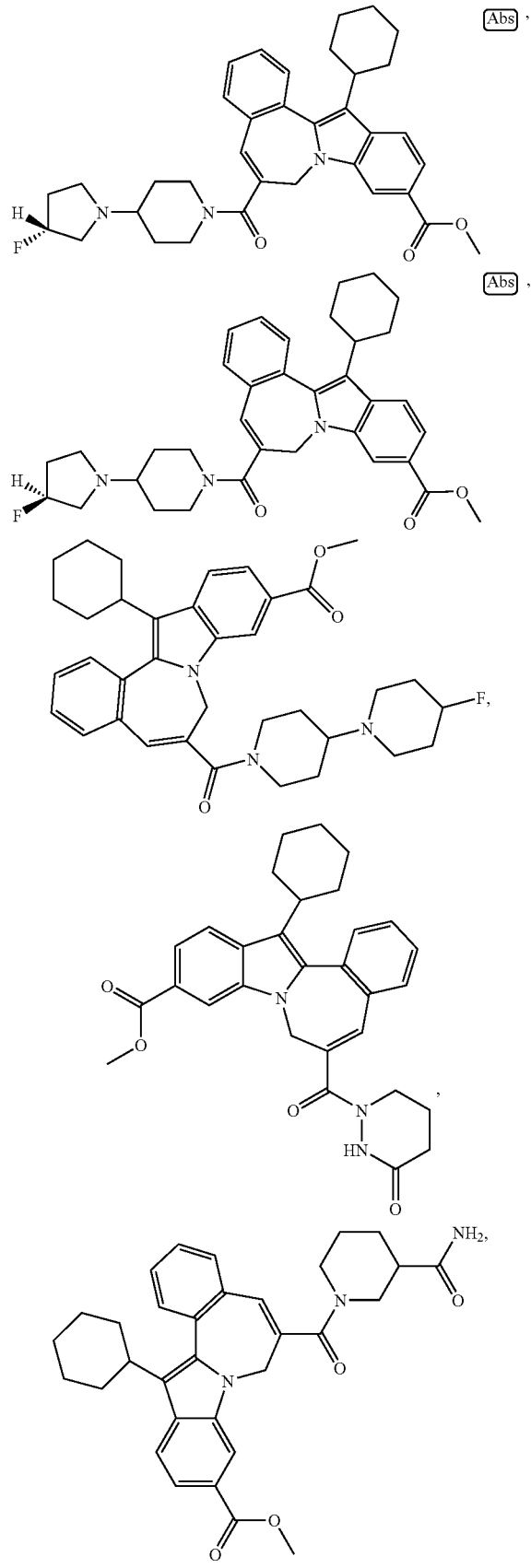
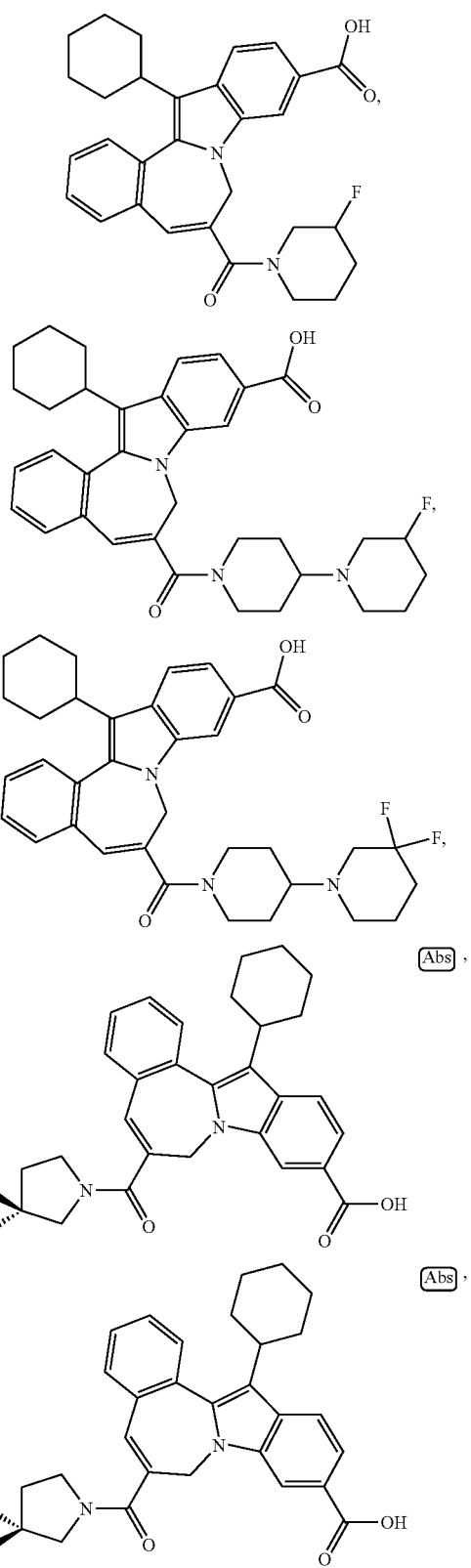

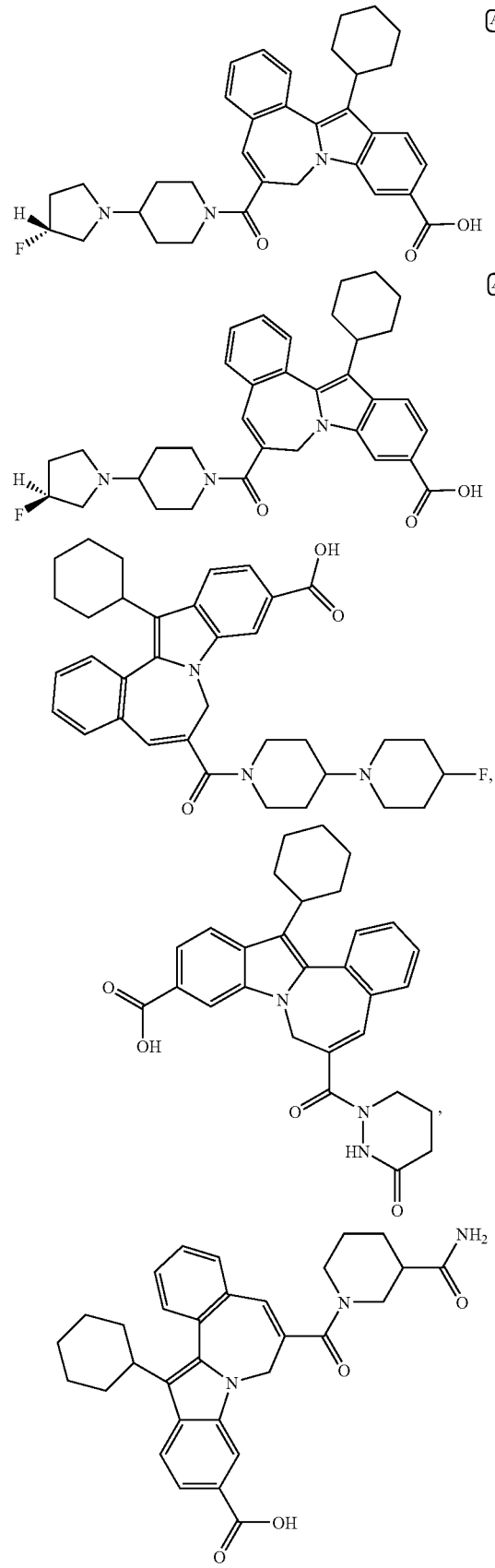
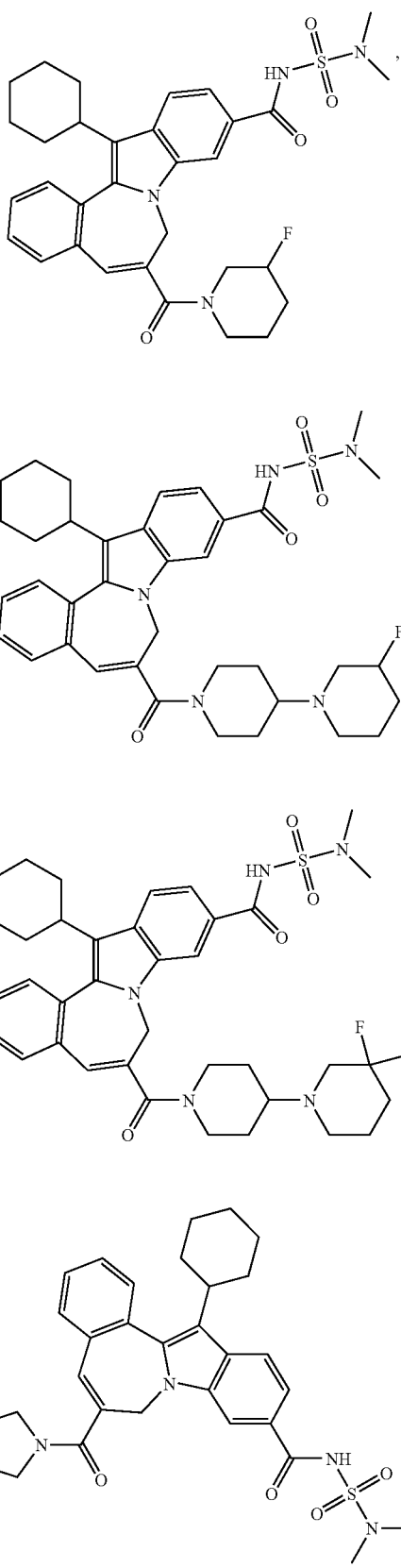

655
-continued
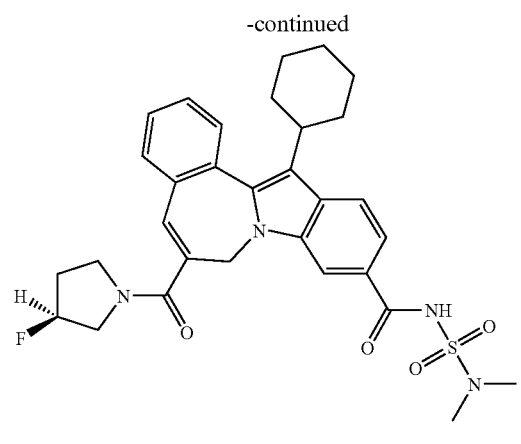
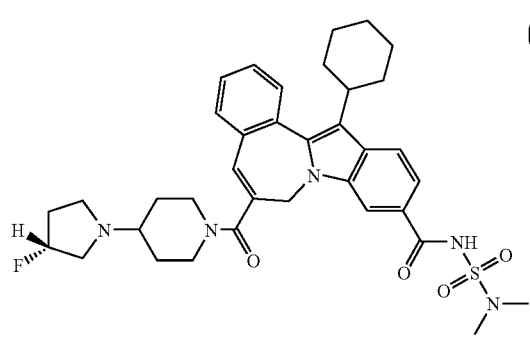
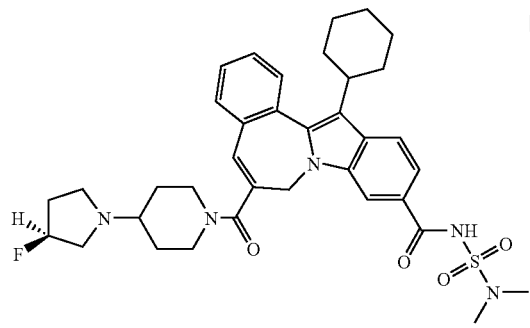
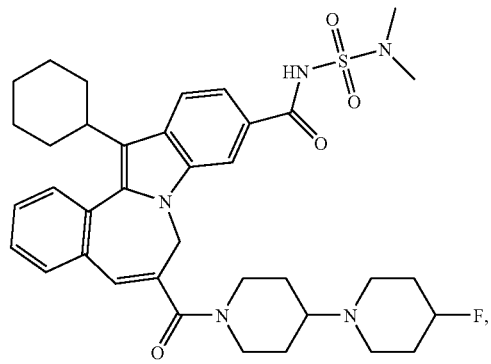
656
-continued
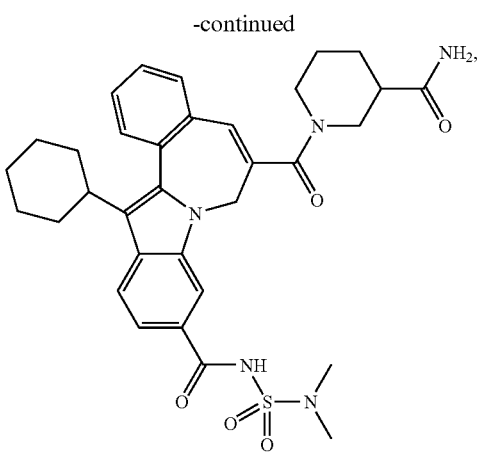
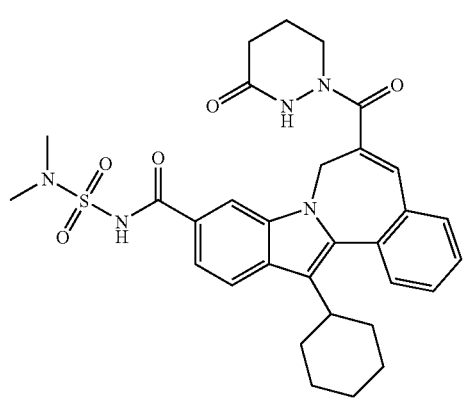
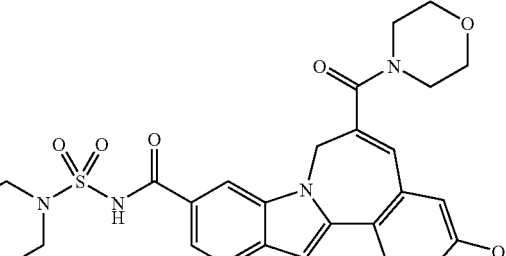
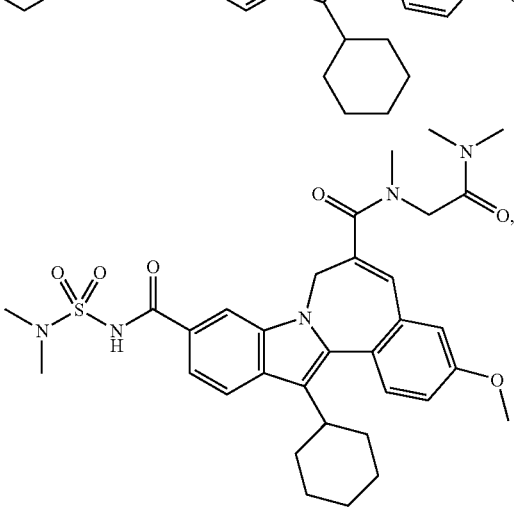

657
-continued
658
-continued
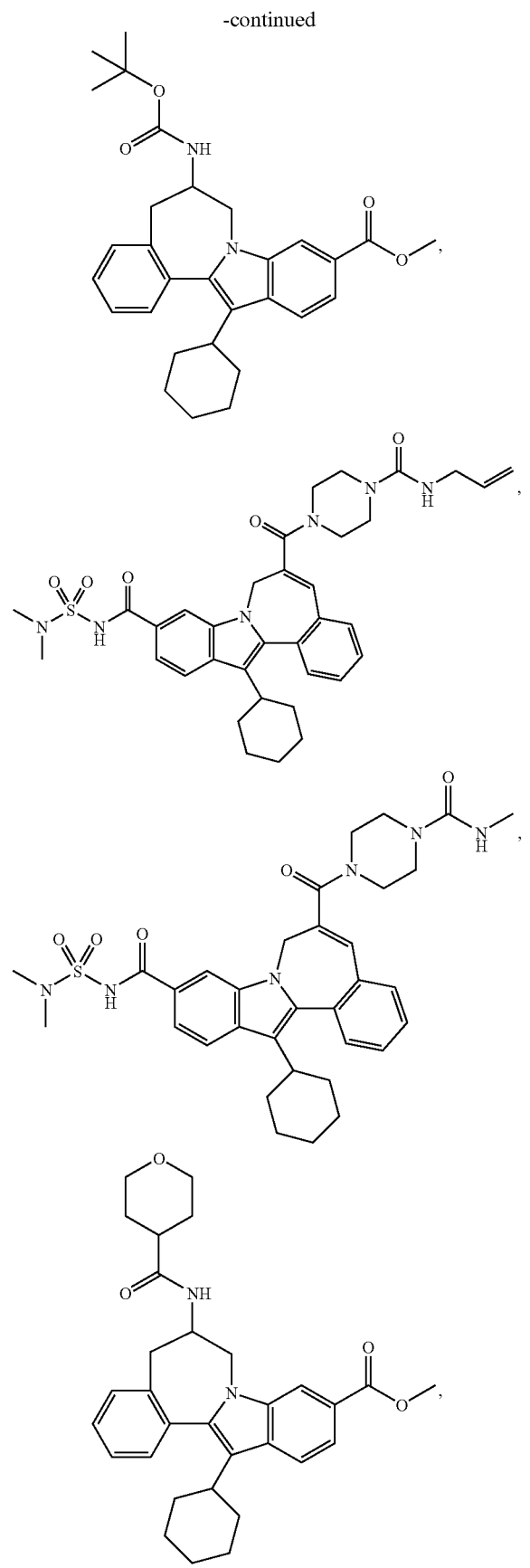
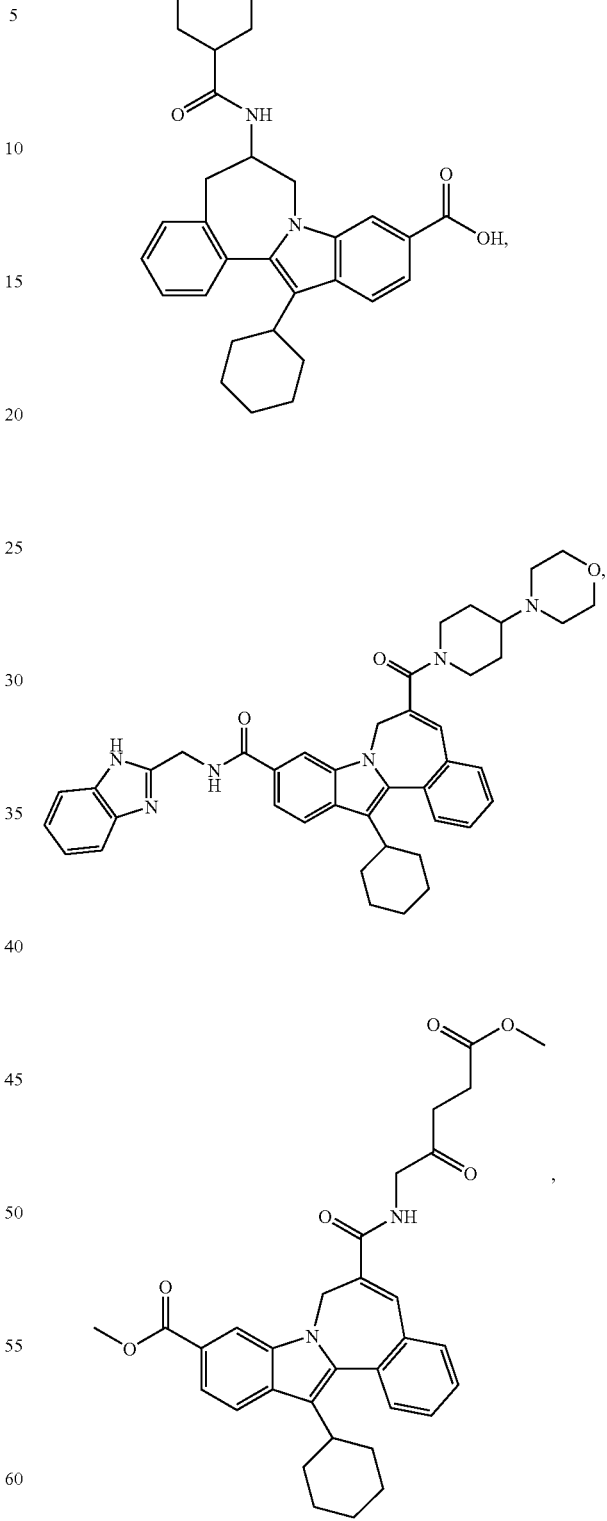

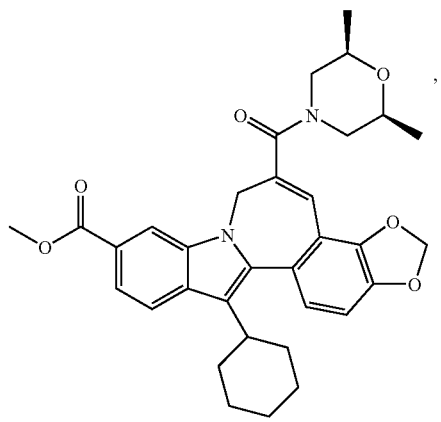
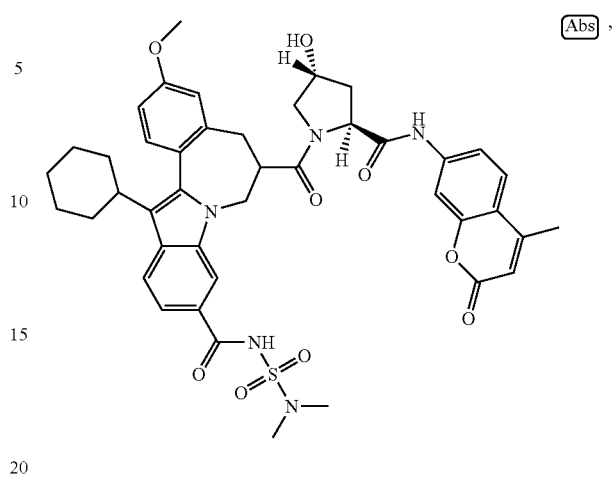
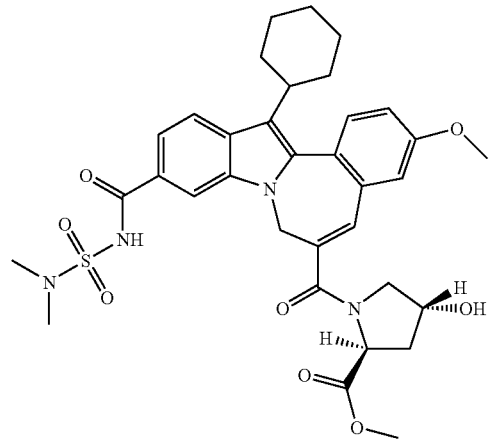
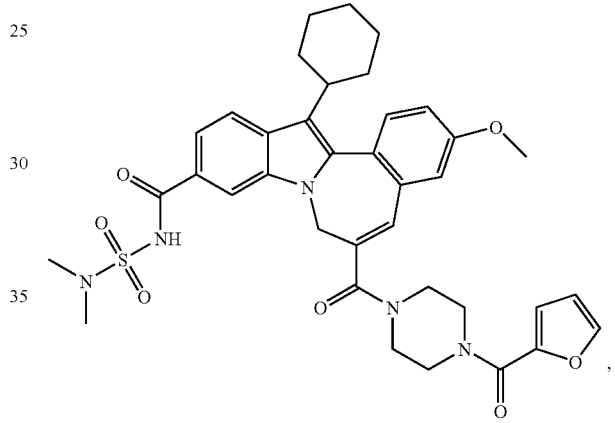
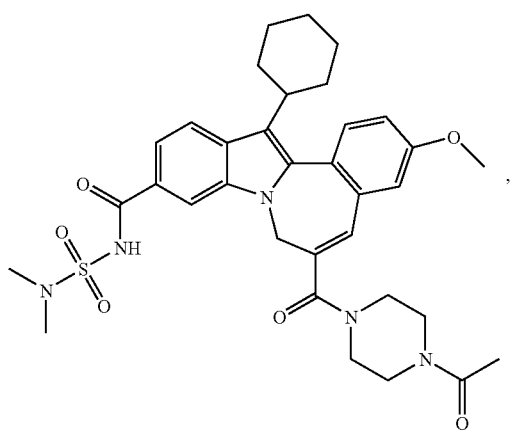
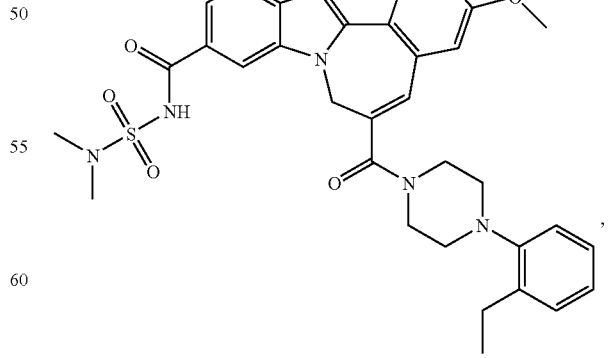

661
-continued
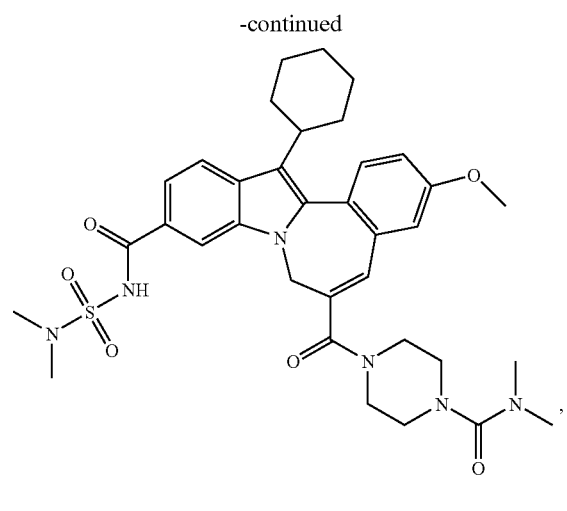
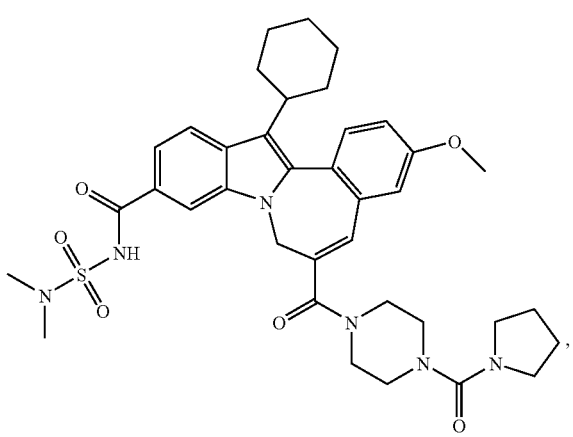
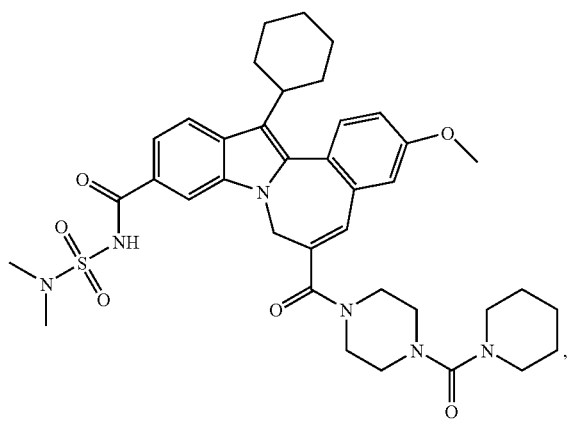
662
-continued
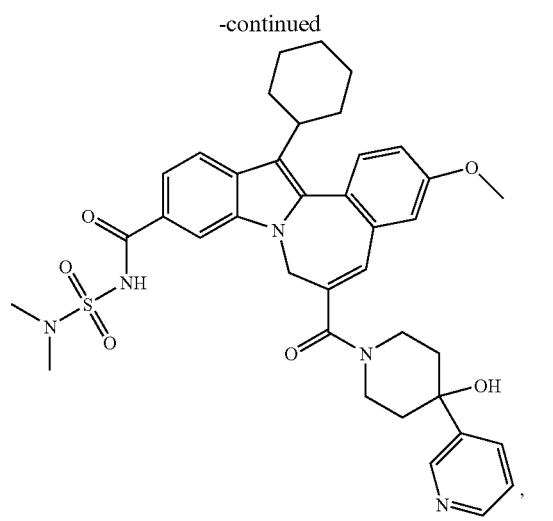
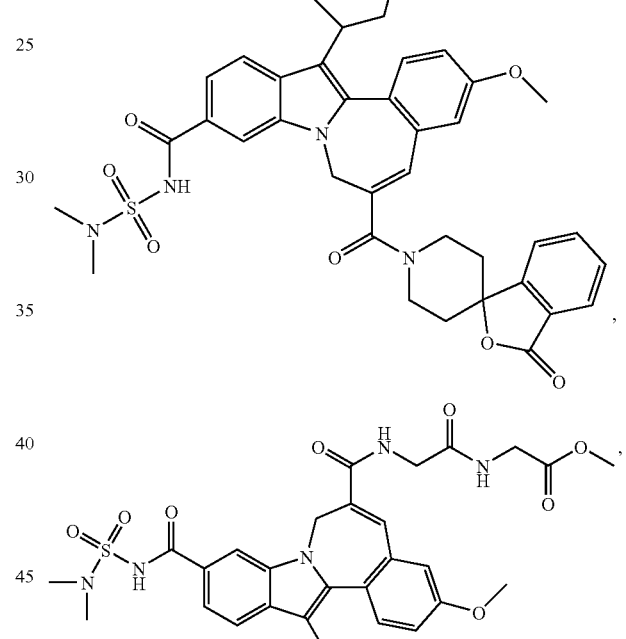
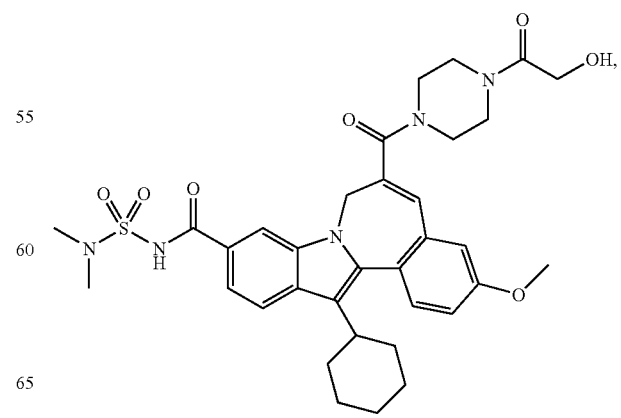

663
-continued
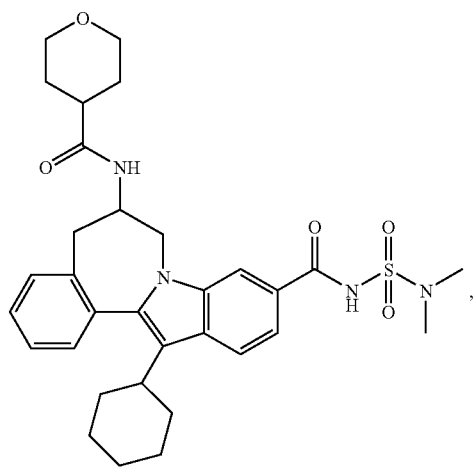
664
-continued
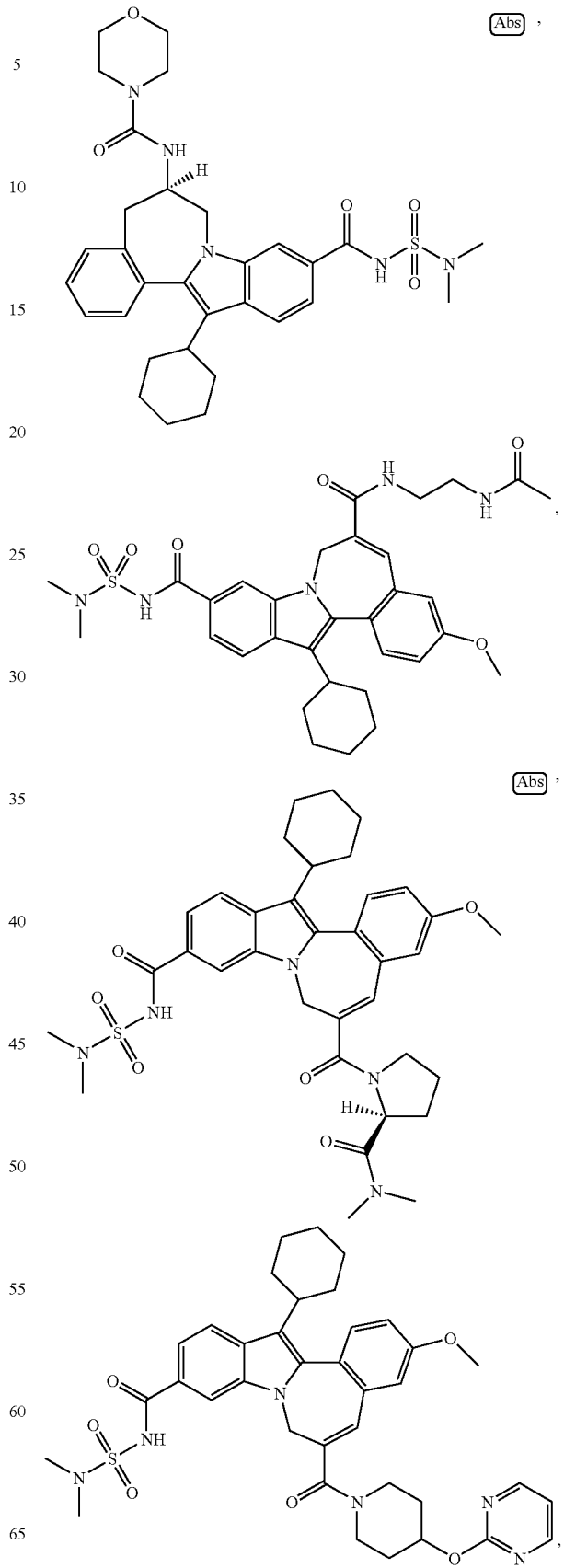

665
-continued
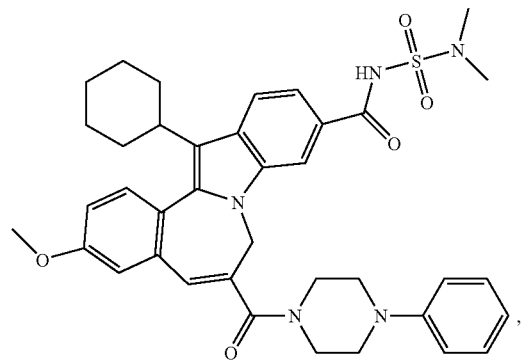
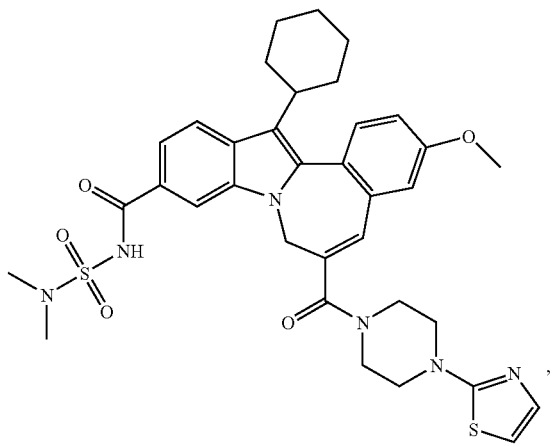
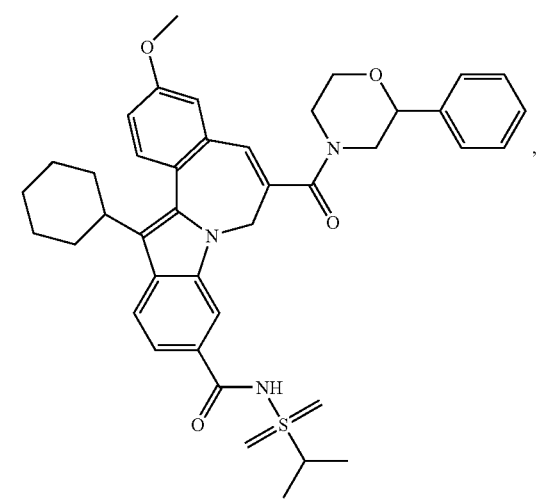
666
-continued
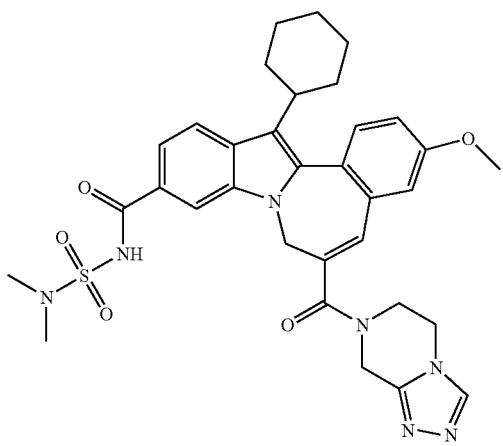
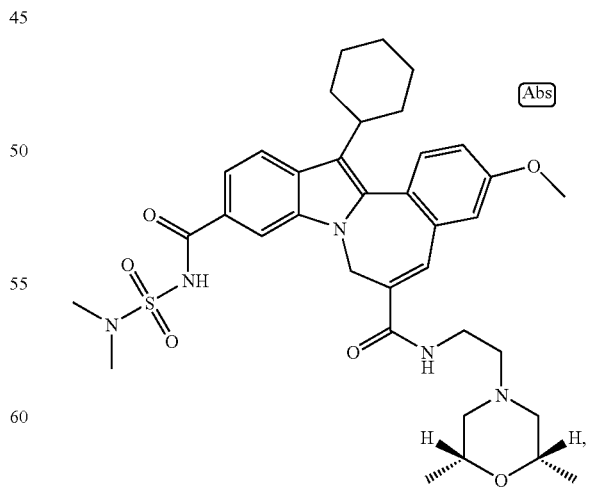

667
-continued
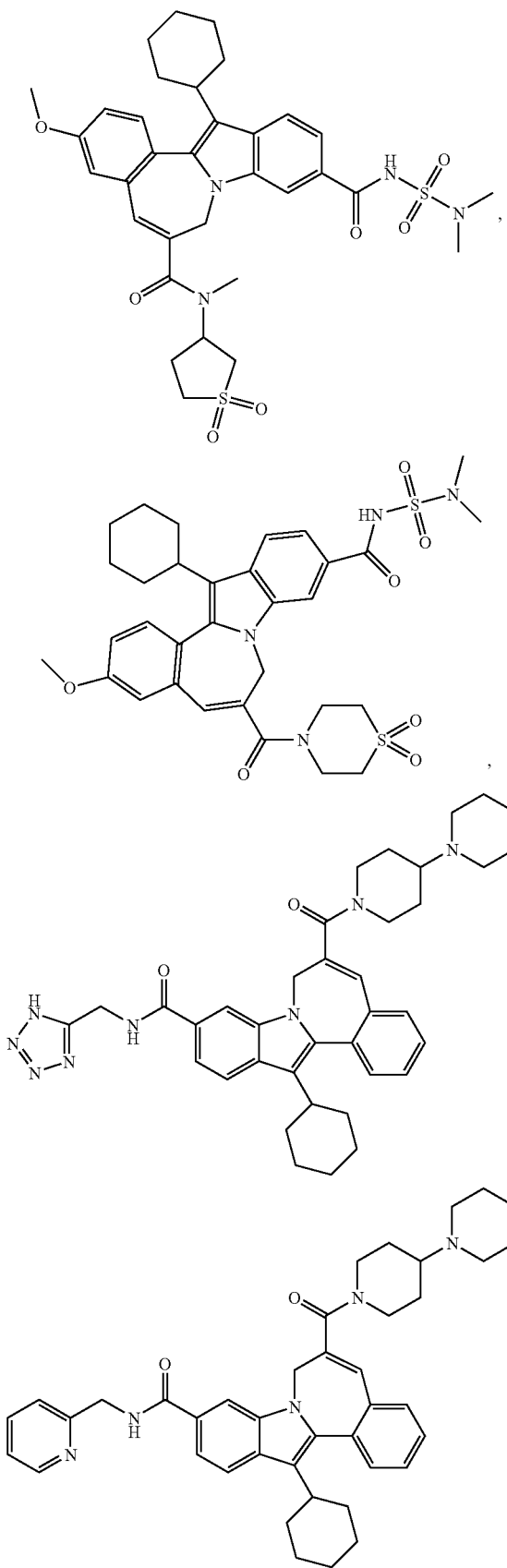
668
-continued
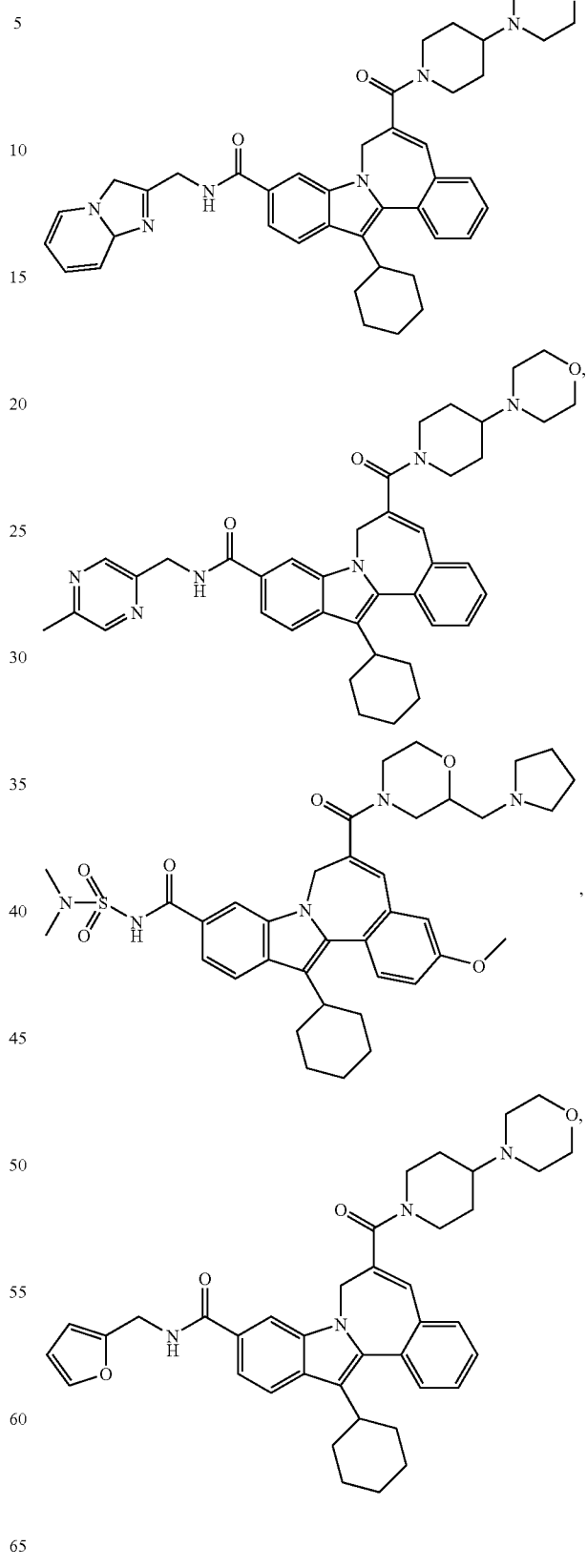

669
-continued
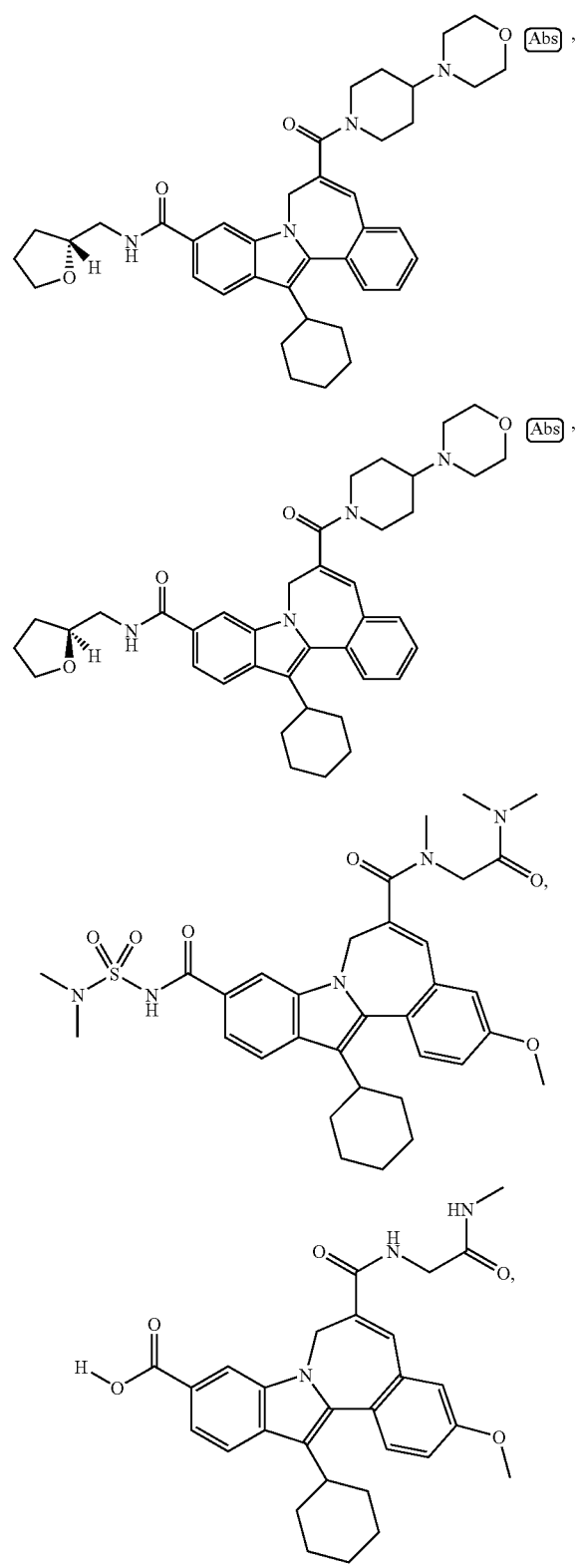
670
-continued
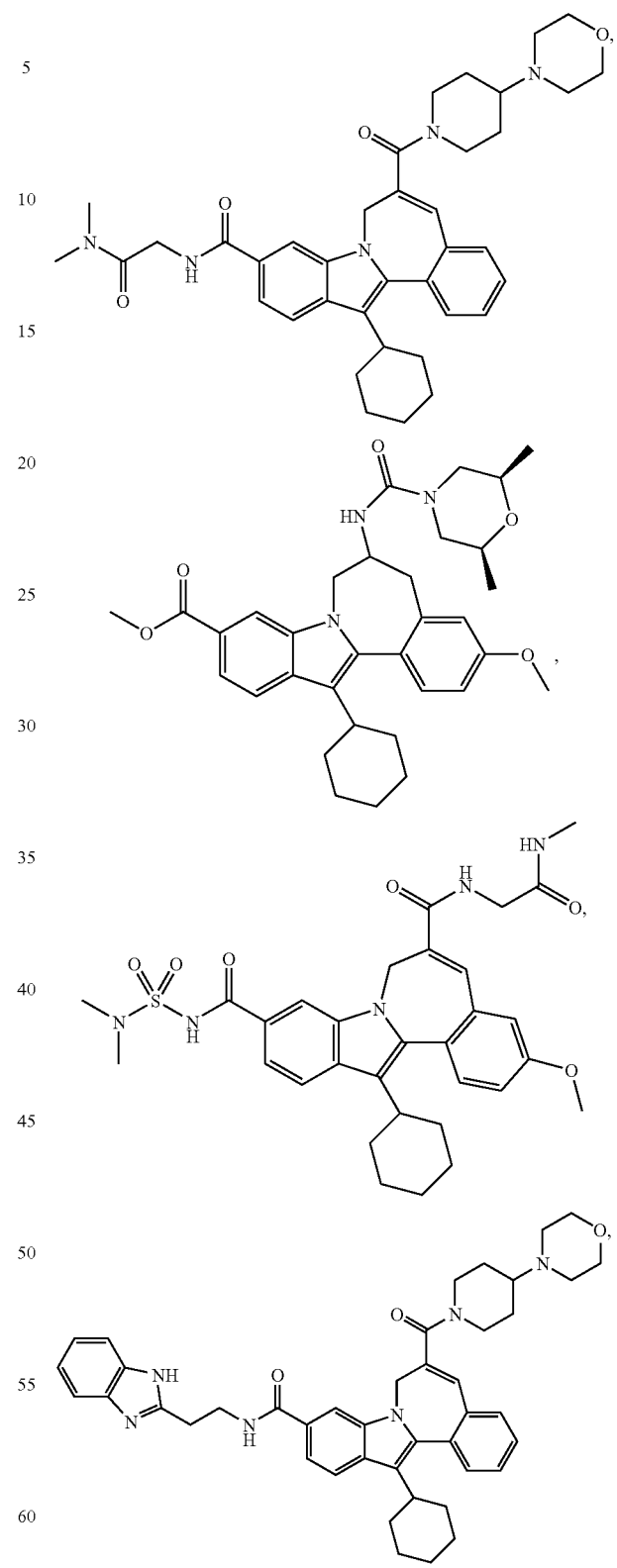

671
-continued
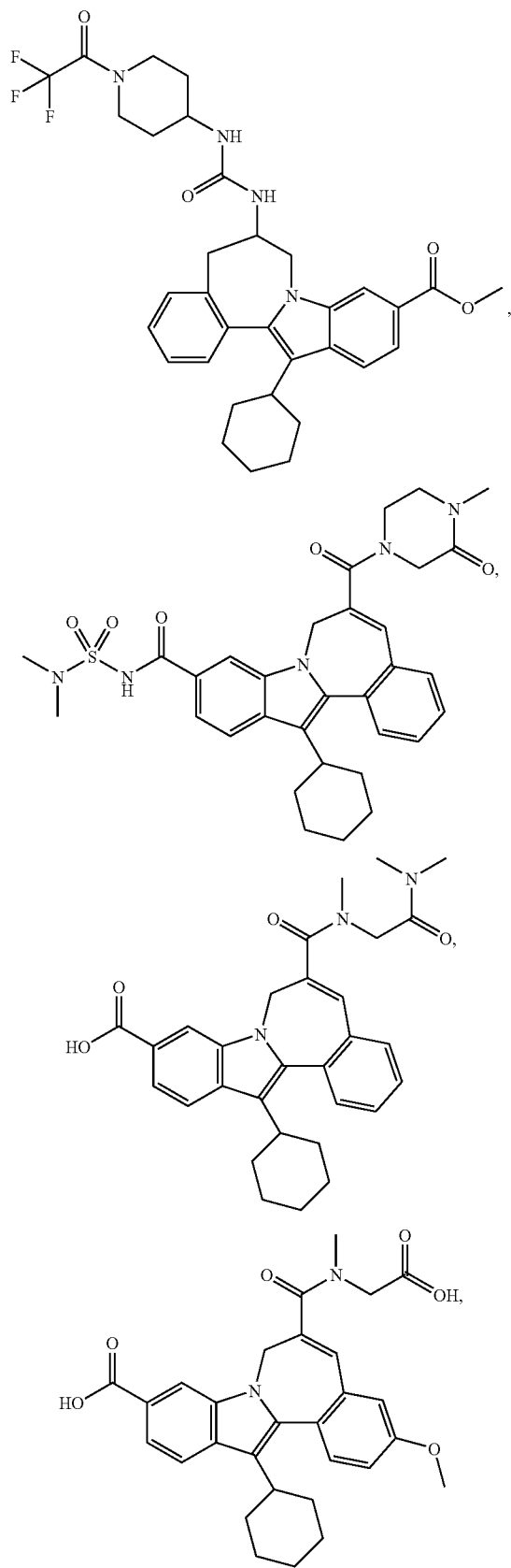
672
-continued
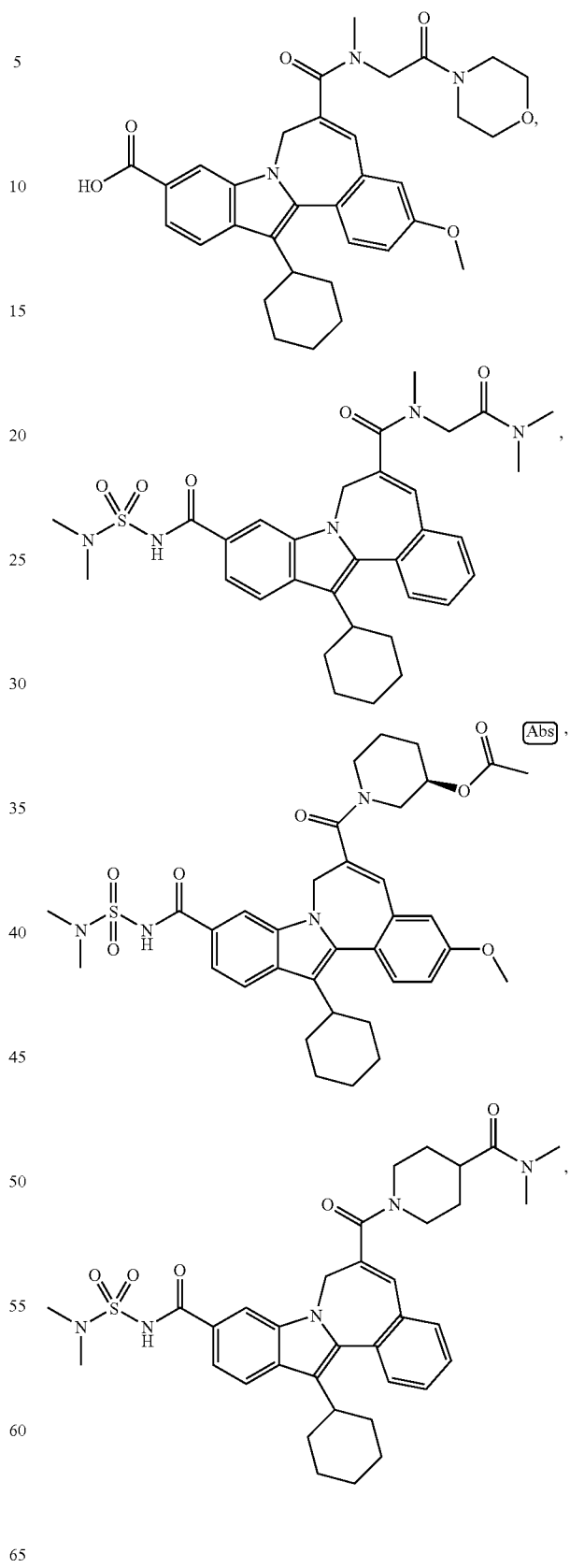

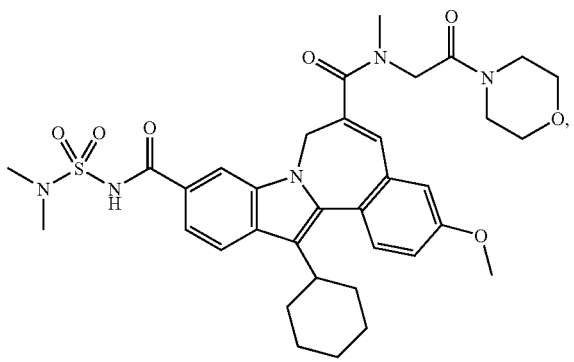
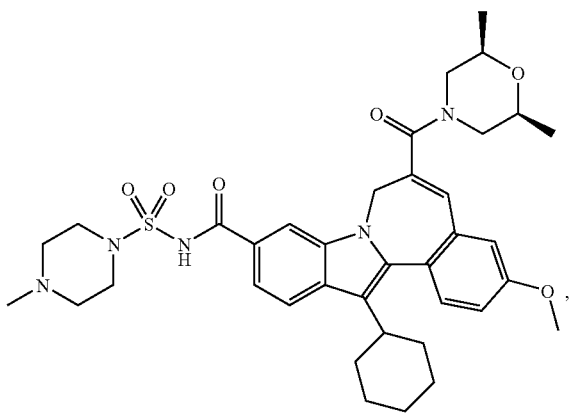
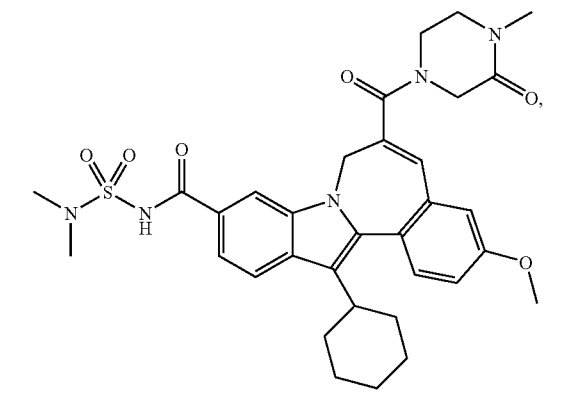
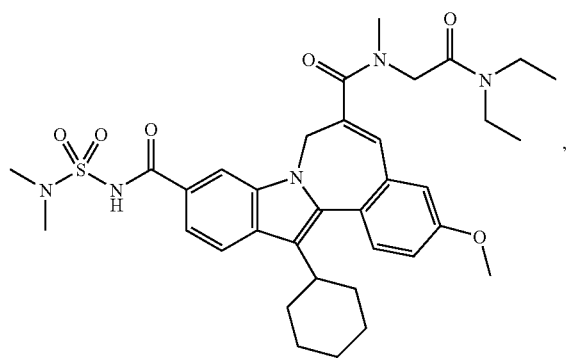
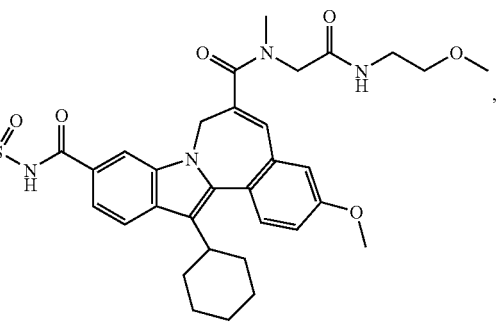
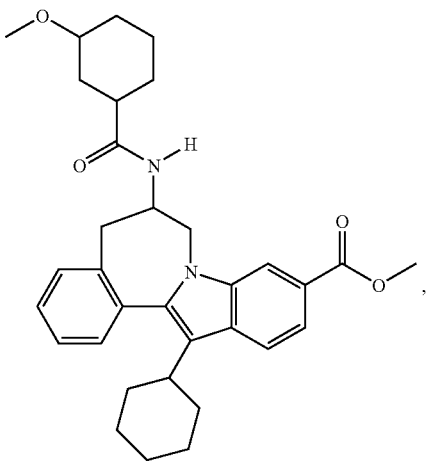
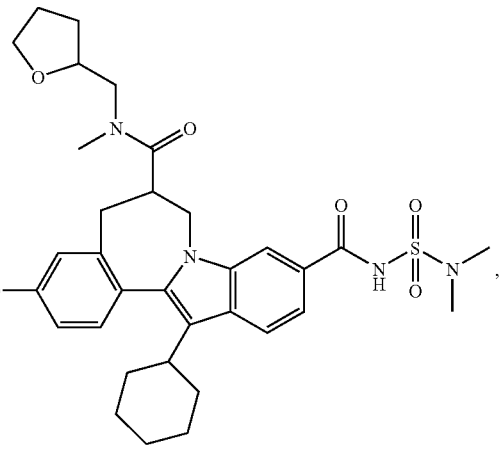
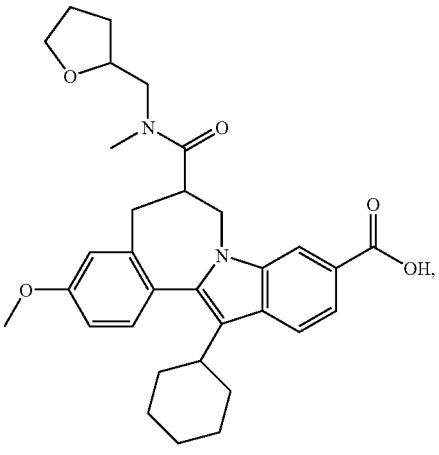

675
-continued
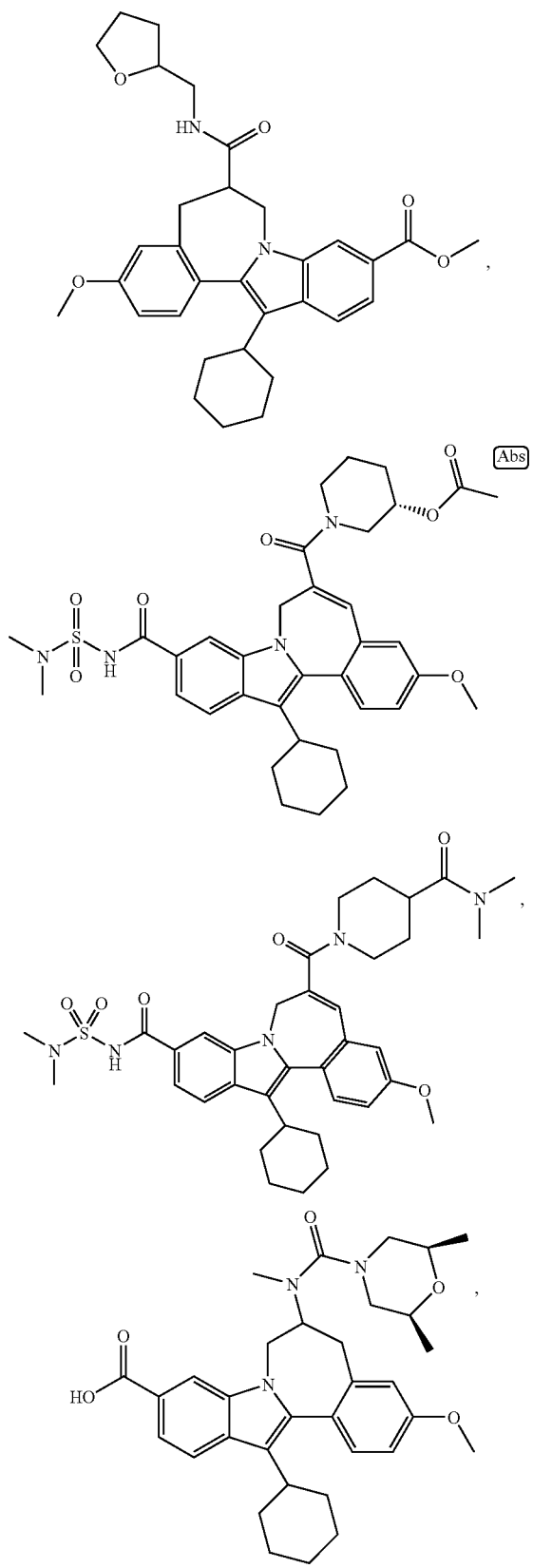
676
-continued
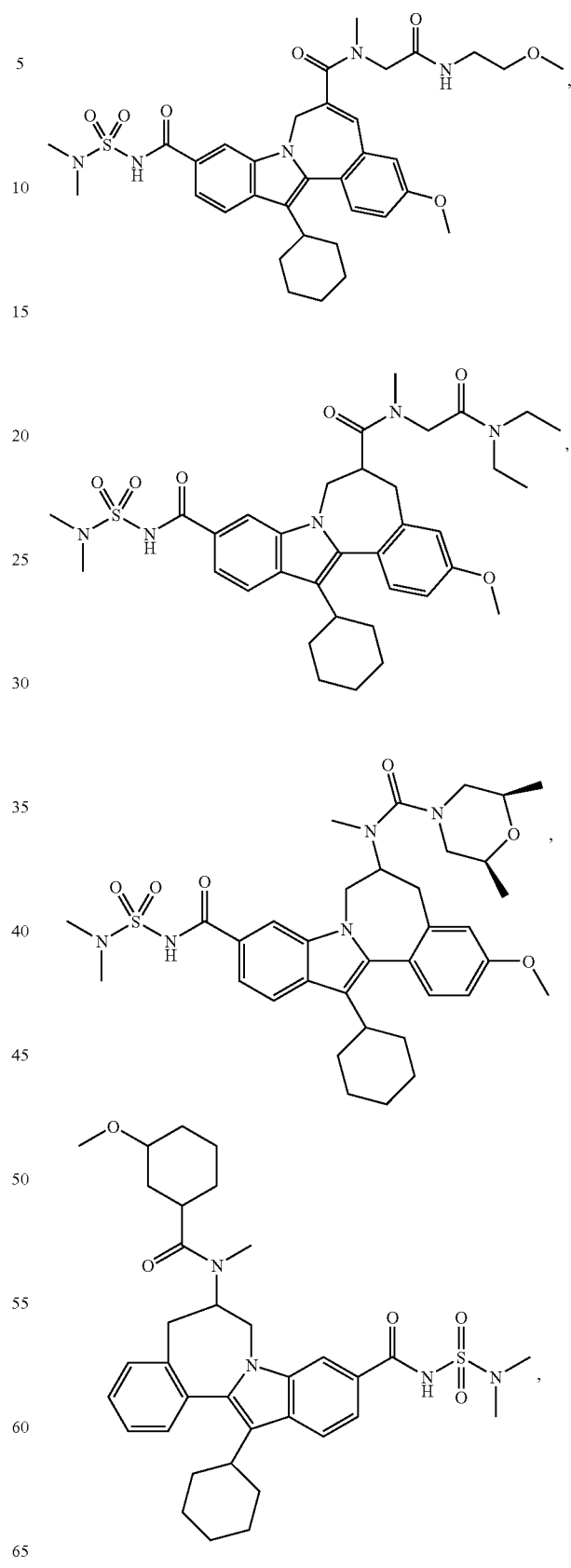

677 678
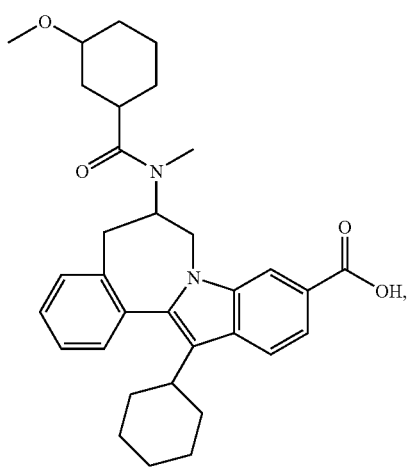
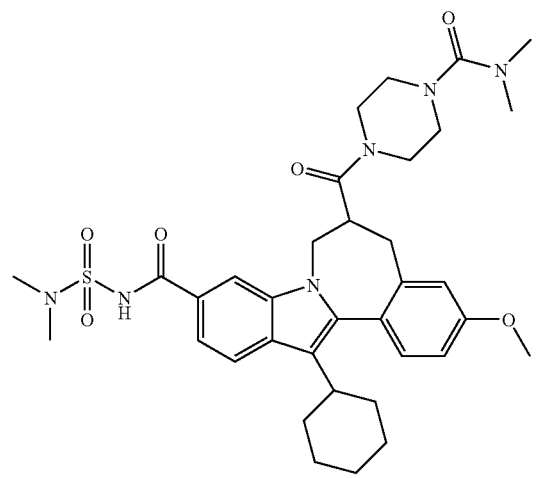
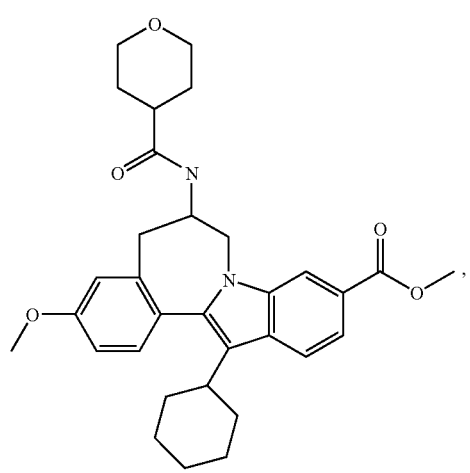
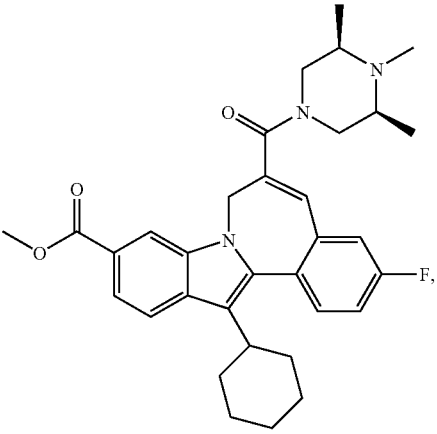
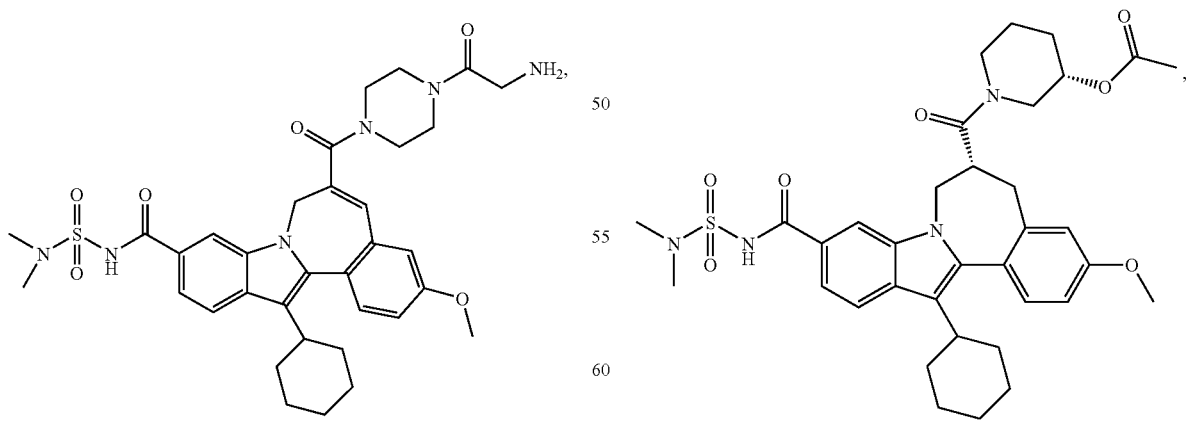

679
-continued
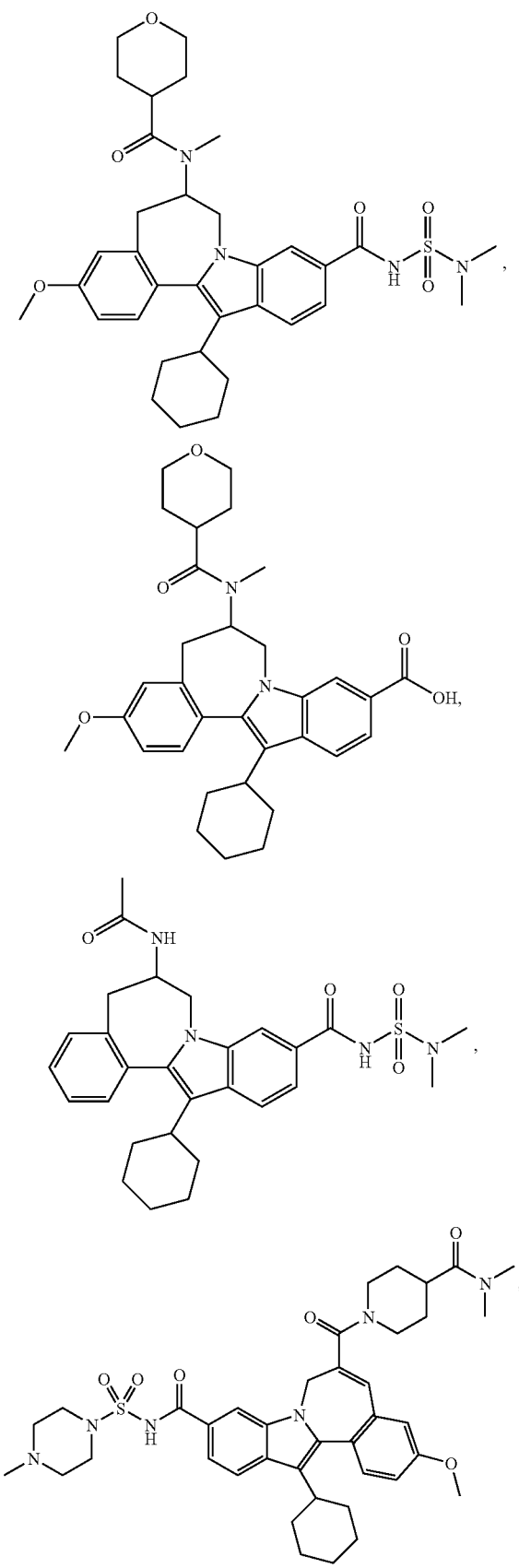
680
-continued
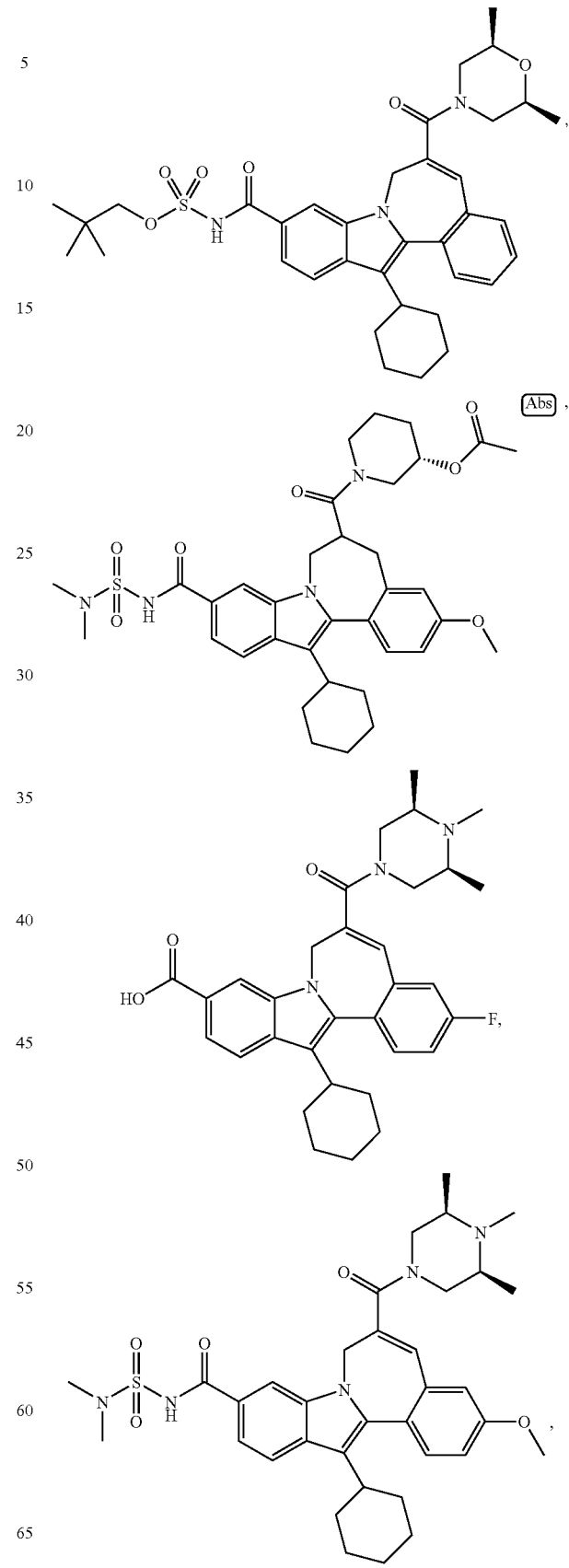

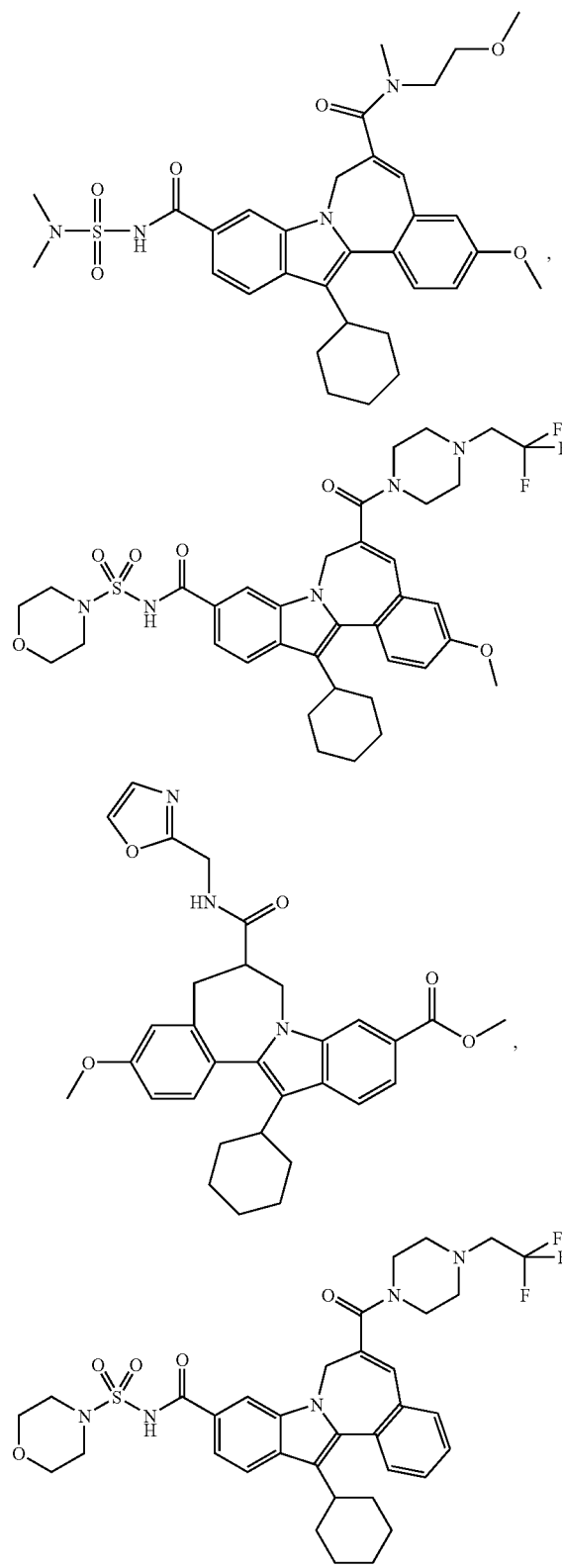
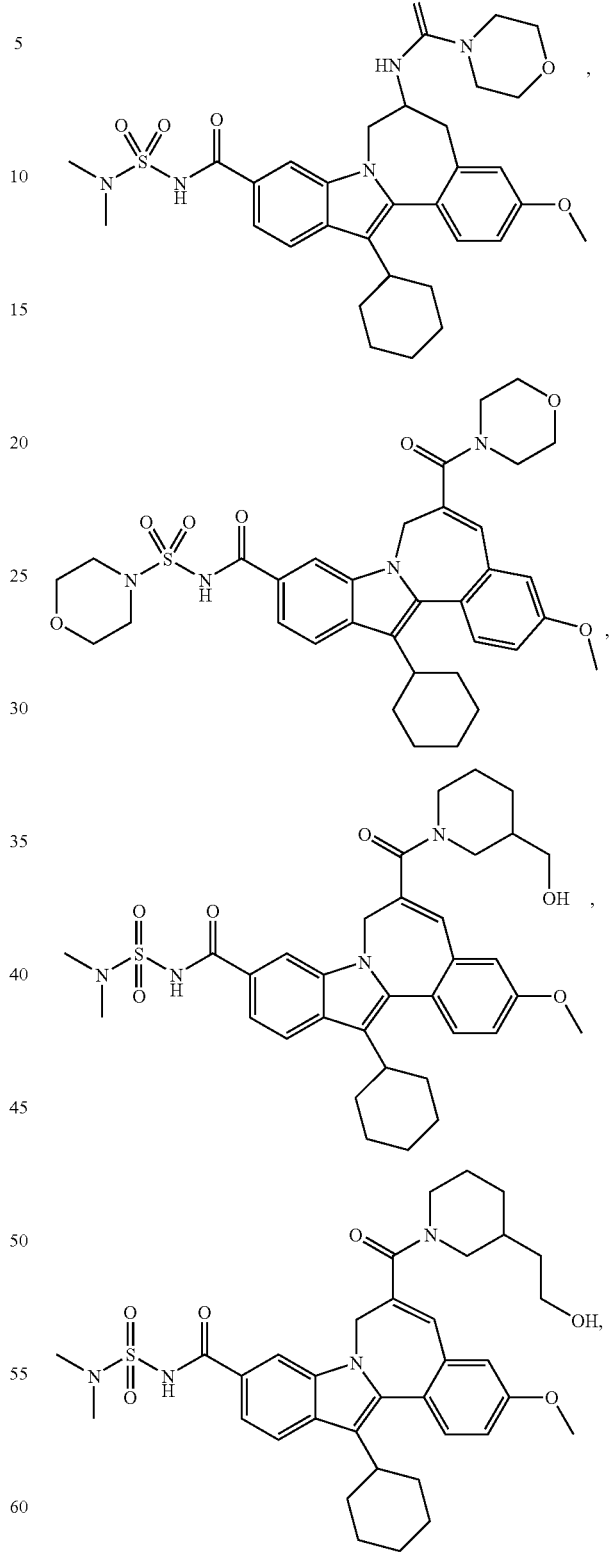

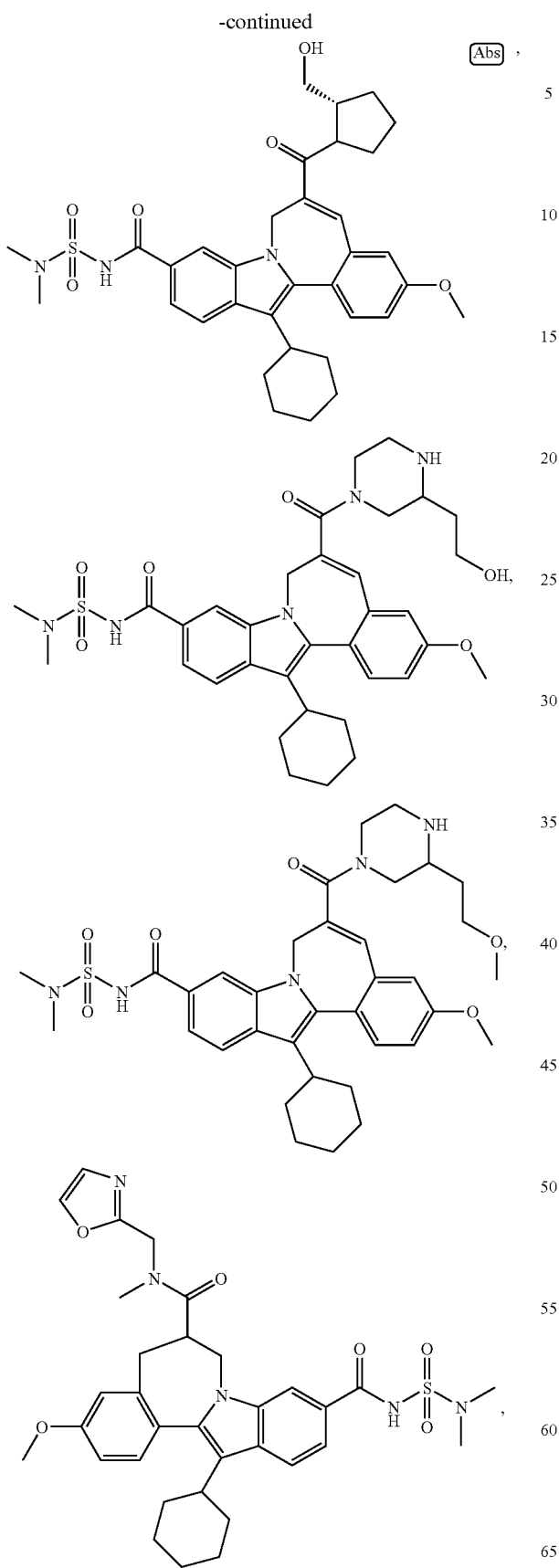
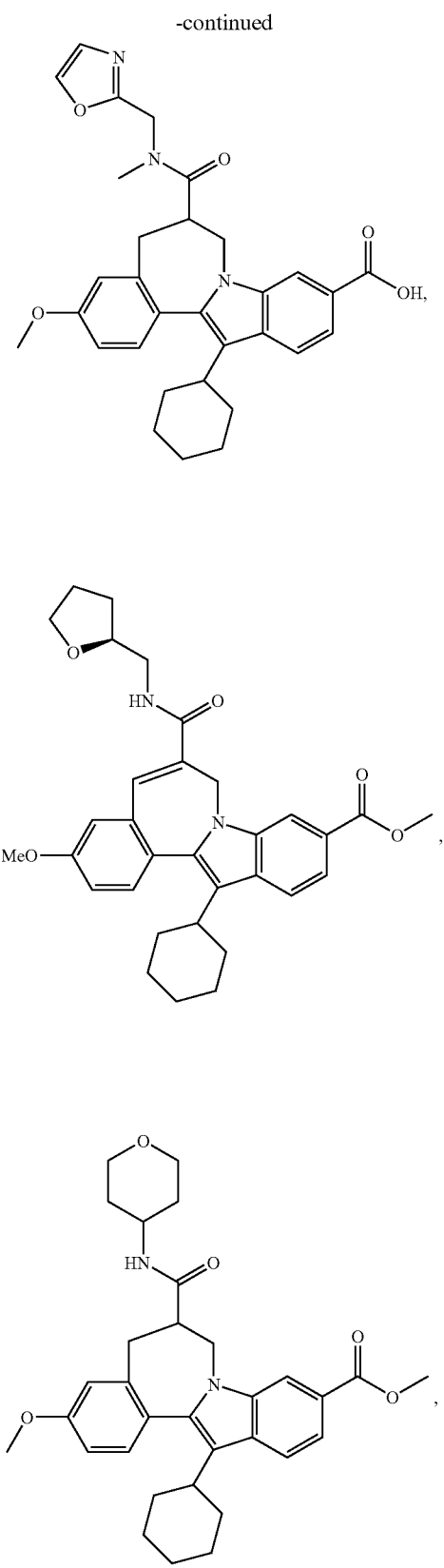

685
-continued
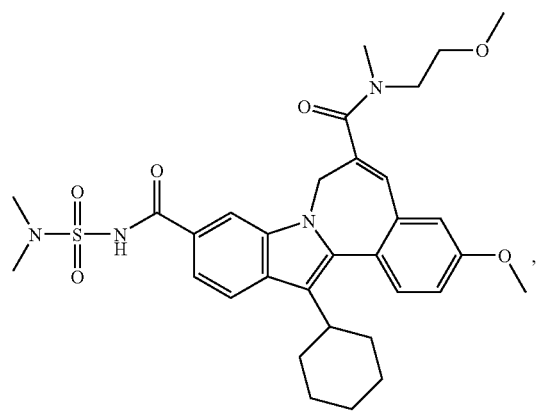
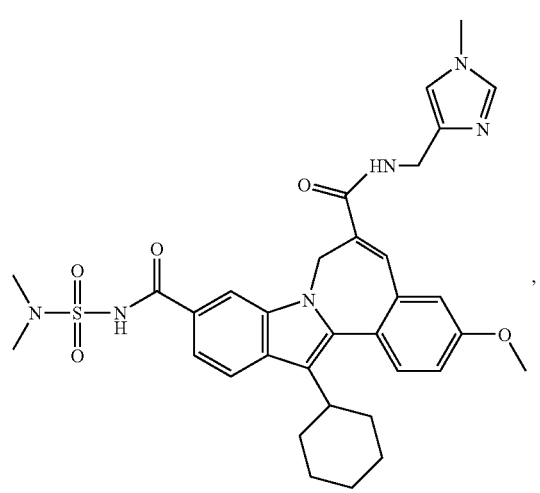
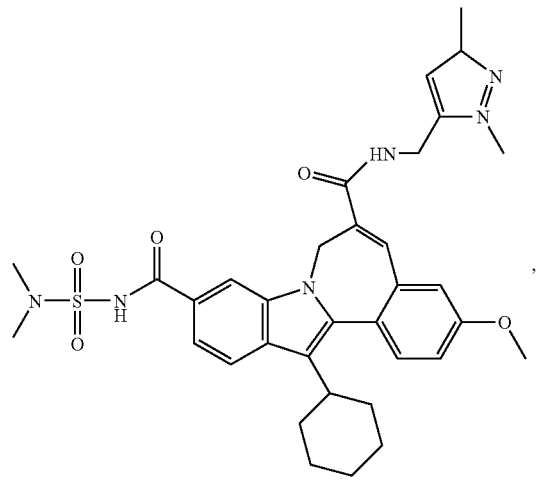
686
-continued
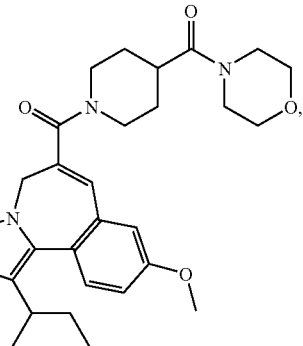
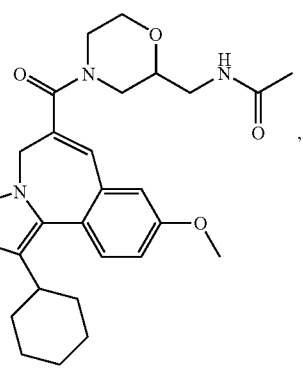
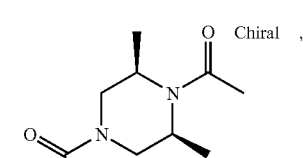
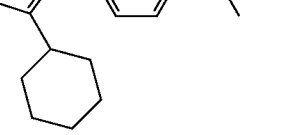
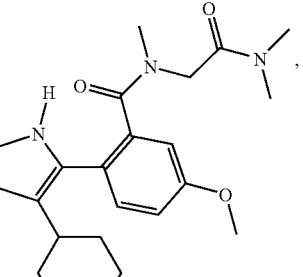

687
-continued
688
-continued
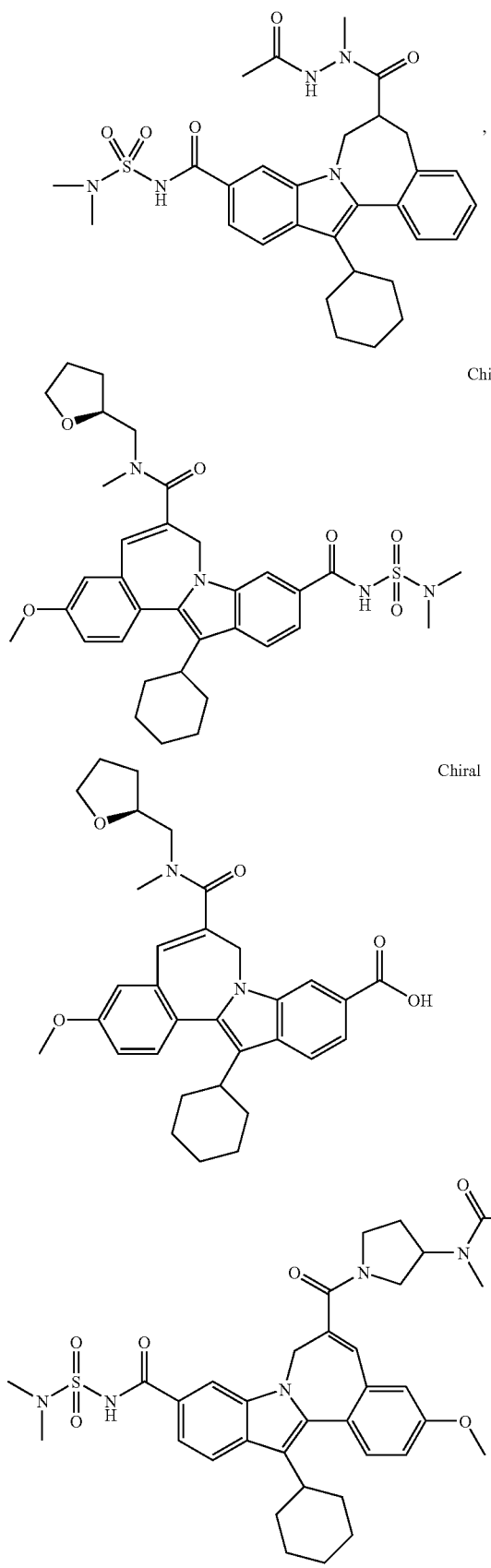
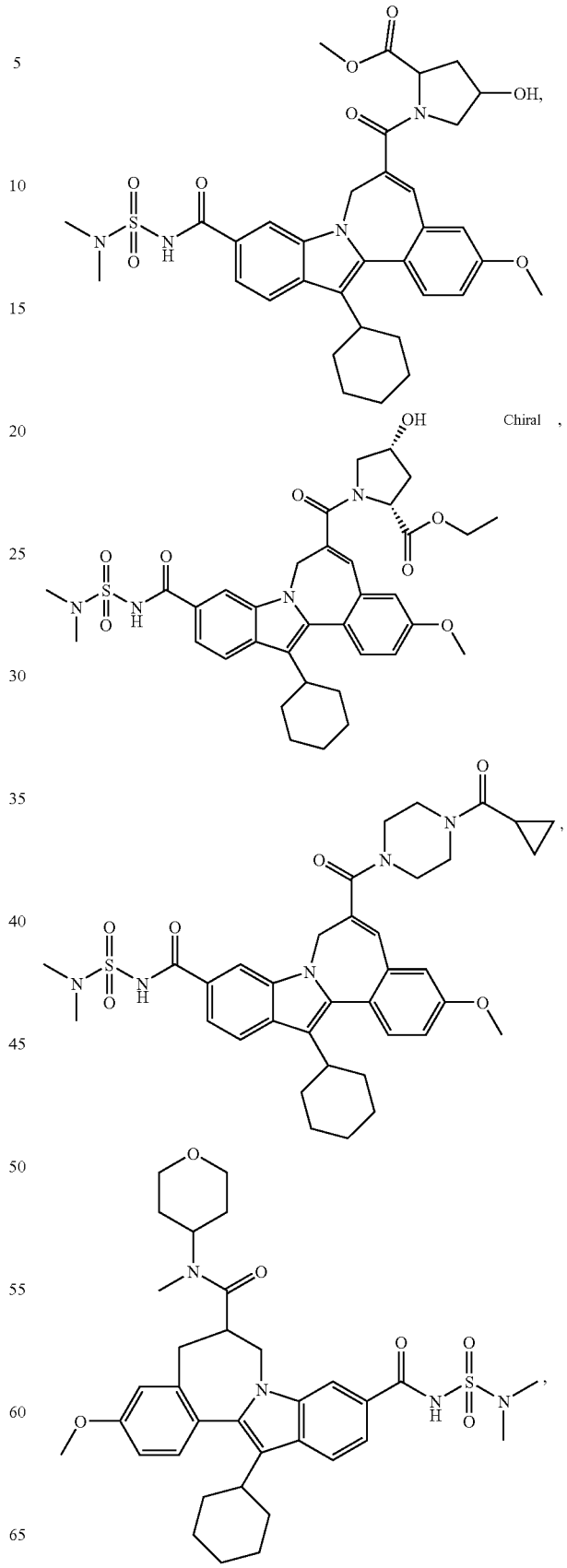

689
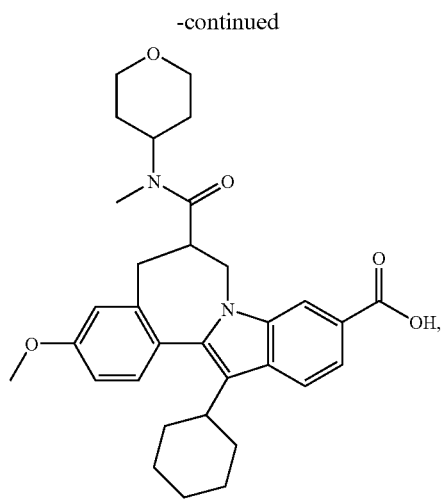
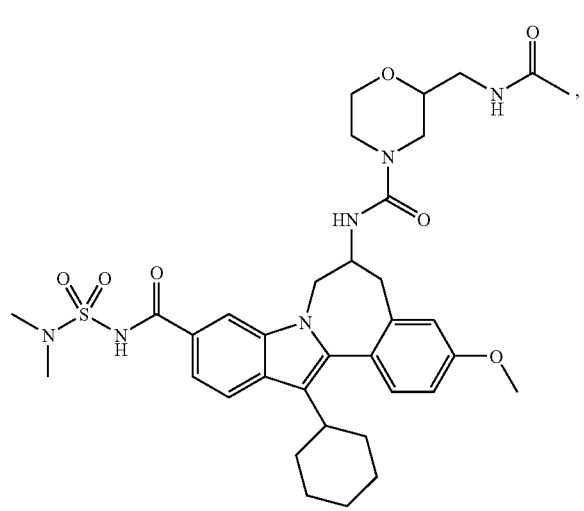
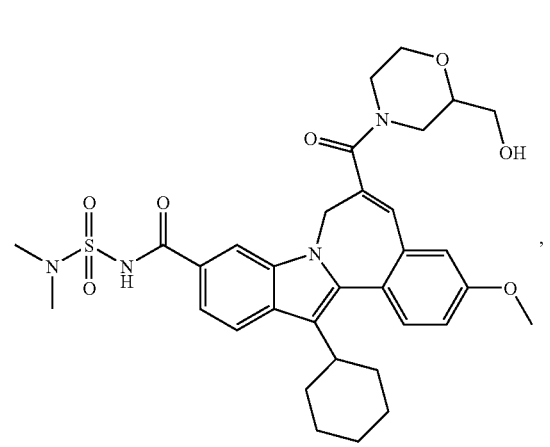
690
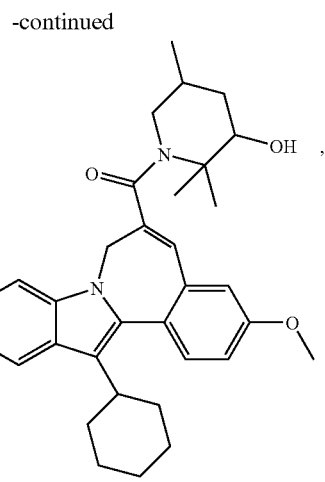
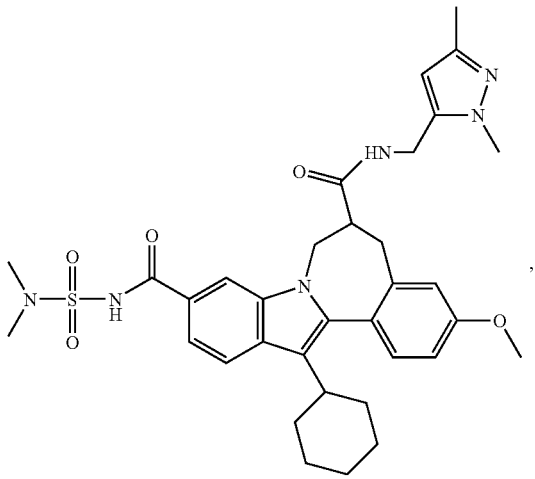
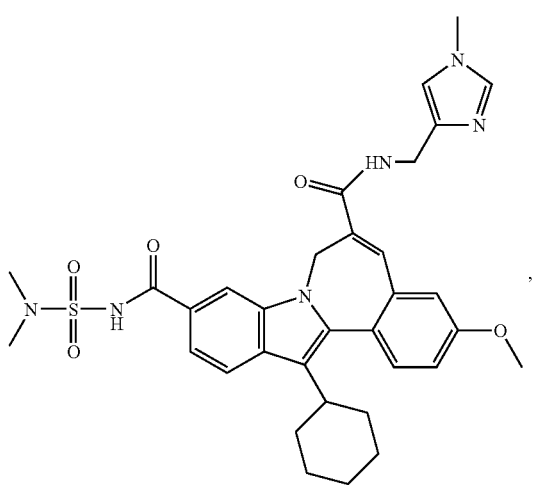

691
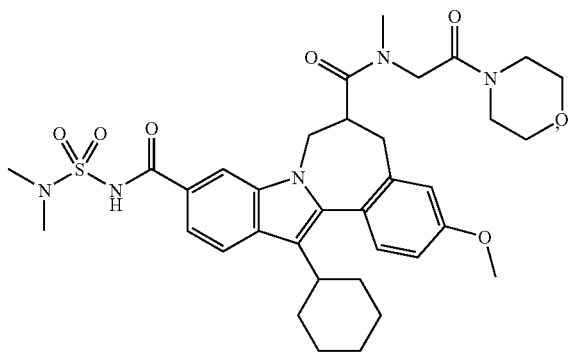
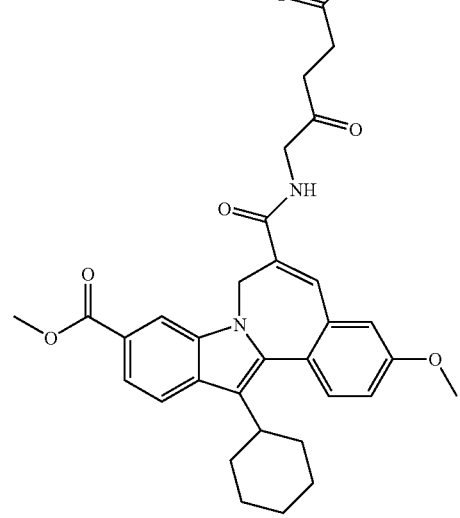
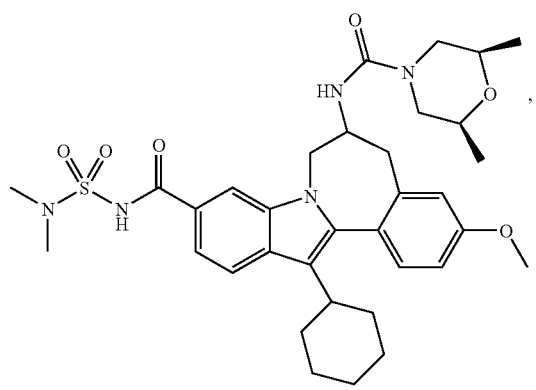
692
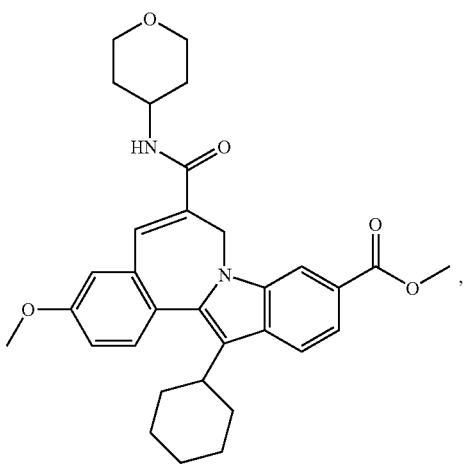
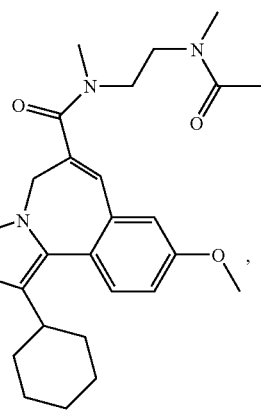
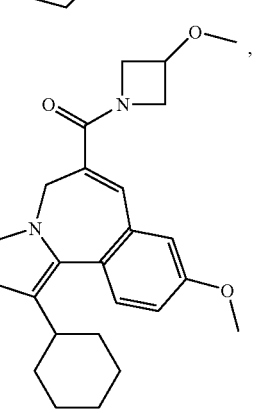
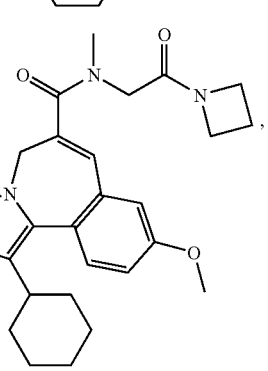

693 -continued
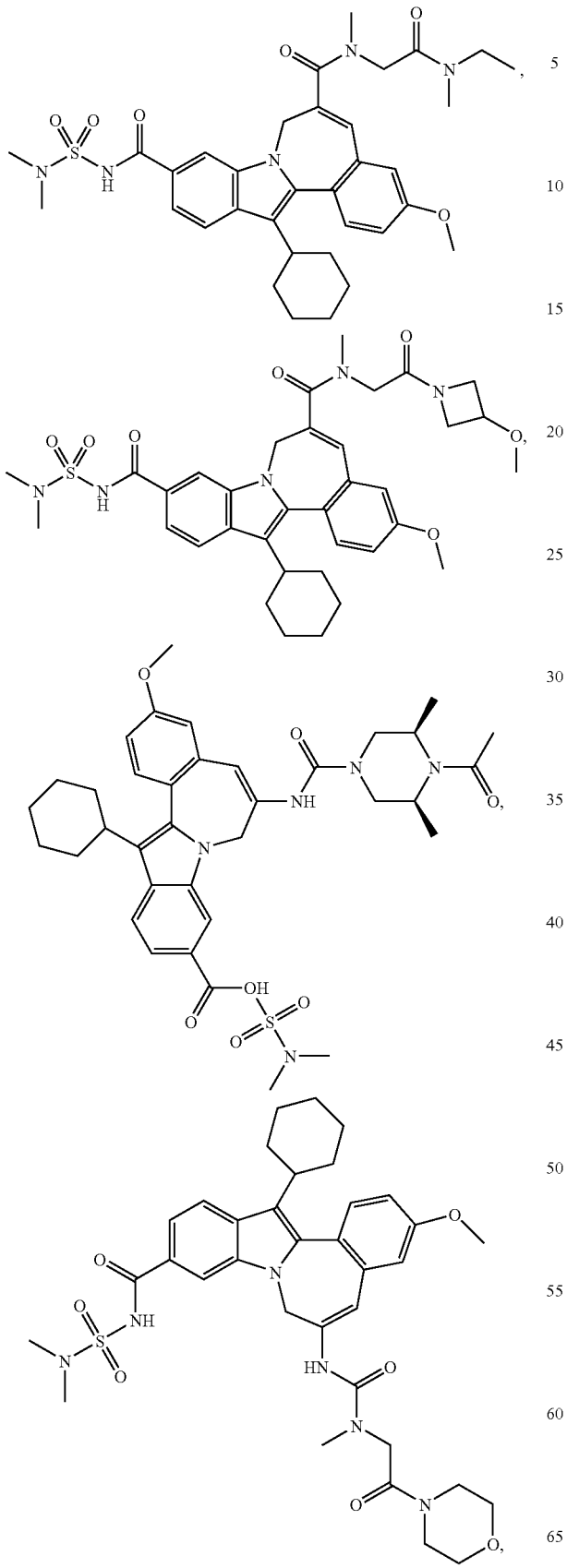
694 -continued
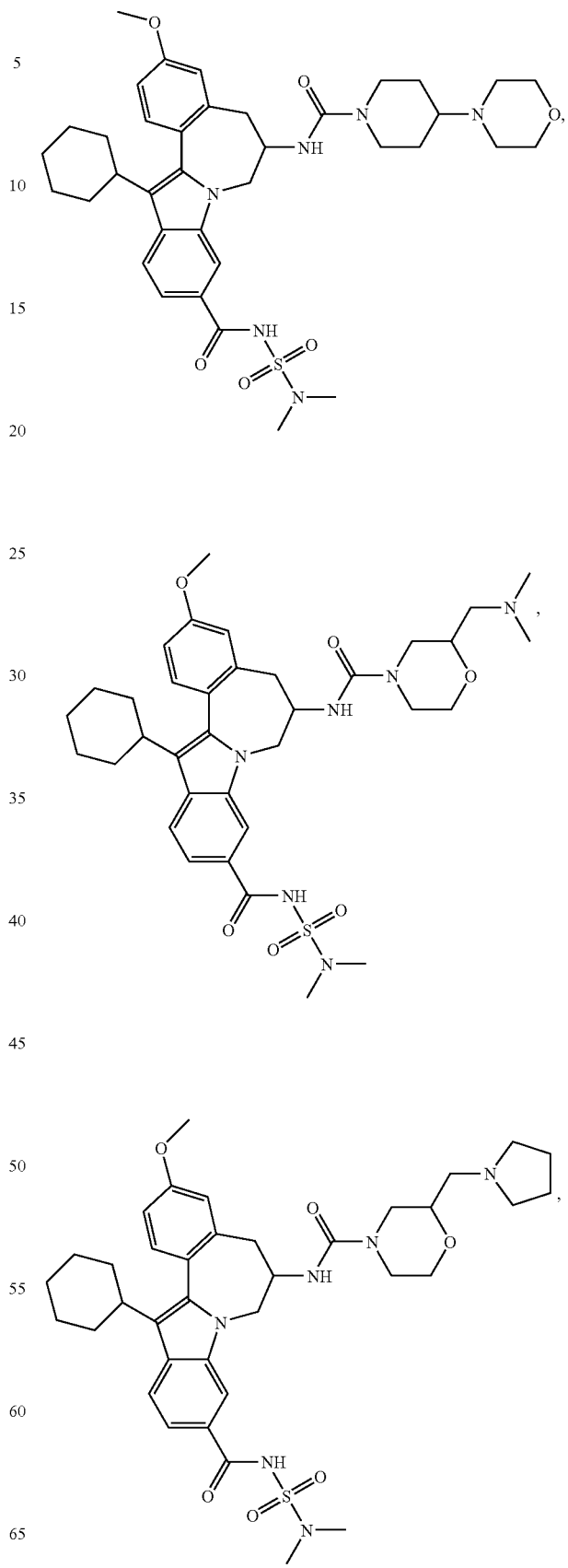

695
-continued
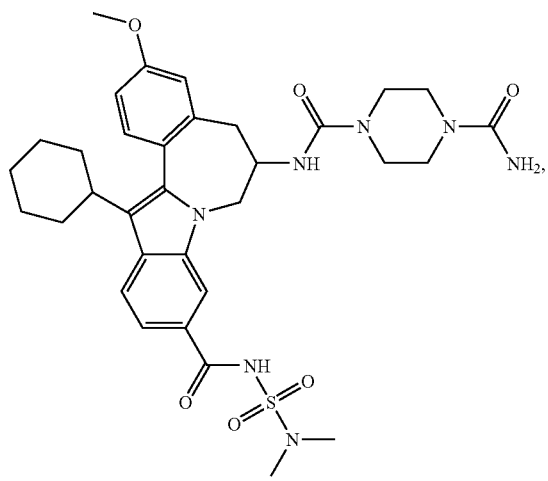
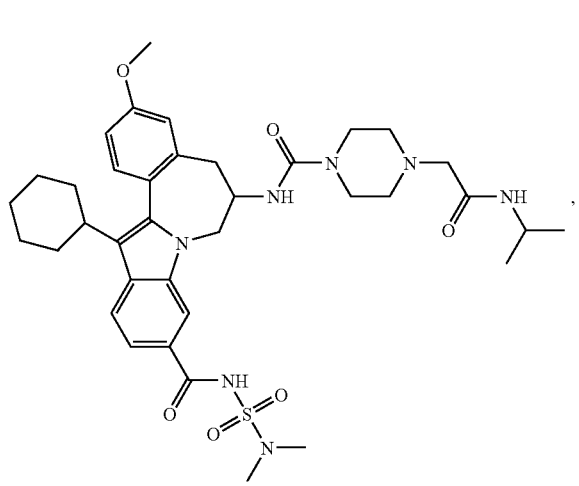
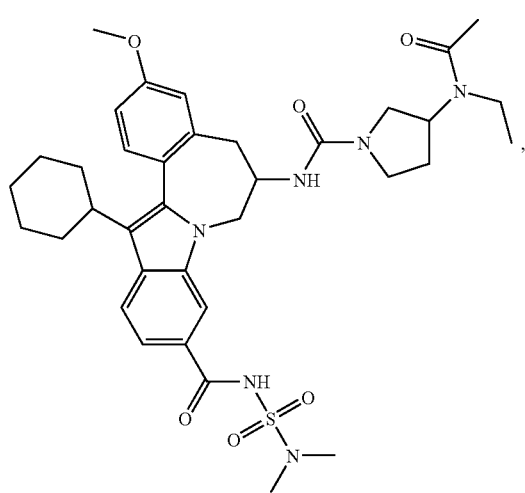
696
-continued
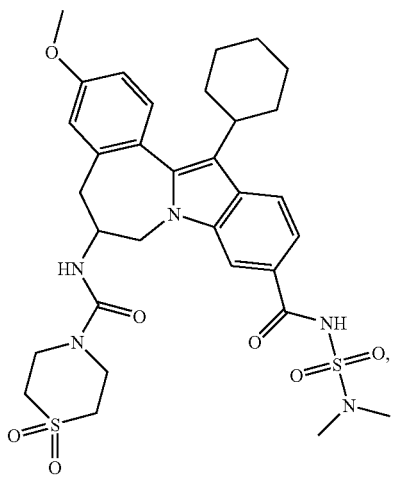
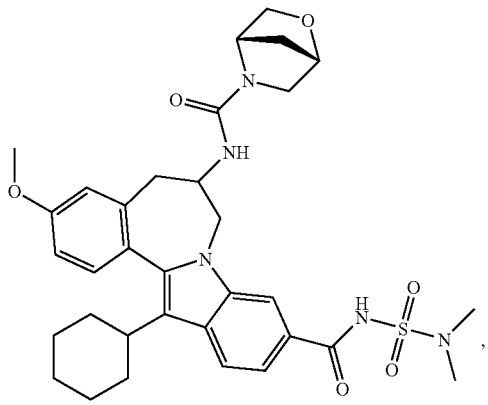
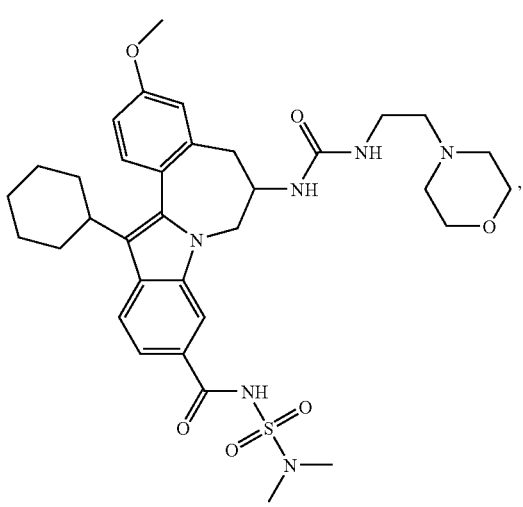

| 697 | 698 |
|---|---|
| 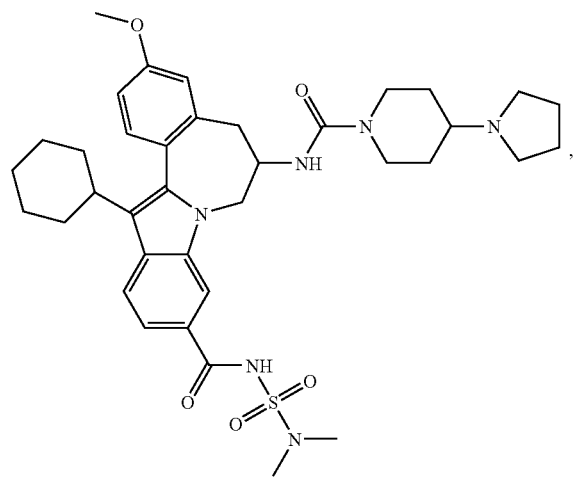 | 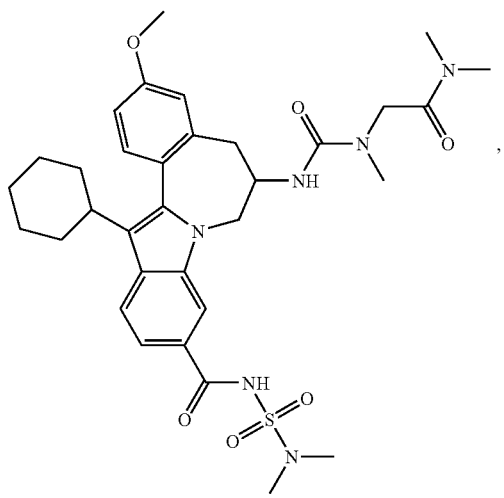 |
| 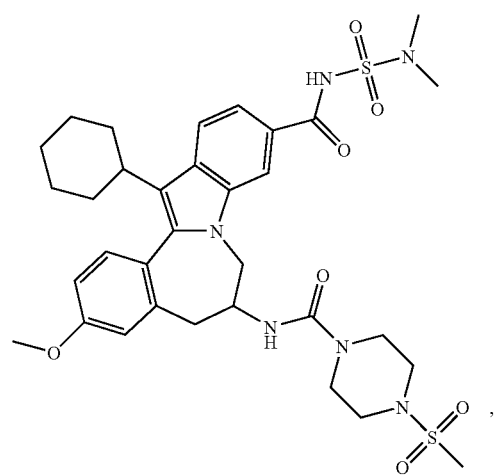 | 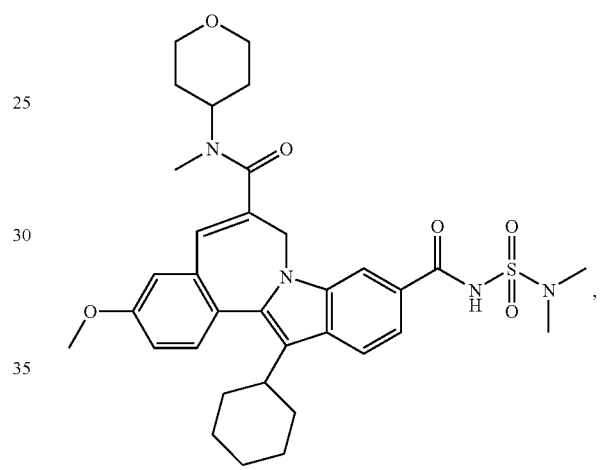 |
| 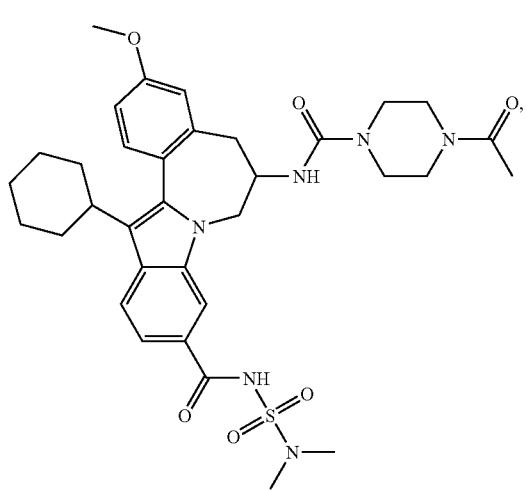 | |

699 700
-continued -continued
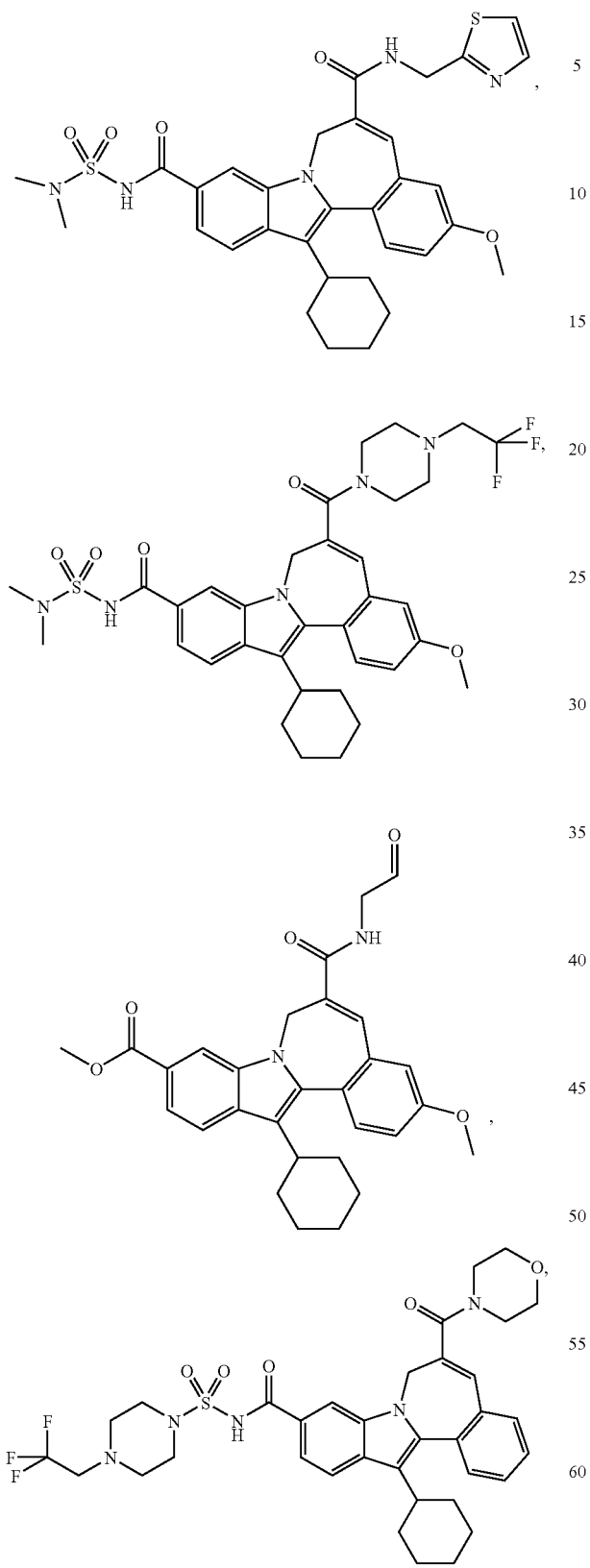
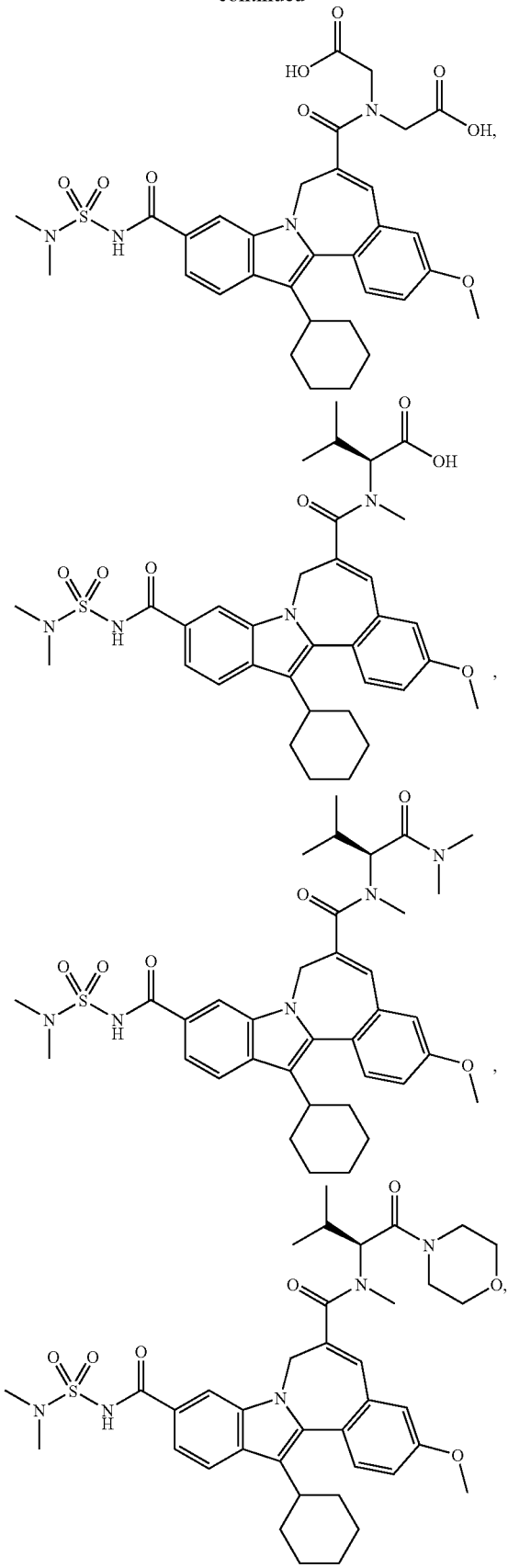

701                                            702
-continued                                    -continued
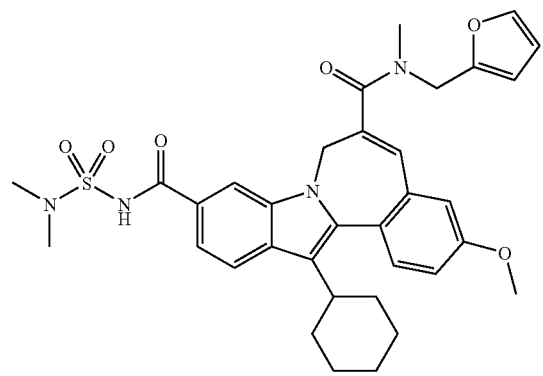,
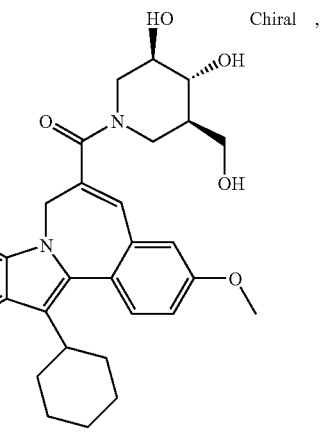,
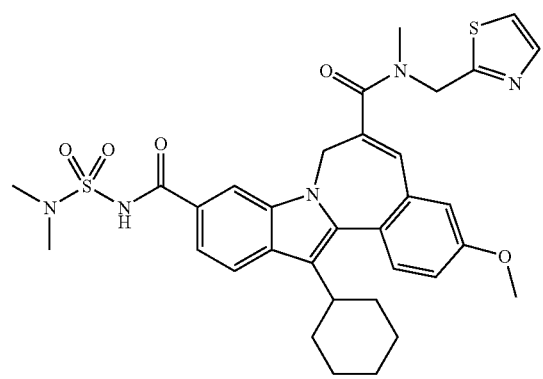,
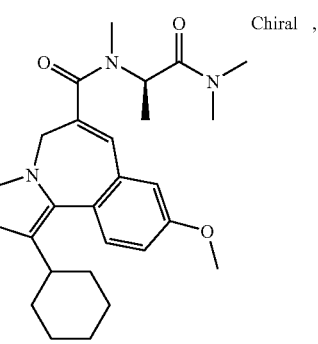,
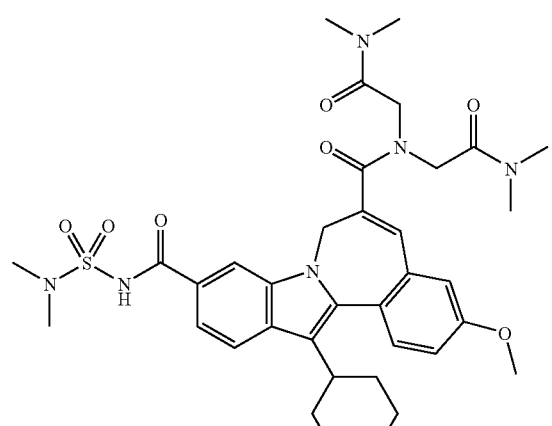,
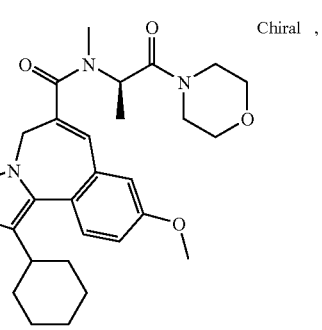,
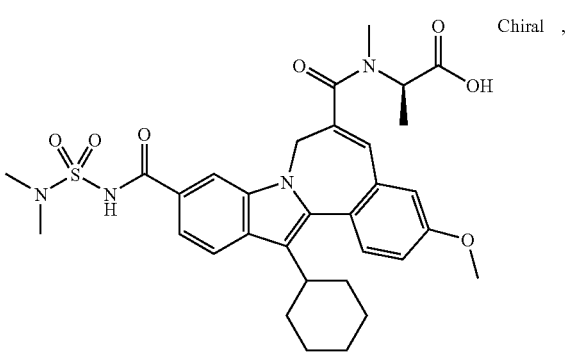
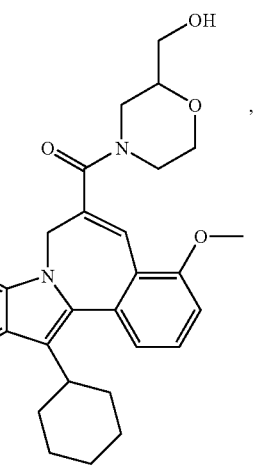, 703
-continued
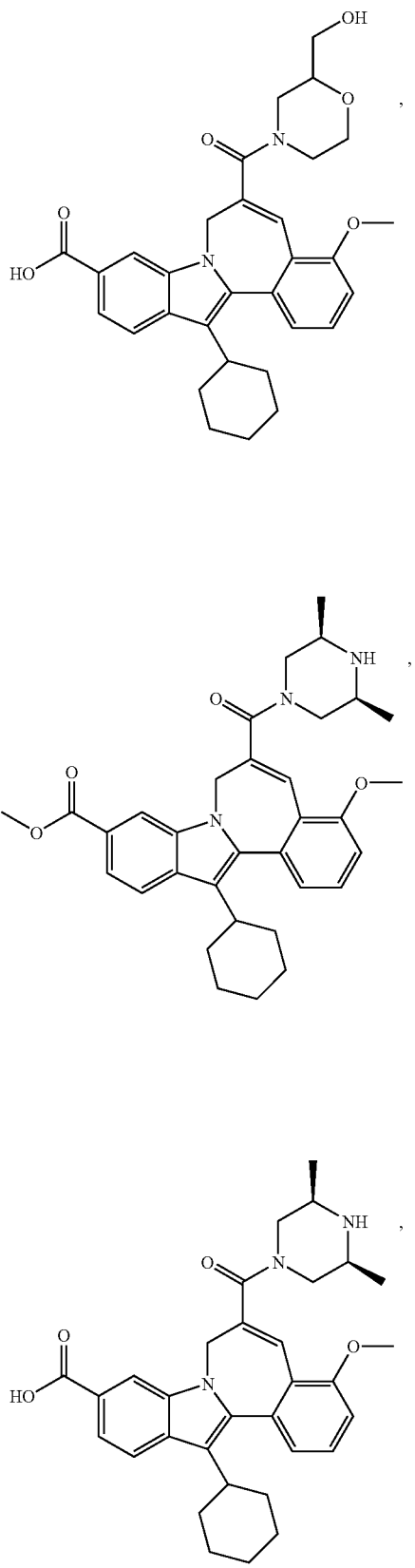
704
-continued
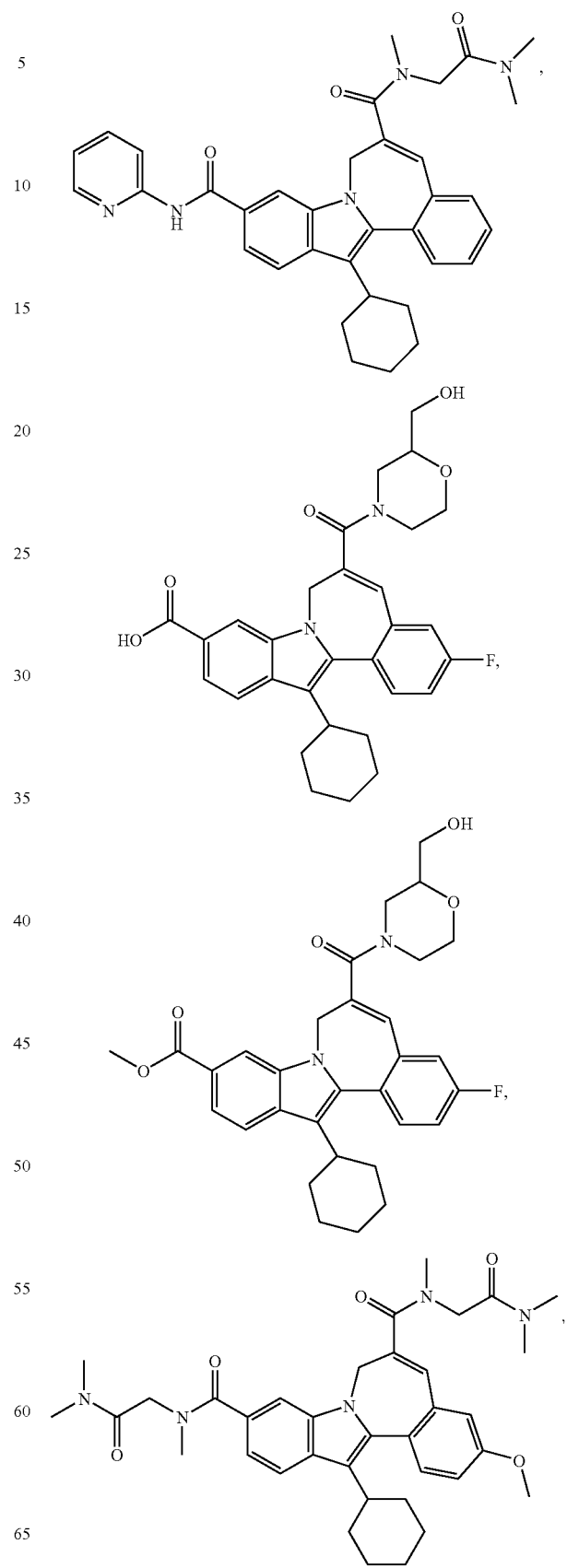

705
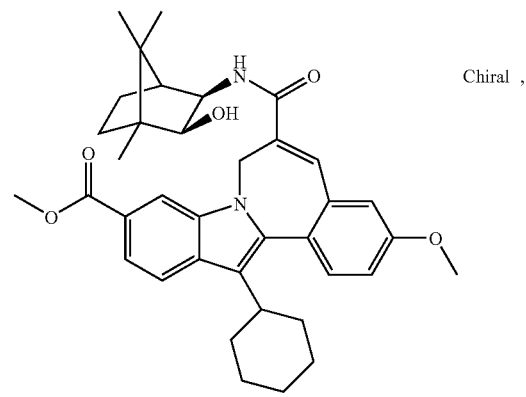
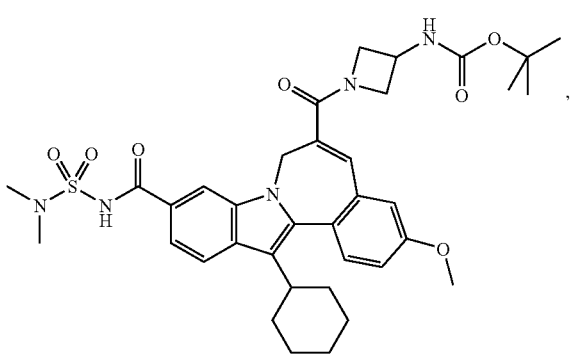
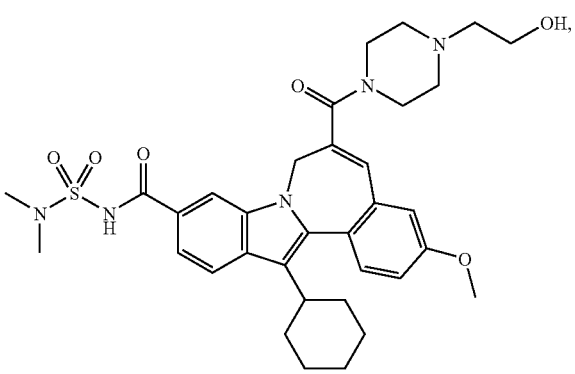
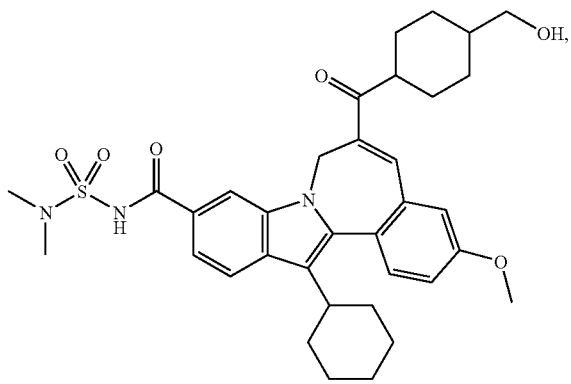
706
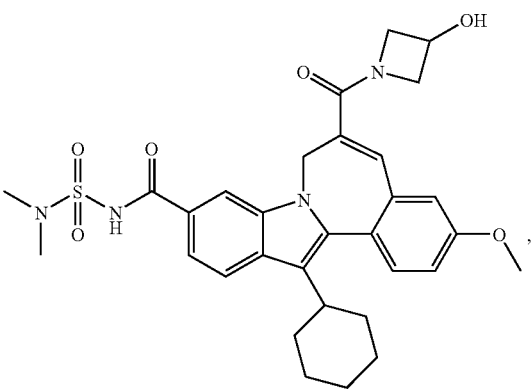
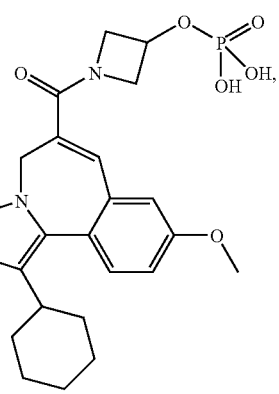
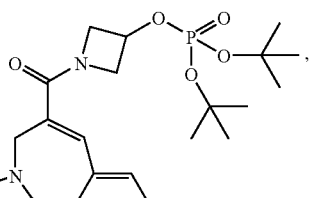
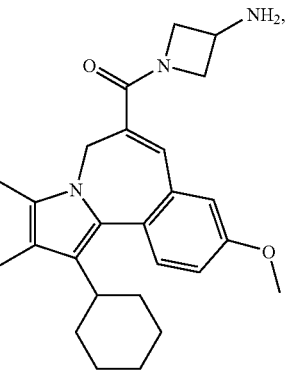

707
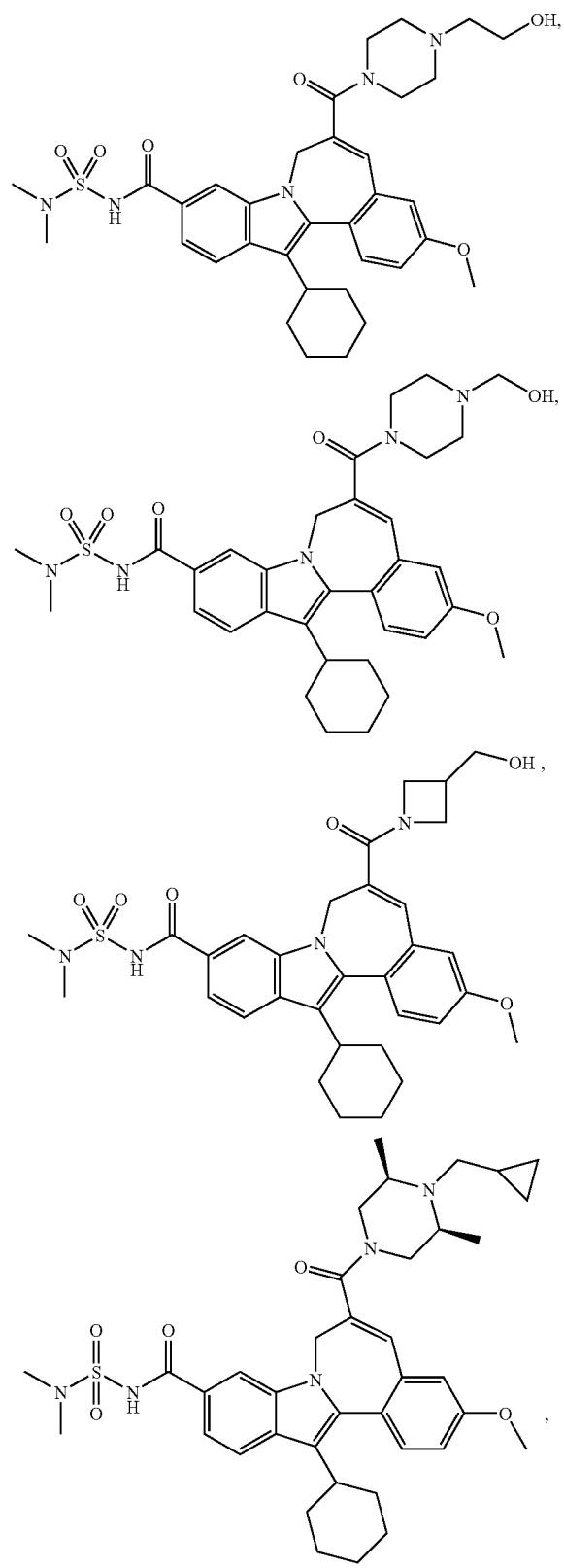
708
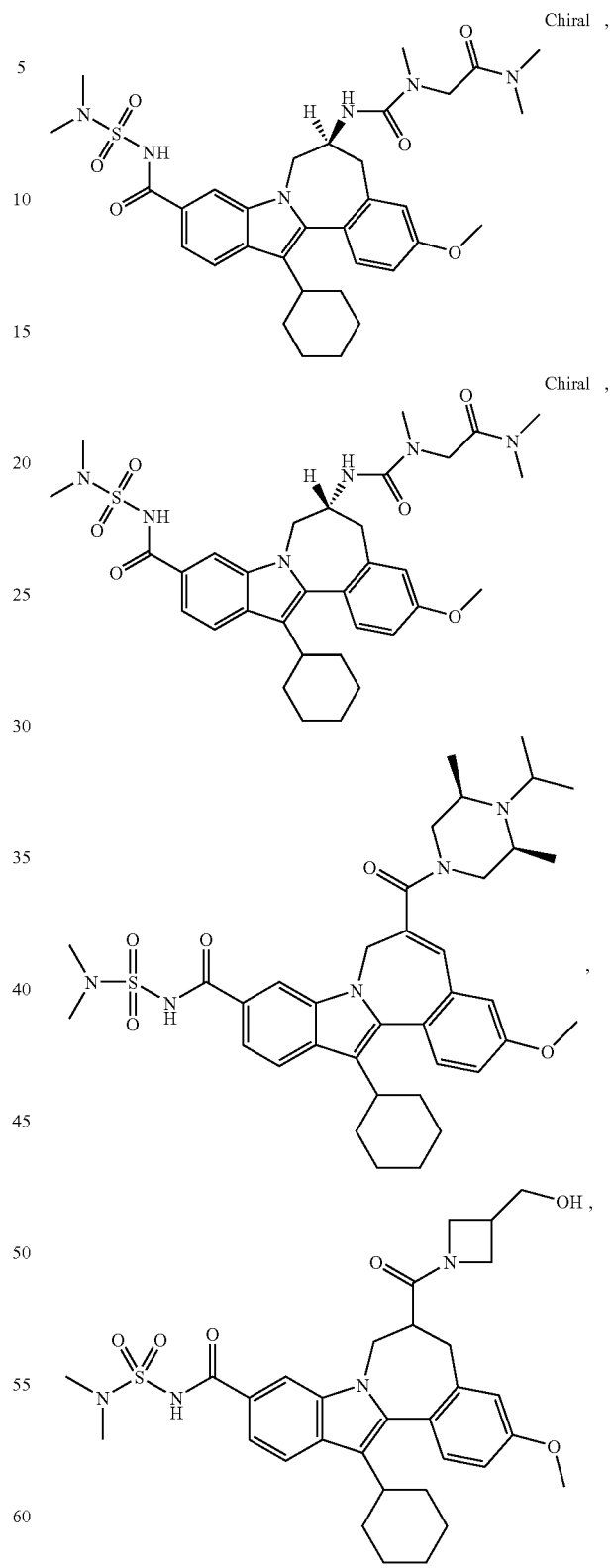

709                                                710
-continued                                         -continued
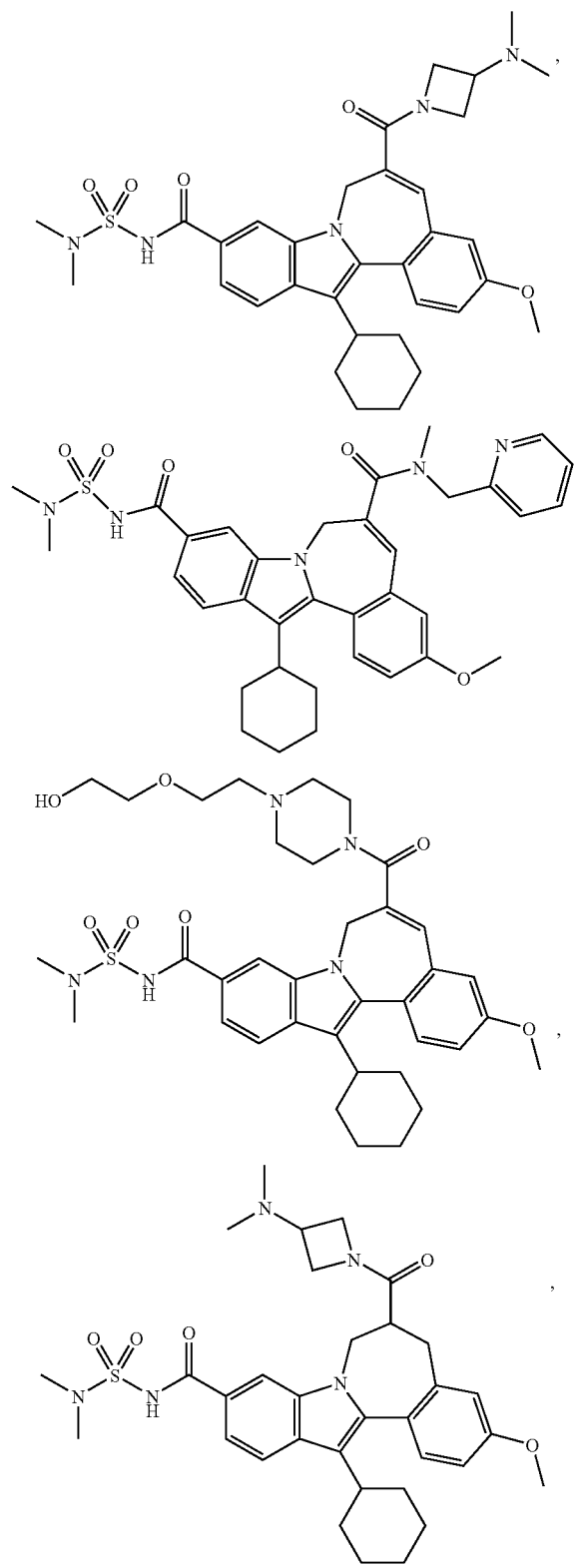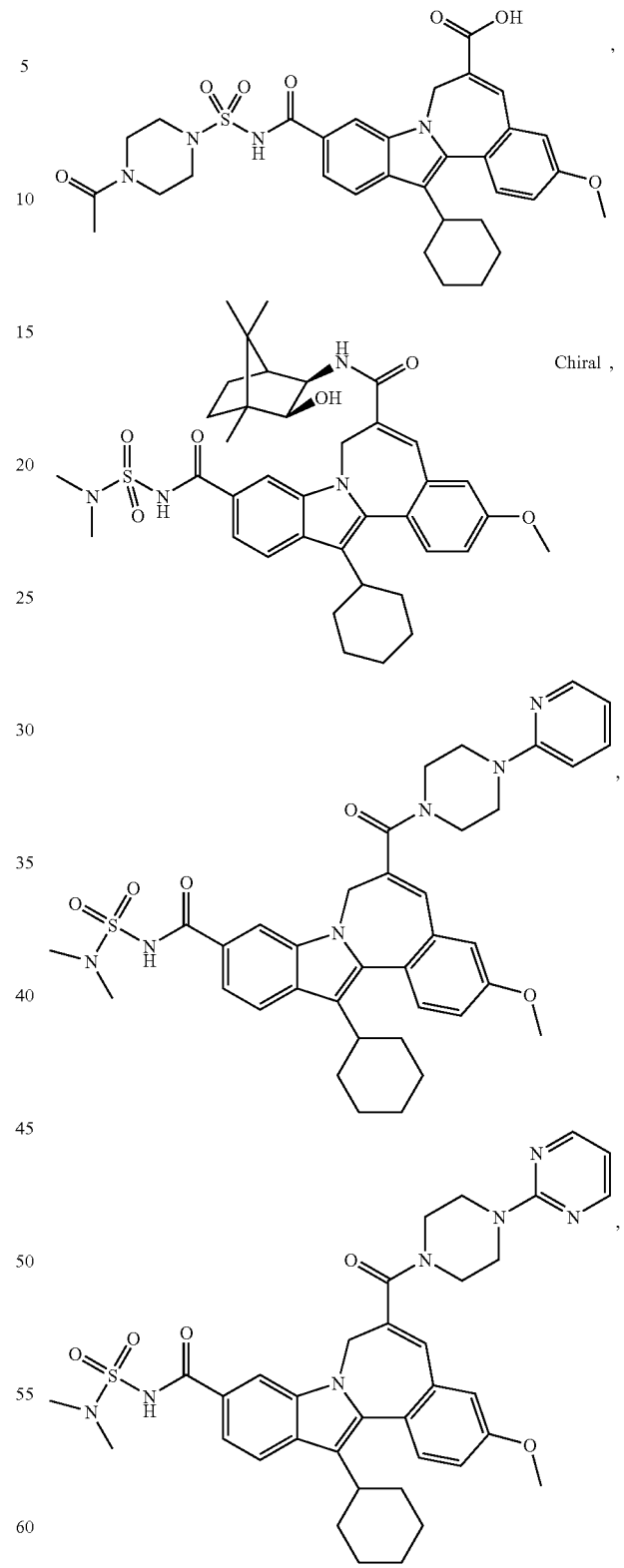

711
-continued
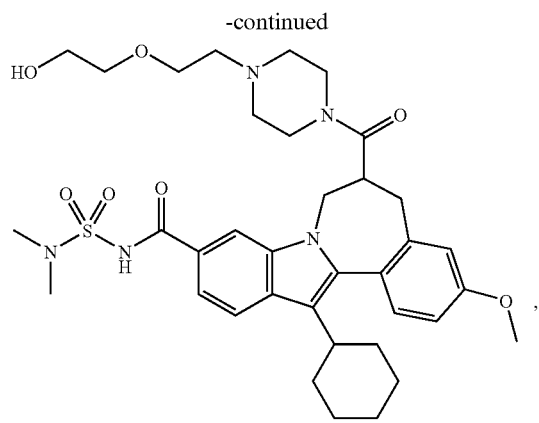
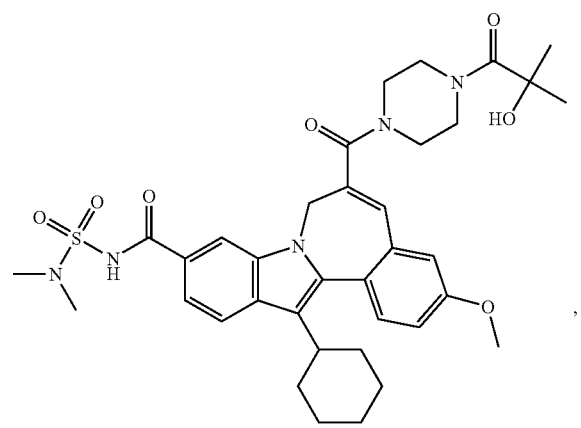
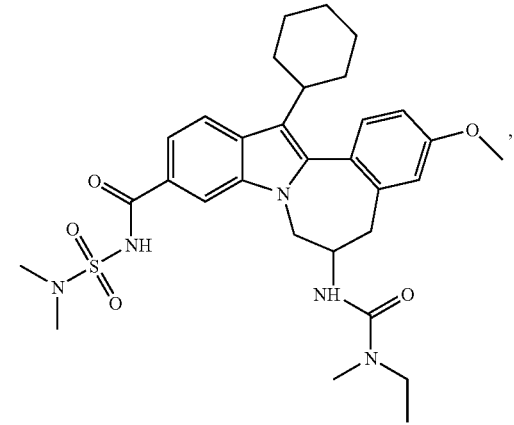
712
-continued
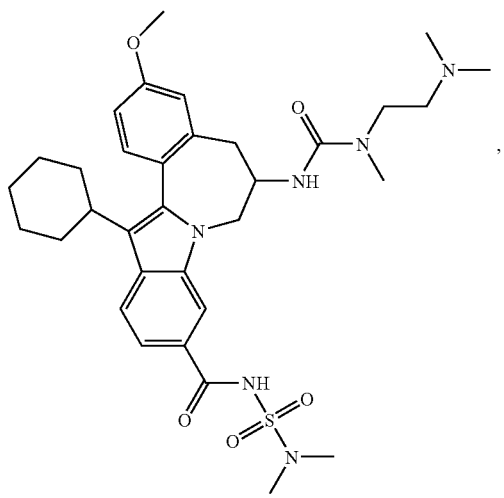
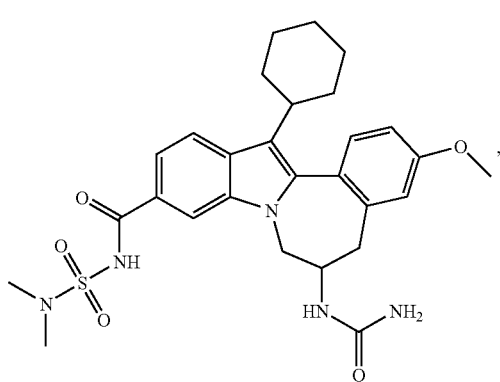
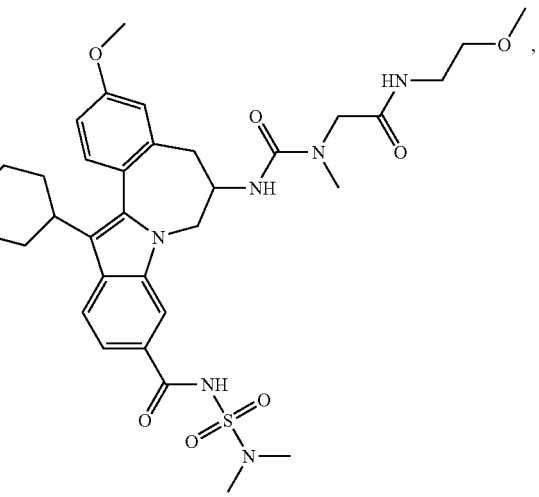

713
-continued
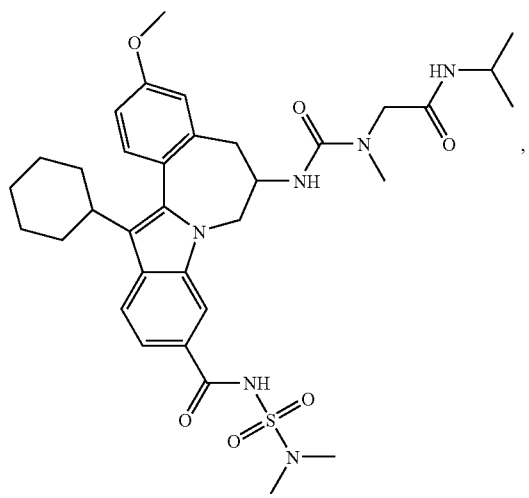
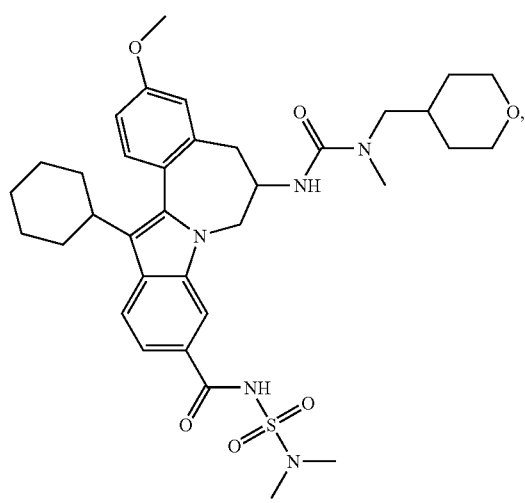
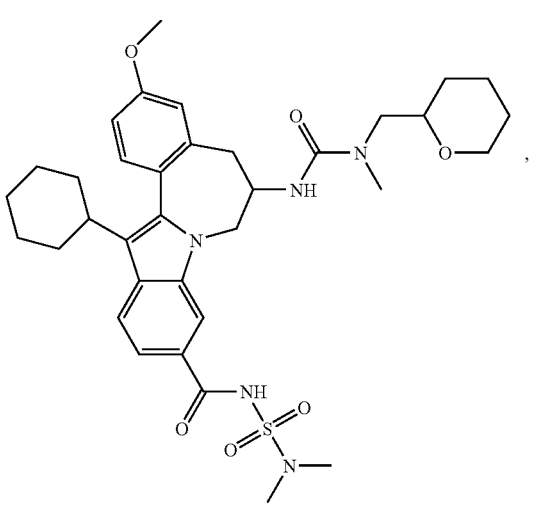
714
-continued
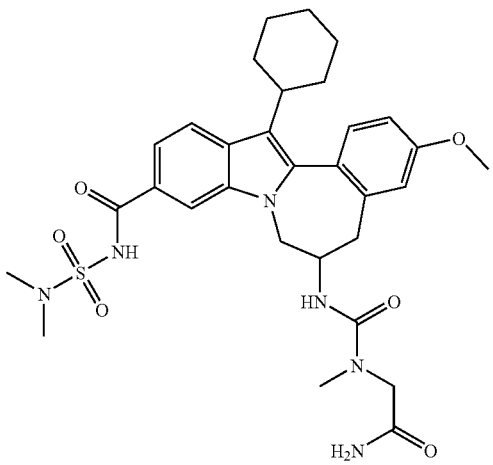
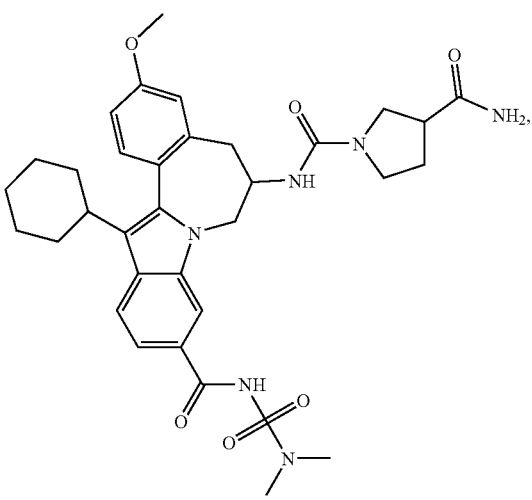
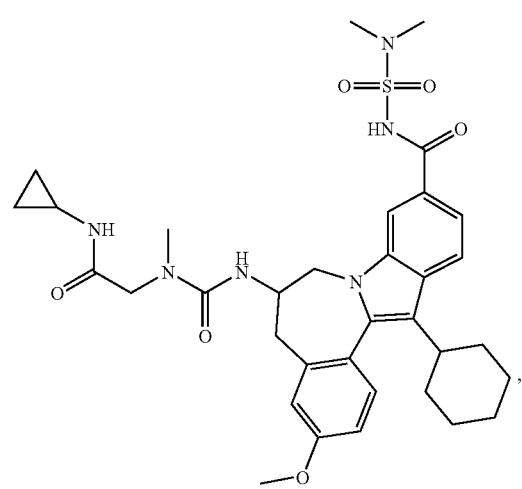

715
-continued
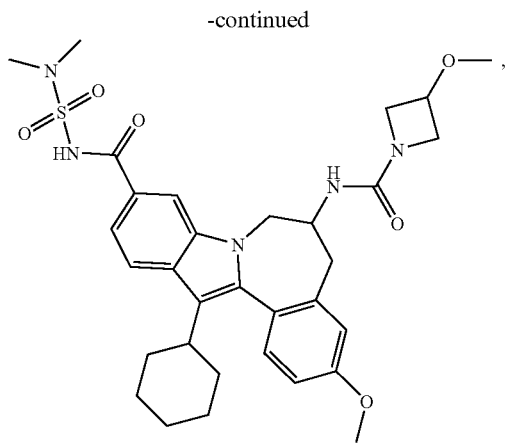
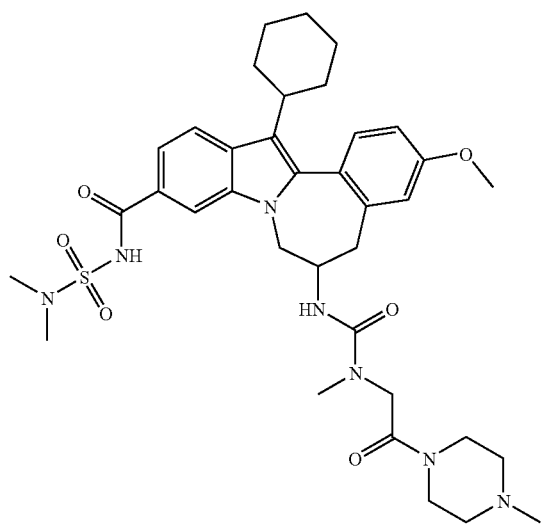
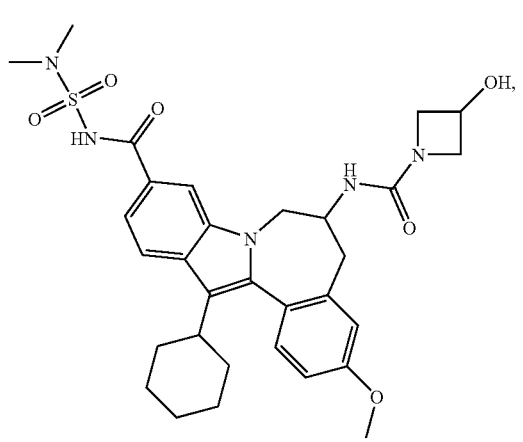
716
-continued
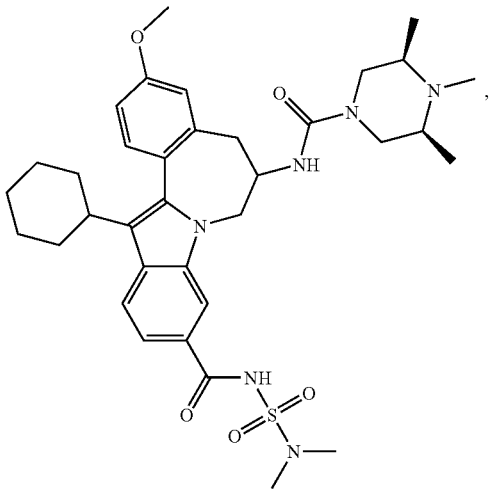
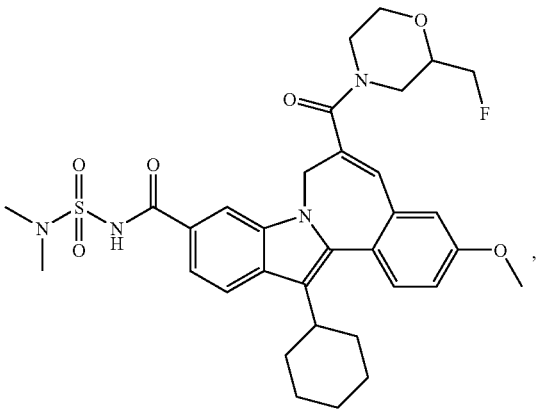
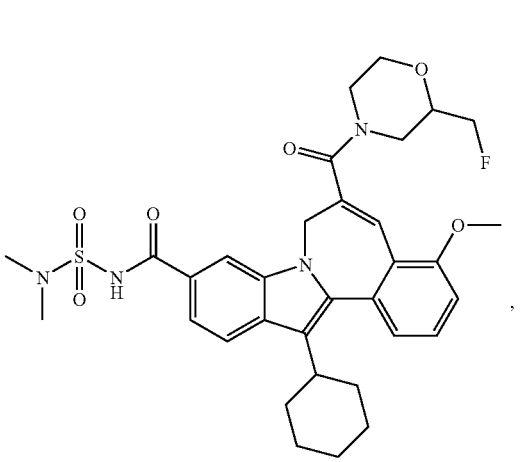

717 718
-continued
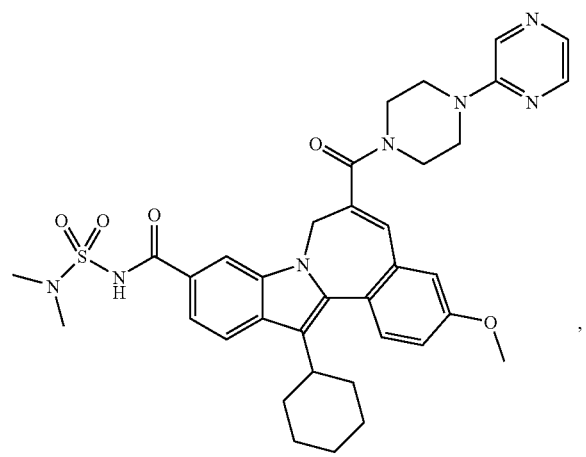
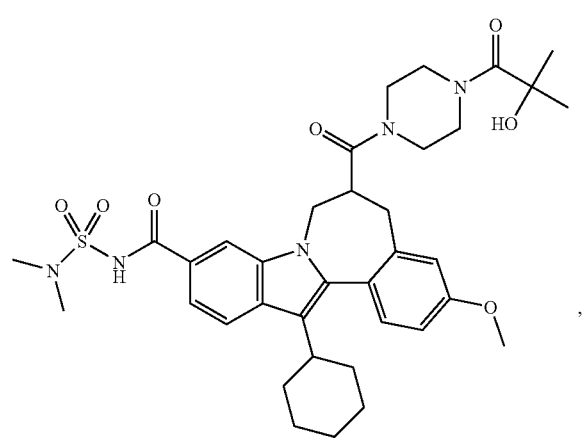
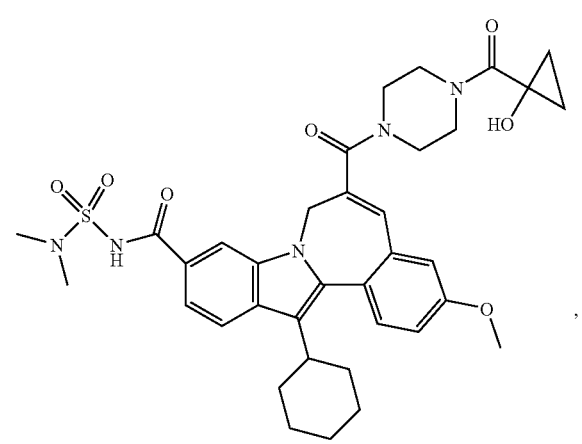
-continued
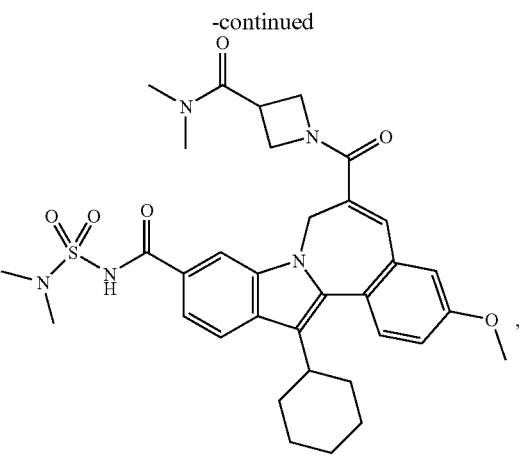
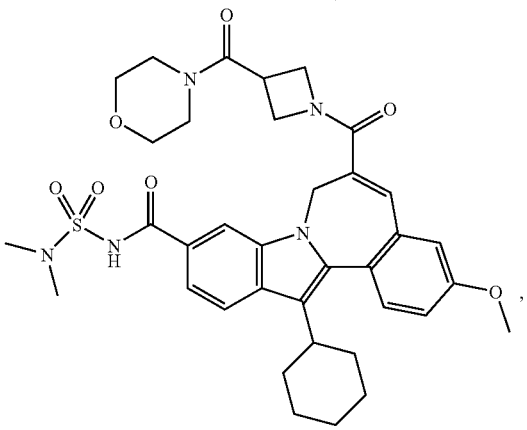
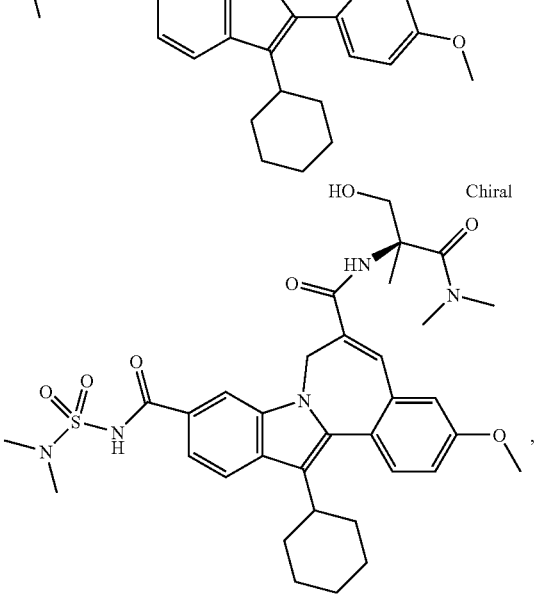

-continued
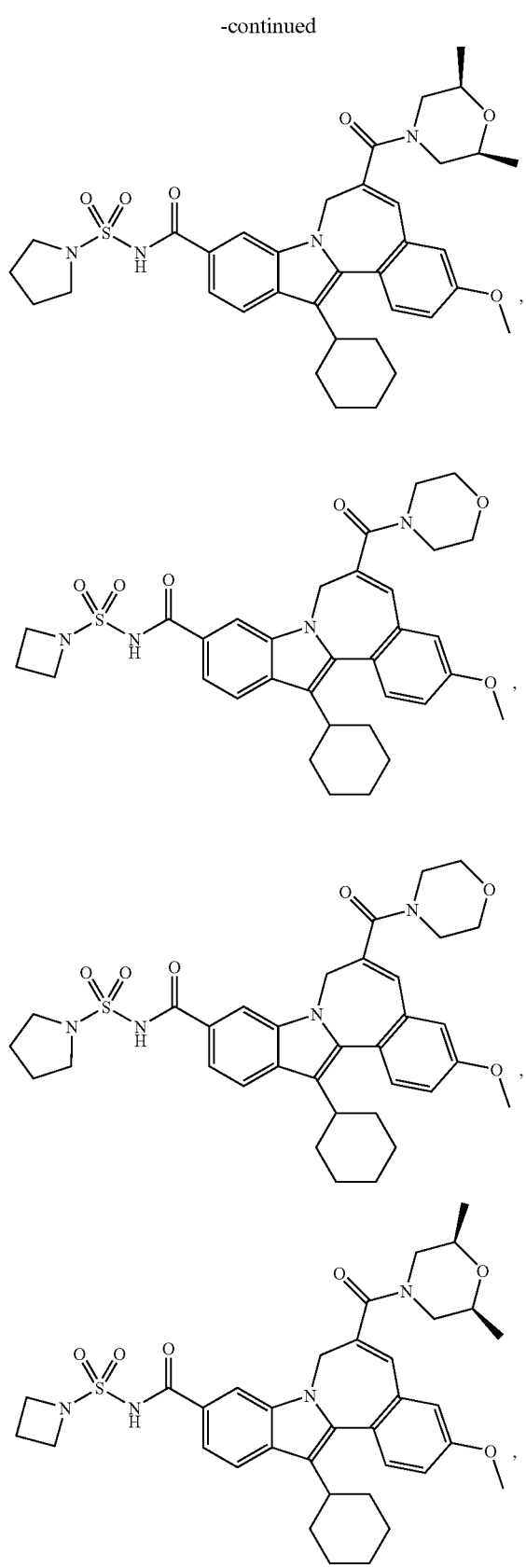
-continued
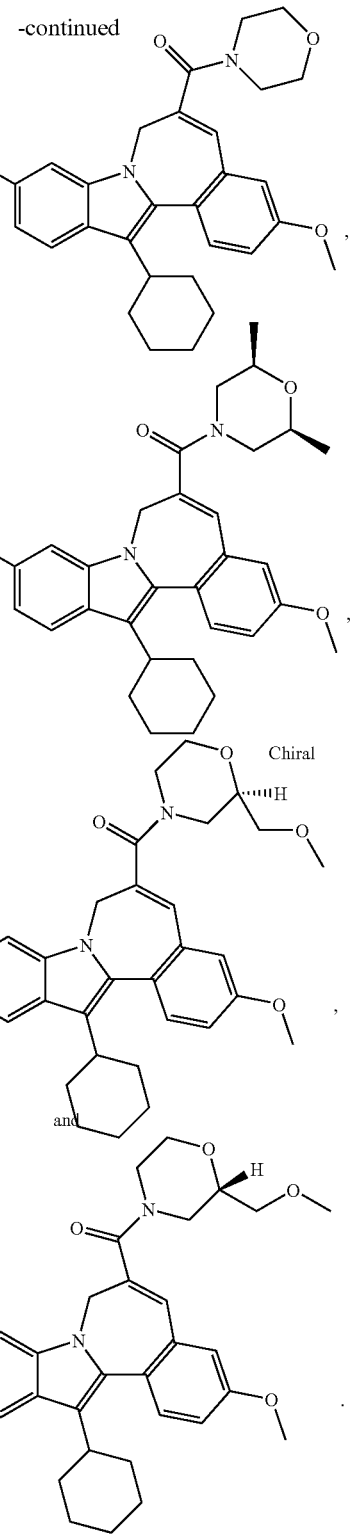
14. A composition comprising a compound of claim 1, 9, 10, 11, or 12, or a pharmaceutically acceptable salt thereof, and a pharmaceutically acceptable carrier.
15. A method of treating hepatitis C infection comprising administering a therapeutically effective amount of a compound of claim 1, 9, 10, 11, or 12 to a patient.
* * * * *